United States Patent
Dong et al.

(10) Patent No.: US 10,023,593 B2
(45) Date of Patent: Jul. 17, 2018

(54) ALK KINASE INHIBITOR, AND PREPARATION METHOD AND USES THEREOF

(71) Applicant: BEIJING PEARL BIOTECHNOLOGY LIMITED LIABILITY COMPANY, Beijing (CN)

(72) Inventors: Jiaqiang Dong, Taicang (CN); Boyu Zhong, Taicang (CN); Hongbin Yuan, Taicang (CN); Chuan Shih, Taicang (CN); Shaosong Chu, Taicang (CN); Deyi Zhang, Taicang (CN); Ruihao Zhang, Taicang (CN)

(73) Assignee: Beijing Pearl Biotechnology Limited Liability Company, Beijing (CN)

( * ) Notice: Subject to any disclaimer, the term of this patent is extended or adjusted under 35 U.S.C. 154(b) by 0 days.

(21) Appl. No.: 15/314,876

(22) PCT Filed: May 29, 2015

(86) PCT No.: PCT/CN2015/080273
§ 371 (c)(1),
(2) Date: Apr. 25, 2017

(87) PCT Pub. No.: WO2015/180685
PCT Pub. Date: Dec. 3, 2015

(65) Prior Publication Data
US 2017/0247392 A1 Aug. 31, 2017

(30) Foreign Application Priority Data

May 30, 2014 (CN) .......................... 2014 1 0238263

(51) Int. Cl.
| | |
|---|---|
| C07D 401/14 | (2006.01) |
| C07D 403/14 | (2006.01) |
| C07D 498/08 | (2006.01) |
| C07D 403/12 | (2006.01) |
| C07D 471/04 | (2006.01) |
| C07D 409/14 | (2006.01) |
| C07D 405/14 | (2006.01) |

(52) U.S. Cl.
CPC ......... *C07D 498/08* (2013.01); *C07D 401/14* (2013.01); *C07D 403/12* (2013.01); *C07D 403/14* (2013.01); *C07D 405/14* (2013.01); *C07D 409/14* (2013.01); *C07D 471/04* (2013.01)

(58) Field of Classification Search
CPC .. C07D 401/14; C07D 403/12; C07D 403/14; C07D 405/14; C07D 409/14; C07D 417/14; C07D 471/04; C07D 498/08; A61K 31/506; A61K 31/5386; A61K 31/55

USPC ................. 544/295, 324; 514/252.19, 275
See application file for complete search history.

(56) References Cited

U.S. PATENT DOCUMENTS 8,519,129 B2 * 8/2013 Marsilje, III ........ C07D 401/14
544/122

OTHER PUBLICATIONS

Gura et al., Systems for identifying new drugs are often faulty, Science, 278:1041-1042, (1997).*
Johnson et al., Relationships between drug activity in NCI preclinical in vitro and in vivo models and early clinical trials, British Journal of Cancer, 84(10):1424-1431, (2001).*
Simone, Oncology: Introduction, Cecil Textbook of Medicine, 20th Edition, vol. 1, pp. 1004-101 O, (1996).*
Pearce et al., Failure modes in anticancer drug discovery and development, Cancer Drug Design and Discovery Edited by Stephen Neidle, Chapter 18, pp. 424-435 (2008).*
Li, Youzhi et al., Suppression of cancer relapse and metastasis by inhibiting cancer sternness, PNAS, vol. 112, No. 6, pp. 1839-1844 (2015).*
Martelli et al., EML4-ALK Rearrangement in Non-Small Cell Lung Cancer and Non-Tumor Lung Tissues, The American Journal of Pathology, vol. 174, No. 2, pp. 661-670 (2009).*
Zhang et al., Discovery of 2-arylamino-4-(1-methyl-3-isopropylsulfonyl-4-pyrazol-amino)pyrimidines as potent anaplastic lymphoma kinase (ALK) inhibitors, Bioorganic & Medicinal Chemistry Letters, vol. 25, pp. 3738-3743 (2015).*

* cited by examiner

*Primary Examiner* — Deepak R Rao
(74) *Attorney, Agent, or Firm* — Lewis Roca Rothgerber Christie LLP

(57) ABSTRACT

An ALK kinase inhibitor compound as represented by Formula I, pharmaceutical composition containing the compound, and preparation method and use thereof in the preparation of drugs serving as an ALK inhibitor for treating cancer.

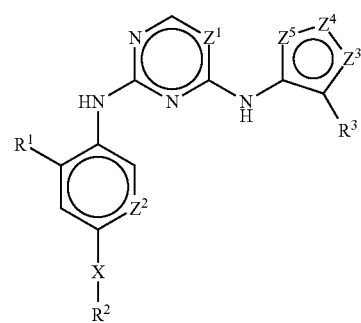

37 Claims, No Drawings

ALK KINASE INHIBITOR, AND PREPARATION METHOD AND USES THEREOF

CROSS-REFERENCE TO RELATED APPLICATION(S)

This application is a U.S. National Phase Patent Application and claims priority to and the benefit of International Application Number PCT/CN2015/080273, filed on May 29, 2015, which claims priority to Chinese Patent Application No. 201410238263.6, filed May 30, 2014, the entire content of all of which are incorporated herein by reference.

TECHNICAL FIELD

The present invention relates to the field of pharmaceutical chemistry, specifically relates to compounds for inhibiting, regulating and/or modulating ALK kinase signal transduction, method for preparing the same, pharmaceutical compositions containing the same and uses thereof as drugs.

BACKGROUND ART

Protein kinases are enzymatic components of the signal transduction pathways, which catalyze the transfer of the terminal phosphate from ATP to the hydroxyl group of tyrosine, serine and/or threonine residues of proteins. Thus, compounds which inhibit protein kinase functions are valuable tools for assessing the physiological consequences of protein kinase activation. The overexpression or inappropriate expression of normal or mutant protein kinases in mammals has been a topic of extensive study and has been demonstrated to play a significant role in the development of many diseases, including diabetes, angiogenesis, psoriasis, restenosis, ocular disease, schizophrenia, rheumatoid arthritis, atherosclerosis, cardiovascular disease and cancer. Inhibitors of protein kinases have particular utility in the treatment of human and animal disease.

One of the principal mechanisms by which cellular regulation is effected is through the transduction of extracellular signal across the membrane that in turn modulates biochemical pathways within the cell. Protein phosphorylation represents one course by which intracellular signals propagated from molecule to molecule resulting eventually in a cellular response. Phosphorylation of proteins occurs predominantly at serine, threonine or tyrosine residues and protein kinases have therefore been classified by their specificity of phosphorylation sites, i.e. serine/threonine kinases and tyrosine kinases. Because phosphorylation is such a ubiquitous process within cells, and because cellular phenotypes are largely influenced by the activity of these pathways, it is currently believed that a number of diseases states and/or disorders are a result of either aberrant activation or functional mutations in the molecular components of kinase cascades.

Anaplastic lymphoma kinase (ALK) is a member of the receptor tyrosine kinase family, which can collect downstream protein molecules through autophosphorylation, express specific genes and modulate the growth and metabolism of cells. Anaplastic lymphoma kinase was firstly discovered in anaplastic large cell lymphoma (ALCL). Abnormal expression of ALK in certain ALCL comes from the ectopias of different chromosomes, the fusion proteins produced from ALK ectopia play a role of oncogene. Such fusion proteins retain the intracellular kinase portion of ALK and fuse the N-terminal fragment of the fusion protein, resulting in high expression and over-activation of intracellular ALK kinases and causing the malignant transformation of cells. Currently known genes which can fuse with ALK have reached 22 or more. On the other hand, just as other members of the receptor tyrosine kinase family, ALK also can lead to over-activation of intracellular ALK kinases through gene mutations and overexpression from varieties reasons.

So far, ALK fusion protein, ALK gene overexpression and ALK mutation have been identified in large numbers of human diseases, including tumors and cancers, such as melanoma, neuroblastoma, glioblastoma, rhabdomyosarcoma, astrocytoma, Ewing's sarcoma, retinoblastoma, anaplastic large cell lymphoma (ALCL), inflammatory myofibroblastic tumor (IMT), diffuse large B-cell lymphoma (DLBCL), non-small cell lung cancer (NSCLC), renal medullary carcinoma (RMC), renal cell carcinoma (RCC), breast cancer, colon cancer, ovarian serous carcinoma (SOC) and esophageal squamous cell carcinoma (ESCC).

SUMMARY OF THE INVENTION

The object of the present invention is to provide a compound as ALK kinase inhibitors or a pharmaceutical salt (pharmaceutically acceptable salt) thereof. Another object of the present invention is to provide a method for preparing the compound as ALK kinase inhibitors. Still another object of the present invention is to provide a pharmaceutical composition comprising the compound as ALK kinase inhibitors or the pharmaceutical acceptable salt thereof. Even another object of the present invention is to provide the use of the compound as ALK kinase inhibitors or the pharmaceutically acceptable salt thereof in the preparation of anti-tumor drugs. Yet a further object of the present invention is to provide a method for treating tumors.

The above objects of the present invention are achieved by the following technical solutions.

In one aspect, the present invention provides a compound as ALK kinase inhibitors or a pharmaceutically acceptable salt thereof, wherein the compound as ALK kinase inhibitors has the structure represented by the following Formula I,

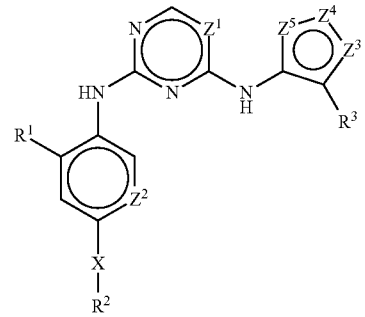

Formula I wherein, $R^1$ is alkyl, haloalkyl or —O—$R^4$, wherein $R^4$ is hydrogen, $C_{1-8}$ alkyl, halo $C_{1-8}$ alkyl, $C_{3-8}$ cycloalkyl, halo $C_{3-8}$ cycloalkyl, $C_{1-8}$ alkyl-$C_{3-8}$ cycloalkyl, $C_{3-8}$ cycloalkyl-$C_{1-8}$ alkyl, substituted or unsubstituted heterocyclyl, or substituted or unsubstituted heterocyclyl-$C_{1-8}$ alkyl;

$R^2$ is alkyl, cycloalkyl, heterocycloalkyl or heterocycloalkenyl, which may optionally be substituted with 1 to 3 substituents independently selected from the group consisting of oxo, $C_{1-8}$ alkyl, halo $C_{1-8}$ alkyl, $C_{1-8}$ alkoxy, halo $C_{1-8}$ alkoxy, $C_{3-8}$ cycloalkyl, halo $C_{3-8}$ cycloalkyl, $C_{3-8}$ cycloalkoxy, halo $C_{3-8}$ cycloalkoxy, $C_{1-8}$ alkoxy-$C_{1-8}$ alkyl, hydroxy-$C_{1-8}$ alkyl, amino —$C_{1-8}$ alkyl, carboxy-$C_{1-8}$ alkyl, $C_{1-8}$ alkyl -amino-$C_{1-8}$ alkyl, halogen, hydroxy, cyano, cyano-$C_{1-8}$ alkyl, amino, $C_{1-8}$ alkyl-amino, di ($C_{1-8}$ alkyl)-amino, $C_{3-8}$ cycloalkyl -amino, substituted or unsubstituted aromatic group, substituted or unsubstituted heteroaromatic group, substituted or unsubstituted heterocyclyl, substituted or unsubstituted heterocyclyl-alkyl, $(CH_2)_nCONR^5R^6$, —$COR^5$, —$SO_2R^5$ and —$NR^5SO_2R^6$, wherein n is an integer of 0-8, $R^5$ and $R^6$ are independently hydrogen, alkyl, haloalkyl, cycloalkyl, halocycloalkyl, amino, $C_{1-8}$ alkyl-amino, di ($C_{1-8}$ alkyl)-amino, cyano-$C_{1-8}$ alkyl, $C_{1-8}$ alkyl-amino-$C_{1-8}$ alkyl or di ($C_{1-8}$ alkyl)-amino-$C_{1-8}$ alkyl, wherein the substituent groups may optionally form a ring with the carbon atoms to which they are attached. $R^3$ is —$SO_2R^7$, —$SO_2NR^7R^8$, —CN, —$CONR^7R^8$, or —$COR^7$, wherein $R^7$ and $R^8$ are independently hydrogen, alkyl or cycloalkyl.

X is a chemical bond, O, S, CO, $NR^9$, $SO_2$ or S(O), wherein $R^9$ is hydrogen, $C_{1-8}$ alkyl, halo $C_{1-8}$ alkyl, $C_{3-8}$ cycloalkyl, halo $C_{3-8}$ cycloalkyl, $C_{1-8}$ alkyl-CO or 4-6 membered heterocyclyl.

$Z^1$ is N or C—$R^{10}$, wherein $R^{10}$ is hydrogen, halogen, alkyl, haloalkyl, cycloalkyl, halocycloalkyl, alkoxy, haloalkoxy or cyano;

$Z^2$ is C—$R^{11}$ or N, wherein $R^{11}$ is hydrogen, $C_{1-8}$ alkyl, halo $C_{1-8}$ alkyl, $C_{3-8}$ cycloalkyl, halo $C_{3-8}$ cycloalkyl, $C_{1-8}$ alkoxy, halo $C_{1-8}$ alkoxy, $C_{3-8}$ cycloalkoxy, halo $C_{3-8}$ cycloalkoxy, halogen, amino, $C_{1-8}$ alkyl-amino, di($C_{1-8}$ alkyl)-amino or cyano, wherein $R^{11}$ and $R^2$ may optionally form a ring together with the carbon atoms to which they are attached, the ring may be optionally substituted with 1 to 3 substituents independently selected from the group consisting of oxo, $C_{1-8}$ alkyl, halo $C_{1-8}$ alkyl, $C_{1-8}$ alkoxy, halo $C_{1-8}$ alkoxy, $C_{3-8}$ cycloalkyl, halo $C_{3-8}$ cycloalkyl, $C_{3-8}$ cycloalkoxy, halo $C_{3-8}$ cycloalkoxy, $C_{1-8}$ alkoxy-$C_{1-8}$ alkyl, hydroxy-$C_{1-8}$ alkyl, amino-$C_{1-8}$ alkyl, carboxy-$C_{1-8}$ alkyl, $C_{1-8}$ alkyl-amino-$C_{1-8}$ alkyl, halogen, hydroxy, cyano, cyano-$C_{1-8}$ alkyl, amino, $C_{1-8}$ alkyl-amino, di($C_{1-8}$ alkyl)-amino, $C_{3-8}$ cycloalkyl-amino, substituted or unsubstituted aromatic group, substituted or unsubstituted heteroaromatic group, substituted or unsubstituted heterocyclyl, substituted or unsubstituted heterocyclyl alkyl, $(CH_2)nCONR^{12}R^{13}$, —$COR^{12}$, —$SO_2R^{12}$ and —$NR^{12}SO_2R^{13}$, wherein n is an integer of 0-8, $R^{12}$ and $R^{13}$ are independently hydrogen, alkyl, haloalkyl, cycloalkyl, halocycloalkyl, amino, $C_{1-8}$ alkyl-amino, di($C_{1-8}$ alkyl)-amino, cyano-$C_{1-8}$ alkyl, $C_{1-8}$ alkyl-amino-$C_{1-8}$ alkyl or di($C_{1-8}$ alkyl)-amino-$C_{1-8}$ alkyl;

$Z^3$, $Z^4$ and $Z^5$ are selected from the following groups:
$Z^3$ is N, $Z^4$ is N—$R^{14}$, $Z^5$ is CH or N;
$Z^3$ is N, $Z^4$ is C—$R^{14}$, $Z^5$ is N, O or S;
$Z^3$ is O or S, $Z^4$ is N—$R^{14}$, $Z^5$ is CH;
$Z^3$ is O or S, $Z^4$ is C—$R^{14}$, $Z^5$ is N; and
$Z^3$ is C, $Z^4$ is N—$R^{14}$, $Z^5$ is O or S;
wherein $R^{14}$ is hydrogen, alkyl, haloalkyl, $C_{3-8}$ cycloalkyl, halo$C_{3-8}$ cycloalkyl or 4-6 membered heterocyclyl.

In some embodiments, $R^1$ is $C_{1-8}$ alkyl, halo $C_{1-8}$ alkyl, or —O—$R^4$, wherein $R^4$ is hydrogen, $C_{1-8}$ alkyl, halo $C_{1-8}$ alkyl, $C_{3-8}$ cycloalkyl, halo $C_{3-8}$ cycloalkyl, $C_{1-8}$ alkyl-$C_{3-8}$ cycloalkyl, $C_{3-8}$ cycloalkyl-$C_{1-8}$ alkyl, substituted or unsubstituted 4-7 membered heterocyclyl group or substituted or unsubstituted 4-7 membered heterocyclyl-$C_{1-8}$ alkyl. In some embodiments, the substituted or unsubstituted 4-7 membered heterocyclyl is substituted or unsubstituted 4-7 membered heterocyclyl containing one or two heteroatoms selected from a group consisting of N, O, and S. In some embodiments, the substituted or unsubstituted 4-7 membered heterocyclyl-$C_{1-8}$ alkyl is substituted or unsubstituted 4-7 membered heterocyclyl-$C_{1-8}$ alkyl containing one or two heteroatoms selected from a group consisting of N, O, and S.

In some embodiments, $R^1$ is $C_{1-8}$ alkyl or —O—$R^4$, wherein $R^4$ is $C_{1-5}$ alkyl, halo $C_{1-5}$ alkyl, $C_{3-7}$ cycloalkyl, halo $C_{3-7}$ cycloalkyl or $C_{3-7}$ cycloalkyl-methyl. In some embodiments, $R^4$ is methyl, ethyl, n-propyl, isopropyl, cyclopropyl, trifluoromethyl, cyclobutyl, or cyclopropylmethyl.

In some embodiments, $R^2$ is $C_{1-8}$ alkyl, $C_{3-8}$ cycloalkyl, 4-7 membered heterocycloalkyl or 4-7 membered heterocycloalkenyl, which may optionally be substituted with 1-3 substituents independently selected from the group consisting of oxo, $C_{1-8}$ alkyl, halo $C_{1-8}$ alkyl, $C_{1-8}$ alkoxy, halo $C_{1-8}$ alkoxy, $C_{3-8}$ cycloalkyl, halo $C_{3-8}$ cycloalkyl, $C_{3-8}$ cycloalkoxy, halo-$C_{3-8}$ cycloalkoxy, $C_{1-8}$ alkoxy-$C_{1-8}$ alkyl, hydroxy-$C_{1-8}$ alkyl, amino-$C_{1-8}$ alkyl, carboxy-$C_{1-8}$ alkyl, $C_{1-8}$ alkyl-amino-$C_{1-8}$ alkyl, halogen, hydroxy, cyano, cyano-$C_{1-8}$ alkyl, amino, $C_{1-8}$ alkyl-amino, di ($C_{1-8}$ alkyl)-amino, $C_{3-8}$ cycloalkyl-amino, substituted or unsubstituted aromatic group, substituted or unsubstituted heteroaromatic group, substituted or unsubstituted 4-7 membered heterocyclyl, substituted or unsubstituted 4-7 membered heterocyclyl-$C_{1-8}$ alkyl, —$(CH_2)_nCONR^5R^6$, —$COR^5$, —$SO_2R^5$ and —$NR^5SO_2R^6$, wherein n is an integer of 0-8, $R^5$ and $R^6$ are independently hydrogen, $C_{1-8}$ alkyl, halo $C_{1-8}$ alkyl, $C_{3-8}$ cycloalkyl, halo $C_{3-8}$ cycloalkyl, amino, $C_{1-8}$ alkyl-amino, di ($C_{1-8}$ alkyl)-amino, cyano-$C_{1-8}$ alkyl, $C_{1-8}$ alkyl-amino-$C_{1-8}$ alkyl or di-($C_{1-8}$ alkyl)-amino —$C_{1-8}$ alkyl, wherein the substituent groups may optionally form a substituted or unsubstituted ring with the carbon atoms to which they are attached; preferably, wherein the substituent groups and the carbon atoms to which they are attached form a substituted or unsubstituted ring.

In some embodiments, $R^2$ is $C_{1-8}$ alkyl, $C_{3-8}$ cycloalkyl, 4-7 membered heterocycloalkyl containing one or two heteroatoms selected from a group consisting of N, O and S or 4-7 membered heterocycloalkenyl containing one or two heteroatoms selected from a group consisting of N, O and S, which may optionally be substituted with 1-3 substituent groups independently selected from the following group: oxo, $C_{1-8}$ alkyl, halo $C_{1-8}$ alkyl, $C_{1-8}$ alkoxy, halo $C_{1-8}$ alkoxy, $C_{3-8}$ cycloalkyl, halo $C_{3-8}$ cycloalkyl, $C_{3-8}$ cycloalkoxy, halo $C_{3-8}$ cycloalkoxy, $C_{1-8}$ alkoxy-$C_{1-8}$ alkyl, hydroxy-$C_{1-8}$ alkyl, amino-$C_{1-8}$ alkyl, carboxy-$C_{1-8}$ alkyl, $C_{1-8}$ alkyl-amino-$C_{1-8}$ alkyl, halogen, hydroxy, cyano, cyano-$C_{1-8}$ alkyl, amino, $C_{1-8}$ alkyl-amino, di ($C_{1-8}$ alkyl)-amino, $C_{3-8}$ cycloalkyl-amino, substituted or unsubstituted aromatic group, substituted or unsubstituted heteroaromatic group, substituted or unsubstituted 4-7 membered heterocyclyl, substituted or unsubstituted 4-7 membered heterocyclyl —$C_{1-8}$ alkyl, —$(CH_2)_nCONR^5R^6$, —$COR^5$, —$SO_2R^5$ and —$NR^5SO_2R^6$, wherein n is an integer of 0-8, $R^5$ and $R^6$ are independently hydrogen, $C_{1-8}$ alkyl, halo $C_{1-8}$ alkyl, $C_{3-8}$ cycloalkyl, halo $C_{3-8}$ cycloalkyl, amino, $C_{1-8}$ alkyl-amino, di ($C_{1-8}$ alkyl)-amino, or cyano-$C_{1-8}$ alkyl, $C_{1-8}$ alkyl-amino-$C_{1-8}$ alkyl or di-($C_{1-8}$ alkyl)-amino-$C_{1-8}$ alkyl, wherein the substituent groups may optionally form a substituted or unsubstituted ring with the carbon atoms to which they are attached.

In some embodiments, $R^2$ is cyclohexyl, piperidinyl, pyrrolidinyl, azetidinyl, tetrahydropyranyl, morpholinyl or 3-4 alkenyl piperidinyl, which are optionally substituted with 1-3 substituents independently selected from the following group: methyl, ethyl, n-propyl, isopropyl, n-butyl, sec-butyl, isobutyl, tert-butyl, cyclopropyl, cyclobutyl, oxetane, methoxy, methoxymethyl, methoxyethyl, fluoro, chloro, cyano, amino, cyclopropylamino, (isopropyl, methyl)-amino, formyl, acetyl, trifluoroacetyl, cyclopropanecarbonyl, —$COR^5$, —$SO_2R^5$ and —$NR^5SO_2R^6$, wherein $R^5$ and $R^6$ are independently hydrogen, $C_{1-5}$ alkyl, dimethylamino, dimethylaminomethyl, ethylamino or cyanomethyl.

In some embodiments, $R^3$ is —$SO_2R^7$, —$SO_2NR^7R^8$, —CN, —$CONR^7R^8$, or —$COR^7$, wherein $R^7$ and $R^8$ are independently hydrogen, $C_{1-8}$ alkyl or $C_{3-8}$ cycloalkyl.

In some embodiments, $R^3$ is —$SO_2R^7$, wherein $R^7$ is hydrogen, $C_{1-8}$ alkyl or $C_{3-8}$ cycloalkyl. In some embodiments, $R^7$ is isopropyl, sec-butyl or isobutyl.

In some embodiments, X is a chemical bond or CO.

In some embodiments, $Z^1$ is C—$R^{10}$, wherein $R^{10}$ is hydrogen, halogen, $C_{1-8}$ alkyl, halo $C_{1-8}$ alkyl, $C_{3-8}$ cycloalkyl, halo $C_{3-8}$ cycloalkyl, $C_{1-8}$ alkoxy, halo $C_{1-8}$ alkoxy, or cyano; preferably, $R^{10}$ is halogen; more preferably, $R^{10}$ is chloro.

In some embodiments, $Z^2$ is C—$R^{11}$, wherein $R^{11}$ is hydrogen, $C_{1-8}$ alkyl, halogen or cyano, wherein $R^{11}$ and $R^2$ may optionally together form a ring with the carbon atoms to which they are attached, the ring may optionally be substituted with 1-3 substituents independently selected from the group consisting of: oxo, $C_{1-8}$ alkyl, halo $C_{1-8}$ alkyl, $C_{1-8}$ alkoxy, halo $C_{1-8}$ alkoxy, $C_{3-8}$ cycloalkyl, halo $C_{3-8}$ cycloalkyl, $C_{3-8}$ cycloalkoxy, halo $C_{3-8}$ cycloalkoxy, $C_{1-8}$ alkoxy-$C_{1-8}$ alkyl, hydroxy-$C_{1-8}$ alkyl, amino-$C_{1-8}$ alkyl, carboxyl-$C_{1-8}$ alkyl, $C_{1-8}$ alkyl-amino-$C_{1-8}$ alkyl, halogen, hydroxy, cyano, cyano-$C_{1-8}$ alkyl, amino, $C_{1-8}$ alkyl-amino, di ($C_{1-8}$ alkyl) amino, $C_{3-8}$ cycloalkyl-amino, substituted or unsubstituted aromatic group, substituted or unsubstituted heteroaromatic group, substituted or unsubstituted heterocyclyl, substituted or unsubstituted heterocyclyl-alkyl, —$(CH_2)_nCONR^{12}R^{13}$, —$COR^{12}$, —$SO_2R^{12}$ and —$NR^{12}SO_2R^{13}$, wherein n is an integer of 0-8, $R^{12}$ and $R^{13}$ are independently hydrogen, alkyl, haloalkyl, cycloalkyl, halocycloalkyl, amino, $C_{1-8}$ alkyl-amino, di ($C_{1-8}$ alkyl)-amino, cyano $C_{1-8}$ alkyl, $C_{1-8}$ alkyl -amino-$C_{1-8}$ alkyl or di-($C_{1-8}$ alkyl)-amino-$C_{1-8}$ alkyl.

In some embodiments, $R^{11}$ and $R^2$ together with the carbon atoms to which they are attached form a ring.

In some embodiments, $Z^2$ is C—$R^{11}$, wherein $R^{11}$ is hydrogen, $C_{1-8}$ alkyl, halogen or cyano. In some embodiments, $R^{11}$ is hydrogen, methyl, fluoro, chloro or cyano.

In some embodiments, $Z^3$, $Z^4$ and $Z^5$ are selected from the following group:
$Z^3$ is N, $Z^4$ is N—$R^{14}$, $Z^5$ is CH or N;
$Z^3$ is N, $Z^4$ is C—$R^{14}$, $Z^5$ is N, O or S;
$Z^3$ is O or S, $Z^4$ is N—$R^{14}$, $Z^5$ is CH;
$Z^3$ is O or S, $Z^4$ is C—$R^{14}$, $Z^5$ is N; and
$Z^3$ is C, $Z^4$ is N—$R^{14}$, $Z^5$ is O or S,
wherein $R^{14}$ is hydrogen, $C_{1-8}$ alkyl, $C_{3-8}$ cycloalkyl, halo $C_{3-8}$ cycloalkyl, 4-6 membered heterocyclyl containing 1 or 2 heteroatoms selected from the group consisting of N, O and S or halo 4-6 membered heterocyclyl containing 1 or 2 heteroatoms selected from the group consisting of N, O and S.

In some embodiments, $Z^3$ is N, $Z^4$ is N—$R^{14}$, $Z^5$ is CH, wherein $R^{14}$ is hydrogen, $C_{1-8}$ alkyl, $C_{3-8}$ cycloalkyl, halo $C_{3-8}$ cycloalkyl, 4-6 membered heterocyclyl containing 1 or 2 heteroatoms selected from the group consisting of N, O and S or halo 4-6 membered heterocyclyl containing 1 or 2 heteroatoms selected from the group consisting of N, O and S. In some embodiments, $R^{14}$ is $C_{1-8}$ alkyl or $C_{3-8}$ cycloalkyl. In some embodiments, $R^{14}$ is methyl or cyclopropyl.

In some embodiments, $Z^3$ is N, $Z^4$ is C—$R^{14}$, $Z^5$ is S, wherein $R^{14}$ is $C_{1-8}$ alkyl or $C_{3-8}$ cycloalkyl; preferably, $R^{14}$ is methyl or cyclopropyl.

In some embodiments, the compounds have the following structures:

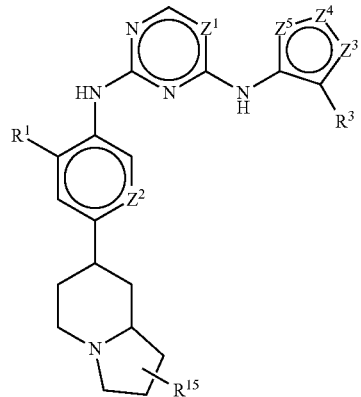

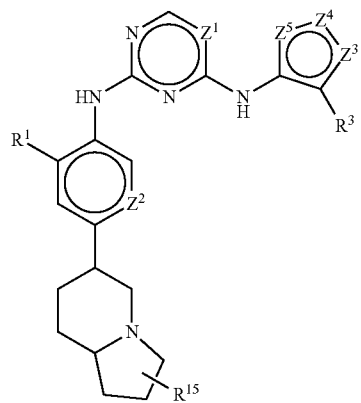

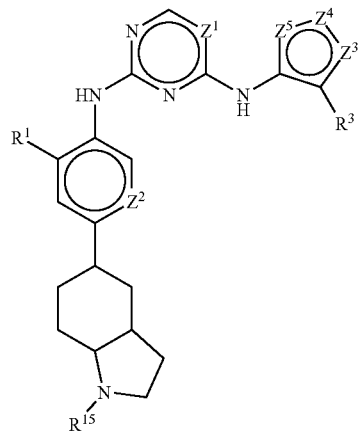

-continued
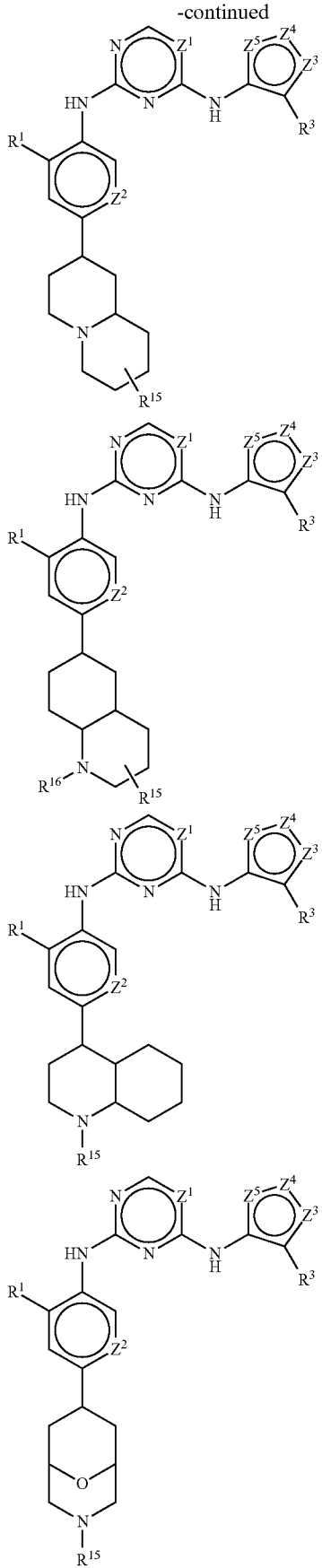
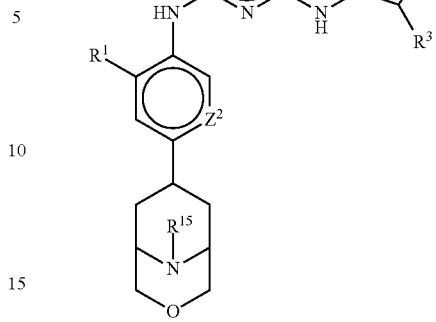
Wherein $R^{15}$ and $R^{16}$ are independently $C_{1-8}$ alkyl, $C_{3-8}$ cycloalkyl, $C_{1-8}$ alkoxy-$C_{1-8}$ alkyl, hydroxy-$C_{1-8}$ alkyl, amino-$C_{1-8}$ alkyl, $C_{1-8}$ alkyl-CO, $C_{1-8}$ alkyl-amino-$C_{1-8}$ alkyl or di ($C_{1-8}$ alkyl)-amino-$C_{1-8}$ alkyl. Wherein, $R^1$, $R^3$, $Z^1$, $Z^2$, $Z^3$, $Z^4$, $Z^5$ are defined as previously described.
In some embodiments, the compounds have the following structures:
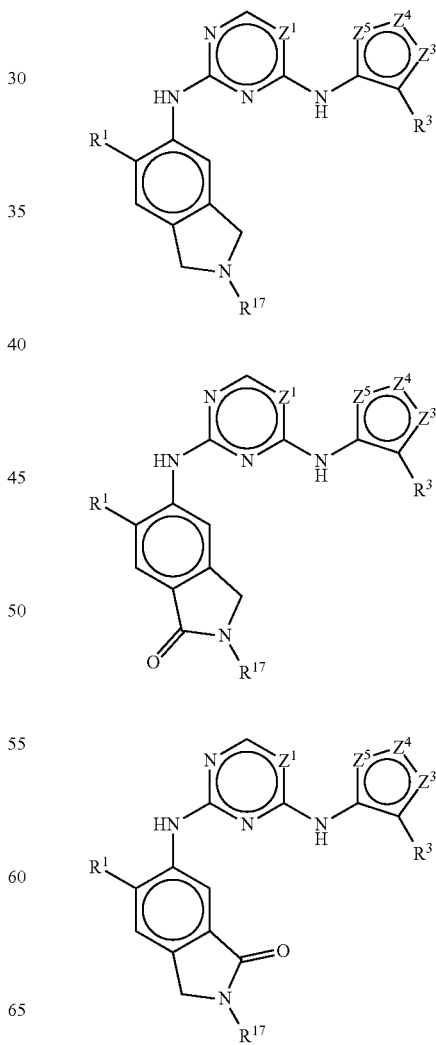

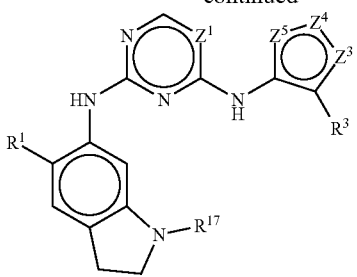
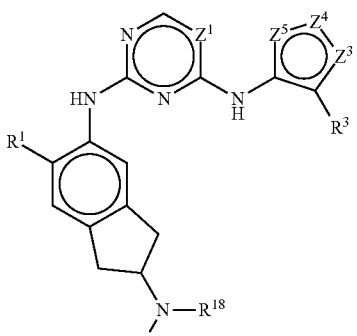
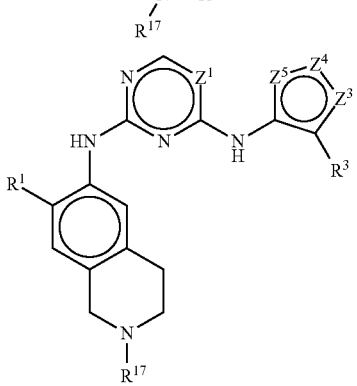
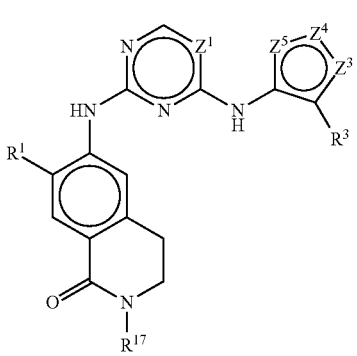
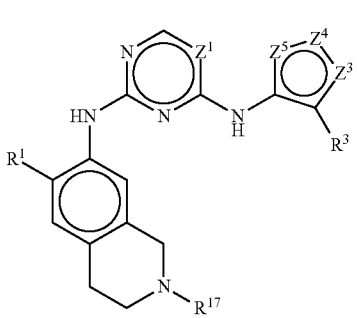
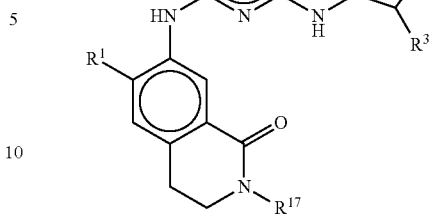
Wherein $R^{17}$ and $R^{18}$ are independently $C_{1-8}$ alkyl, $C_{3-8}$ cycloalkyl, $C_{1-8}$ alkoxy-$C_{1-8}$ alkyl, hydroxy-$C_{1-8}$ alkyl, amino-$C_{1-8}$ alkyl, $C_{1-8}$ alkyl-CO, $C_{1-8}$ alkyl-amino-$C_{1-8}$ alkyl or di ($C_{1-8}$ alkyl)-amino-$C_{1-8}$ alkyl. Wherein, $R^1$, $R^3$, $Z^1$, $Z^3$, $Z^4$, $Z^5$ are defined as previously described.
In one specific embodiment, the compounds as Formula I are selected from the following compounds:
1
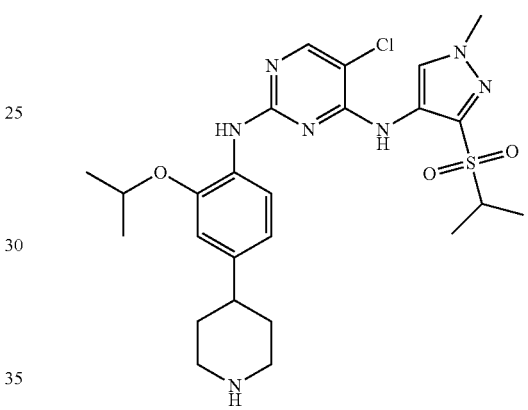
2
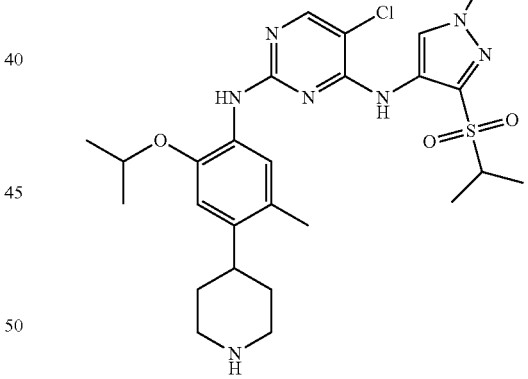
3
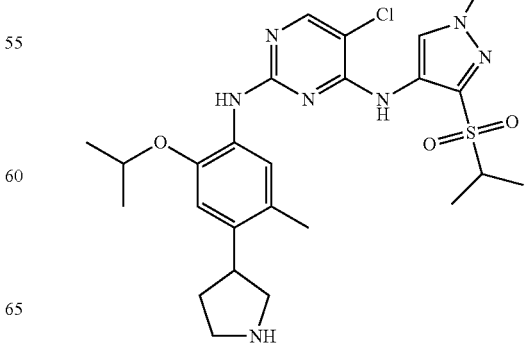

| | |
|---|---|
| 4 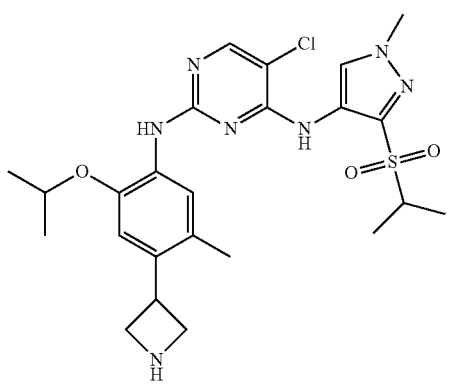 | 8 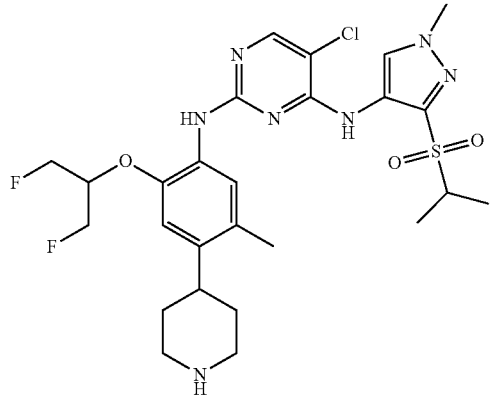 |
| 5 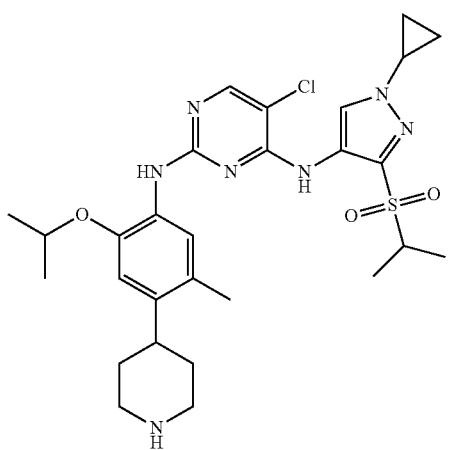 | 9 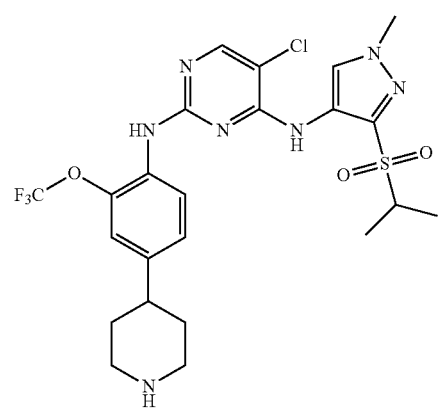 |
| 6 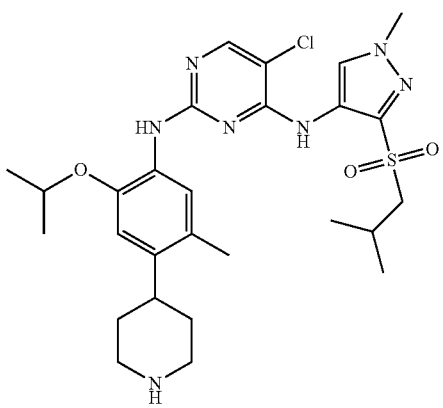 | 10 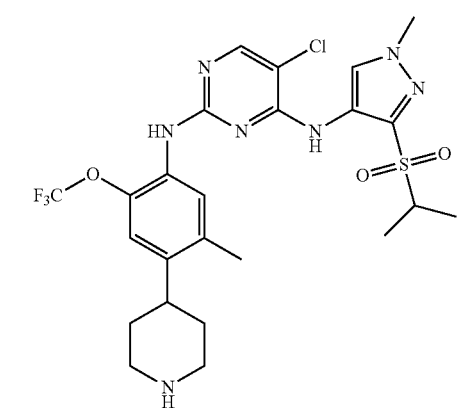 |
| 7 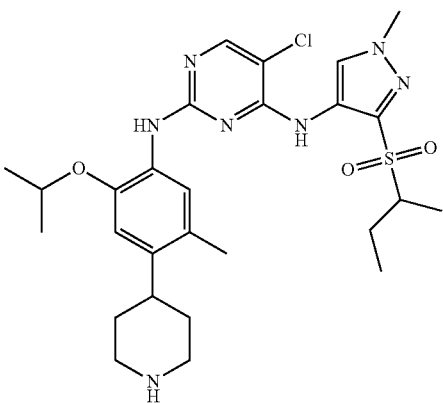 | 11 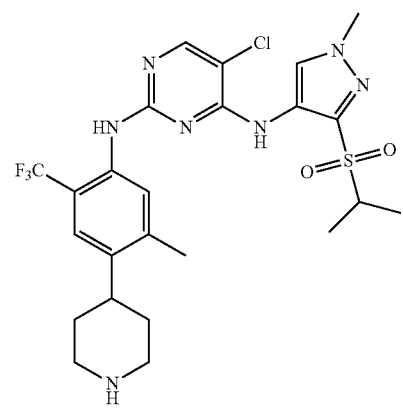 |

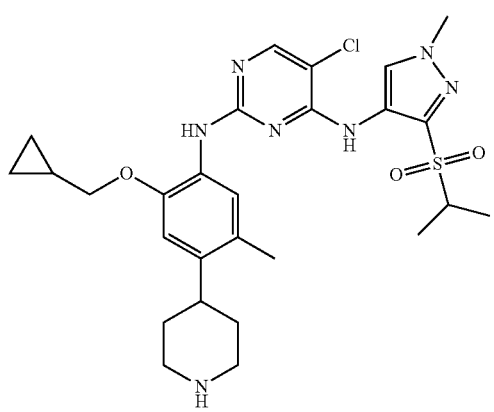
12
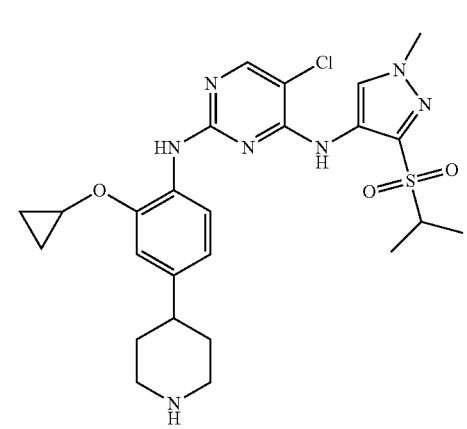
13
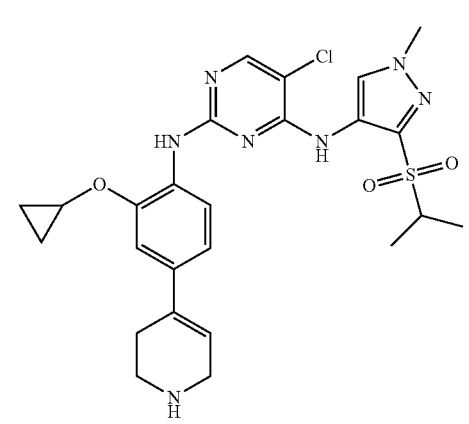
14
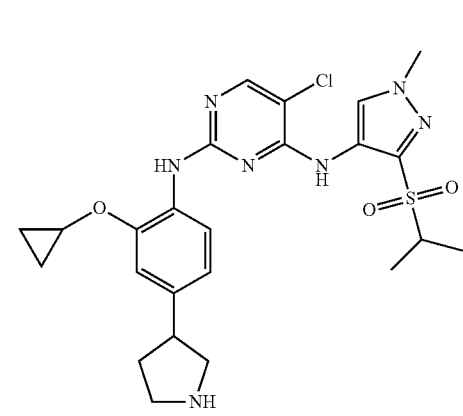
15
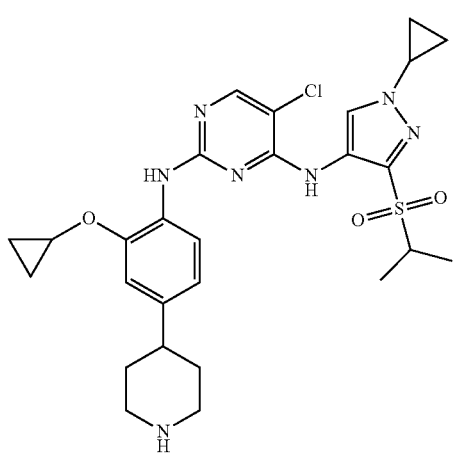
16
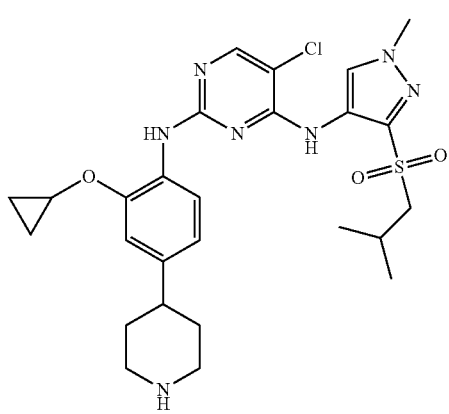
17
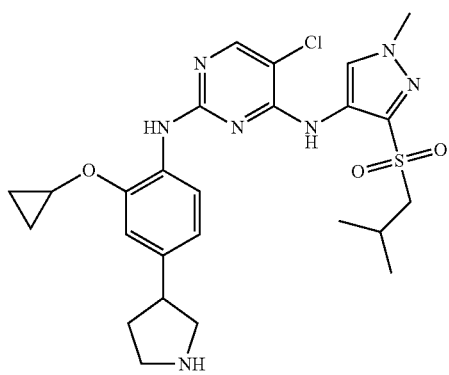
18
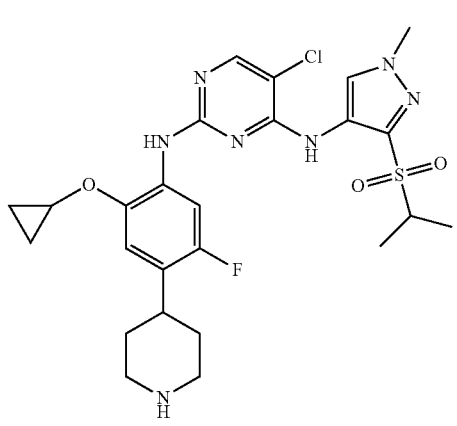
19

20 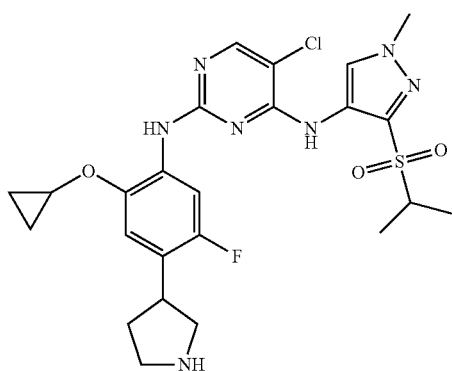
21 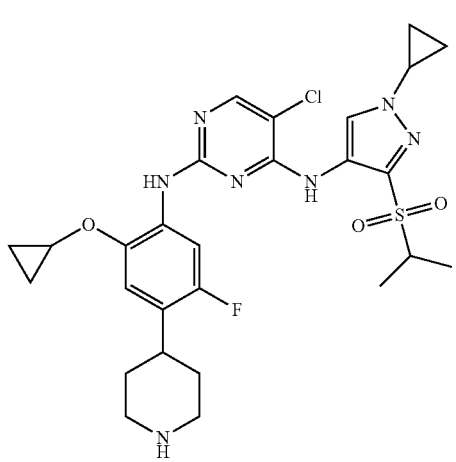
22 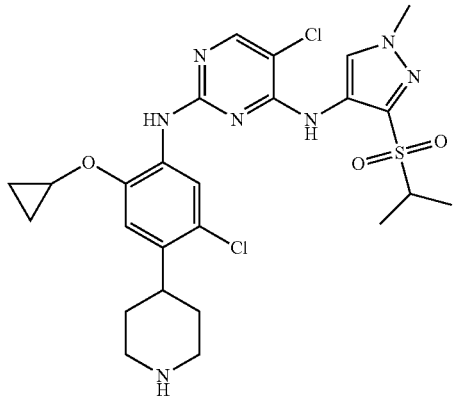
23 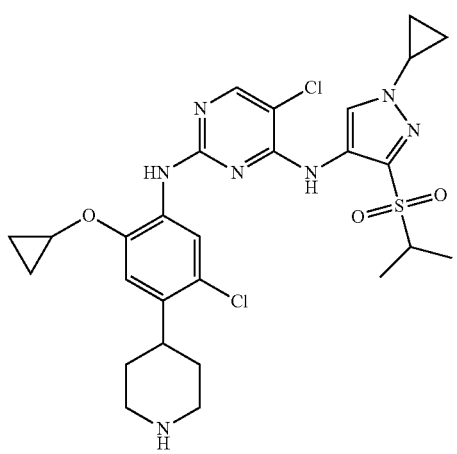
24 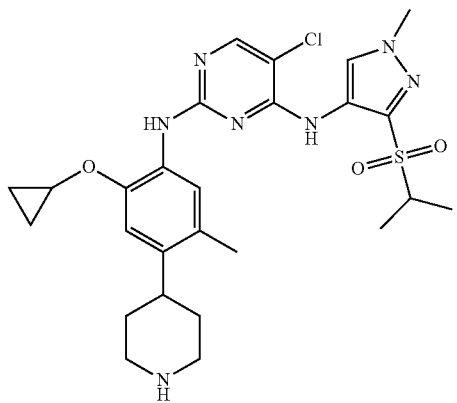
25 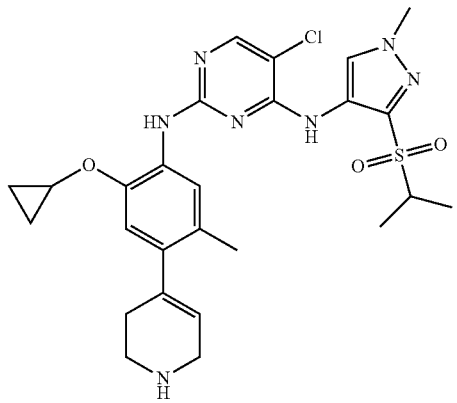
26 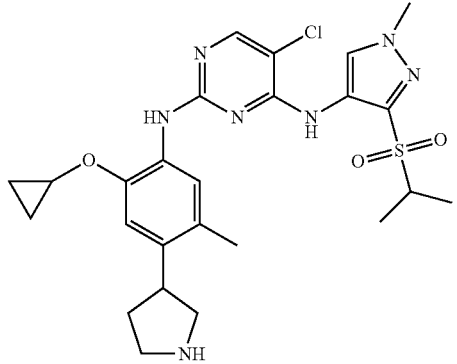

27
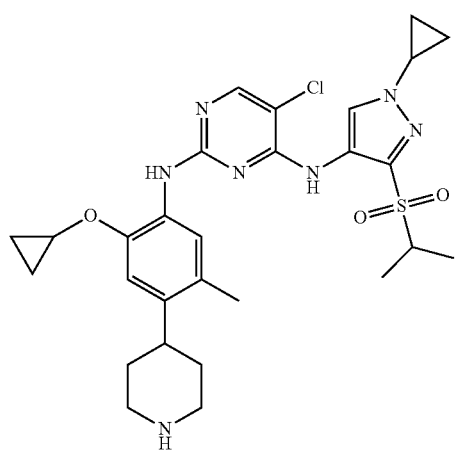
28

29
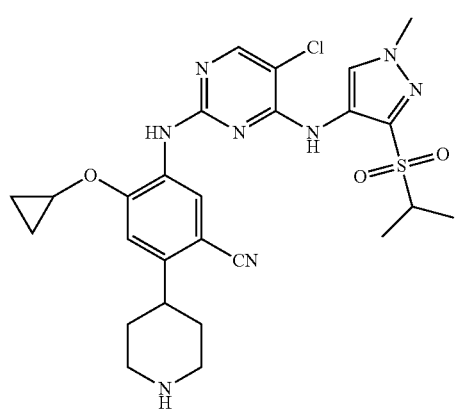
30
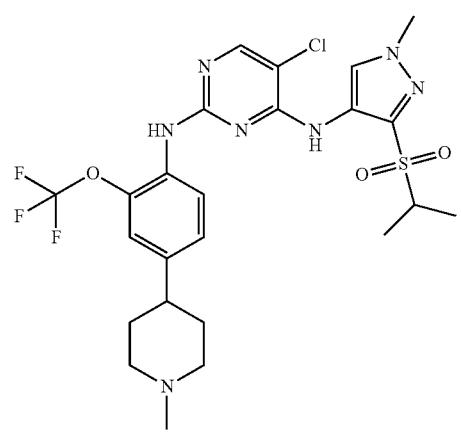
31
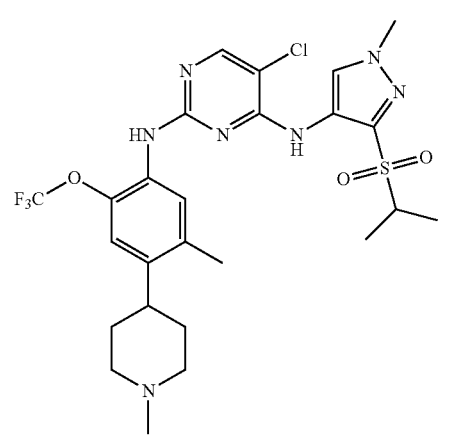
32
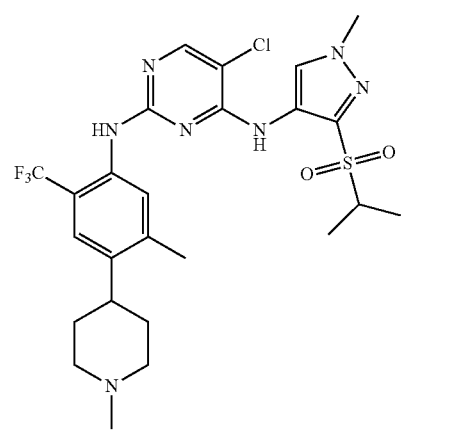

33
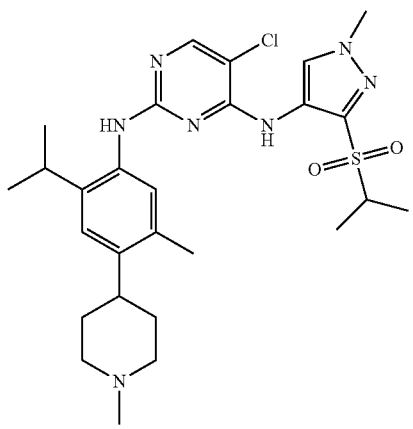
34
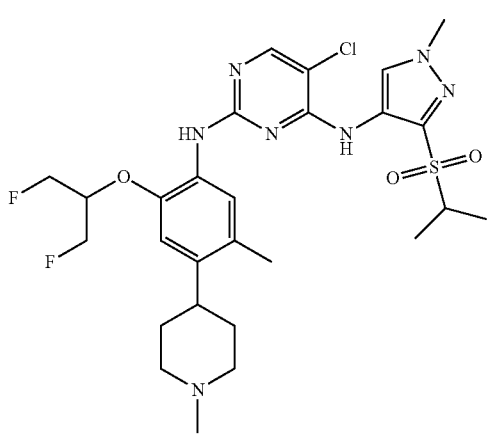
35
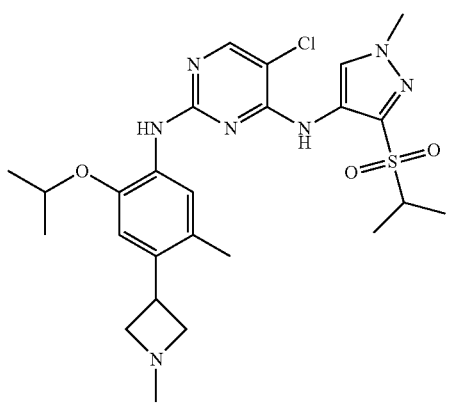
36
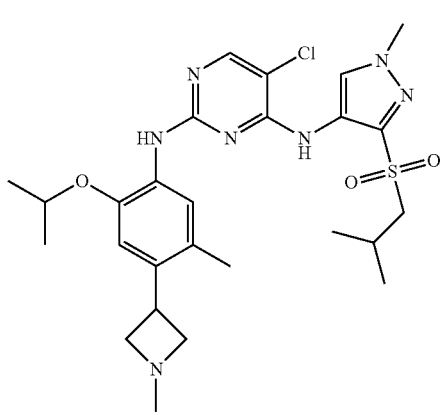
37
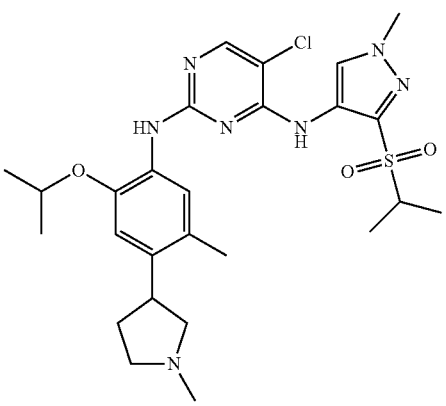
38
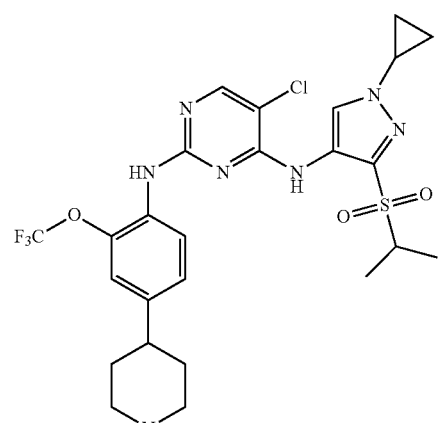
39
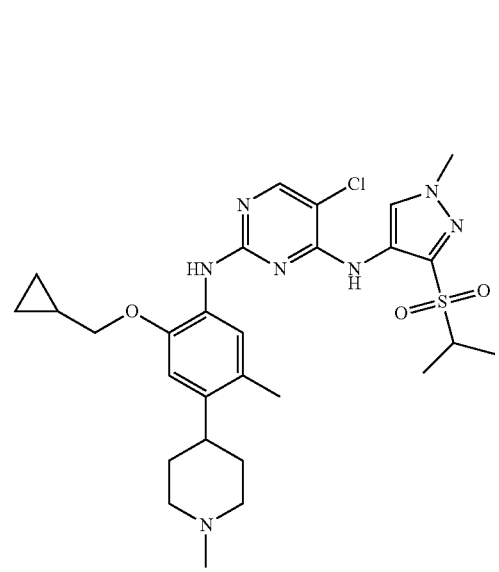

40
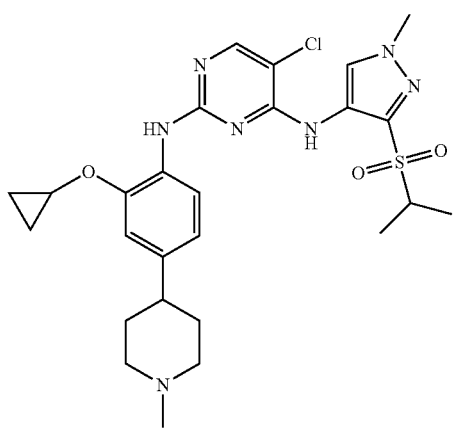
41
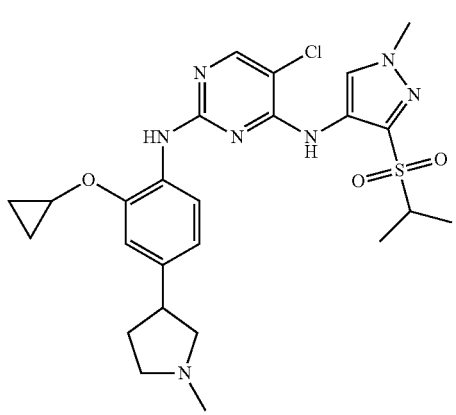
42
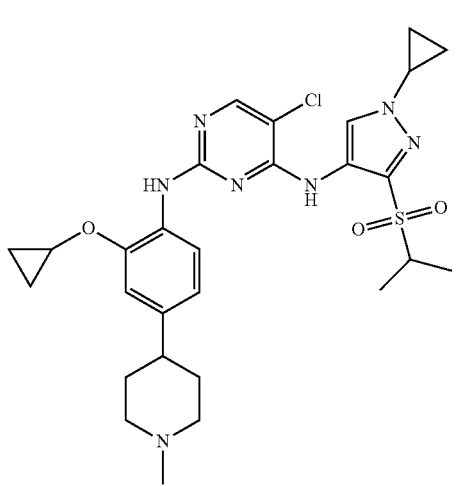
43
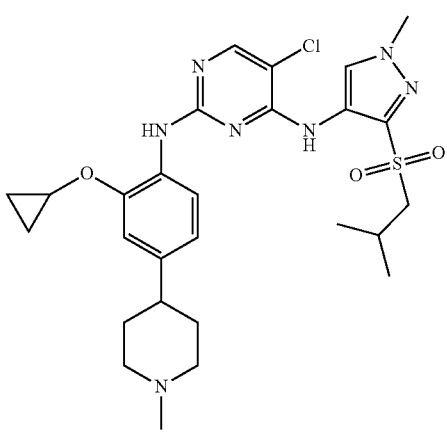
44
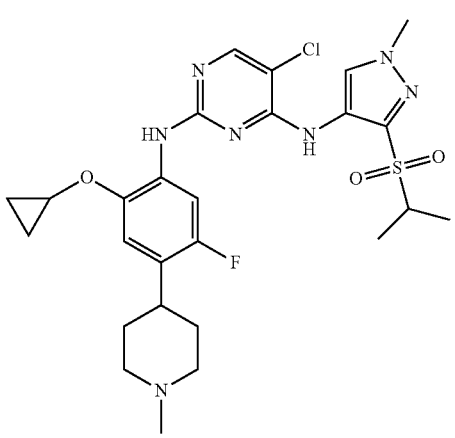
45
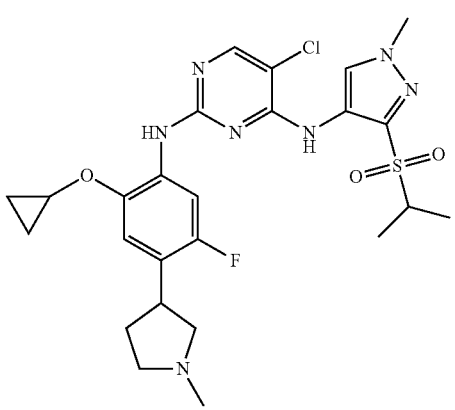

46
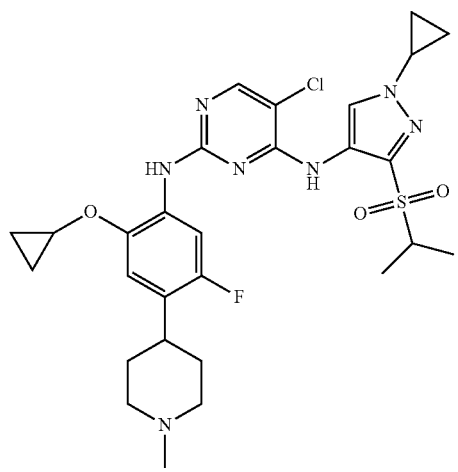
47
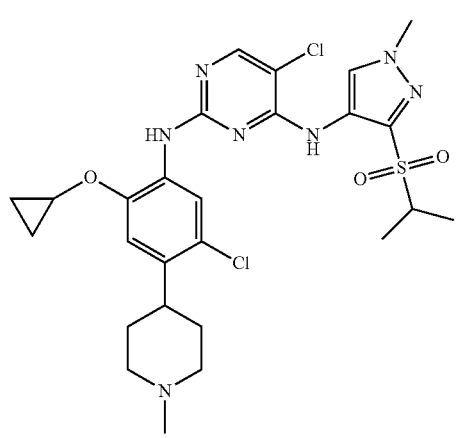
48
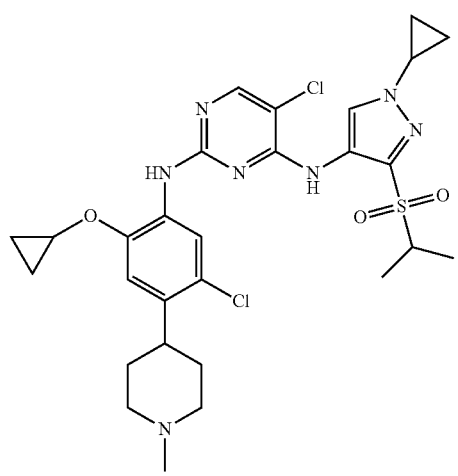
49
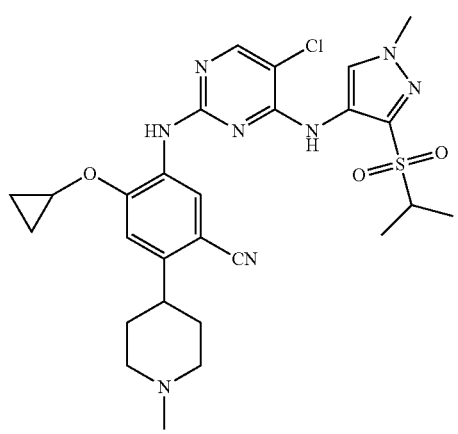
50
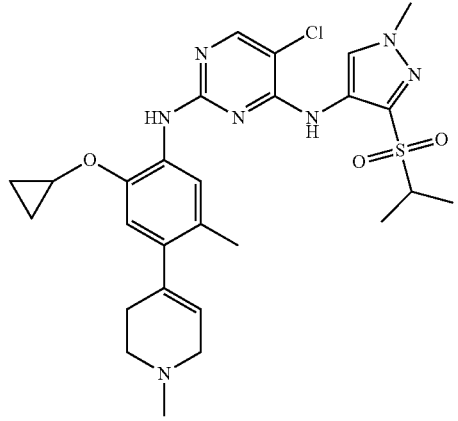
51
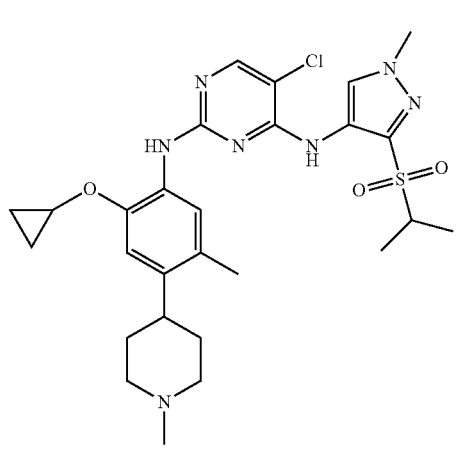

52
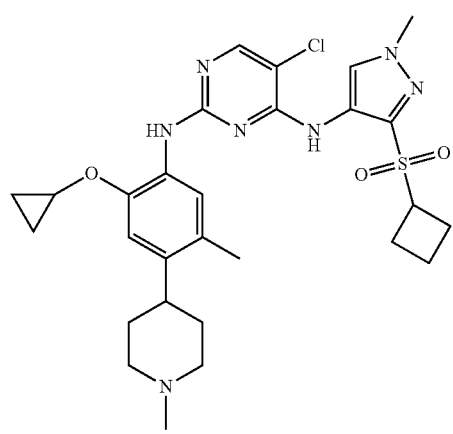
53
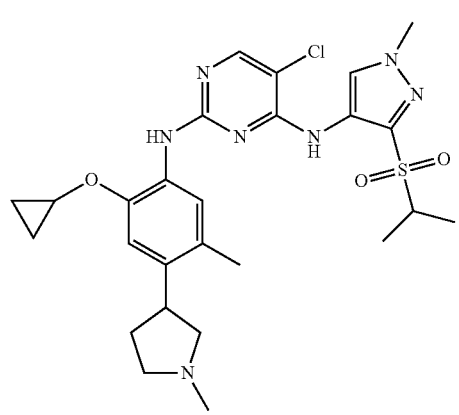
54
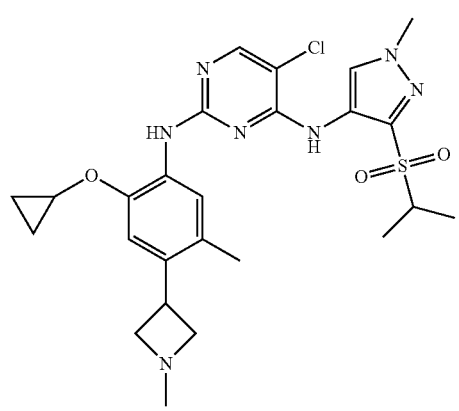
55
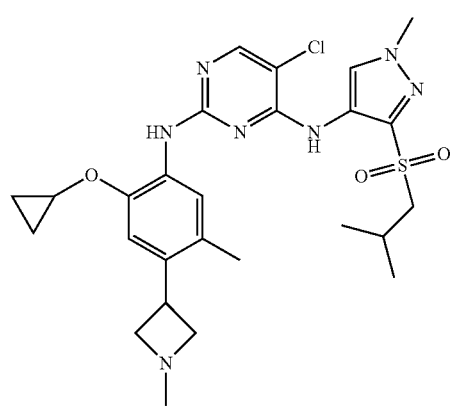
56
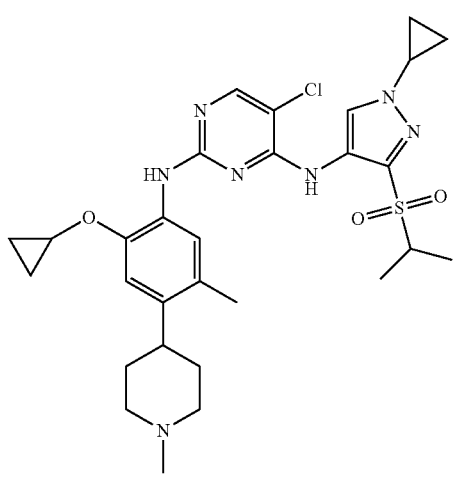
57
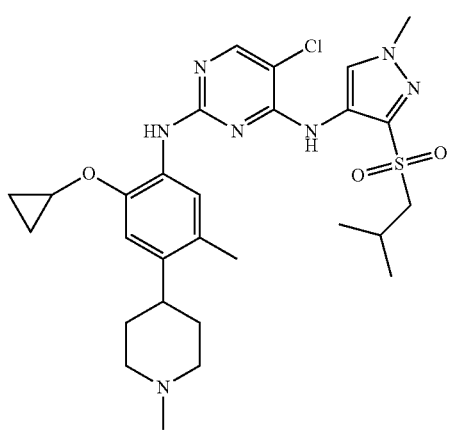
58
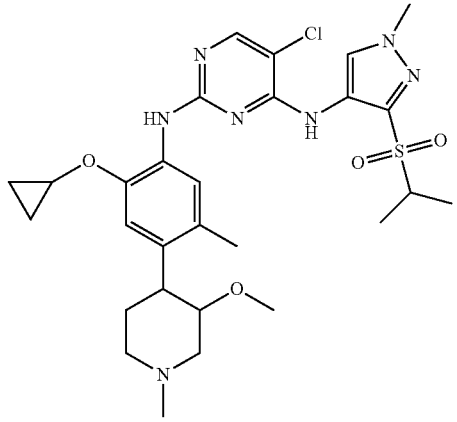

59
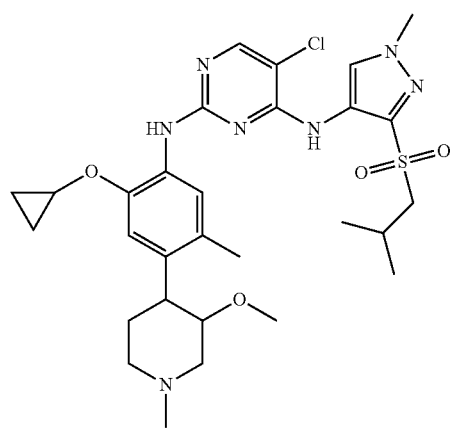
60
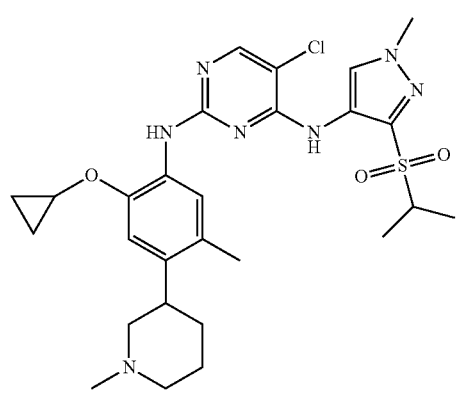
61
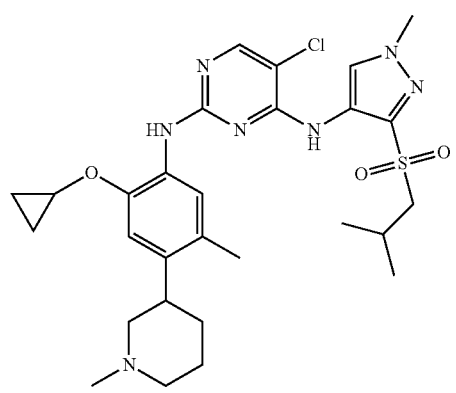
62
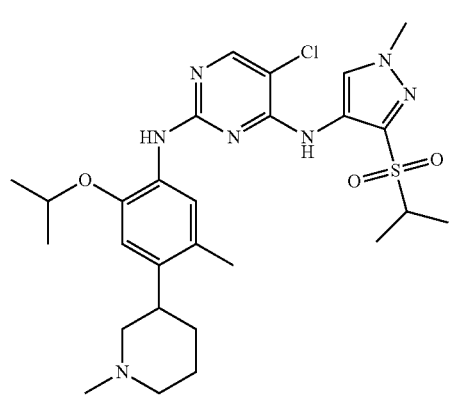
63
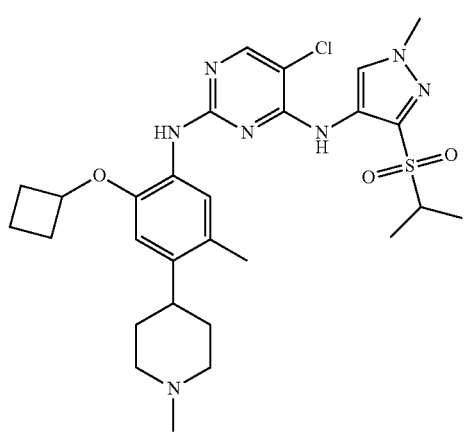
64
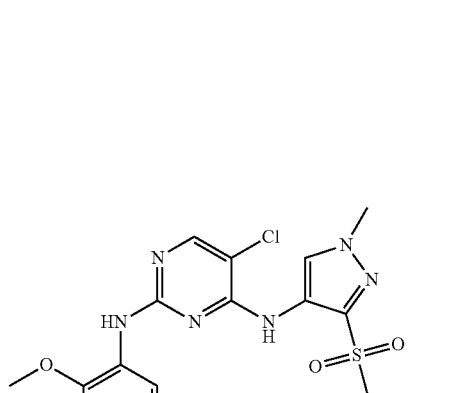
65
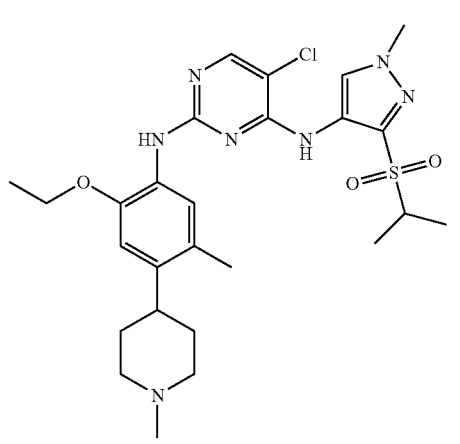

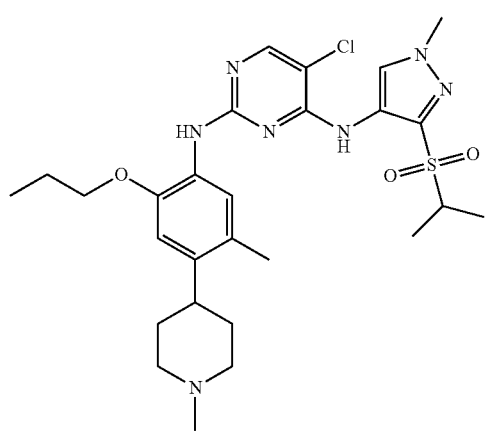
66
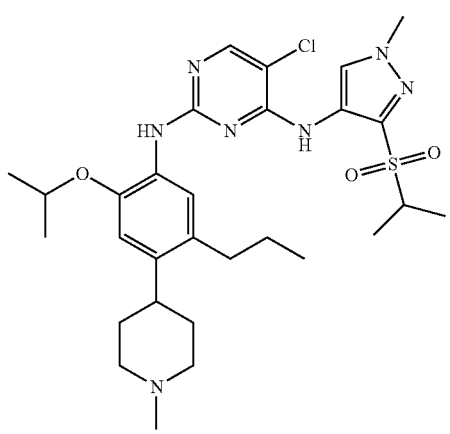
69
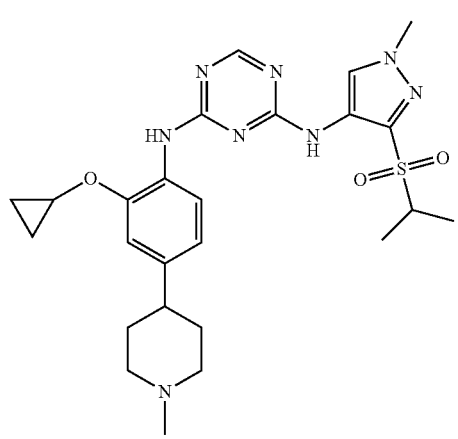
67
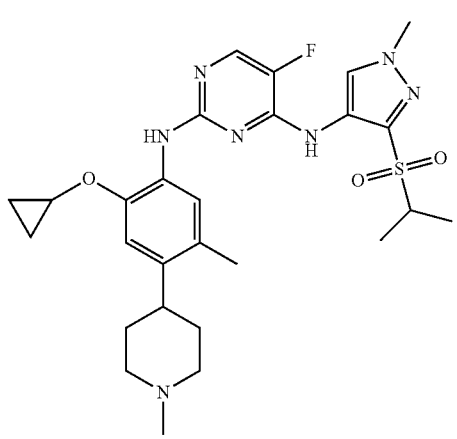
70
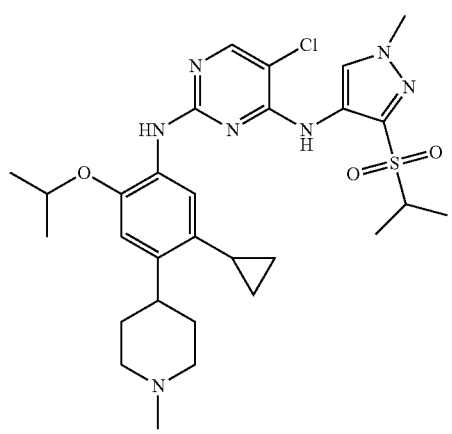
68
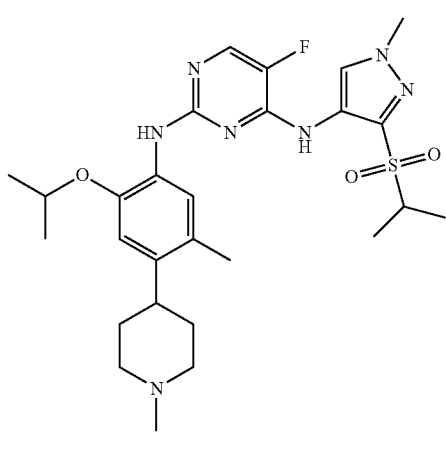
71

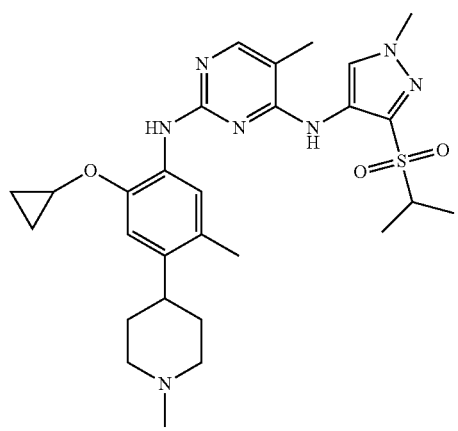
72
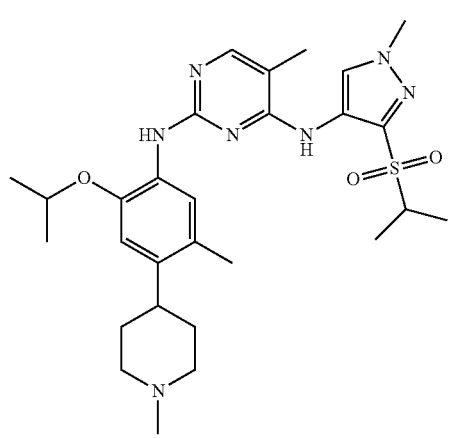
73
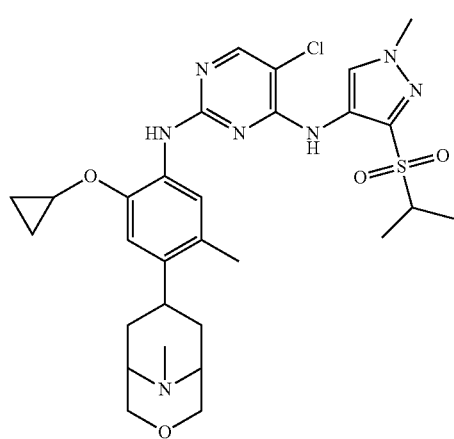
74
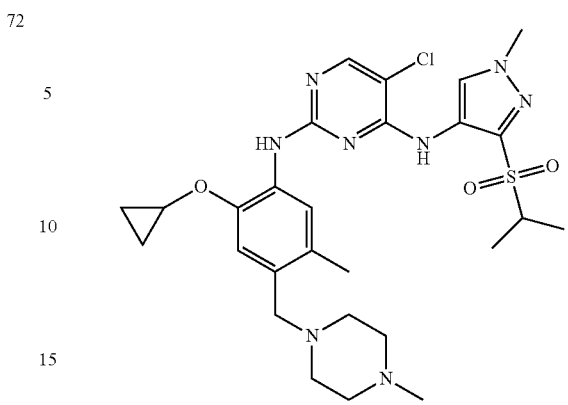
75
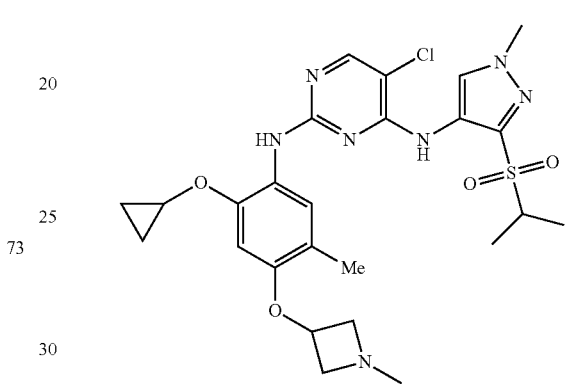
76
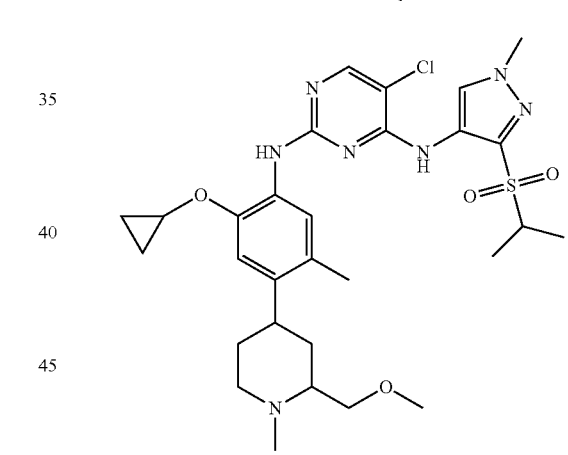
77
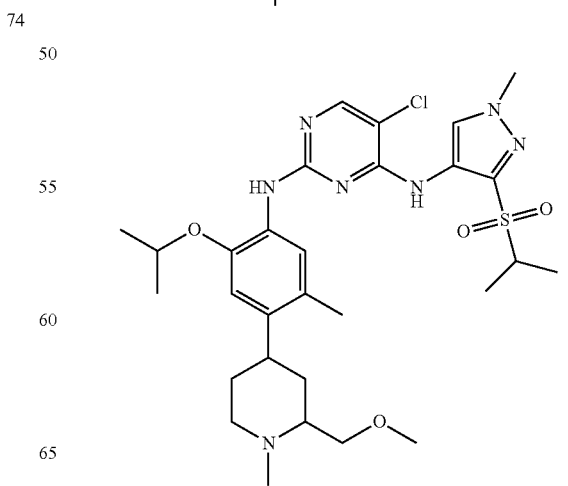
78

33
-continued
79
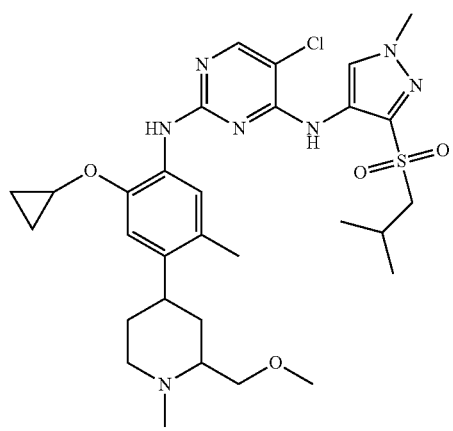
80
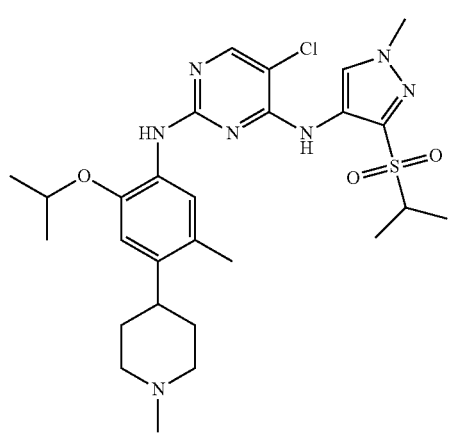
81
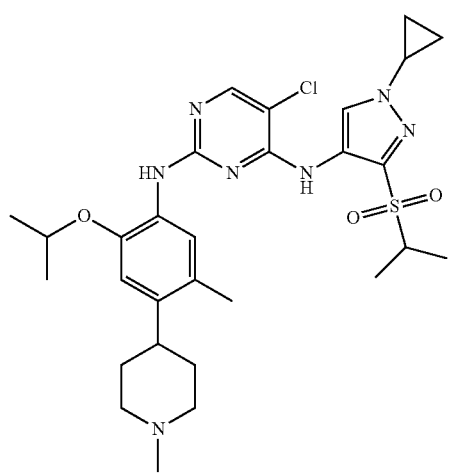
34
-continued
82
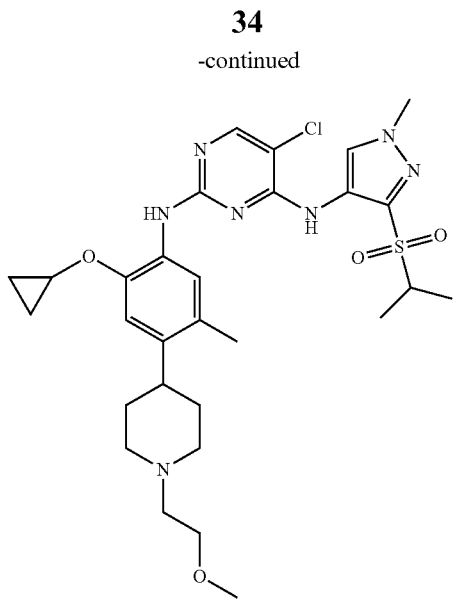
83
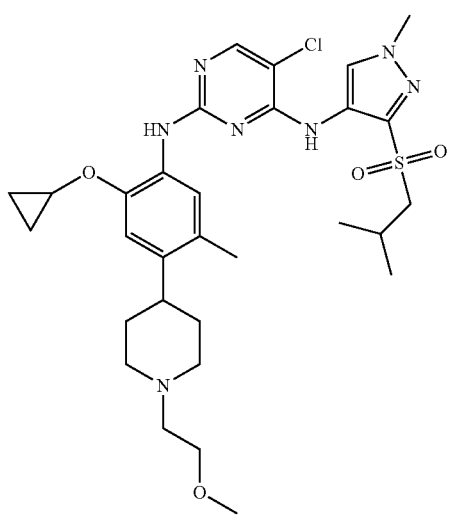
84
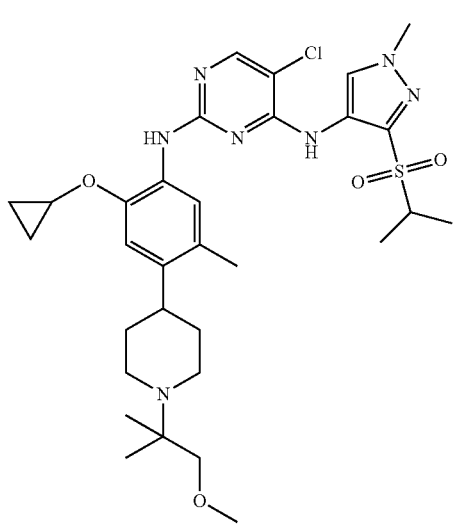

85
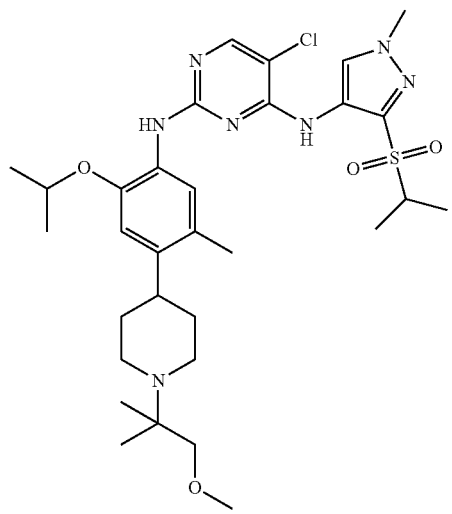
86
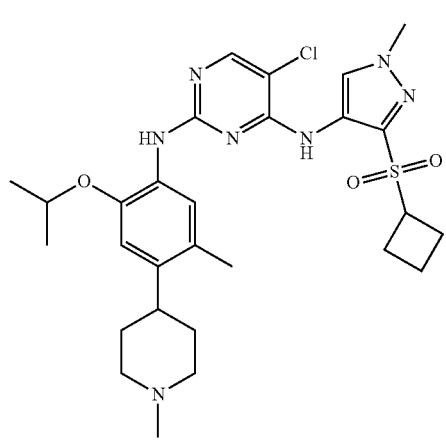
87
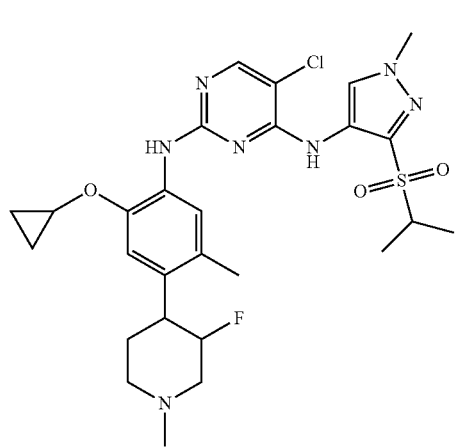
88
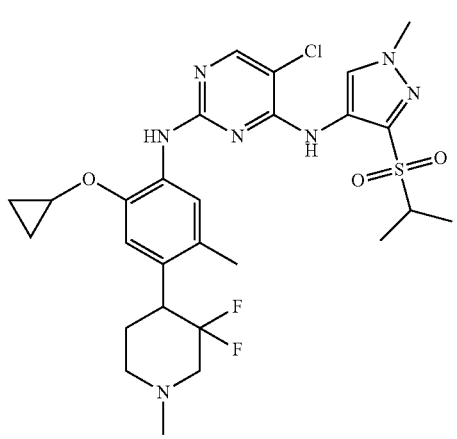
89
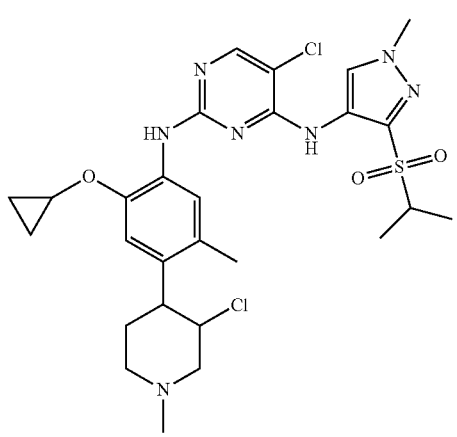
90

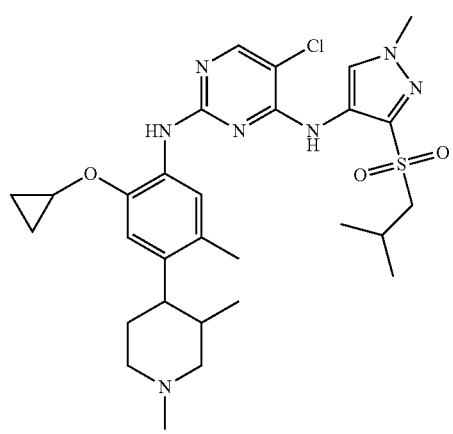
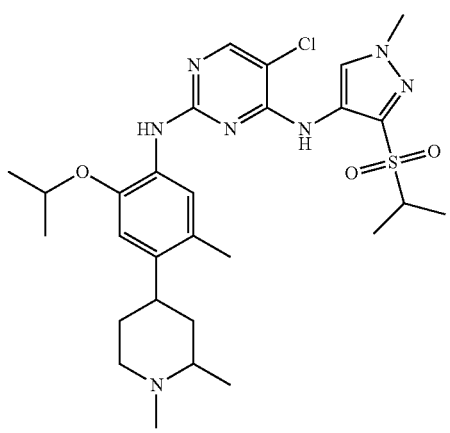

97
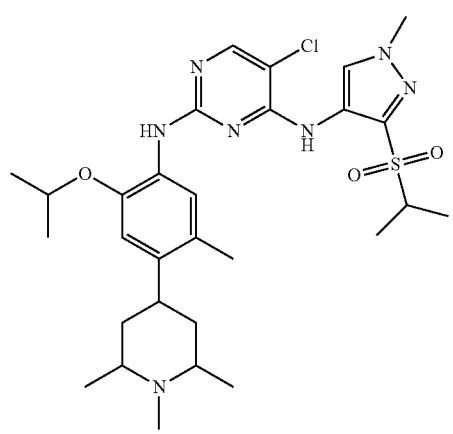
98
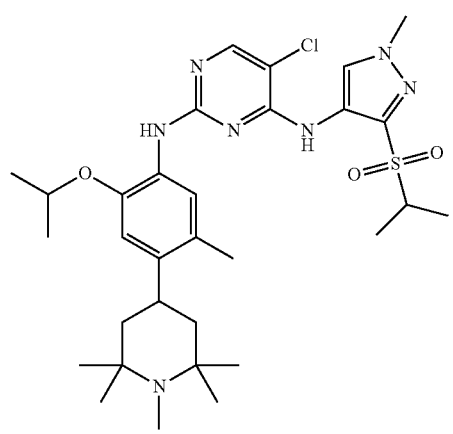
99
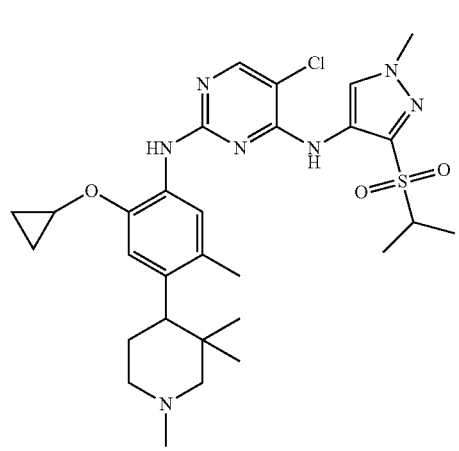
100
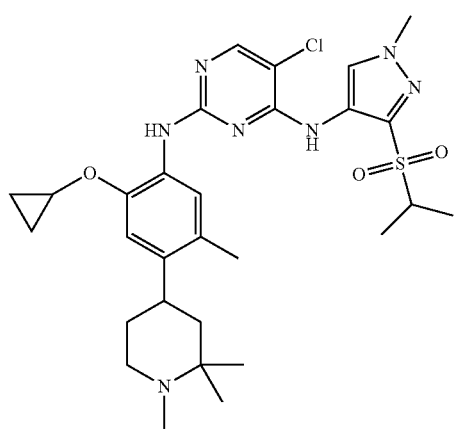
101
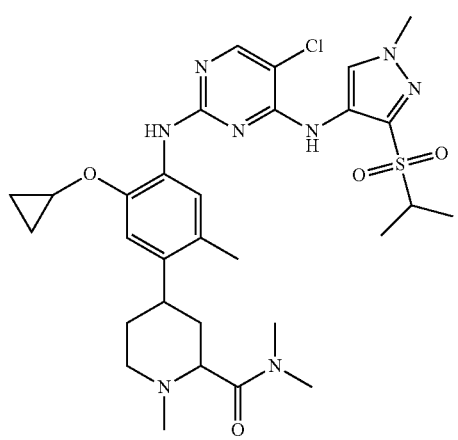
102
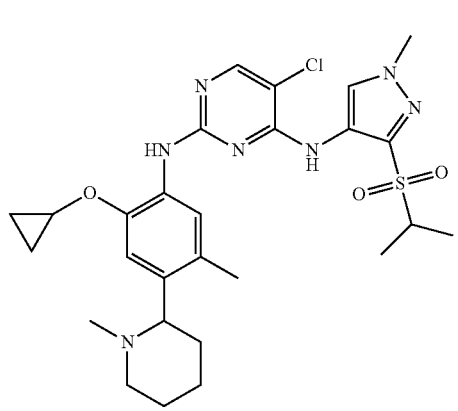

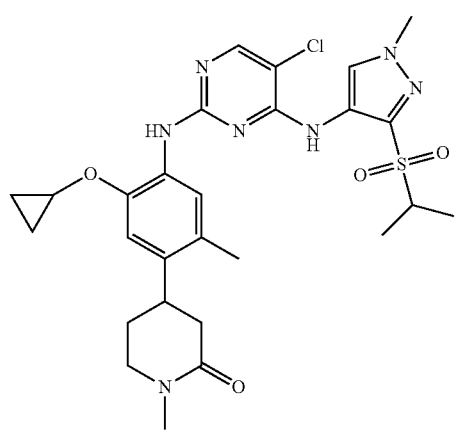
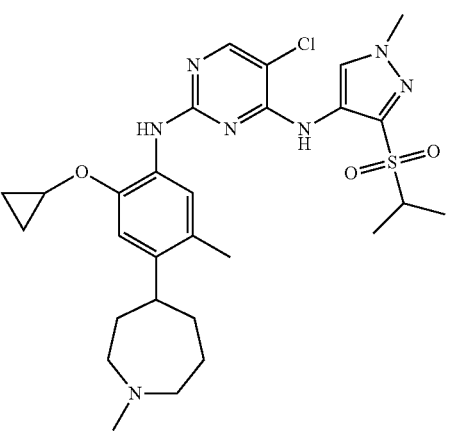

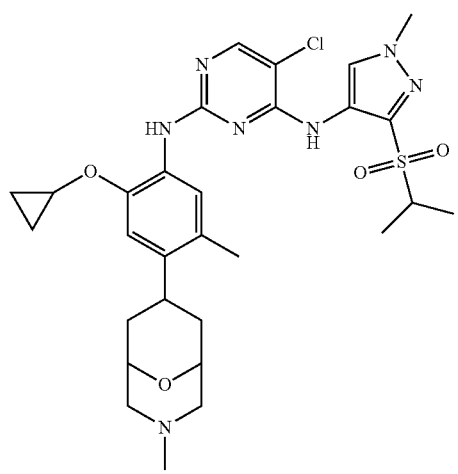
109
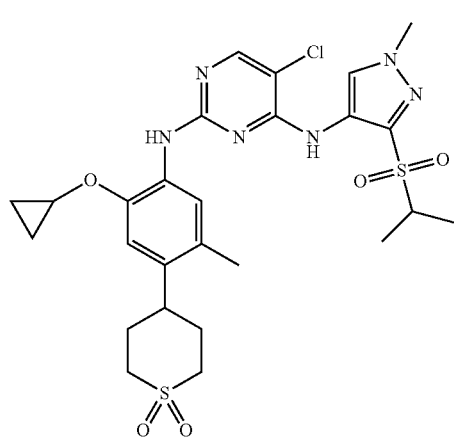
110
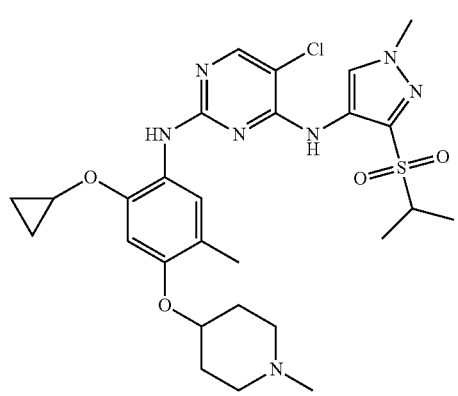
111
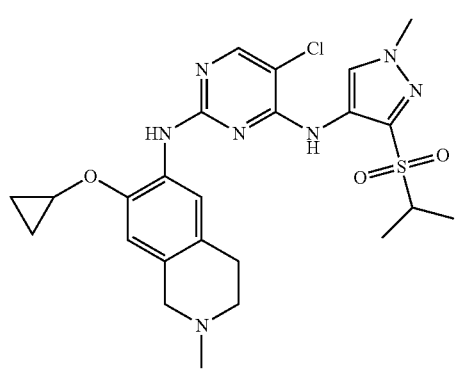
112
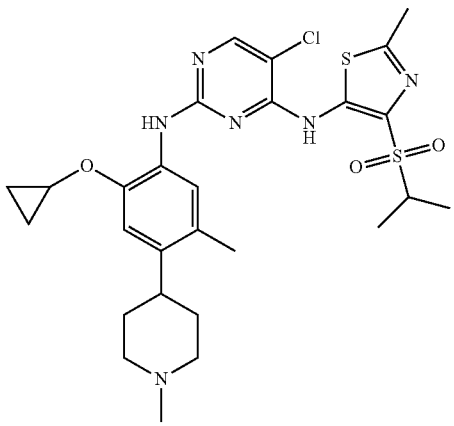
113
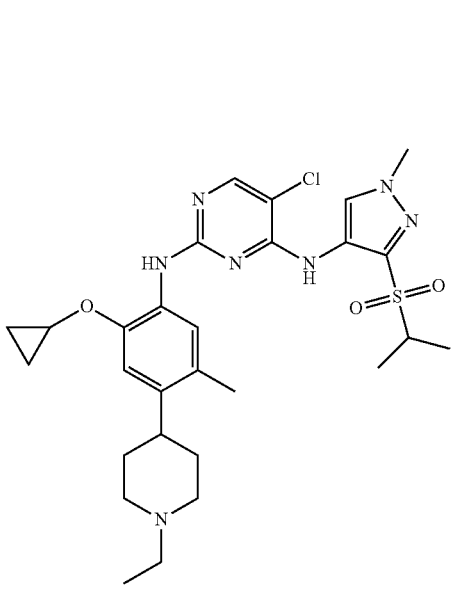
114
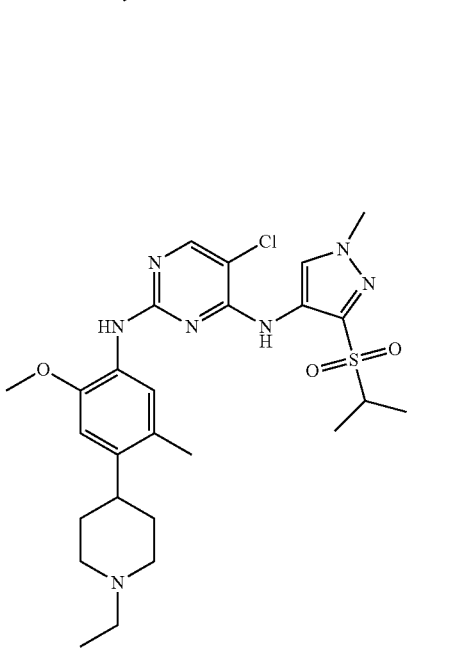
115

116 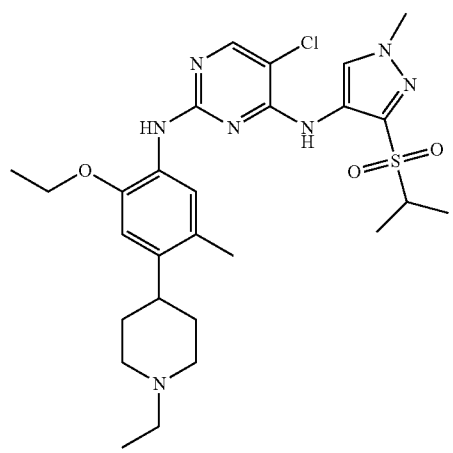
117 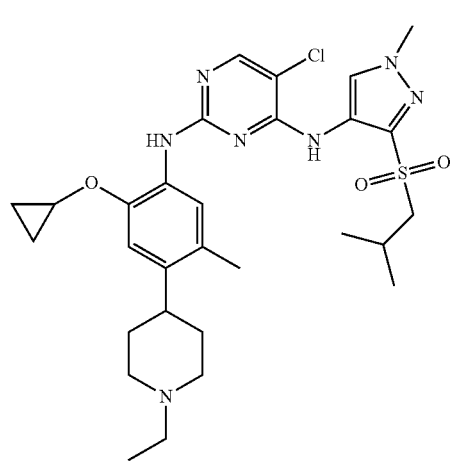
118 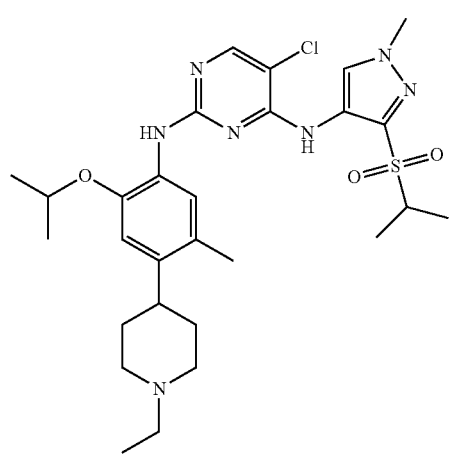
119 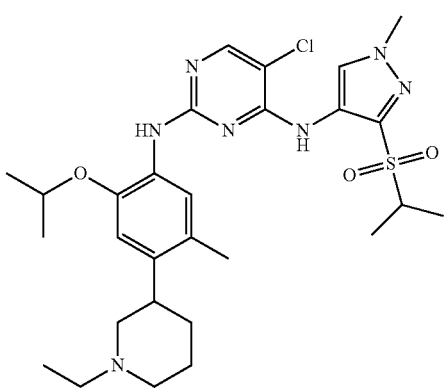
120 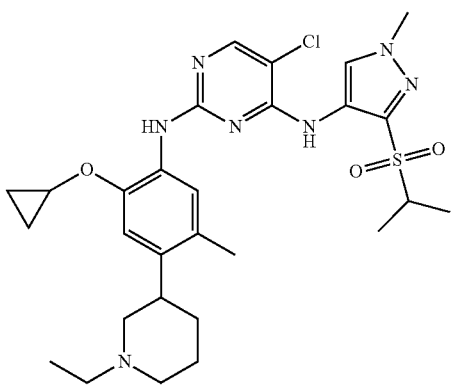
121 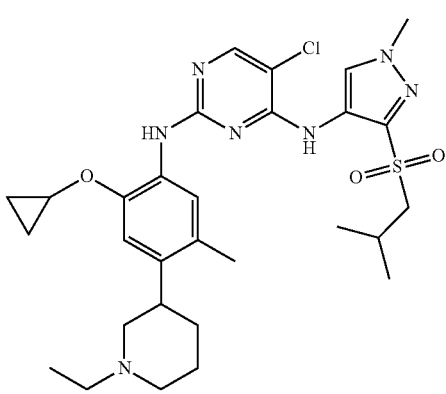
122 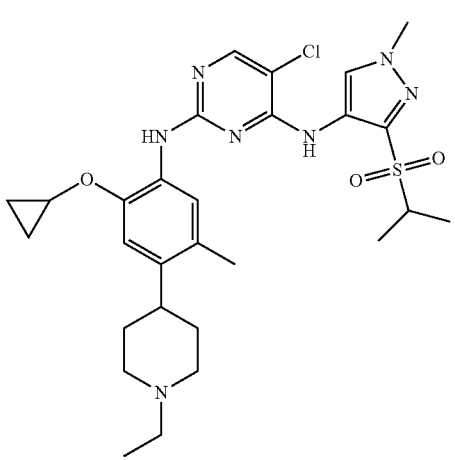

-continued
123
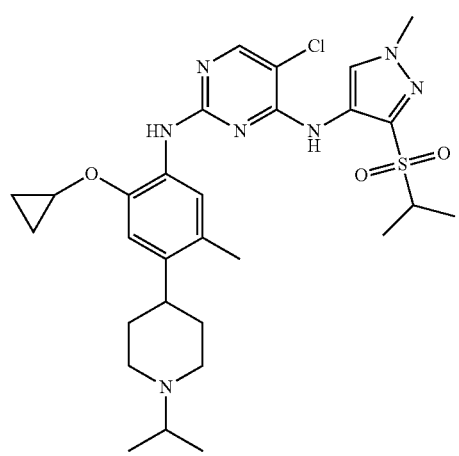
124
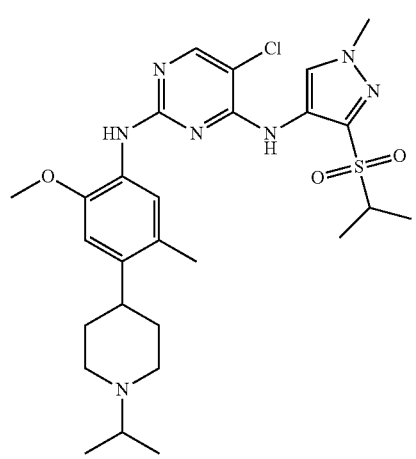
125
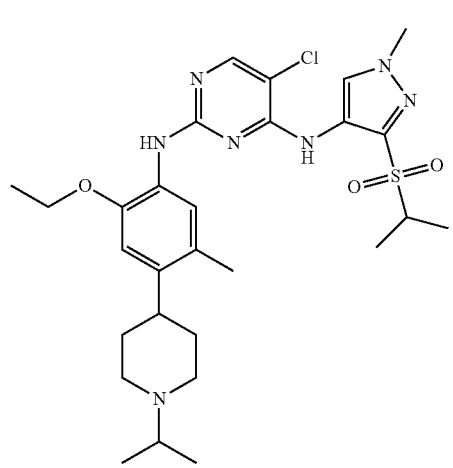
-continued
126
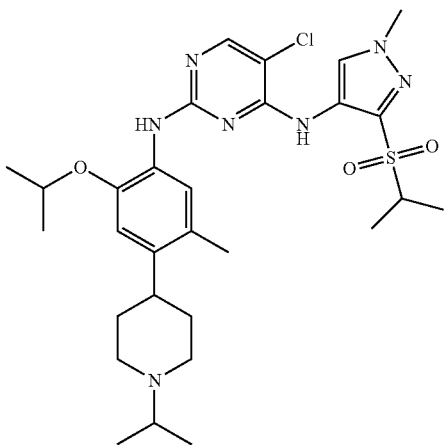
127
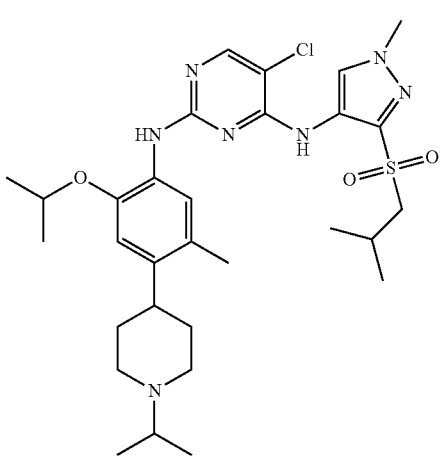
128
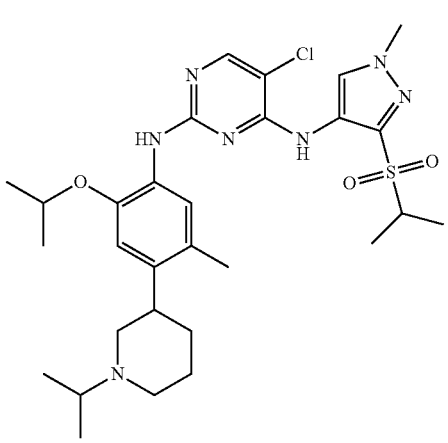

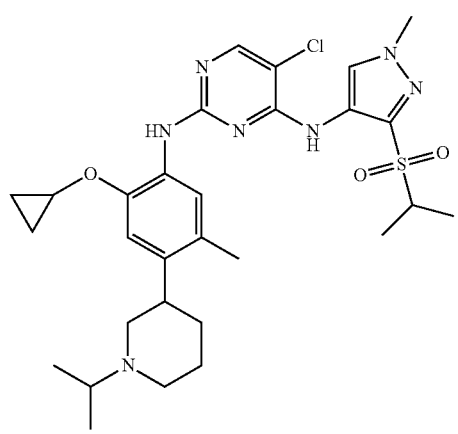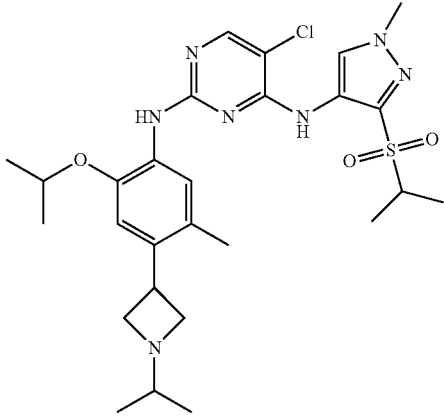

135
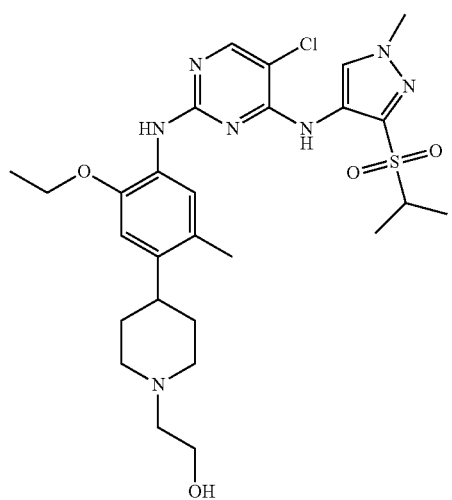
136
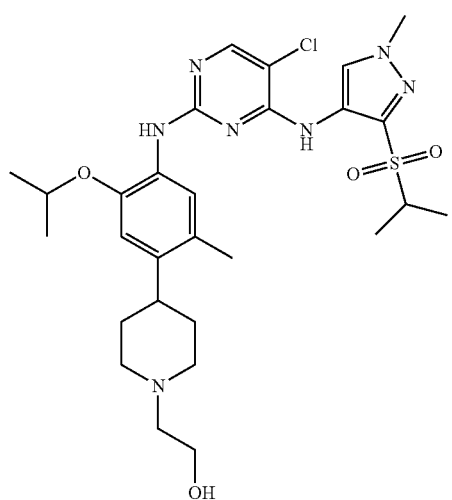
137
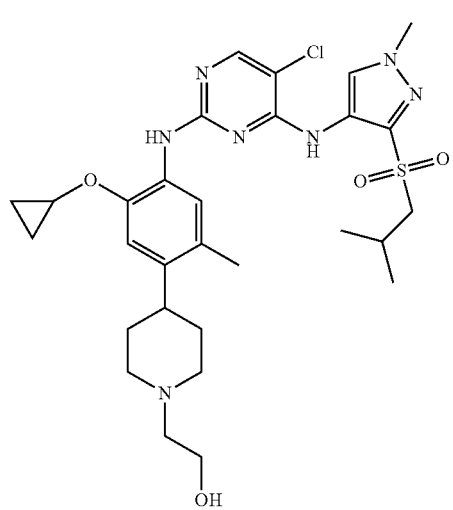
138
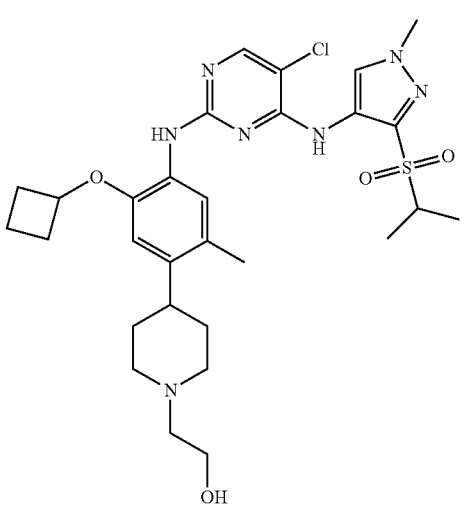
139
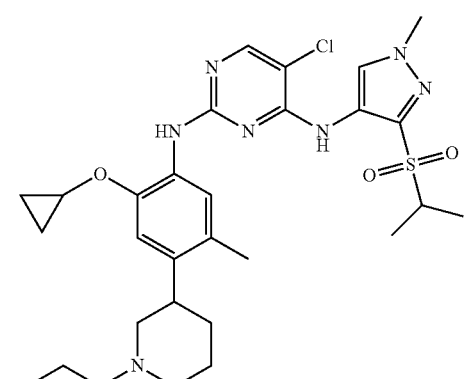
140
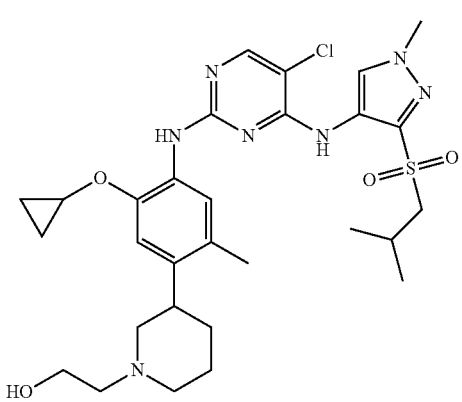

-continued
141
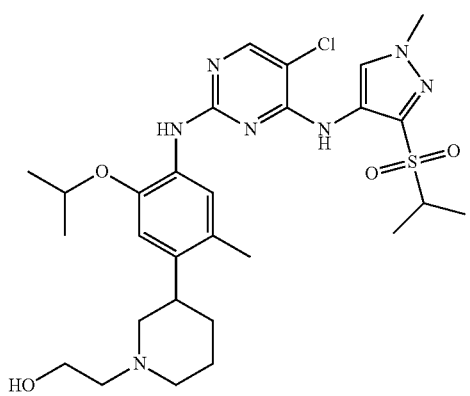
142
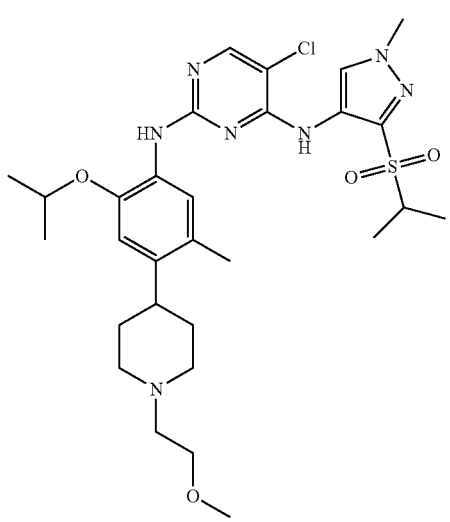
143
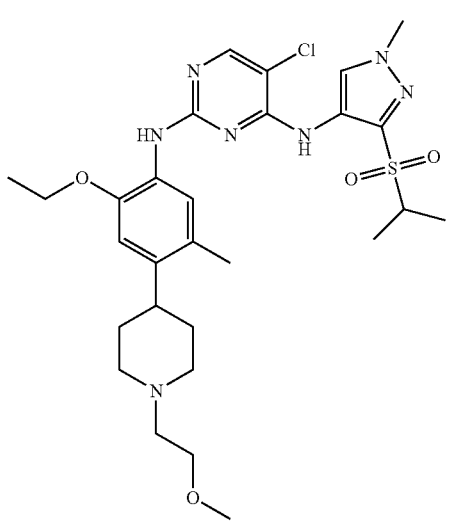
144
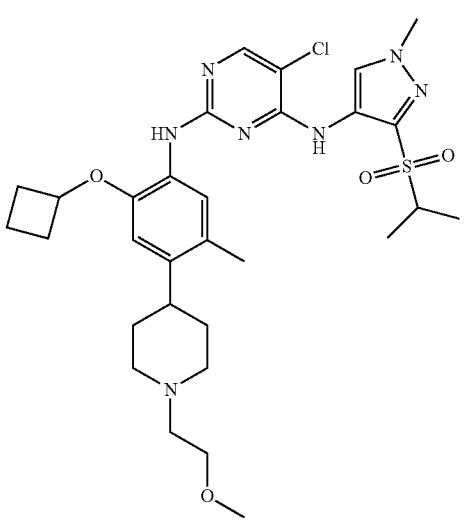
145
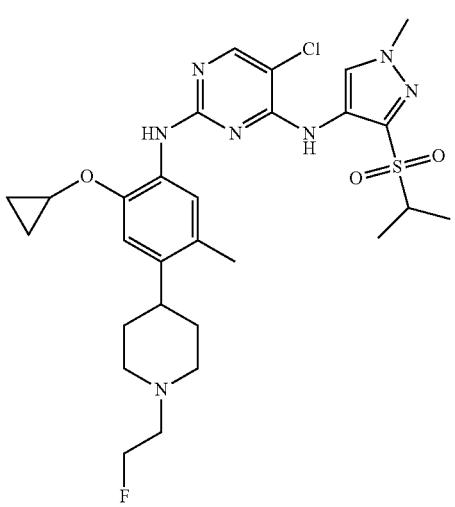
146
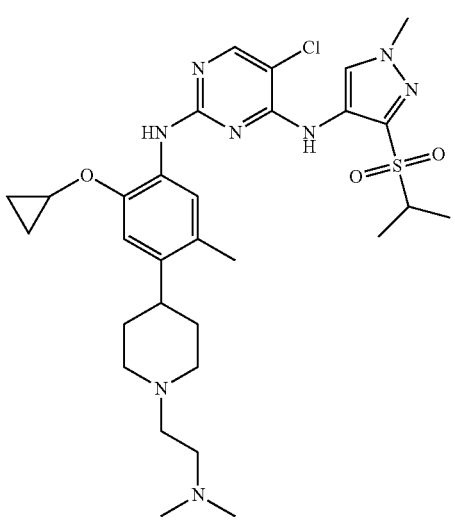

147
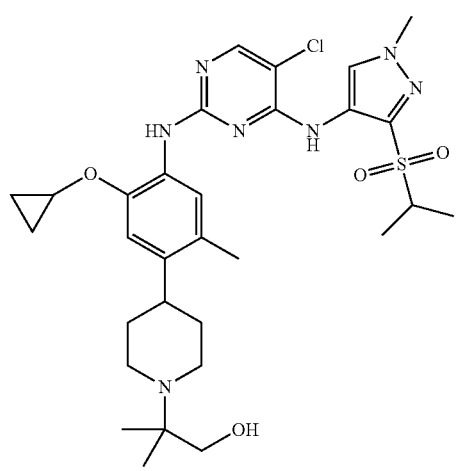
150
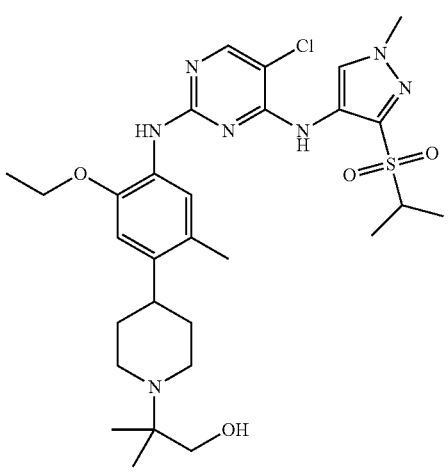
148
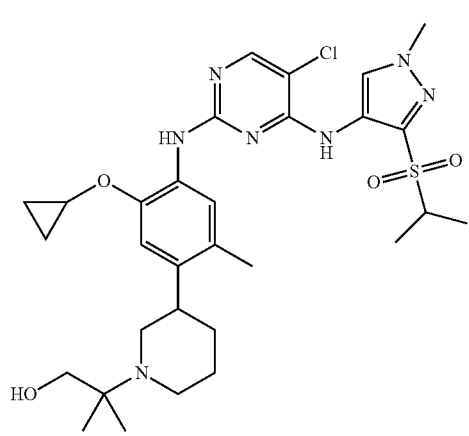
151
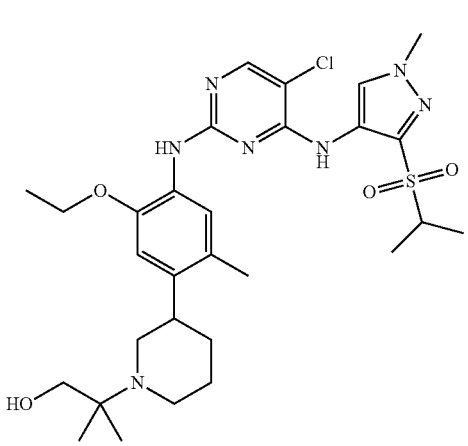
149
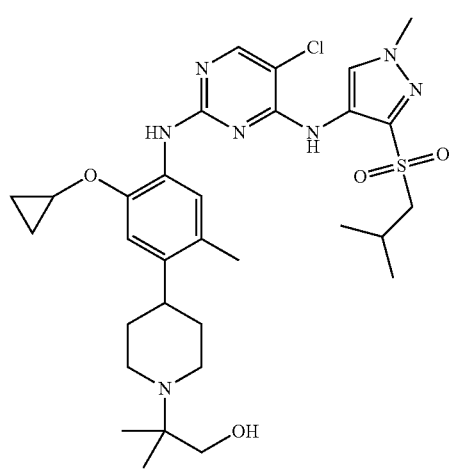
152
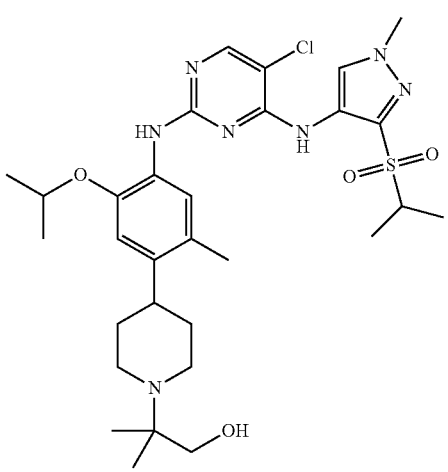

153 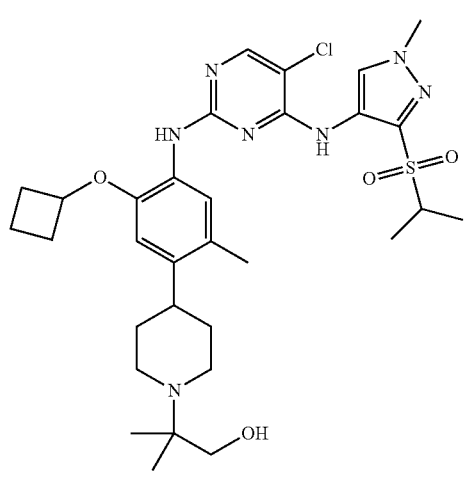
154 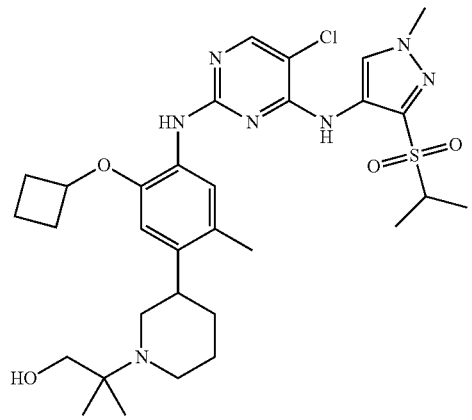
155 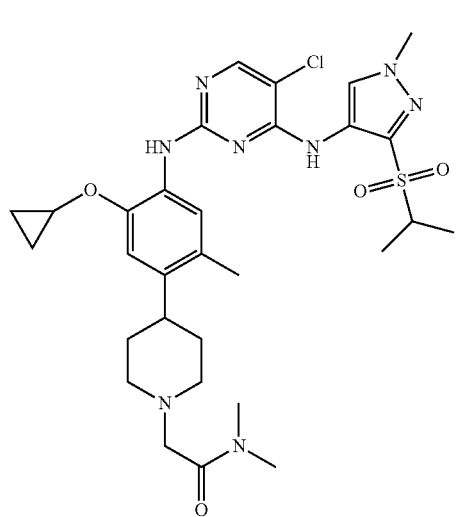
156 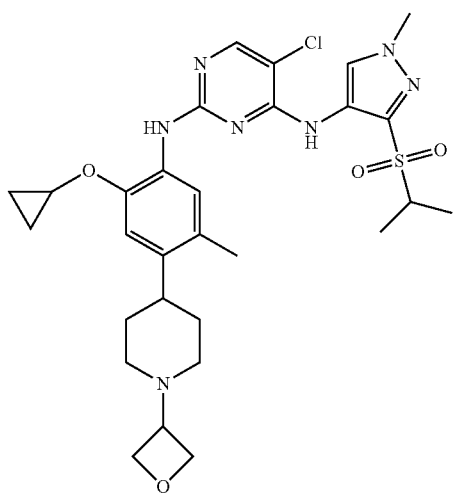
157 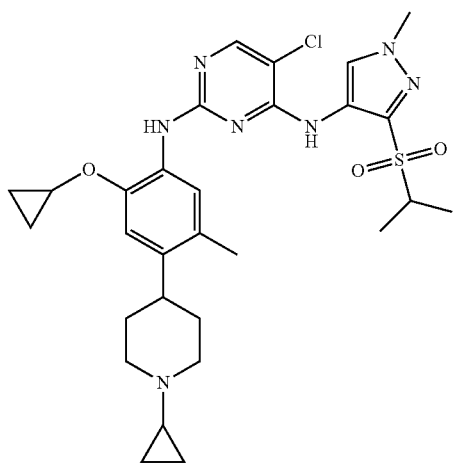
158 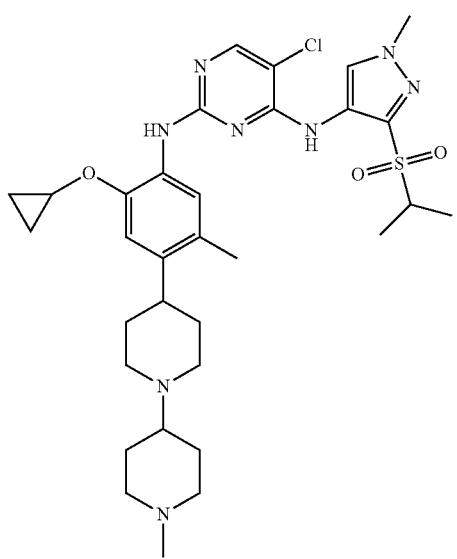

159
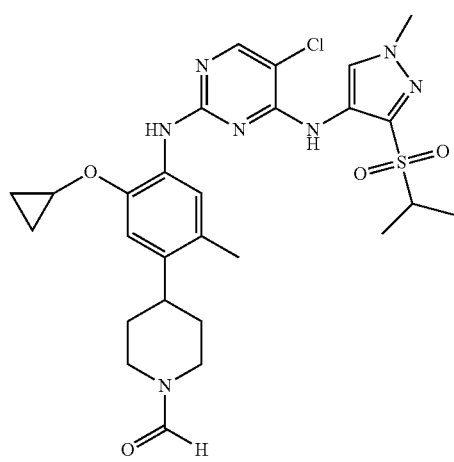
162
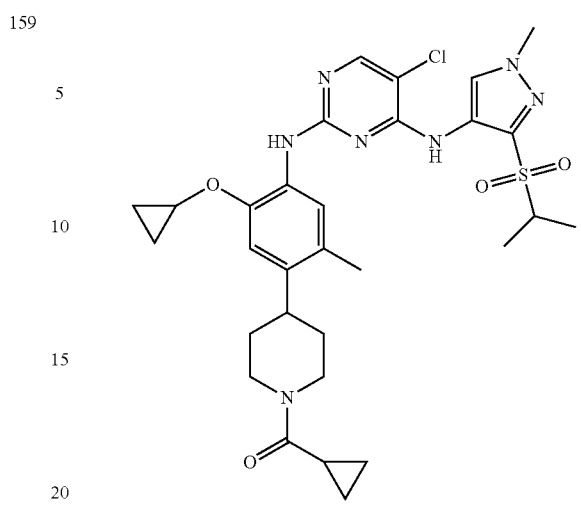
160
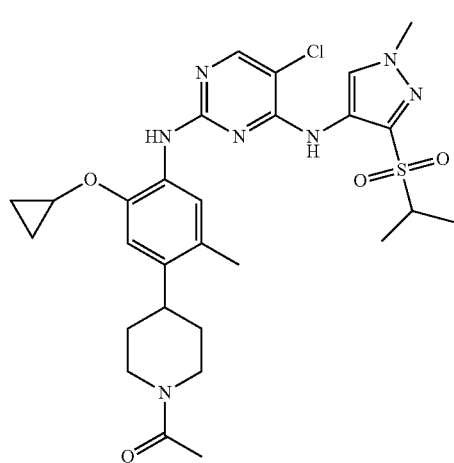
163
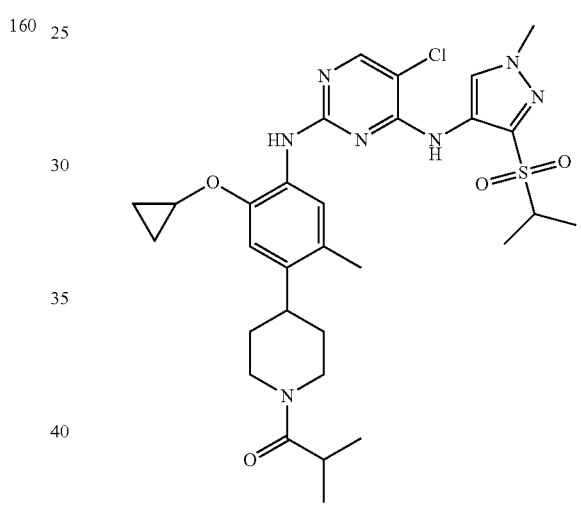
161
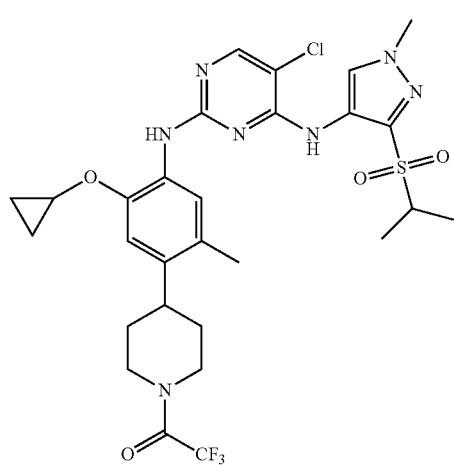
164
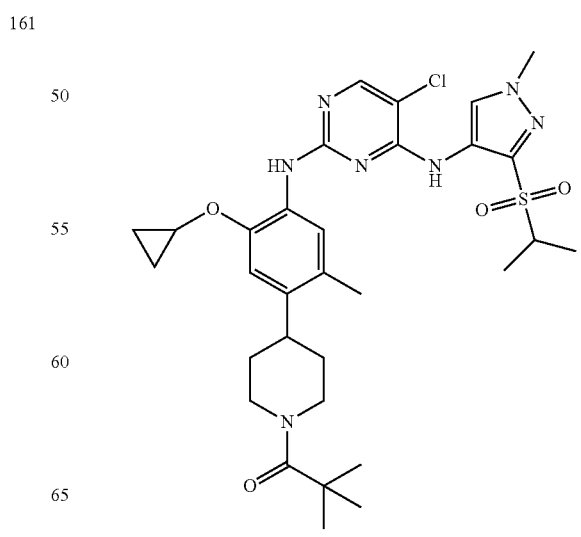

-continued
165
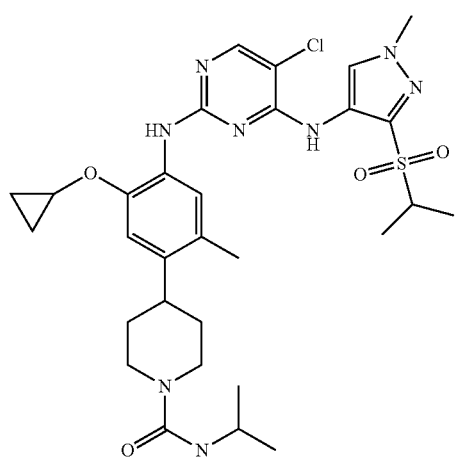
166
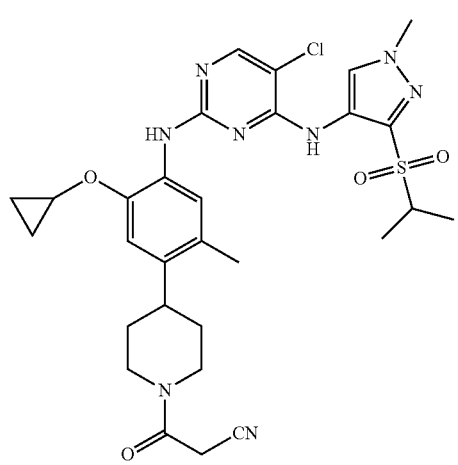
167
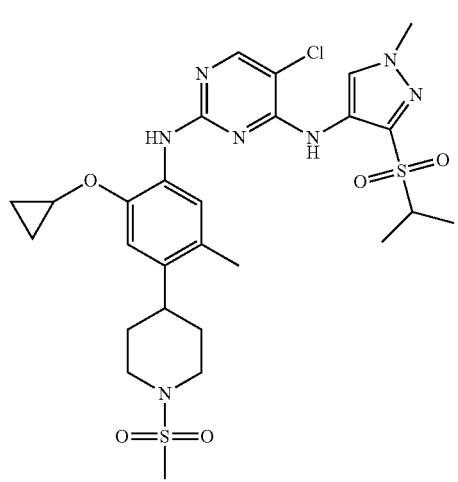
-continued
168
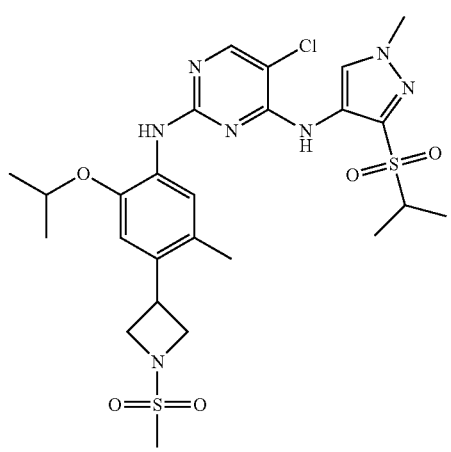
169
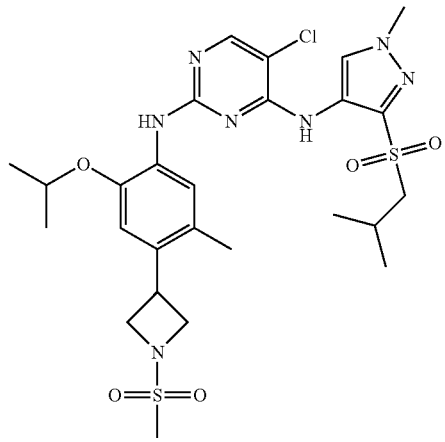
170
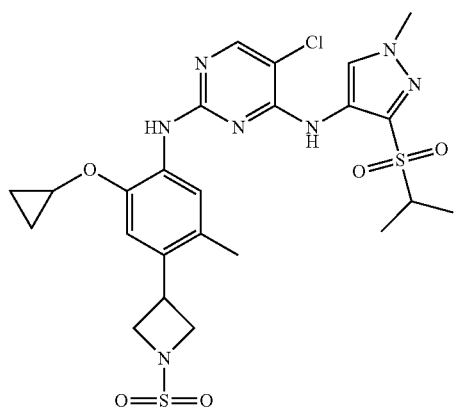

-continued
171
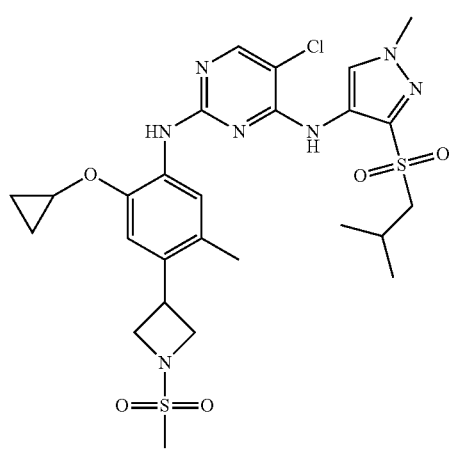
172
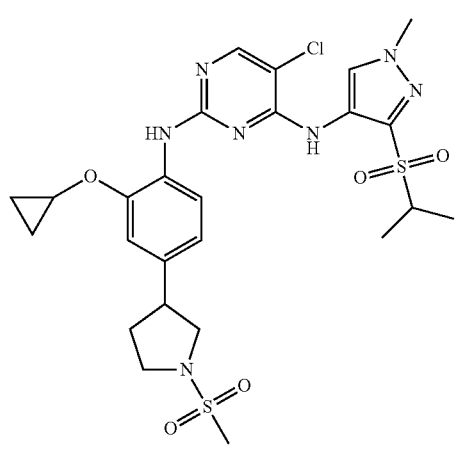
173
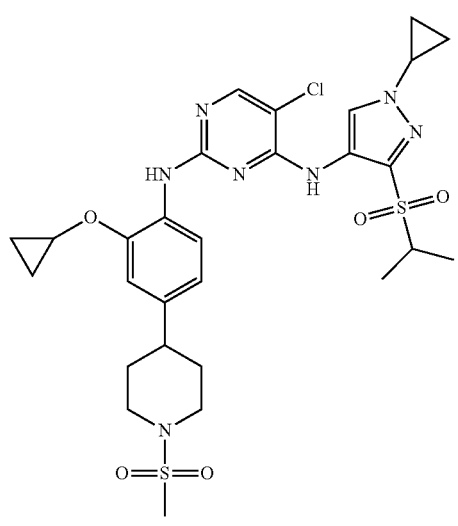
-continued
174
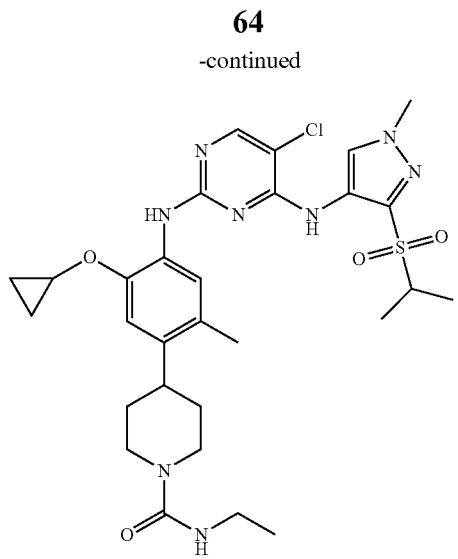
175
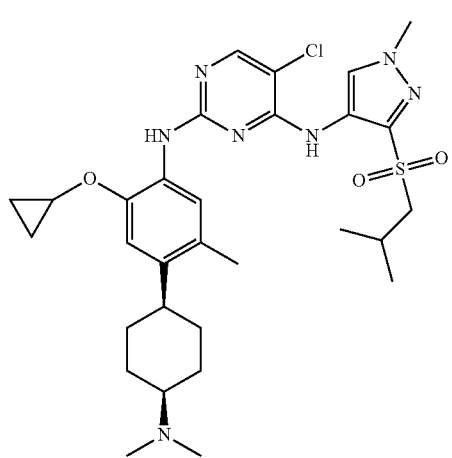
176
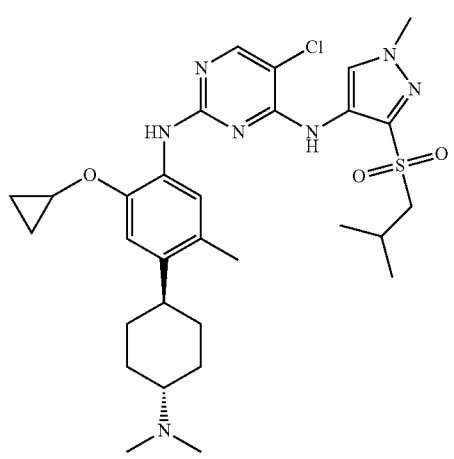

177 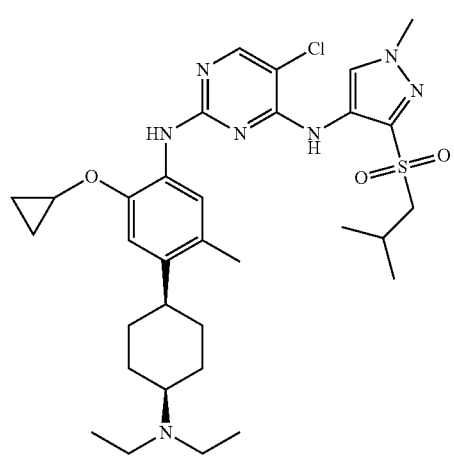
178 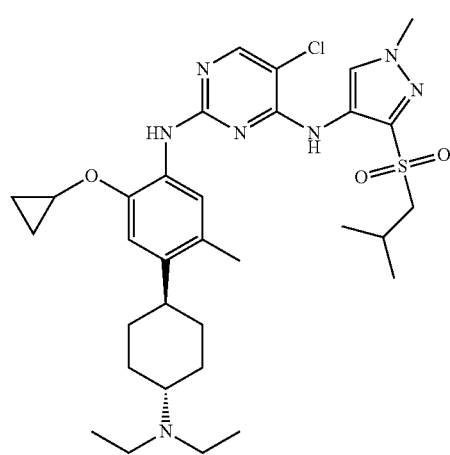
179 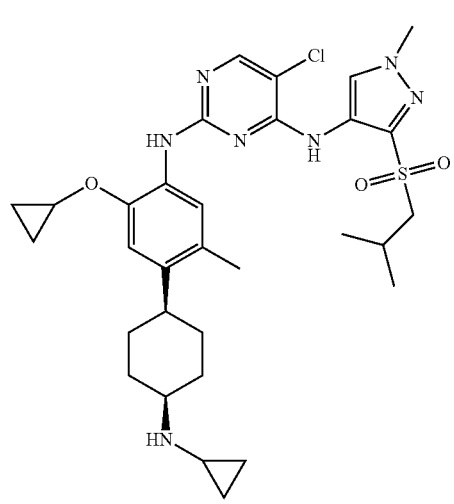
180 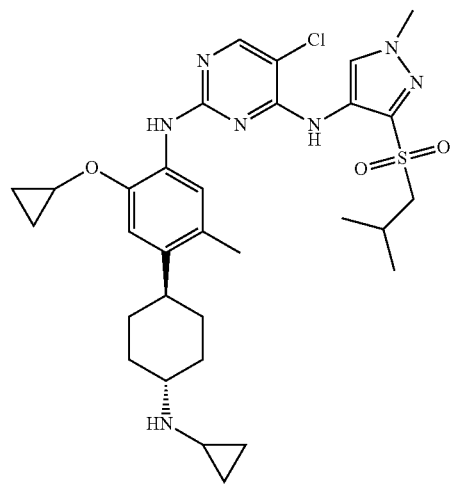
181 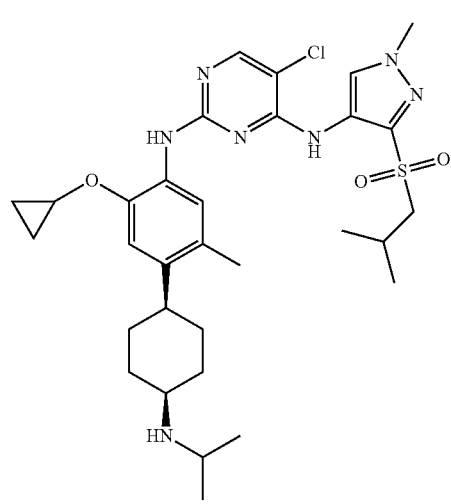
182 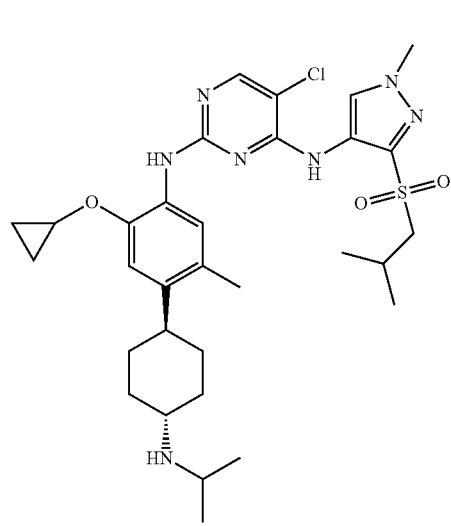

183
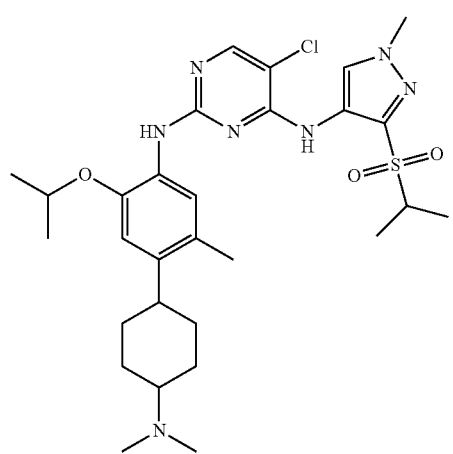
184
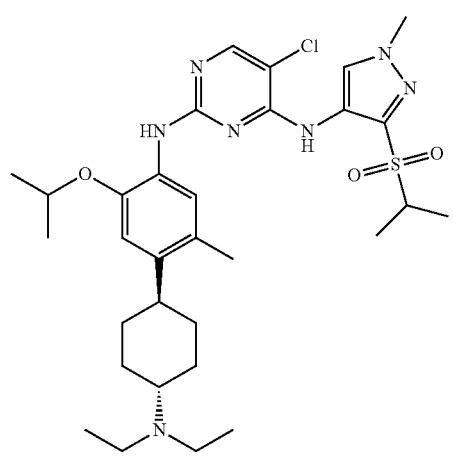
185
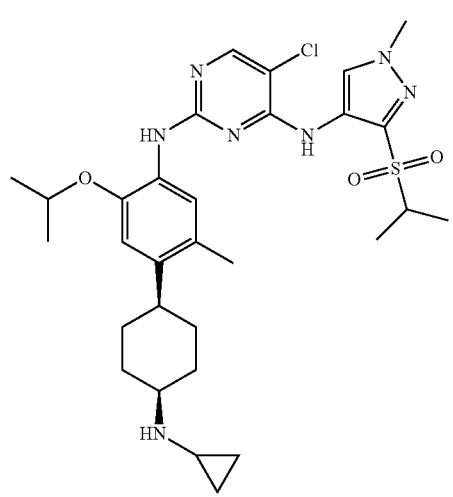
186
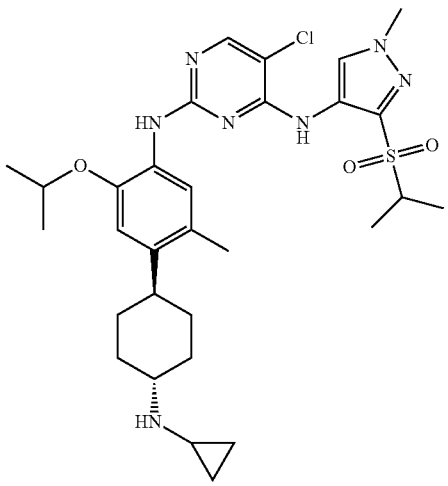
187
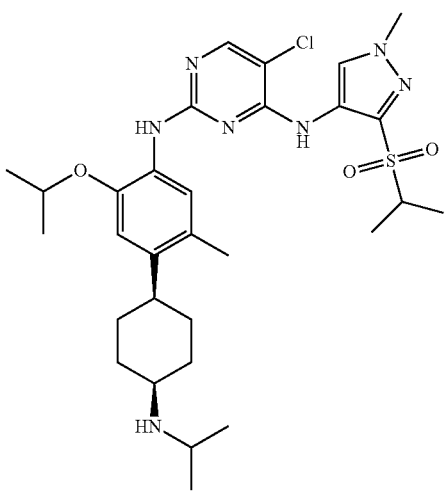
188
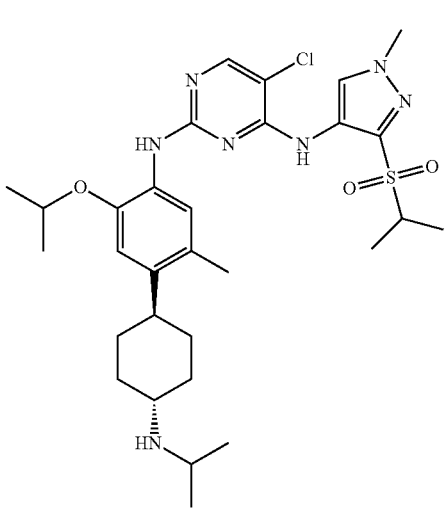

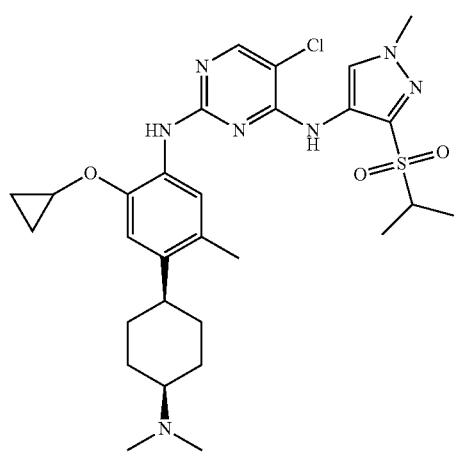
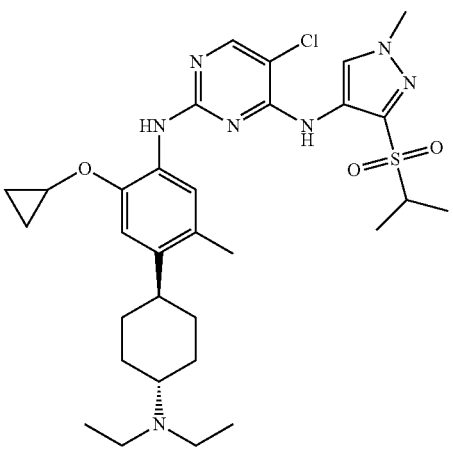

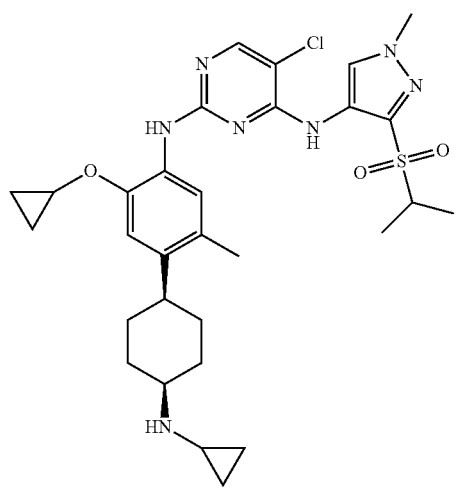
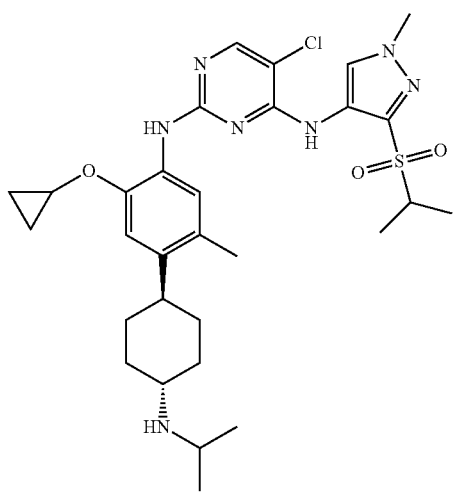

201 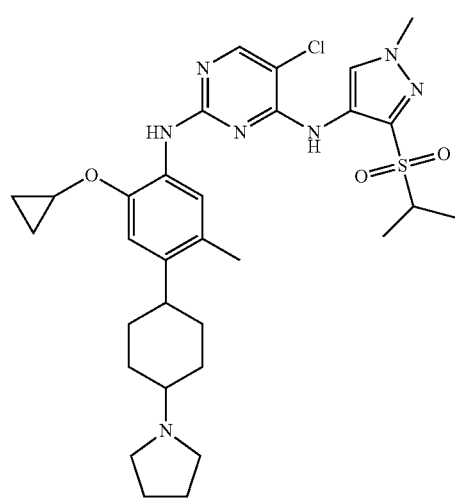
202 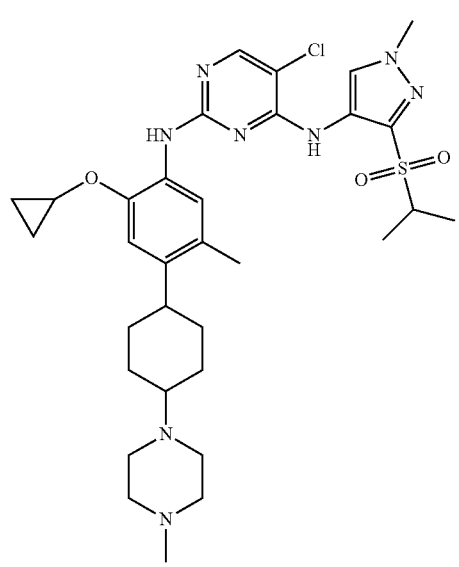
203 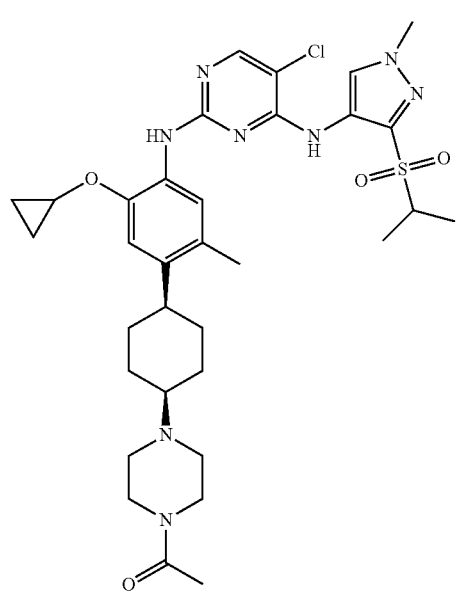
204 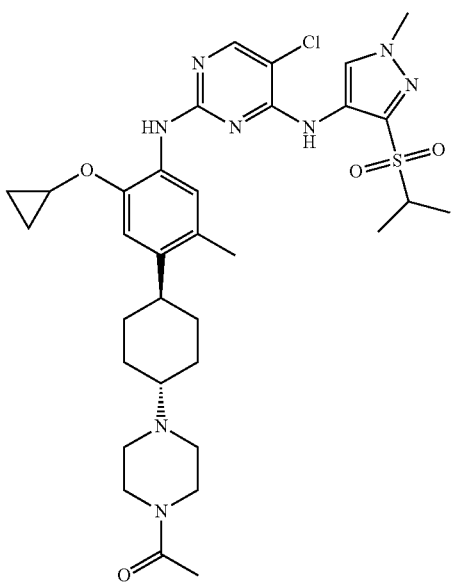
205 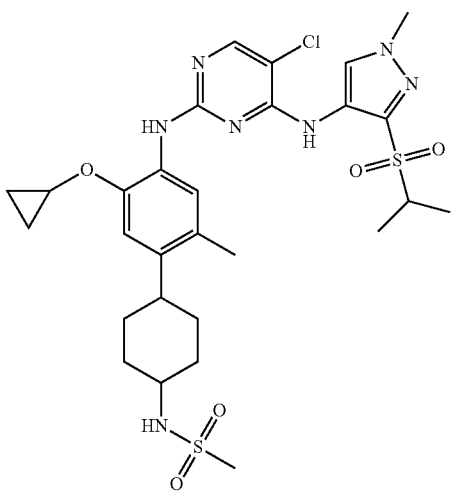
206 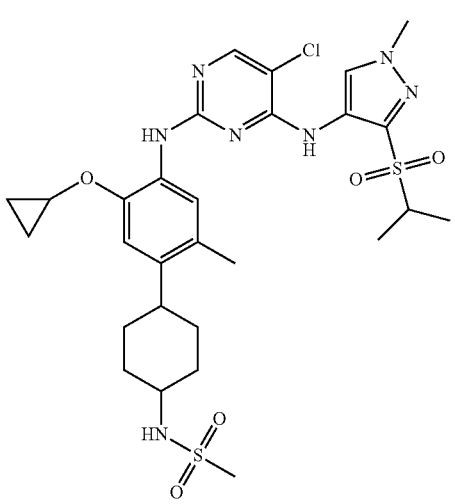

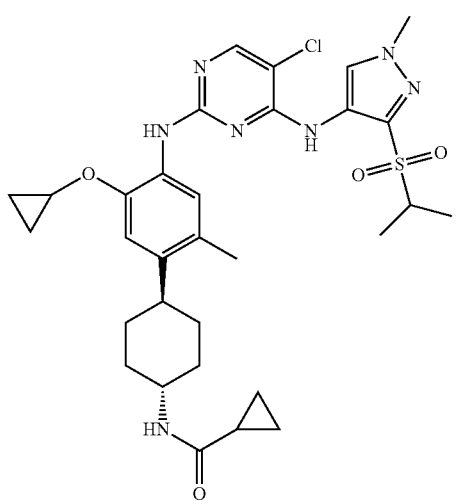
207
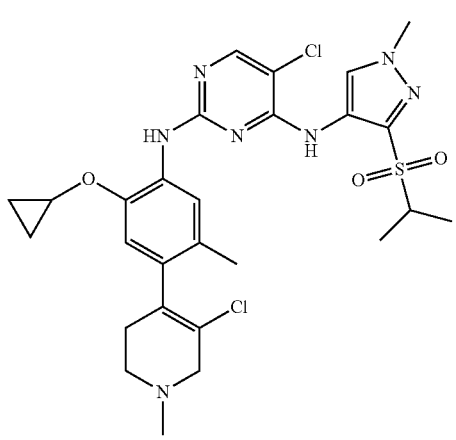
208
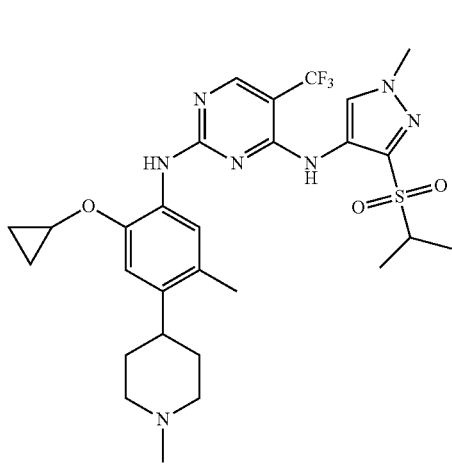
209
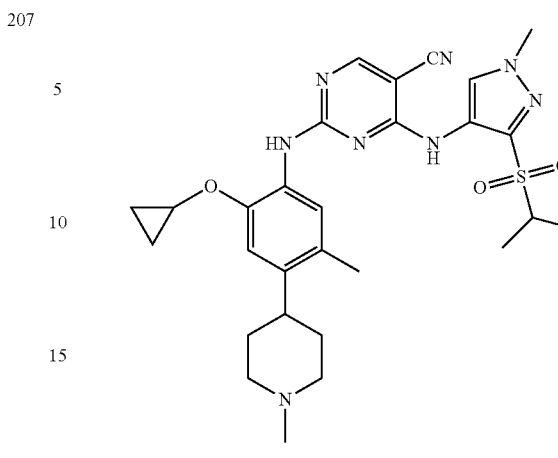
210
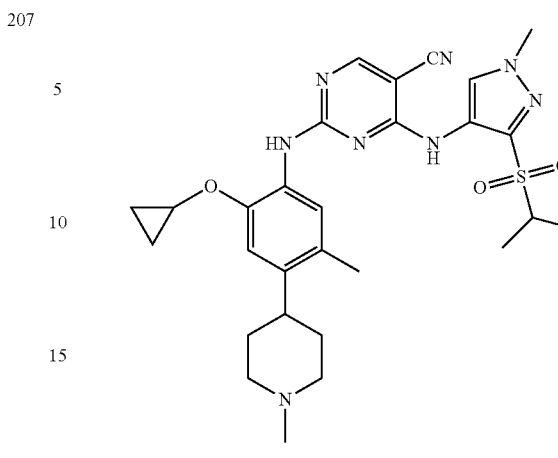
211
On the other hand, the present invention provides a method for preparing the above compound of Formula I, comprising the following steps:
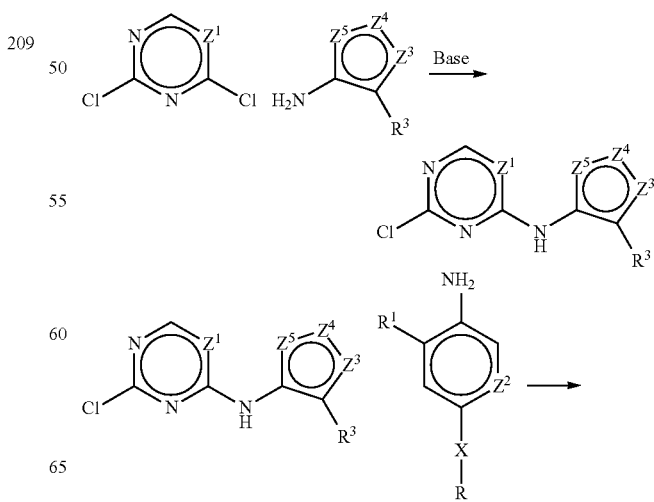

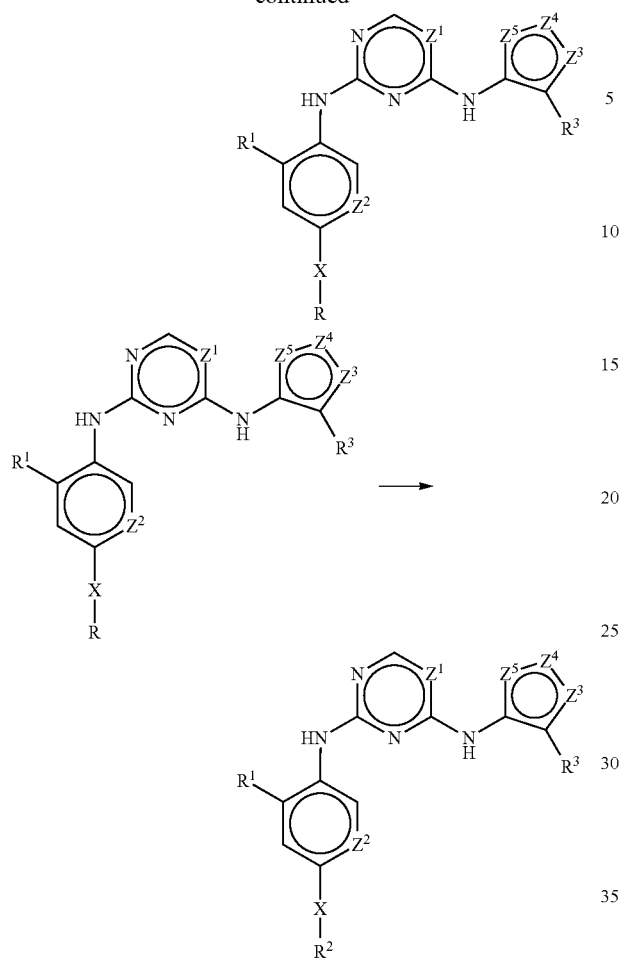

wherein $R^1$, $R^2$, $R^3$, X, $Z^1$, $Z^2$, $Z^3$, $Z^4$ and $Z^5$ are defined as above, R is the precursor of $R^2$ and generally has a protecting group, which may be for example t-butyloxycarbonyl, trifluoroacetyl and the like.

In some embodiments, the method for preparing the compound of Formula I comprises the following steps:

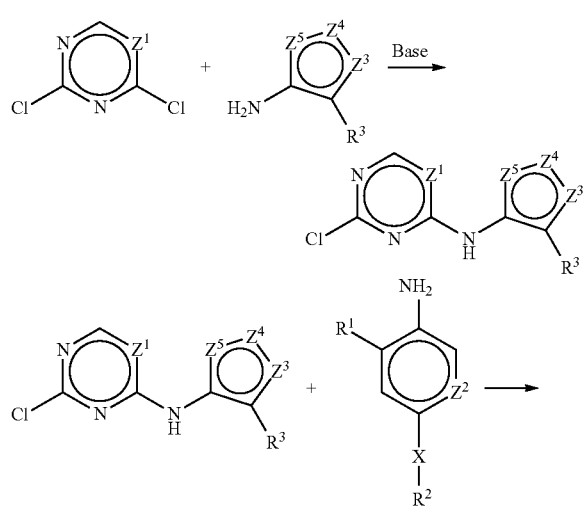

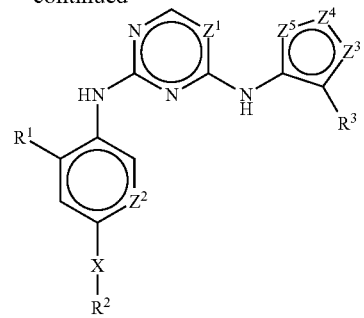

wherein $R^1$, $R^2$, $R^3$, X, $Z^1$, $Z^2$, $Z^3$, $Z^4$ and $Z^5$ are defined as above.

On the other hand, the present invention provides a pharmaceutical composition comprising the above compound or the pharmaceutical salts thereof, wherein the pharmaceutical composition comprises a pharmaceutically acceptable carrier or excipient.

In some embodiments, the pharmaceutical composition is in the form of a tablet, a capsule, a pill, a granule, a powder, a suppository, an injection, a solution, a suspension, an ointment, a patch, a lotion, a drop, a liniment or a spray.

In another aspect, the present invention provides a use of the above compound or pharmaceutical salts thereof and/or pharmaceutical compositions in the manufacture of an anti-tumor drug.

In some embodiments, the anti-tumor drugs are applied to the following diseases: melanoma, neuroblastoma, glioblastoma, rhabdomyosarcoma, astrocytoma, Ewing's sarcoma, retinoblastoma, anaplastic large cell lymphoma, inflammatory myofibroblastic tumor, diffuse large B-cell lymphoma, non-small cell lung cancer, renal medullary carcinoma, renal cell carcinoma, breast cancer, colon cancer, serous ovarian cancer and esophageal squamous cell carcinoma.

In still another aspect, the present invention provides a method for treating a tumor in subject, comprising administering to the subject a therapeutically effective amount of the above compound or pharmaceutically acceptable salts or pharmaceutical compositions thereof.

In some embodiments, the subject is a mammal.

In some embodiments, the subject is a human.

In some embodiments, the modes of administration include oral, mucosal, sublingual, ocular, topical, parenteral, rectal, intracisternal, vagina, peritoneum, bladder, nasal administration.

Other features and advantages of the present invention are described in details as follows. The following examples and specific embodiments are aimed at describing the technical solutions of the present invention and technical effects and advantages thereof, rather than limiting the scope the present invention.

Structure of the Compound as ALK Kinase Inhibitors

One aspect of the present invention provides a compound as ALK kinase inhibitors or pharmaceutically acceptable salt thereof, wherein the compound has the structure as expressed in the Formula I below,

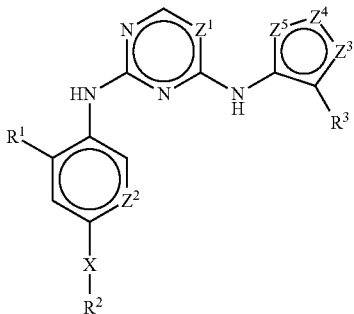

Formula I wherein, $R^1$ is alkyl, haloalkyl or —O—$R^4$, wherein $R^4$ is hydrogen, $C_{1-8}$ alkyl, halo $C_{1-8}$ alkyl, $C_{3-8}$ cycloalkyl, halo $C_{3-8}$ cycloalkyl, $C_{1-8}$ alkyl-$C_{3-8}$ cycloalkyl, $C_{3-8}$ cycloalkyl-$C_{1-8}$ alkyl, substituted or unsubstituted heterocyclyl, or substituted or unsubstituted heterocyclyl —$C_{1-8}$ alkyl;

$R^2$ is alkyl, cycloalkyl, heterocycloalkyl or heterocycloalkenyl, which may be optionally substituted with 1 to 3 substituent groups independently selected from the group consisting of oxo, $C_{1-8}$ alkyl, halo $C_{1-8}$ alkyl, $C_{1-8}$ alkoxy, halo $C_{1-8}$ alkoxy, $C_{3-8}$ cycloalkyl, halo $C_{3-8}$ cycloalkyl, $C_{3-8}$ cycloalkoxy, halo $C_{3-8}$ cycloalkoxy, $C_{1-8}$ alkoxy-$C_{1-8}$ alkyl, hydroxy-$C_{1-8}$ alkyl, amino group-$C_{1-8}$ alkyl, carboxy-$C_{1-8}$ alkyl, $C_{1-8}$ alkyl-amino-$C_{1-8}$ alkyl, halogen, hydroxy, cyano, cyano-$C_{1-8}$ alkyl, amino, $C_{1-8}$ alkyl-amino, di ($C_{1-8}$ alkyl)-amino, $C_{3-8}$ cycloalkyl amino, substituted or unsubstituted aromatic group, substituted or unsubstituted heteroaromatic group, substituted or unsubstituted heterocyclyl, substituted or unsubstituted heterocyclyl-alkyl, $(CH_2)_n CONR^5R^6$, —$COR^5$, —$SO_2R^5$ and —$NR^5SO_2R^6$, wherein n is an integer of 0-8, $R^5$ and $R^6$ are independently hydrogen, alkyl, haloalkyl, cycloalkyl, halocycloalkyl, amino, $C_{1-8}$ alkyl-amino, di ($C_{1-8}$ alkyl)-amino, cyano-$C_{1-8}$ alkyl, $C_{1-8}$ alkyl-amino-$C_{1-8}$ alkyl or di ($C_{1-8}$ alkyl)-amino-$C_{1-8}$ alkyl, wherein the substituent groups may optionally form a ring with the carbon atoms to which they are attached.

$R^3$ is —$SO_2R^7$, —$SO_2NR^7R^8$, —CN, —$CONR^7R^8$, or —$COR^7$, wherein $R^7$ and $R^8$ are independently hydrogen, alkyl or cycloalkyl.

X is a chemical bond, O, S, CO, $NR^9$, $SO_2$ or $S(O)$, wherein $R^9$ is hydrogen, $C_{1-8}$ alkyl, halo $C_{1-8}$ alkyl, $C_{3-8}$ cycloalkyl, halo $C_{3-8}$ cycloalkyl, $C_{1-8}$ alkyl-CO or 4-6 membered heterocyclyl.

$Z^1$ is N or C—$R^{10}$, wherein $R^{10}$ is hydrogen, halogen, alkyl, haloalkyl, cycloalkyl, halocycloalkyl, alkoxy, haloalkoxy or cyano;

$Z^2$ is C—$R^{11}$ or N, wherein $R^{11}$ is hydrogen, $C_{1-8}$ alkyl, halo $C_{1-8}$ alkyl, $C_{3-8}$ cycloalkyl, halo $C_{3-8}$ cycloalkyl, $C_{1-8}$ alkoxy, halo $C_{1-8}$ alkoxy, $C_{3-8}$ cycloalkoxy, halo $C_{3-8}$ cycloalkoxy, halogen, amino, $C_{1-8}$ alkyl-amino, di($C_{1-8}$ alkyl)-amino or cyano, wherein $R^{11}$ and $R^2$ may optionally form a ring together with the carbon atoms to which they are attached, the ring may be optionally substituted with 1 to 3 substituent groups selected from the group consisting of oxo, $C_{1-8}$ alkyl, halo $C_{1-8}$ alkyl, $C_{1-8}$ alkoxy, halo $C_{1-8}$ alkoxy, $C_{3-8}$ cycloalkyl, halo $C_{3-8}$ cycloalkyl, $C_{3-8}$ cycloalkoxy, halo $C_{3-8}$ cycloalkoxy, $C_{1-8}$ alkoxy-$C_{1-8}$ alkyl, hydroxy-$C_{1-8}$ alkyl, amino-$C_{1-8}$ alkyl, carboxy-$C_{1-8}$ alkyl, $C_{1-8}$ alkyl-amino-$C_{1-8}$ alkyl, halogen, hydroxy, cyano, cyano-$C_{1-8}$ alkyl, amino, $C_{1-8}$ alkyl-amino, di($C_{1-8}$ alkyl)-amino, $C_{3-8}$ cycloalkyl-amino, substituted or unsubstituted aromatic group, substituted or unsubstituted heteroaromatic group, substituted or unsubstituted heterocyclyl, substituted or unsubstituted heterocyclyl alkyl, $(CH_2)_n CONR^{12}R^{13}$, —$COR^{12}$, —$SO_2R^{12}$ and —$NR^{12}SO_2R^{13}$, wherein n is an integer of 0-8, $R^{12}$ and $R^{13}$ are independently hydrogen, alkyl, haloalkyl, cycloalkyl, halocycloalkyl, amino, $C_{1-8}$ alkyl-amino, di($C_{1-8}$ alkyl)-amino, cyano-$C_{1-8}$ alkyl, $C_{1-8}$ alkyl-amino-$C_{1-8}$ alkyl or di($C_{1-8}$ alkyl)-amino-$C_{1-8}$ alkyl;

$Z^3$, $Z^4$ and $Z^5$ are selected from the following group:
$Z^3$ is N, $Z^4$ is N—$R^{14}$, $Z^5$ is CH or N;
$Z^3$ is N, $Z^4$ is C—$R^{14}$, $Z^5$ is N, O or S;
$Z^3$ is O or S, $Z^4$ is N—$R^{14}$, $Z^5$ is CH;
$Z^3$ is O or S, $Z^4$ is C—$R^{14}$, $Z^5$ is N; and
$Z^3$ is C, $Z^4$ is N—$R^{14}$, $Z^5$ is O or S;

wherein $R^{14}$ is hydrogen, alkyl, haloalkyl, $C_{3-8}$ cycloalkyl, halo-$C_{3-8}$ cycloalkyl or 4-6 membered heterocyclyl.

In some embodiments of the present invention, $R^1$ is $C_{1-8}$ alkyl. Preferably, $R^1$ is $C_{1-6}$ alkyl. More preferably, $R^1$ is $C_{1-4}$ alkyl. In some embodiments, $R^1$ is haloalkyl. Preferably, $R^1$ is halo $C_{1-4}$ alkyl. In some embodiments, $R^1$ is —O—$R^4$, wherein $R^4$ is hydrogen, $C_{1-8}$ alkyl, halo $C_{1-8}$ alkyl, $C_{3-8}$cycloalkyl, halo $C_{3-8}$ cycloalkyl, $C_{1-8}$ alkyl-$C_{3-8}$ cycloalkyl, $C_{3-8}$ cycloalkyl-$C_{1-8}$ alkyl, substituted or unsubstituted 4-7 membered heterocyclyl or substituted or unsubstituted 4-7 membered heterocyclyl-$C_{1-8}$ alkyl. Preferably, $R^4$ is $C_{1-6}$ alkyl, halo $C_{1-6}$ alkyl, $C_{3-6}$ cycloalkyl, halo $C_{3-6}$ cycloalkyl, $C_{1-6}$ alkyl-$C_{3-6}$ cycloalkyl, $C_{3-6}$ cycloalkyl-$C_{1-6}$ alkyl, substituted or unsubstituted 4-6 membered heterocyclyl group or substituted or unsubstituted 4-6 membered heterocyclyl-$C_{1-6}$ alkyl. More preferably, $R^4$ is $C_{1-4}$ alkyl, halo $C_{1-4}$ alkyl, $C_{3-4}$ cycloalkyl, halo $C_{3-4}$ cycloalkyl, $C_{1-4}$ alkyl-$C_{3-4}$ cycloalkyl, $C_{3-4}$ cycloalkyl-$C_{1-4}$ alkyl. In some embodiments, the heterocyclyl is the heterocyclyl containing one or two heteroatoms selected from the group consisting of N, O and S. In some embodiments, $R^4$ is $C_{1-5}$ alkyl, halo $C_{1-5}$ alkyl, $C_{3-7}$ cycloalkyl, halo $C_{3-7}$ cycloalkyl or $C_{3-7}$ cycloalkyl-methyl. In some embodiments, $R^4$ is methyl, ethyl, n-propyl, isopropyl, cyclopropyl, trifluoromethyl, cyclobutyl or cyclopropylmethyl.

In some embodiments, $R^2$ is $C_{1-8}$ alkyl, $C_{3-8}$ cycloalkyl, 4-7 membered heterocycloalkyl or 4-7 membered heterocycloalkenyl, which may optionally be substituted with 1-3 substituent groups independently selected from the group consisting of oxo, $C_{1-8}$ alkyl, halo $C_{1-8}$ alkyl, $C_{1-8}$ alkoxy, halo $C_{1-8}$ alkoxy, $C_{3-8}$ cycloalkyl, halo $C_{3-8}$ cycloalkyl, $C_{3-8}$ cycloalkoxy, halo-$C_{3-8}$ cycloalkoxy, $C_{1-8}$ alkoxy-$C_{1-8}$ alkyl, hydroxy-$C_{1-8}$ alkyl, amino-$C_{1-8}$ alkyl, carboxy-$C_{1-8}$ alkyl, $C_{1-8}$ alkyl-amino-$C_{1-8}$ alkyl, halogen, hydroxy, cyano, cyano-$C_{1-8}$ alkyl, amino, $C_{1-8}$ alkyl-amino, di ($C_{1-8}$ alkyl)-amino, $C_{3-8}$ cycloalkyl-amino, substituted or unsubstituted aromatic group, substituted or unsubstituted heteroaromatic group, substituted or unsubstituted 4-7 membered heterocyclyl, substituted or unsubstituted 4-7 membered heterocyclyl-$C_{1-8}$ alkyl, —$(CH_2)_n CONR^5R^6$, —$COR^5$, —$SO_2R^5$ and —$NR^5SO_2R^6$, wherein n is an integer of 0-8, $R^5$ and $R^6$ are independently hydrogen, $C_{1-8}$ alkyl, halo $C_{1-8}$ alkyl, $C_{3-8}$ cycloalkyl, halo $C_{3-8}$ cycloalkyl, amino, $C_{1-8}$ alkyl-amino, di ($C_{1-8}$ alkyl)-amino, cyano-$C_{1-8}$ alkyl, $C_{1-8}$ alkyl-amino-$C_{1-8}$ alkyl or di-($C_{1-8}$ alkyl)-amino-$C_{1-8}$ alkyl, cyano-$C_{1-8}$ alkyl, $C_{1-8}$ alkyl-amino-$C_{1-8}$ alkyl or di ($C_{1-8}$ alkyl)-amino-$C_{1-8}$ alkyl, wherein the substituents may optionally form a substituted or unsubstituted ring with the carbon atoms to which they are attached.

In some embodiments, $R^2$ is $C_{1-8}$ alkyl, $C_{3-8}$ cycloalkyl, 4-7 membered heterocycloalkyl containing 1 or 2 heteroatoms selected from the group consisting of N, O and S or 4-7 membered heterocycloalkenyl containing 1 or 2 heteroatoms selected from the group consisting of N, O and S, which may optionally be substituted with 1-3 substituent groups independently selected from the group consisting of: oxo, $C_{1-8}$ alkyl, halo $C_{1-8}$ alkyl, $C_{1-8}$alkoxy, halo $C_{1-8}$ alkoxy, $C_{3-8}$ cycloalkyl, halo $C_{3-8}$ cycloalkyl, $C_{3-8}$ cycloalkoxy, halo $C_{3-8}$ cycloalkoxy, $C_{1-8}$ alkoxy-$C_{1-8}$ alkyl, hydroxy-$C_{1-8}$ alkyl, amino-$C_{1-8}$ alkyl, carboxy-$C_{1-8}$ alkyl, $C_{1-8}$ alkyl-amino-$C_{1-8}$ alkyl, halogen, hydroxy, cyano, cyano-$C_{1-8}$ alkyl, amino, $C_{1-8}$ alkyl-amino, di ($C_{1-8}$ alkyl)-amino, $C_{3-8}$ cycloalkyl-amino, substituted or unsubstituted aromatic group, substituted or unsubstituted heteroaromatic group, substituted or unsubstituted 4-7 membered heterocyclyl, substituted or unsubstituted 4-7 membered heterocyclyl-$C_{1-8}$ alkyl, —$(CH_2)_n CONR^5 R^6$, —$COR^5$, —$SO_2 R^5$ and —$NR^5 SO_2 R^6$, wherein n is an integer of 0-8, $R^5$ and $R^6$ are independently hydrogen, $C_{1-8}$ alkyl, halo $C_{1-8}$ alkyl, $C_{3-8}$ cycloalkyl, halo $C_{3-8}$ cycloalkyl, amino, $C_{1-8}$ alkyl-amino, di ($C_{1-8}$ alkyl)-amino, or cyano-$C_{1-8}$ alkyl, $C_{1-8}$ alkyl-amino-$C_{1-8}$ alkyl or di-($C_{1-8}$ alkyl)-amino-$C_{1-8}$ alkyl, wherein the substituents may optionally form a substituted or unsubstituted ring with the carbon atoms to which they are attached.

In some embodiments, $R^2$ is $C_{1-6}$ alkyl, $C_{3-6}$ cycloalkyl, 4-6 membered heterocycloalkyl containing 1 or 2 heteroatoms selected from the group consisting of N, O and S or 4-6 membered heterocycloalkenyl containing 1 or 2 heteroatoms selected from the group consisting of N, O and S, which may optionally be substituted with 1-3 substituent groups independently selected from the group consisting of: oxo, $C_{1-6}$ alkyl, halo $C_{1-6}$ alkyl, $C_{1-6}$ alkoxy, halo $C_{1-6}$ alkoxy, $C_{3-6}$ cycloalkyl, halo $C_{3-6}$ cycloalkyl, $C_{3-6}$ cycloalkoxy, halo $C_{3-6}$ cycloalkoxy, $C_{1-6}$ alkoxy-$C_{1-6}$ alkyl, hydroxy-$C_{1-6}$alkyl, amino-$C_{1-6}$ alkyl, carboxy-$C_{1-6}$ alkyl, $C_{1-6}$ alkyl-amino-$C_{1-6}$ alkyl, halogen, hydroxy, cyano, cyano-$C_{1-6}$ alkyl, amino, $C_{1-6}$ alkyl-amino, di($C_{1-6}$ alkyl)-amino, $C_{3-6}$ cycloalkyl-amino, substituted or unsubstituted aromatic group, substituted or unsubstituted heteroaromatic group, substituted or unsubstituted 4-6 membered heterocyclyl, substituted or unsubstituted 4-6 membered heterocyclyl-$C_{1-6}$ alkyl, —$(CH_2)_n CONR^5 R^6$, —$COR^5$, —$SO_2 R^5$ and —$NR^5 SO_2 R^6$, wherein n is an integer of 0-8, $R^5$ and $R^6$ are independently hydrogen, $C_{1-6}$ alkyl, halo $C_{1-6}$ alkyl, $C_{3-6}$ cycloalkyl, halo $C_{3-6}$ cycloalkyl, amino, $C_{1-6}$ alkyl-amino, di ($C_{1-6}$ alkyl)-amino, or cyano-$C_{1-6}$ alkyl, $C_{1-6}$ alkyl-amino-$C_{1-6}$ alkyl or di-($C_{1-6}$ alkyl)-amino-$C_{1-6}$ alkyl, wherein the substituent groups may optionally form a substituted or unsubstituted ring with the carbon atoms to which they are attached.

In some embodiments, $R^2$ is $C_{1-6}$ alkyl, $C_{3-6}$ cycloalkyl, 4-6 membered heterocycloalkyl containing 1 or 2 heteroatoms selected from the group consisting of N, O and S or 4-6 membered heterocycloalkenyl containing 1 or 2 heteroatoms selected from the group consisting of N, O and S, which may optionally be substituted with 1-3 substituent groups independently selected from the group consisting of: oxo, $C_{1-5}$ alkyl, halo $C_{1-5}$ alkyl, $C_{1-5}$ alkoxy, halo $C_{1-5}$ alkoxy, $C_{3-5}$ cycloalkyl, halo $C_{3-5}$ cycloalkyl, $C_{3-5}$ cycloalkoxy, halo $C_{3-5}$ cycloalkoxy, $C_{1-5}$ alkoxy-$C_{1-5}$ alkyl, hydroxy-$C_{1-5}$ alkyl, amino-$C_{1-5}$ alkyl, carboxy-$C_{1-5}$ alkyl, $C_{1-5}$ alkyl-amino-$C_{1-5}$ alkyl, halogen, hydroxy, cyano, cyano-$C_{1-5}$ alkyl, amino, $C_{1-5}$ alkyl-amino, di ($C_{1-5}$ alkyl)-amino, $C_{3-5}$ cycloalkyl-amino, substituted or unsubstituted aromatic group, substituted or unsubstituted heteroaromatic group, substituted or unsubstituted 4-6 membered heterocyclyl, substituted or unsubstituted 4-6 membered heterocyclyl-$C_{1-5}$alkyl, —$(CH_2)_n CONR^5 R^6$, —$COR^5$, —$SO_2 R^5$ and —$NR^5 SO_2 R^6$, wherein n is an integer of 0-8, $R^5$ and $R^6$ are independently hydrogen, $C_{1-5}$ alkyl, halo $C_{1-5}$ alkyl, $C_{3-5}$ cycloalkyl, halo $C_{3-5}$ cycloalkyl, amino, $C_{1-5}$ alkyl-amino, di ($C_{1-5}$ alkyl)-amino, or cyano-$C_{1-5}$ alkyl, $C_{1-5}$ alkyl-amino-$C_{1-5}$ alkyl or di-($C_{1-5}$ alkyl)-amino-$C_{1-5}$ alkyl, wherein the substituents may optionally form a substituted or unsubstituted ring with the carbon atoms to which they are attached.

In some embodiments, $R^2$ is $C_{1-6}$ alkyl, $C_{3-6}$ cycloalkyl, 4-6 membered heterocycloalkyl containing 1 or 2 heteroatoms selected from the group consisting of N, O and S or 4-6 membered heterocycloalkenyl containing 1 or 2 heteroatoms selected from the group consisting of N, O and S, which may optionally be substituted with 1-3 substituent groups independently selected from the group consisting of: oxo, $C_{1-4}$ alkyl, halo $C_{1-4}$ alkyl, $C_{1-4}$ alkoxy, halo $C_{1-4}$ alkoxy, $C_{3-4}$ cycloalkyl, halo $C_{3-4}$ cycloalkyl, $C_{3-4}$ cycloalkoxy, halo $C_{3-4}$ cycloalkoxy, $C_{1-4}$ alkoxy-$C_{1-4}$ alkyl, hydroxy-$C_{1-4}$ alkyl, amino-$C_{1-4}$ alkyl, carboxy-$C_{1-6}$ alkyl, $C_{1-4}$ alkyl-amino—$C_{1-4}$ alkyl, halogen, hydroxy, cyano, cyano-$C_{1-4}$ alkyl, amino, $C_{1-4}$ alkyl-amino, di ($C_{1-4}$ alkyl)-amino, $C_{3-4}$ cycloalkyl-amino, substituted or unsubstituted aromatic group, substituted or unsubstituted heteroaromatic group, substituted or unsubstituted 4-6 membered heterocyclyl, substituted or unsubstituted 4-6 membered heterocyclyl-$C_{1-6}$ alkyl, —$(CH_2)_n CONR^5 R^6$, —$COR^5$, —$SO_2 R^5$ and —$NR^5 SO_2 R^6$, wherein n is an integer of 0-8, $R^5$ and $R^6$ are independently hydrogen, $C_{1-4}$ alkyl, halo $C_{1-4}$ alkyl, $C_{3-4}$ cycloalkyl, halo $C_{3-6}$ cycloalkyl, amino, $C_{1-6}$ alkyl-amino, di ($C_{1-4}$ alkyl)-amino, or cyano-$C_{1-4}$ alkyl, $C_{1-4}$ alkyl-amino-$C_{1-4}$ alkyl or di-($C_{1-4}$ alkyl)-amino-$C_{1-4}$ alkyl, wherein the substituent groups may optionally form a substituted or unsubstituted ring with the carbon atoms to which they are attached.

In some embodiments, $R^2$ is cyclohexyl, piperidinyl, pyrrolidinyl, azetidinyl, tetrahydropyranyl, morpholinoe group or 3-4 alkenyl piperidinyl, which are optionally substituted with 1-3 substituent groups independently selected from the group consisting of: methyl, ethyl, n-propyl, isopropyl, n-butyl, sec-butyl, isobutyl, tert-butyl, cyclopropyl, cyclobutyl, dioxetane, methoxy, methoxymethyl, methoxyethyl, fluoro, chloro, cyano, amino, cyclopropylamino, (isopropyl, methyl)-amino, formyl, acetyl, trifluoroacetyl, cyclopropylformyl, —$COR^5$, —$SO_2 R^5$ and —$NR^5 SO_2 R^6$, wherein $R^5$ and $R^6$ are independently hydrogen, $C_{1-5}$ alkyl, dimethylamino, dimethylaminomethyl, ethylamino or cyanomethyl.

In some embodiments, $R^3$ is —$SO_2 R^7$, —$SO_2 NR^7 R^8$, —CN, —$CONR^7 R^8$, or —$COR^7$, wherein $R^7$ and $R^8$ are independently hydrogen, $C_{1-8}$ alkyl or $C_{3-8}$ cycloalkyl. Preferably, $R^7$ and $R^8$ are independently hydrogen, $C_{1-6}$ alkyl or $C_{3-6}$ cycloalkyl. More preferably, $R^7$ and $R^8$ are independently hydrogen, $C_{1-5}$ alkyl or $C_{3-5}$ cycloalkyl. More preferably, $R^7$ and $R^8$ are independently hydrogen, $C_{1-4}$ alkyl or $C_{3-4}$ cycloalkyl. More preferably, $R^7$ and $R^8$ are independently hydrogen, $C_{1-3}$ alkyl.

In some embodiments, $R^3$ is —$SO_2 R^7$, wherein $R^7$ is hydrogen, $C_{1-8}$ alkyl or $C_{3-8}$ cycloalkyl. Preferably, $R^7$ is hydrogen, $C_{1-6}$ alkyl or $C_{3-6}$ cycloalkyl. More preferably, $R^7$ is hydrogen, $C_{1-5}$ alkyl or $C_{3-5}$ cycloalkyl. More preferably, $R^7$ is hydrogen, $C_{1-4}$ alkyl or $C_{3-4}$ cycloalkyl. In some embodiments, $R^7$ is isopropyl, sec-butyl or isobutyl.

In some embodiments, X is a chemical bond or CO.

In some embodiments, $Z^1$ is C—$R^{10}$, wherein $R^{10}$ is hydrogen, halogen, $C_{1-8}$alkyl, halo $C_{1-8}$ alkyl, $C_{3-8}$ cycloalkyl, halo $C_{3-8}$ cycloalkyl, $C_{1-8}$ alkoxy, halo $C_{1-8}$ alkoxy, or cyano; preferably, $R^{10}$ is halogen; more preferably, $R^{10}$ is chloro.

In some embodiments, $Z^2$ is C—$R^{11}$, wherein $R^{11}$ is hydrogen, $C_{1-8}$ alkyl, halogen or cyano, wherein $R^{11}$ and $R^2$ may optionally form a ring together with the carbon atoms to which they are attached, the ring may be optionally substituted with 1-3 substituent groups independently selected from the group consisting of: oxo, $C_{1-8}$ alkyl, halo $C_{1-8}$ alkyl, $C_{1-8}$ alkoxy, halo $C_{1-8}$ alkoxy, $C_{3-8}$ cycloalkyl, halo $C_{3-8}$ cycloalkyl, $C_{3-8}$ cycloalkoxy, halo $C_{3-8}$ cycloalkoxy, $C_{1-8}$ alkoxy-$C_{1-8}$ alkyl, hydroxy-$C_{1-8}$ alkyl, amino-$C_{1-8}$ alkyl, carboxyl-$C_{1-8}$ alkyl, $C_{1-8}$ alkyl-amino-$C_{1-8}$ alkyl, halogen, hydroxy, cyano, cyano-$C_{1-8}$ alkyl, amino, $C_{1-8}$ alkyl-amino, di ($C_{1-8}$ alkyl) amino, $C_{3-8}$ cycloalkyl-amino, substituted or unsubstituted aromatic group, substituted or unsubstituted heteroaromatic group, substituted or unsubstituted heterocyclyl, substituted or unsubstituted heterocyclyl-alkyl, —(CH$_2$)$_n$CONR$^{12}$R$^{13}$, —COR$^{12}$, —SO$_2$R$^{12}$ and —NR$^{12}$SO$_2$R$^{13}$, wherein n is an integer of 0-8, $R^{12}$ and $R^{13}$ are independently hydrogen, $C_{1-8}$ alkyl, halo $C_{1-8}$ alkyl, $C_{3-8}$ cycloalkyl, halo $C_{3-8}$ cycloalkyl, amino, $C_{1-8}$ alkyl-amino, di ($C_{1-8}$ alkyl)-amino, cyano $C_{1-8}$ alkyl, $C_{1-8}$ alkyl-amino-$C_{1-8}$ alkyl or di ($C_{1-8}$ alkyl)-amino-$C_{1-8}$ alkyl.

In some embodiments, $Z^2$ is C—$R^{11}$, wherein $R^{11}$ is hydrogen, $C_{1-6}$ alkyl, halogen or cyano, wherein $R^{11}$ and $R^2$ may optionally form a ring together with the carbon atoms to which they are attached, the ring may be optionally substituted with 1-3 substituent groups independently selected from the group consisting of: oxo, $C_{1-6}$ alkyl, halo $C_{1-6}$ alkyl, $C_{1-6}$ alkoxy, halo $C_{1-6}$ alkoxy, $C_{3-6}$ cycloalkyl, halo $C_{3-6}$ cycloalkyl, $C_{3-6}$ cycloalkoxy, halo $C_{3-6}$ cycloalkoxy, $C_{1-6}$ alkoxy-$C_{1-6}$ alkyl, hydroxy-$C_{1-6}$ alkyl, amino-$C_{1-6}$ alkyl, carboxyl-$C_{1-6}$ alkyl, $C_{1-6}$ alkyl-amino-$C_{1-6}$ alkyl, halogen, hydroxy, cyano, cyano-$C_{1-6}$ alkyl, amino, $C_{1-6}$ alkyl-amino, di ($C_{1-6}$ alkyl) amino, $C_{3-6}$ cycloalkyl-amino, substituted or unsubstituted aromatic group, substituted or unsubstituted heteroaromatic group, substituted or unsubstituted heterocyclyl, substituted or unsubstituted heterocyclyl-alkyl, —(CH$_2$)$_n$CONR$^{12}$R$^{13}$, —COR$^{12}$, —SO$_2$R$^{12}$ and —NR$^{12}$SO$_2$R$^{13}$, wherein n is an integer of 0-8, $R^{12}$ and $R^{13}$ are independently hydrogen, $C_{1-6}$ alkyl, halo $C_{1-6}$ alkyl, $C_{3-6}$ cycloalkyl, halo $C_{3-6}$ cycloalkyl, amino, $C_{1-6}$ alkyl-amino, di ($C_{1-6}$ alkyl)-amino, cyano $C_{1-6}$ alkyl, $C_{1-6}$ alkyl-amino-$C_{1-6}$ alkyl or di ($C_{1-6}$ alkyl)-amino-$C_{1-6}$ alkyl.

In some embodiments, $Z^2$ is C—$R^{11}$, wherein $R^{11}$ is hydrogen, $C_{1-6}$ alkyl, halogen or cyano, wherein $R^{11}$ and $R^2$ may optionally form a ring together with the carbon atoms to which they are attached, the ring may be optionally substituted with 1-3 substituent groups independently selected from the group consisting of: oxo, $C_{1-4}$alkyl, halo $C_{1-4}$ alkyl, $C_{1-4}$ alkoxy, halo $C_{1-4}$ alkoxy, $C_{3-5}$ cycloalkyl, halo $C_{3-5}$ cycloalkyl, $C_{3-5}$ cycloalkoxy, halo $C_{3-5}$ cycloalkoxy, $C_{1-4}$ alkoxy-$C_{1-4}$ alkyl, hydroxy-$C_{1-4}$ alkyl, amino-$C_{1-4}$ alkyl, carboxyl-$C_{1-4}$ alkyl, $C_{1-4}$ alkyl-amino-$C_{1-4}$ alkyl, halogen, hydroxy, cyano, cyano-$C_{1-6}$ alkyl, amino, $C_{1-4}$ alkyl-amino, di ($C_{1-4}$ alkyl) amino, $C_{3-4}$ cycloalkyl-amino, substituted or unsubstituted aromatic group, substituted or unsubstituted heteroaromatic group, substituted or unsubstituted heterocyclyl, substituted or unsubstituted heterocyclyl-alkyl, —(CH$_2$)$_n$CONR$^{12}$R$^{13}$, —COR$^{12}$, —SO$_2$R$^{12}$ and —NR$^{12}$SO$_2$R$^{13}$, wherein n is an integer of 0-8, $R^{12}$ and $R^{13}$ are independently hydrogen, $C_{1-4}$ alkyl, halo $C_{1-4}$ alkyl, $C_{3-5}$ cycloalkyl, halo $C_{3-5}$ cycloalkyl, amino, $C_{1-4}$ alkyl-amino, di ($C_{1-4}$ alkyl)-amino, cyano $C_{1-4}$ alkyl, $C_{1-4}$ alkyl-amino-$C_{1-4}$ alkyl or di ($C_{1-4}$ alkyl)-amino-$C_{1-4}$ alkyl.

In some embodiments, $Z^2$ is C—$R^{11}$, wherein $R^{11}$ is hydrogen, $C_{1-8}$ alkyl, halogen or cyano. In some embodiments, $R^{11}$ is hydrogen, methyl, fluoro, chloro or cyano.

In some embodiments, $Z^3$, $Z^4$ and $Z^5$ are selected from the following group:

$Z^3$ is N, $Z^4$ is N—$R^{14}$, $Z^5$ is CH or N;

$Z^3$ is N, $Z^4$ is C—$R^{14}$, $Z^5$ is N, O or S;

$Z^3$ is O or S, $Z^4$ is N—$R^{14}$, $Z^5$ is CH;

$Z^3$ is O or S, $Z^4$ is C—$R^{14}$, $Z^5$ is N; and $Z^3$ is C, $Z^4$ is N—$R^{14}$, $Z^5$ is O or S;

wherein $R^{14}$ is hydrogen, $C_{1-8}$ alkyl, $C_{3-8}$ cycloalkyl, halo $C_{3-8}$ cycloalkyl, 4-6 membered heterocycloalkyl group containing 1 or 2 heteroatoms selected from the group consisting of N, O and S or halo 4-6 membered heterocyclyl containing 1 or 2 heteroatoms selected from the group consisting of N, O and S. Preferably, $R^{14}$ is $C_{1-6}$ alkyl, $C_{3-6}$ cycloalkyl, halo $C_{3-6}$ cycloalkyl, 4-5 membered heterocyclyl containing for 2 heteroatoms selected from the group consisting of N, O and S or halo 4-5 membered heterocyclyl containing 1 or 2 heteroatoms selected from the group consisting of N, O and S. More preferably, $R^{14}$ is $C_{1-4}$ alkyl, $C_{3-4}$ cycloalkyl, halo $C_{3-4}$ cycloalkyl.

In some embodiments, $Z^3$ is N, $Z^4$ is N—$R^{14}$, $Z^5$ is CH, wherein $R^{14}$ is hydrogen, $C_{1-8}$ alkyl, $C_{3-8}$ cycloalkyl, halo $C_{3-8}$ cycloalkyl, 4-6 membered heterocyclyl containing 1 or 2 heteroatoms selected from the group consisting of N, O and S or halo 4-6 membered heterocyclyl containing 1 or 2 heteroatoms selected from the group consisting of N, O and S. Preferably, $R^{14}$ is $C_{1-6}$ alkyl, $C_{3-6}$ cycloalkyl, halo $C_{3-6}$ cycloalkyl, 4-5 membered heterocyclyl containing 1 or 2 heteroatoms selected from the group consisting of N, O and S or halo 4-5 membered heterocyclyl containing 1 or 2 heteroatoms selected from the group consisting of N, O and S. More preferably, $R^{14}$ is $C_{1-4}$ alkyl, $C_{3-4}$ cycloalkyl, or halo $C_{3-4}$ cycloalkyl. In some embodiments, $R^{14}$ is $C_{1-8}$ alkyl or $C_{3-8}$ cycloalkyl. In some embodiments, $R^{14}$ is methyl or cyclopropyl.

In some embodiments, the compounds are expressed in formulas as below:

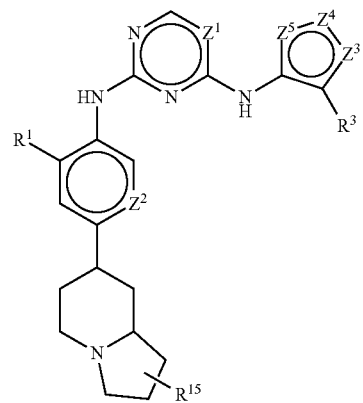

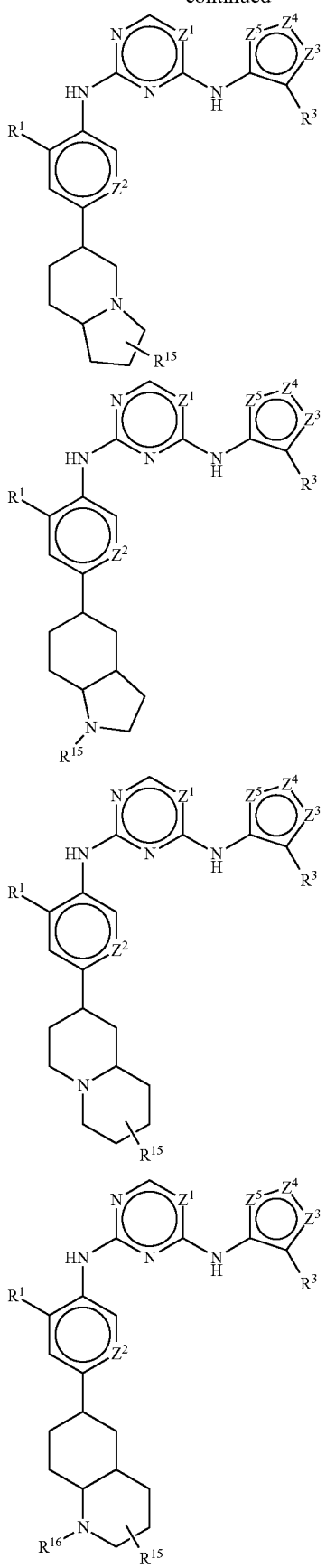
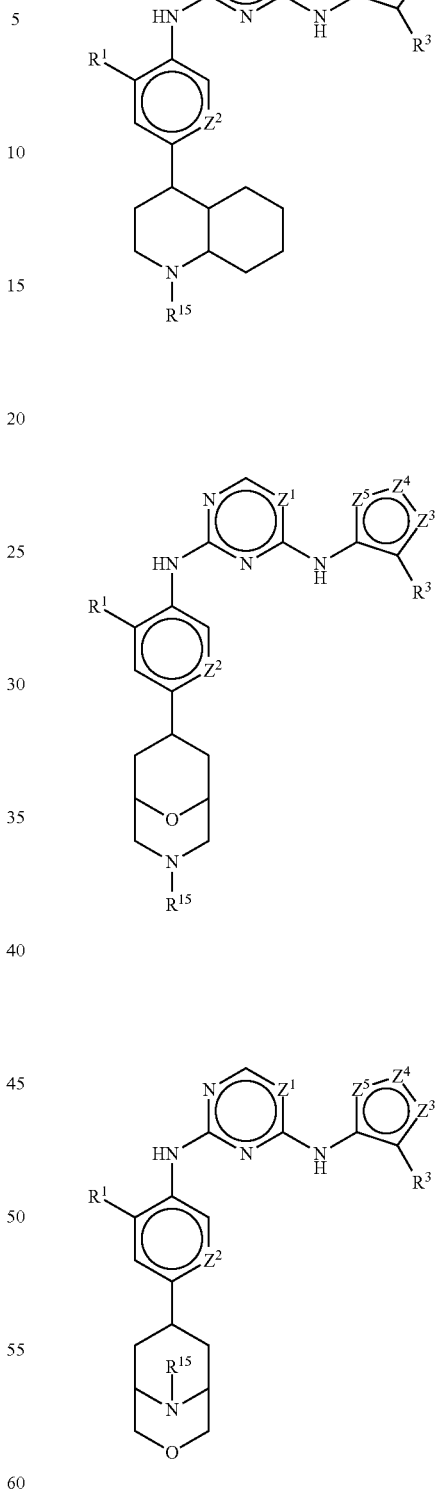
Wherein $R^{15}$ and $R^{16}$ are independently $C_{1-8}$ alkyl, $C_{3-8}$ cycloalkyl, $C_{1-8}$ alkoxy-$C_{1-8}$ alkyl, hydroxy-$C_{1-8}$ alkyl, amino-$C_{1-8}$ alkyl, $C_{1-8}$ alkyl-CO, $C_{1-8}$ alkyl-amino-$C_{1-8}$ alkyl or di ($C_{1-8}$ alkyl)-amino-$C_{1-8}$ alkyl.
In some embodiments, the compounds are expressed in formulas as below:

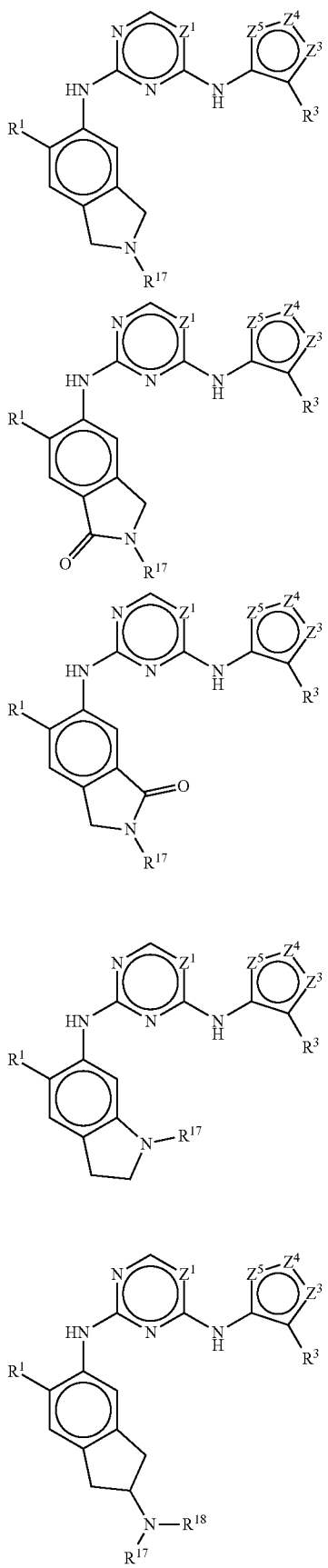
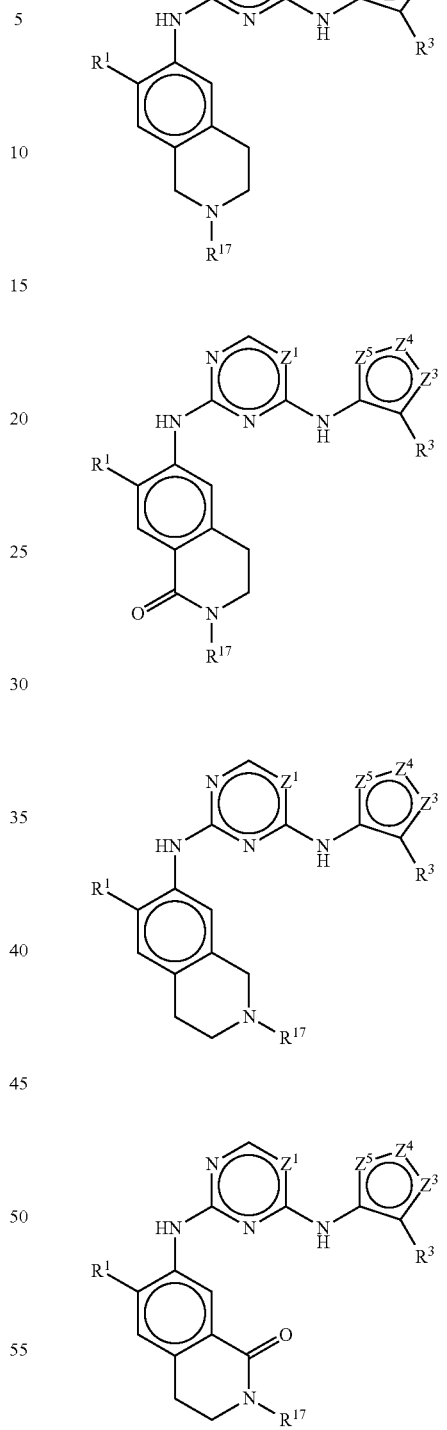
Wherein $R^{17}$ and $R^{18}$ are independently $C_{1-8}$ alkyl, $C_{3-8}$ cycloalkyl, $C_{1-8}$ alkoxy-$C_{1-8}$ alkyl, hydroxy-$C_{1-8}$ alkyl, amino-$C_{1-8}$ alkyl, $C_{1-8}$ alkyl-CO, $C_{1-8}$ alkyl-amino-$C_{1-8}$ alkyl or di ($C_{1-8}$ alkyl)-amino-$C_{1-8}$ alkyl.
In a specific embodiment, the compounds of Formula I of the present invention are selected from the following compounds:

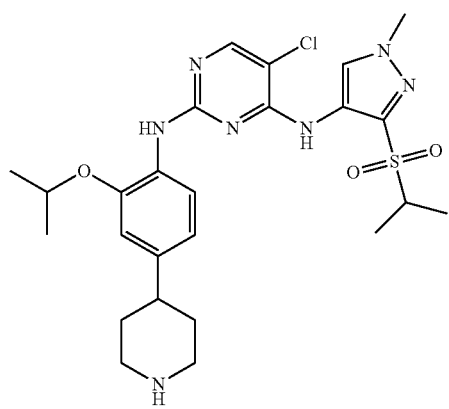
1
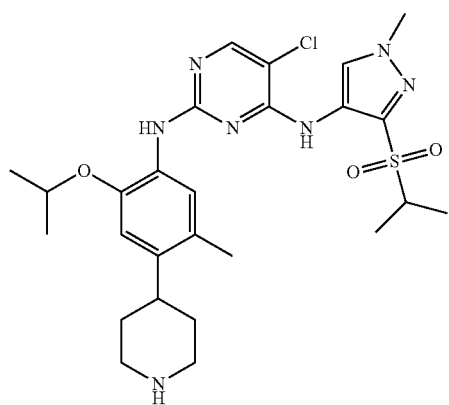
2
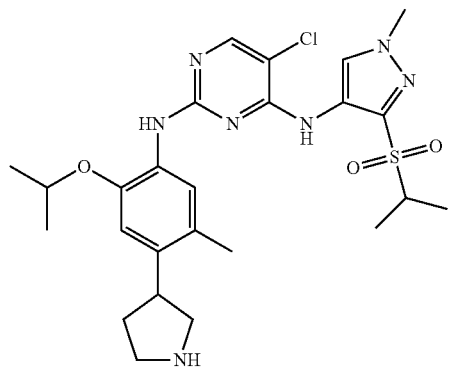
3
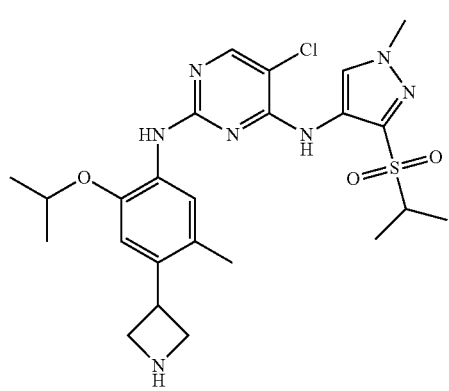
4
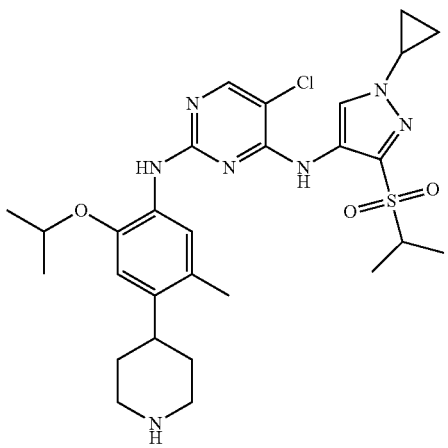
5
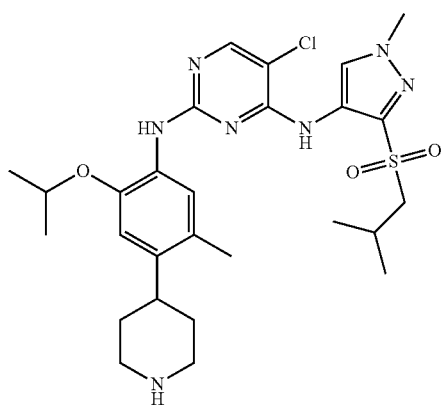
6
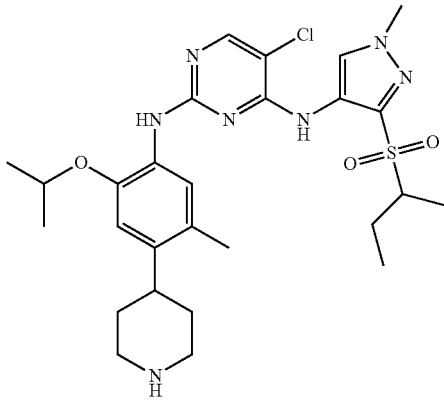
7
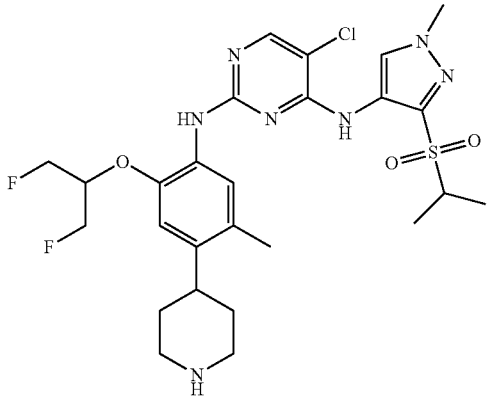
8

9
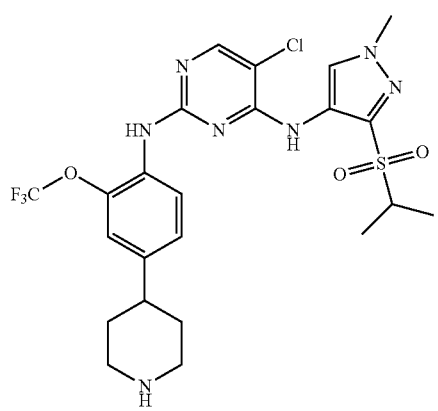
10
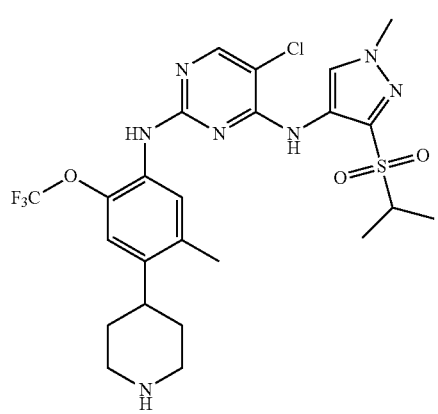
11
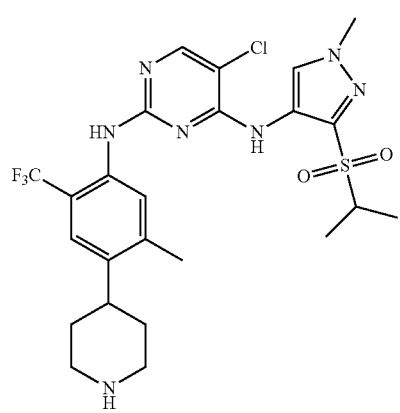
12
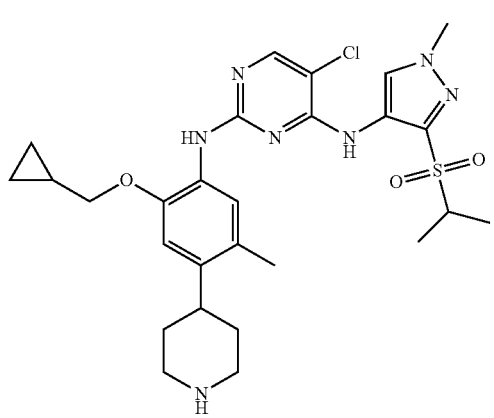
13
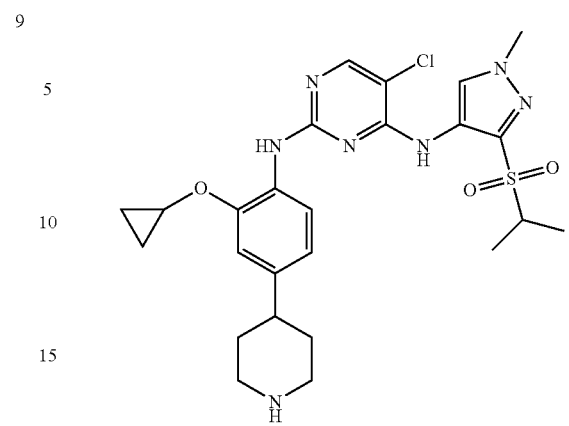
14
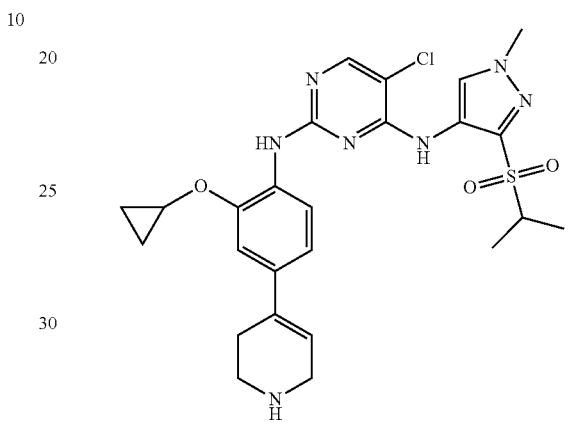
15
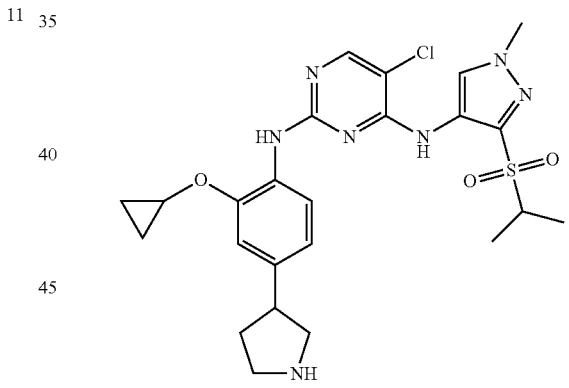
16
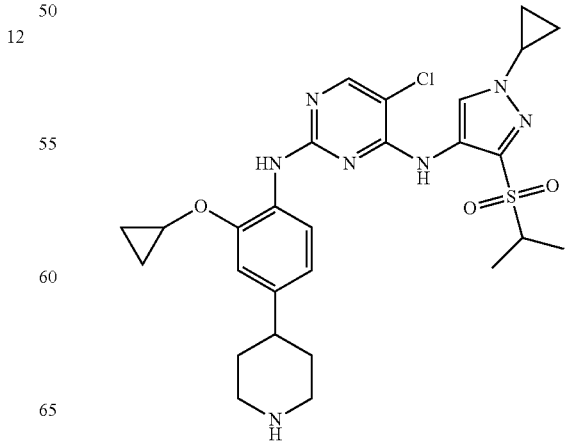

17
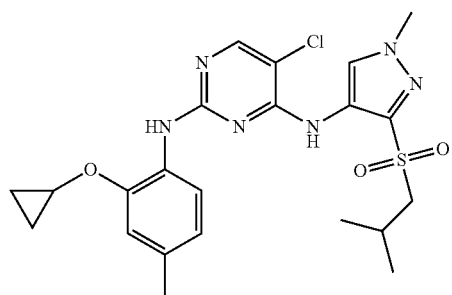
18
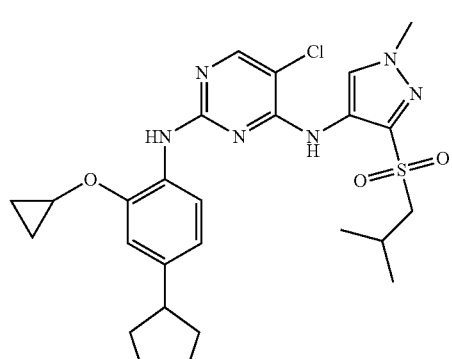
19
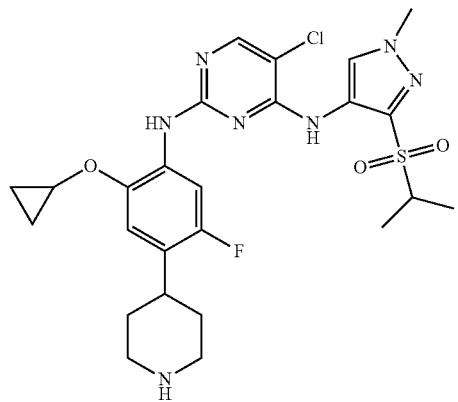
20
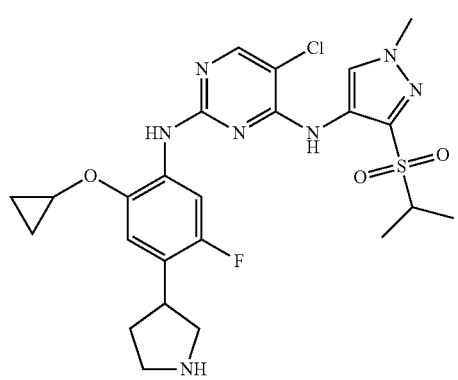
21
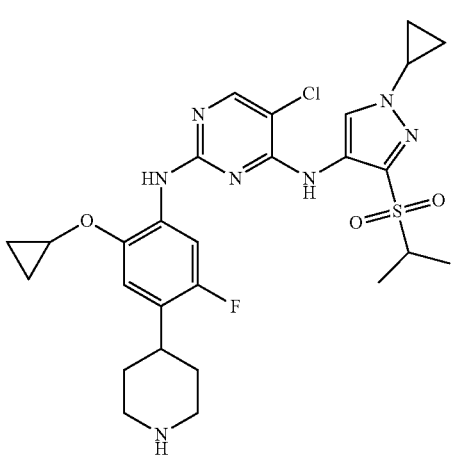
22
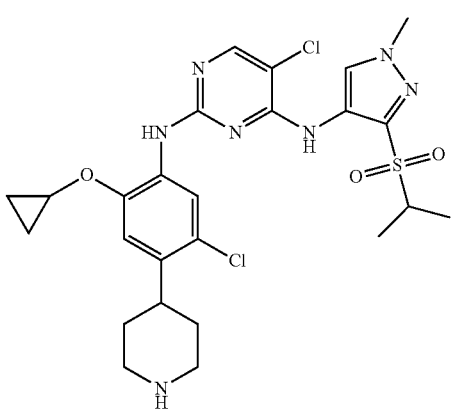
23
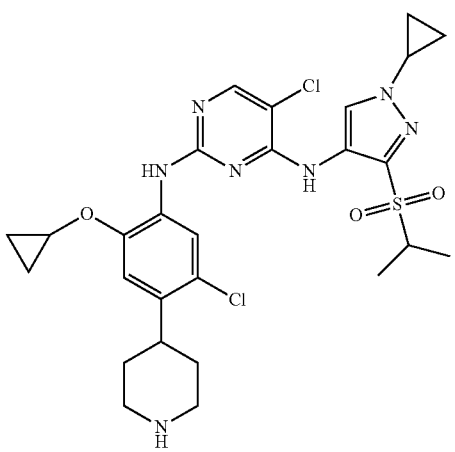

24
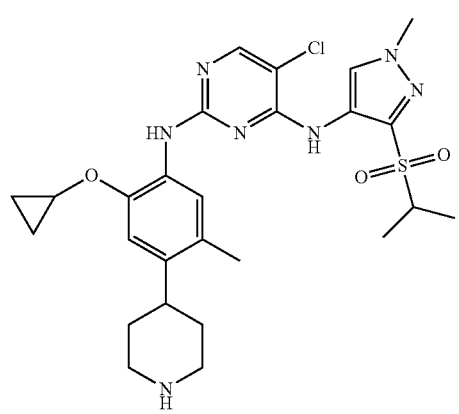
25
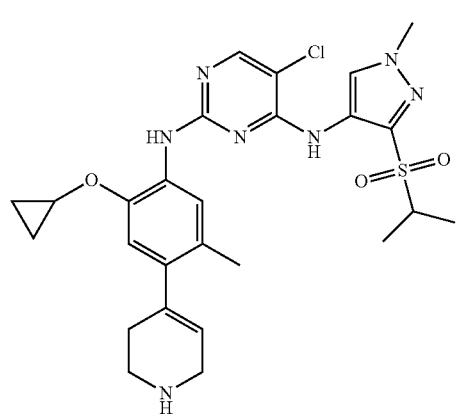
26
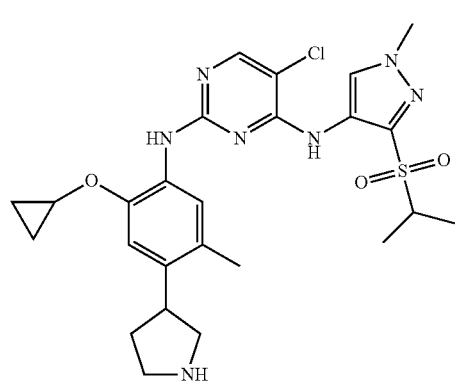
27
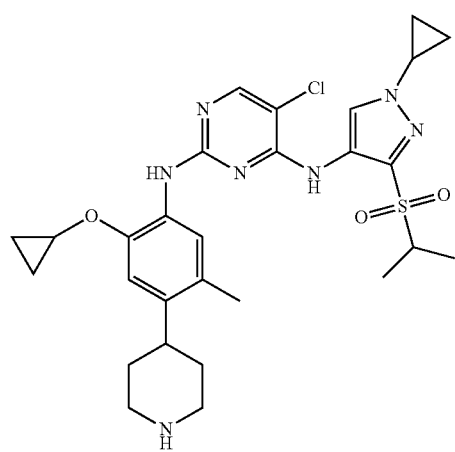
28
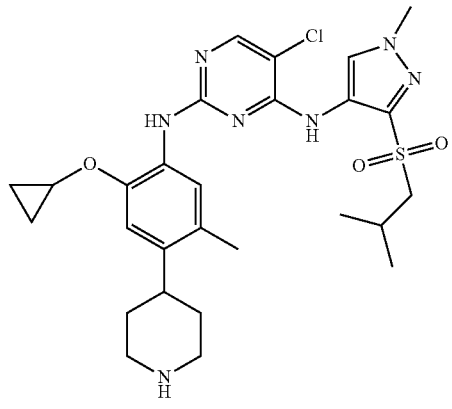
29
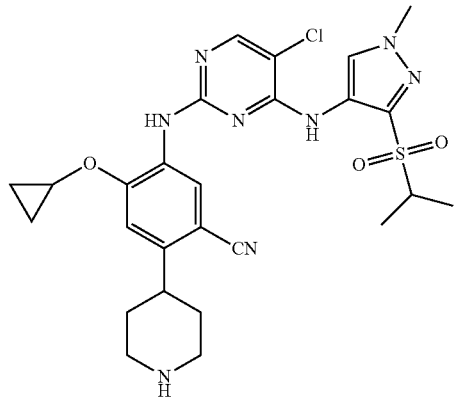
30
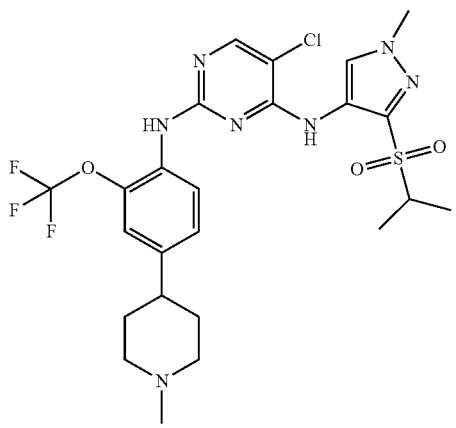
31
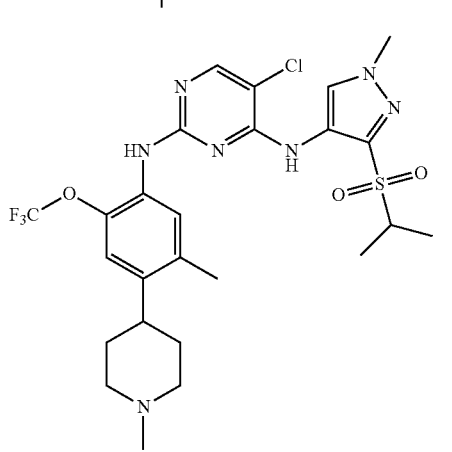

32
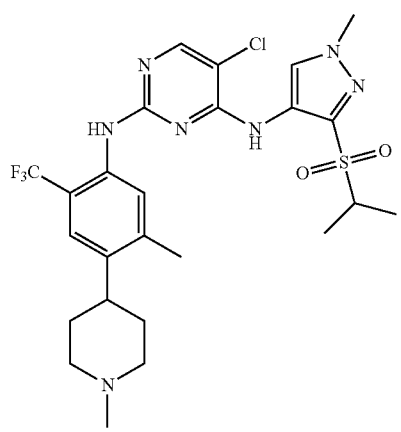
35
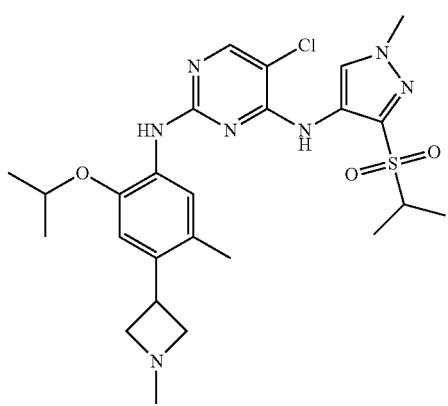
33
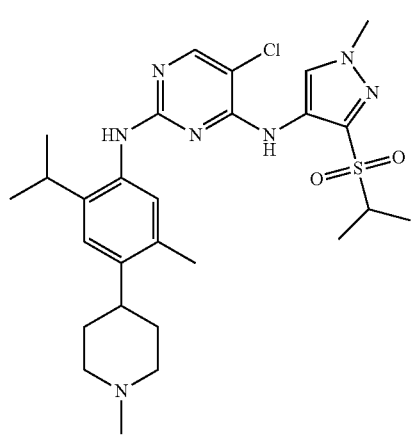
36
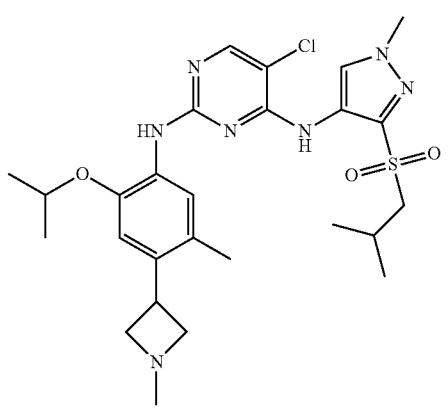
34
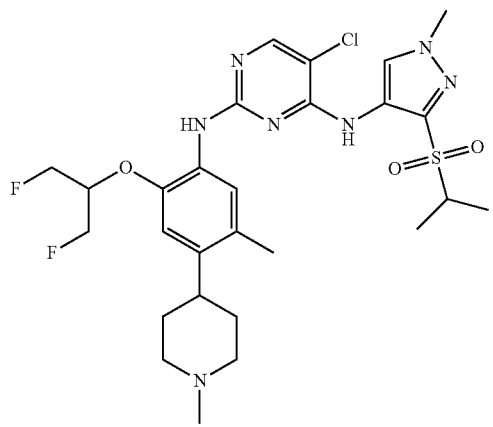
37
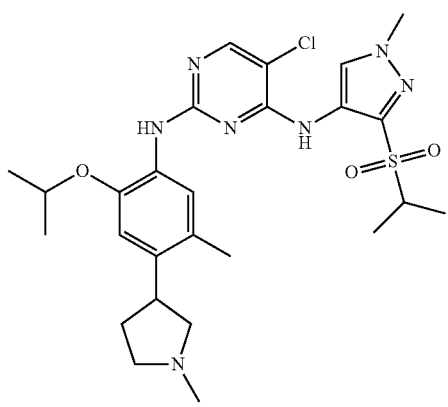

99
-continued
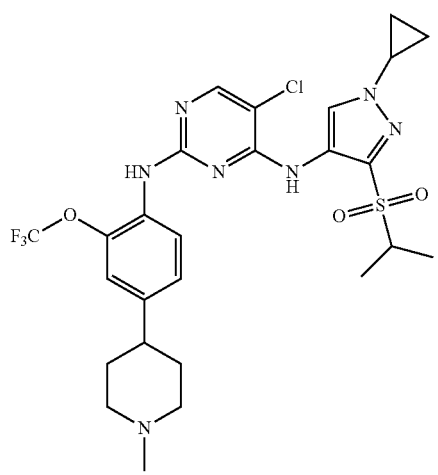
38
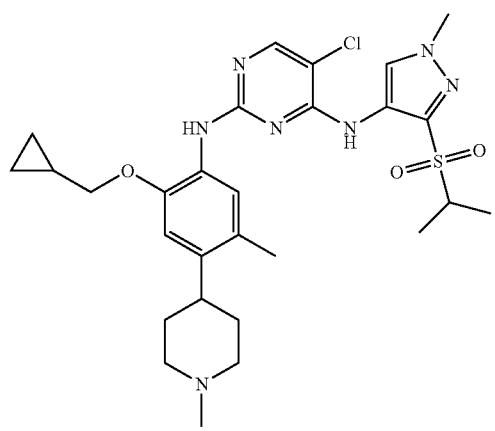
39
100
-continued
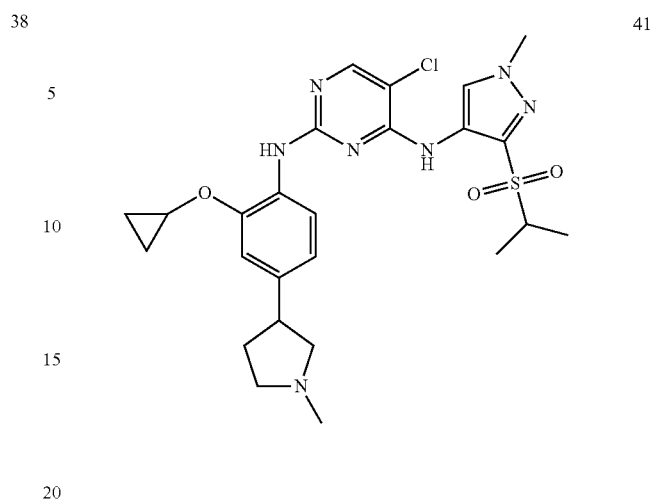
41
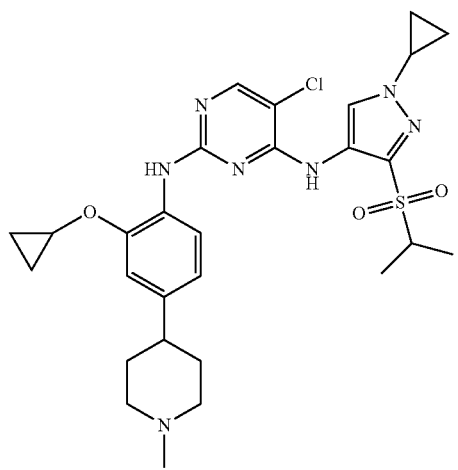
42
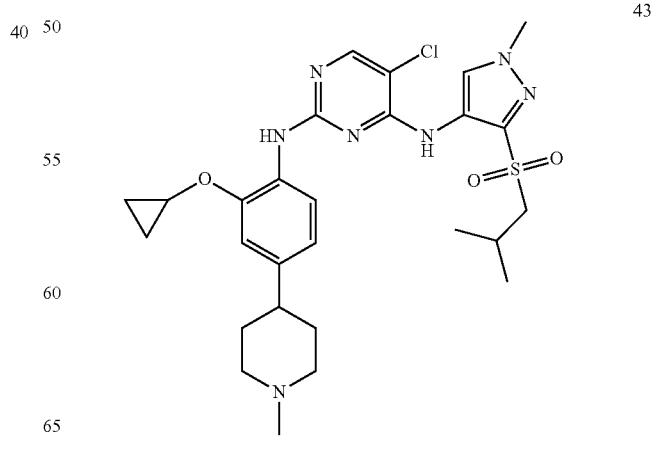
43

44
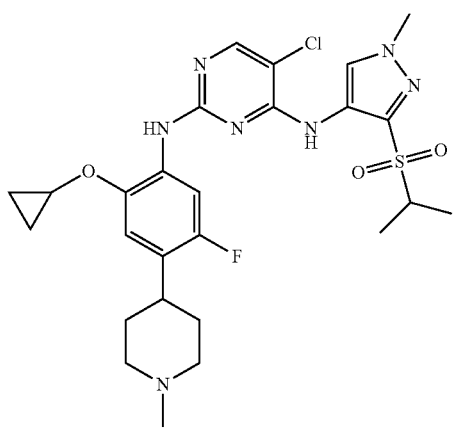
45
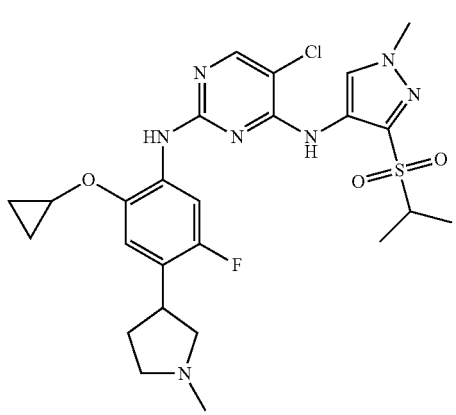
46
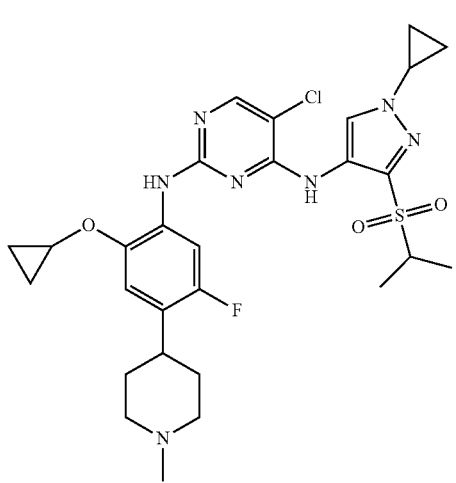
47
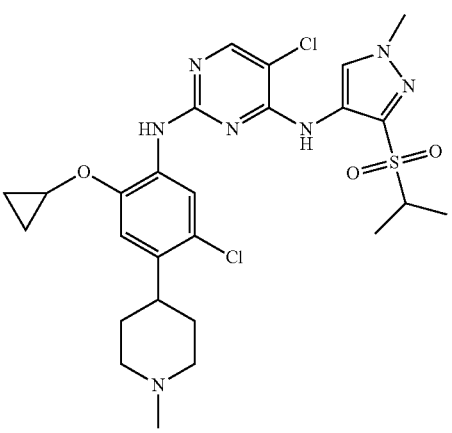
48
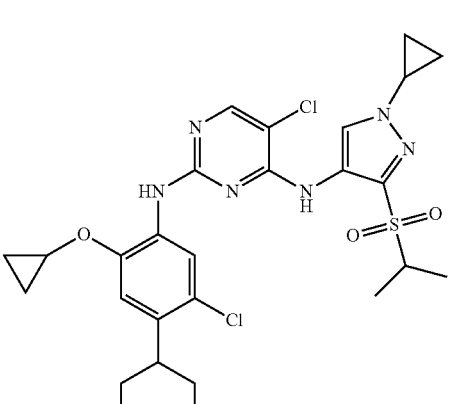
49
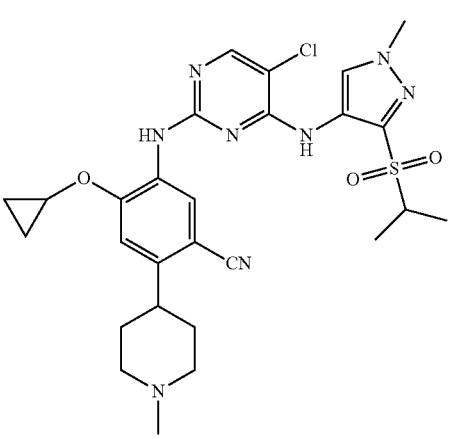

50
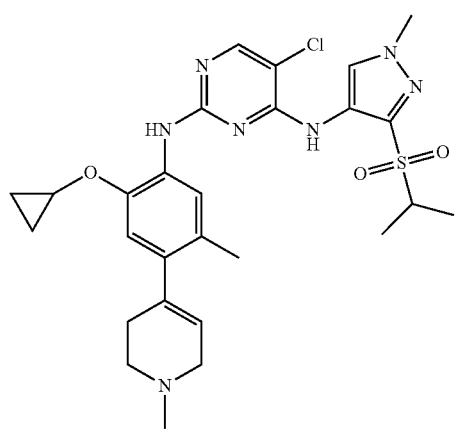
51
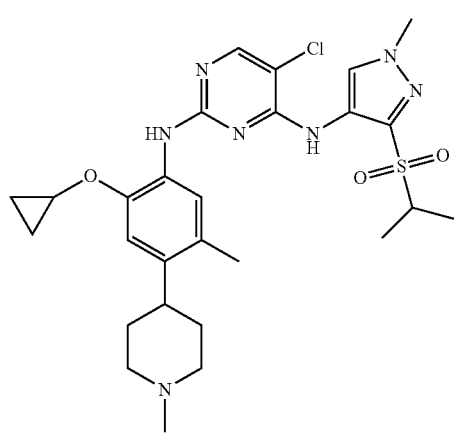
52
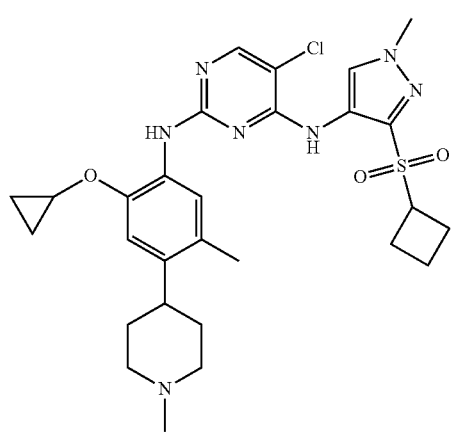
53
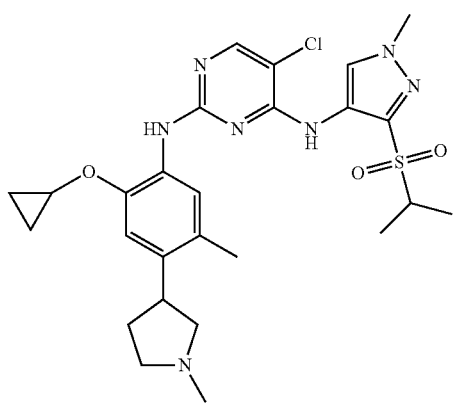
54
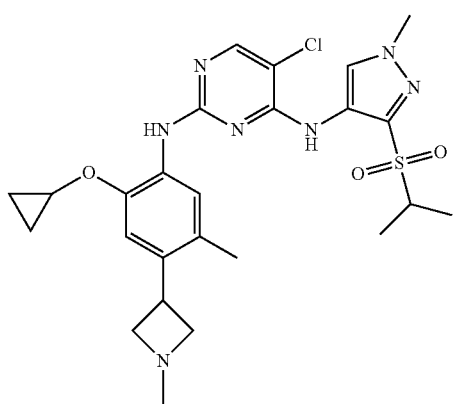
55
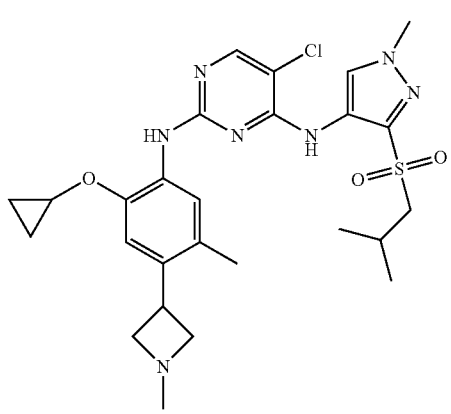

56
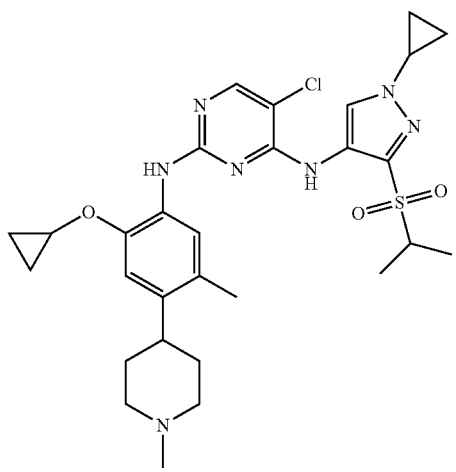
57
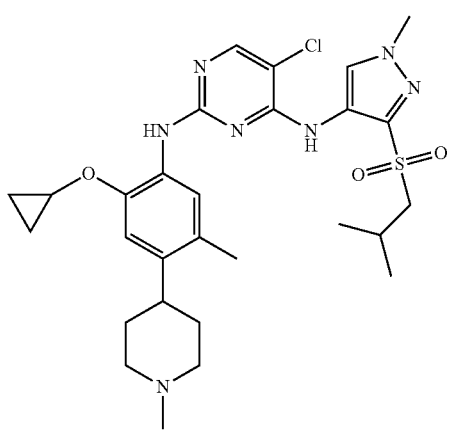
58
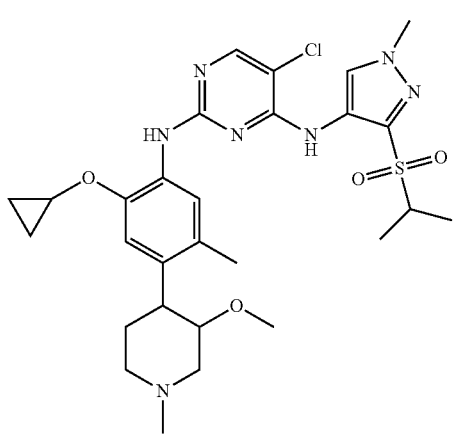
59
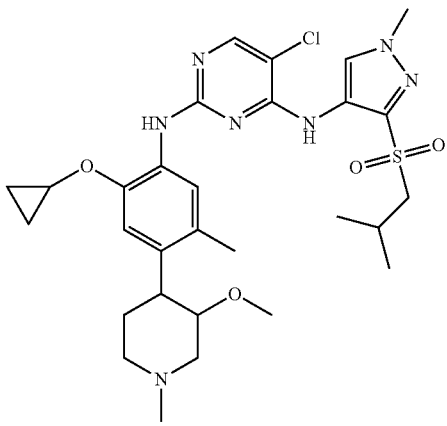
60
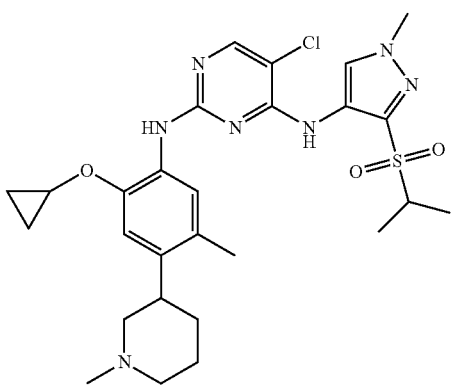
61
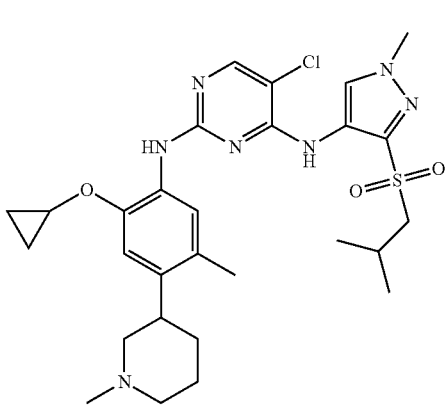
62
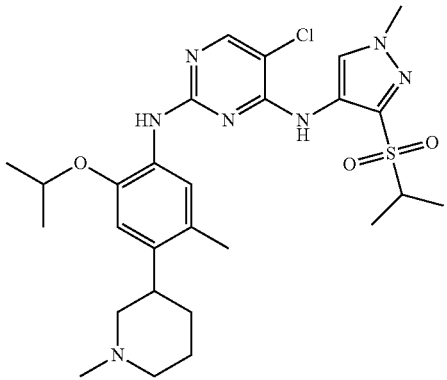

63
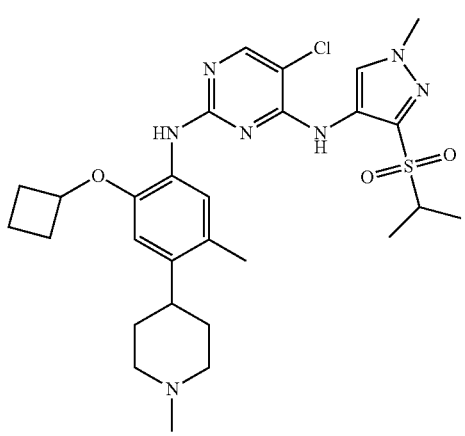
64
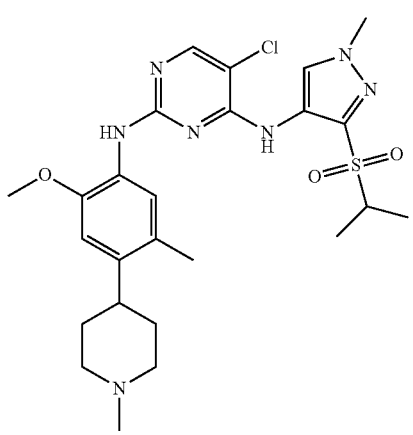
65
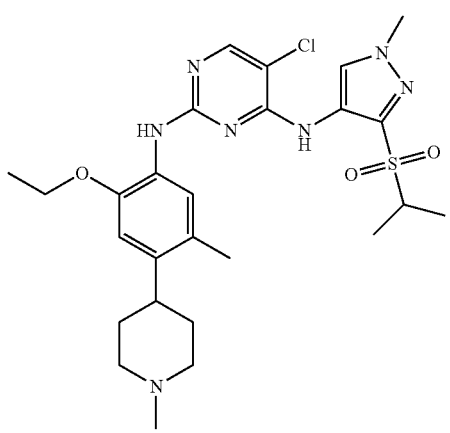
66
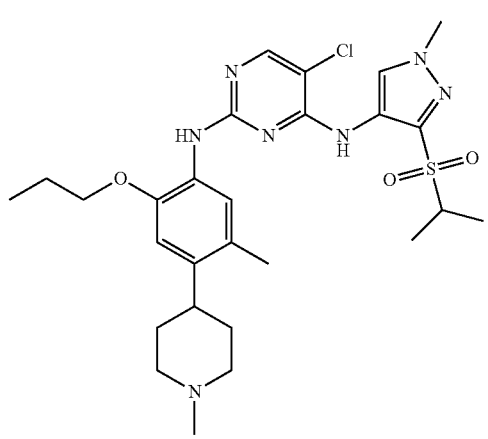
67
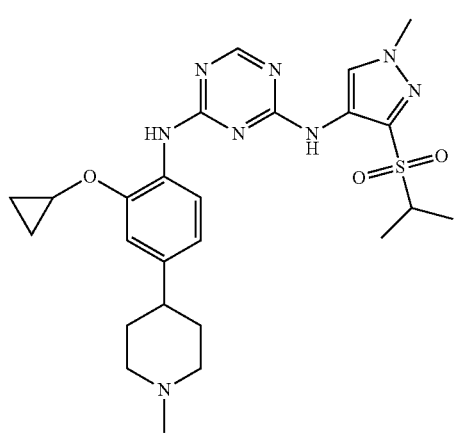
68
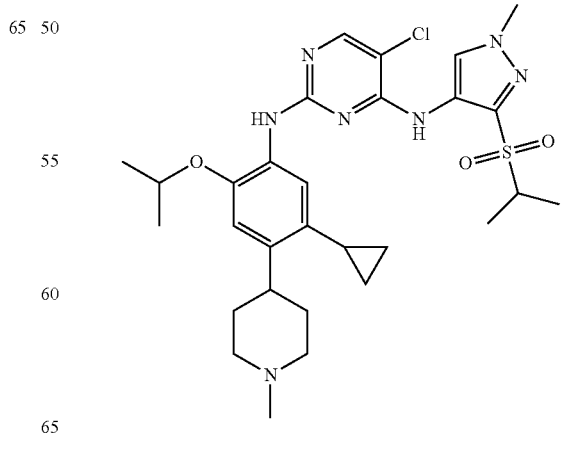

69
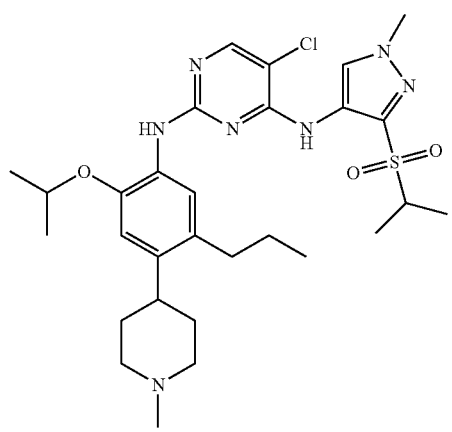
70
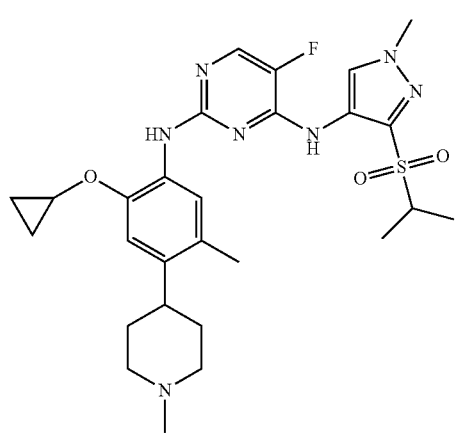
71
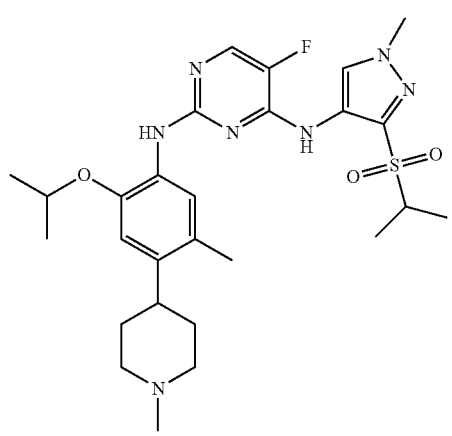
72
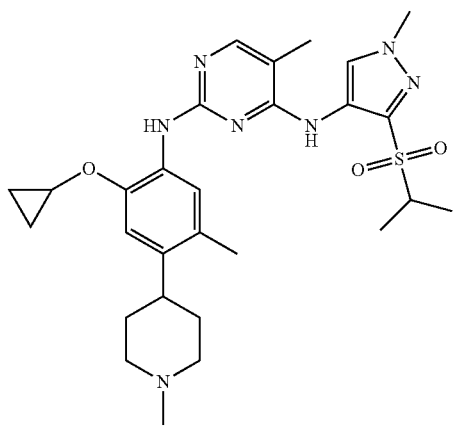
73
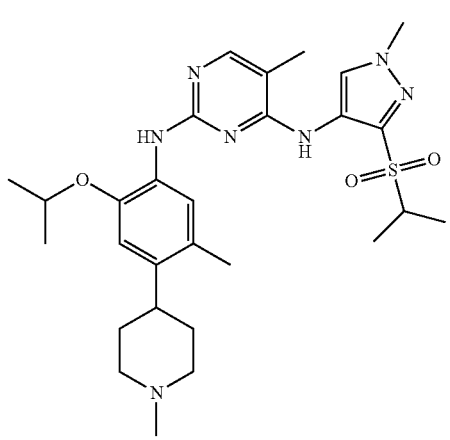
74
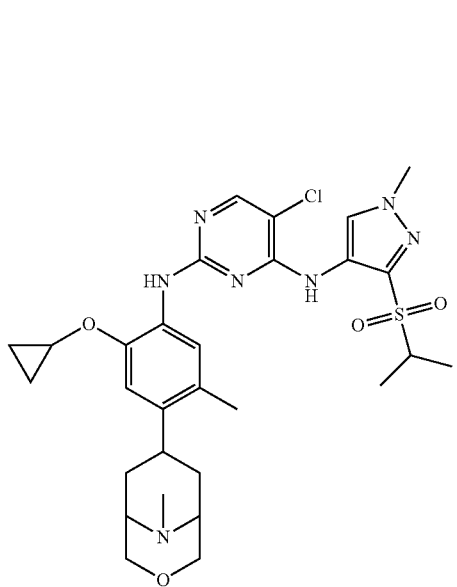

75
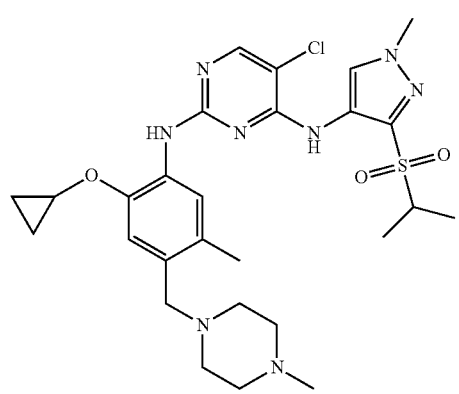
76
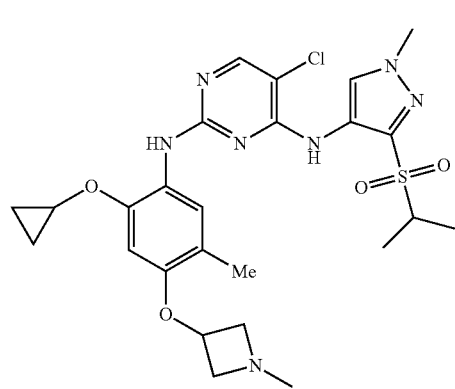
77
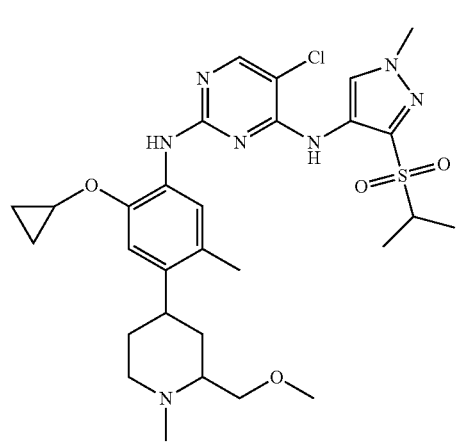
78
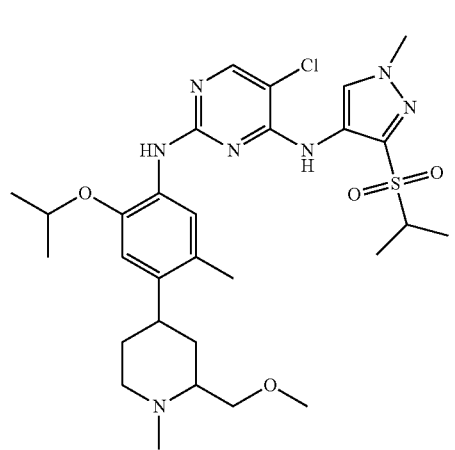
79
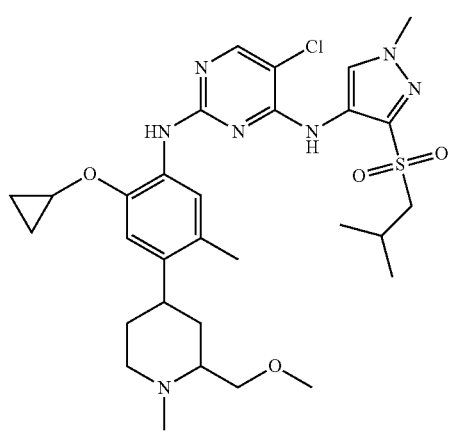
80
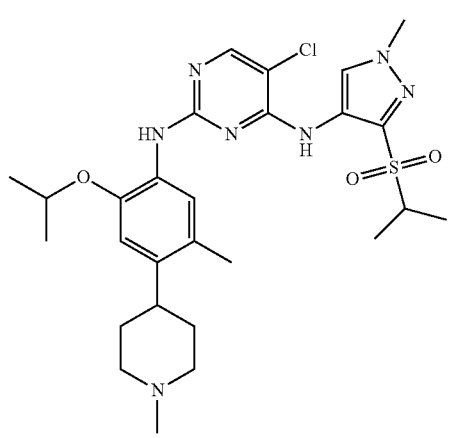
81
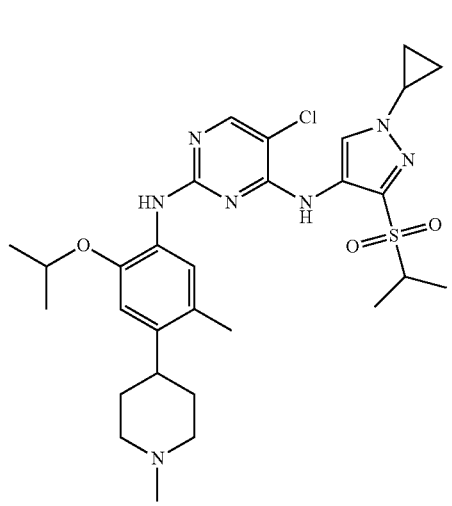

82
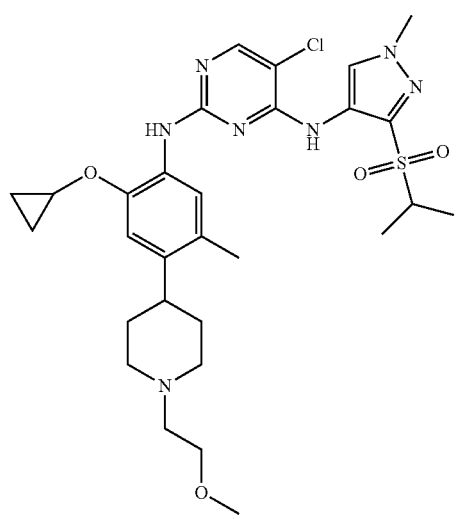
83
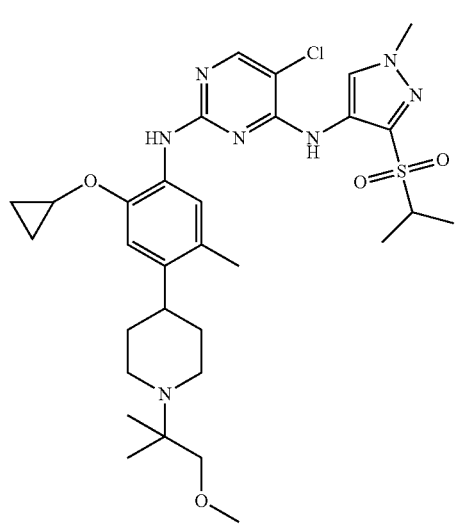
85
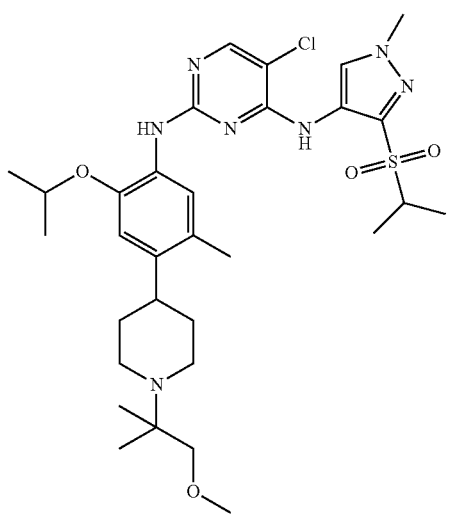
86
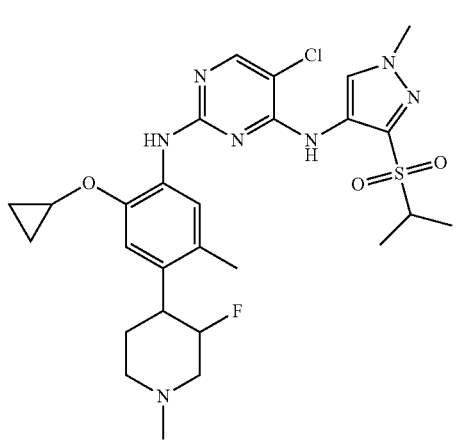
87

88
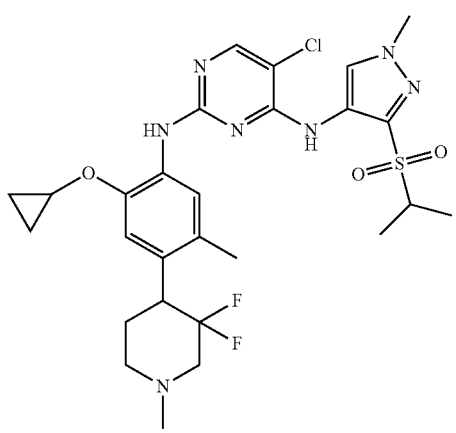
89
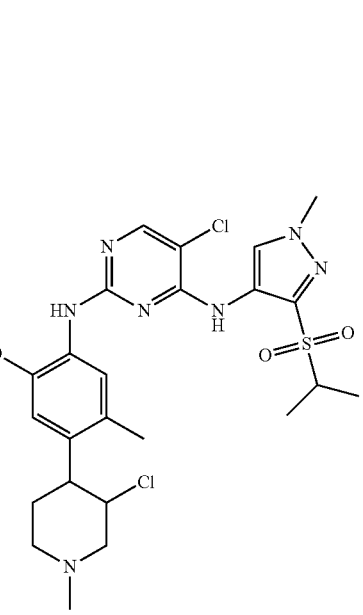
90
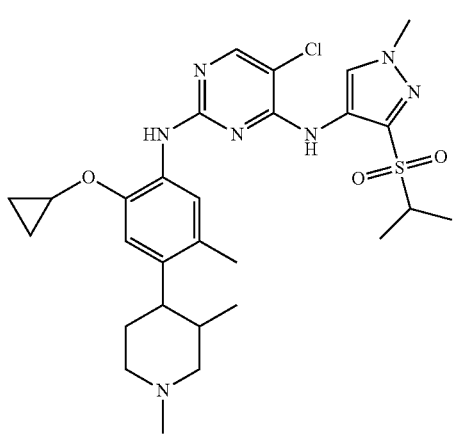
91
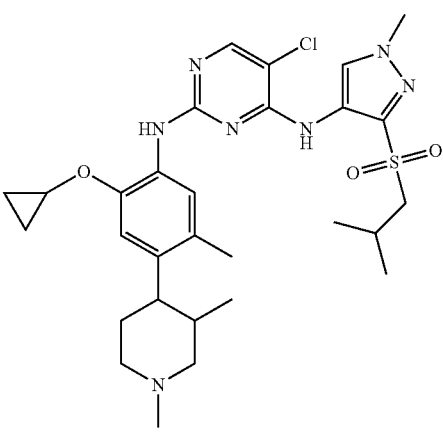
92
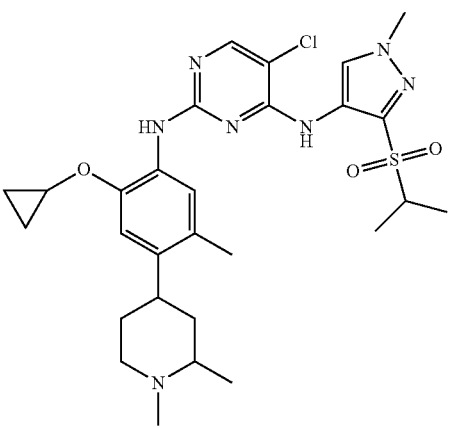
93

94
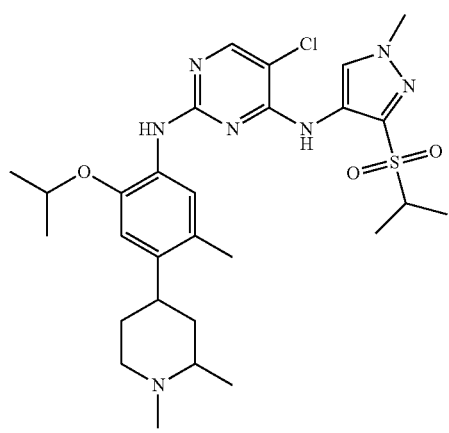
95
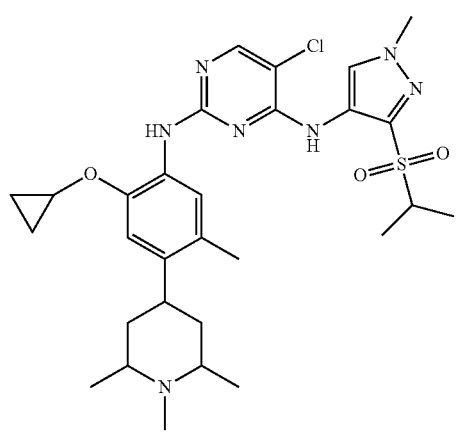
96
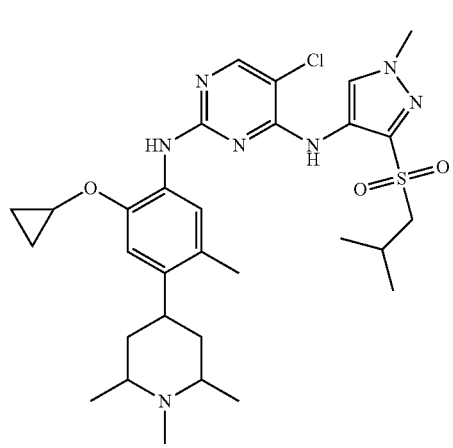
97
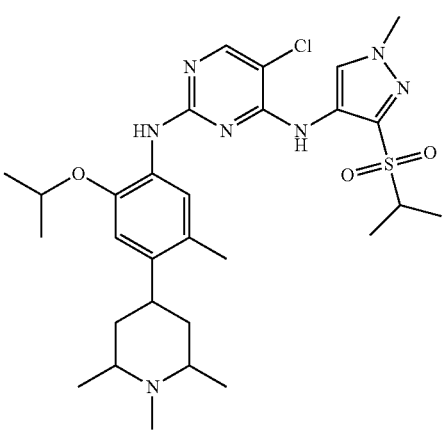
98
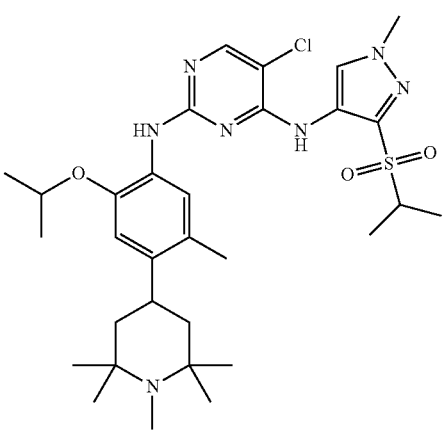
99
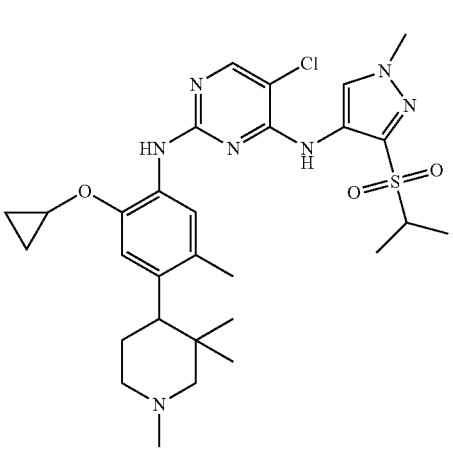

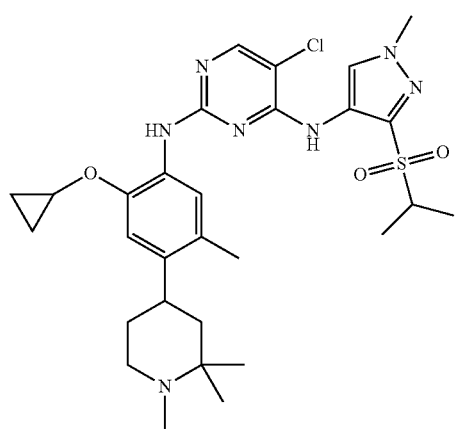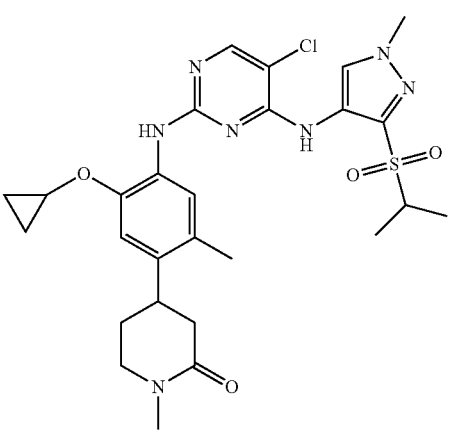

106
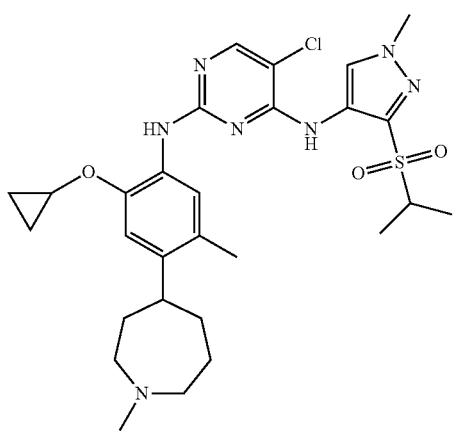
107
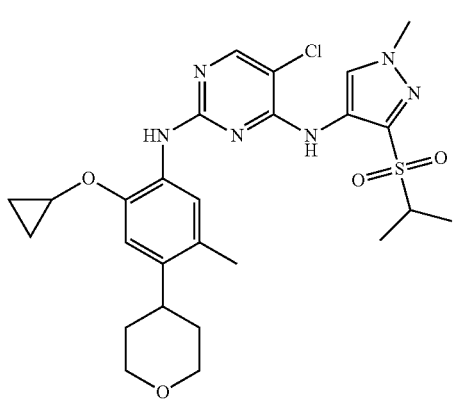
108
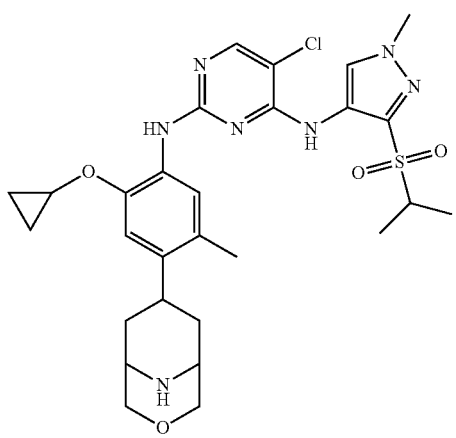
109
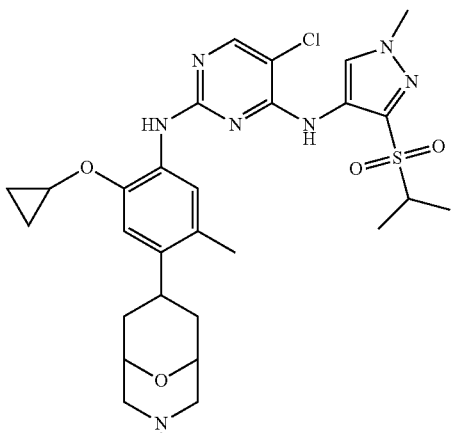
110
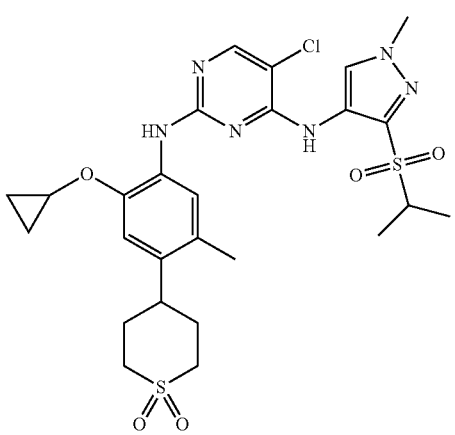
111
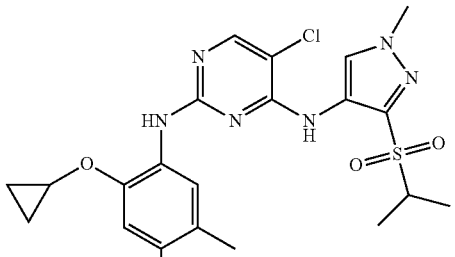
112
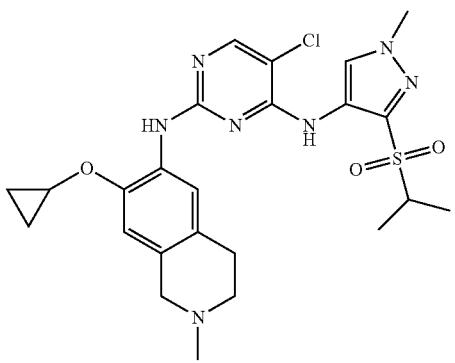

113
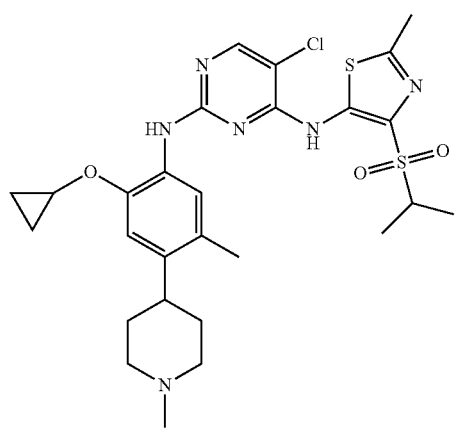
114
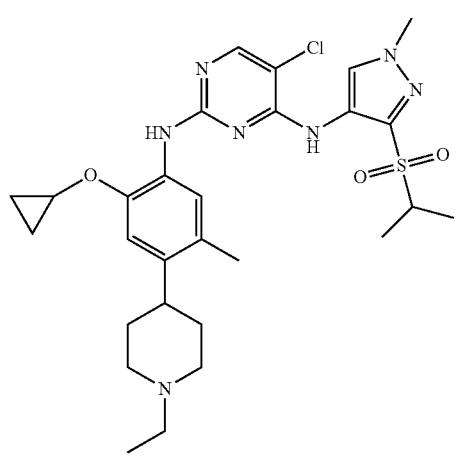
115
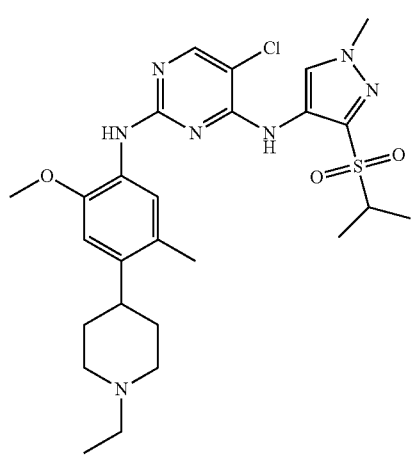
116
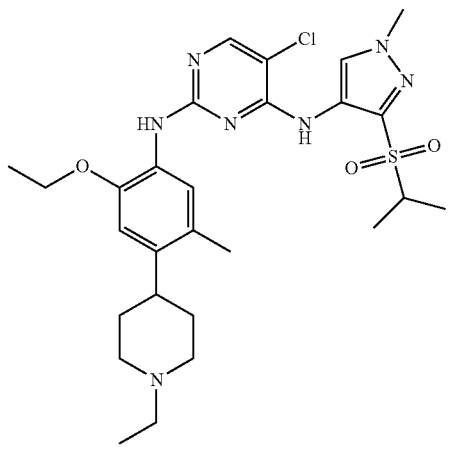
117
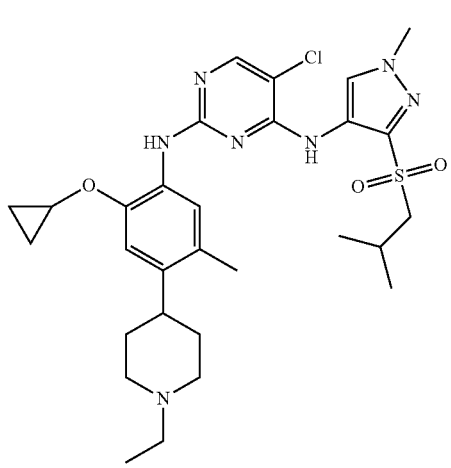
118
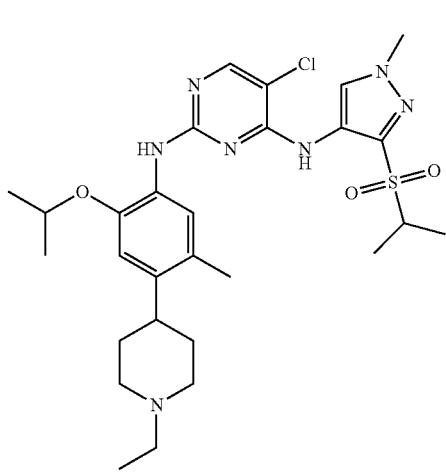

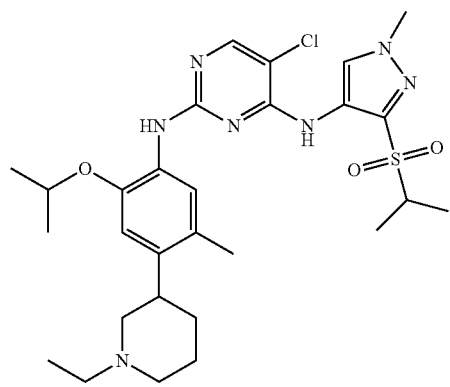
119
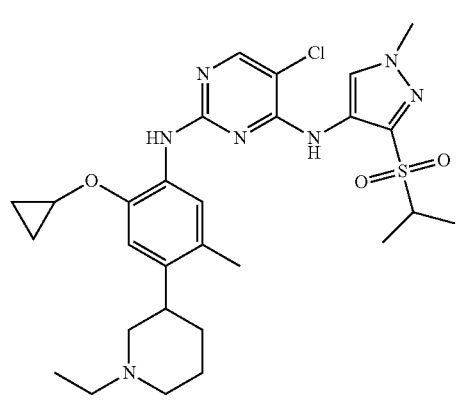
120
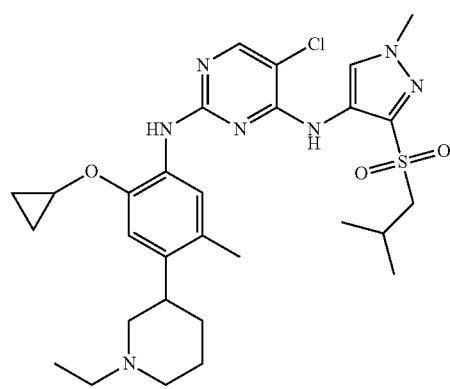
121
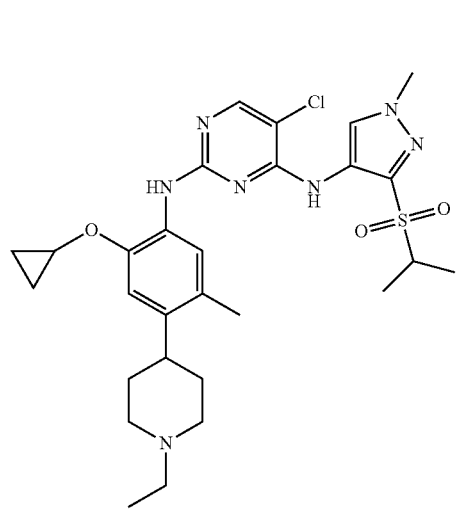
122
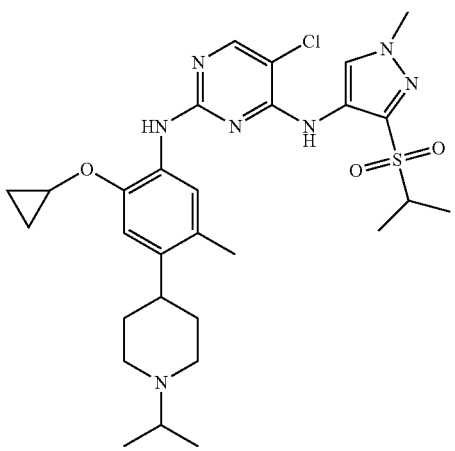
123
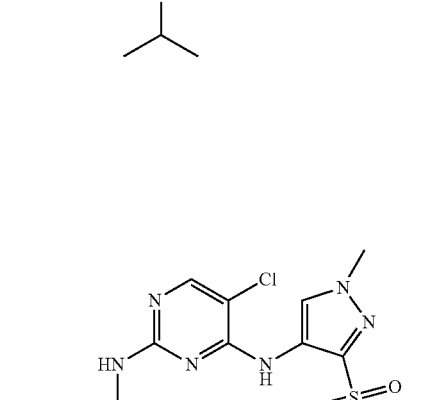
124
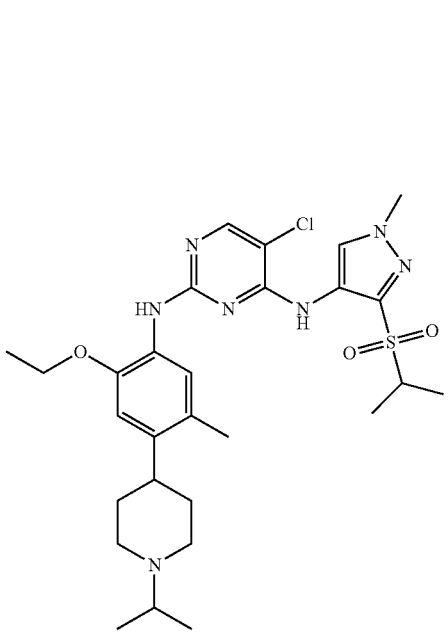
125

-continued
126
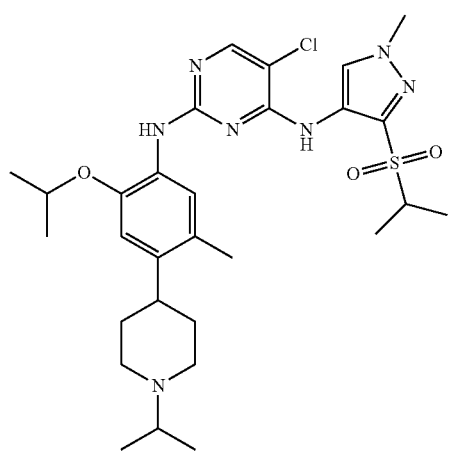
127
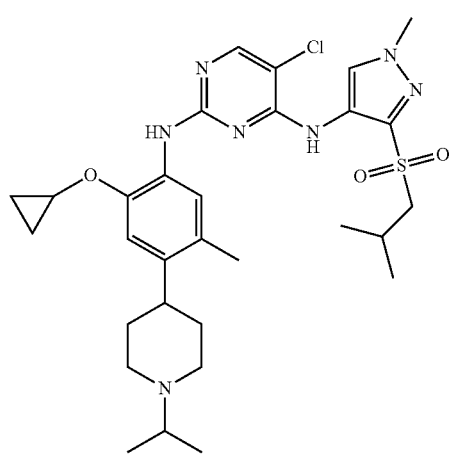
128
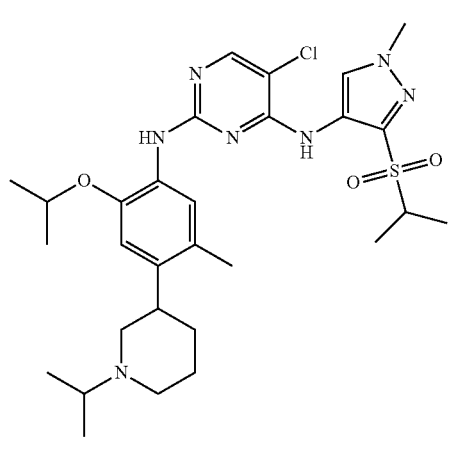
-continued
129
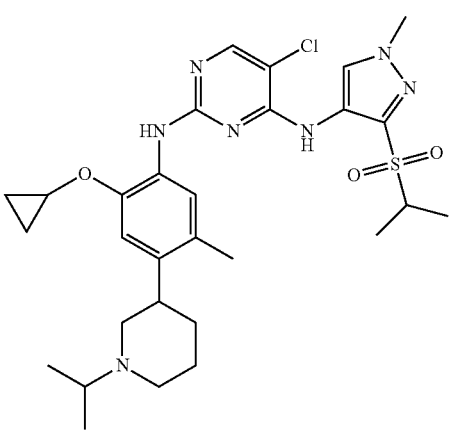
130
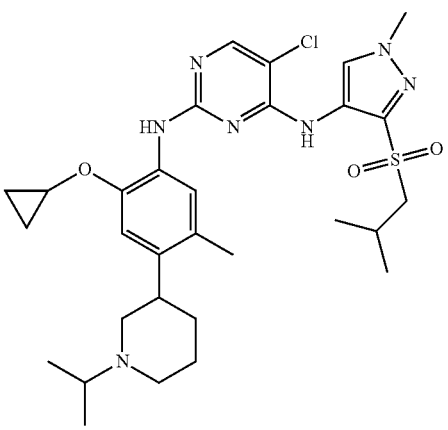
131
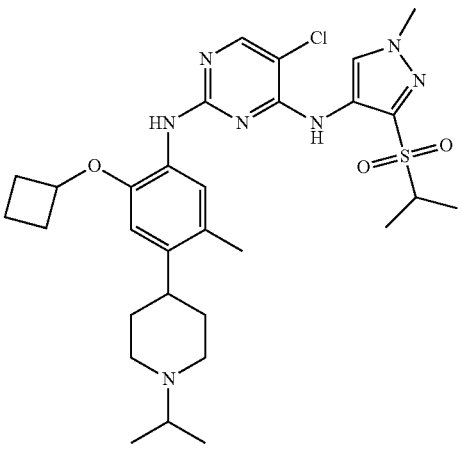

129
-continued
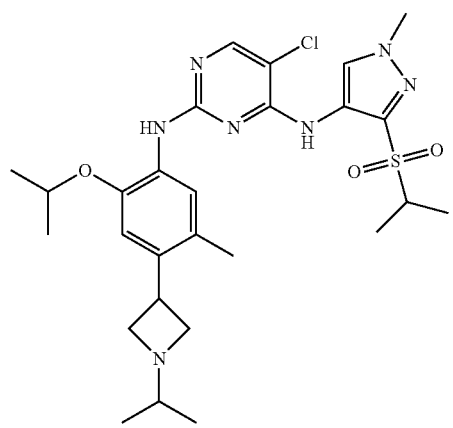
132
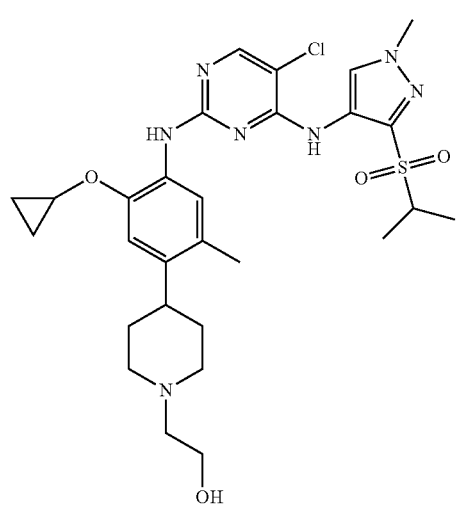
133
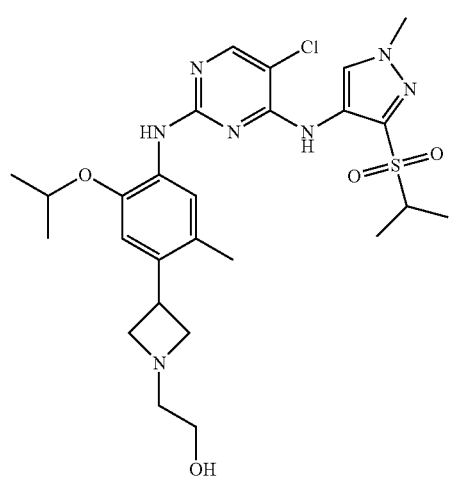
134
130
-continued
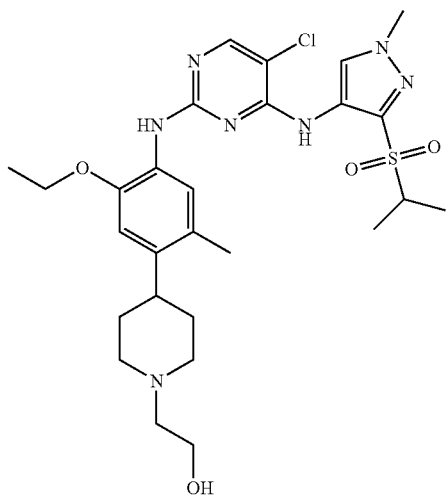
135
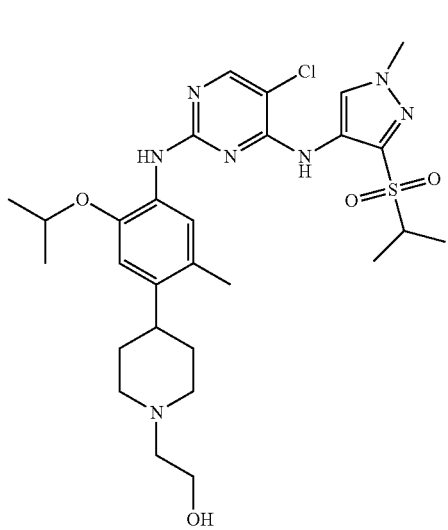
136
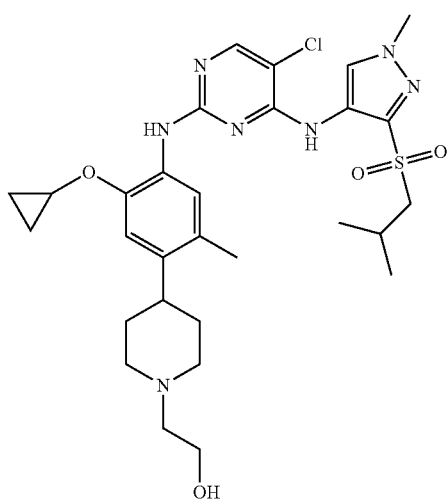
137

138 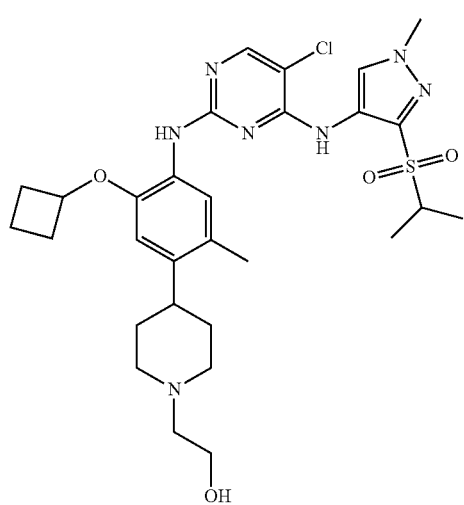
139 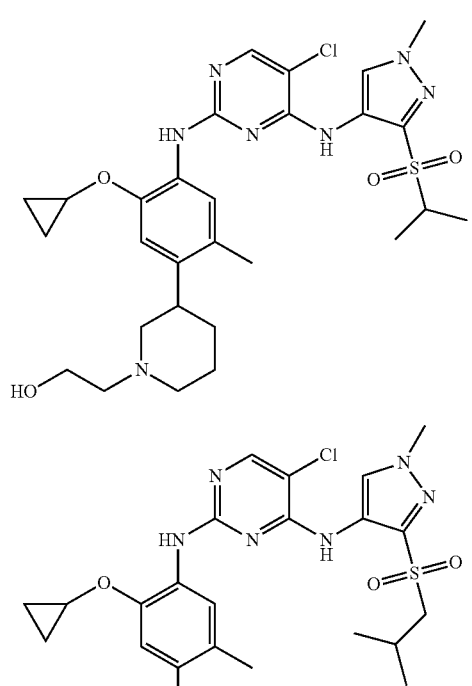
140 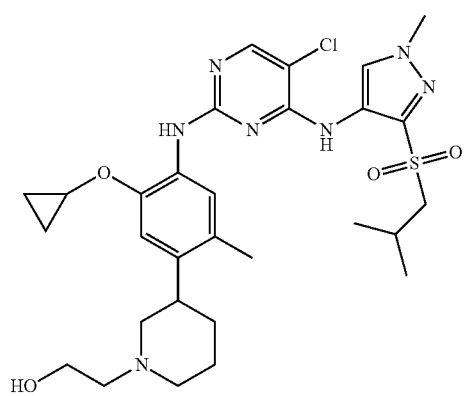
141 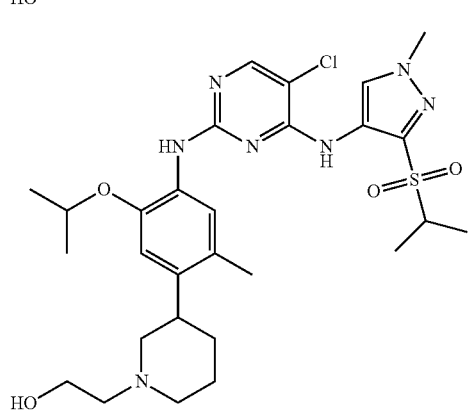
142 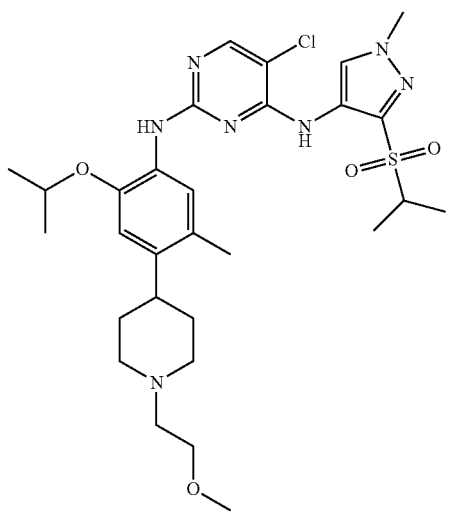
143 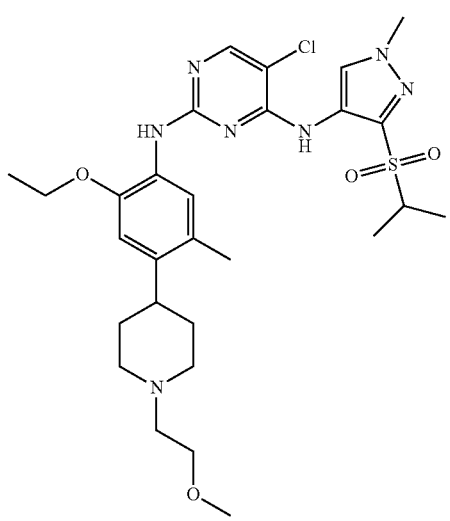
144 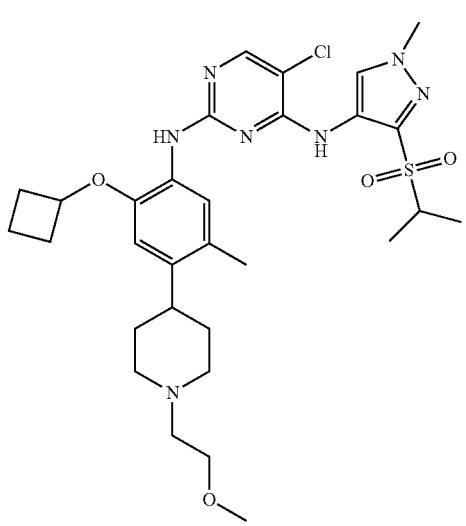

133
-continued
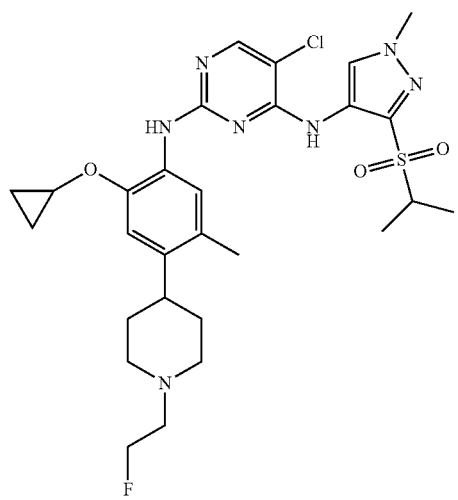
145
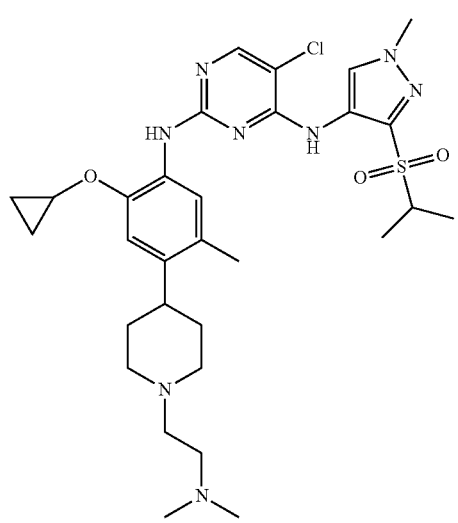
146
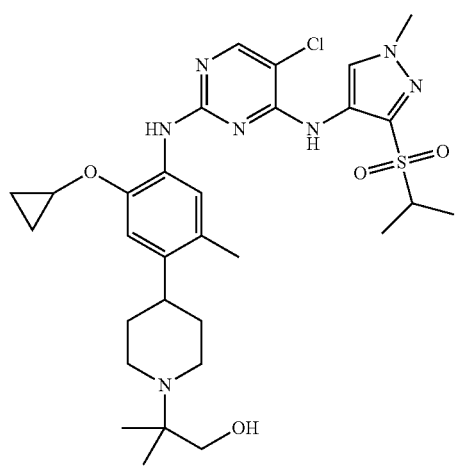
147
134
-continued
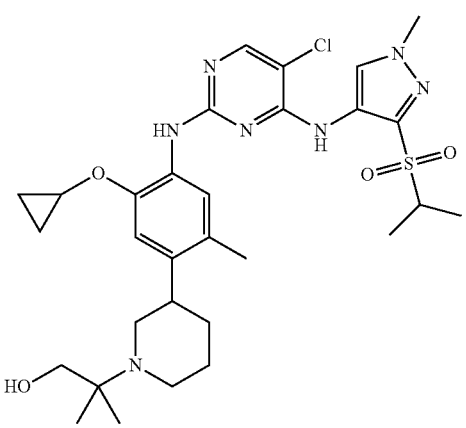
148
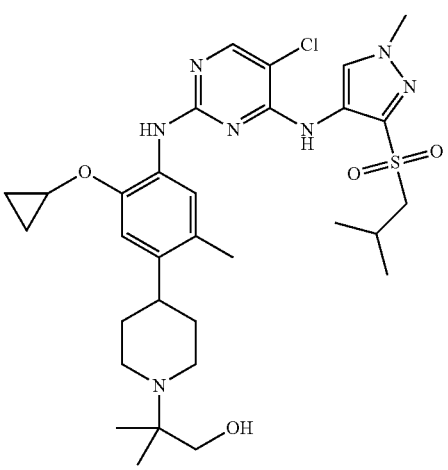
149
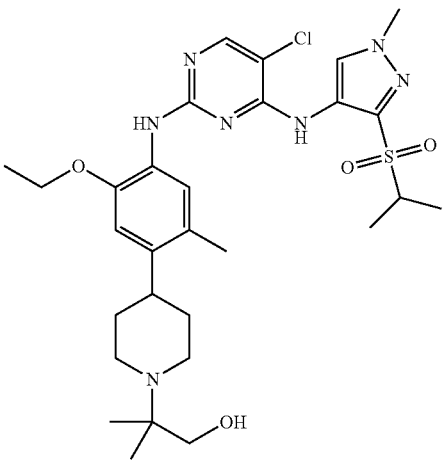
150

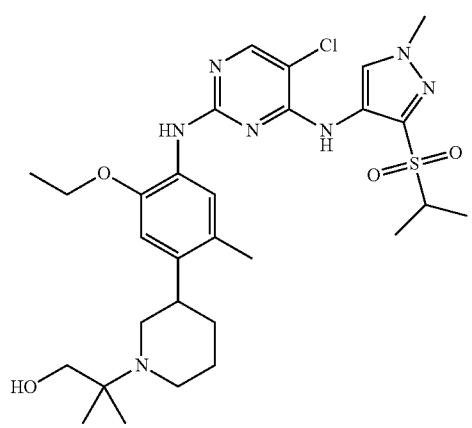
151
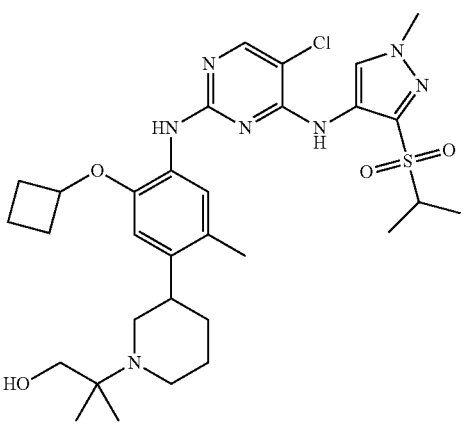
154
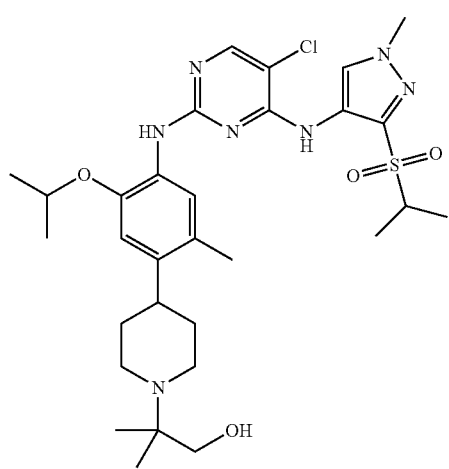
152
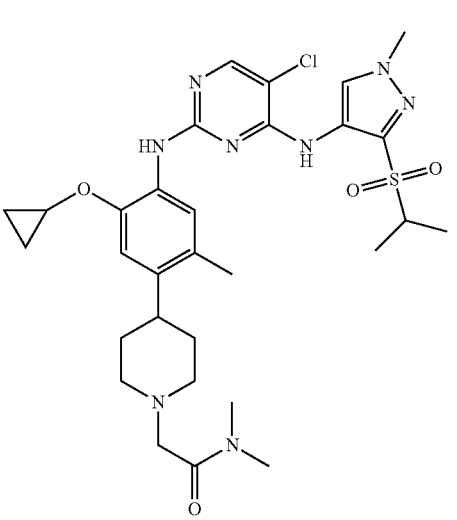
155
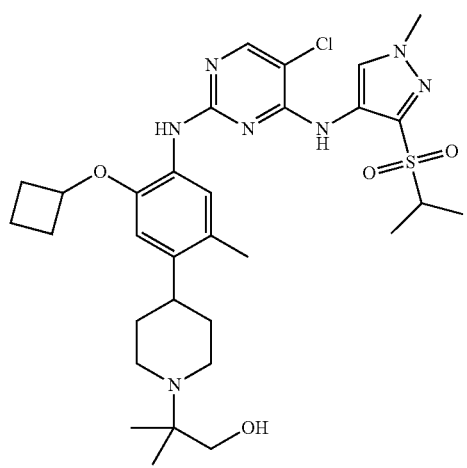
153
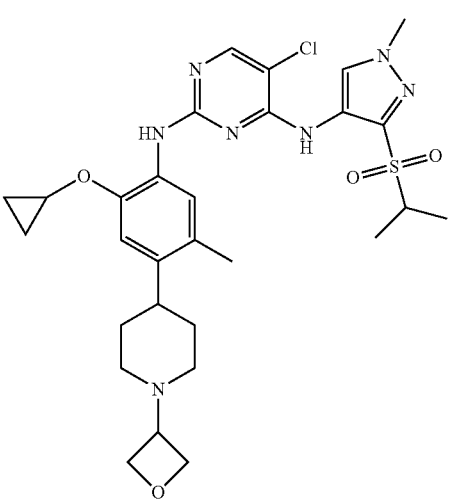
156

157
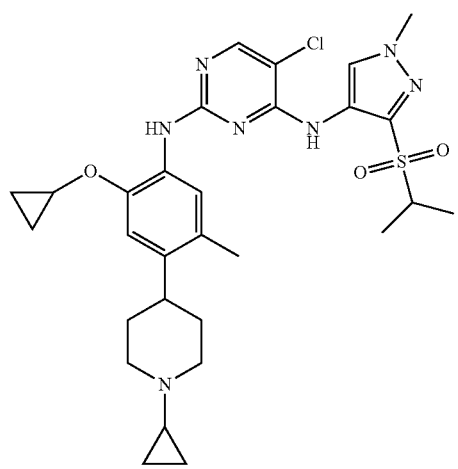
158
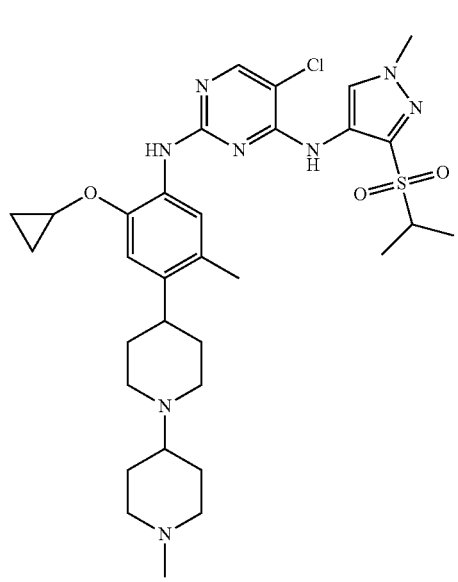
159
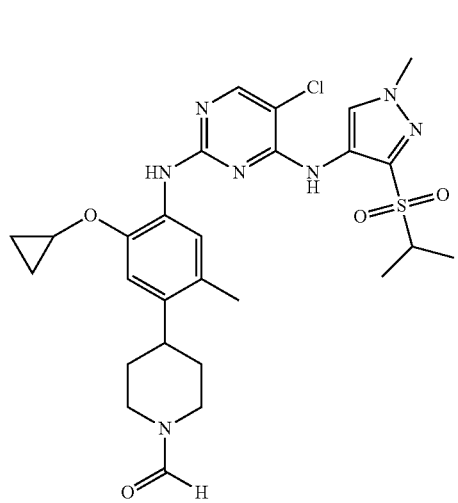
160
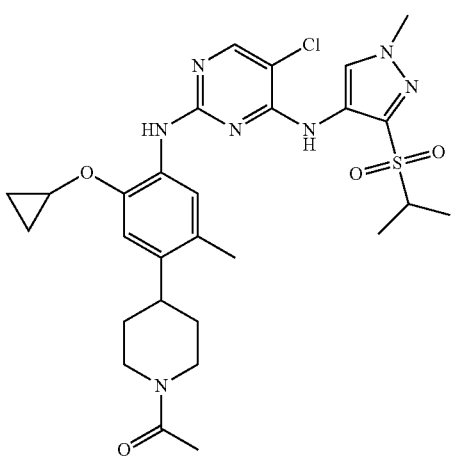
161
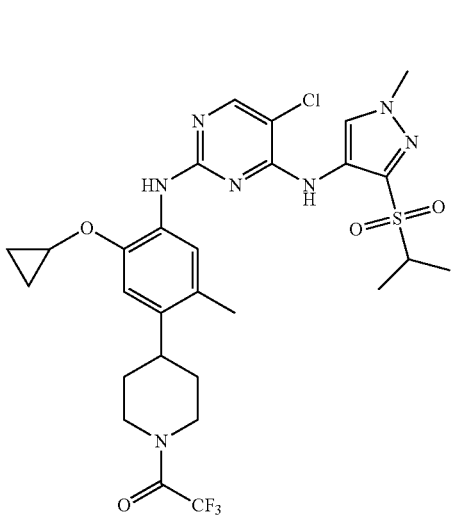
162
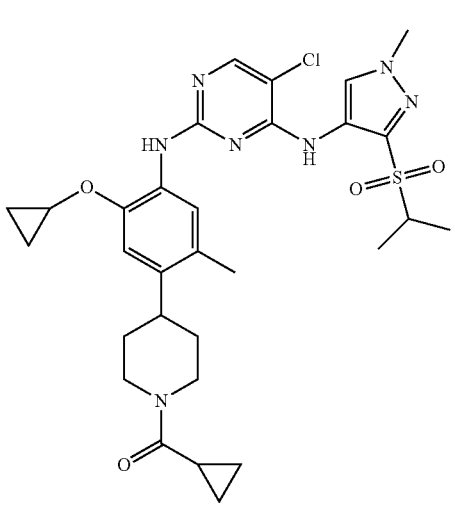

163
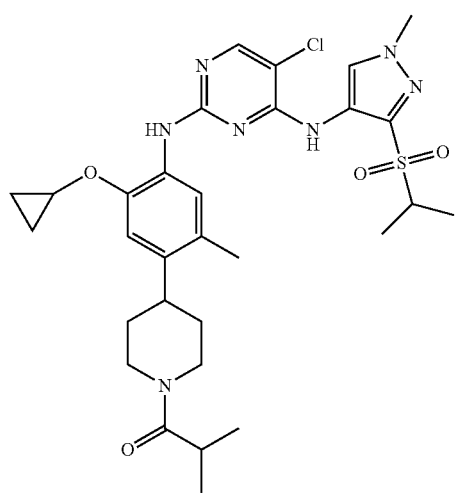
164
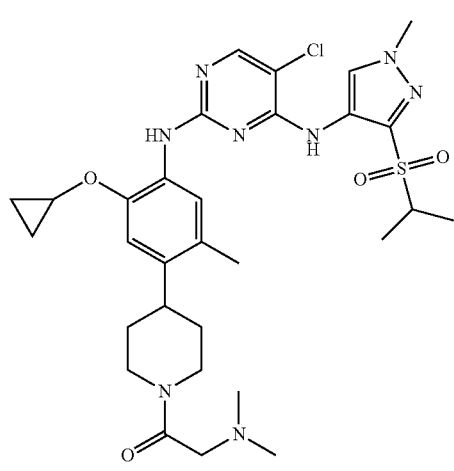
165
166
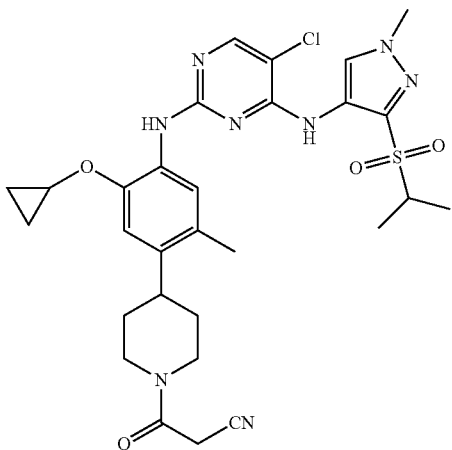
167
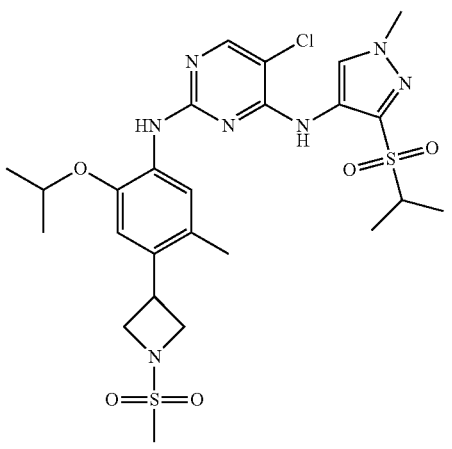
168

-continued
169
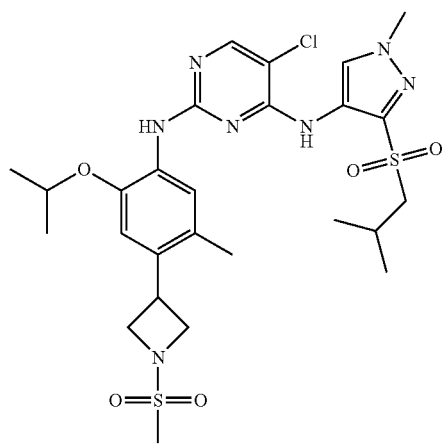
170
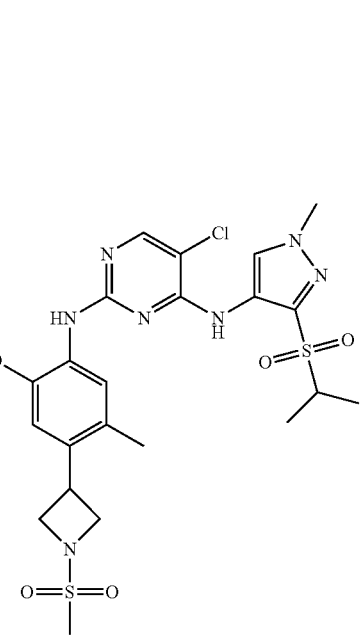
171
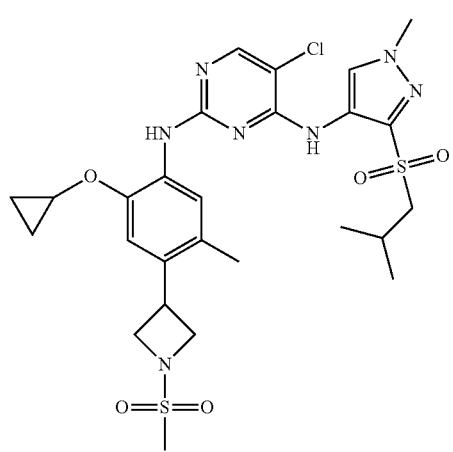
-continued
172
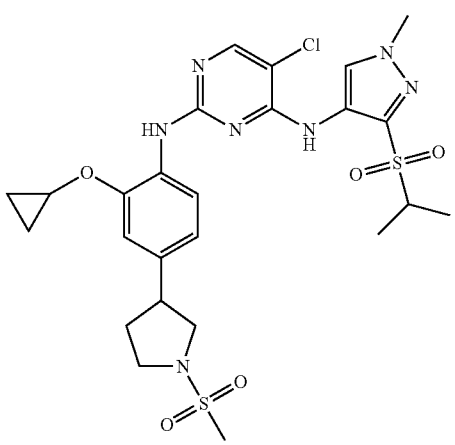
173
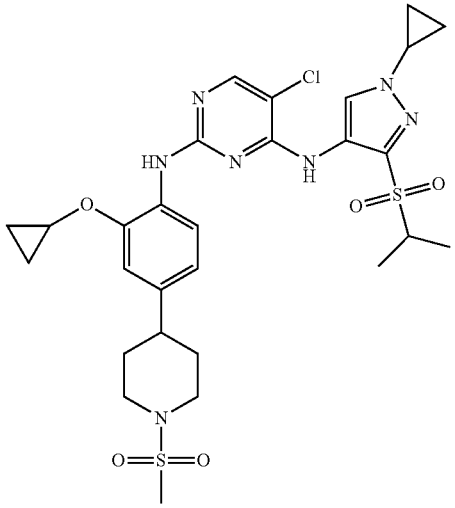
174
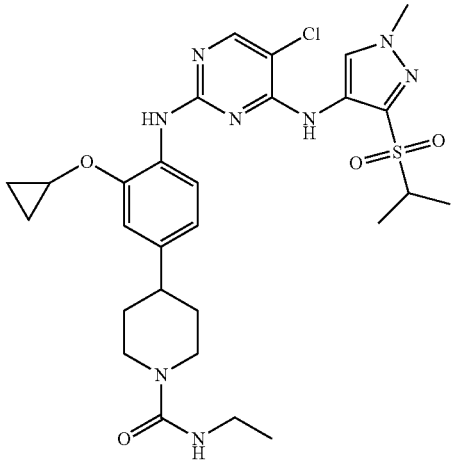

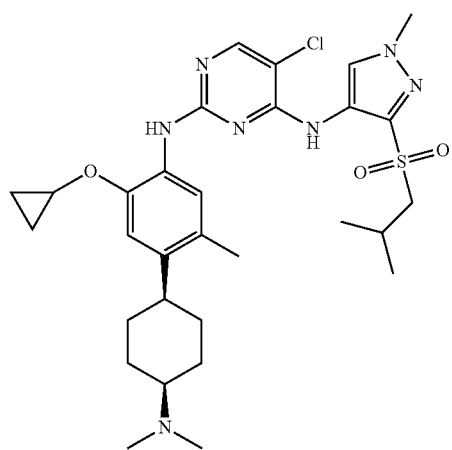
175
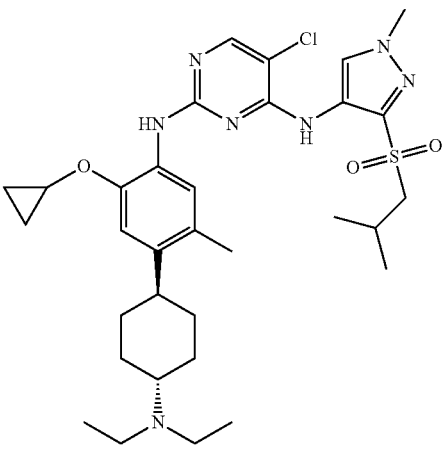
178
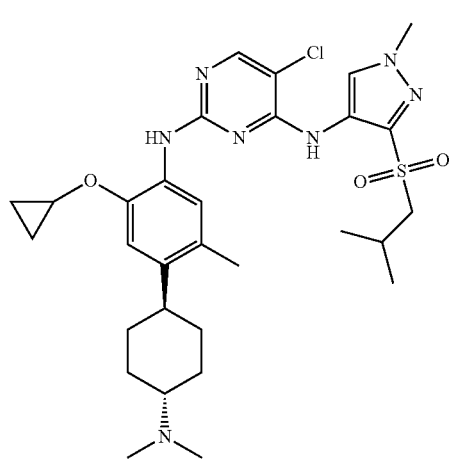
176
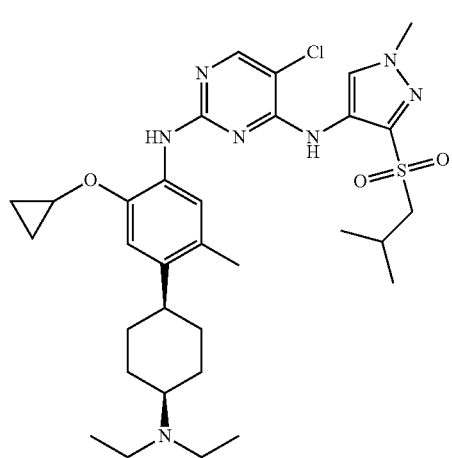
177
179
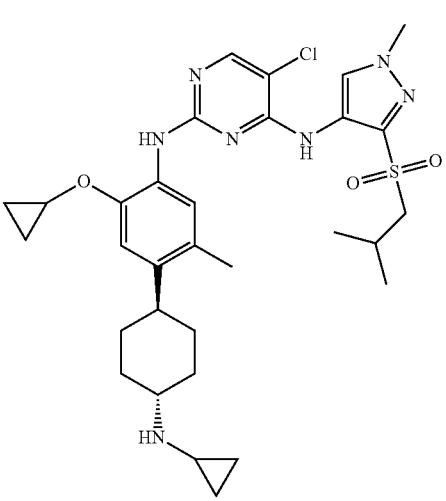
180

181
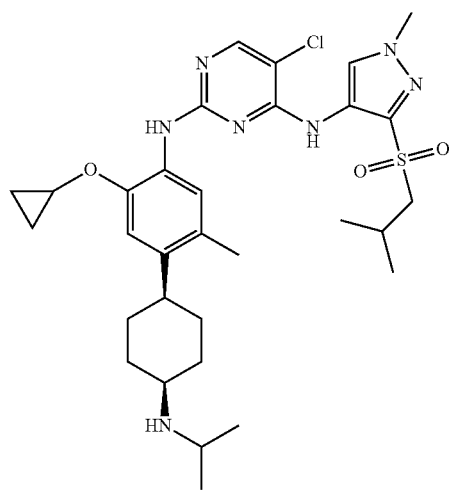
182
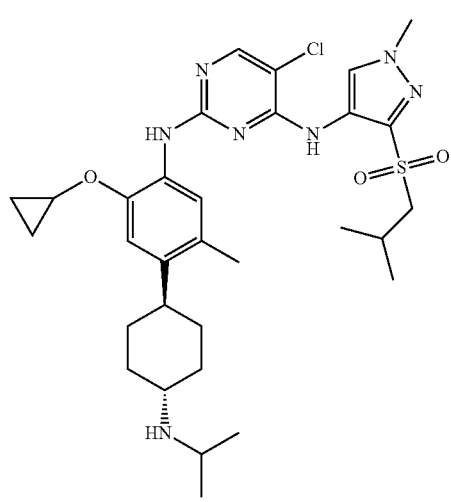
183
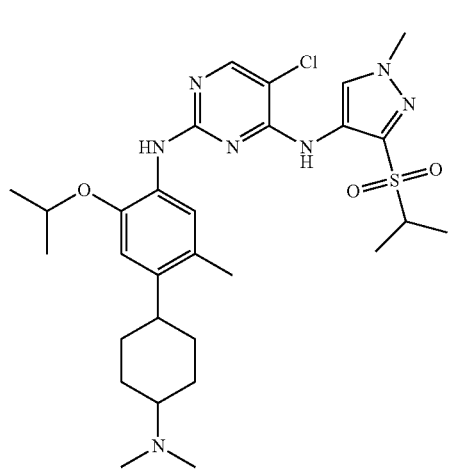
184
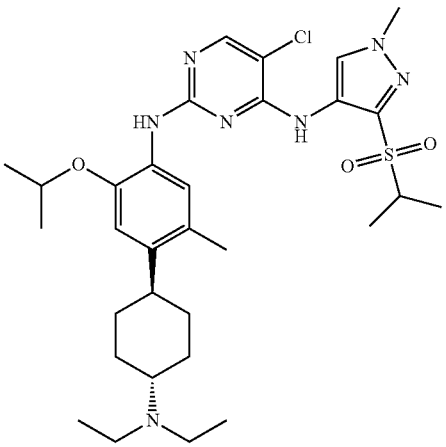
185
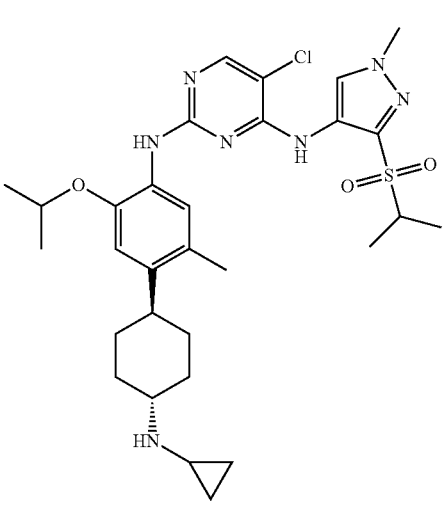
186

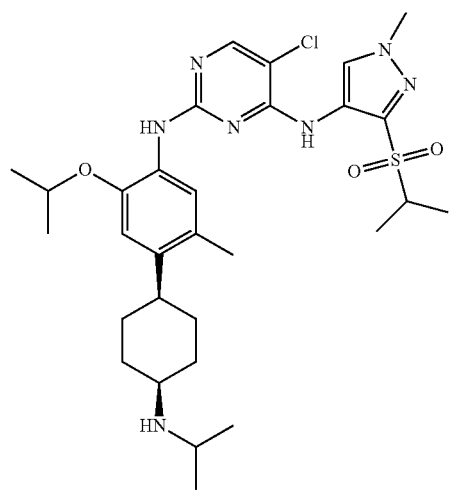
187
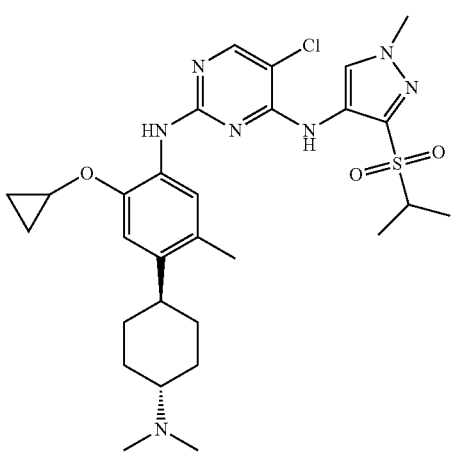
190
188
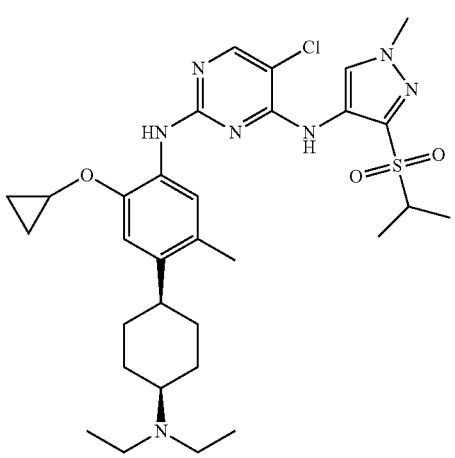
191
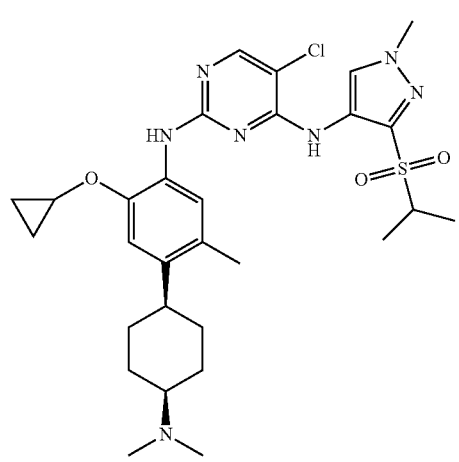
189
192

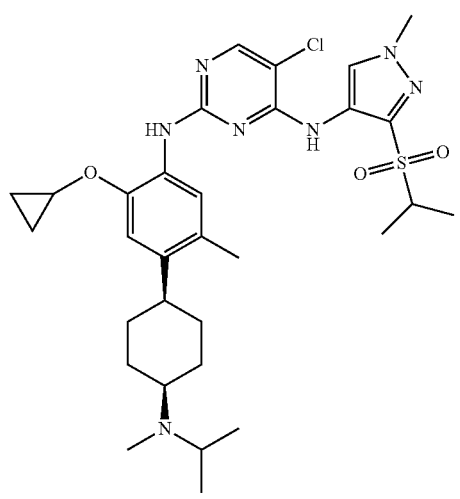
193
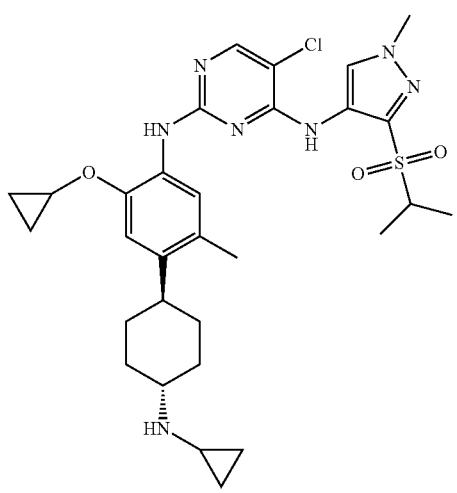
196
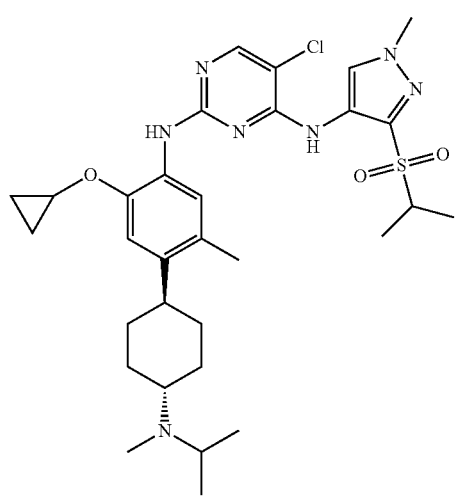
194
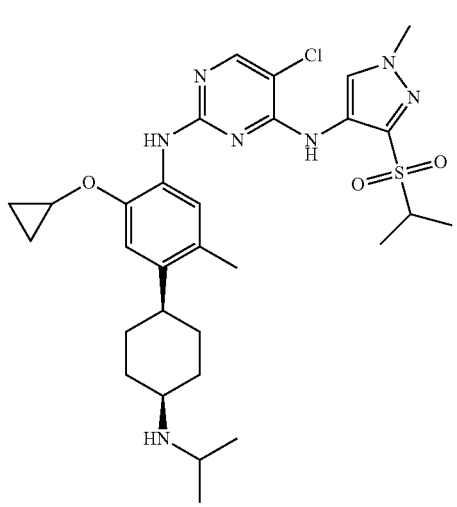
197
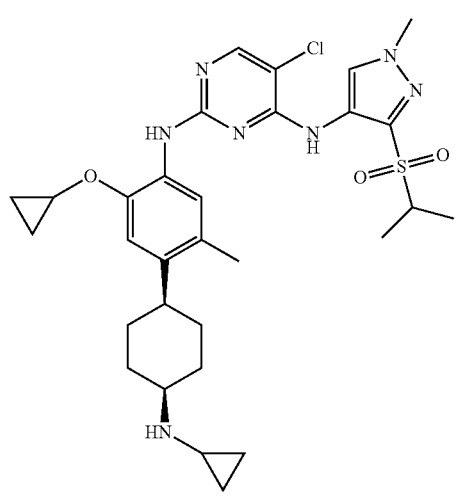
195
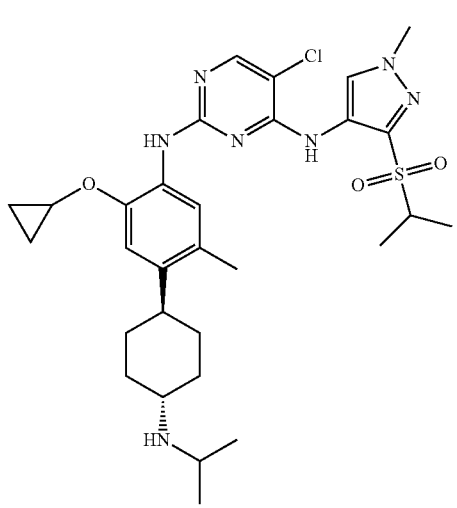
198

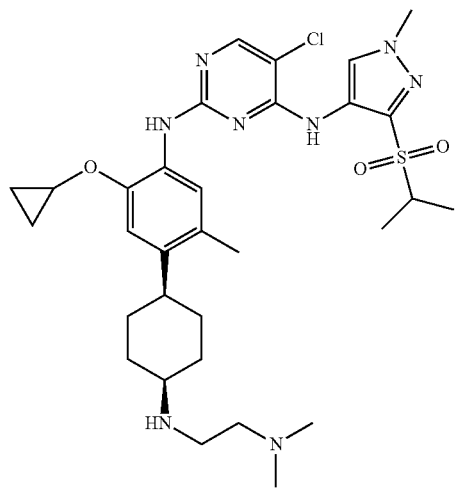
199
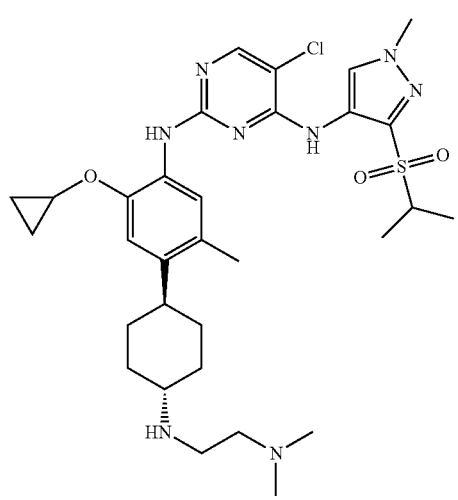
200
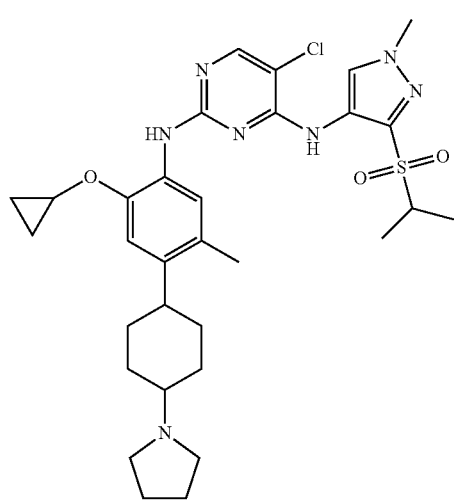
201
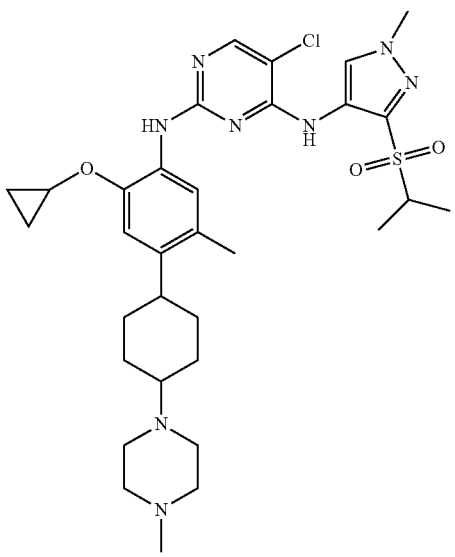
202
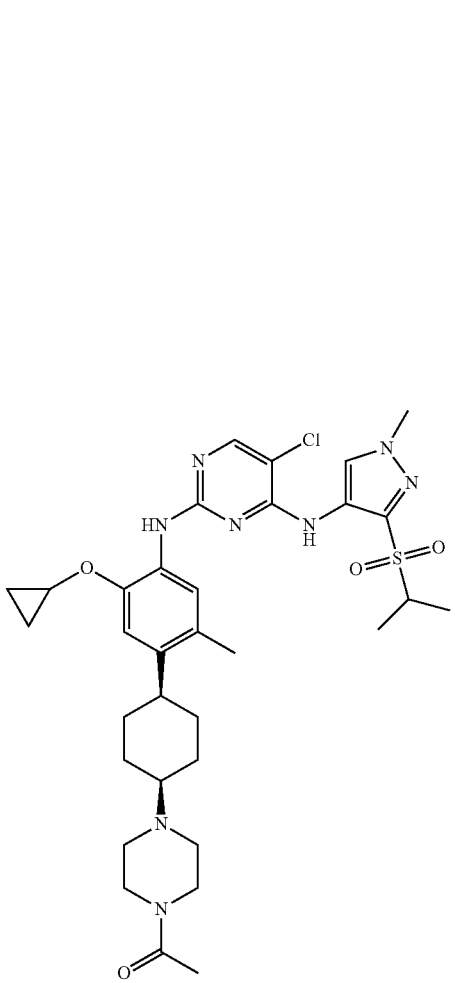
203

204
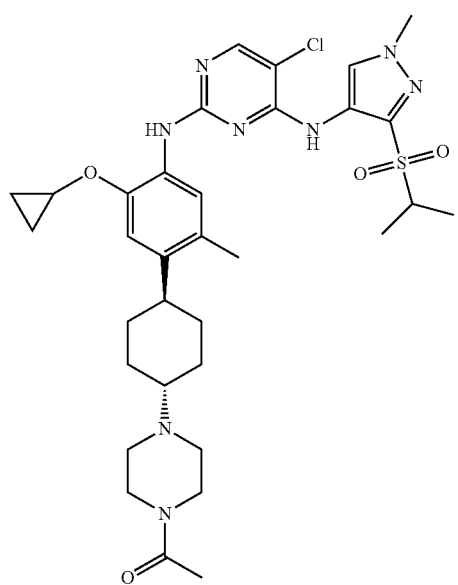
205
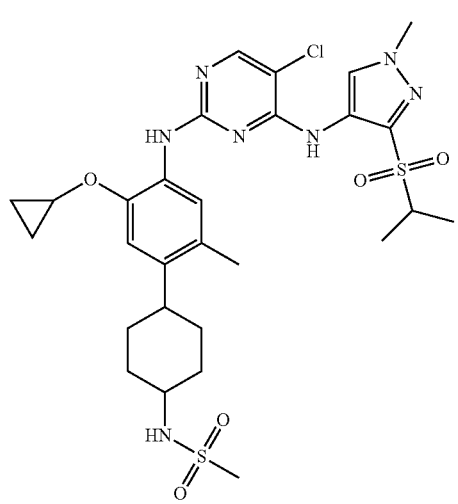
206
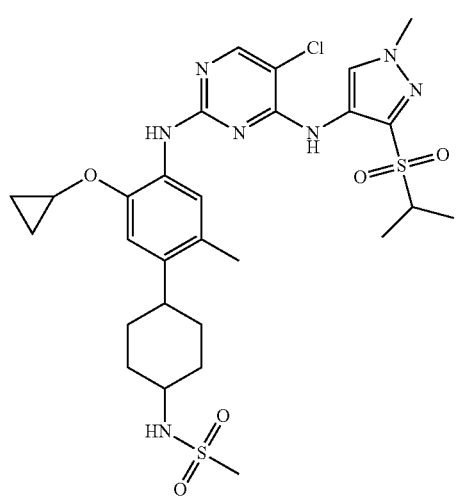
207
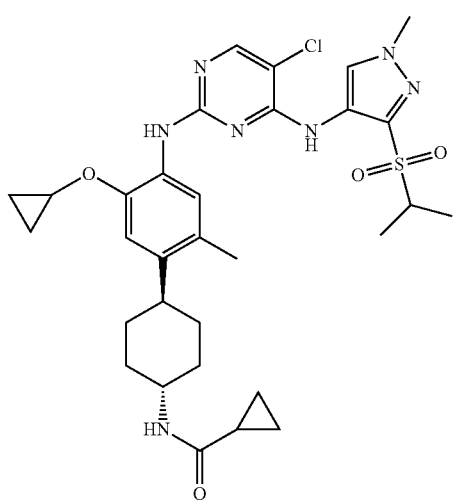
208
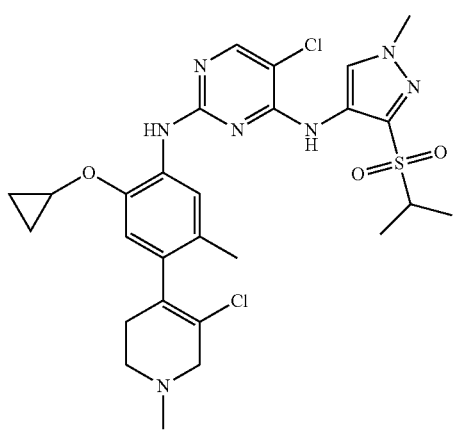
209
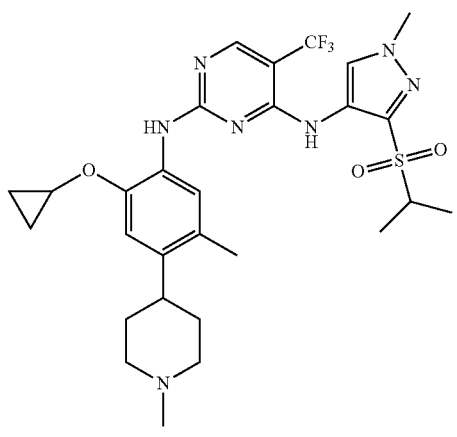

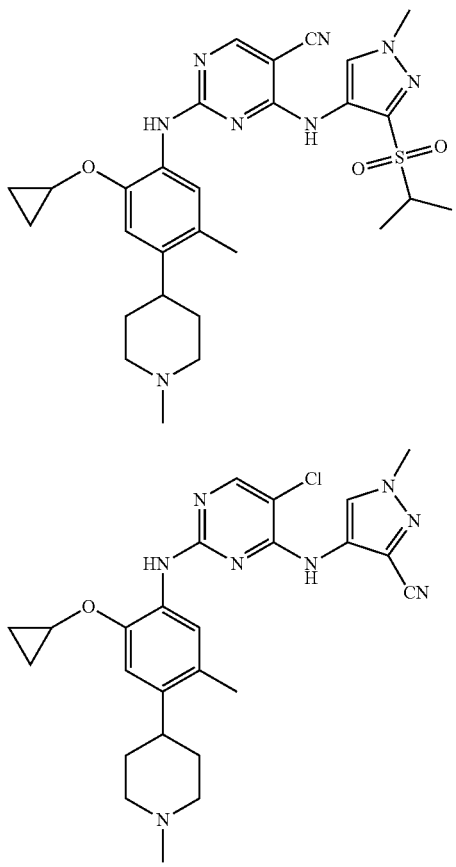

The compounds and their derivatives of the present application are named in accordance with IUPAC (International Union of Pure and Applied Chemistry) or CAS (Chemical Abstracts Service, which is located in Columbus, Ohio) nomenclature system.

The minimum and maximum values of carbon atoms content of hydrocarbon groups are represented by a prefix, for example, the prefix ($C_{a-b}$) alkyl refers to any alkyl groups containing "a" to "b" carbon atoms. Thus, for example, ($C_{1-6}$) alkyl means an alkyl including one to six carbon atoms. The alkyl is branched chain or linear chain.

The atoms in the compounds of the present application include isotopic atoms, for example, hydrogen may be deuterium or tritium.

"Alkyl" refers to a linear or branched, monovalent, saturated aliphatic radical, including but not limited to, e.g. methyl, ethyl, n-propyl, isopropyl, n-butyl, isobutyl, sec-butyl, tert-butyl, pentyl, isopentyl, hexyl and other similar groups, preferably $C_{1-8}$ alkyl, more preferably $C_{1-6}$ alkyl, more preferably $C_{1-4}$ alkyl.

"Cycloalkyl" refers to a saturated monocyclic or polycyclic alkyl, possibly in combination with other groups. Cycloalkyl includes but not limited to such as cyclopropyl, cyclobutyl, cyclopentyl, cyclohexyl, cycloheptyl, preferably $C_{3-8}$ cycloalkyl, more preferably $C_{3-6}$ cycloalkyl, more preferably $C_{3-4}$ cycloalkyl.

"Alkoxy" refers to linear chain or branched chain, monovalent, saturated aliphatic radical bonding with an oxygen atom, including but not limited to such as methoxy, ethoxy, propoxy, butoxy, isobutoxy, tert-butoxy, and other similar groups, preferably $C_{1-8}$ alkoxy, more preferably $C_{1-6}$ alkoxy, more preferably $C_{1-4}$ alkoxy.

"Halogen" refers to fluorine, chlorine, bromine and iodine, preferably fluorine and chlorine.

"Haloalkyl" means alkyl as defined herein, wherein one or more hydrogen have been substituted with the same or different halogens. Exemplary haloalkyls include —$CH_2Cl$, —$CH_2CF_3$, $CH_2CCl_3$, perfluoroalkyl (e.g., —$CF_3$) and the like.

"Heterocyclyl" refers to non-aromatic monocyclic groups, containing heteroatoms selected from the group consisting of N, O, or S, and the remaining atoms are C. Examples of heterocyclic moieties include, but not limited to: piperidinyl, piperazinyl, homopiperazinyl, pyrrolidinyl, pyrazolidinyl, imidazolidinyl, imidazolinyl, morpholinyl, pyridyl, pyridazinyl, pyrimidinyl, oxazolidinyl, isoxazolidinyl, thiazolidinyl, isothiazolidinyl, quinuclidinyl, thiadiazolizinyl, dihydrofuranyl, tetrahydrofuranyl, dihydropyranyl, tetrahydropyranyl, thiomorpholinyl, thiomorpholinyl sulfoxide, thiomorpholinyl sulfone, preferably 4-7 membered heterocyclyl, more preferably 4-6 membered heterocyclyl.

"Aryl" refers to a cyclic aromatic hydrocarbon, including but not limited to such as phenyl, naphthyl, anthryl, phenanthryl and other similar groups, preferably phenyl.

"Heteroaryl" refers to monocyclic or polycyclic aromatic hydrocarbons, wherein one or more carbon atoms have been substituted with heteroatoms such as nitrogen, oxygen or sulfur and so on. If heteroaryl contains more than one heteroatoms, the heteroatoms may be the same or different. Heteroaryls include but not limited to such as furyl, pyridyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzimidazolyl, indolyl, indazolyl, iso-indazolyl, benzisothiazole, benzoxazolyl, benzisoxazole and quinolinyl. Preferred heteroaryl is pyridinyl, oxazolyl or triazolyl.

A cyclic group may bond with another group by a variety of ways. If the bonding way is not indicated, it is meant to include all possible ways. For example, "pyridyl" includes 2-, 3-, or 4-pyridyl, and "thienyl" includes 2- or 3-thienyl.

"Pharmaceutically salts" refer to conventional acid addition salts or base addition salts which keep biological effectiveness and properties of the compounds expressed by Formula I, which are formed by suitable non-toxic organic or inorganic acids or organic or inorganic bases. Examples of acid addition salts include those salts derived from inorganic acids and organic acids, wherein the inorganic acids include such as hydrochloric acid, hydrobromic acid, hydroiodic acid, sulfuric acid, sulfamic acid, phosphoric acid and nitric acid. The organic acids include such as p-methyl benzenesulfonic acid, salicylic acid, methanesulfonic acid, oxalic acid, succinic acid, citric acid, maleic acid, lactic acid, fumaric acid and the like. Examples of alkali addition salts include salts derived from ammonium, potassium, sodium and quaternary ammonium hydroxide, such as tetramethylammonium hydroxide. It is well known for pharmacists to change pharmaceutical compounds (i.e. drugs) into salts to improve physical and chemical stability, hygroscopicity, flowability and solubility of the compounds.

The toxicity of the compounds of the present invention is low, specifically, the inventors selected several compounds of the present invention (for example, final products 40, 43, 44, 46, 47, 51, 57, 60, 67, 77, 80, 82, 95, 97, 114, 133, 146, 156, 160, 161, 166, 167, 202, 204, 205, etc.) and tested the inhibitory activity of these compounds on common subfamilies of cytochrome P450 (1A2, 2C9, 2C19, 2D6, 3A4) and as a result, no significant inhibition (all of IC50 is greater than 10 μM) is found. In addition, the inventors of the present application also selected some compounds to repeat this test in rats. The result shows that no significant gap appears between male and female after administrating repeatedly for 4 days, there is no serious toxicity in blood biochemical and pathology and the maximum tolerated dose amount is greater than 86.3 mg/kg. A test of repeated drug administration for 14 days showed that the amount of drug exposure increases with the increase of the dosage, there is no significant gap between male and female and the maximum tolerated dose is 75 mg/kg, the safety window (the exposure amount of the maximum tolerated dose/the exposure amount of the onset dose) is more than 40 times.

Method for Preparing the Compounds as ALK Kinase Inhibitors

The compounds of the present invention can be synthesized by the following procedure. The procedure is an illustrative example without limiting other methods for preparing the compounds. In addition, the steps in the procedure are just for explaining better the method for preparing the compounds of the present invention. The steps may be modified according to actual needs without departing from the scope of the invention described herein.

In some embodiments, the present application provides a method for preparing the compound expressed as Formula I, wherein the chemical reaction scheme of the method is as follows:

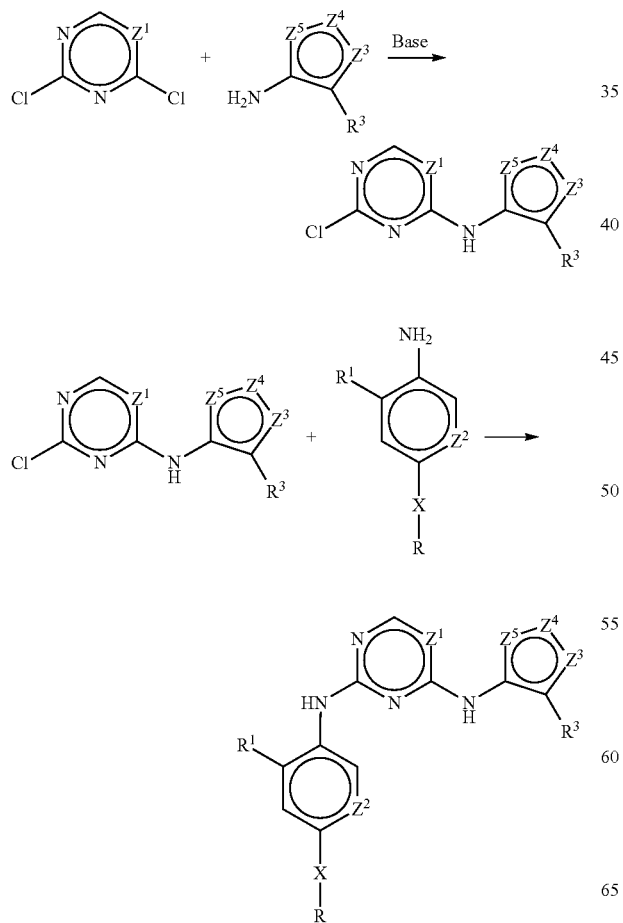

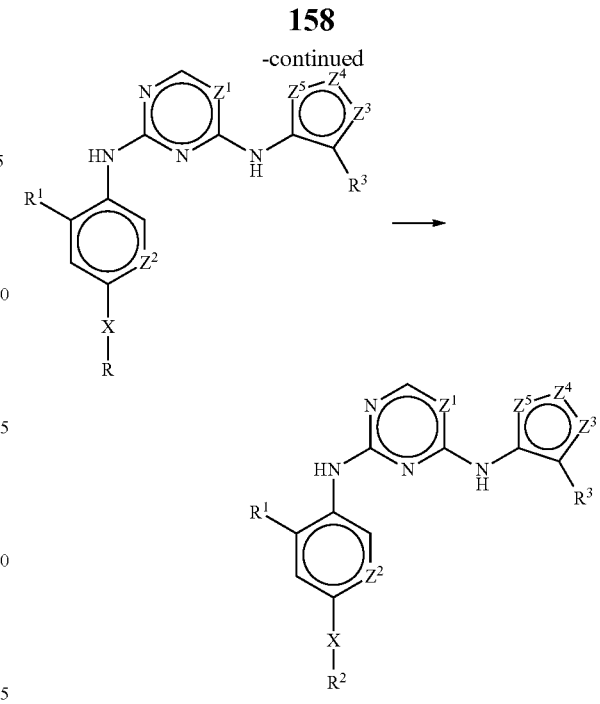

Wherein $R^1$, $R^2$, $R^3$, X, $Z^1$, $Z^2$, $Z^3$, $Z^4$ and $Z^5$ are defined as above, R is the precursor of $R^2$, generally is $R^2$ having a protecting group which may be for example, t-butyloxycarbonyl, trifluoroacetyl and the like.

In some embodiments, wherein the chemical reaction scheme of the method for preparing the compound expressed as Formula I is as follows:

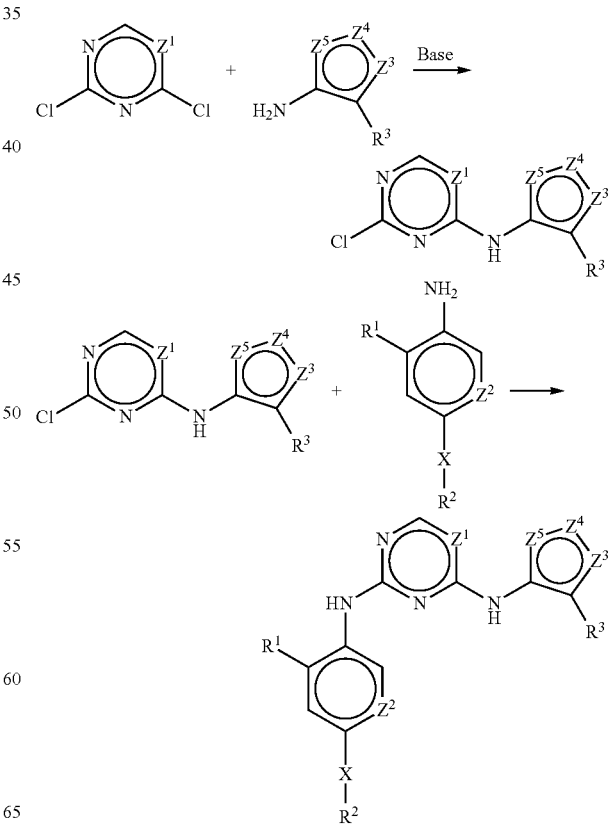

wherein $R^1$, $R^2$, $R^3$, X, $Z^1$, $Z^2$, $Z^3$, $Z^4$ and $Z^5$ are defined as above.

The Pharmaceutical Compositions as ALK Kinase Inhibitors

The present invention also provides a composition including the compounds as ALK kinase inhibitors or a pharmaceutically acceptable salt thereof, wherein the pharmaceutical composition comprises a pharmaceutically acceptable carrier or excipient.

The term "pharmaceutically acceptable carrier" refers to a pharmaceutically acceptable material, component or medium, such as liquid or solid filler, diluting agent, excipient, solvent or packaging material, which participates in loading or delivering the compounds of the present invention from one location, body fluids, tissues, organs (internal or external), or part of the body into another location, body fluids, tissues, organs (internal or external) or part of the body. The pharmaceutically acceptable carrier can be media, diluting agent, excipient or other materials which do not have excessive toxicity or side-effects and can contact with animal tissues. Typical pharmaceutically acceptable carriers include saccharides, starches, cellulose, maltose, tragacanth gum, gelatin, Ringer's solution, alginic acid, physiological saline, buffers and the like.

Each pharmaceutically acceptable carrier should be compatible with other components. For example they may form preparations with the compounds of the present invention, do not have excessive toxicity, stimulus, allergic response, immunogenicity or other problems or complications and have a more reasonable benefit/risk ratio.

Some pharmaceutically acceptable carriers include: (1) saccharides, such as lactose, glucose and sucrose; (2) starches, such as corn starch and potato starch; (3) cellulose and derivatives thereof, such as sodium carboxymethyl cellulose, ethyl cellulose, cellulose acetate; (4) gum tragacanth powder; (5) maltose; (6) gelatin; (7) talcum powder; (8) excipients, such as cocoa butter and suppository wax; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) lipids, such as ethyl oleate, ethyl laureate; (13) agaropectin; (14) buffering agents, such as magnesium hydroxide and aluminum hydroxide; (15) alginic acid; (16) sterile pyrogen-free water; (17) physiologicalsaline; (18) Ringer's solution; (19) alcohols, such as ethanol and propanol; (20) phosphate buffer; (21) other non-toxic and compatible substances in pharmaceutical dosage forms, such as acetone.

The pharmaceutical compositions can include pharmaceutically acceptable adjuvants to simulate physiological conditions, such as pH adjusting and buffering agents, toxicity adjusting agents and the like, such as sodium acetate, sodium chloride, potassium chloride, calcium chloride, sodium lactate and the like.

Drug ingredients can be made into any suitable dosage forms, such as solid dosage forms (e.g. tablets, capsules, powder, granules etc.) and liquid dosage forms (e.g. aqueous solution, emulsion, elixirs, syrups etc.). The methods for preparing pharmaceutical compositions has been well known, which can be prepared by conventional process, such as provided by Remington in The Science and Practice of Pharmacy (Gennaro ed. 20th edition, Williams & Wilkins PA, USA) (2000).

In some embodiments, the compounds or pharmaceutical compositions of the present invention can be made into suitable dosage forms for drug release, which are administrated by injection (such as subcutaneous, intravenous, intramuscular, intraarterial, hydrocele, intracystic, box, intracardiac, intradermal, intraperitoneal, intratracheal, epidermis, intra-articular, subcapsular, subarachnoid, intraspinal, intrasternal, and/or infusion) or non-injection (such as oral, parenteral, buccal, nasal, intranasal, mucosal, epidermal, emplastrum, dermal, ophthalmic, pulmonary, sublingual, rectal, vaginal or surface skin local application).

Suitable dosage forms include (but not limited to) injectable dosage forms such as emulsion, solution and suspension, oral dosage forms such as tablet, capsule, pill, dragee, powder and granule, local application dosage forms or the dosage forms absorbed by skin such as spray, ointment, paste, cream, lotion, gel, solution, patche and inhalant drugs, vaginal or rectal dosage forms such as suppository. These dosage forms can be prepared in accordance with compounds and suitable excipients under suitable conditions. The preparation method and process are well known, such as provided by Remington in The Science and Practice of Pharmacy (Gennaro ed. 20th edition, Williams & Wilkins PA, USA) (2000).

In some embodiments, the present application provides a pharmaceutical composition including the compounds or pharmaceutically acceptable salts thereof and pharmaceutically acceptable carriers or excipients thereof. In some embodiments, the pharmaceutical composition is formulated in a form of tablet, capsule, pill, granule, powder, suppository, injection, solution, suspension, ointment, patche, lotion, drop, liniment, spray.

Use of the Pharmaceutical Compositions as ALK Kinase Inhibitors

The present invention also provides a use of the above compounds or pharmaceutically salts thereof and/or pharmaceutical compositions for preparing drugs and treating diseases.

In some embodiments, the present invention provides a use of the above compounds or pharmaceutically salts thereof and/or pharmaceutical compositions for preparing anti-tumor drugs.

In some embodiments, the present invention provides a use of the above compounds or pharmaceutically salts thereof and/or pharmaceutical compositions for preparing anti-tumor drugs. In some embodiments, wherein the anti-tumor drugs are applied for the following diseases: melanoma, neuroblastoma, glioblastoma, rhabdomyosarcoma, astrocytoma, Ewing's sarcoma, retinoblastoma, anaplastic large cell lymphoma, inflammatory myofibroblastic tumor, diffuse large B-cell lymphoma, non-small cell lung cancer, renal medullary carcinoma, renal cell carcinoma, breast cancer, colon cancer, ovarian serous carcinoma and esophageal squamous cell carcinoma.

In some embodiments, the present invention provides a method for treating tumors in a subject, comprising administering to the subject a therapeutically effective amount of the compounds or pharmaceutically acceptable salts thereof or pharmaceutical compositions. In some embodiments, the subject is a mammal. In some embodiments, the subject is a human. In some embodiments, the modes of administration include oral, mucosal, sublingual, ocular, topical, parenteral, rectal, intracisternal, vagina, peritoneum, bladder, nasal administration.

The compounds or pharmaceutically salts thereof or pharmaceutical compositions of the present invention may enter the organisms by any suitable ways, such as oral, intravenous, intranasal, topical, intramuscular, intradermal injection, percutaneous, or subcutaneous administration. In some embodiments, the modes of administration of compounds or pharmaceutically salts thereof or pharmaceutical compositions of the present invention include oral, mucosal, sublingual, ocular, topical, parenteral, rectal, intracisternal, vagina, peritoneum, bladder, nasal administration.

In some embodiments, the compounds or pharmaceutically salts thereof or pharmaceutical compositions of the present invention may be administrated concurrently with a second active substance to obtain a superimposed and even synergistic effect in organisms. For example, the compounds of the present invention may be combined into a pharmaceutical composition with a second active substance and administrated simultaneously or sequentially in a separate manner. The second active substances which can be administrated simultaneously with the compounds of the present invention for the treatment of cancers include, but not limited to fluorouracil, doxorubicin, daunorubicin, tamoxifen, leuprolide, goserelin, flutamide, nilutamide, finasteride, dexamethasone, aminoglutethimide, amsacrine, anastrozole, asparaginase, bacille calmette-guerin, bicalutamide, bleomycin, clinical, busulfan, camptothecin, capecitabine, carboplatin, carmustine, chlorambucil, cisplatin, cladribine, colchicine, cyclophosphamide, drugs, cyproterone, cytarabine, dacarbazine, actinomycin d, daunorubicin, dienestrol, diethylstilbestrol, docetaxel, doxorubicin, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, tamoxifen, teniposide, testosterone, titanocene dichloride, Rio Pu Taikang, trastuzumab, tretinoin, vinblastine, hydroxyurea, idarubicin, ifosfamide, imatinib, interferon, irinotecan, irinotecan, letrozole, leucovorin, pentostatin, mithramycin, procarbazine, raltitrexed porfimer, rituximab streptozotocin, suramin, leuprolide, levamisole, cyclohexyl nitrosourea, mechlorethamine, medroxyprogesterone, megestrol, melphalan, mercaptopurine, mesna, methotrexate, mitomycin, mitotane, mitoxantrone, nilutamide, nocodazole, octreotide, platinum, paclitaxel, pamidronate, thioguanine, thiotepa, methyl chloride, Topotecan Ermao titanium, trastuzumab, accutane, vinblastine, vincristine, vindesine, vinorelbine.

In some embodiments, the compounds or pharmaceutically salts thereof of the present invention maybe performed simultaneously with non-chemical methods for the treatment of cancers. In some embodiments, the compounds or pharmaceutically salts thereof of the present invention may be performed simultaneously with radiation therapy. In some embodiments, the compounds of the present invention can be used in combination with surgery, cancer heat treatment, focused ultrasound therapy, cryotherapy or the above several therapies.

In some embodiments, the compounds or pharmaceutically acceptable salts thereof of the present invention can be administrated simultaneously with steroids. Suitable steroids include, but not limited to: amcinonide, beclomethasone, betamethasone, budesonide, chloroprednisone, clobetasol, corticosterone, cortisone, desonide, desoximetasone, dexamethasone, diflorasone, diflucortolone, difluprednate, glycyrrhetinic acid, fluazacort, flumethasone, flunisolide, fluclorolone acetonide, fluocinolone acetonide acetate, fluocinonide, fluocortin butyl, fluocortolone, flurandrenolone, fluperolone acetate, fluprednidene acetate, fluprednisolone, fludroxycortide, fluoro-propionic acid, formocortal, clobetasol propionate, halcinonide, halometasone, hydrocortisone, loteprednol etabonate ethyl carbonate, mazipredone, medrysone, meprednisone, 6-methylprednisolone, furoate, paramethasone, prednisolone, dexamethasone and 25-prednisolone diethylaminoacetate.

In some embodiments, the compounds of the present invention can be administrated simultaneously with immunotherapeutic agents. Suitable immunotherapeutic agents include tumor cell multidrug resistance reversal agent (such as verapamil), rapamycin, mycophenolate, thalidomide, cyclophosphamide, cyclosporine, and monoclonal antibodies.

PREFERRED EMBODIMENTS OF THE INVENTION

Additional objects, advantages and novel features of this invention will become apparent to those skilled in the art upon examination of the following examples thereof, which are intended to be illustrative and not intended to be limiting.

Unless otherwise specified, raw materials used in the following examples are commercially available.

Example 1 Preparation of Intermediate A1

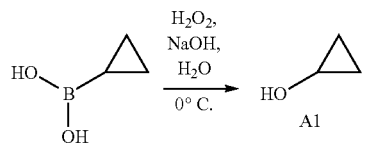

Step 1: Cyclopropanol

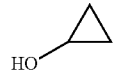

Cyclopropylboronic acid (10 g, 0.116 mol), sodium hydroxide aqueous solution (8.37 g, 0.209 mol, added to 100 ml water) were added into a 1 L reaction flask, and hydrogen peroxide (34%, 80 mL) was slowly dropped thereinto under ice bath and the temperature was kept not higher than 5° C. during the process of dropping. After adding, the mixture was stirred at 5° C. for 1 hour. After completion of the reaction, a saturated sodium thiosulfate aqueous solution was slowly dropped to terminate the reaction until the potassium iodide-starch test paper does not change color. The reaction solution was extracted with diethyl ether for three times and the combined organic phase was washed with saturated brine, dried, filtered and concentrated at 0° C. to obtain the title compound (colorless oil, 4 g, 60%), which may be used directly for the subsequent reaction. (MS: [M+1] none)

Example 2 Preparation of Intermediate A2

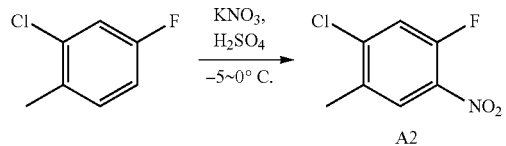

Step 1: 1-chloro-5-fluoro-2-methyl-4-nitrobenzene

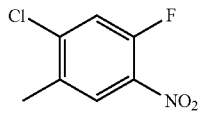

2-chloro-4-fluoro-1-methyl benzene (1.5 g, 10.4 mmol) and concentrated sulfuric acid (15 mL) were added into a 50 mL reaction flask. The reaction mixture was cooled down to −5° C.~0° C. and then potassium nitrate (1.4 g, 13.8 mmol) was added in batches at this temperature. The reaction mixture was slowly increased up to room temperature and stirred for 16 hours. After completion of the reaction, the reaction mixture was poured into ice water and extracted by using ethyl acetate, and washed with saturated aqueous sodium bicarbonate and saturated brine, dried and concentrated. The crude product thus obtained was separated and purified by column chromatography (silica gel column, eluent:ethyl acetate/petroleum ether=1:50) to obtain the title compound (yellow solid, 1.1 g, 56%). (MS: [M+1] none)

Example 3 Preparation of Intermediate A3

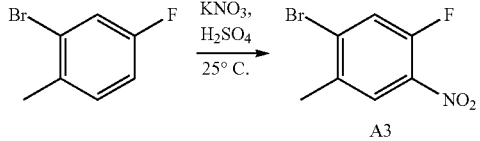

Step 1: 1-bromo-5-fluoro-2-methyl-4-nitrobenzene

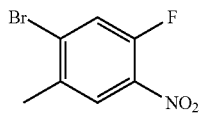

Intermediate A3 (100 g, 58%) was synthesized by using the above method for preparing intermediate A2. (MS: [M+1] none)

Example 4 Preparation of Intermediate A4

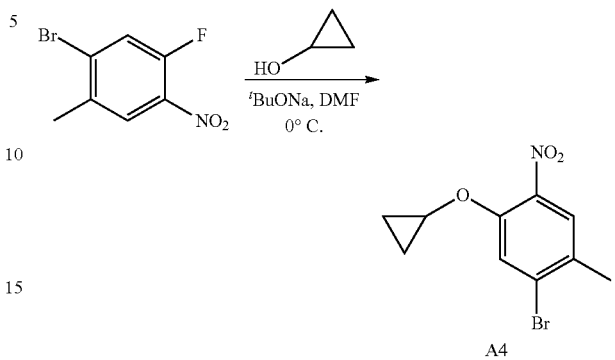

Step 1: 1-bromo-5-cyclopropyloxy-2-methyl-4-nitrobenzene

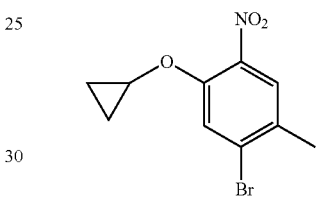

1-bromo-5-fluoro-2-methyl-4-nitrobenzene (70 g, 0.3 mol), freshly prepared cyclopropanol diethyl ether complex (23 g, ~0.4 mol) and N,N-dimethylformamide (260 mL) were added into a 500 mL reaction flask. Sodium tert-butoxide (35 g, 0.36 mol) was added slowly thereinto at 0° C. and the reaction mixture was stirred at 0° C. for 1.5 hours. After completion of the reaction, the reaction mixture was poured into ice water slowly, and the precipitated solid was filtered to obtain the crude product. The filter cake was then washed with a lot of water and dried through air to obtain the title compound (yellow solid, 78 g, 96%), which may be used directly for the subsequent reaction. (MS: [M+1] none)

Example 5-14 Preparation of Intermediates A5-14

Intermediates A5-A14 (table 1) were synthesized by using the above method for preparing intermediate A4.

TABLE 1

| | Intermediates A5-A14 | | |
|---|---|---|---|
| Nos. | Starting Materials | Intermediates | Molecular Ion Peaks [M + 1]+ |
| A5 | Cl-benzene(F, NO2, CH3) | Cl-benzene(O-cyclopropyl, NO2, CH3) | none |
| A6 | Cl-benzene(F, NO2, CH3) | Cl-benzene(O-isopropyl, NO2, CH3) | none |

TABLE 1-continued

Intermediates A5-A14

| Nos. | Starting Materials | Intermediates | Molecular Ion Peaks [M + 1]+ |
|---|---|---|---|
| A7 | Br—[ring]—F, NO₂, CH₃ | Br—[ring]—O-iPr, NO₂, CH₃ | none |
| A8 | Cl—[ring]—F, NO₂ | Cl—[ring]—O-iPr, NO₂ | none |
| A9 | Br—[ring]—F, NO₂, CH₃ | Br—[ring]—O-cyclobutyl, NO₂, CH₃ | none |
| A10 | Br—[ring]—F, NO₂, CH₃ | Br—[ring]—OMe, NO₂, CH₃ | none |
| A11 | Br—[ring]—F, NO₂, CH₃ | Br—[ring]—OEt, NO₂, CH₃ | none |
| A12 | Br—[ring]—F, NO₂, CH₃ | Br—[ring]—O-nPr, NO₂, CH₃ | none |
| A13 | Br—[ring]—F, Cl, NO₂ | Br—[ring]—O-cyclopropyl, Cl, NO₂ | none |
| A14 | Br—[ring]—F, NO₂, CH₃ | Br—[ring]—O-CH(CH₂F)₂, NO₂, CH₃ | none |

Example 15 Preparation of Intermediate A15

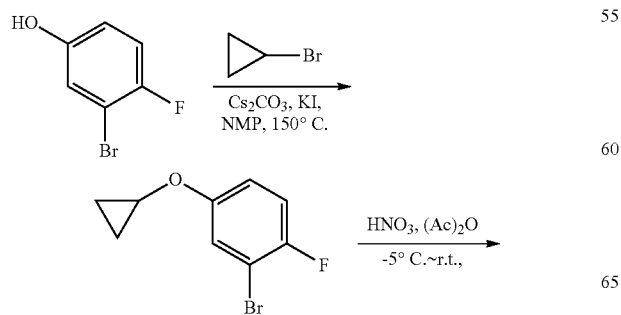

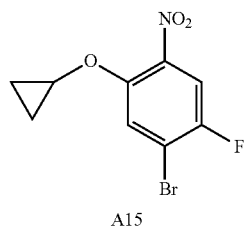

-continued

A15

Step 1: 1-bromo-5-cyclopropyloxy-2-fluoro-benzene

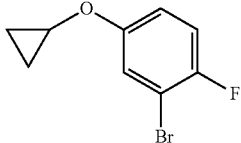 [SMILES: Fc1ccc(OC2CC2)cc1Br]

3-bromo-4-fluoro-phenol (1.5 g, 7.9 mmol), bromocyclopropane (4.7 g, 38.8 mmol), cesium carbonate (3.8 g, 11.7 mmol), potassium iodide (1.3 g, 7.9 mmol) N-methylpyrrolidinone (6 mL) were added into a 20 mL reaction flask. The reaction mixture was heated up to 150° C. in a closed system and stirred for 20 hours. Ethyl acetate was added to the reaction mixture, and the organic phase was washed with saturated brine, dried and concentrated, the crude product obtained was separated and purified by column chromatography (silica gel column, eluent: dichloromethane/petroleum ether, gradient: 0~100% dichloromethane) to obtain the title compound (0.77 g, 42%). (MS: [M+1] none)

Step 2: 1-bromo-5-cyclopropyloxy-2-fluoro-4-nitrobenzene

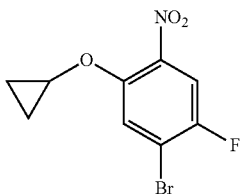 [SMILES: O=[N+]([O-])c1cc(F)c(Br)cc1OC1CC1]

1-bromo-5-cyclopropyloxy-2-fluoro-benzene (465 mg, 2 mmol) and acetic anhydride (10 mL) were added to a 25 mL reaction flask. The reaction mixture was cooled down to −5° C. and concentrated nitric acid (1.5 mL, 22 mmol) was added slowly at this temperature. The reaction mixture was maintained at −5° C. and stirred for 30 minutes. After completion of the reaction, the reaction mixture was poured into ice water, neutralized with saturated aqueous sodium bicarbonate, extracted with ethyl acetate, washed with saturated saline, dried and concentrated. The crude product obtained was separated and purified by column chromatography (silica gel column, eluent:ethyl acetate/petroleum ether, gradient: 0~5% ethyl acetate) to obtain the title compound (yellow oil, 400 mg, 72%). (MS: [M+1] none)

Example 16 Preparation of Intermediate A16

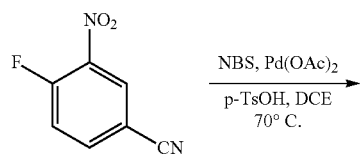

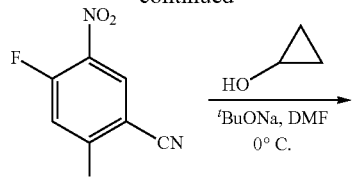

Step 1: 2-bromo-4-fluoro-5-nitrobenzonitrile

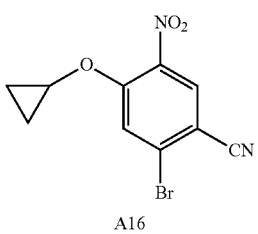

4-fluoro-3-nitrobenzonitrile (3.32 g, 20 mmol), N-bromosuccinimide (3.92 g, 22 mmol), palladium acetate (0.45 g, 2 mmol), p-toluenesulfonic acid (1.72 g, 10 mmol) and 1,2-dichloroethane (50 ml) were added to a 250 mL reaction flask. The reaction mixture was heated up to 70° C. and stirred for 12 hours. After completion of the reaction and the reaction mixture was cooled down, ethyl acetate (50 mL) was added and then filtered. The reaction mixture was concentrated and purified by column chromatography (ethyl acetate/petroleum ether=1:4) to obtain the title compound (white solid, 1.76 g, 36%). (MS: [M+1] none)

Step 2: 2-bromo-4-cyclopropyloxy-5-nitrobenzonitrile

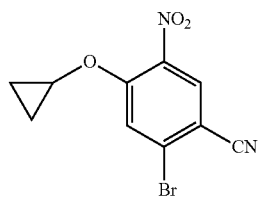 [SMILES: N#Cc1cc([N+](=O)[O-])c(OC2CC2)cc1Br]

2-bromo-4-fluoro-5-nitrobenzonitrile (660 mg, 2.7 mmol), N,N-dimethylformamide (10 mL) were added to a 250 mL reaction flask. Sodium tert-butoxide (285 mg, 2.97 mmol) was added slowly at 0° C. After the reaction mixture was stirred for 10 minutes, cyclopropanol (313 mg, 5.4 mmol) was added slowly into the reaction system. The reaction mixture was stirred for 30 minutes at 0° C. After completion of the reaction, the reaction mixture was poured into ethyl acetate and the organic phase was washed with saturated aqueous lithium chloride solution and saturated aqueous sodium chloride solution, dried, concentrated and purified by column chromatography (eluent:ethyl acetate/petroleum ether=1:10) to obtain the title compound (yellow solid, 201 mg, 26%). (MS: [M+1] none)

Example 17 Preparation of Intermediate A17

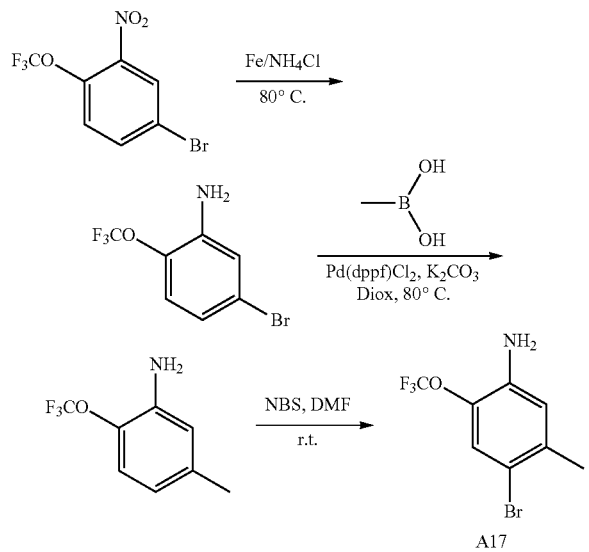

Step 1: 5-bromo-2-(trifluoromethoxy)aniline

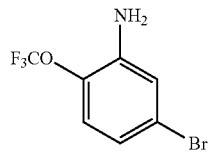

5-bromo-2-(trifluoromethoxy) nitrobenzene (2.86 g, 10 mmol), iron powder (2.86 g) and saturated aqueous ammonium chloride solution (50 mL) were added to a 250 mL reaction flask. The reaction mixture was heated up to 80° C. under the protection of nitrogen and stirred for 1 hour. After completion of the reaction, the reaction mixture was filtered and concentrated to obtain the title compound (yellow solid, 2.5 g, 98%), which may be used directly for the subsequent reaction. (MS: [M+1] none)

Step 2: 5-methyl-2-(trifluoromethoxy)aniline

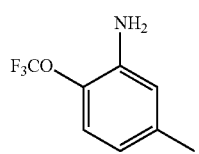

5-bromo-2-(trifluoromethoxy) aniline (1.14 g, 4.46 mmol) obtained from the last step, methyl boronic acid (0.72 g, 12 mmol), potassium carbonate (1.66 g, 12 mmol), [1,1'-bis (diphenylphosphino) ferrocene]dichloropalladium (0.29 g, 0.4 mmol) and 1,4-dioxane (25 mL) were added to a 100 mL reaction flask. The reaction mixture was heated up to 80° C. and stirred overnight. After completion of the reaction, the reaction solution was concentrated and dissolved in ethyl acetate. The organic phase was washed with saturated ammonium chloride and saturated brine, dried, concentrated and purified by column chromatography (ethyl acetate/petroleum ether=1:15) to obtain the title compound (yellow oil, 0.61 g, 72%). (MS: [M+1] 192.1)

Step 3: 4-bromo-5-methyl-2-(trifluoromethoxy) aniline

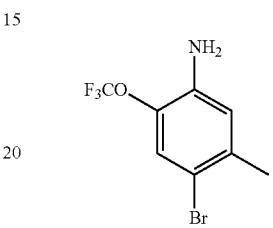

N-bromosuccinimide (0.53 g, 3 mmol) was added to 5-methyl-2-(trifluoromethoxy) aniline (0.57 g, 3 mmol) in N,N-dimethylformamide (20 mL) in a 100 mL reaction flask. The reaction mixture was stirred at room temperature for 1 hour. After completion of the reaction, ethyl acetate (100 mL) was added to dilute the mixture and then mixture is filtered. The filtrate was washed with saturated aqueous ammonium chloride solution and saturated aqueous sodium chloride solution, dried and concentrated to obtain the title compound (yellow oil, 0.8 g, 99%), and the crude product was used directly for the subsequent reaction. (MS: [M+1] 270.1)

Example 18 Preparation of Intermediate A18

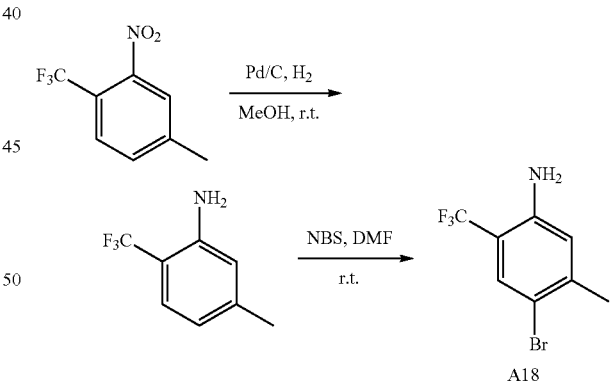

Step 1: 5-methyl-2-(trifluoromethyl) aniline

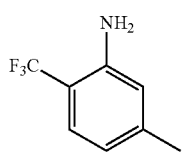

Pd/C (0.2 g, 10% content) was added to 4-methyl-2-nitro-1-trifluoromethylbenzene (1 g, 4.8 mmol) in methanol (30 mL) in a 100 mL reaction flask. The reaction mixture was stirred for 4 hours under hydrogen atmosphere of 1 atmospheric pressure at 25° C. After completion of the reaction, the reaction solution was filtered and concentrated and the residue was separated and purified by column chromatography (ethyl acetate/petroleum ether=1:10) to obtain the title compound (0.68 g, 80%). (MS: [M+1] 176.2)

Step 2: 4-bromo-5-methyl-2-(trifluoromethyl) aniline

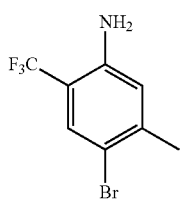

N-bromosuccinimide (0.69 g, 3.88 mmol) was added to 5-methyl-2-(trifluoromethyl) aniline (0.68 g, 3.88 mmol) in N,N-dimethylformamide (20 mL) in a 100 mL reaction flask. The reaction mixture was stirred for 1 hour at room temperature. After completion of the reaction, ethyl acetate (100 mL) was added to dilute the mixture and then mixture is filtered. The filtrate was washed with saturated ammonium chloride and saturated sodium chloride solution, dried and concentrated. The crude product was separated by column chromatography (ethyl acetate/petroleum ether=1:10) to obtain the title compound (0.78 g, 80%). (MS: [M+1] 254.1)

Example 19 Preparation of Intermediate A19

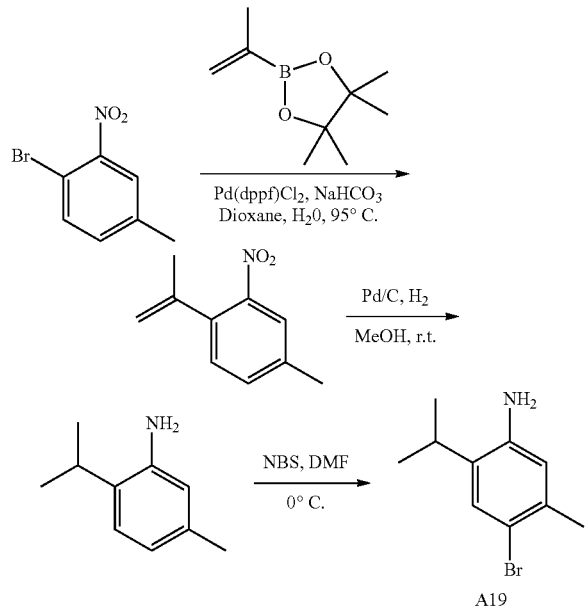

Step 1: 4-methyl-2-nitro-1-(propylene-2-yl)benzene

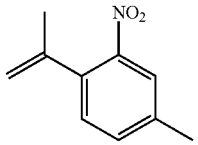

1-bromo-4-methyl-2-nitrobenzene (2.16 g, 10 mmol), propylene-2-boronic acid pinacol ester (2 g, 12 mmol), [1,1'-bis (diphenylphosphino) ferrocene]dichloropalladium (366 mg, 0.5 mmol), sodium bicarbonate (1.26 g, 15 mmol), 1,4-dioxane (100 mL) and water (30 mL) were added to a 250 mL reaction flask. The reaction mixture was heated up to 95° C. under the protection of nitrogen in an oil bath and stirred for 5 hours. After the completion of the reaction, dichloromethane was added to the reaction solution. The organic phase was washed with saturated brine, dried and concentrated. The obtained crude product was separated and purified by column chromatography (silica gel column, eluent: dichloromethane/petroleum ether, gradient: 0~50% dichloromethane) to obtain the title compound (1.5 g, 85%). (MS: [M+1] none)

Step 2: 2-isopropyl-5-methyl aniline

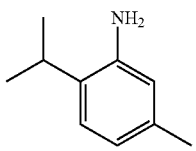

4-methyl-2-nitro-1-(propylene-2-yl) benzene (1.5 g, 8.47 mmol), Pd/C (1.3 g, 10% content) and methanol (30 mL) were added to a 100 mL reaction flask. The reaction mixture was stirred overnight under hydrogen atmosphere of 1 atmospheric pressure at 25° C. After completion of the reaction, the reaction solution was filtered and concentrated to obtain the title compound (1 g, 79%). The crude product was used directly for the subsequent reaction. (MS: [M+1] 150.1)

Step 3: 4-bromo-2-isopropyl-5-methyl aniline

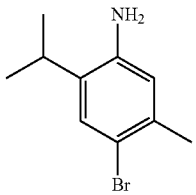

2-isopropyl-5-methyl aniline (1 g, 6.67 mmol), N-bromosuccinimide (1.18 g, 6.67 mmol) and DMF (20 mL) were added to a 50 mL reaction flask. The reaction mixture was stirred for 3 hours in an ice bath. After completion of the reaction, ethyl acetate was added to the reaction solution and washed with saturated brine, dried and concentrated. The obtained crude product was separated and purified by col-

Example 20 Preparation of Intermediate A20

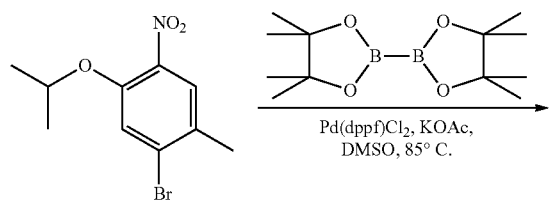

Step 1: 2-(5-isopropoxy-2-methyl-4-nitrophenyl)-4,4,5,5-tetramethyl-1,3,2-dioxide cyclopentaborane

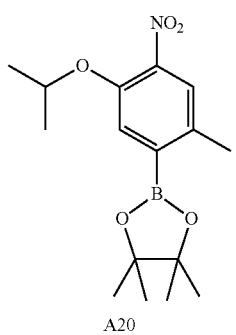

1-bromo-5-isopropoxy-2-methyl-4-nitrobenzene (100 mg, 0.365 mmol), boronic acid pinacol ester (102 mg, 0.401 mmol), [1,1'-bis (diphenylphosphino) ferrocene] dichloropalladium (8 mg, 0.011 mmol), potassium acetate (107 mg, 1.10 mmol) and anhydrous dimethyl sulfoxide (5 mL) were added to a 25 mL reaction flask. The reaction mixture was heated up to 85° C. under nitrogen atmosphere for 18 hours. After completion of the reaction, the reaction solution was cooled down to room temperature and diluted with ethyl acetate, and then filtered with diatomite. The obtained filtrate was washed with water and saturated brine, and then dried with anhydrous sodium sulfate followed by concentration. The obtained crude product was separated and purified by column chromatography (silica gel column, ethyl acetate/petroleum ether=1/30) to obtain the title compound (yellow oil, 80 mg, yield:68%). (MS: [M+1] 322.1)

Example 21 Preparation of Intermediate A21

Intermediate A21 was synthesized by the above method of preparing intermediate A20. (MS: [M+1] none)

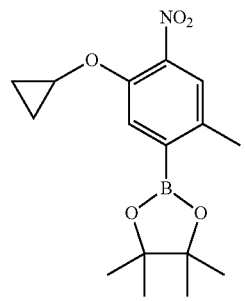

Example 22 Preparation of Intermediate A22

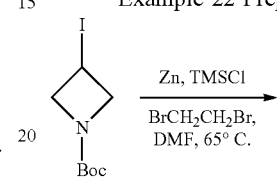

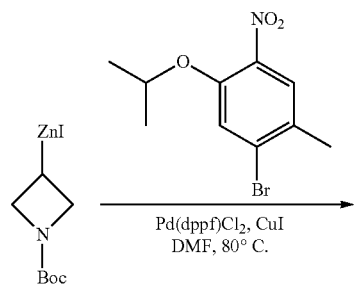

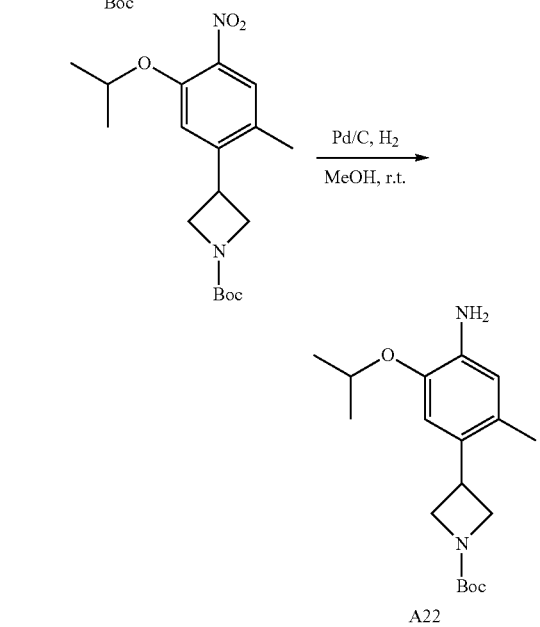

Step 1: (1-(t-butyloxycarbonyl)azetidin-3-yl)zinc iodide (Divalent)

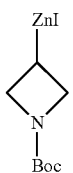

A mixture solution of trimethylchlorosilane and 1,2-dibromoethane (1.8 mL, with a volume ratio of 7:5, the dropping was completed within 10 minutes) were added slowly to zinc powder (1.78 g, 27.3 mmol) in N,N-dimethylformamide (4.2 mL) suspension in a 25 mL reaction flask. The internal temperature was controlled lower than 65° C. during the addition process. After continuing to stir for 14 minutes, 1-bromo-5-isopropoxy-2-methyl-4-nitrobenzene (6.3 g, 22 mmol) in N,N-dimethylformamide (11 mL) solution was added slowly thereinto and the internal temperature was controlled lower than 65° C. during the addition process. The reaction mixture was stirred for 5 minutes at 65° C. and then cooled down to room temperature and stirred for 30 minutes. The reaction solution was filtered to remove insoluble matters and obtain the title compound in N,N-dimethylformamide solution, which was used directly for the subsequent reaction.

Step 2: 1-(t-butyloxycarbonyl)-3-(5-isopropoxy-2-methyl-4-nitrophenyl)azetidine

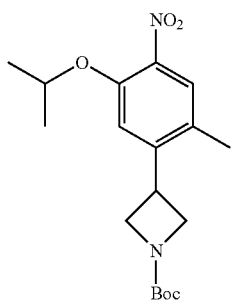 [SMILES: Cc1cc([N+](=O)[O-])c(OC(C)C)cc1C1CN(C(=O)OC(C)(C)C)C1]

[1,1'-bis (diphenylphosphino) ferrocene] palladium dichloride (0.44 g, 0.6 mmol) and cuprous iodide (0.23 g, 1.2 mmol) were added to 1-chloro-5-isopropyl-2-methyl-4-nitrobenzene (1.71 g, 6.24 mmol) in N,N-dimethylformamide (10 mL) solution under $N_2$ in a 50 mL reaction flask. And then the above (1-(t-butyloxycarbonyl) azetidin-3-yl) zinc iodide (divalent) in N,N-dimethylformamide solution (about 3-4 times equivalents) was added thereinto. The reaction mixture was stirred for 4 hours at 80° C., cooled down to room temperature, added with water and extracted with ethyl acetate and washed with saturated brine, dried and concentrated. The residue was separated by column chromatography (ethyl acetate/petroleum ether=1:10) to obtain the title compound (yellow liquid, 1 g, 50%). (MS: [M+1] none)

Step 3: 1-t-butyloxycarbonyl-3-(4-amino-5-isopropoxy-2-methylphenyl)azetidine

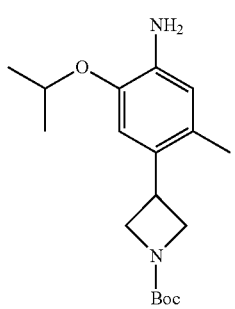

Pd/C (0.2 g, with a content of 10%) was added to 1-t-butyloxycarbonyl-3-(5-isopropoxy-2-methyl-4-nitrophenyl) azetidine (1 g, 2.8 mmol) in methanol (30 mL) in a 100 mL reaction flask. The reaction mixture was stirred for 4 hours under hydrogen atmosphere of 1 atmospheric pressure at 25° C. After completion of the reaction, the reaction solution was filtered and concentrated, and the residue was separated by column chromatography (ethyl acetate/petroleum ether=1:10) to obtain the title compound (0.63 g, 70%). (MS: [M+1] 321.2)

Example 23 Preparation of Intermediate A23

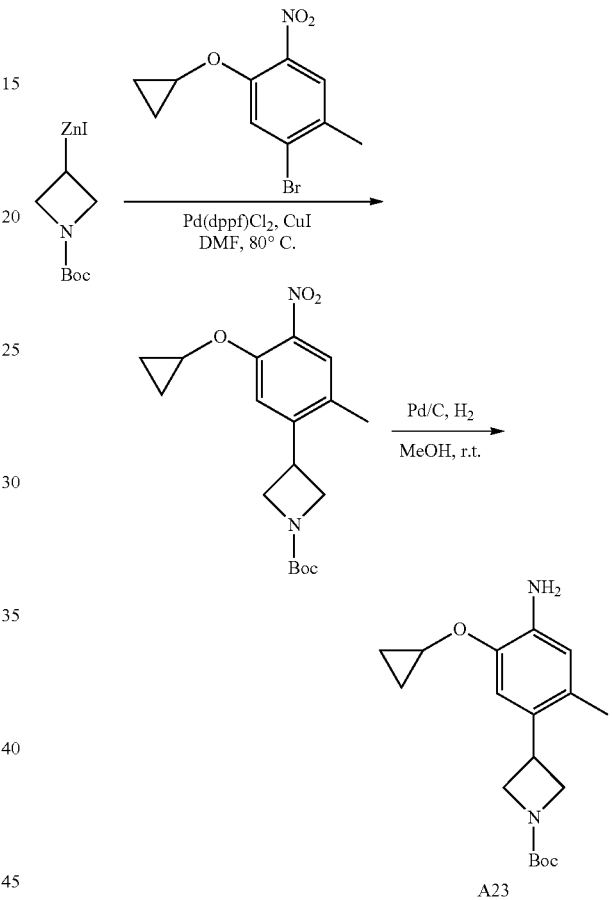

Intermediate A23, i.e., 1-t-butyloxycarbonyl-3-(4-amino-5-cyclopropyloxy-3-methylphenyl)azetidine (0.35 g) was synthesized by the above method for preparing intermediate A22, and the total yield of the two steps is 13.8%. (MS: [M+1] 319.2)

Example 24 Preparation of Intermediate A24

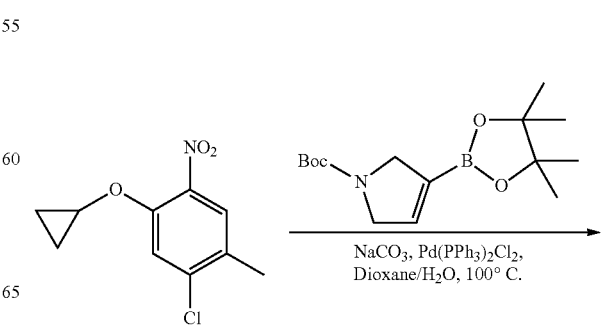

Step 1: 1-t-butyloxycarbonyl-3-(5-cyclopropyloxy-2-methyl-4-methyl phenyl)-2,5-dihydro-1H-porrole

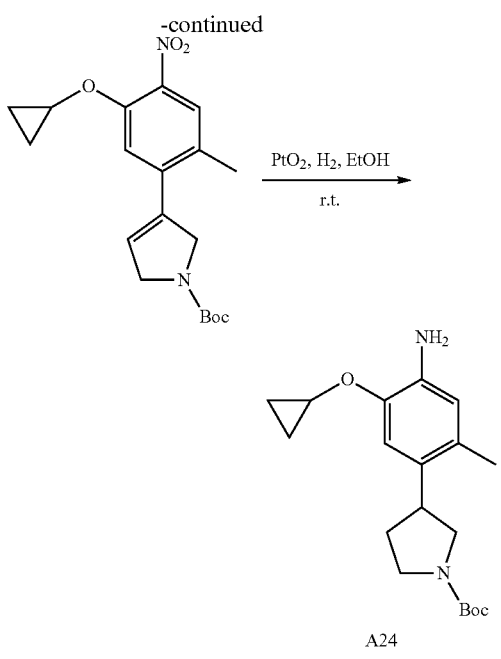

A24

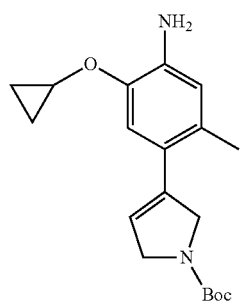 [SMILES: Cc1cc(N)c(OC2CC2)cc1C1=CCN(C(=O)OC(C)(C)C)C1]

1-t-butyloxycarbonyl-2,5-dihydro-1H-pyrrole-3-boronic acid pinacol ester (0.54 g, 1.83 mmol), 1-chloro-5-cyclopropyloxy-2-methyl-4-nitrobenzene (0.4 g, 1.76 mmol), bis(triphenylphosphine) palladium dichloride (0.12 g, 0.17 mmol), sodium carbonate (0.37 g, 3.49 mmol), 1,4-dioxane (dioxane/diox) (5 mL) and water (2 mL) were added to a 25 mL reaction flask. The reaction mixture was heated up to 100° C. in a microwave reaction meter under the protection of nitrogen and stirred for 45 minutes. After completion of the reaction, the reaction mixture was dissolved in water and extracted with ethyl acetate, and the organic layer was washed with water, dried, concentrated and purified by column chromatography (ethyl acetate/petroleum ether=1:4) to obtain the title compound (white solid, 0.35 g, 55%). (MS: [M+1] none)

Step 2: 1-t-butyloxycarbonyl-3-(4-amino-5-cyclopropyloxy-2-methyl phenyl)-pyrrolidine

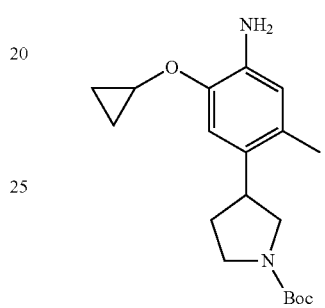

1-t-butyloxycarbonyl-3-(5-cyclopropyloxy-2-methyl-4-nitrophenyl)-2,5-dihydro-1H-porrole (0.23 g, 0.64 mmol), platinum dioxide (80 mg, with a content of 80%, 0.2 mmol) and ethanol (5 mL) were added to a 25 mL reaction flask. The reaction mixture was stirred for 2 hours under hydrogen atmosphere at room temperature. After completion of the reaction, the mixture was filtered and concentrated to obtain the crude title compound (brown oil, 0.16 g, 76%), which is used directly for the subsequent reaction. (MS: [M+1] 333.2)

Example 25-35 Preparation of Intermediate A25-A35

Intermediates A25-A35 was synthesized by the above method for preparing intermediate A24 (table 2).

TABLE 2

Intermediates A25-A35

| Nos. | Starting Materials | Intermediates | Molecular Ion Peaks [M + 1]+ |
|---|---|---|---|
| A25 | | | 347.2 |

TABLE 2-continued

Intermediates A25-A35

| Nos. | Starting Materials | Intermediates | Molecular Ion Peaks [M + 1]+ |
|---|---|---|---|
| A26 | | | 361.2 |
| A27 | | | 321.1 |
| A28 | | | 335.2 |
| A29 | | | 349.2 |

TABLE 2-continued
Intermediates A25-A35
| Nos. | Starting Materials | Intermediates | Molecular Ion Peaks [M + 1]+ |
|---|---|---|---|
| A30 | 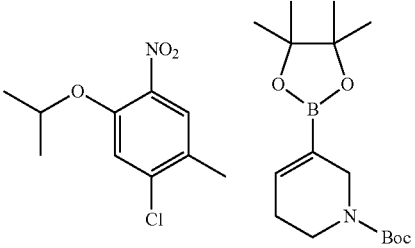 | 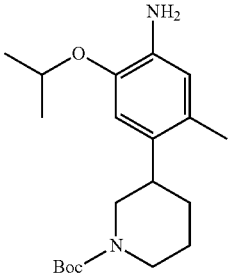 [SMILES: Cc1cc(N)c(OC(C)C)cc1C1CCCN(C(=O)OC(C)(C)C)C1] | 349.2 |
| A31 | 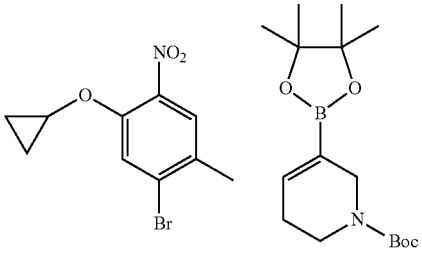 | 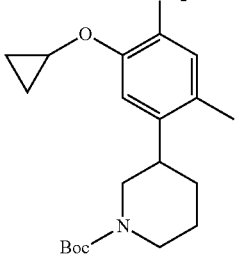 | 347.2 |
| A32 | 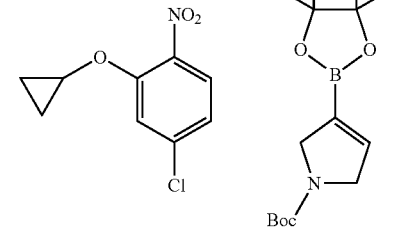 | 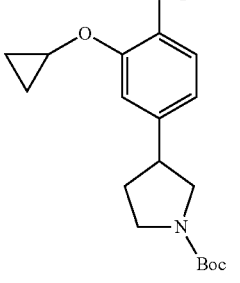 | 319.1 |
| A33 | 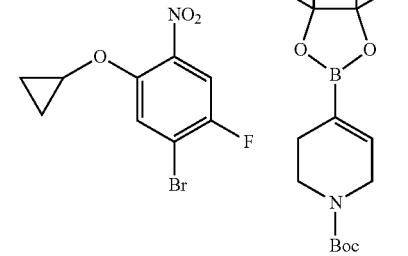 | 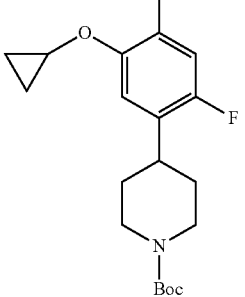 | 351.1 |
| A34 | 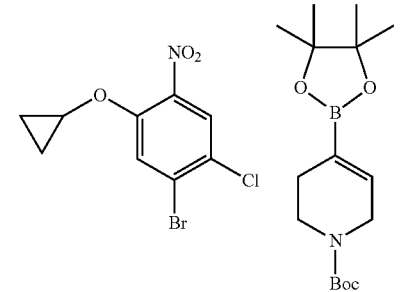 | 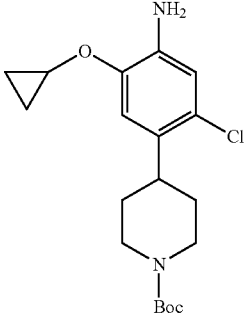 [SMILES: CC(C)(C)OC(=O)N1CCC(c2cc(OC3CC3)c(N)cc2Cl)CC1] | 367.1 |

TABLE 2-continued

Intermediates A25-A35

| Nos. | Starting Materials | Intermediates | Molecular Ion Peaks [M + 1]+ |
|---|---|---|---|
| A35 | | | 385.2 |

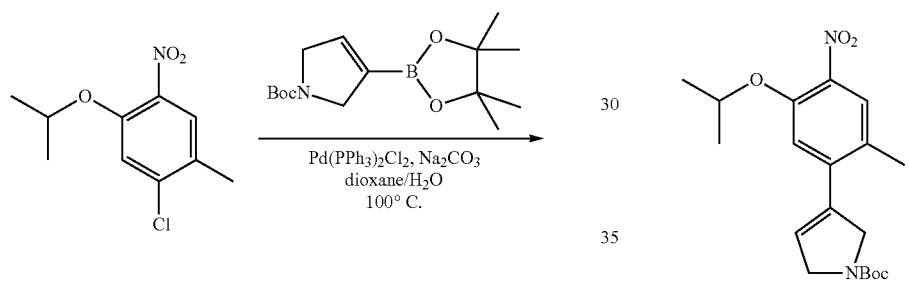

Example 36 Preparation of Intermediate A36

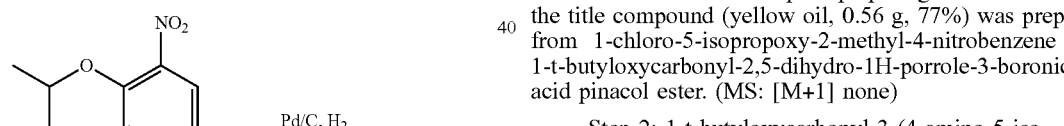

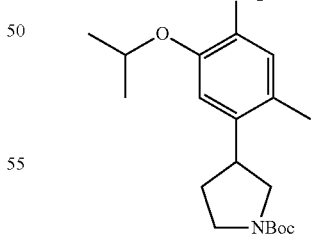

A36

Step 1: 1-t-butyloxycarbonyl-3-(5-isopropoxy-2-methyl-4-nitrophenyl)-2,5-dihydro-1H-porrole With reference to the steps of preparing intermediate A15, the title compound (yellow oil, 0.56 g, 77%) was prepared from 1-chloro-5-isopropoxy-2-methyl-4-nitrobenzene and 1-t-butyloxycarbonyl-2,5-dihydro-1H-porrole-3-boronic acid pinacol ester. (MS: [M+1] none)

Step 2: 1-t-butyloxycarbonyl-3-(4-amino-5-isopropoxy-2-methylphenyl)pyrrolidine 1-t-butyloxycarbonyl-3-(5-isopropoxy-2-methyl-4-nitrophenyl)-2,5-dihydro-1H-porrole (160 mg, 0.44 mmol), Pd/C (45 mg, 10% content) and ethanol (5 mL) were added to a 25 mL reaction flask. The reaction mixture was stirred for 4 hours under hydrogen atmosphere of 1 atmospheric pressure at 25° C. After completion of the reaction, the reaction solution was filtered and concentrated to obtain the title compound (147 mg, 100%), the crude product was used directly for the subsequent reaction. (MS: [M+1] 335.2)

Example 37-45 Preparation of Intermediate A37-A45
Intermediates A37-A45 was synthesized by the above method for preparing intermediate A36 (table 3).
TABLE 3
Intermediates A37-A45
| Nos. | Starting Material | Intermediates | Molecular Ion Peaks [M + 1]⁺ |
|---|---|---|---|
| A37 | 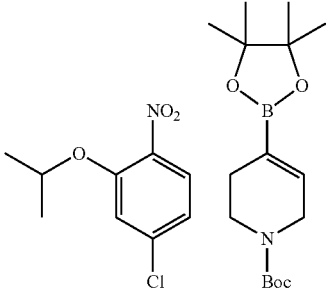 | 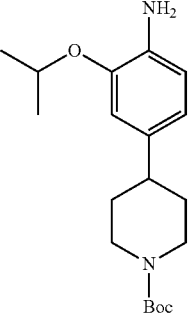 [SMILES: CC(C)Oc1cc(C2CCN(C(=O)OC(C)(C)C)CC2)ccc1N] | 335.2 |
| A38 | 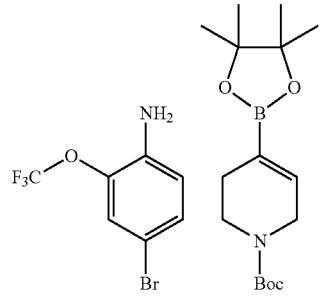 | 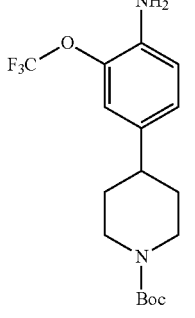 | 361.1 |
| A39 | 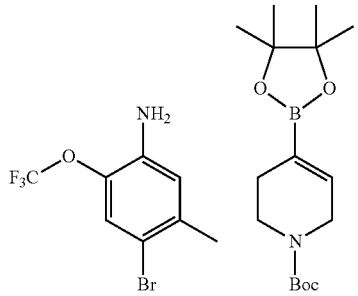 | 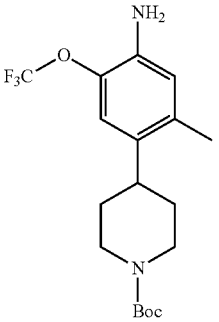 [SMILES: Cc1cc(N)c(OC(F)(F)F)cc1C1CCN(C(=O)OC(C)(C)C)CC1] | 375.1 |
| A40 | 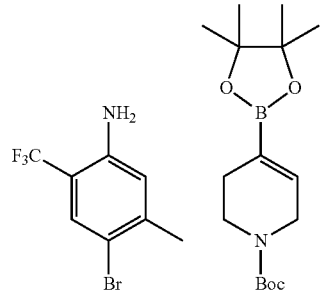 | 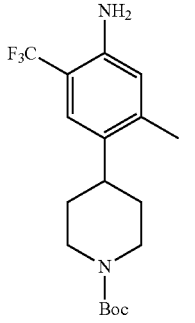 [SMILES: Cc1cc(N)c(C(F)(F)F)cc1C1CCN(C(=O)OC(C)(C)C)CC1] | 359.2 |

TABLE 3-continued
Intermediates A37-A45
| Nos. | Starting Material | Intermediates | Molecular Ion Peaks [M + 1]+ |
|---|---|---|---|
| A41 | 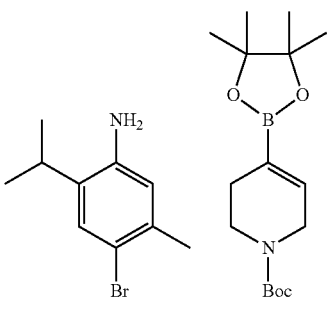 | 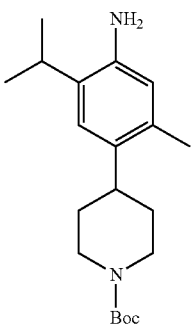 [SMILES: Cc1cc(N)c(C(C)C)cc1C1CCN(C(=O)OC(C)(C)C)CC1] | 333.2 |
| A42 | 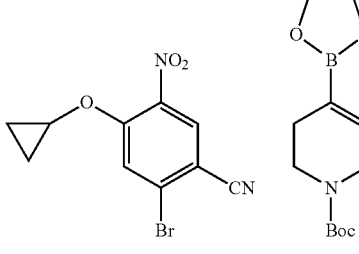 | 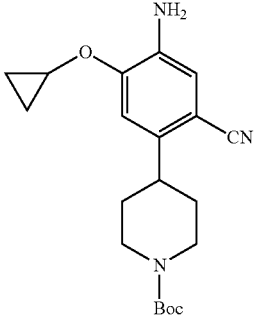 [SMILES: CC(C)(C)OC(=O)N1CCC(c2cc(OC3CC3)c(N)cc2C#N)CC1] | 358.1 |
| A43 | 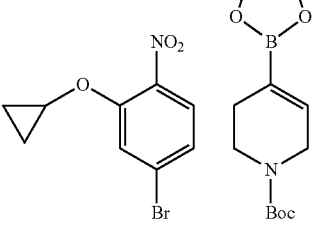 | 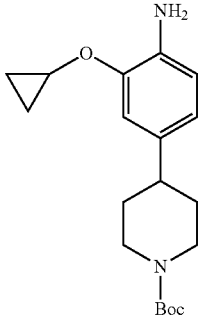 [SMILES: CC(C)(C)OC(=O)N1CCC(c2ccc(N)c(OC3CC3)c2)CC1] | 333.2 |
| A44 | 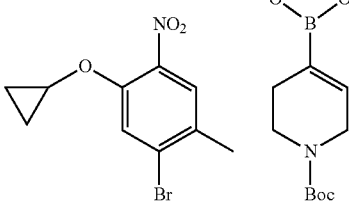 | 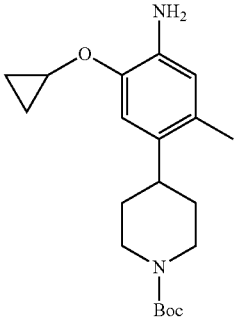 [SMILES: Cc1cc(N)c(OC2CC2)cc1C1CCN(C(=O)OC(C)(C)C)CC1] | 347.2 |

TABLE 3-continued

Intermediates A37-A45

| Nos. | Starting Material | Intermediates | Molecular Ion Peaks [M + 1]+ |
|---|---|---|---|
| A45 | 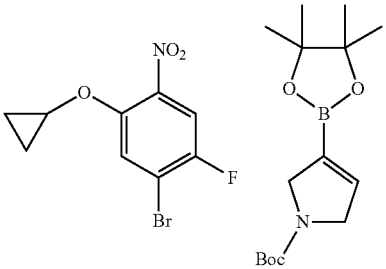 | 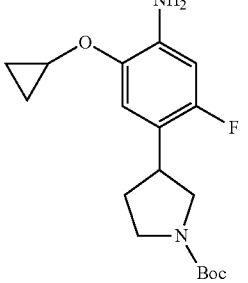 | 337.2 |

Example 46 Preparation of Intermediate A46

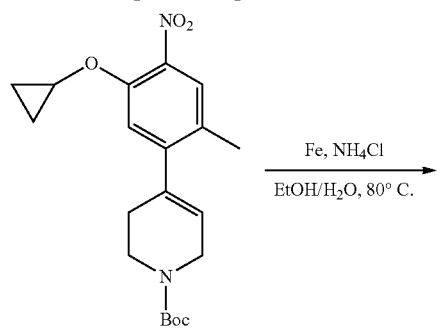

Step 1: 1(2H)-t-butyloxycarbonyl-4-(4-amino-5-cyclopropyloxy-2-methylphenyl)-5,6-dihydropyridine

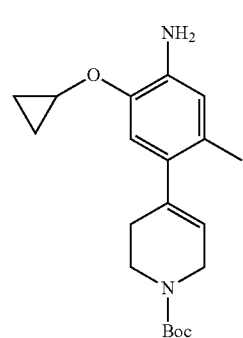 [SMILES: Cc1cc(N)c(OC2CC2)cc1C1=CCN(C(=O)OC(C)(C)C)CC1]

A46

1(2H)-t-butyloxycarbonyl-4-(5-cyclopropyloxy-2-methyl-4-nitrophenyl)-5,6-dihydropyridine (100 mg, 0.27 mmol), iron powder (90 mg, 1.60 mol), ammonium chloride (14 mg, 0.27 mmol), ethanol (8 mL) and water (4 mL) were added to a 25 ml reaction flask. The reaction mixture was heated up to 80° C. under the protection of nitrogen and stirred for 1.5 hours. After completion of the reaction, the reaction solution was filtered and concentrated, and the residue was dissolved in ethyl acetate, washed with saturated aqueous sodium bicarbonate solution and saturated brine, dried and concentrated to obtain the title compound (90 mg, 97%). The crude product was used directly for the subsequent reaction. (MS: [M+1] 345.2)

Example 47 Preparation of Intermediate A47

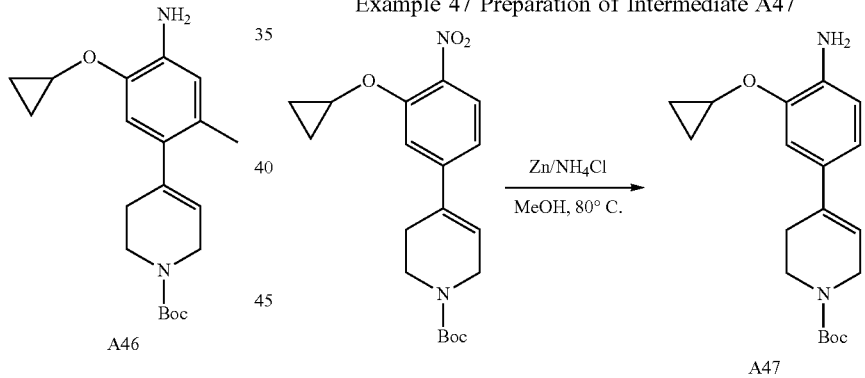

Step 1: 1(2H)-t-butyloxycarbonyl-4-(4-amino-3-cyclopropyloxyphenyl)-5,6-dihydropyridine

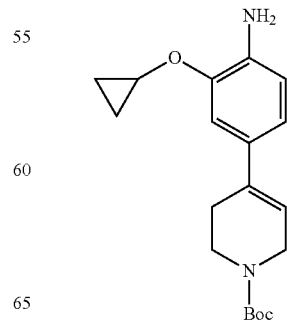

1(2H)-t-butyloxycarbonyl-4-(3-cyclopropyloxy-4-nitrophenyl)-5,6-dihydropyridine (200 mg, 0.55 mmol), zinc powder (50 mg, 0.77 mol), ammonium chloride (53 mg, 1 mmol), methanol (10 mL) and water (5 mL) were added to a 25 ml reaction flask. The reaction mixture was heated up to 80° C. under the protection of nitrogen and stirred for 2 hours. After completion of the reaction, the reaction solution was filtered and concentrated, and the residue was dissolved with ethyl acetate and washed with saturated aqueous sodium bicarbonate solution and saturated brine, dried and concentrated to obtain the title crude compound (180 mg, 98%). (MS: [M+1] 331.2)

Example 48 Preparation of Intermediate A48

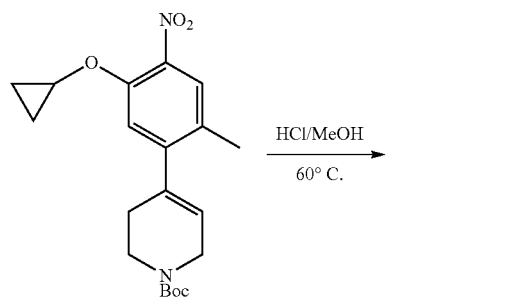

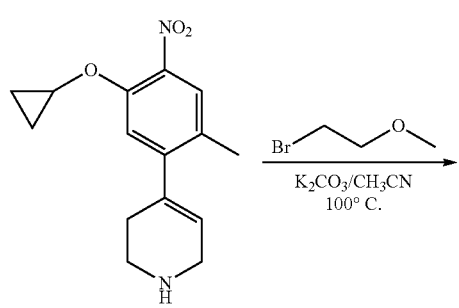

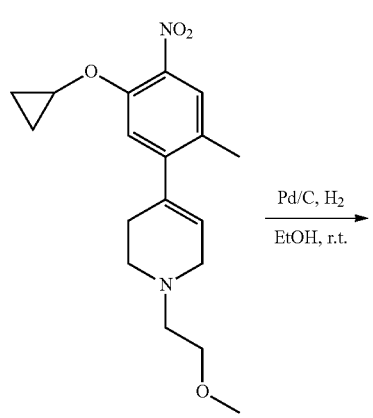

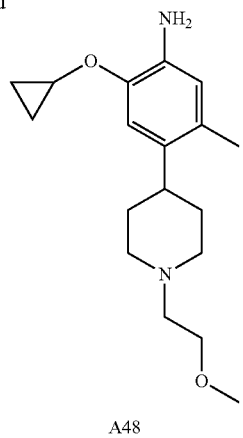

A48

Step 1: 4-(5-cyclopropyloxy-2-methyl-4-nitrophenyl)-1,2,3,6-tetrahydropyridine

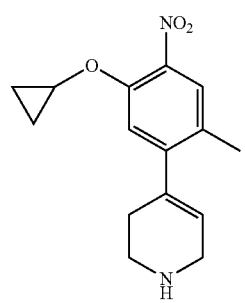 [SMILES: Cc1cc([N+](=O)[O-])c(OC2CC2)cc1C1=CCNCC1]

1(2H)-t-butyloxycarbonyl-4-(5-cyclopropyloxy-2-methyl-4-nitrophenyl)-5,6-dihydropyridine (320 mg, 0.85 mmol), methanol (2 mL) and concentrated hydrochloric acid (1 mL) were added to a 25 mL reaction flask. The reaction mixture was heated up to 60° C. and stirred for 30 minutes. The reaction solution was concentrated and the residue was neutralized with saturated aqueous sodium bicarbonate solution and extracted with ethyl acetate, dried and concentrated to obtain the title compound (210 mg, 90%), which was used directly for the subsequent reaction. (MS: [M+1] 275.1)

Step 2: 4-(5-cyclopropyloxy-2-methyl-4-nitrophenyl)-1-(2-methoxy ethyl)-1,2,3,6-tetrahydropyridine

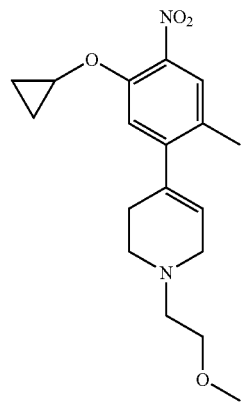 [SMILES: COCCN1CC=C(c2cc(OC3CC3)c([N+](=O)[O-])cc2C)CC1]

4-(5-cyclopropyloxy-2-methyl-4-nitrophenyl)-1,2,3,6-tetrahydropyridine (40 mg, 0.15 mmol), 1-bromo-2-methoxy-ethane (40 mg, 0.29 mmol), potassium carbonate (80 mg, 0.58 mmol) and 2 mL acetonitrile were added to a 25 mL reaction flask. The reaction mixture was heated up to 100° C. under the protection of nitrogen and stirred for 3 hours. The reaction solution was cooled down and filtered, and the filtrate was concentrated to obtain the crude product, which was separated by column chromatography (dichloromethane/methanol=10:1) to obtain the title compound (40 mg, 80%). (MS: [M+1] 333.2)

Step 3: 2-cyclopropyloxy-4-(1-(2-methoxyethyl)piperidine-4-yl)-5-methylaniline

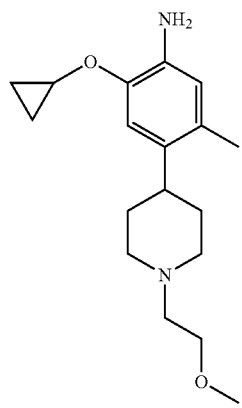 [SMILES: COCCN1CCC(c2cc(OC3CC3)c(N)cc2C)CC1]

4-(5-cyclopropyloxy-2-methyl-4-nitrophenyl)-1-(2-methoxyethyl)-1,2,3,6-tetrahydropyridine (40 mg, 0.12 mmol), Pd—C (20 mg, 10% content) and ethanol (5 mL) were added to a 25 mL reaction flask. The reaction mixture was stirred for 4 hours under hydrogen atmosphere of 1 atmospheric pressure at 25° C. After completion of the reaction, the reaction solution was filtered and concentrated to obtain the title compound (37 mg, 100%). The crude product was used directly for the subsequent reaction. (MS: [M+1] 305.2)

Example 49 Preparation of Intermediate A49

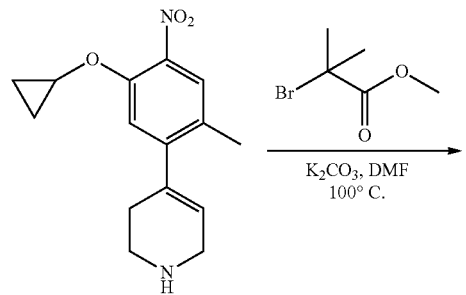

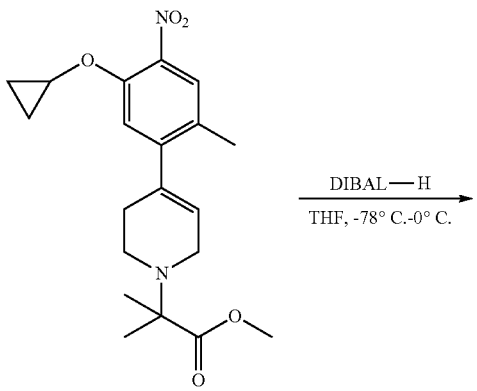

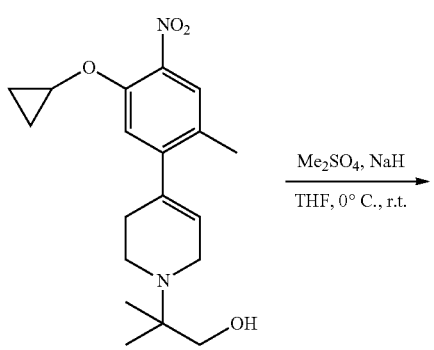

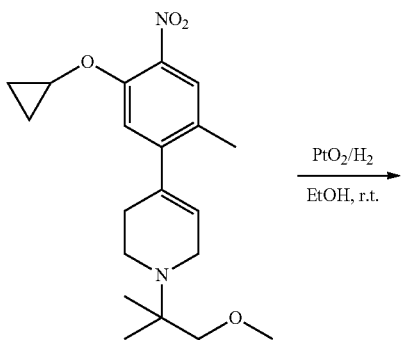

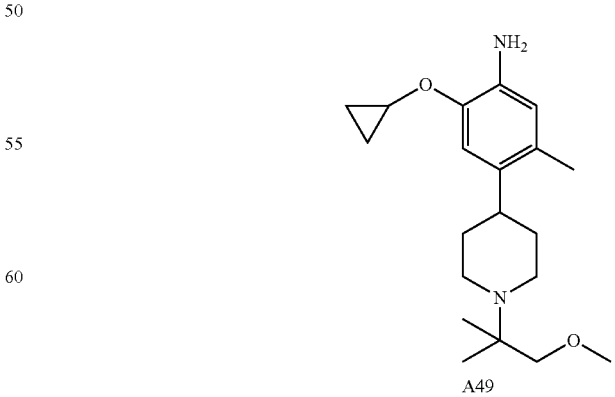

Step 1: Methyl 2-(4-(5-cyclopropyloxy-2-methyl-4-nitrophenyl)-5,6-dihydropyridine-1(2H)-2-methyl propanoate

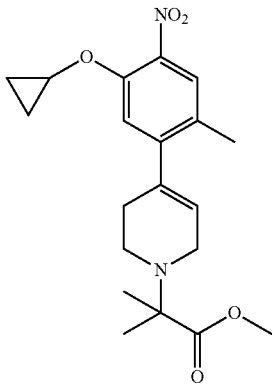 [SMILES: COC(=O)C(C)(C)N1CC=C(c2cc(OC3CC3)c([N+](=O)[O-])cc2C)CC1]

4-(5-cyclopropyloxy-2-methyl-4-nitrophenyl) 1,2,3,6-tetrahydropyridine (1 g, 6.65 mmol), methyl 2-bromo-2-methyl propanoate (2.6 g, 14.4 mmol), potassium carbonate (1 g, 7.3 mmol) and N,N-dimethylformamide (10 mL) were added to a 20 mL microwave tube. The reaction mixture was heated up to 100° C. by microwave under the protection of nitrogen and stirred overnight. After completion of the reaction, the reaction solution was added with ethyl acetate and water, and the organic layer was washed with saturated brine, dried and concentrated. The thus obtained crude product was separated and purified by column chromatography (silica gel column, eluent:ethyl acetate/petroleum ether, gradient: 0~50% ethyl acetate) to obtain the title compound (0.7 g, 51%). (MS: [M+1] 375.2)

Step 2: 2-(4-(5-cyclopropyloxy-2-methyl-4-nitrophenyl)-5,6-dihydropyridine-1(2H)-2-methyl-1-propanol

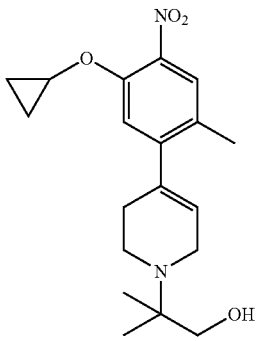 [SMILES: Cc1cc([N+](=O)[O-])c(OC2CC2)cc1C1=CCN(C(C)(C)CO)CC1]

Methyl 2-(4-(5-cyclopropyloxy-2-methyl-4-nitrophenyl)-5,6-dihydropyridin-1(2H)-yl)-2-methyl propanoate (700 mg, 1.87 mmol) and dried methylene chloride (7 mL) were added to a 25 mL reaction flask. The reaction mixture was cooled down to −78° C., and 1.5 M diisobutylaluminum hydride (6.2 mL, 9.3 mmol) was added slowly at this temperature, and then the reaction solution temperature was raised up to 0° C. and stirred overnight. After completion of the reaction, the reaction solution was poured into saturated ammonium chloride solution, and the organic layer was dried and concentrated. The thus obtained crude product was separated and purified by column chromatography (silica gel column, eluent:ethyl acetate/petroleum ether, gradient: 0~30% ethyl acetate) to obtain the title compound (330 mg, 51%). (MS: [M+1] 349.2)

Step 3: 4-(5-cyclopropyloxy-2-methyl-4-nitrophenyl)-1-(1-methoxy-2-methylpropane-2-yl)-1,2,3,6-tetrahydropyridine

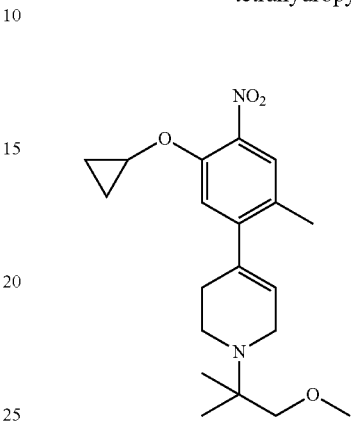

2-(4-(5-cyclopropyloxy-2-methyl-4-nitrophenyl)-5,6-dihydropyridine-1(2H)-yl)-2-methyl-1-propanol (330 mg, 0.95 mmol) and tetrahydrofuran (10 mL) were added to a 25 mL reaction flask. The mixture was cooled down to 0° C. under the protection of $N_2$, added with NaH (60%, 305 mg, 7.63 mmol) and then stirred for 20 minutes and added slowly with dimethyl sulfate (360 mg, 2.85 mmol). The reaction solution was slowly heated up to room temperature and stirred overnight. After completion of the reaction, saturated aqueous sodium bicarbonate solution and ethyl acetate were added and stirred for 10 minutes, and the organic layer was collected and washed with saturated brine, dried and concentrated. The thus obtained crude product was separated and purified by column chromatography (silica gel column, eluent:ethyl acetate/petroleum ether, gradient: 0~30% ethyl acetate) to obtain the title compound (170 mg, 50%). (MS: [M+1] 361.2)

Step 4: 2-cyclopropyloxy-4-(1-(1-methoxy-2-methylpropan-2-yl)-piperidin-4-yl)-5-methyl-aniline

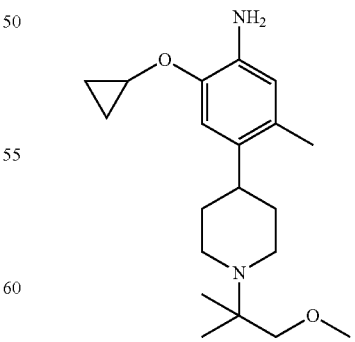

4-(5-cyclopropyloxy-2-methyl-4-nitrobenzene)-1-(1-methoxy-2-methylpropan-2-yl)-1,2,3,6-tetrahydropyridine (50 mg, 0.14 mmol), $PtO_2$ (25 mg) and ethanol (5 mL) were added to a 25 mL reaction flask. The reaction mixture was stirred for 3 hours under hydrogen atmosphere of 1 atmospheric pressure at 25° C. After completion of the reaction, the reaction solution was filtered and concentrated to obtain the title compound (35 mg) and the crude product was used directly for the subsequent reaction. (MS: [M+1] 333.2)

Example 50 Preparation of Intermediate A50

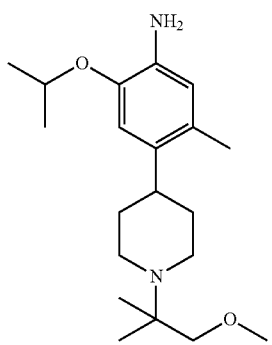 [SMILES: COCC(C)(C)N1CCC(c2cc(OC(C)C)c(N)cc2C)CC1]

Intermediate A50 (35 mg) was synthesized by the above method for preparing intermediate A49, and the crude product was used directly for the subsequent reaction. (MS: [M+1] 335.2)

Example 51 Preparation of Intermediate A51

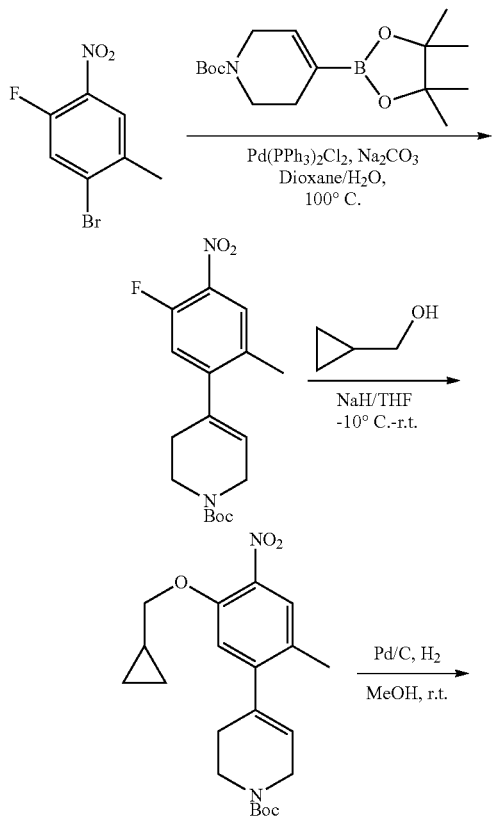

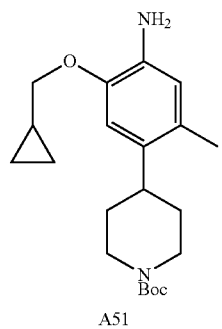

A51

Step 1: (2H)-t-butyloxycarbonyl-4-(5-fluoro-2-methyl-4-nitrophenyl)-5,6-dihydropyridine

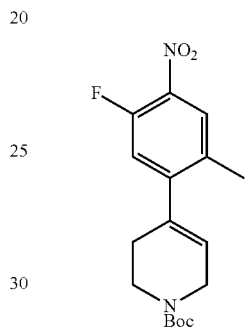

With reference to the steps of preparing intermediate A24, the title compound (240 mg, 70%) was prepared from 1-bromo-5-fluoro-2-methyl-4-nitrobenzene and 1-t-butyloxycarbonyl-1,2,3,6-tetrahydropyridin-4-boronic acid pinacol ester. (MS: [M+1] none)

Step 2: 1(2H)-t-butyloxycarbonyl-4-(5-(cyclopropylmethoxy)-2-methyl-4-nitrophenyl)-5,6-dihydropyridine

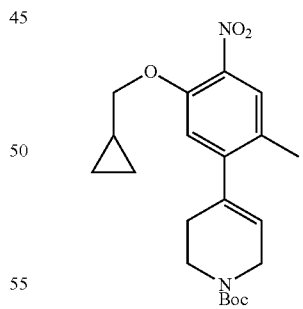

Under the protection of nitrogen, 5 mL tetrahydrofuran was added to a 25 mL round-bottomed flask and stirred, added with sodium-hydrogen (53 mg, with a content of 60%, 1.3 mmol) and cooled down to −10° C. Cyclopropanemethanol (100 mg, 1.4 mmol) in tetrahydrofuran solution prepared in advance was dropped to the above solution and stirred for 10 minutes, and then 1(2H)-t-butyloxycarbonyl-4-(5-fluoro-2-methyl-4-nitrophenyl)-5,6-dihydropyridine (100 mg, 0.3 mmol) was dropped and the reaction solution was heated up slowly to room temperature. The reaction solution was concentrated and the residue was added with water and ethyl acetate and extracted twice with ethyl acetate. The organic phase was dried and concentrated, and the crude product was purified by column chromatography (ethyl acetate/petroleum ether=1:10) to obtain the title compound (light yellow solid, 110 mg, 95%). (MS: [M+1] none)

Step 3: 1-t-butyloxycarbonyl-4-(4-amino-5-(cyclopropylmethoxy)-2-methylphenyl)piperidine

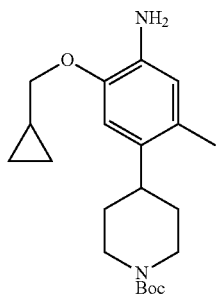 [SMILES: Cc1cc(N)c(OCC2CC2)cc1C1CCN(C(=O)OC(C)(C)C)CC1]

1(2H)-t-butyloxycarbonyl-4-(5-(cyclopropylmethoxy)-2-methyl-4-nitrophenyl)-5,6-dihydropyridine (110 mg, 0.28 mmol), Pd/C (40 mg, 10% content) and ethanol (5 mL) were added to a 25 mL reaction flask. The reaction mixture was stirred for 4 hours under hydrogen atmosphere of 1 atmospheric pressure at 25° C. After completion of the reaction, the reaction solution was filtered, concentrated, and separated by column chromatography (ethyl acetate/petroleum ether=1:10) to obtain the title compound (99 mg, 98%). (MS: [M+1] 361.2)

Example 52 Preparation of Intermediate A52

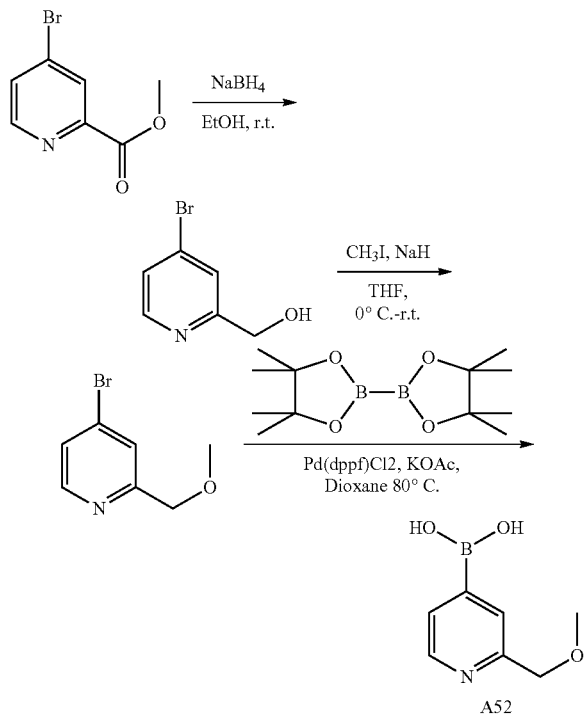

Step 1: 2-hydroxymethyl-4-bromopyridine

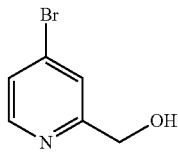

Methyl 4-bromo-pyridine formate (990 mg, 4.58 mmol) and ethanol (250 mL) were added to a 250 mL reaction flask. Under stirring, sodium borohydride (380 mg, 10 mg) was slowly added to the reaction system in batches. The reaction mixture was stirred for 18 hours under the protection of nitrogen at room temperature. After completion of the reaction, 5 mL acetone was added to the reaction system, followed by stirring for 15 minutes. The reaction solution was filtered, concentrated and added with ethyl acetate and water, and the layers were separated. The organic phase was dried and concentrated to obtain the title compound (yellow liquid, 760 mg, 88%), the crude product was used directly for the subsequent reaction. (MS: [M+1] 187.9)

Step 2: 4-bromo-2-methoxy-methylpyridine

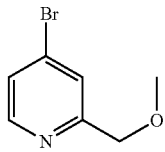

2-hydroxymethyl-4-bromopyridine (760 mg, 4 mmol) in tetrahydrofuran (10 mL) solution obtained in last step was slowly added with sodium hydrogen (325 mg, with a content of 60%, 8.13 mmol) at 0° C. in a 250 mL reaction flask. The reaction mixture was stirred for 0.5 hours at 0° C., slowly added with methyl iodide (692 mg, 4.87 mmol), and then heated up to room temperature, followed by stirring for 5 hours. After completion of the reaction, the reaction solution was poured into ethyl acetate, added with saturated aqueous ammonium chloride solution to neutralize until pH value was 8-9. The organic phase was dried, filtered, concentrated and purified by column chromatography (ethyl acetate/petroleum ether=1:2) to obtain the title compound (yellow oil, 420 mg, 52%). (MS: [M+1] 201.9)

Step 3: 2-methoxy-methylpyridine-4-boronic acid

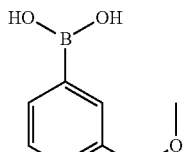

4-bromo-2-methoxy-methylpyridine (402 mg, 2 mmol), bis(pinacolato) diboron (762 mg, 3 mg), potassium acetate (588 mg, 6 mmol), [1,1'-bis (diphenylphosphino) ferrocene] palladium dichloride (147 mg, 0.2 mmol) and 1,4-dioxane (10 mL) were added to a 250 mL reaction flask. The reaction mixture was heated up to 80° C. and stirred for 3 hours. After completion of the reaction, the mixture was cooled down and added with ethyl acetate (50 mL), and washed with saturated aqueous ammonium chloride. The organic phase was dried, filtered and concentrated to obtain the title compound (black oil, 300 mg, 89%). The crude product was used directly for the subsequent reaction. (MS: [M+1] 168.0)

Example 53 Preparation of Intermediate A53

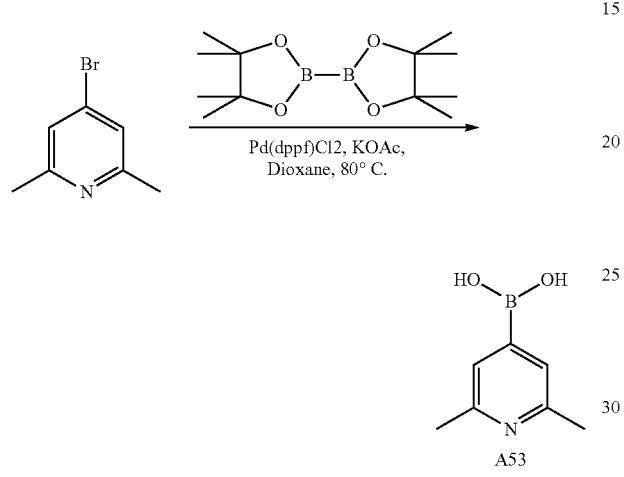

Step 1: 2,6-dimethylpyridine-4-boronic acid

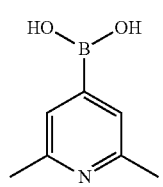

With reference to the steps of preparing intermediate A52, the title compound (brown oil, 370 mg, 81%) was prepared from 4-bromo-2, 6-dimethylpyridine and bis(pinacolato)diboron. (MS: [M+1] 152.1)

Example 54 Preparation of Intermediate A54

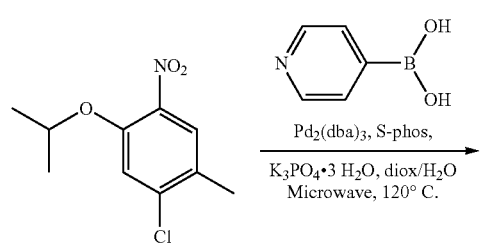

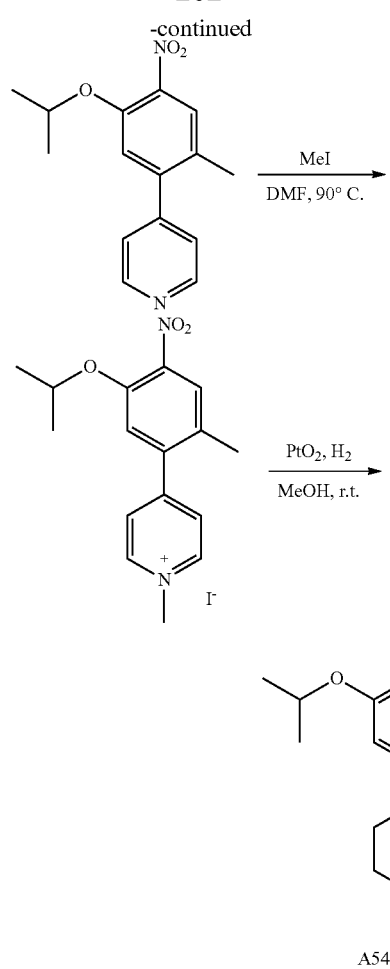

Step 1: 4-(5-isopropoxy-2-methyl-4-nitrophenyl)pyridine

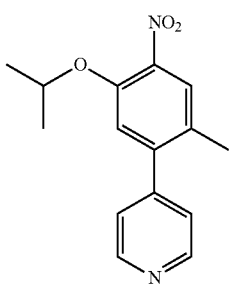 [SMILES: Cc1cc([N+](=O)[O-])c(OC(C)C)cc1-c1ccncc1]

1-chloro-5-isopropoxy-2-methyl-4-nitrobenzene (0.85 g, 3.7 mmol), 4-pyridine boronic acid (0.5 g, 4.1 mmol), tris(dibenzylideneacetone) dipalladium (0.34 g, 0.37 mmol), 2-dicyclohexyl phosphino-2',6'-dimethoxy-biphenyl (S-phos) (0.38 g, 0.93 mmol), potassium phosphate trihydrate (2 g, 7.51 mmol), 1,4-dioxane (6 mL) and water (3 mL) were added to a 20 mL microwave tube. The reaction mixture was heated up to 120° C. by microwave under the protection of nitrogen and stirred for 40 minutes. After completion of the reaction, the reaction solution was added with ethyl acetate, washed with saturated brine, dried and concentrated. The thus obtained crude product was separated and purified by column chromatography (silica gel column, eluent:ethyl acetate/petroleum ether, gradient: 0~50% ethyl acetate) to obtain the title compound (yellow solid, 0.81 g, 81%). (MS: [M+1] 273.1)

Step 2: 4-(5-isopropoxy-2-methyl-4-nitrophenyl)-1-methyl-pyridinium iodide

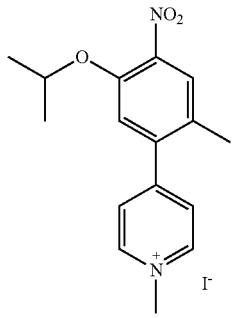

4-(5-isopropyl-2-methyl-4-nitrophenyl) pyridine (400 mg, 1.47 mmol), methyl iodide (570 mg, 4 mg), N,N-dimethylformamide (10 mL) were added to a 25 mL reaction flask. The reaction mixture was heated up to 90° C. under the protection of nitrogen and stirred overnight. The reaction solution was concentrated to obtain the title compound (yellow solid, 610 mg, 100%). The crude product was used directly for the subsequent reaction. (MS: [M+1] 287.1)

Step 3: 2-isopropoxy-5-methyl-4-(1-methyl-piperidin-4-yl)-phenylamine

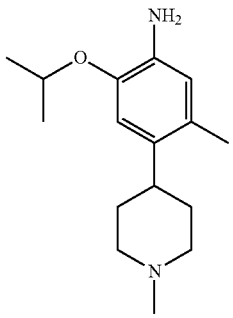 [SMILES: Cc1cc(N)c(OC(C)C)cc1C1CCN(C)CC1]

4-(5-isopropoxy-2-methyl-4-nitrophenyl)-1-methyl-pyridinium iodide (320 mg, 0.77 mmol), platinum dioxide (100 mg, 85% platinum) and methanol (5 mL) were added to a 25 mL reaction flask. The reaction mixture was stirred for 16 hours under hydrogen atmosphere of 1 atmospheric pressure at 25° C. After completion of the reaction, the reaction solution was filtered and concentrated. The thus obtained crude product was separated and purified by column chromatography (silica gel column, eluent:methylene chloride/methanol=10:1) to obtain the title compound (192 mg, 95%). (MS: [M+1] 263.2)

Example 55-63 Preparation of Intermediate A55-A63

Intermediates A55-A63 were synthesized by the above method for preparing intermediate A54 (table 4).

TABLE 4

Intermediates A55-A63

| Nos. | Starting Materials | Intermediate | Molecular Ion Peaks [M + 1]+ |
|---|---|---|---|
| A55 | | | 305.2 |
| A56 | | | 307.4 |

TABLE 4-continued
Intermediates A55-A63
| Nos. | Starting Materials | Intermediate | Molecular Ion Peaks [M + 1]+ |
|---|---|---|---|
| A57 | 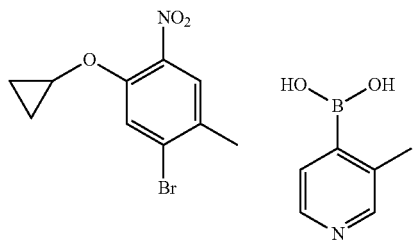 | 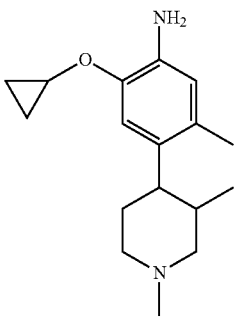 [SMILES: Cc1cc(N)c(OC2CC2)cc1C1CCN(C)CC1C] | 275.1 |
| A58 | 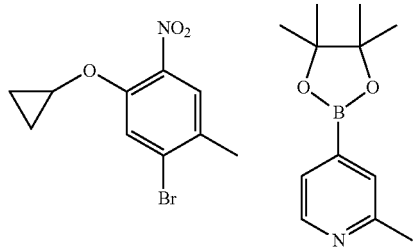 | 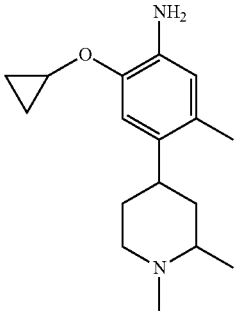 [SMILES: Cc1cc(N)c(OC2CC2)cc1C1CCN(C)C(C)C1] | 275.1 |
| A59 | 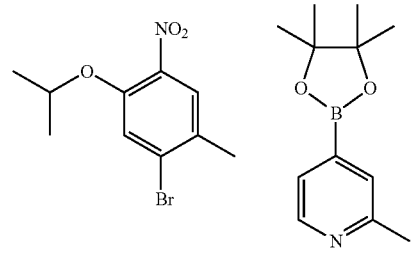 | 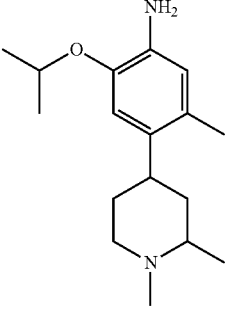 [SMILES: Cc1cc(N)c(OC(C)C)cc1C1CCN(C)C(C)C1] | 277.3 |
| A60 | 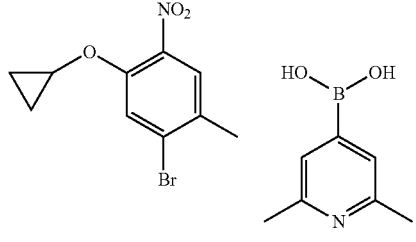 | 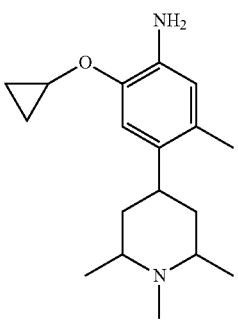 [SMILES: Cc1cc(N)c(OC2CC2)cc1C1CC(C)N(C)C(C)C1] | 289.2 |

TABLE 4-continued
Intermediates A55-A63
| Nos. | Starting Materials | Intermediate | Molecular Ion Peaks [M + 1]+ |
|---|---|---|---|
| A61 | 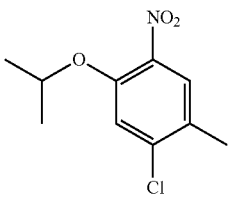 | 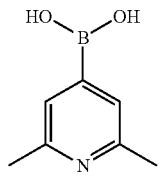 | 291.2 |
| A62 | 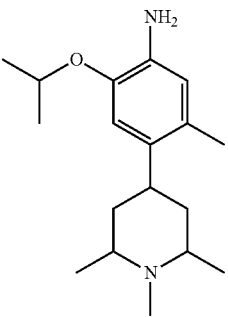 [SMILES: Cc1cc(N)c(OC(C)C)cc1C1CC(C)N(C)C(C)C1] | 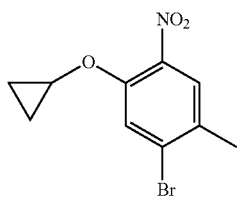 | 261.2 |
| A63 | 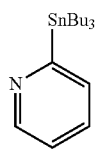 | 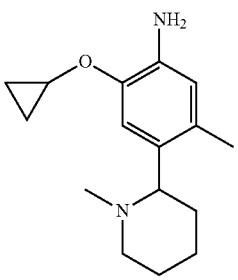 [SMILES: Cc1cc(N)c(OC2CC2)cc1C1CCCCN1C] | 332.2 |
Example 64 Preparation of Intermediate A64
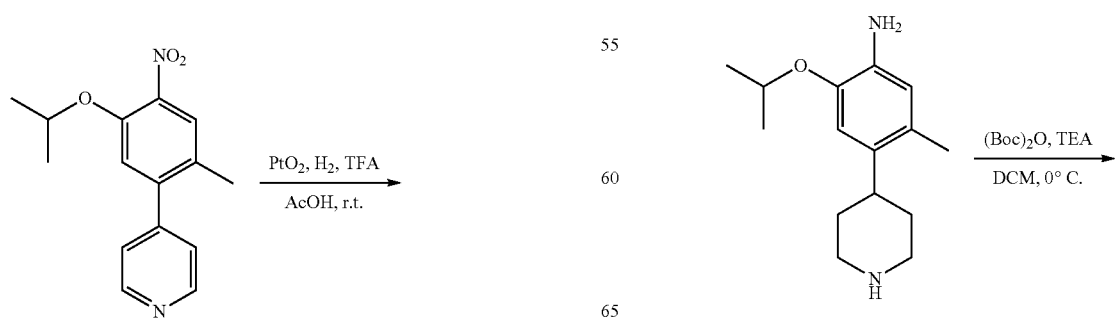
-continued 2-isopropoxy-5-methyl-4-(piperidin-4-)-phenylamine (960 mg, 3.86 mmol), triethylamine (1.1 mL, 7.72 mmol) and dichloromethane (20 mL) were added to a 50 mL reaction flask. The reaction mixture was cooled down to 0° C., slowly added with di-tert-butyl dicarbonate (841 mg, 3.86 mmol) in dichloromethane solution (3 mL). The reaction mixture was stirred for 1 hour at 0° C. After completion of the reaction, the reaction solution was concentrated, and the thus obtained crude product was separated and purified by column chromatography (silica gel column, eluent:ethyl acetate/petroleum ether, gradient: 0~20% ethyl acetate) to obtain the title compound (yellow solid, 672 mg, the total yield of the two steps is 47%). (MS: [M+1] 371.3)

Example 65 Preparation of Intermediate A65

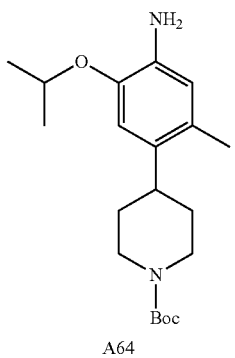
A64

Step 1:
2-isopropoxy-5-methyl-piperidin-4-yl-aniline

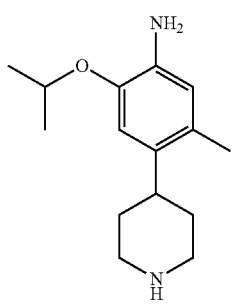 [SMILES: Cc1cc(N)c(OC(C)C)cc1C1CCNCC1]

4-(5-isopropyl-2-methyl-4-nitrophenyl) pyridine (1.05 g, 3.86 mmol), platinum dioxide (415 mg, 85% platinum), trifluoroacetic acid (880 mg, 7.72 mmol) and acetic acid (5 mL) were added to a 100 mL reaction flask. The reaction mixture was stirred for 16 hours under hydrogen atmosphere of 1 atmospheric pressure at 25° C. After completion of the reaction, the reaction solution was filtered and concentrated. The residue was neutralized with saturated aqueous sodium bicarbonate solution, and extracted with methylene chloride/isopropanol (2:1 by volume), dried and concentrated to obtain the title compound (brown oil, 960 mg). The crude product was used directly for the subsequent reaction. (MS: [M+1] 249.2)

Step 2: 2-isopropoxy-5-methyl-4-(N-t-butyloxycarbonyl-piperidin-4-)-phenylamine

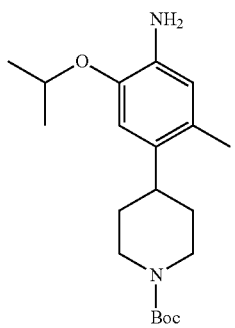 [SMILES: Cc1cc(N)c(OC(C)C)cc1C1CCN(C(=O)OC(C)(C)C)CC1]

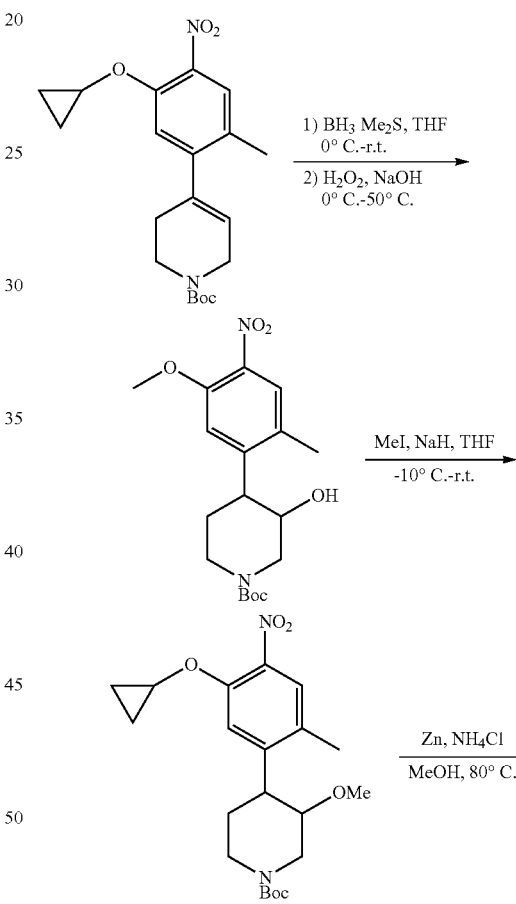

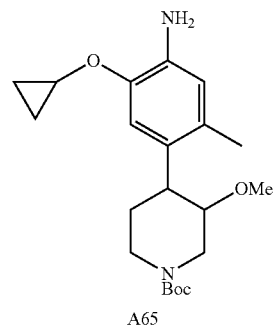
A65

Step 1: 1-t-butyloxycarbonyl-4-(5-cyclopropoxy-2-methyl-4-nitrophenyl)-3-hydroxy-piperidine

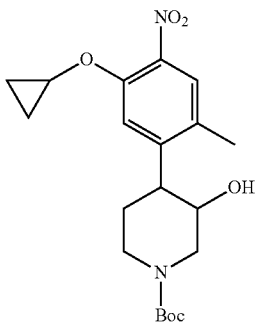 [SMILES: Cc1cc([N+](=O)[O-])c(OC2CC2)cc1C1CCN(C(=O)OC(C)(C)C)CC1O]

1-t-butyloxycarbonyl-4-(5-cyclopropoxy-2-methyl-4-nitrophenyl)-3,6-dihydro-2H-pyridine (500 mg, 1.34 mmol) and tetrahydrofuran (7 mL) were added to a 25 mL reaction flask. The reaction mixture was cooled down to 0° C., slowly added with borane-dimethyl sulfide complex (1.34 mL, 2M tetrahydrofuran solution, 2.68 mmol) at this temperature. The reaction mixture was heated up to room temperature and stirred for 16 hours. The reaction mixture was cooled down again to 0° C. and added very slowly with 4N aqueous sodium hydroxide solution (1 mL, 4 mmol) at this temperature, followed by adding slowly 30% hydrogen peroxide (0.46 mL, 4 mmol). The reaction mixture was heated up to 50° C. and stirred for 2 hours. After completion of the reaction, the reaction solution was poured into water, extracted with ethyl acetate, and washed with sodium bisulfite solution and saturated brine, dried and concentrated. The thus obtained crude product was separated and purified by column chromatography (silica gel column, eluent:ethyl acetate/petroleum ether, gradient: 0~30% ethyl acetate) to obtain the title compound (yellow solid, 260 mg, 50%). (MS: [M+1] 415.2)

Step 2: 1-t-butyloxycarbonyl-4-(5-cyclopropoxy-2-methyl-4-nitrophenyl)-3-methoxy-piperidine

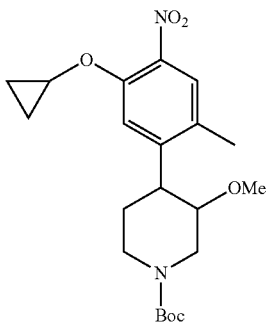 [SMILES: COC1CN(C(=O)OC(C)(C)C)CCC1c1cc(OC2CC2)c([N+](=O)[O-])cc1C]

Under the protection of nitrogen, 5 mL tetrahydrofuran was added to a 25 mL round-bottomed flask and stirred, added with sodium-hydrogen (53 mg, with a content of 60%, 1.33 mmol) and cooled down to −10° C. 1-t-butyloxycarbonyl-4-(5-cyclopropoxy-2-methyl-4-nitrophenyl)-3-hydroxy-piperidine in tetrahydrofuran solution prepared in advance was dropped to the above solution and stirred for 10 minutes, and then iodomethane (70 mg, 0.42 mmol) was dropped and the reaction solution was heated up slowly to room temperature. After completion of the reaction, the reaction solution was concentrated and the residue was diluted with water and extracted with ethyl acetate. The organic phase was dried and concentrated to obtain the title compound. The crude product was used directly for the subsequent reaction. (MS: [M+1] 407.2)

Step 3: 1-t-butyloxycarbonyl-4-(4-amino-5-cyclopropoxy-2-nitrophenyl)-3-methoxypiperidine

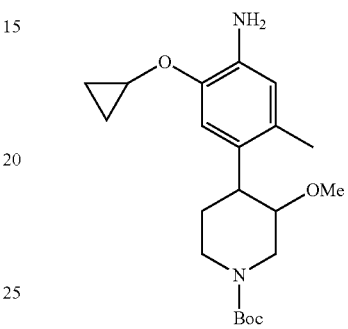

1-t-butyloxycarbonyl-4-(5-cyclopropoxy 2-methyl-4-nitrophenyl)-3-methoxypiperidine (90 mg, 0.22 mmol), zinc powder (95 mg, 1.45 mmol), ammonium chloride (54 mg, 1 mmol), methanol (10 mL) and water (5 mL) were added to a 25 mL reaction flask. The reaction mixture was heated up to 80° C. under the protection of nitrogen and stirred for 2 hours. After completion of the reaction, the reaction solution was filtered and concentrated, and the residue was dissolved with ethyl acetate, washed with saturated sodium bicarbonate solution and saturated brine, dried and concentrated and separated by preparative chromatography (ethyl acetate/petroleum ether=1:4) to obtain the title compound (63 mg, 76%). (MS: [M+1] 377.2)

Example 66 Preparation of Intermediate A66 and A67

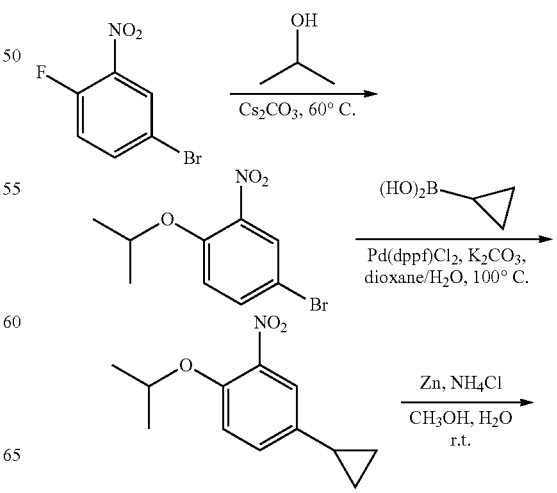

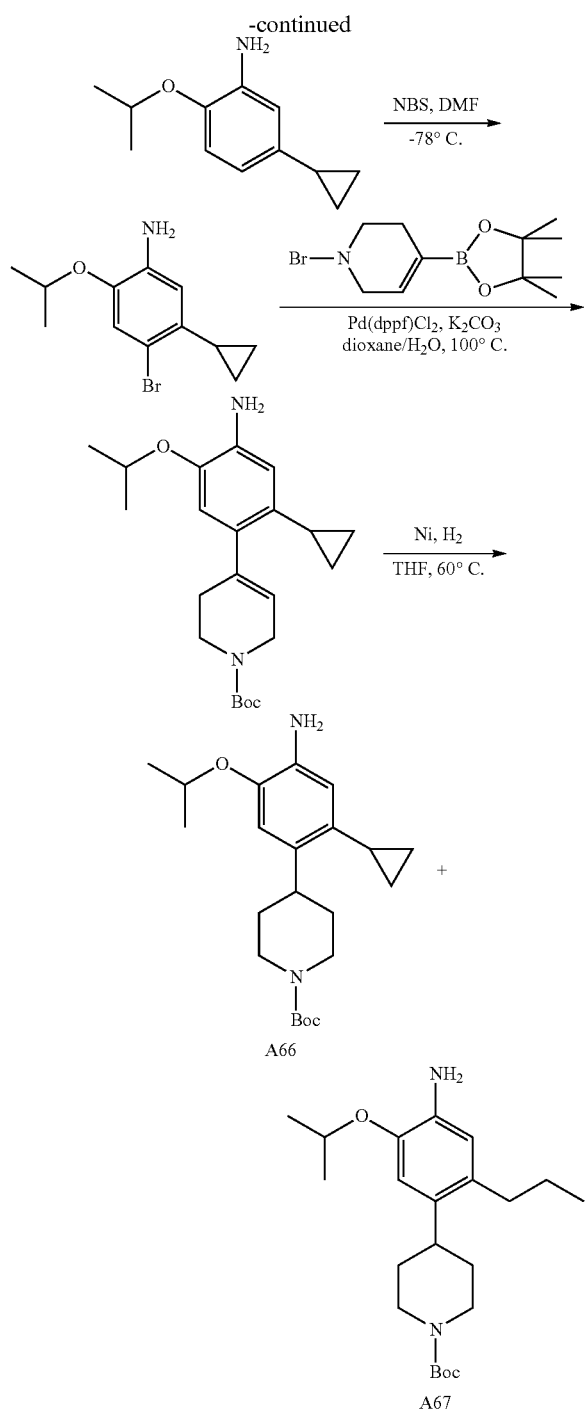

A66

A67

Step 1: 4-bromo-1-isopropoxy-2-nitrobenzene

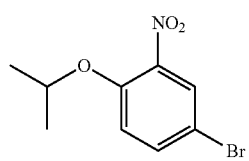

4-bromo-1-fluoro-2-nitrobenzene (5.0 g, 22.8 mmol), cesium carbonate (14.9 g, 45.7 mmol) and cyclopropanol (40 mL) were added to a 100 ml single-port reaction flask. The reaction mixture was stirred and reacted at 60° C. overnight. After completion of the reaction, ethyl acetate was added for dilution. The organic phase was washed with saturated brine, dried and concentrated. The thus obtained crude product was separated and purified by column chromatography (eluent:ethyl acetate/petroleum ether, gradient: 0~15% ethyl acetate) to obtain the title compound (yellow solid, 5.2 g, 88%). (MS: [M+1] none)

Step 2: 4-cyclopropyl-1-isopropoxy-2-nitrobenzene

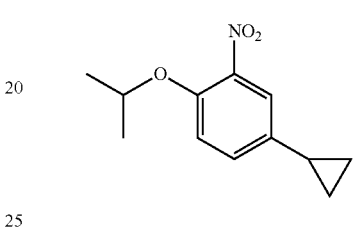

4-bromo-1-isopropoxy-2-nitrobenzene (2 g, 7.7 mmol), cyclopropyl boronic acid pinacol ester (1.32 g, 15.4 mmol), potassium carbonate (2.13 g, 15.4 mmol), [1,1'-bis (diphenylphosphino) ferrocene] palladium dichloride (264 mg, 0.36 mmol) and 1, 4-dioxane/water (20 mL/2 mL) were added to a 100 ml single-port reaction flask. The reaction mixture was heated up to 100° C. in an oil bath under the protection of nitrogen and stirred overnight. After completion of the reaction, the reaction solution was filtered with diatomite, and the filtrate was added with ethyl acetate, washed with saturated brine, dried and concentrated. The thus obtained crude product was separated and purified by column chromatography (eluent:ethyl acetate/petroleum ether, gradient: 0~20% ethyl acetate) to obtain the title compound (yellow solid, 1.4 g, 82%). (MS: [M+1] none)

Step 3:5-cyclopropyl-2-isopropoxy-aniline

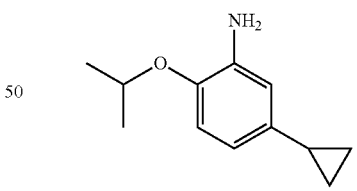

4-cyclopropyl-1-isopropoxy-2-nitrobenzene (1.4 g, 6.3 mmol), zinc powder (412 mg, 6.3 mmol), saturated ammonium chloride solution (40 mL) and methanol (20 mL) were added to a 100 ml single-port reaction flask. The reaction mixture was stirred and reacted for 3 hours at room temperature. After completion of the reaction, ethyl acetate was added for dilution and washed with saturated brine, dried and concentrated. The thus obtained crude product was separated and purified by column chromatography (eluent: ethyl acetate/petroleum ether, gradient: 0~50% ethyl acetate) to obtain the title compound (yellow solid, 547 mg, 45%). (MS: [M+1] 192.1)

Step 4: 4-bromo-5-cyclopropyl-2-isopropoxyaniline

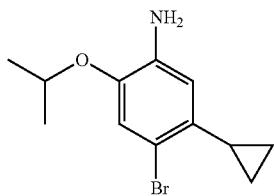

4-cyclopropyl-1-isopropoxy-2-nitrobenzene (547 mg, 2.86 mmol), N-bromosuccinimide (507 mg, 1.7 mmol) and N,N-dimethylformamide (8 mL) were added to a 100 ml single-port reaction flask. The reaction mixture was stirred and reacted for 1 hour at −78° C. After completion of the reaction, ethyl acetate was added for dilution and washed with saturated brine, dried and concentrated. The thus obtained crude product was separated and purified by column chromatography (eluent: ethyl acetate/petroleum ether, gradient: 0~40% ethyl acetate) to obtain the title compound (yellow solid, 634 mg, 82%). (MS: [M+1] 270.0)

Step 5: t-butyl 4-(4-amino-2-cyclopropyl-5-isopropoxy-phenyl)-5,6-dihydro-piperidine-1(2H) carbonate

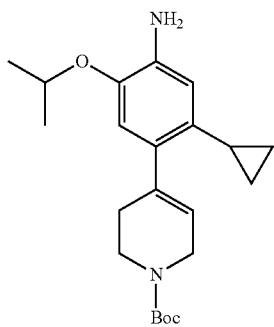 [SMILES: CC(C)Oc1cc(C2=CCN(C(=O)OC(C)(C)C)CC2)c(C2CC2)cc1N]

4-bromo-5-cyclopropyl-2-isopropoxy aniline (538 mg, 2 mmol), N-t-butoxycarbonyl-1,2,5,6-tetrahydropyridin-4-boronic acid pinacol ester (742 mg, 2.4 mmol), potassium carbonate (552 mg, 4 mg), [1,1'-bis (diphenylphosphino) ferrocene] dichloropalladium (73 mg, 0.1 mmol) and 1,4-dioxane/water (10 mL/1 mL) were added to a 100 ml single-port reaction flask. The reaction mixture was heated up to 100° C. in an oil bath under the protection of nitrogen and stirred for 3 hours. After completion of the reaction, the reaction solution was filtered with diatomite, and the filtrate was added with ethyl acetate, washed with saturated brine, dried and concentrated. The thus obtained crude product was separated and purified by column chromatography (eluent: ethyl acetate/petroleum ether, gradient: 0~30% ethyl acetate) to obtain the title compound (light yellow solid, 597 mg, 80%). (MS: [M+1] 373.3)

Step 3: t-butyl 4-(4-amino-5-isopropoxy-2-cyclopropylphenyl)piperidine-1-carbonate and t-butyl 4-(4-amino-5-isopropoxy-2-propylphenyl)piperidine-1-carbonate

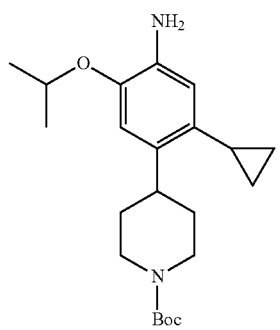

A66

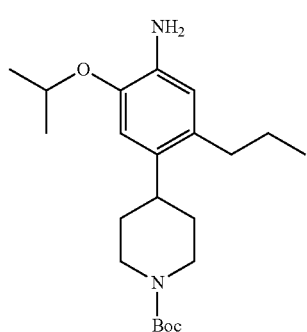

A67 t-butyl 4-(4-amino-2-cyclopropyl-5-isopropoxy-phenyl)-5,6-dihydropiperidine-1(2H)-carbonate (250 mg, 0.67 mmol), raney nickel (250 mg) and tetrahydrofuran (50 mL) were added to a 100 ml single-port reaction flask. The reaction mixture was reacted for 2 hours under the protection of hydrogen at 60° C. After completion of the reaction, the reaction solution was filtered and concentrated with diatomite. The thus obtained crude product was separated and purified by column chromatography (eluent:ethyl acetate/petroleum ether, gradient: 0~30% ethyl acetate) to obtain the title compound A66 (light yellow solid, 50 mg, 20%) and A67 (light yellow solid, 102 mg, 41%). (MS: [M−56+1] 321.3)

Example 67 Preparation of Intermediate A68

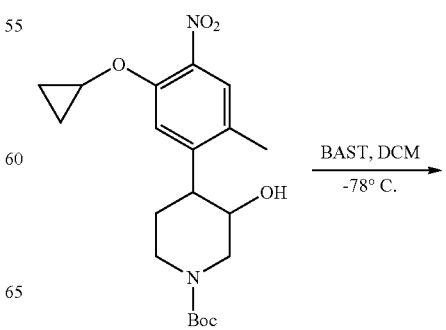

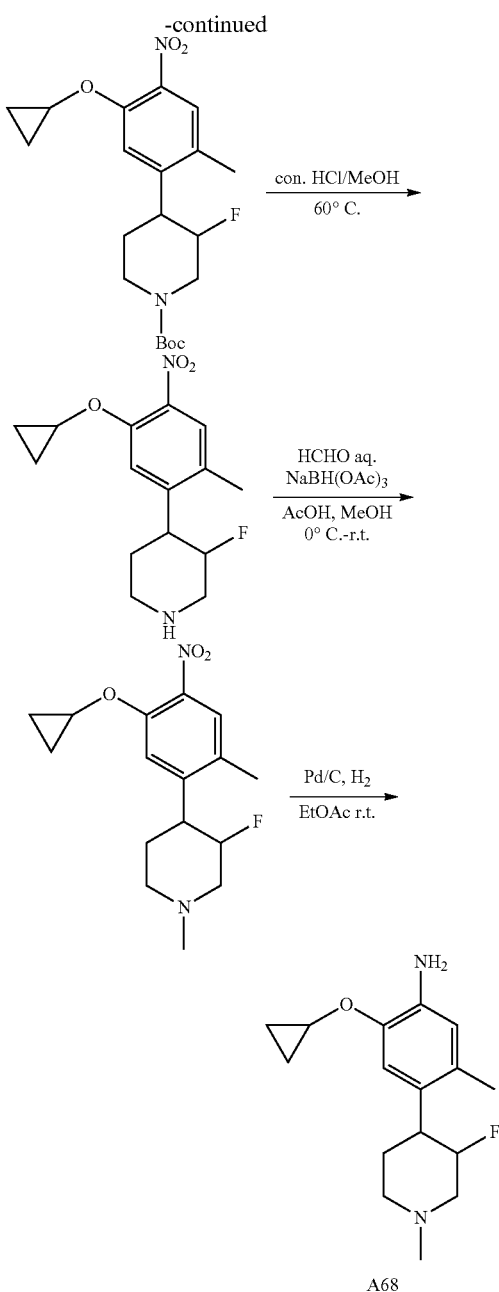

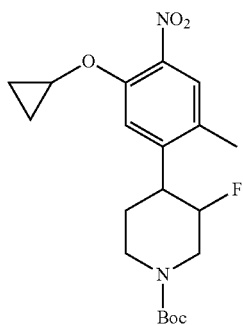 [SMILES: Cc1cc([N+](=O)[O-])c(OC2CC2)cc1C1CCN(C(=O)OC(C)(C)C)CC1F]

A68

Step 1: 1-t-butyloxycarbonyl-4-(5-cyclopropoxy-2-methyl-4-nitrophenyl)-3-fluoropiperidine Bis (2-methoxyethyl) amino sulfur trifluoride (304 mg, 1.38 mmol) and dichlormethane (8 mL) were added to a 25 ml reaction flask. The reaction mixture was cooled down to −78° C., and slowly added with 1-t-butyloxycarbonyl-4-(5-cyclopropoxy-2-methyl-4-nitrophenyl)-3-hydroxypiperidine (180 mg, 0.46 mmol) in dichlormethane (8 mL) solution at this temperature. The reaction mixture was maintained at −78° C. and stirred for 1 hour. After completion of the reaction, the reaction solution was poured into cold aqueous ammonium chloride solution and extracted with dichlormethane, dried and concentrated. The thus obtained crude product was purified by preparative plates (developing solvent:ethyl acetate/petroleum ether=1:2) to obtain the title compound (70 mg, 39%). (MS: [M+Na] 417.1)

Step 2: 4-(5-cyclopropoxy-2-methyl-4-nitrophenyl)-3-fluoropiperidine

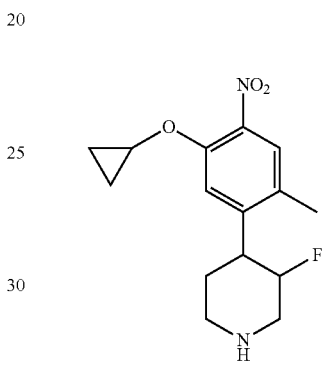

1-t-butyloxycarbonyl-4-(5-cyclopropoxy-2-methyl-4-nitrophenyl)-3-fluoropiperidine (50 mg, 0.13 mmol), methanol (2 mL) and concentrated hydrochloric acid (1 mL) were added to a 10 ml reaction flask. The reaction mixture was heated up to 60° C. and stirred for 30 minutes. The reaction solution was concentrated, and the residue was neutralized with saturated aqueous sodium bicarbonate solution, extracted with ethyl acetate, dried and concentrated to obtain the title compound (40 mg). The crude product was used directly for the subsequent reaction. (MS: [M+1] 295.1)

Step 3: 4-(5-cyclopropoxy-2-methyl-4-nitrophenyl)-3-fluoro-1-methyl-piperidine

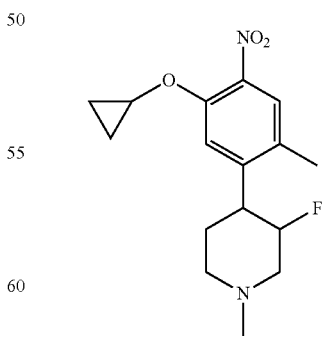

4-(5-cyclopropoxy-2-methyl-4-nitrophenyl)-3-fluoropiperidine (40 mg, 0.1 mmol) and methanol (4 mL) were added to a 25 ml reaction flask. The reaction mixture was cooled down to 0° C., and added with 36% aqueous formaldehyde solution (0.11 mL, 1.3 mmol) and acetic acid (15 mg, 0.25 mmol) at this temperature, followed by adding with sodium triacetoxyborohydride (70 mg, 0.33 mmol). The reaction mixture was heated up to room temperature and stirred for 3.5 hours. After completion of the reaction, saturated aqueous sodium bicarbonate solution was added and stirred for 10 minutes, followed by extracting with ethyl acetate, washed with saturated brine, dried and concentrated. The thus obtained crude product was separated and purified by column chromatography (silica gel column, eluent:ethyl acetate/petroleum ether, gradient: 50~100% ethyl acetate) to obtain the title compound (31 mg, the total yield of the two steps is 77%). (MS: [M+1] 309.1)

Step 4: 2-cyclopropoxy-4-(3-fluoro-1-methyl-piperidin-4-yl)-5-methyl-aniline

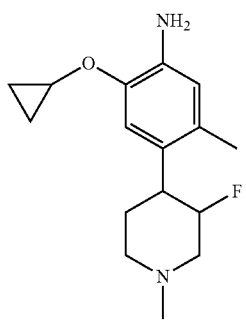 [SMILES: Cc1cc([N+](=O)[O-])c(OC2CC2)cc1C1CCN(C)CC1F]

4-(5-cyclopropoxy-2-methyl-4-nitrophenyl)-3-fluoro-1-methylpiperidine (31 mg, 0.1 mmol), 10% Pd/C (15 mg) and ethyl acetate (2 ml) were added to a 10 ml reaction flask. The reaction mixture was stirred for 22 hours under hydrogen atmosphere of 1 atmospheric pressure at room temperature. After completion of the reaction, the reaction solution was filtered, concentrated to obtain the title compound (28 mg, 100%). The crude product was used directly for the subsequent reaction. (MS: [M+1] 279.2)

Example 68 Preparation of Intermediate A69

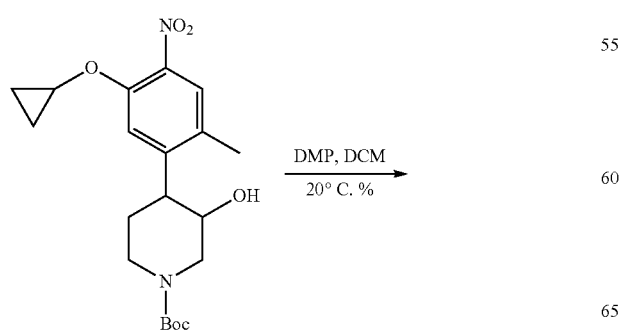

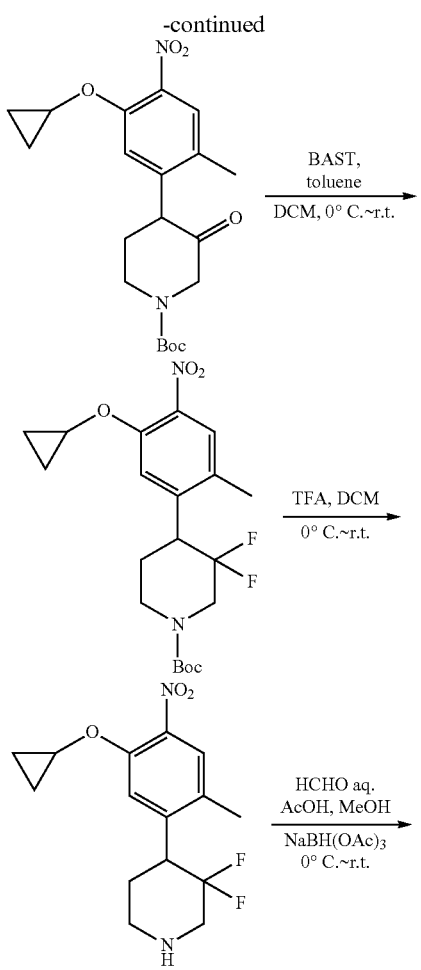

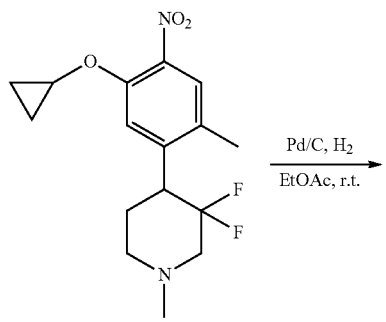

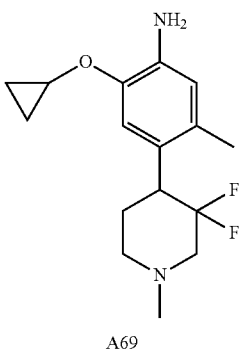

A69

Step 1: 1-t-butyloxycarbonyl-4-(5-cyclopropoxy-2-methyl-4-nitrophenyl)-3-piperidinone

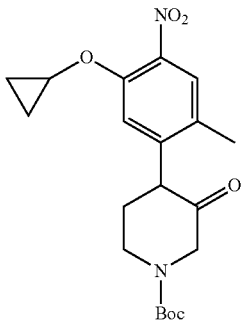

1-t-butyloxycarbonyl-4-(5-cyclopropoxy-2-methyl-4-nitrophenyl)-3-hydroxy-piperidine (150 mg, 0.38 mmol) and dichloromethane (2.5 mL) were added to a 10 ml reaction flask. The reaction mixture was cooled down to 0° C., added with (1,1,1-triacetoxy)-1,1-dihydro-1,2-benziodoxol-3(1H)-one (242 mg, 0.57 mmol) in batches at this temperature. The reaction mixture was heated up to 20° C. and stirred for 16 hours. After completion of the reaction, the reaction solution was poured into water and extracted with dichloromethane, washed with aqueous sodium bisulfite solution and saturated brine, dried and concentrated. The thus obtained crude product was separated and purified by column chromatography (silica gel column, eluent:ethyl acetate/petroleum ether, gradient: 0~30% ethyl acetate) to obtain the title compound (140 mg, 95%). (MS: [M+Na] 413.2)

Step 2: 1-t-butyloxycarbonyl-4-(5-cyclopropoxy-2-methyl-4-nitrophenyl)-3,3-difluoropiperidine

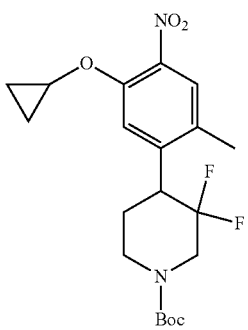 [SMILES: Cc1cc([N+](=O)[O-])c(OC2CC2)cc1C1CCN(C(=O)OC(C)(C)C)CC1(F)F]

1-t-butyloxycarbonyl-4-(5-cyclopropoxy-2-methyl-4-nitrophenyl)-3-piperidone (116 mg, 0.3 mmol) and dichloromethane (4 mL) were added to a 25 ml reaction flask. The reaction mixture was cooled down to 0° C., and slowly added with bis(2-methoxyethyl)amino sulfur trifluoride (195 mg, 0.88 mmol) in toluene solution (0.16 mL). The reaction mixture was heated up to room temperature and stirred for 16 hour. After completion of the reaction, the reaction solution was combined, poured into cold aqueous sodium bicarbonate solution and extracted with dichloromethane, dried and concentrated. The thus obtained crude product was separated by preparative plates (developing solvent:ethyl acetate/petroleum=1:3) to obtain the title compound (59 mg, 48%). (MS: [M+Na] 413.2)

Step 3: 4-(5-cyclopropoxy-2-methyl-4-nitrophenyl)-3,3-difluoropiperidine

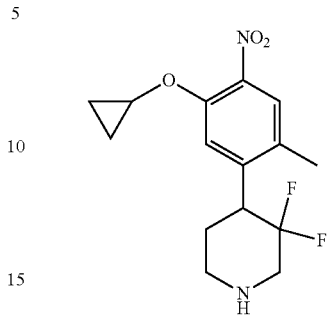

1-t-butyloxycarbonyl-4-(5-cyclopropoxy-2-methyl-4-nitrophenyl)-3,3-difluoropiperidine (59 mg, 0.14 mmol) and dichloromethane (2 mL) were added to a 10 ml reaction flask. The reaction mixture was cooled down to 0° C., and slowly added with trifluoroacetic acid (0.30 mL). The reaction mixture was heated up to room temperature and stirred for 1 hour. The reaction solution was neutralized with saturated aqueous sodium bicarbonate solution, extracted with dichloromethane, dried and concentrated to obtain the title compound (43 mg, 98%). (MS: [M+1] 313.1)

Step 4: 4-(5-cyclopropoxy-2-methyl-4-nitrophenyl)-3,3-difluoro-1-methyl-piperidine

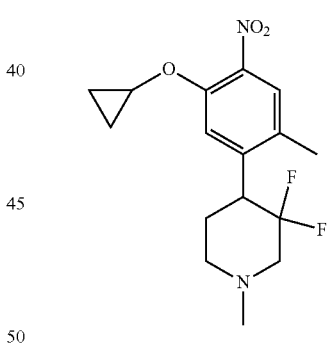

4-(5-cyclopropoxy-2-methyl-4-nitrophenyl)-3,3-difluoropiperidine (43 mg, 0.14 mmol) and methanol (3 mL) were added to a 10 ml reaction flask. The reaction mixture was cooled down to 0° C., and added with 36% aqueous formaldehyde solution (0.12 mL, 1.4 mmol) and acetic acid (16.6 mg, 0.28 mmol) at this temperature, followed by adding with sodium triacetoxyborohydride (153 mg, 0.69 mmol). The reaction mixture was heated up to room temperature and stirred for 16 hours. After completion of the reaction, saturated aqueous sodium bicarbonate solution was added and stirred for 10 minutes, followed by extracting with dichloromethane, washed with saturated brine, dried and concentrated. The thus obtained crude product was separated by preparative plates (eluent:dichloromethane/methanol=15:1) to obtain the title compound (46 mg, 100%). (MS: [M+1] 327.1)

Step 5: 2-cyclopropoxy-4-(3,3-difluoro-1-methyl-piperidin-4-yl)-5-methyl-aniline

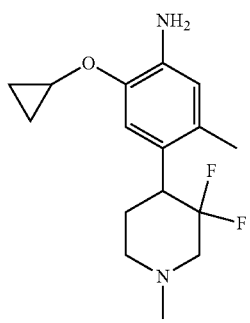 [SMILES: Cc1cc(N)c(OC2CC2)cc1C1CCN(C)CC1(F)F]

4-(5-cyclopropoxy-2-methyl-4-nitrophenyl)-3,3-difluoro-1-methyl-piperidine (40 mg, 0.12 mmol), 10% Pd/C (15 mg) and ethyl acetate (4 mL) were added to a 25 ml reaction flask. The reaction mixture was stirred for 16 hours under hydrogen atmosphere of 1 atmospheric pressure at room temperature. After completion of the reaction, the reaction solution was filtered and concentrated to obtain the title compound (colorless oil, 32 mg, 89%). The crude product was used directly for the subsequent reactions. (MS: [M+1] 297.1)

Example 69 Preparation of Intermediate A70

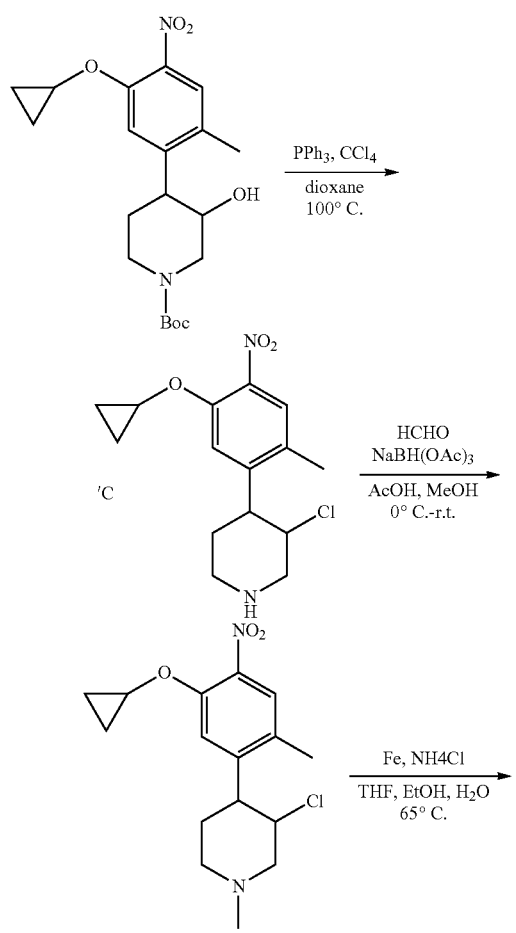

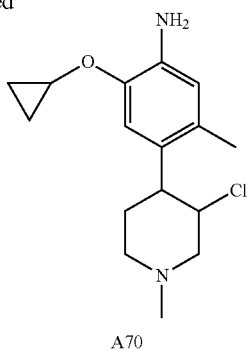

A70

Step 1: 3-chloro-4-(5-cyclopropoxy-2-methyl-4-nitrophenyl)piperidine

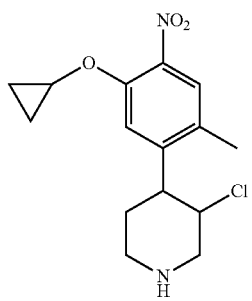 [SMILES: Cc1cc([N+](=O)[O-])c(OC2CC2)cc1C1CCNCC1Cl]

t-butyl 4-(5-cyclopropoxy-2-methyl-4-nitrophenyl)-3-hydroxy-piperidin-1-carboxylate (40 mg, 0.1 mmol), triphenylphosphine (28 mg, 0.19 mmol), carbon tetrachloride (18 mg, 0.19 mmol) and 1,4-dioxane (5 ml) were added to a 25 ml reaction flask. The reaction was heated up to 100° C. and stirred for 24 hours. After completion of the reaction, the reaction solution was concentrated, and the residue was neutralized with saturated aqueous sodium bicarbonate solution, extracted with dichloromethane, dried and concentrated. The thus obtained crude product was separated and purified by column chromatography (silica gel column, eluent:dichloromethane/methanol=9/1), and then purified by preparative HPLC to remove residual ligands and the title compound was obtained (10 mg, 32%). (MS: [M+1] 311.1)

Step 2: 3-chloro-4-(5-cyclopropoxy-2-methyl-4-nitrophenyl)-1-methyl-piperidine

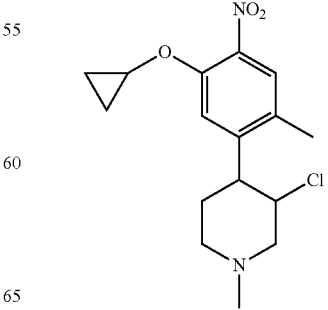

3-chloro-4-(5-cyclopropoxy-2-methyl-4-nitrophenyl)-piperidine (20 mg, 0.064 mmol) and methanol (5 mL) were added to a 25 ml reaction flask. The reaction mixture was cooled down to 0° C., and added with 36% aqueous formaldehyde solution (40 μL, 0.64 mmol) and acetic acid (2 mg, 0.032 mmol) at this temperature, followed by adding with sodium triacetoxyborohydride (130 mg, 0.32 mmol). The reaction mixture was heated up to room temperature and stirred for 3.5 hours. After completion of the reaction, saturated aqueous sodium bicarbonate solution was added and stirred for 10 minutes, followed by extracting with ethyl acetate, washed with saturated brine, dried and concentrated to obtain the title compound (20 mg). The crude product was used directly for the subsequent reaction. (MS: [M+1] 325.1)

Step 3: 3-chloro-4-(5-cyclopropoxy-2-methyl-4-aminophenyl)-1-methylpiperidine

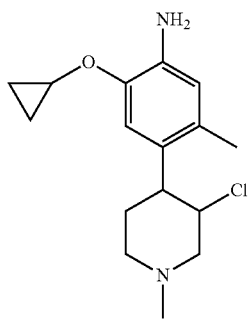 [SMILES: Cc1cc([N+](=O)[O-])c(OC2CC2)cc1C1CCN(C)CC1Cl]

3-chloro-4-(5-cyclopropoxy-2-methyl-4-nitrophenyl)-1-methylpiperidine (20 mg, 0.06 mmol), iron powder (14 mg, 0.25 mmol), ammonium chloride (6 mg, 0.11 mmol), water (0.5 ml), tetrahydrofuran (0.5 mmol) and ethanol (0.5 mL) were added to a 25 ml reaction flask. The reaction solution was heated up to 60° C., reacted and stirred for 3.5 hours. The reaction solution was filtered, concentrated, added with saturated aqueous sodium bicarbonate solution and stirred for 10 minutes, and extracted with ethyl acetate, washed with saturated brine, dried and concentrated to obtain the title compound (10 mg, 55%). The crude product was used directly for the subsequent reaction. (MS: [M+1] 295.1)

Example 70 Preparation of Intermediate A71

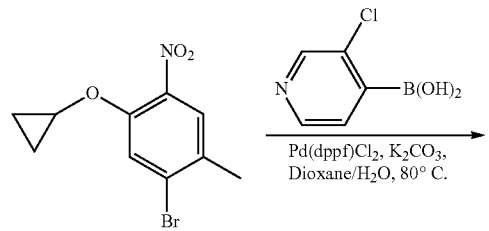

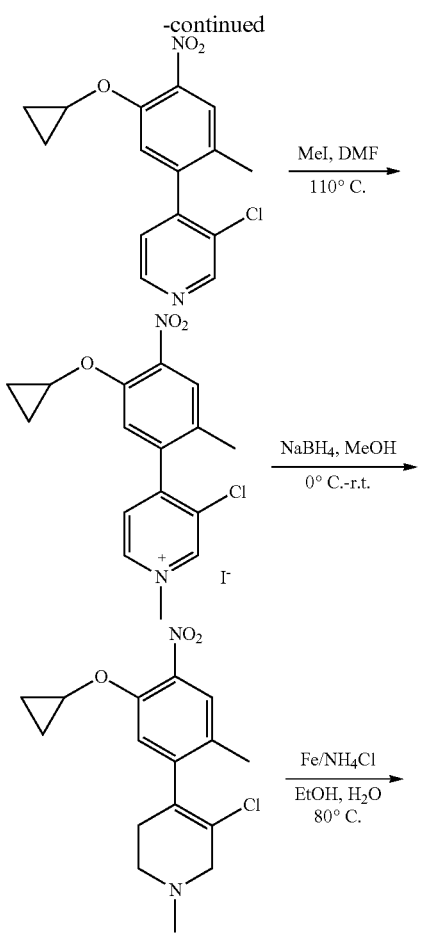

Step 1: 3-chloro-4-(5-cyclopropoxy-2-methyl-4-nitro-phenyl)-pyridine

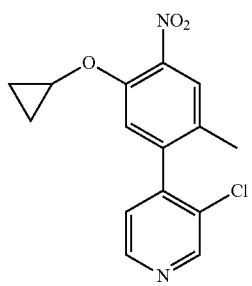 [SMILES: Cc1cc([N+](=O)[O-])c(OC2CC2)cc1-c1ccncc1Cl]

1-bromo-5-cyclopropoxy-2-methyl-4-nitro-benzene (200 mg, 0.74 mmol), 3-chloropyridin-4-boronic acid monohydrate (140 mg, 0.8 mmol), 1,1'-bis (diphenylphosphino) ferrocene palladium dichloride (113 mg, 0.15 mmol), potassium carbonate (153 mg, 1.11 mmol), 1,4-dioxane (9 mL) and water (3 mL) were added to a 25 ml reaction flask. The reaction mixture was heated up to 80° C. in an oil bath under the protection of nitrogen and stirred for 4 hours. After completion of the reaction, the reaction solution was added with ethyl acetate, washed with saturated brine, dried and concentrated. The thus obtained crude product was separated by column chromatography (silica gel column, eluent: ethyl acetate/petroleum ether, gradient: 0~50% ethyl acetate) to obtain the title compound (brown oil, 176 mg, 78%). (MS: [M+1] 305.0)

Step 2: 3-chloro-4-(5-cyclopropoxy-2-methyl-4-nitrophenyl)-1-methyl-pyridinium iodide

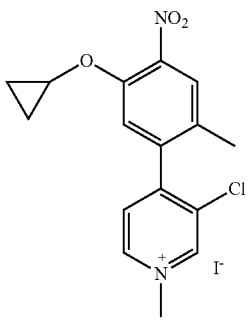

3-chloro-4-(5-cyclopropoxy-2-methyl-4-nitro-phenyl)-pyridine (176 mg, 0.58 mmol), methyl iodide (0.37 mL, 5.9 mmol) and N,N-dimethylformamide (2.5 mL) were added to a 25 ml reaction flask. The reaction mixture was heated up to 110° C. in a sealed tube under the protection of nitrogen and stirred for 16 hours. The reaction solution was concentrated to obtain the title compound (brown oil, 310 mg, 100%). The crude product was used directly for the subsequent reaction. (MS: [M+1] 319.1)

Step 3: 5-chloro-4-(5-cyclopropoxy-2-methyl-4-nitrophenyl)-1-methyl-1,2,3,6-tetrahydro-pyridine

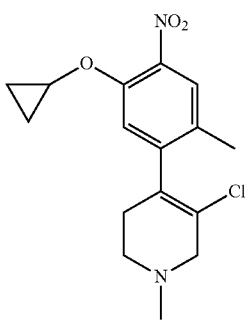 [SMILES: Cc1cc([N+](=O)[O-])c(OC2CC2)cc1C1=C(Cl)CN(C)CC1]

3-chloro-4-(5-cyclopropoxy-2-methyl-4-nitrophenyl)-1-methyl-pyridinium iodide (280 mg crude product, 0.52 mmol) and methanol (10 mL) were added to a 25 ml reaction flask. The reaction mixture was cooled down to 0° C., added with sodium borohydride (60 mg, 1.58 mmol) in batched at this temperature, followed by heating up to room temperature and stirred for 16 hours. After completion of the reaction, saturated aqueous sodium bicarbonate solution was added and stirred for 10 minutes, and extracted with ethyl acetate, washed with saturated brine, dried and concentrated. The thus obtained crude product was separated by column chromatography (silica gel column, eluent: dichloromethane/methanol, gradient: 0~2% methanol) to obtain the title compound (brown oil, 116 mg, 69%). (MS: [M+1] 323.0)

Step 4: 4-(5-chloro-1-methyl-1,2,3,6-tetrahydro-pyridin-4-yl)-2-cyclopropoxy-5-methyl aniline

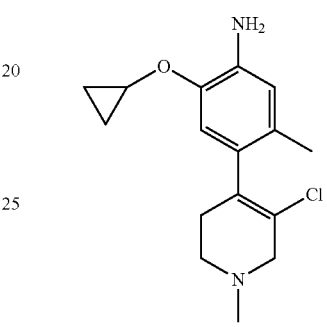

5-chloro-4-(5-cyclopropoxy-2-methyl-4-nitro-phenyl)-1-methyl-1,2,3,6-tetrahydro-pyridine (90 mg, 0.28 mmol), iron powder (78 mg, 1.40 mmol), ammonium chloride (15 mg, 0.28 mmol), ethanol (8 mL) and water (4 mL) were added to a 25 ml reaction flask. The reaction mixture was heated up to 80° C. under the protection of nitrogen and stirred for 2 hours. After completion of the reaction, the reaction solution was filtered, concentrated, and the residue was dissolved with ethyl acetate, washed with saturated sodium bicarbonate solution and saturated brine, dried and concentrated to obtain the title compound (brown oil, 80 mg, 97%), which was used directly for the subsequent reaction. (MS: [M+1] 293.1)

Example 71 Preparation of Intermediate A72

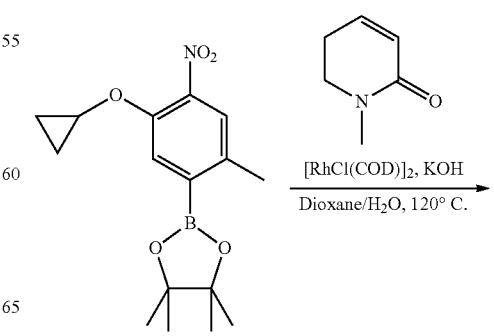

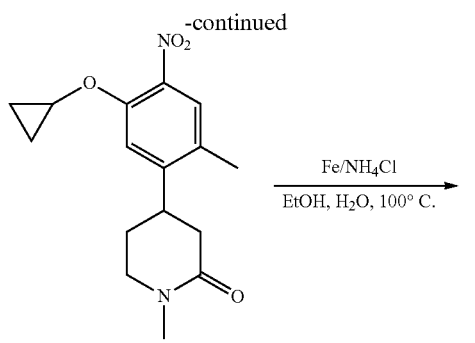

Step 2: 4-(4-amino-5-cyclopropoxy-2-methylphenyl)-1-methylpiperidin-2-one

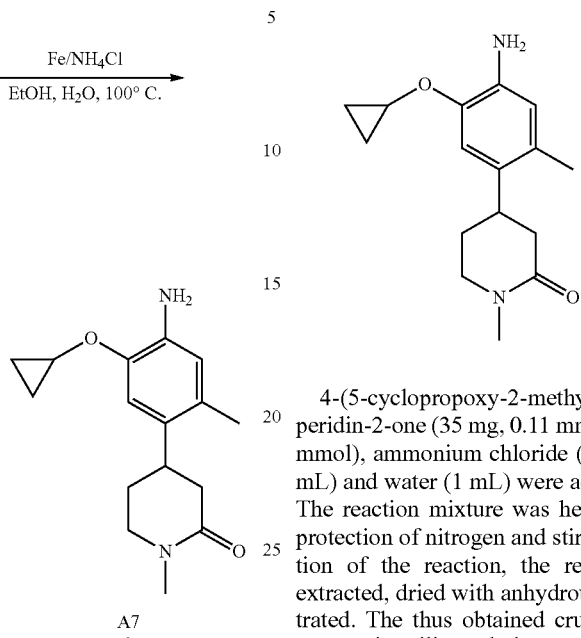

4-(5-cyclopropoxy-2-methyl-4-nitrophenyl)-1-methylpiperidin-2-one (35 mg, 0.11 mmol), iron powder (36 mg, 0.64 mmol), ammonium chloride (7 mg, 0.13 mmol), ethanol (3 mL) and water (1 mL) were added to a 10 ml reaction flask. The reaction mixture was heated up to 100° C. under the protection of nitrogen and stirred for 2 hours. After completion of the reaction, the reaction solution was filtered, extracted, dried with anhydrous sodium sulfate and concentrated. The thus obtained crude product was separated by preparative silica gel plates to obtain the title compound (18 mg, 60%). (MS: [M+1] 275.0)

Example 72 Preparation of Intermediate A73

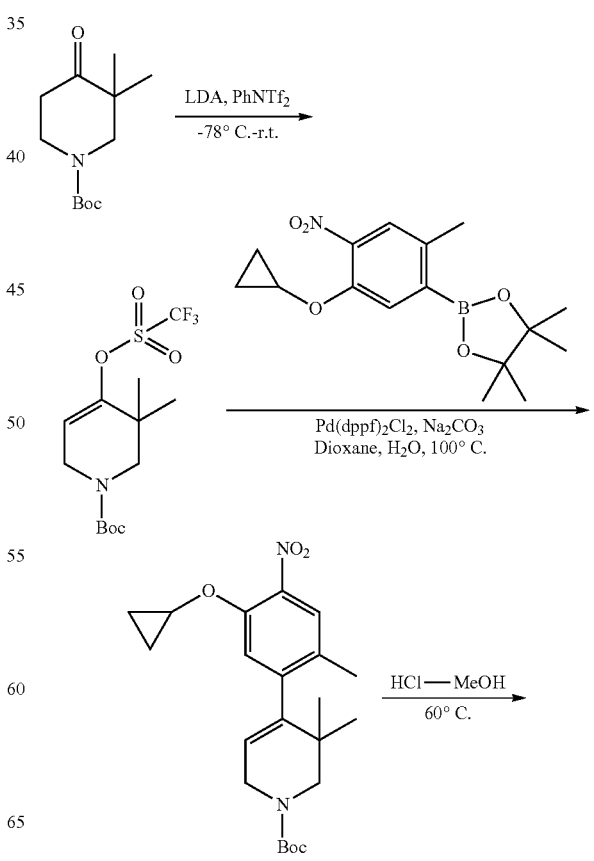

Step 1: 4-(5-cyclopropoxy-2-methyl-4-nitrophenyl)-1-methylpiperidin-one

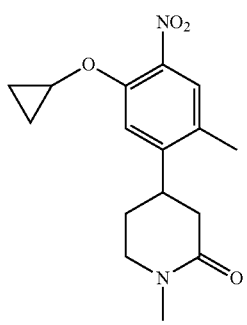 [SMILES: Cc1cc(N)c(OC2CC2)cc1C1CCN(C)C(=O)C1]

2-(5-cyclopropoxy-2-methyl-4-nitrophenyl)-4,4,5,5-tetramethyl-1,3,2-dioxaborolane (50 mg, 0.157 mmol), 1-methyl-5,6-dihydropyridin-2(1H)-one (19.2 mg, 0.172 mmol), potassium hydroxide (1 mmol/L in $H_2O$, 0.0785 mmol), (1,5-cyclooctadiene) rhodium (I) dimer (7.8 mg, 0.016 mmol) and 1,4-dioxane (3 mL) were added to a 10 ml microwave tube. The reaction mixture was reacted at 120° C. by microwave for 20 minutes under the protection of nitrogen. After completion of the reaction, the reaction solution was filtered, extracted with ethyl acetate, washed with saturated brine, dried with anhydrous sodium sulfate and concentrated. The thus obtained crude product was separated and purified by column chromatography (silica gel column, eluent:ethyl acetate/petroleum ether=1:3) to obtain the title compound (yellow solid, 35 mg, 73%). (MS: [M+1] 305.0)

-continued

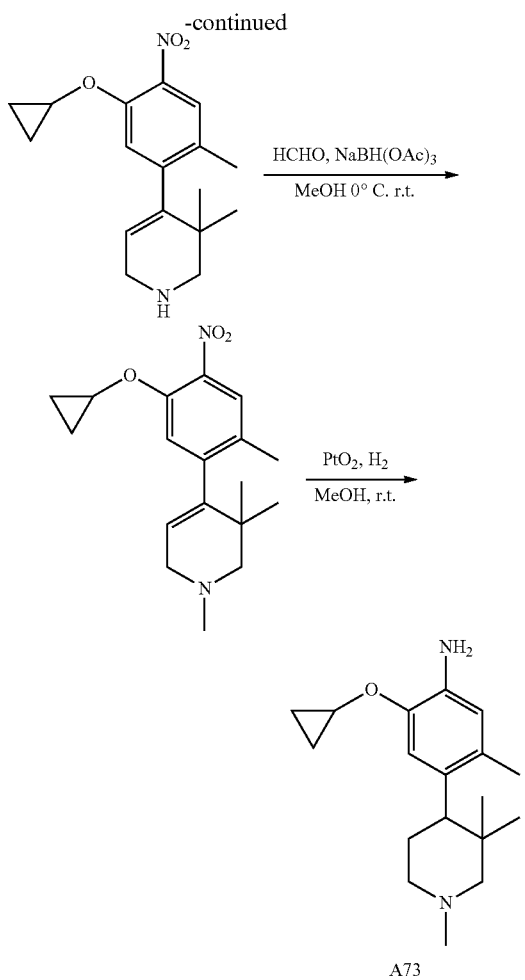

A73

Step 1: 5, tert-butyl 5-dimethyl-4-(trifluoromethyl-sulfonyloxy)-5,6-dihydropiperidin-1(2H)-carbonate

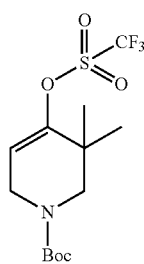

Diisopropylamine (0.76 g, 7.5 mmol) and tetrahydrofuran (20 mL) were added to a 25 ml reaction flask. The reaction mixture was cooled down to −78° C., slowly added with N-butyl lithium (3 mL, 2.5M). The reaction solution was stirred for 1 hour at −78° C. and then slowly added with tert-butyl 3,3-dimethyl-4-oxopiperidin-1-carbonate (1.1 g, 4.84 mmol) in tetrahydrofuran solution (5 mL). Followed by reacting for another 1 hour, the reaction solution was added with 1,1,1-trifluoro-N-phenyl-N-(trifluoromethylsulfonyl) methyl sulfonamide (2 g, 5.60 mmol) in tetrahydrofuran solution (6.3 mL), and the reaction was increased naturally to room temperature. After completion of the reaction, the reaction solution was quenched with ammonium chloride solution, extracted with ethyl acetate, washed with saturated brine, dried and concentrated. The thus obtained crude product was separated and purified by column chromatography (silica gel column, eluent:ethyl acetate/petroleum ether=1:10) to obtain the title compound (yellow liquid, 417 mg, 24%). (MS: none)

Step 2: tert-butyl 4-(5-cyclopropoxy-2-methyl-4-nitrophenyl)-5,5-dimethyl-5,6-dihydropyridin-1(2H)-carbonate

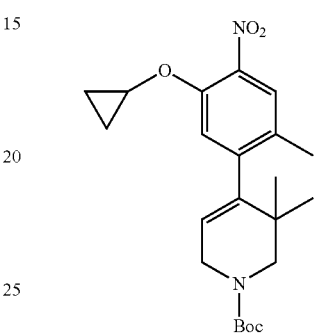

tert-butyl 5,5-dimethyl-4-(trifluoromethylsulfonyloxy)-5,6-dihydropiperidin-1(2H)-carbonate (101 mg, 0.28 mmol), 2-(5-cyclopropoxy-2-methyl-4-nitrophenyl)-4,4,5,5,-tetramethyl-1,3,2-dioxo boric acid ester (90 mg, 0.28 mmol), [1,1'-bis (diphenylphosphino) ferrocene] dichloropalladium (21 mg, 0.028 mmol), saturated sodium carbonate solution (0.5 mL), 1,4-dioxane (2.5 mL) were added to a 5 ml microwave tube. The reaction mixture was heated up to 100° C. under the protection of nitrogen and stirred overnight. After completion of the reaction, the reaction solution was added with ethyl acetate, washed with saturated brine, dried and concentrated. The thus obtained crude product was separated and purified by column chromatography (silica gel column, eluent:ethyl acetate/petroleum ether, gradient: 0~10% ethyl acetate) to obtain the title compound (yellow solid, 70 mg, 62%). (MS: none)

Step 3: 4-(5-cyclopropoxy-2-methyl-4-nitrophenyl)-3,3-dimethyl-1,2,3,6-tetrahydropyridine

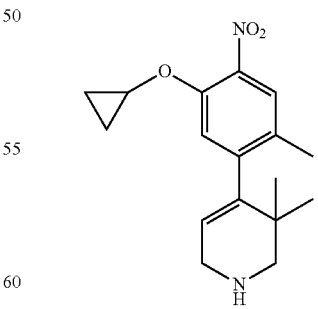

tert-butyl 4-(5-cyclopropoxy-2-methyl-4-nitrophenyl)-5,5-dimethyl-5,6-dihydropiperidin-1(2H)-carbonate (70 mg, 0.17 mmol), methanol (5 mL) and concentrated hydrochloric acid (0.5 mL) were added to a 25 ml reaction flask. The reaction mixture was heated up to 60° C. and stirred for 3 hours. After completion of the reaction, the mixture was concentrated, and the residue was neutralized with saturated aqueous sodium bicarbonate solution, extracted with ethyl acetate, washed with saturated brine, dried and concentrated to obtain the title compound (yellow oil, 50 mg, 97%). The crude product was used directly for the subsequent reaction. (MS: [M+1] 303.2)

Step 4: 4-(5-cyclopropoxy-2-methyl-4-nitrophenyl)-1,3,3-trimethyl-1,2,3,6-tetrahydropyridine

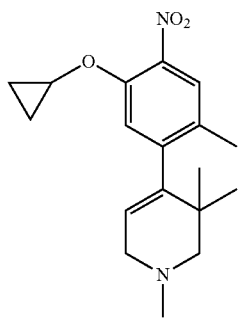 [SMILES: Cc1cc([N+](=O)[O-])c(OC2CC2)cc1C1=CCN(C)CC1(C)C]

4-(5-cyclopropoxy-2-methyl-4-nitrophenyl)-3,3-dimethyl-1,2,3,6-tetra hydropyridine (50 mg, 0.17 mmol), aqueous formaldehyde solution (142 mg, 1.7 mmol), acetic acid (21 mg, 0.34 mmol) and methanol (6 mL) were added to a 25 ml reaction flask. The reaction mixture was cooled down 0° C. and reacted for 15 minutes. The reaction solution was slowly added with sodium triacetoxyborohydride (189 mg, 0.85 mmol) and reacted for 4 hours at room temperature. After completion of the reaction, the mixture was concentrated and residue was neutralized with saturated aqueous sodium bicarbonate solution, extracted with ethyl acetate, washed with saturated brine, dried and concentrated to obtain the title compound (yellow oil, 50 mg, 93%). The crude product was used directly for the subsequent reaction. (MS: [M+1] 317.2)

Step 5: 2-cyclopropoxy-5-methyl-4-(1,3,3-trimethyl-pyridin-4-yl)aniline

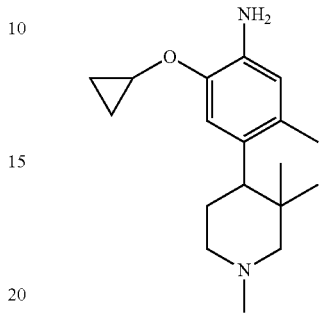

4-(5-cyclopropoxy-2-methyl-4-nitrophenyl)-1,3,3-trimethyl-1,2,3,6-tetrahydropyridine (42 mg, 0.13 mmol), platinum dioxide (21 mg, 85% platinum) and methanol (2 mL) were added to a 25 ml reaction flask. The reaction mixture was stirred for 9 hours under hydrogen atmosphere of 1 atmospheric pressure at room temperature. After completion of the reaction, the reaction solution was filtered and concentrated, and residue was neutralized with saturated aqueous sodium bicarbonate solution, extracted with dichloromethane, dried and concentrated to obtain the title compound (yellow oil, 28 mg, 75%). The crude product was used directly for the subsequent reaction. (MS: [M+1] 289.2)

Example 73 Preparation of Intermediate A74-A78

Intermediates A74-A78 were synthesized by the above method for preparing intermediate A73 (table 5).

TABLE 5

| Nos. | Starting Materials | Intermediates | Molecular Ion Peaks [M + 1]+ |
|---|---|---|---|
| A74 | (structure) | (structure) | 319.3 |

TABLE 5-continued
Intermediates A74-A78
| Nos. | Starting Materials | Intermediates | Molecular Ion Peaks [M + 1]+ |
|---|---|---|---|
| A75 | 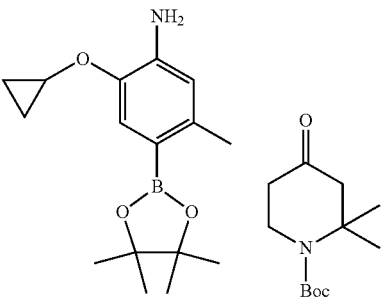 | 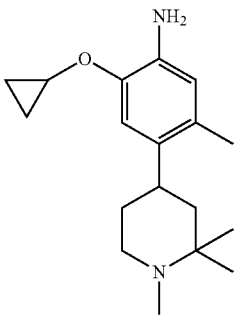 [SMILES: Cc1cc(N)c(OC2CC2)cc1C1CCN(C)C(C)(C)C1] | 289.2 |
| A76 | 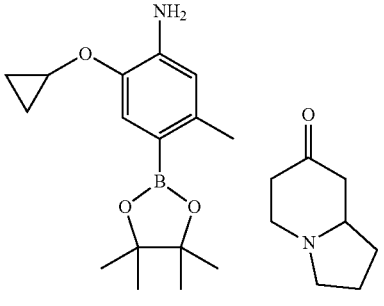 | 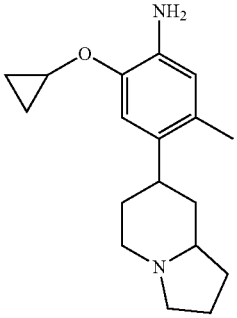 [SMILES: Cc1cc(N)c(OC2CC2)cc1C1CCN2CCCC2C1] | 287.2 |
| A77 | 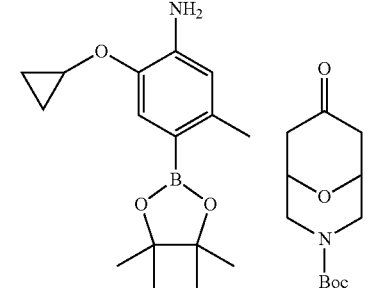 | 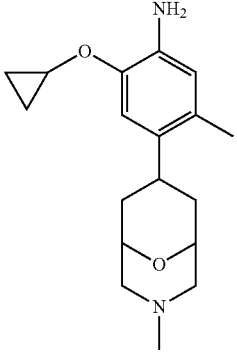 [SMILES: Cc1cc(N)c(OC2CC2)cc1C1CC2CN(C)CC(C1)O2] | 303.2 |
| A78 | 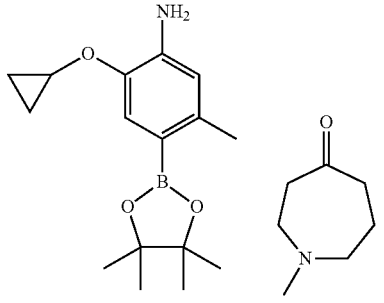 | 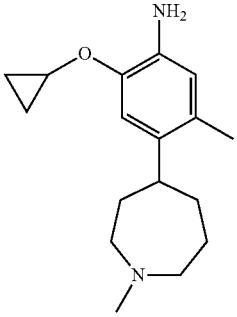 [SMILES: Cc1cc(N)c(OC2CC2)cc1C1CCCN(C)CC1] | 275.2 |

Example 78 Preparation of Intermediate A79

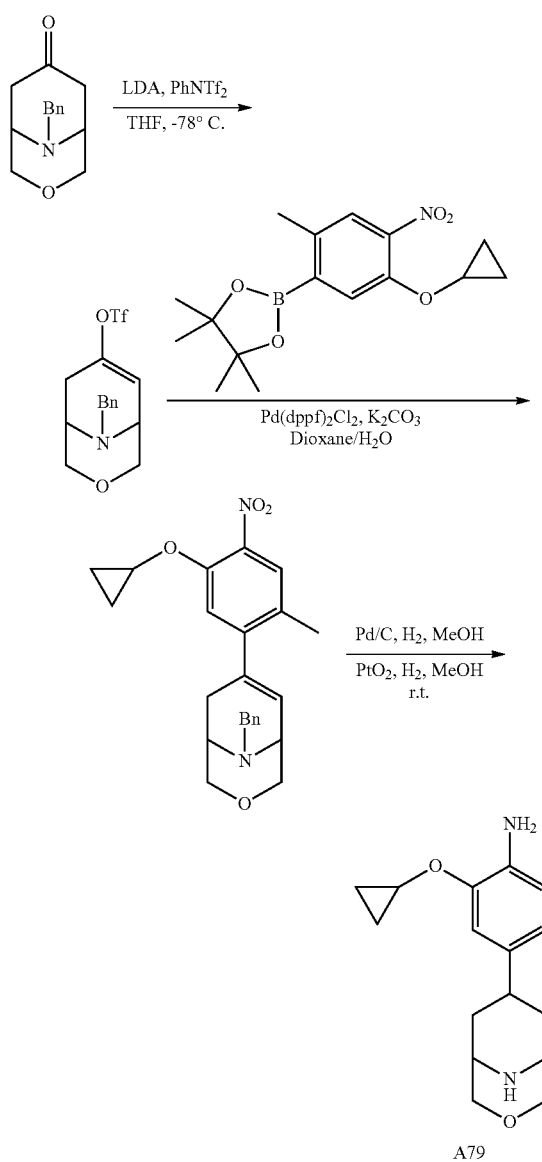

A79

Step 1: 9-benzyl-3-oxa-9-azabicyclo[3.3.1]non-6-ene-7-yl triflate

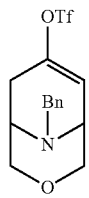

The title compound (light yellow liquid, 3 g, 56%) was synthesized by the above method for preparing intermediate A73. (MS: [M+1] 364.1)

Step 2: 9-benzyl-7-(5-cyclopropoxy-2-methyl-4-nitrophenyl)-3-oxa-9-azabicyclo[3.3.1]non-6-ene

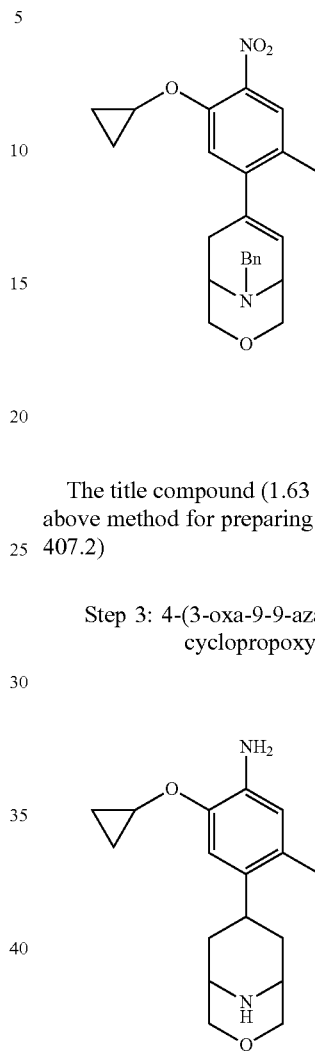

The title compound (1.63 g, 87%) was synthesized by the above method for preparing intermediate A73. (MS: [M+1] 407.2)

Step 3: 4-(3-oxa-9-9-azabicyclo[3.3.1]non-7-yl)-2-cyclopropoxy-5-methylaniline

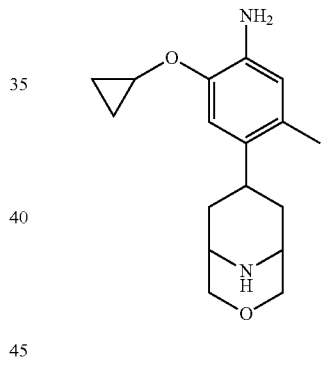

9-benzyl-7-(5-cyclopropoxy-2-methyl-4-nitrophenyl)-3-oxa-9-azabicyclo[3.3.1] non-6-ene (1.53 g, 3.76 mmol), Pd/C (410 mg) and methanol (20 mL) were added to a 50 ml hydrogenated bottle. The reaction mixture was stirred and reacted for 22 hours under hydrogen pressure (60 psi) at room temperature. A small amount of products in which the double bonds were not hydrogenated were detected by liquid chromatography-mass spectrometry. The filter cake was suction filtered and washed with methanol. The mother liquor was concentrated and dissolved in methanol (10 mL), added with platinum dioxide (570 mg), and followed by stirring overnight under hydrogen atmosphere (60 psi) at room temperature. After completion of the reaction, the mixture was filtered, and the crude product obtained by concentrating the mother liquor was separated and purified by column chromatography (silica gel column, eluent: methanol/dichloromethane=1/16) to obtain the title compound (431 mg, yield: 40%). (MS: [M+1] 289.2)

Example 79 Preparation of Intermediate A80

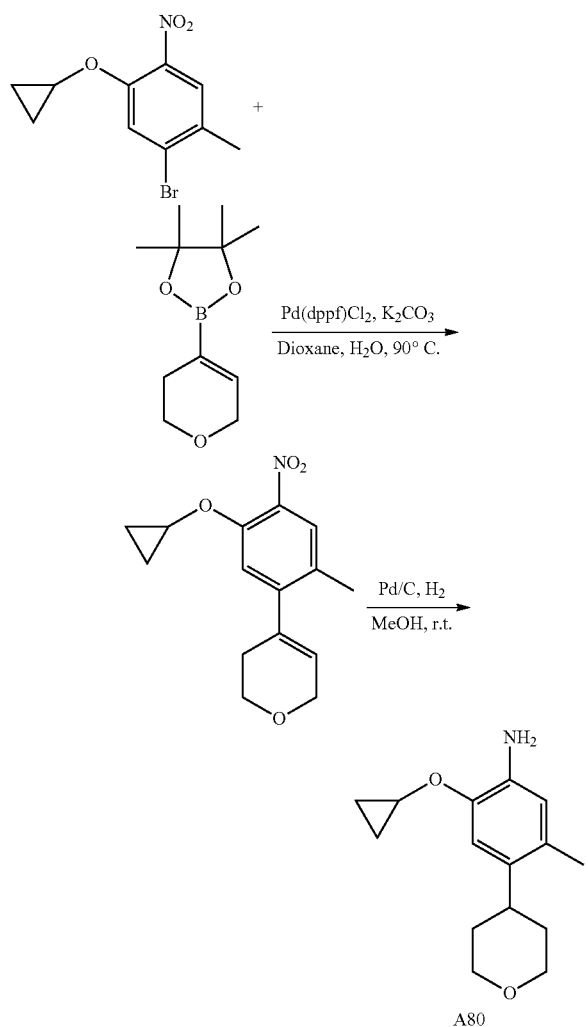

Step 1: 4-(5-cyclopropoxy-2-methyl-4-nitrophenyl)-3,6-dihydro-2H-pyran

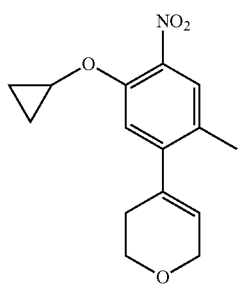 [SMILES: Cc1cc([N+](=O)[O-])c(OC2CC2)cc1C1=CCOCC1]

1-bromo-5-cyclopropoxy-2-methyl-4-nitrobenzene (271 mg, 1 mmol), 3,6-dihydro-2H-pyran-4-boronic acid pinacol ester (210 mg, 1 mmol), [1,1'-bis (diphenylphosphino) ferrocene] dichloropalladium (73 mg, 0.1 mmol), potassium carbonate (207 mg, 1.5 mg), 1,4-dioxane (10 mL) and water (1 mL) were added to a 25 ml reaction flask. The reaction mixture was heated up to 90° C. in an oil bath under the protection of nitrogen and stirred and reacted for 5 hours. After completion of the reaction, the reaction solution was added with ethyl acetate, washed with saturated brine, dried and concentrated. The thus obtained crude product was separated and purified by column chromatography (silica gel column, eluent:ethyl acetate/petroleum ether, gradient: 0~50% ethyl acetate) to obtain the title compound (yellow solid, 198 mg, 72%). (MS: [M+1] none)

Step 2: 2-cyclopropoxy-4-(tetrahydro-2H-pyran)-5-methyl-aniline

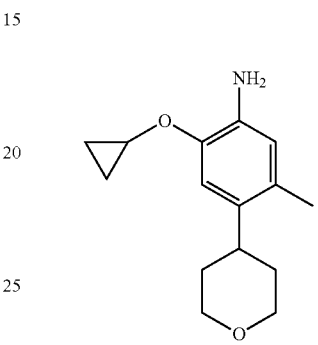

4-(5-cyclopropoxy-2-methyl-4-nitrophenyl)-3,6-dihydro-2H-pyran (198 mg, 0.72 mmol), Pd/C (40 mg, with a content of 10%) and ethanol (20 ml) were added to a 50 ml reaction flask. The reaction mixture was stirred for 4 hours under hydrogen atmosphere of 1 atmospheric pressure at room temperature. After completion of the reaction, the reaction solution was filtered and concentrated to obtain the title compound (160 mg, 90%). The crude product was used directly for the subsequent reaction. (MS: [M+1] 248.2)

Example 80 Preparation of Intermediate A81

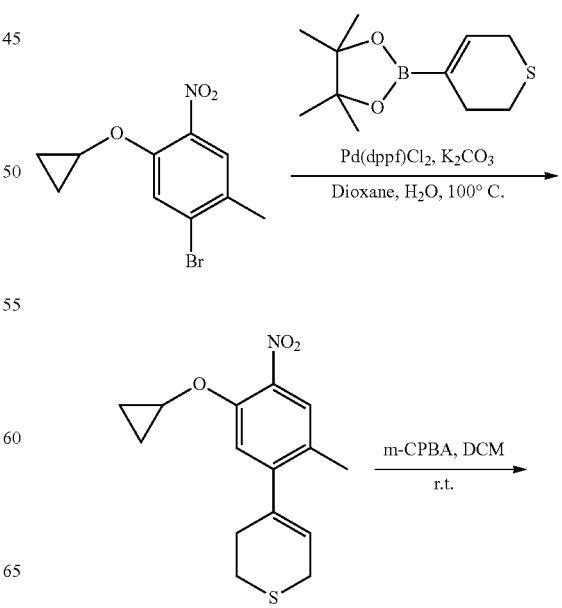

Step 2: 4-(5-cyclopropoxy-2-methyl-4-nitrophenyl)-3,6-dihydro-2H-thiopyran-1,1-dioxide

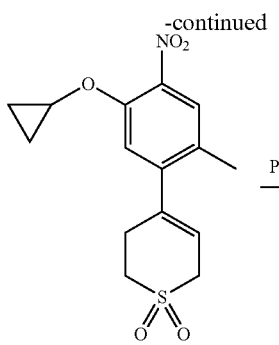

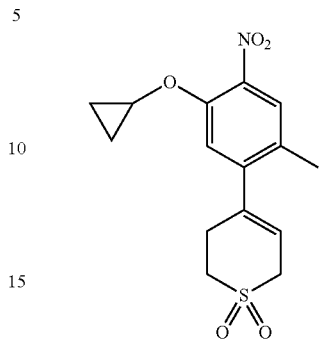

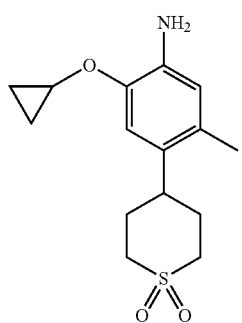

A81

4-(5-cyclopropoxy-2-methyl-4-nitrophenyl)-3,6-dihydro-2H-thiopyran (150 mg, 0.52 mmol), m-chloroperoxybenzoic acid (233 mg, 1.28 mmol) and dichloromethane (10 mL) were added to a 25 ml reaction flask. The reaction mixture was stirred and reacted for 3 hours at room temperature. After completion of the reaction, dichloromethane (50 mL) was added and filtered. The mother liquor was washed with saturated aqueous sodium bicarbonate solution and saturated aqueous sodium thiosulfate, dried, concentrated and purified by column chromatography (petroleum ether/ethyl acetate=1:1) to obtain the title compound (yellow solid, 130 mg, 78%), which was used directly for the subsequent reaction. (MS: [M+1] none)

Step 1: 4-(5-cyclopropoxy-2-methyl-4-nitrophenyl)-3,6-dihydro-2H-thiopyran

Step 3: 2-cyclopropoxy-4-(1,1-dioxo-4-tetrahydrothiopyranyl)-5-methyl-aniline

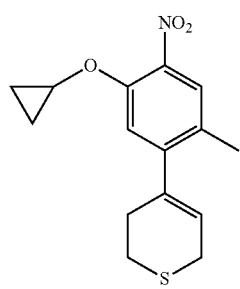 [SMILES: Cc1cc([N+](=O)[O-])c(OC2CC2)cc1C1=CCSCC1]

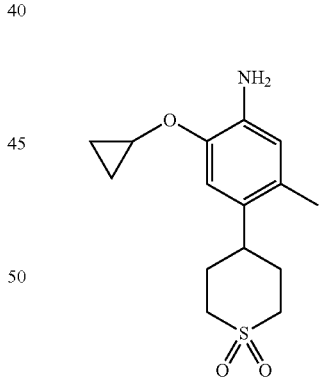

3,6-dihydro-thiopyran-4-boronic acid pinacol ester (497 mg, 2.2 mmol), 1-bromo-5-cyclopropoxy-2-methyl-4-nitrobenzene (544 mg, 2 mmol), potassium carbonate (552 mg, 4 mg), [1,1'-bis (diphenylphosphino) ferrocene] dichloropalladium (146.4 mg, 0.2 mmol), water (1 mL), 1,4-dioxane (10 mL) were added to a 25 ml reaction flask. The reaction mixture was heated up to 100° C. and stirred for 5 hours. After completion of the reaction, the reaction solution was cooled down and added with ethyl acetate, filtered, and then washed with saturated brine. The aqueous phase was extracted with ethyl acetate, and the organic phase was dried, filtered, concentrated and purified by column chromatography (petroleum ether/ethyl acetate=10:1) to obtain the title compound (yellow oil, 480 mg, 82%). (MS: [M+1] none)

4-(5-cyclopropoxy-2-methyl-4-nitrophenyl)-3,6-dihydro-2H-thiopyran-1,1-dioxide (70 mg, 0.22 mmol), 10% Pd/C (50 mg) and methanol (2 mL) were added to a 100 ml reaction flask. The reaction mixture was stirred for 3 hours under hydrogen atmosphere of 1 atmospheric pressures at room temperature. After completion of the reaction, the mixture was filtered, dried and concentrated to obtain the title compound (yellow oil, 60 mg, 92%), which was used directly for the subsequent reaction. (MS: [M+1] 296.1)

Example 81 Preparation of Intermediate A82

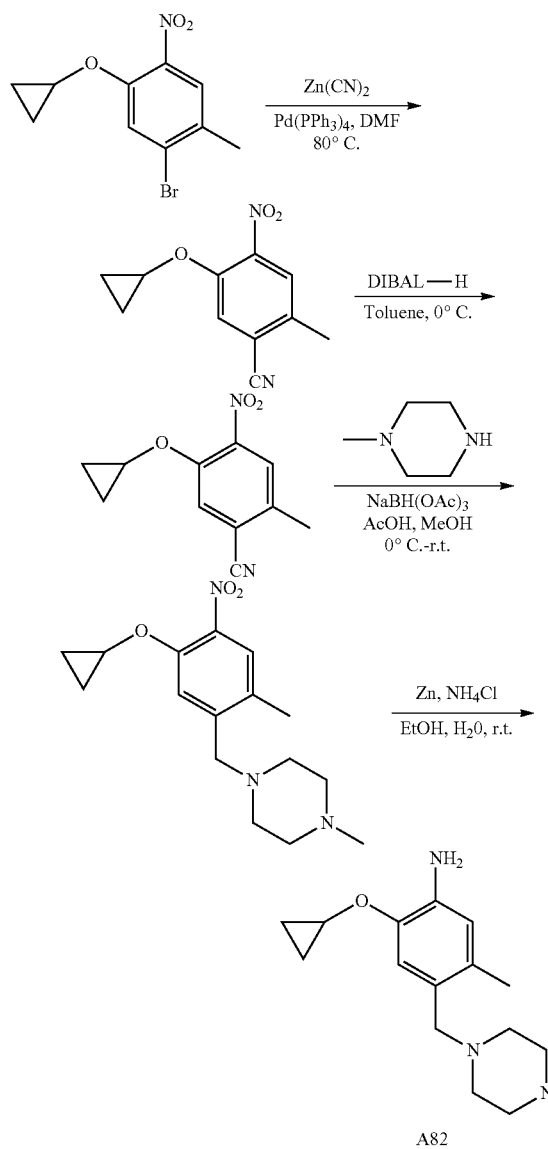

A82

Step 1: 5-cyclopropoxy-2-methyl-4-nitrobenzonitrile 1-bromo-5-cyclopropoxy-2-methyl-4-nitrobenzene (542 mg, 2 mmol), zinc cyanide (468 mg, 4 mg), tetrakis(triphenylphosphine)palladium (116 mg, 0.1 mg) and N,N-dimethylformamide (10 mL) were added to a 50 ml single-ported reaction flask. The reaction mixture was heated up to 80° C. in an oil bath under the protection of nitrogen and reacted for 1 hour. After completion of the reaction, the reaction solution was filtered with diatomite, and the filtrate was added with ethyl acetate, washed with saturated brine, dried and concentrated. The thus obtained crude product was separated and purified by silica gel column (eluent: ethyl acetate/petroleum ether, gradient: 0~25% ethyl acetate) to obtain the title compound (yellow solid, 390 mg, 89%). (MS: [M+1] none)

Step 2: 5-cyclopropoxy-2-methyl-4-nitrobenzaldehyde 5-cyclopropoxy-2-methyl-4-nitrobenzonitrile (327 mg, 1.5 mmol) and toluene (15 mL) were added to a 50 ml reaction flask, and added with diisobutylaluminum hydride in methylbenzene solution (3.8 mL, 3.8 mmol) at 0° C. The reaction mixture was reacted at 0° C. for 3 hours, and the reaction was quenched with water, filtered, and the filtrate was extracted with ethyl acetate, washed with saturated brine, dried and concentrated. The thus obtained crude product was separated and purified by silica gel column (silica gel column, eluent:ethyl acetate/petroleum ether, gradient: 0~40% ethyl acetate) to obtain the title compound (245 mg, 74%). (MS: [M+1] none)

Step 3: 1-(5-cyclopropoxy-2-methyl-4-nitrophenyl)-4-methylpiperazine 5-cyclopropoxy-2-methyl-4-nitrobenzaldehyde (111 mg, 0.5 mmol), N-methylpiperazine (100 mg, 1 mmol), acetic acid (60 mg, 1 mmol) and dichloromethane (5 mL) were added to a 25 ml reaction flask, and stirred at 0° C. for 5 to 10 minutes, followed by adding sodium triacetoxyborohydride (117 mg, 0.55 mmol) in batches. The reaction mixture was reacted at room temperature overnight, and added with saturated sodium bicarbonate solution to quench the reaction, extracted with ethyl acetate, washed with saturated brine, dried and concentrated. The thus obtained crude product was separated and purified by column chromatography (silica gel column, eluent:ethyl acetate/petroleum ether, gradient: 20~60% ethyl acetate) to obtain the title compound (97 mg, 64%). (MS: [M+1] 306.2)

Step 4: 2-cyclopropoxy-5-methyl-4-((4-methylpiperazin-1-yl)methyl)aniline

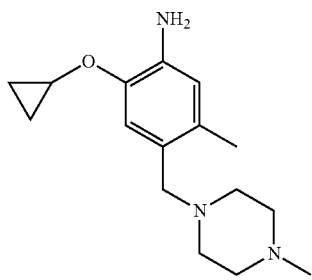 [SMILES: Cc1cc(N)c(OC2CC2)cc1CN1CCN(C)CC1]

1-(5-cyclopropoxy-2-methyl-4-nitrophenyl)-4-methyl-piperazine (87 mg, 0.29 mmol), zinc powder (180 mg, 2.9 mmol), ammonium chloride (31 mg, 0.58 mmol) and ethanol/water (5/2.5 mL) were added to a 25 ml reaction flask. The reaction mixture was reacted at room temperature for 1 hour, filtered, and the filtrate was extracted with ethyl acetate, washed with saturated brine, dried and concentrated. The thus obtained crude product was separated by thin layer silica gel (silica gel plate, developing solvent: dichloromethane/methanol, 10% methanol) to obtain the title compound (72 mg, 90%). (MS: [M+1] 276.1)

Example 82 Preparation of Intermediate A83

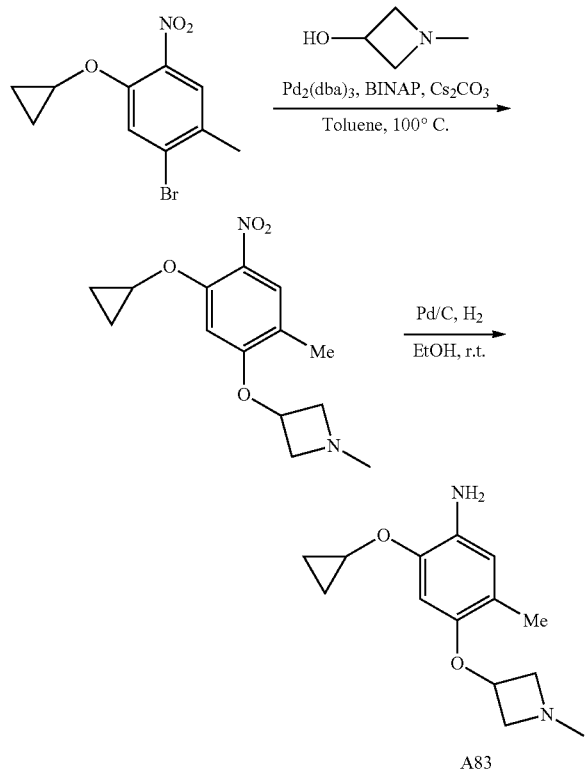

Step 1: 3-(5-cyclopropoxy-2-methyl-4-nitrophenoxy)-1-methyl azetidine

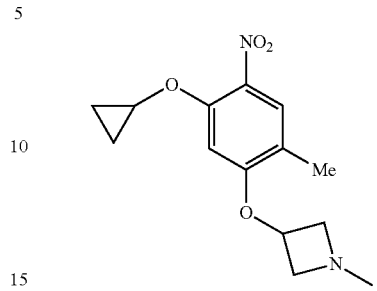

1-methyl-3-hydroxy-azetidine (348 mg, 4 mmol), 1-bromo-5-cyclopropoxy-2-methyl-4-nitrobenzene (54 mg, 2 mmol), cesium carbonate (1.3 g, 4 mmol), tris (dibenzylideneacetone) dipalladium (230 mg, 0.4 mg), 1,1'-binaphthyl-2,2'-bis diphenyl phosphine (497 mg, 0.8 mmol) and toluene (20 mL) were added to a 250 ml reaction flask. The reaction mixture was heated up to 100° C. and stirred overnight. After completion of the reaction, the mixture was cooled down, added with ethyl acetate, filtered, and layered with 40 ml water, and the organic phase was extracted twice with ethyl acetate. The combined organic phase was washed with saturated aqueous sodium chloride solution, filtered and dried. The crude product obtained by concentrating the reaction solution was purified by column chromatography (dichloromethane:methanol=20:1) to obtain the title compound (yellow oil, 121 mg, 75%), which was used directly for the subsequent reaction. (MS: [M+1] 279.1)

Step 2: 2-cyclopropoxy-5-methyl-4-(1-methyl-azetidinyl-3-yloxy)aniline

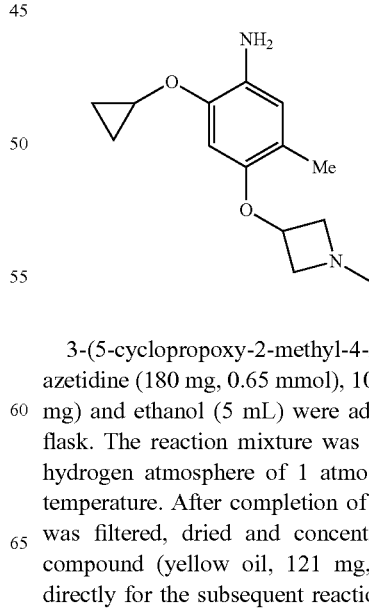

3-(5-cyclopropoxy-2-methyl-4-nitrophenyl)-1-methyl-azetidine (180 mg, 0.65 mmol), 10% palladium/carbon (180 mg) and ethanol (5 mL) were added to a 100 ml reaction flask. The reaction mixture was stirred for 3 hours under hydrogen atmosphere of 1 atmospheric pressure at room temperature. After completion of the reaction, the mixture was filtered, dried and concentrated to obtain the title compound (yellow oil, 121 mg, 75%), which was used directly for the subsequent reaction. (MS: [M+1] 249.2)

Example 83 Preparation of Intermediate A84

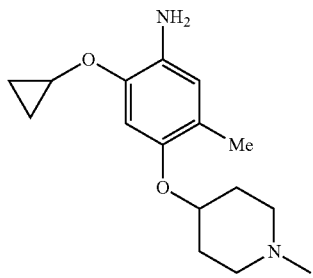

Intermediate A84 was synthesized by the above method for preparing intermediate A83. (MS: [M+1] 277.2)

Example 84 Preparation of Intermediate A85

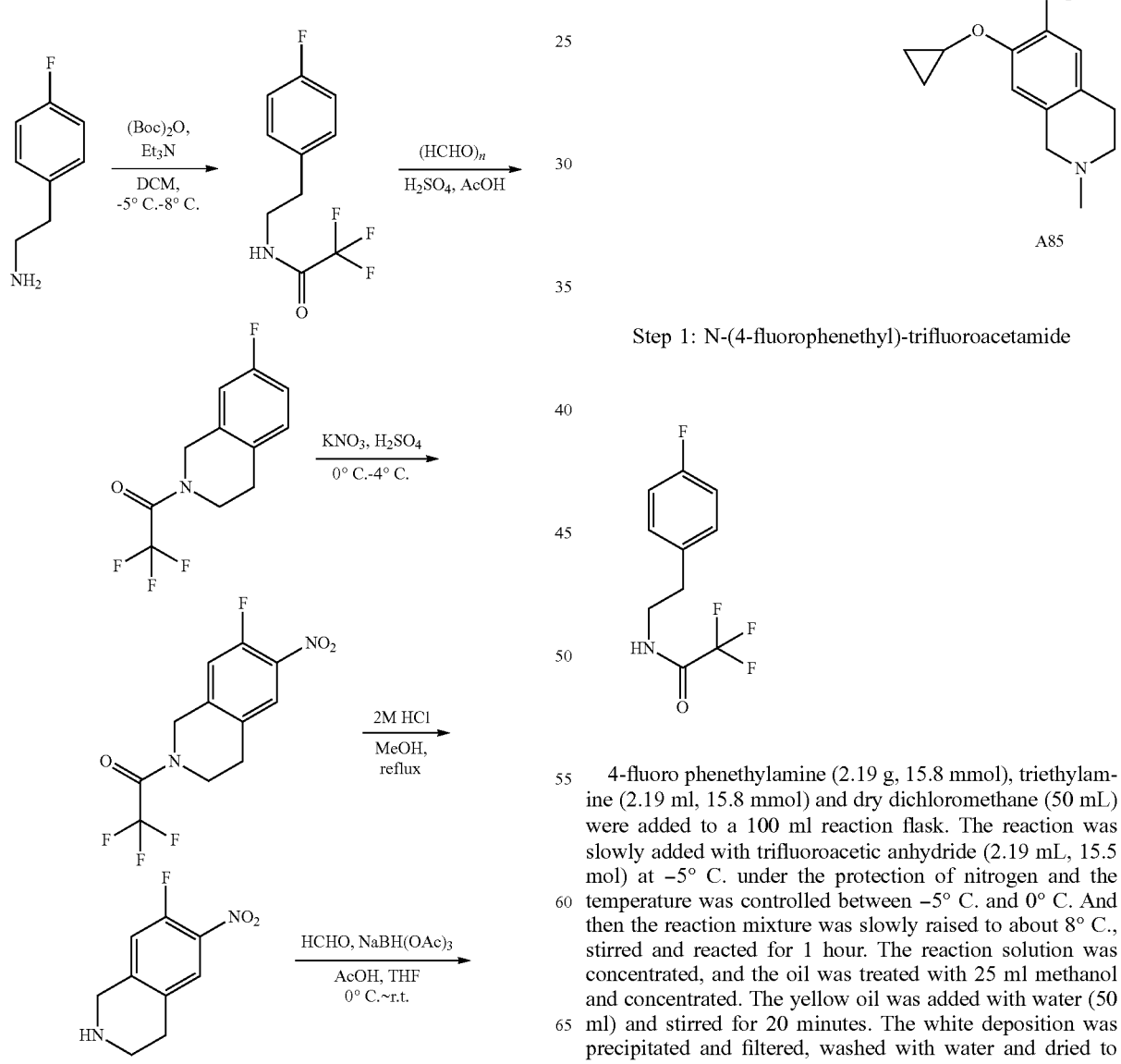

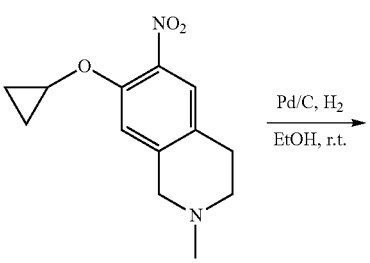

Step 1: N-(4-fluorophenethyl)-trifluoroacetamide

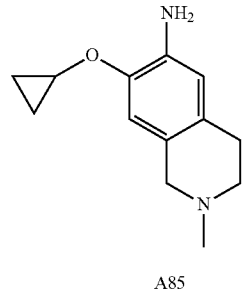

4-fluoro phenethylamine (2.19 g, 15.8 mmol), triethylamine (2.19 ml, 15.8 mmol) and dry dichloromethane (50 mL) were added to a 100 ml reaction flask. The reaction was slowly added with trifluoroacetic anhydride (2.19 mL, 15.5 mol) at −5° C. under the protection of nitrogen and the temperature was controlled between −5° C. and 0° C. And then the reaction mixture was slowly raised to about 8° C., stirred and reacted for 1 hour. The reaction solution was concentrated, and the oil was treated with 25 ml methanol and concentrated. The yellow oil was added with water (50 ml) and stirred for 20 minutes. The white deposition was precipitated and filtered, washed with water and dried to obtain the title compound (2.73 g, 75%). (MS: [M+1] none)

Step 2: N-trifluoroacetyl-7-fluoro-1,2,3,4-tetrahydroisoquinoline

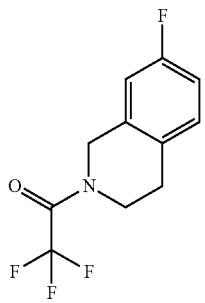 [SMILES: O=C(N1CCc2ccc(F)cc2C1)C(F)(F)F]

N-(4-fluorophenethyl) trifluoroacetamide (2.66 g, 11.3 mmol), paraformaldehyde (0.56 g) and concentrated sulfuric acid/acetic acid (5.5 mL/8.2 mL) were added to a 150 ml reaction flask. The reaction was stirred for 20 hours under the protection of nitrogen at room temperature. The reaction solution was poured into water (50 ml), and extracted three times with ethyl acetate. The organic phases were combined, washed sequentially with saturated aqueous sodium bicarbonate solution and saturated brine, dried, concentrated, and the obtained crude product was separated and purified by column chromatography (silica gel column, eluent:ethyl acetate/petroleum ether, gradient: 0~30%) to obtain the title compound (1.98 g, 71%). (MS: [M+1] none)

Step 3: N-trifluoroacetyl-7-fluoro-6-nitro-1,2,3,4-tetrahydroisoquinoline

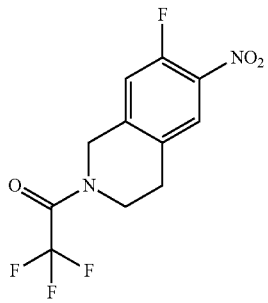 [SMILES: O=C(N1CCc2cc([N+](=O)[O-])c(F)cc2C1)C(F)(F)F]

Concentrated sulfuric acid (4 mL) was added to a 25 ml reaction flask and cooled down to 0° C., and N-trifluoroacetyl-7-fluoro-1,2,3,4-tetrahydroisoquinoline (1 g, 4.05 mmol) was slowly added to the reaction flask. And then potassium nitrate (410 mg, 4.05 mmol) in concentrated sulfuric acid (6 mL) solution was added at this temperature, and the temperature was controlled between 0° C. and 4° C., followed by stirring for 45 minutes at 4° C. After completion of the reaction, the reaction solution was poured into ice water and extracted with ethyl acetate. The organic phases were combined, washed sequentially with water and saturated brine, dried and concentrated to obtain the crude product. The crude product was heated and dissolved with a small amount of methylene chloride, cooled down to room temperature, and added with n-hexane. White solid was precipitated, the deposition was collected and dried to obtain the title compound (770 mg, 65%). (MS: [M+1] none)

Step 4: 7-fluoro-6-nitro-1,2,3,4-tetrahydroisoquinoline

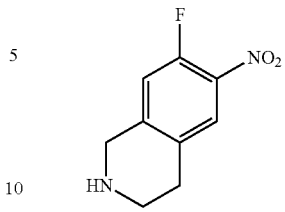

N-trifluoroacetyl-7-fluoro-6-nitro-1,2,3,4-tetrahydroisoquinoline (660 mg, 2.3 mmol) and methanol (10 mL) were added to a 25 ml reaction flask, and hydrochloric acid (2M, 6 mL) was added under the protection of nitrogen. The reaction solution was heated to reflux and reacted overnight, and then concentrated. The residue was ground in diethyl ether, and the solid was collected by filtration to obtain the title compound (450 mg). The crude product was used directly for the subsequent reaction. (MS: [M+1] 197.1)

Step 5: N-methyl-7-fluoro-6-nitro-1,2,3,4-tetrahydroisoquinoline

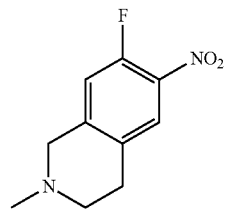

7-fluoro-6-nitro-1,2,3,4-tetrahydroisoquinoline (150 mg, 0.77 mmol) and methanol (10 mL) were added to a 25 ml reaction flask. The reaction mixture was cooled down to 0° C., and added with 36% aqueous formaldehyde solution (340 mg, 7.7 mmol) and acetic acid (92 mg, 1.53 mmol), followed by adding with sodium triacetoxyborohydride (806 mg, 3.8 mmol) in batches. The reaction mixture was heated up to room temperature and stirred overnight. After completion of the reaction, saturated aqueous sodium bicarbonate solution was added and stirred for 10 minutes, and then extracted with ethyl acetate, washed with saturated brine, dried and concentrated to obtain the title compound (150 mg). The crude product was used directly for the subsequent reaction. (MS: [M+1] 211.1)

Step 6: N-methyl-7-cyclopropoxy-6-nitro-1,2,3,4-tetrahydroisoquinoline

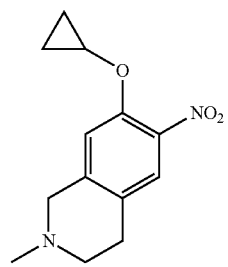 [SMILES: CN1CCc2cc([N+](=O)[O-])c(OC3CC3)cc2C1]

N-methyl-7-fluoro-6-nitro-1,2,3,4-tetrahydroisoquinoline (150 mg, 0.72 mmol), sodium tert-butoxide (83 mg, 0.86 mmol) and N,N-dimethylformamide (5 mL) were added to a 25 ml reaction flask under nitrogen protection. The reaction was stirred for 10 minutes at 0° C., and added with cyclopropanol (54 mg, 0.93 mmol) in N,N-dimethylformamide (5 mL) solution. The reaction was stirred and reacted for 1 hour at 0° C. After completion of the reaction, ethyl acetate and water were added to the reaction solution, and the reaction solution was extracted with ethyl acetate twice additionally. The combined organic phase was washed with saturated brine, dried and concentrated. The obtained crude product was separated and purified by column chromatography (silica gel column, eluent:ethyl acetate/petroleum ether, gradient: 0~50%) to obtain the title compound (140 mg, 79%). (MS: [M+1] 249.1)

Step 7: N-methyl-7-cyclopropoxy-1,2,3,4-tetrahydroisoquinoline-6-amine

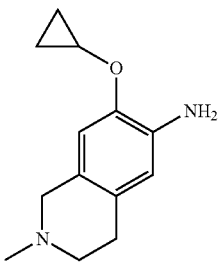

N-methyl-7-cyclopropoxy-6-nitro-1,2,3,4-tetrahydroisoquinoline (100 mg, 0.4 mmol), 10% Pd/C (50 mg) and ethanol (5 mL) were added to a 25 ml reaction flask. The reaction mixture stirred for 3 hours under hydrogen atmosphere of 1 atmospheric pressure at 25° C. After completion of the reaction, the reaction solution was filtered and concentrated to obtain the title compound (80 mg, 91%). The crude product was used directly for the subsequent reaction. (MS: [M+1] 219.1)

Example 85 Preparation of Intermediate A86

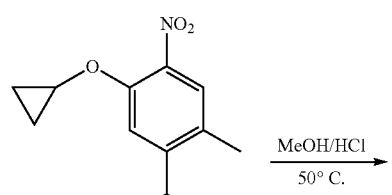

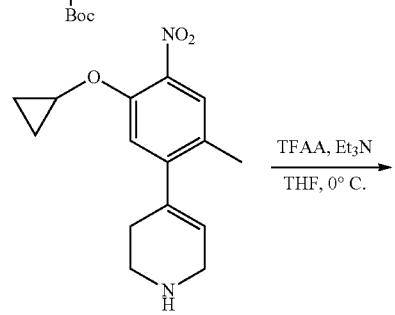

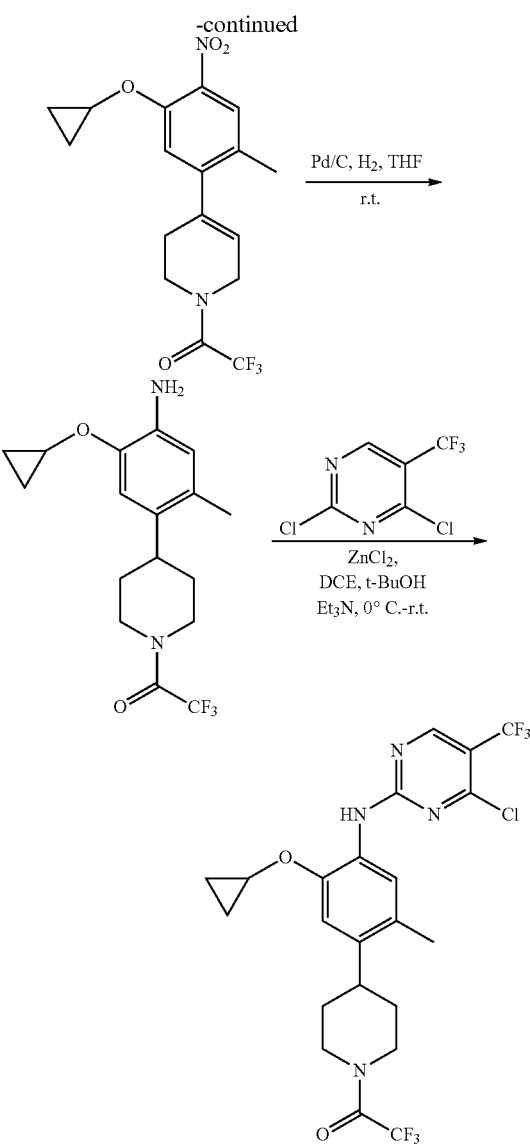

Step 1: 4-(5-cyclopropoxy-2-methyl-4-nitrophenyl)-1,2,3,6-tetrahydropyridine

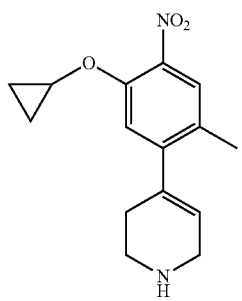 [SMILES: Cc1cc([N+](=O)[O-])c(OC2CC2)cc1C1=CCNCC1]

tert-butyl 4-(5-cyclopropoxy-2-methyl-4-nitrophenyl)-5,6-dihydropyridin-1(2H)-carboxylate (13.8 g, 36.9 mmol)

and concentrated hydrochloric acid/methanol (40/200 mL) were added to a 500 ml single-ported reaction flask. The reaction mixture was heated up to 50° C. in an oil bath, stirred and reacted for 2 hours. After completion of the reaction, the reaction solution was concentrated and quenched with saturated sodium bicarbonate solution, extracted with ethyl acetate, washed with saturated brine, dried and concentrated to obtain the title compound (yellow oil, 14 g), which was used directly for the next reaction. (MS: [M+1] 275.1)

Step 2: 1-(4-(5-cyclopropoxy-2-methyl-4-nitrophenyl)-5,6-dihydropyridin-1(2H)-yl) 2,2,2-trifluoroacetamide

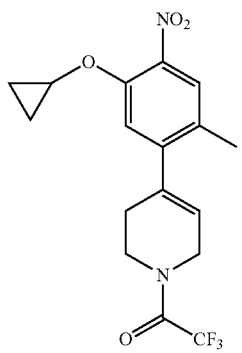 [SMILES: Cc1cc([N+](=O)[O-])c(OC2CC2)cc1C1=CCN(C(=O)C(F)(F)F)CC1]

4-(5-cyclopropoxy-2-methyl-4-nitrophenyl)-1,2,3,6-tetrahydropyridine (14 g, 36.9 mmol meter), trifluoroacetic anhydride (8.14 g, 38.75 mmol), triethylamine (3.9 g, 38.75 mmol) and tetrahydrofuran (200 mL) were added to a 500 ml single-ported reaction flask. The reaction mixture was stirred and reacted for 1 hour under the protection of nitrogen at 0° C. After completion of the reaction, the reaction solution was added with ethyl acetate, washed with saturated brine, dried and concentrated. The obtained crude product was separated and purified by silica gel column (eluent:ethyl acetate/petroleum ether, gradient: 0~30% ethyl acetate) to obtain the title compound (yellow solid, 12 g, the total yield of the two steps is 88%). (MS: [M+1] none)

Step 3: 1-(4-(4-amino-5-cyclopropoxy-2-methylphenyl) piperidin-1-yl)-2,2,2-trifluoroacetamide

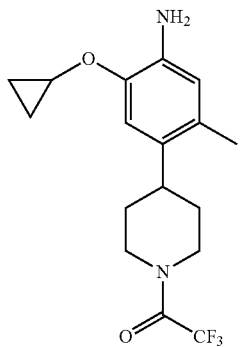 [SMILES: Cc1cc(N)c(OC2CC2)cc1C1CCN(C(=O)C(F)(F)F)CC1]

1-(4-(5-cyclopropoxy-2-methyl-4-nitrophenyl)-5,6-dihydropyridin-1(2H)-yl) 2,2,2-trifluoroacetamide (5 g, 13.51 mmol), 10% palladium/carbon (1.5 g) and tetrahydrofuran (200 mL) were added to a 500 ml single-ported reaction flask. The reaction mixture was reacted for 5 hours under the protection of hydrogen at room temperature. After completion of the reaction, the reaction solution was filtered and concentrated with diatomite to obtain the title compound (colorless foamy solid, 4.08 g), which was used directly for the next reaction. (MS: [M+1] 343.2)

Step 4: 1-(4-(4-(4-chloro-5-(trifluoromethyl) pyrimidin-2-amino)-5-cyclopropoxy-2-methyl-phenyl)-1-yl)-N-2,2,2-trifluoroacetyl-piperidine

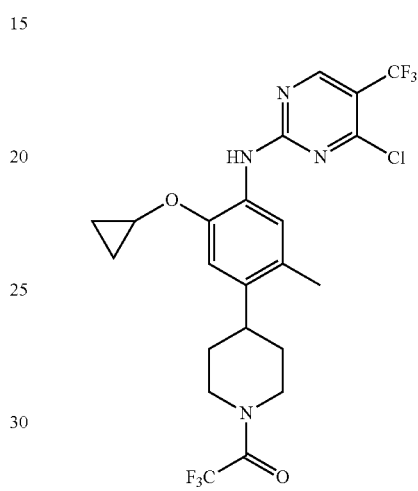

Anhydrous zinc chloride (94 mg, 0.7 mmol) and 2,4-dichloro-5-(trifluoromethyl) pyrimidine (139 mg, 0.64 mmol) were added to 1,2-dichloroethane (10 mL) and tert-butanol (10 mL). After stirring for 1 hour at 0° C., 1-(4-(5-cyclopropoxy-2-methyl-4-nitrophenyl)-5,6-dihydropyridin-1(2H)-yl) 2,2,2-trifluoroacetamide (200 mg, 0.58 mmol) in 1,2-dichloroethane (2 mL) solution was added to the above reaction solution, followed by adding with triethylamine (64 mg, 0.63 mmol). The reaction mixture was stirred for 30 minutes at 0° C. and then heated up to room temperature and stirred overnight. The reaction solution was poured into water, extracted with dichloromethane, dried, concentrated and purified by thin-layer chromatography (developing solvent:petroleum ether/ethyl acetate=4:1) to obtain the title compound (200 mg, 66%). (MS: [M+1] 523.1)

Example 86 Preparation of Intermediate A87

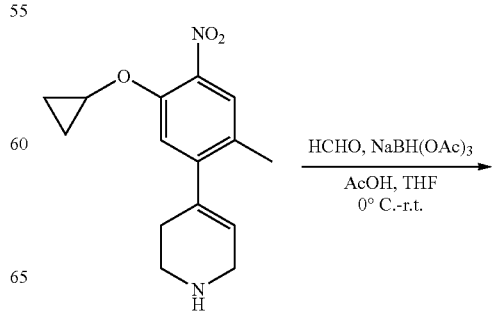

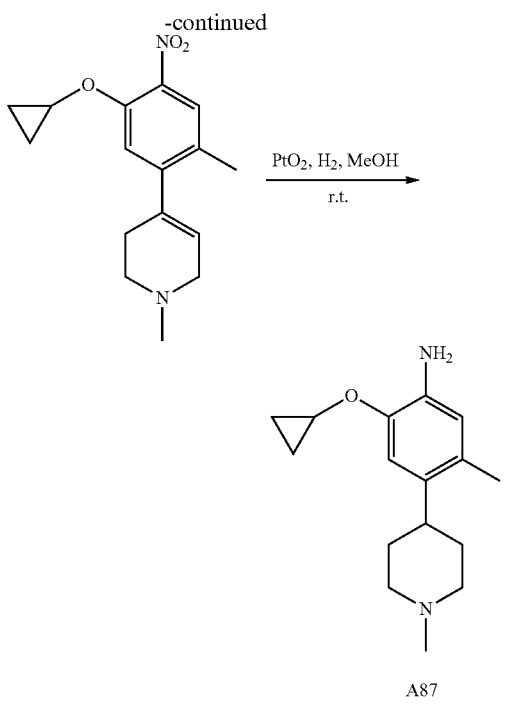

Step 1: 4-(5-cyclopropoxy-2-methyl-4-nitrophenyl)-1-methyl-1,2,3,6-tetrahydropyridine

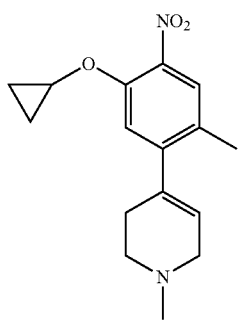 [SMILES: Cc1cc([N+](=O)[O-])c(OC2CC2)cc1C1=CCN(C)CC1]

The title compound was prepared by using the method for preparing intermediate A73 in step 4.

Step 2: 2-cyclopropoxy-5-methyl-4(1-methyl-piperidin-4-yl)aniline

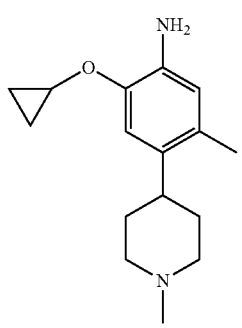 [SMILES: Cc1cc(N)c(OC2CC2)cc1C1CCN(C)CC1]

The title compound was prepared by using the method for preparing intermediate A73 in step 5.

Example 87 Preparation of Intermediate B1

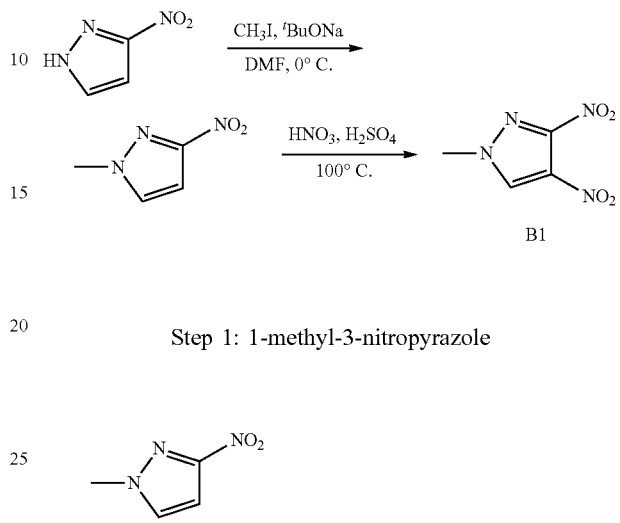

Step 1: 1-methyl-3-nitropyrazole

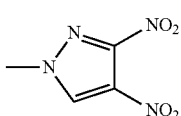

3-nitropyrazole (20 g, 0.177 mol) and N,N-dimethylformamide (300 mL) were added to a 1 L reaction flask. The reaction mixture was stirred in an ice-salt bath for 20 minutes, and then sodium tert-butoxide (20.35 g, 0.212 mol) was slowly and carefully added in batches. The reaction mixture was stirred for 3 hours at 0° C. After completion of the reaction, excess saturated aqueous ammonium chloride solution was added to terminate the reaction, and then ethyl acetate was used to extract. The organic phase was washed with saturated aqueous sodium chloride solution, dried and concentrated to obtain the title compound (yellow solid, 20.7 g, 92%), which was used directly for the next reaction. (MS: [M+1] none)

Step 2: 1-methyl-3,4-dinitropyrazole

In a 1 L reaction flask, the obtained 1-methyl-3-nitropyrazole (20.7 g, 0.163 mol) in the last step was slowly added with concentrated sulfuric acid (600 mL), and then concentrated nitric acid (60 mL) was slowly added to the reaction system. The reaction mixture was heated up to 100° C. and stirred for 6 hours. After completion of the reaction, the reaction system was poured into ice water, and saturated aqueous sodium carbonate solution was added for neutralization until the pH value was 8 to 9. Ethyl acetate was added to extract the reaction solution, and the organic phase was filtered and dried to obtain the title compound (yellow oil, 22.1 g, 79%), which was used directly for the next reaction. (MS: [M+1] none)

Example 88 Preparation of Intermediate B2

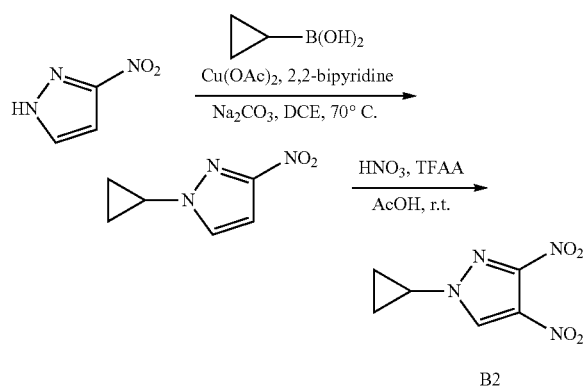

Step 1: 1-cyclopropyl-3-nitropyrazole

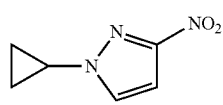 [SMILES: O=[N+]([O-])c1ccn(C2CC2)n1]

3-nitropyrazole (1.0 g, 8.9 mmol), 2,2-bipyridine (1.4 g, 8.9 mmol), anhydrous sodium carbonate (1.8 g, 17 mmol) and dichloroethane (20 mL) were added to a 100 mL reaction flask. The reaction mixture was stirred for 30 minutes under the protection of nitrogen at room temperature, and then added with anhydrous copper acetate (1.6 g, 8.9 mmol) in batches and stirred for 1 hour, and then heated up to 70° C. and stirred overnight. After completion of the reaction, dichloromethane was added for dilution, and filtered. The organic phase was washed with hydrochloric acid (20 mL, 2M) and saturated brine, and then dried and concentrated to obtain the title compound (brown oil, 0.82 g, 60%), which was used directly for the next reaction. (MS: [M+1] none)

Step 2: 1-cyclopropyl-3,4-dinitropyrazole

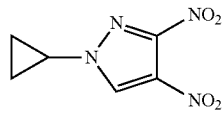

Glacial acetic acid (10 mL), trifluoroacetic anhydride (3 mL), and 1-cyclopropyl-3-nitro-pyrazole (0.82 g, 5.36 mmol) were added to a 50 mL reaction flask, and fuming nitric acid (2.5 mL) was added thereinto under stirring, followed by stirring for 4 hours at room temperature. After completion of the reaction, the reactant was poured into ice water, and sodium bicarbonate was added to adjust the pH value to 8 to 9, and extracted with ethyl acetate, dried and concentrated to obtain the crude title compound (brown oil, 1.05 g, 100%), which was used directly for the next reaction. (MS: [M+1] none)

Example 89 Preparation of Intermediate B3

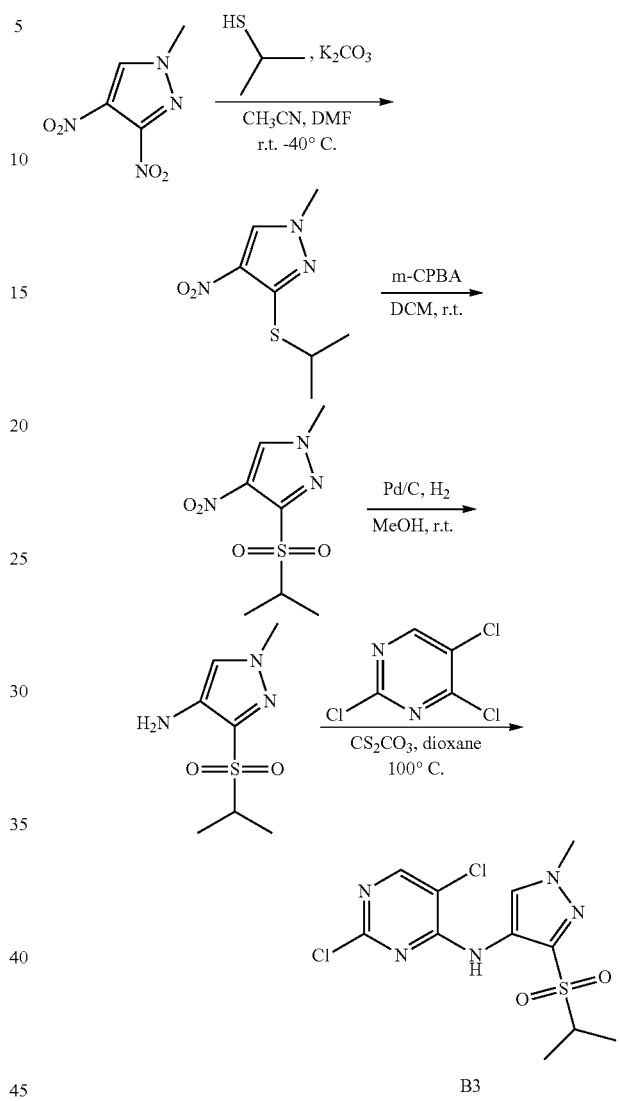

Step 1: 3-isopropylmercapto-1-methyl-4-nitropyrazole

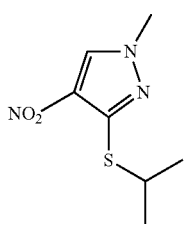

1-methyl-3,4-dinitropyrazole (21.6 g, 0.125 mol), isopropyl mercaptan (12.4 mL, 0.134 mol), potassium carbonate (19 g, 0.138 mol) and acetonitrile (400 mL) were added to a 1 L reaction flask. The reaction mixture was stirred vigorously at room temperature for 12 hours, and supplemented with isopropyl mercaptan (6.2 mL, 67 mmol), cesium carbonate (22.5 g, 69 mmol), and N,N-dimethylformamide (50 mL). The reaction mixture was heated up to 40° C. and stirred overnight. After completion of the reaction, the reaction solution was cooled down and slowly poured into water, extracted with ethyl acetate, and then washed with saturated aqueous sodium chloride solution and saturated aqueous lithium chloride solution, dried and concentrated. The obtained crude product was crystallized with a mixed solution of ethyl acetate and diethyl ether (ethyl acetate:diethyl ether=1:10) to obtain the title compound (yellow solid, 24.2 g, 96%). (MS: [M+1] 202.1)

Step 2: 3-isopropylsulfonyl-1-methyl-4-nitropyrazole

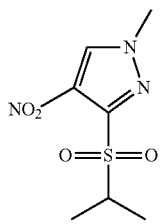

3-isopropylmercapto-1-methyl-4-nitropyrazole (13.2 g, 65.7 mmol) and dichloromethane (200 mL) were added to a 500 mL reaction flask, and then m-chloroperoxybenzoic acid (22.7 g, 0.132 mol) was slowly added to the reaction system in batches. The reaction mixture was stirred overnight at room temperature. After completion of the reaction, saturated aqueous sodium sulfite was added until starch potassium iodide paper does not turn into blue, filtered, dried and concentrated to obtain the title compound (white solid, 15 g, 98%), which was used directly for the subsequent reaction. (MS: [M+1] 234.1)

Step 3: 3-isopropylsulfonyl-1-methyl-4-aminopyrazole

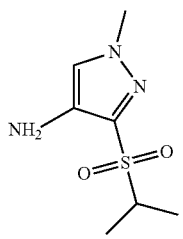

3-isopropylsulfonyl-1-methyl-4-nitropyrazole (15 g, 64 mmol), 10% Pd/C (1.5 g) and methanol (150 mL) were added to a 500 mL reaction flask. The reaction mixture was stirred overnight under hydrogen atmosphere of 1 atmospheric pressure at room temperature. After completion of the reaction, filtered, washed with diethyl ether, dried and concentrated to obtain the title compound (purple solid, 10 g, 77%). (MS: [M+1] 204.1)

Step 4: 2,5-dichloro-N-(3-isopropylsulfonyl-1-methyl-1H-pyrazol-4-yl)-pyrimidin-4-amine

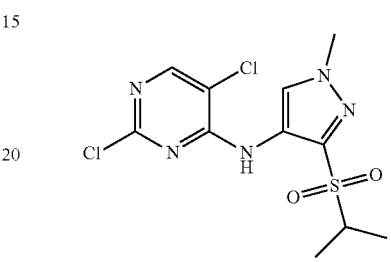

3-isopropylsulfonyl-1-methyl-4-nitropyrazole (2.04 g, 10 mmol), 2,4,5-trichloropyrimidine (2.73 g, 15 mmol), triethylamine (2.02 g, 20 mmol) and anhydrous ethanol (20 mL) were added to a 100 mL reaction flask. The reaction mixture was heated up to 70° C. under the protection of nitrogen and stirred for 24 hours, concentrated, and dissolved with ethyl acetate, washed with water, dried and concentrated. The thus obtained crude product was recrystallized with isopropanol to obtain the title compound (white solid, 2.45 g, 70%). (MS: [M+1] 350.0) (the reaction in this step can also be carried out by heating up to 100° C. in a cesium carbonate/1,4-dioxane system to obtain the title compound)

Example 90-97 Preparation of Intermediates B4-B11

Intermediates B4-B11 were synthesized by using the above method for preparing intermediate B3 (table 6).

TABLE 6

Intermediates B4-B11

| Nos. | Starting Materials | | | Intermediates | Molecular Ion Peaks [M + 1]⁺ |
|---|---|---|---|---|---|
| B4 | 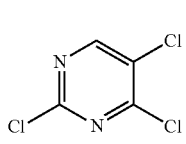 | 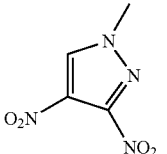 |  | 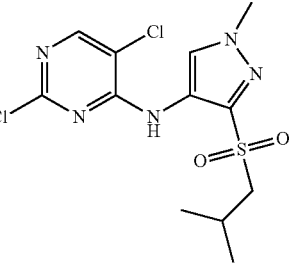 | 364.0 |

TABLE 6-continued

Intermediates B4-B11

| Nos. | Starting Materials | Intermediates | Molecular Ion Peaks [M + 1]+ |
|---|---|---|---|
| B5 | | | 364.1 |
| B6 | | | 362.0 |
| B7 | | | 376.1 |
| B8 | | | 317.0 |
| B9 | | | 334.1 |

TABLE 6-continued

Intermediates B4-B11

| Nos. | Starting Materials | Intermediates | Molecular Ion Peaks [M + 1]+ |
|---|---|---|---|
| B10 | 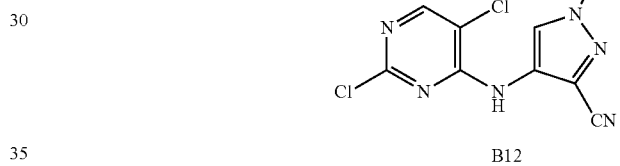 | | 330.1 |
| B11 | 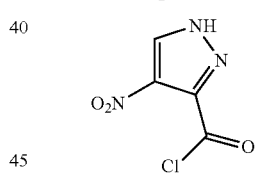 |  | 394.0 |

Example 98 Preparation of Intermediate B12

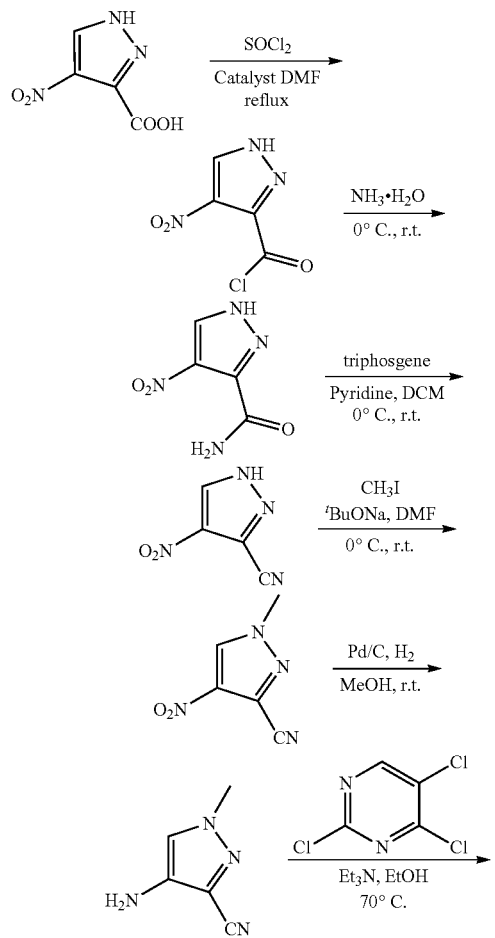

Step 1: 4-nitropyrazol-3-carbonyl chloride 4-nitro-pyrazol-3-formic acid (3 g, 19.1 mmol), thionyl chloride (100 mL) and N,N-dimethylformamide (0.1 mL) were added to a 250 mL reaction flask. The reaction mixture was heated up to reflux and stirred for 3 hours. After completion of the reaction, the reaction solution was concentrated to obtain the title compound (3.33 g), the crude product was used directly for the subsequent reaction. (MS: [M+1] none)

Step 2: 4-nitropyrazol-3-carboxamide

Aqueous ammonia (60 mL) was added to a 250 mL reaction flask and cooled down to 0° C., and added with 4-nitropyrazol-3-carbonyl chloride (3.33 g, 19.1 mmol) in tetrahydrofuran solution (60 mL) at this temperature. The reaction mixture was slowly heated up to room temperature and stirred for 18 hours. After completion of the reaction, the reaction mixture was concentrated, washed with water and petroleum ether, and the filter cake was dried to obtain the title compound (1.7 g, the yield of the two steps is 57%). (MS: [M+1] 157.0)

Step 3: 3-cyano-4-nitropyrazole

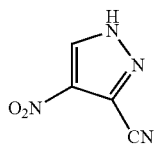

4-nitropyrazol-3-carboxamide (400 kg, 2.56 mmol), pyridine (1.62 g, 20.5 mmol) and anhydrous dichloromethane (40 mL) were added to a 250 mL reaction flask. The reaction mixture was cooled down to 0° C., and added with triphosgene (780 mg, 2.64 mmol) at this temperature. The reaction mixture was slowly heated up to room temperature and stirred for 18 hours. After completion of the reaction, the reaction solution was added with water to quench the reaction, and the extracted organic phase was washed with dilute hydrochloric acid (3N) and saturated brine, dried and concentrated. The thus obtained crude product was purified by column chromatography (developing solvent:methanol/water=2:1) to obtain the title compound (200 mg, 56%). (MS: [M+1] 139.0)

Step 4: 1-methyl-3-cyano-4-nitropyrazole

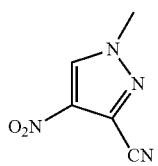

3-cyano-4-nitropyrazole (139 mg, 1 mmol), sodium tert-butoxide (144 mg, 1.5 mmol) and N,N-dimethylformamide (5 mL) were added to a 25 mL reaction flask. The reaction mixture was cooled down to 0° C., and added with methyl iodide (213 mg, 1.5 mg) at this temperature. The reaction mixture was slowly heated up to room temperature and stirred for 2 hours. After completion of the reaction, the reaction solution was added with water to quench the reaction, extracted with ethyl acetate, and the organic phase was washed with saturated brine, dried and concentrated. The thus obtained crude product was purified by column chromatography (developing solvent:petroleum ether/ethyl acetate=1:1) to obtain the title compound (110 mg, 72%). (MS: [M+1] 153.0)

Step 5: 1-methyl-3-cyano-4-aminopyrazole

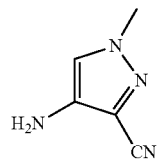

1-methyl-3-cyano-4-nitropyrazole (91 mg, 0.6 mmol), Pd/C (20 mg) and methanol (5 mL) were added to a 25 mL reaction flask. The reaction mixture was stirred under hydrogen atmosphere of 1 atmospheric pressure at room temperature for 3 hours. After completion of the reaction, the reaction solution was filtered and concentrated to obtain the title compound (65 mg). The crude product was used directly for the subsequent reaction. (MS: [M+1] 123.1)

Step 6: 2,5-dichloro-N-(3-cyano-1-methyl-1H-pyrazol-4-yl)-pyrimidin-4-amine

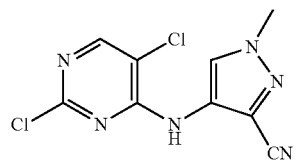 [SMILES: Cn1cc(Nc2nc(Cl)ncc2Cl)c(C#N)n1]

1-methyl-4-amino-1H-pyrazole-3-carbonitrile (65 mg, 0.53 mmol meter), 2,4,5-trichloro-pyrimidine (146 mg, 0.8 mmol), triethylamine (101 mg, 1 mmol) and ethanol (6 mL) were added to a 15 mL reaction flask. The reaction mixture was heated up to 70° C. and stirred for 18 hours. After completion of the reaction, the reaction solution was concentrated and purified by column chromatography (developing solvent:petroleum ether/ethyl acetate=1:1) to obtain the title compound (65 mg, the yield of the two steps is 40%). (MS: [M+1] 269.0)

Example 99 Preparation of Intermediate B13

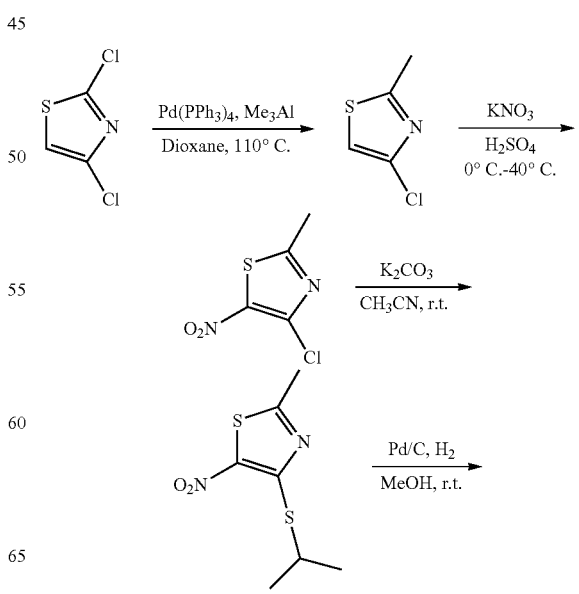

-continued

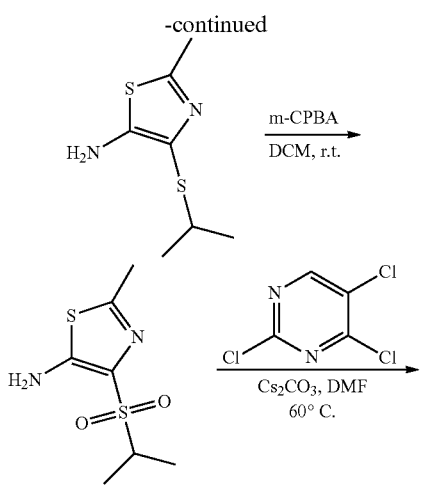

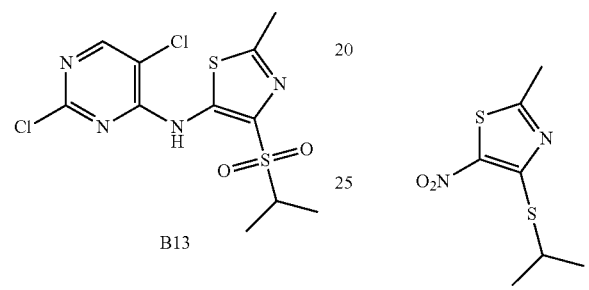

B13

Step 1: 4-chloro-2-methylthiazole

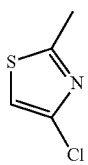

2,4-dichlorothiazole (770 mg, 5 mg), trimethyl aluminum (5 mL, 5 mmol, 1 mol/L), tetrakis(triphenylphosphine) palladium (710 mg, 0.5 mmol) and anhydrous 1,4-dioxane (10 mL) were added to a 30 mL microwave tube. The reaction mixture was heated up to 100° C. by microwave under the protection of nitrogen and stirred for 20 minutes. After completion of the reaction, the reaction solution was cooled down and poured into saturated sodium bicarbonate solution, extracted with ethyl acetate, washed with saturated brine, dried and concentrated. The thus obtained crude product was separated and purified by column chromatography (silica gel column, eluent:ethyl acetate/petroleum ether, gradient: 0-20% ethyl acetate) to obtain the title compound (440 mg, 66%). (MS: [M+1] none)

With reference to the above procedures, more than 2 g product was obtained.

Step 2: 4-chloro-2-methyl-5-nitrothiazole

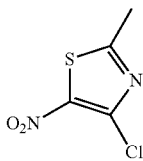

4-chloro-2-methylthiazole (1.8 g, 13.5 mmol) and concentrated sulfuric acid (15 mL) were added to a 100 mL reaction flask. The reaction mixture was cooled down to about −5° C. to 0° C., and added with potassium nitrate (1.78 g, 17.6 mmol) in batches at this temperature. The reaction mixture was slowly heated up to 40° C. and stirred overnight. After completion of the reaction, the reaction solution was poured into ice water and extracted with ethyl acetate, washed with saturated sodium bicarbonate solution and saturated brine, dried and concentrated. The thus obtained crude product was separated and purified by column chromatography (silica gel column, eluent:ethyl acetate/petroleum ether, gradient: 0-20% ethyl acetate) to obtain the title compound (2.162 g, 90%). (MS: [M+1] 179.0)

Step 3: 4-(isopropyl mercapto)-2-methyl-5-nitrothiazole

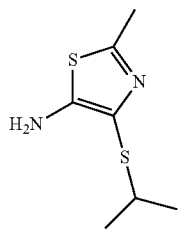

4-chloro-2-methyl-5-nitrothiazol (1.43 g, 8 mmol), potassium carbonate (1.66 g, 12 mmol), isopropyl mercaptan (0.79 g, 10.4 mmol) and acetonitrile (20 mL) were added to a 50 ml reaction flask. The reaction mixture was reacted at room temperature overnight and filtered. The filtrate was concentrated under reduced pressure, added with water, extracted with ethyl acetate, washed with saturated brine, dried and concentrated to obtain the crude product (350 mg, 20%), which was used directly for the subsequent reaction. (MS: [M+1] 219.1)

Step 4: 4-(isopropyl mercapto)-2-methylthiazol-5-amine 4-(isopropyl mercapto)-2-methyl-5-nitrothiazol (280 mg, 1.3 mmol), Pd/C (280 mg, 5%) and ethanol (5 mL) were added to a 25 mL reaction flask. The reaction mixture was reacted under hydrogen atmosphere of 1 atmospheric pressure at room temperature for 2 hours. After completion of the reaction, the reaction solution was filtered and concentrated. The thus obtained crude product was separated and purified by column chromatography (silica gel column, eluent: methylene chloride/methanol, gradient: 0-5% methanol) to obtain the title compound (150 mg, 61%). (MS: [M+1] 189.1)

Step 5: 4-(isopropylsulfonyl)-2-methylthiazol-5-amine

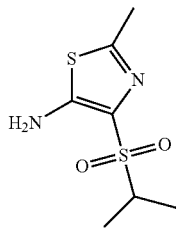

4-(isopropyl mercapto)-2-methylthiazol-5-amine (150 mg, 0.8 mmol) and dichloromethane (8 mL) were added to a 25 ml reaction flask. m-chloroperbenzoic acid (414 mg, 2.4 mmol) was added in batches, and then the reaction mixture was reacted at room temperature overnight. After completion of the reaction, the reaction solution was added with saturated sodium sulfite solution, extracted with ethyl acetate and concentrated. The thus obtained crude product was separated and purified by column chromatography (silica gel column, eluent: methylene chloride/methanol, gradient: 0-5% methanol) to obtain the title compound (161 mg, 91%). (MS: [M+1] 221.1)

Step 6: N-(2, 5-dichloro-pyrimidin-4-yl)-4-(isopropylsulfonyl)-2-methylthiazole-5-amine

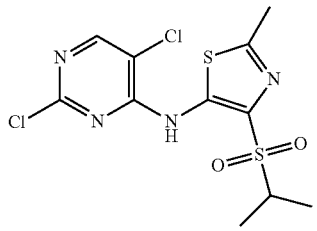 [SMILES: Cc1nc(S(=O)(=O)C(C)C)c(Nc2nc(Cl)ncc2Cl)s1]

4-(isopropylsulfonyl)-2-methylthiazol-5-amine (82 mg, 0.37 mmol), cesium carbonate (248 mg, 0.74 mmol), 2, 4, 5-trichloro-pyrimidine (171 mg, 0.93 mmol) and N,N-dimethylformamide (8 mL) were added to a 25 mL reaction flask. The reaction mixture was heated up to 60° C. and reacted for 3 hours. After completion of the reaction, the reaction solution was cooled down and added with water, extracted with ethyl acetate and concentrated. The thus obtained crude product was separated and purified by column chromatography (silica gel column, eluent:petroleum ether/ethyl acetate, gradient: 0-60% ethyl acetate) to obtain the title compound (53.4 mg, 50%). (MS: [M+1] 367.0)

Example 100 Preparation of Intermediate B14

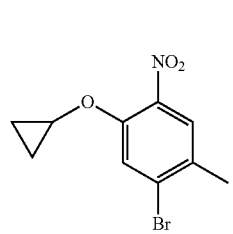 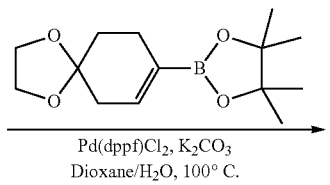

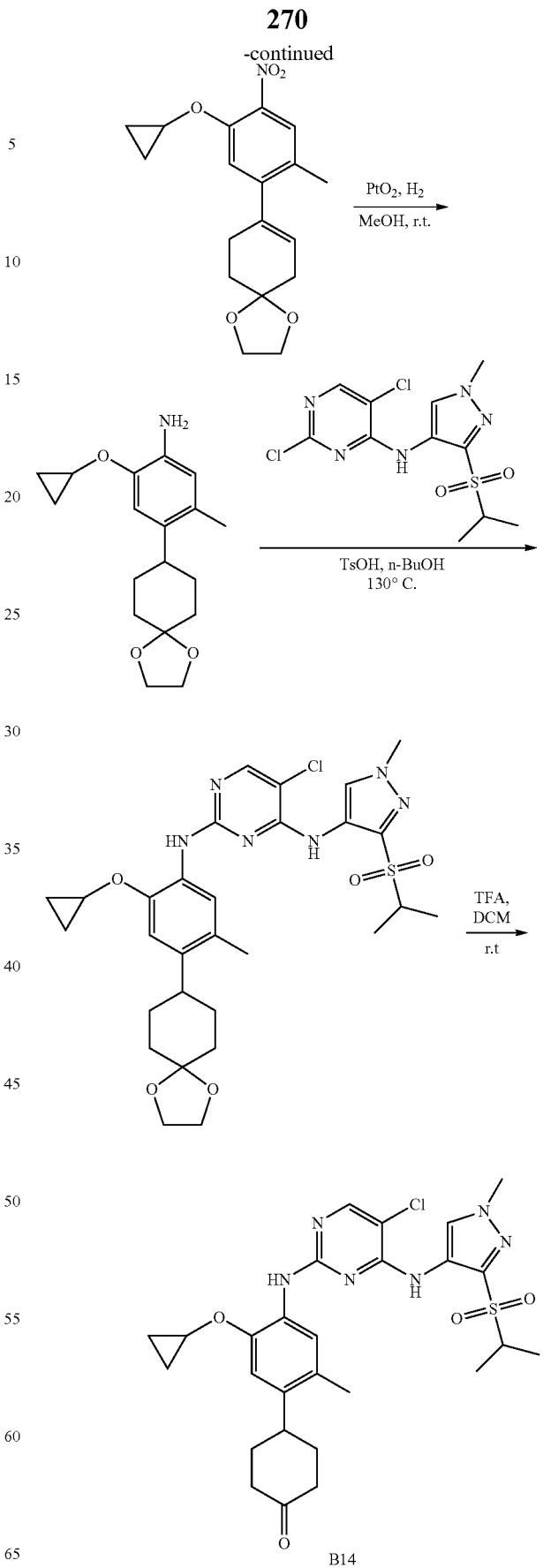

Step 1: 8-(5-cyclopropoxy-2-methyl-4-nitrophenyl)-1,4-dioxaspiro[4.5]dec-7-ene

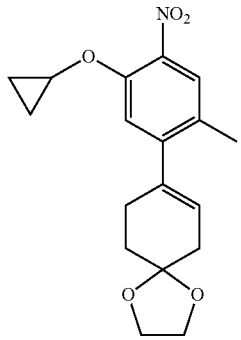 [SMILES: Cc1cc([N+](=O)[O-])c(OC2CC2)cc1C1=CCC2(CC1)OCCO2]

1,4-dioxaspiro[4.5]dec-7-ene-8-boronic acid pinacol ester (0.38 g, 1.43 mmol), 1-bromo-5-cyclopropoxy-2-methyl-4-nitrobenzene (0.35 g, 1.29 mmol), bis (triphenylphosphine) palladium dichloride (0.18 g, 0.26 mmol), sodium carbonate (0.27 g, 2.55 mmol), 1,4-dioxane (3.5 mL) and water (1.4 mL) were added to a 25 ml reaction flask. The reaction mixture was heated up to 100° C. under the protection of nitrogen and reacted for 3 hours. After completion of the reaction, water was added to dissolve, ethyl acetate was added to extract and the organic layer was washed with water, dried, concentrated and purified by column chromatography (ethyl acetate/petroleum ether=1:5) to obtain the title compound (white solid, 0.3 g, 70%). (MS: [M+1] 332.1)

Step 2: 2-cyclopropoxy-5-methyl-4-(1,4-dioxaspiro[4.5]dec-8-yl) aniline

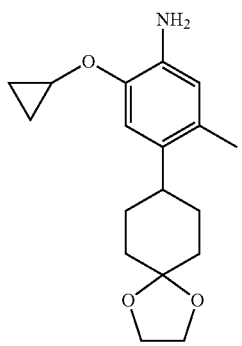 [SMILES: Cc1cc(N)c(OC2CC2)cc1C1CCC2(CC1)OCCO2]

8-(5-cyclopropoxy-2-methyl-4-nitrophenyl)-1,4-dioxaspiro[4.5]dec-7-ene (140 mg, 0.42 mmol), platinum dioxide (80 mg, 80% content) and methanol (5 mL) were added to a 25 ml reaction flask. The reaction mixture was stirred under the condition of hydrogen at room temperature for 2 hours. After completion of the reaction, the mixture was filtered and concentrated to obtain the crude title compound (brown oil, 100 mg, 78%), which was used directly for the subsequent reaction. (MS: [M+1] 304.1)

Step 3: 5-chloro-N²-(2-cyclopropoxy-5-methyl-4-(1,4-dioxa-spiro[4.5]dec-8-yl) phenyl)-N⁴-(3-(isopropylsulfonyl)-1-methyl-1H-pyrazol-4-yl)pyrimidin-2,4-diamine

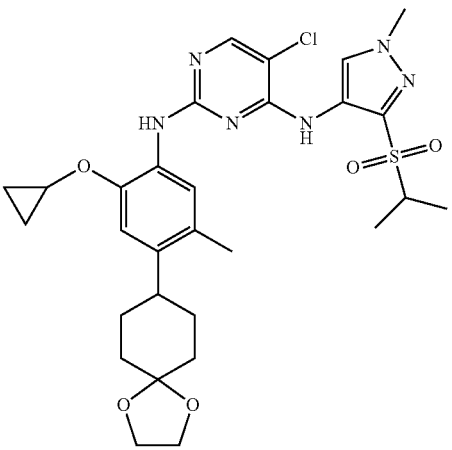 [SMILES: Cc1cc(Nc2ncc(Cl)c(Nc3cn(C)nc3S(=O)(=O)C(C)C)n2)c(OC2CC2)cc1C1CCC2(CC1)OCCO2]

2-cyclopropoxy-5-methyl-4-(1,4-dioxaspiro[4.5]dec-8-yl) aniline (100 mg, 0.33 mmol), 2,5-dichloro-N-(3-(isopropylsulfonyl)-1-methyl-1H-pyrazol-4-yl) pyrimidin-4-amine (125 mg, 0.36 mmol), p-toluenesulfonic acid (57 mg, 0.33 mmol) and n-butanol (3 mL) were added to a 10 mL reaction flask. The reaction mixture was headed up to 130° C. under the protection of nitrogen in microwave reaction instrument. After stirring for 30 minutes, the pH was adjusted to 9 with saturated sodium bicarbonate and extracted with ethyl acetate. The organic phase was dried, concentrated and purified by thin layer chromatography (ethyl acetate/petroleum ether=1:2) to obtain the title compound (white solid, 59 mg, 29%). (MS: [M+1] 617.2)

Step 4: 4-(4-(5-chloro-4-(3-(isopropylsulfonyl)-1-methyl-1H-pyrazol-4-amine)pyrimidin-2-amine)-5-cyclopropoxy-2-methylphenyl)cyclohexanone

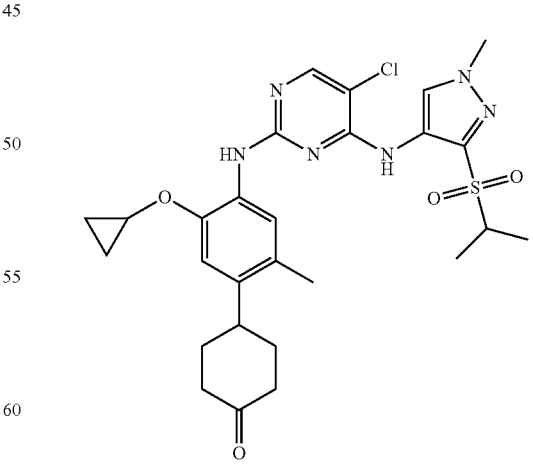

5-chloro-N²-(2-cyclopropoxy-5-methyl-4-(1,4-dioxaspiro[4.5]dec-8-yl) phenyl)-N⁴-(3-(isopropylsulfonyl)-1-methyl-1H-pyrazol-4-yl) pyrimidin-2,4-diamine (60 mg, 0.097 mmol), trifluoroacetic acid (0.1 mL), dichloromethane (2 mL) were added to a 5 mL reaction flask. The reaction mixture was stirred under the protection of nitrogen at room temperature for 24 hours, added with saturated aqueous sodium bicarbonate to neutralize till the pH value to 8 to 9, and extracted with ethyl acetate, dried and concentrated to obtain the crude title compound (white solid, 55 mg, 100%), which was used directly for the subsequent reaction. (MS: [M+1] 573.2)

Example 101-102 Preparation of Intermediates B15 and B16

Intermediates 4-(4-(5-chloro-4-(3-(isopropylsulfonyl)-1-methyl-1H-pyrazol-4-amine)pyrimidin-2-amine)-5-isopropoxy-2-methylphenyl)cyclohexanone (B15) and 4-(4-(5-chloro-4-(3-(isobutylsulfonyl)-1-methyl-1H-pyrazol-4-amine)pyrimidin-2-amine)-5-isopropoxy-2-methylphenyl)cyclohexanone (B16) were synthesized by the above method for preparing intermediate B14.

Example 103 5-chloro-N²-[2-isopropoxy-4-(piperidin-4-yl)phenyl]-N⁴-(3-isopropylsulfonyl-1-methyl-1H-pyrazol-4-yl)pyrimidin-2,4-diamine (Final Product 1)

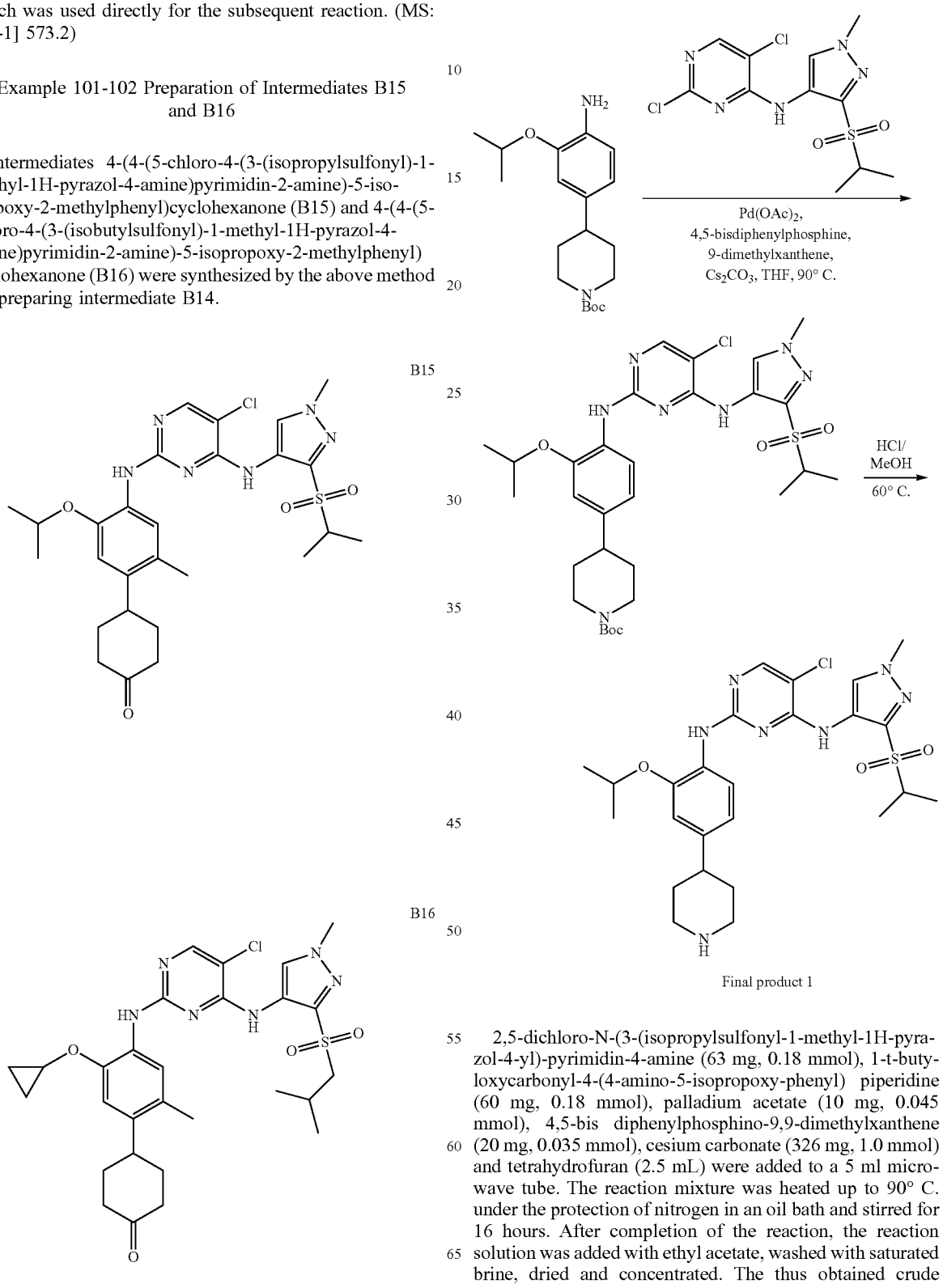

Final product 1

2,5-dichloro-N-(3-(isopropylsulfonyl-1-methyl-1H-pyrazol-4-yl)-pyrimidin-4-amine (63 mg, 0.18 mmol), 1-t-butyloxycarbonyl-4-(4-amino-5-isopropoxy-phenyl) piperidine (60 mg, 0.18 mmol), palladium acetate (10 mg, 0.045 mmol), 4,5-bis diphenylphosphino-9,9-dimethylxanthene (20 mg, 0.035 mmol), cesium carbonate (326 mg, 1.0 mmol) and tetrahydrofuran (2.5 mL) were added to a 5 ml microwave tube. The reaction mixture was heated up to 90° C. under the protection of nitrogen in an oil bath and stirred for 16 hours. After completion of the reaction, the reaction solution was added with ethyl acetate, washed with saturated brine, dried and concentrated. The thus obtained crude product was separated by column chromatography (silica gel column, eluent:ethyl acetate/petroleum ether=1:1) to obtain the protected intermediate (35 mg, 30%). (MS: [M+1] 648.3)

The above intermediate (22 mg, 0.034 mmol), methanol (2 ml) and concentrated hydrochloric acid (1 mL) were added to a 25 ml reaction flask. The reaction solution was concentrated, and the residue was neutralized with saturated aqueous sodium bicarbonate solution, extracted with ethyl acetate, dried and concentrated to obtain the title compound (13 mg, 70%). ($^1$H NMR (400 MHz CDCl$_3$) ppm 1.37-1.41 (m 12H), 1.78-1.92 (m 4H), 2.63 (m 1H), 2.80-2.85 (m 2H), 3.30-3.42 (m 3H), 3.95 (s 3H), 4.60-4.63 (m 1H), 6.82-6.86 (m 2H), 7.29 (s 1H), 8.02 (d 1H), 8.07 (s 1H), 8.38 (s 1H), 8.78 (s 1H); MS: [M+1] 548.3)

Example 104-131 Preparation of Final Products 2-29

Final products 2-29 were synthesized by using the above method for preparing final product 1 from intermediates A and B (table 7).

TABLE 7

| | | Final products 2-29 | |
|---|---|---|---|
| Final Product Nos. | Intermediate Nos. | Structural Formulas of Final Products | NMR or MS |
| Final product 2 | A64, B3 | 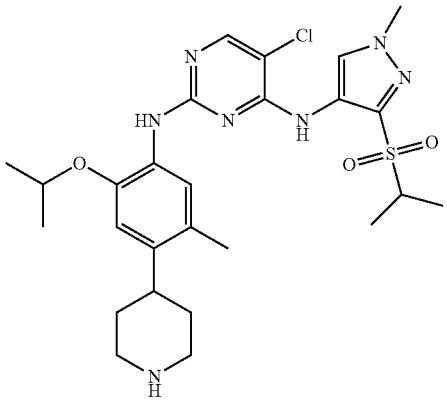 [SMILES: Cc1cc(Nc2ncc(Cl)c(Nc3cn(C)nc3S(=O)(=O)C(C)C)n2)c(OC(C)C)cc1C1CCNCC1] | $^1$H NMR (400 MHz CDCl3) ppm 1.34-1.39 (m 12H), 1.95-1.98 (m 2H), 2.26-2.33 (m 5H), 2.95-3.11 (m 3H), 3.37-3.44 (m 1H), 3.71-3.74 (m 2H), 3.92 (s 3H), 4.57-4.63 (m 1H), 6.90 (s 1H), 7.80 (s 1H), 8.07 (s 1H), 8.24 (s 1H), 9.08 (s 1H), 9.30 (s 1H), 9.49 (s 1H); MS: [M + 1] 562.3 |
| Final product 3 | A36, B3 | 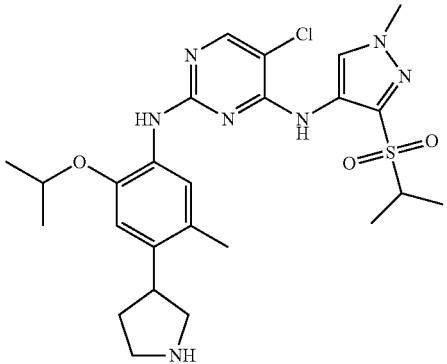 [SMILES: Cc1cc(Nc2ncc(Cl)c(Nc3cn(C)nc3S(=O)(=O)C(C)C)n2)c(OC(C)C)cc1C1CCNC1] | MS: [M + 1] 548.3 |

TABLE 7-continued

Final products 2-29

| Final Product Nos. | Intermediate Nos. | Structural Formulas of Final Products | NMR or MS |
|---|---|---|---|
| Final product 4 | A22, B3 | | MS: [M + 1] 534.3 |
| Final product 5 | A64, B7 | | $^1$H NMR (400 MHz CDCl$_3$) ppm 1.07 (m 2H), 1.21-1.28 (m 2H), 1.36-1.41 (m 12H), 1.96-2.04 (m 2H), 2.22-2.35 (m 5H), 2.95-3.11 (m 3H), 3.40-3.43 (m 1H), 3.66-3.71 (m 3H), 4.61-4.64 (m 1H), 6.90 (s 1H), 7.27 (s 1H), 7.42 (s 1H), 8.09 (s 2H), 8.45 (s 1H), 8.82 (s 1H); MS: [M + 1] 588.3 |
| Final product 6 | A64, B4 | | MS: [M + 1] 576.3 |

TABLE 7-continued
Final products 2-29
| Final Product Nos. | Intermediate Nos. | Structural Formulas of Final Products | NMR or MS |
|---|---|---|---|
| Final product 7 | A64, B5 | 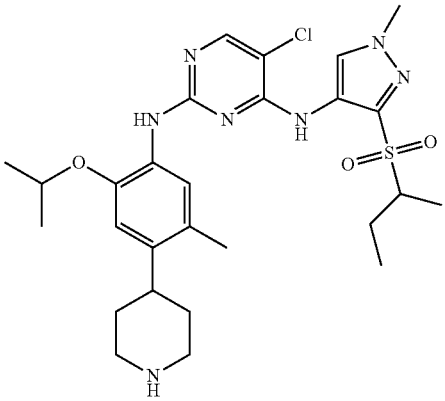 [SMILES: CCC(C)S(=O)(=O)c1nn(C)cc1Nc1nc(Nc2cc(C)c(C3CCNCC3)cc2OC(C)C)ncc1Cl] | $^1$H NMR (400 MHz CDCl$_3$) ppm 1.05-1.07 (m 3H), 1.37-1.40 (m 9H), 1.54-1.61 (m 2H), 1.92-1.96 (m 3H), 2.09-2.13 (m 3H), 2.93-3.02 (m 3H), 3.15-3.21 (m 1H), 3.57-3.60 (m 2H), 4.00 (s 3H), 4.58-4.61 (m 1H), 6.85 (s 1H), 7.33 (s 1H), 8.01 (s 1H), 8.09 (s 2H), 8.39 (s 1H), 8.84 (s 1H); MS: [M + 1] 576.3 |
| Final product 8 | A35, B3 | 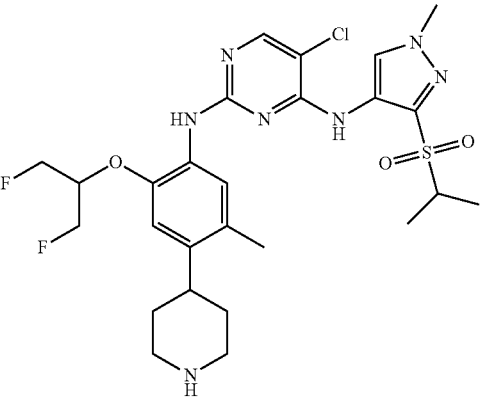 [SMILES: Cc1cc(Nc2ncc(Cl)c(Nc3cn(C)nc3S(=O)(=O)C(C)C)n2)c(OC(CF)CF)cc1C1CCNCC1] | $^1$H NMR (400 MHz CDCl$_3$) ppm 1.36-1.41 (m 6H), 1.67-1.80 (m 4H), 2.33 (s 3H), 2.78-2.83 (m 3H), 3.26-3.28 (m 2H), 3.36-3.43 (m 1H), 3.95 (s 3H), 4.41-4.53 (m 1H), 4.66 (d 2H), 4.78 (d 2H), 6.95 (s 1H), 7.26 (s 1H), 7.46 (s 1H), 8.08-8.10 (m 2H), 8.39 (s 1H), 8.79 (s 1H); MS: [M + 1] 598.3 |
| Final product 9 | A38, B3 | 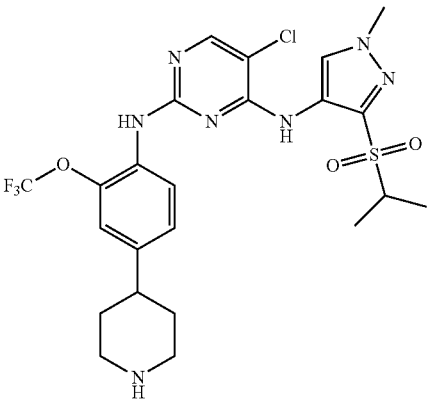 [SMILES: CC(C)S(=O)(=O)c1nn(C)cc1Nc1nc(Nc2ccc(C3CCNCC3)cc2OC(F)(F)F)ncc1Cl] | $^1$H NMR (400 MHz CDCl$_3$) ppm 1.36-1.40 (m 6H), 2.05-2.08 (m 3H), 2.20-2.24 (m 2H), 2.77-2.83 (m 1H), 3.00-3.06 (m 2H), 3.37-3.42 (m 1H), 3.64 (d 2H), 3.97 (s 3H), 7.16 (d 2H), 7.23 (d 1H), 8.08 (s 1H), 8.21-8.24 (m 1H), 8.87 (s 1H); MS: [M + 1] 574.2 |

TABLE 7-continued
Final products 2-29
| Final Product Nos. | Intermediate Nos. | Structural Formulas of Final Products | NMR or MS |
|---|---|---|---|
| Final product 10 | A39, B3 | 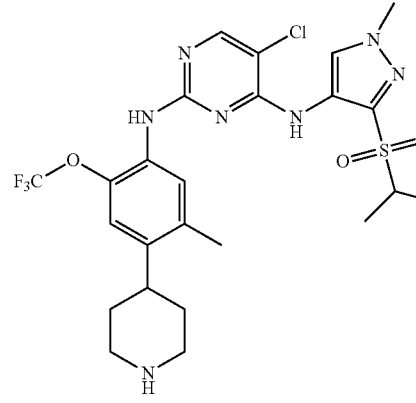 | $^1$H NMR (400 MHz MeOD) ppm 1.37-1.41 (m 6H), 1.94-2.07 (m 4H), 2.46 (s 3H), 2.70 (s 3H), 3.20-3.33 (m 3H), 3.44-3.47 (m 1H), 3.55 (d 2H), 3.95 (s 3H), 7.37 (s 1H), 7.54 (d 1H), 8.17 (s 1H), 8.31 (s 1H) (mesylate); MS: [M + 1] 588.2 |
| Final product 11 | A40, B3 | 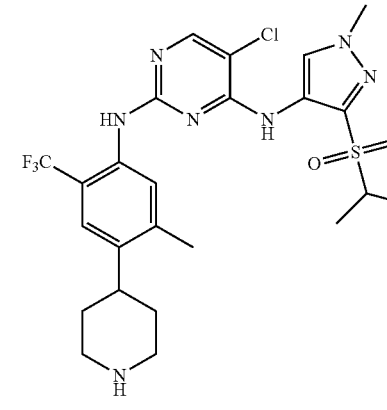 | $^1$H NMR (400 MHz CDCl$_3$) ppm 1.37-1.40 (m 6H), 1.68-1.75 (m 4H), 2.41 (s 3H), 2.75-2.84 (m 3H), 3.25 (d 2H), 3.37-3.41 (m 1H), 3.87 (s 3H), 6.93 (s 1H), 7.52 (s 1H), 7.77 (s 1H), 8.06 (d 2H), 8.87 (s 1H); MS: [M + 1] 572.2 |
| Final product 12 | A51, B3 | 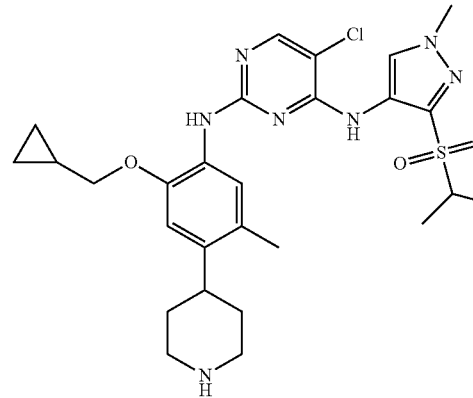 | MS: [M + 1] 574.3 |

TABLE 7-continued
Final products 2-29
| Final Product Nos. | Intermediate Nos. | Structural Formulas of Final Products | NMR or MS |
|---|---|---|---|
| Final product 13 | A43, B3 | 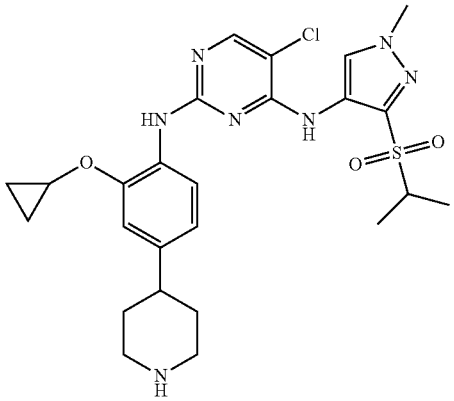 [SMILES: CC(C)S(=O)(=O)c1nn(C)cc1Nc1nc(Nc2ccc(C3CCNCC3)cc2OC2CC2)ncc1Cl] | MS: [M + 1] 546.2 |
| Final product 14 | A47, B3 | 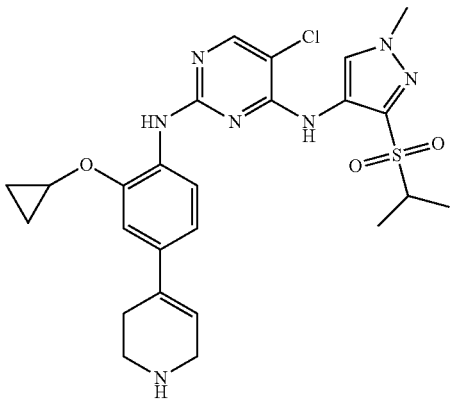 [SMILES: CC(C)S(=O)(=O)c1nn(C)cc1Nc1nc(Nc2ccc(C3=CCNCC3)cc2OC2CC2)ncc1Cl] | MS: [M + 1] 544.2 |
| Final product 15 | A32, B3 | 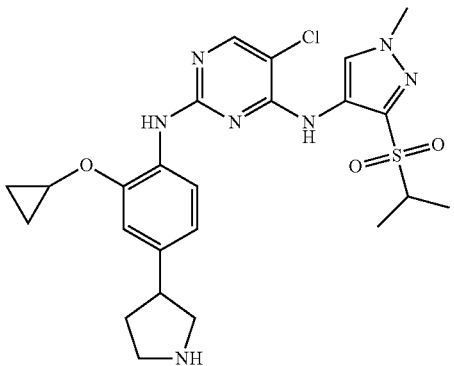 [SMILES: CC(C)S(=O)(=O)c1nn(C)cc1Nc1nc(Nc2ccc(C3CCNC3)cc2OC2CC2)ncc1Cl] | $^1$H NMR (400 MHz CD3OD) ppm 0.57-0.61 (m 2H), 0.73-0.77 (m 2H), 1.33-1.35 (m 6H), 2.20-2.23 (m 1H), 2.57-2.61 (m 1H) 2.70 (s 3H), 3.44-3.49 (m 2H), 3.63-3.67 (m 2H), 3.77-3.82 (m 1H), 3.94-3.97 (m 5H, 7.11-7.14 (m 1H), 7.51 (d 2H), 8.11 (s 1H), 8.33 (s 1H); MS: [M + 1] 532.3 |

TABLE 7-continued

Final products 2-29

| Final Product Nos. | Intermediate Nos. | Structural Formulas of Final Products | NMR or MS |
|---|---|---|---|
| Final product 16 | A43, B7 | | MS: [M + 1] 572.3 |
| Final product 17 | A43, B4 | | MS: [M + 1] 560.3 |
| Final product 18 | A32, B4 | | MS: [M + 1] 546.3 |

TABLE 7-continued

Final products 2-29

| Final Product Nos. | Intermediate Nos. | Structural Formulas of Final Products | NMR or MS |
|---|---|---|---|
| Final product 19 | A33, B3 | | MS: [M + 1] 564.2 |
| Final product 20 | A45, B3 | | MS: [M + 1] 550.3 |
| Final product 21 | A33, B7 | | MS: [M + 1] 590.3 |

TABLE 7-continued

Final products 2-29

| Final Product Nos. | Intermediate Nos. | Structural Formulas of Final Products | NMR or MS |
|---|---|---|---|
| Final product 22 | A34, B3 | | MS: [M + 1] 580.3 |
| Final product 23 | A34, B7 | | MS: [M + 1] 606.3 |
| Final product 24 | A25, B3 | | MS: [M + 1] 560.3 |

TABLE 7-continued

Final products 2-29

| Final Product Nos. | Intermediate Nos. | Structural Formulas of Final Products | NMR or MS |
|---|---|---|---|
| Final product 25 | A46, B3 | (structure) | MS: [M + 1] 558.3 |
| Final product 26 | A24, B3 | (structure) | MS: [M + 1] 546.3 |
| Final product 27 | A25, B7 | (structure) | MS: [M + 1] 586.3 |

TABLE 7-continued

Final products 2-29

| Final Product Nos. | Intermediate Nos. | Structural Formulas of Final Products | NMR or MS |
|---|---|---|---|
| Final product 28 | A25, B4 | (structure shown) | MS: [M + 1] 574.3 |
| Final product 29 | A42, B3 | (structure shown) | MS: [M + 1] 571.3 |

Example 132 5-chloro-$N^2$-(4-(1-methylpiperidin-4-yl)-2-(trifluoromethoxy)phenyl)-$N^4$-(3-(1-isopropyl-sulfonyl-1H-pyrazol-4-yl)pyrimidin-2,4-diamine (Final Product 30)

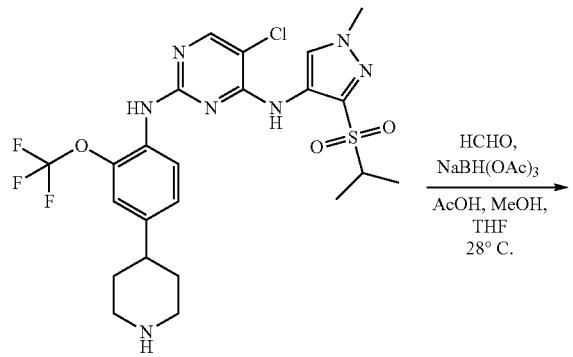

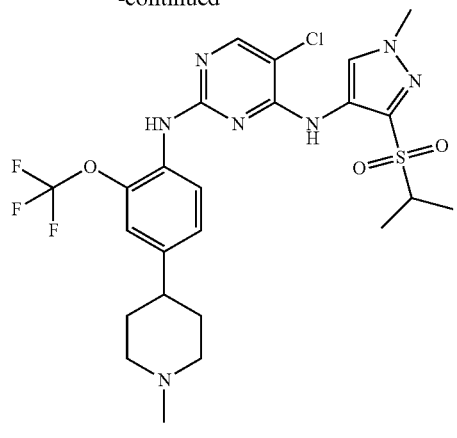

Final product 30

5-chloro-$N^2$-(4-piperidin-4-yl)-2-(trifluoromethoxy) phenyl)-$N^4$-(3-(isopropyl sulfonyl-1-methyl-1H-pyrazol-4-yl) pyrimidin-2,4-diamine (48 mg, 0.083 mmol), tetrahydrofuran (4 mL), methanol (1 mL), aqueous formaldehyde solution (25 mg, 0.83 mmol) and a drop of acetic acid were added to a 25 mL reaction flask. The reaction mixture was heated up to 28° C. under the protection of nitrogen. After stirring for 1 hour, sodium triacetoxyborohydride (175 mg, 0.83 mmol) was added. The reaction mixture was continued to stir at 28° C. for 1 hour, concentrated, and added with saturated aqueous sodium bicarbonate solution to neutralize till the pH value to 8 to 9, and then added with dichloromethane to extract. The organic phase was dried, concentrated and separated by column chromatography (dichloromethane/methanol=10:1) to obtain the title compound (white solid, 34.7 mg, 71%). (MS: [M+1] 588.2)

Example 133-176 Preparation of Final Products 31-74

Final products 31-74 were synthesized by the above method for preparing final product 30 (table 8).

TABLE 8

Final products 31-74

| Final Products No | Structural Formulas of Final Products | NMR or MS |
|---|---|---|
| Final product 31 | 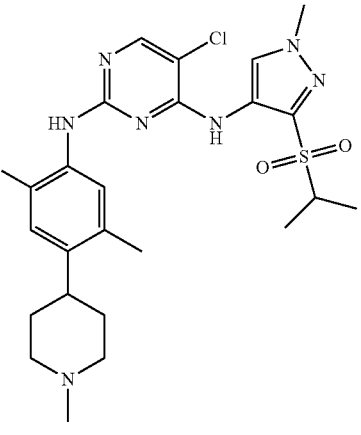 | $^1$H NMR (400 MHz CDCl$_3$) ppm 1.36-1.40 (m 6H), 1.89-1.93 (m 2H), 2.30-2.35 (m 5H), 2.68-2.73 (m 5H), 2.80-2.86 (m 1H), 3.37-3.42 (m 1H), 3.48-3.52 (m 2H), 3.96 (s 3H), 7.08 (s 1H), 7.19 (s 1H), 8.05 (d 2H), 8.08 (s 1H), 8.24 (s 1H), 8.86 (s 1H); MS: [M + 1] 602.3 |
| Final product 32 | 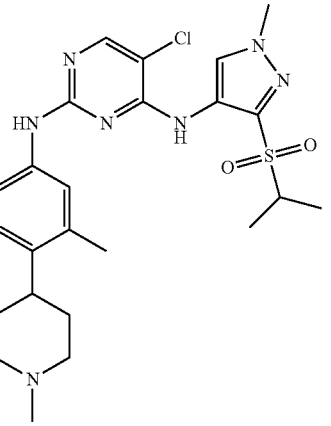 | $^1$H NMR (400 MHz CDCl$_3$) ppm 1.33-1.38 (m 6H), 1.94-1.98 (m 2H), 2.03-2.06 (m 2H), 2.39 (s 3H), 2.47-2.50 (m 1H), 2.85 (s 3H), 2.98 (br 2H), 3.36-3.40 (m 1H), 3.65 (d 2H), 3.89 (s 3H), 7.30 (s 1H), 7.51 (s 1H), 7.83 (s 1H), 8.03 (s 1H), 8.08 (s 1H), 8.85 (s 1H); MS: [M + 1] 586.3 |
| Final product 33 | 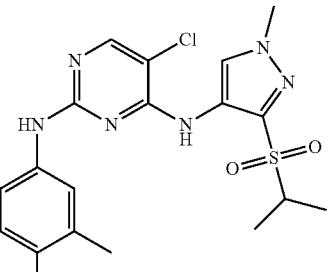 | MS: [M + 1] 560.2 |

TABLE 8-continued

Final products 31-74

| Final Products No | Structural Formulas of Final Products | NMR or MS |
|---|---|---|
| Final product 34 | | MS: [M + 1] 612.3 |
| Final product 35 | | MS: [M + 1] 548.3 |
| Final product 36 | | MS: [M + 1] 561.9 |

TABLE 8-continued

Final products 31-74

| Final Products No | Structural Formulas of Final Products | NMR or MS |
|---|---|---|
| Final product 37 | (structure) | MS: [M + 1] 562.3 |
| Final product 38 | (structure) | MS: [M + 1] 614.1 |
| Final product 39 | (structure) | MS: [M + 1] 588.4 |

TABLE 8-continued

Final products 31-74

| Final Products No | Structural Formulas of Final Products | NMR or MS |
|---|---|---|
| Final product 40 | | MS: [M + 1] 560.3 |
| Final product 41 | | MS: [M + 1] 546.2 |
| Final product 42 | | MS: [M + 1] 586.2 |

TABLE 8-continued
Final products 31-74
| Final Products No | Structural Formulas of Final Products | NMR or MS |
|---|---|---|
| Final product 43 | 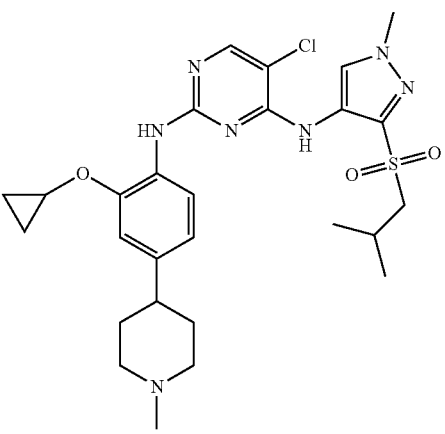 [SMILES: CC(C)CS(=O)(=O)c1nn(C)cc1Nc1nc(Nc2ccc(C3CCN(C)CC3)cc2OC2CC2)ncc1Cl] | MS: [M + 1] 574.3 |
| Final product 44 | 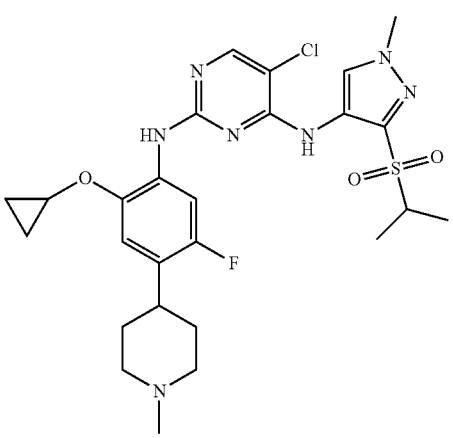 | MS: [M + 1] 578.3 |
| Final product 45 | 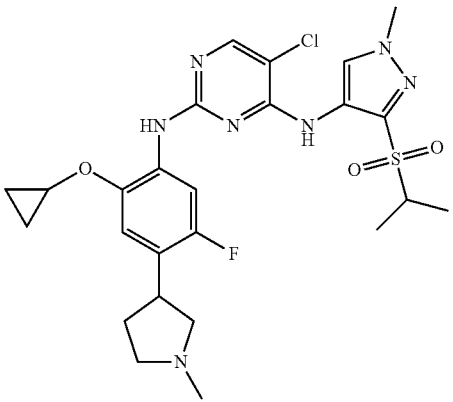 [SMILES: CC(C)S(=O)(=O)c1nn(C)cc1Nc1nc(Nc2cc(F)c(C3CCN(C)C3)cc2OC2CC2)ncc1Cl] | MS: [M + 1] 564.3 |

TABLE 8-continued
| | Final products 31-74 | |
|---|---|---|
| Final Products No | Structural Formulas of Final Products | NMR or MS |
| Final product 46 | 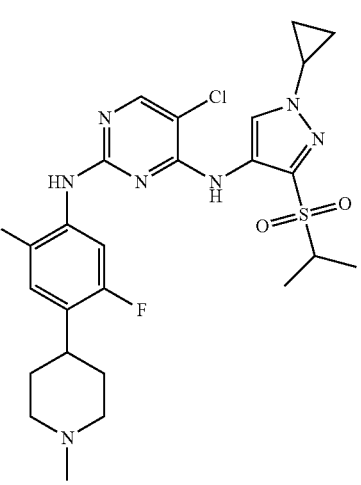 | MS: [M + 1] 604.3 |
| Final product 47 | 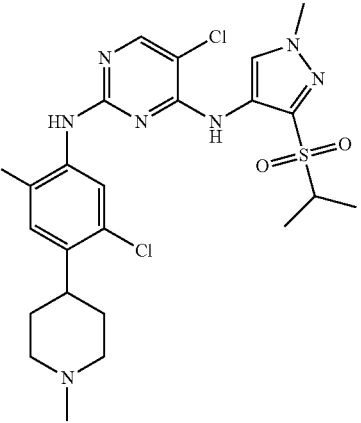 | MS: [M + 1] 594.3 |
| Final product 48 | 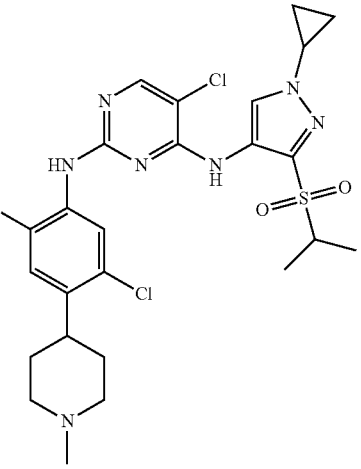 | MS: [M + 1] 620.3 |

TABLE 8-continued

Final products 31-74

| Final Products No | Structural Formulas of Final Products | NMR or MS |
|---|---|---|
| Final product 49 | | MS: [M + 1] 585.3 |
| Final product 50 | | MS: [M + 1] 572.2 |
| Final product 51 | | MS: [M + 1] 574.3 |

TABLE 8-continued
| Final products 31-74 | | |
|---|---|---|
| Final Products No | Structural Formulas of Final Products | NMR or MS |
| Final product 52 | 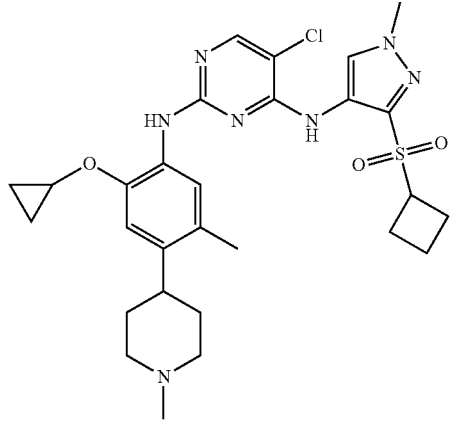 [SMILES: Cc1cc(Nc2ncc(Cl)c(Nc3cn(C)nc3S(=O)(=O)C3CCC3)n2)c(OC2CC2)cc1C1CCN(C)CC1] | MS: [M + 1] 586.1 |
| Final product 53 | 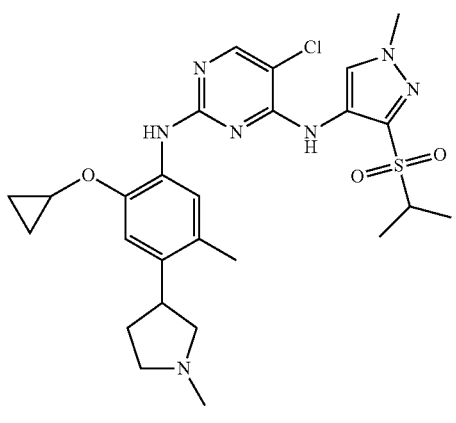 [SMILES: Cc1cc(Nc2ncc(Cl)c(Nc3cn(C)nc3S(=O)(=O)C(C)C)n2)c(OC2CC2)cc1C1CCN(C)C1] | MS: [M + 1] 560.3 |
| Final product 54 | 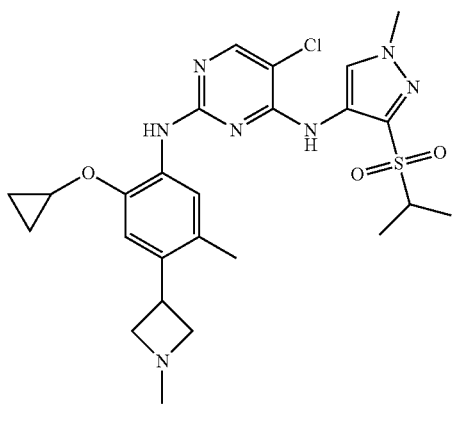 [SMILES: Cc1cc(Nc2ncc(Cl)c(Nc3cn(C)nc3S(=O)(=O)C(C)C)n2)c(OC2CC2)cc1C1CN(C)C1] | MS: [M + 1] 546.1 |

TABLE 8-continued

Final products 31-74

| Final Products No | Structural Formulas of Final Products | NMR or MS |
|---|---|---|
| Final product 55 | | MS: [M + 1] 559.9 |
| Final product 56 | | MS: [M + 1] 600.2 |
| Final product 57 | | MS: [M + 1] 588.4 |

TABLE 8-continued

Final products 31-74

| Final Products No | Structural Formulas of Final Products | NMR or MS |
|---|---|---|
| Final product 58 | | MS: [M + 1] 604.2 |
| Final product 59 | | MS: [M + 1] 617.9 |
| Final product 60 | | MS: [M + 1] 574.3 |

TABLE 8-continued
| Final Products No | Structural Formulas of Final Products | NMR or MS |
|---|---|---|
| Final product 61 | 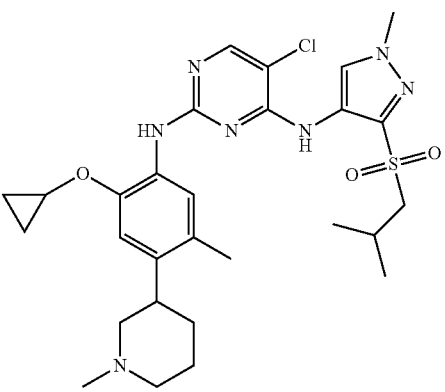 [SMILES: Cc1cc(Nc2ncc(Cl)c(Nc3cn(C)nc3S(=O)(=O)CC(C)C)n2)c(OC2CC2)cc1C1CCCN(C)C1] | MS: [M + 1] 588.3 |
| Final product 62 | 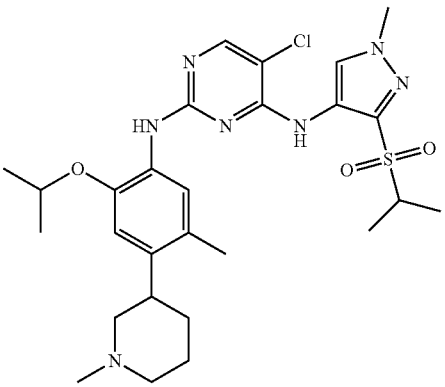 [SMILES: Cc1cc(Nc2ncc(Cl)c(Nc3cn(C)nc3S(=O)(=O)C(C)C)n2)c(OC(C)C)cc1C1CCCN(C)C1] | MS: [M + 1] 576.3 |
| Final product 63 | 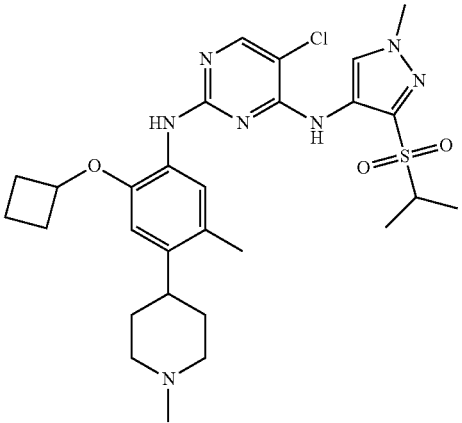 [SMILES: Cc1cc(Nc2ncc(Cl)c(Nc3cn(C)nc3S(=O)(=O)C(C)C)n2)c(OC2CCC2)cc1C1CCN(C)CC1] | MS: [M + 1] 588.2 |

TABLE 8-continued
Final products 31-74
| Final Products No | Structural Formulas of Final Products | NMR or MS |
|---|---|---|
| Final product 64 | 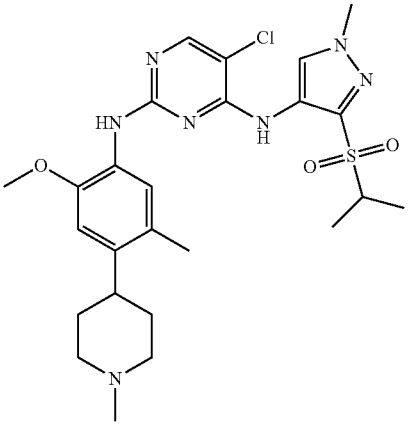 [SMILES: COc1cc(C2CCN(C)CC2)c(C)cc1Nc1ncc(Cl)c(Nc2cn(C)nc2S(=O)(=O)C(C)C)n1] | MS: [M + 1] 548.2 |
| Final product 65 | 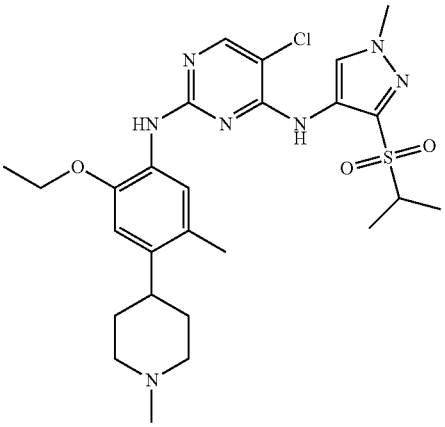 [SMILES: CCOc1cc(C2CCN(C)CC2)c(C)cc1Nc1ncc(Cl)c(Nc2cn(C)nc2S(=O)(=O)C(C)C)n1] | MS: [M + 1] 562.2 |
| Final product 66 | 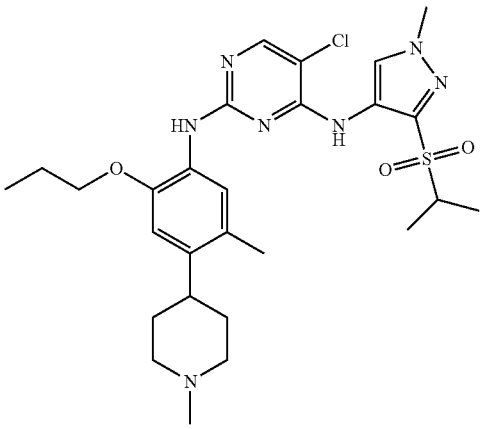 [SMILES: CCCOc1cc(C2CCN(C)CC2)c(C)cc1Nc1ncc(Cl)c(Nc2cn(C)nc2S(=O)(=O)C(C)C)n1] | MS: [M + 1] 576.2 |

TABLE 8-continued
| Final Products No | Structural Formulas of Final Products | NMR or MS |
|---|---|---|
| Final product 67 | 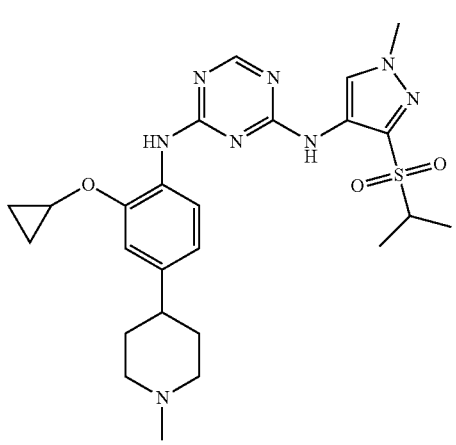 [SMILES: CC(C)S(=O)(=O)c1nn(C)cc1Nc1ncnc(Nc2ccc(C3CCN(C)CC3)cc2OC2CC2)n1] | MS: [M + 1] 527.2 |
| Final product 68 | 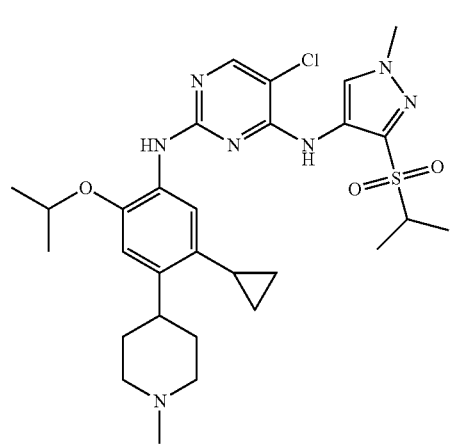 [SMILES: CC(C)Oc1cc(C2CCN(C)CC2)c(C2CC2)cc1Nc1ncc(Cl)c(Nc2cn(C)nc2S(=O)(=O)C(C)C)n1] | MS: [M + 1] 602.3 |
| Final product 69 | 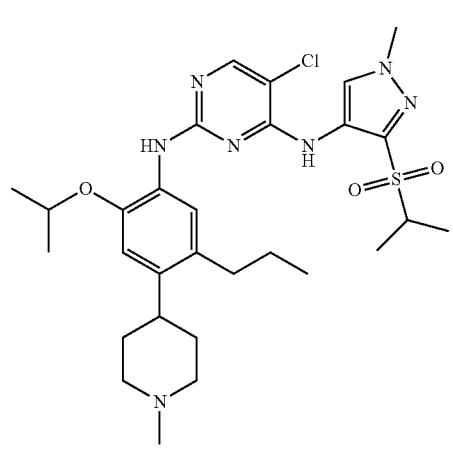 [SMILES: CCCc1cc(Nc2ncc(Cl)c(Nc3cn(C)nc3S(=O)(=O)C(C)C)n2)c(OC(C)C)cc1C1CCN(C)CC1] | MS: [M + 1] 604.3 |

TABLE 8-continued

Final products 31-74

| Final Products No | Structural Formulas of Final Products | NMR or MS |
|---|---|---|
| Final product 70 | | MS: [M + 1] 558.3 |
| Final product 71 | | MS: [M + 1] 560.3 |
| Final product 72 | | MS: [M + 1] 554.3 |

TABLE 8-continued
Final products 31-74
| Final Products No | Structural Formulas of Final Products | NMR or MS |
|---|---|---|
| Final product 73 | | MS: [M + 1] 556.3 |
| Final product 74 | | MS: [M + 1] 616.3 |
Example 177: 5-chloro-N²-(2-cyclopropoxy-5-methyl-4-((4-methylpiperazin-1-yl)methyl)phenyl)-N⁴-(3-(isopropoxysulfonyl)-1-methyl-1H-pyrazol-4-yl)pyrimidin-2,4-diamine (Final Product 75)
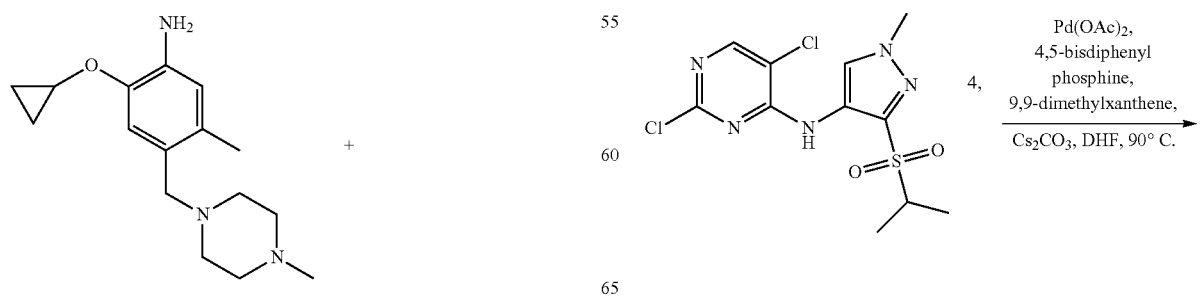
-continued

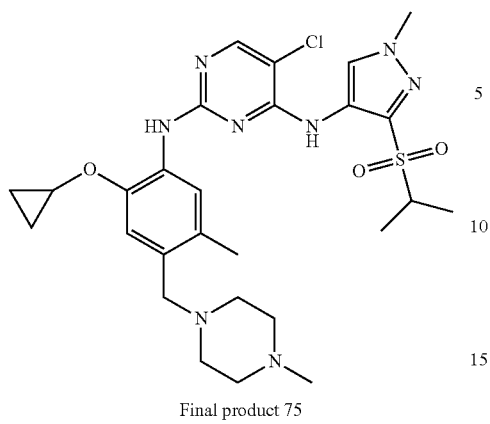

Final product 75

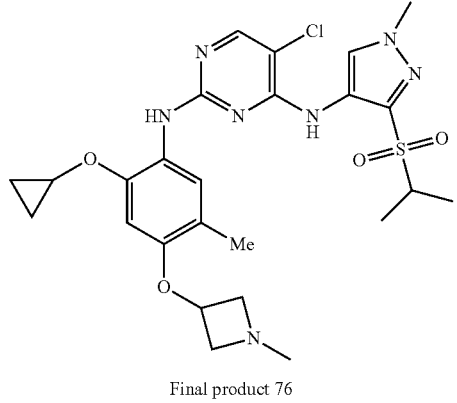

Final product 76

2-cyclopropoxy-5-methyl-4-((4-methyl-piperazin-1-yl)methyl) aniline (28 mg, 0.1 mmol), 2,5-dichloro-N-(3-(isopropylsulfonyl-1-methyl-1H-pyrazol-4-yl)-pyrimidin-4-amine (35 mg, 0.1 mmol), palladium acetate (2 mg, 0.01 mmol), 4,5-bisdiphenylphosphine-9,9-dimethylxanthene (12 mg, 0.02 mmol), cesium carbonate (65 mg, 0.2 mmol) and N,N-dimethylformamide (1 mL) were added to a 10 mL microwave reaction tube. The reaction mixture was heated up to 90° C. by microwave under nitrogen and reacted for 2 hours. After completion of the reaction, the mixture was cooled down, added with water, extracted with ethyl acetate, washed with water and saturated brine, dried and concentrated. The thus obtained crude product was separated by thin layer silica gel plate (silica gel plate, developing solvent:dichloromethane/methanol, 10/1) to obtain the title compound (7.2 mg, 12.2%). (MS: [M+1] 589.2)

Example 178: 5-chloro-N²-(2-cyclopropoxy-5-methyl-4-(1-methylazetidin-3-yloxy)phenyl)-N⁴-(3-(isopropylsulfonyl-1-methyl-1H-pyrazol-4-yl)-pyrimidin-2,4-diamine (Final Product 76)

2,5-dichloro-N-(3-(isopropylsulfonyl-1-methyl-1H-pyrazol-4-yl)-pyrimidin-4-amine (52 mg, 0.15 mmol), 2-cyclopropoxy-5-methyl-4-(1-methyl-butylazetidin-3-yloxy) aniline (40 mg, 0.16 mmol), palladium acetate (4.5 mg, 0.02 mmol), 4,5-bis diphenylphosphine-9,9-dimethylxanthene (23 mg, 0.04 mmol), cesium carbonate (98 mg, 0.30 mmol) and tetrahydrofuran (5 mL) were added to a 5 mL microwave reaction tube. The reaction mixture was heated up to 125° C. by microwave under the protection of nitrogen and reacted for 1 hour. After completion of the reaction, the reaction solution added with ethyl acetate, washed with saturated brine, dried and concentrated. The thus obtained crude product was separated by reverse phase column chromatography to obtain the title compound (10.7 mg, 13%). (MS: [M+1] 562.2)

Example 179: 5-chloro-N²-(2-cyclopropoxy-4-(2-methoxy-1-methyl-piperidin-4-yl)-5-methylphenyl)-N⁴-(3-(isopropylsulfonyl-1-methyl-1H-pyrazol-4-yl)-pyrimidin-2,4-diamine (Final Product 77)

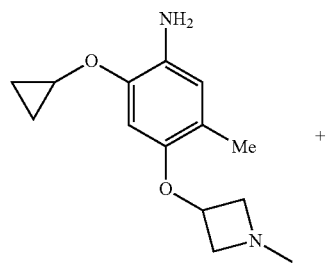

+

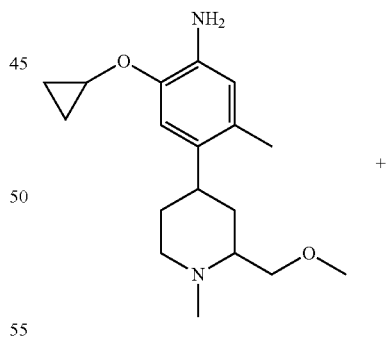

+

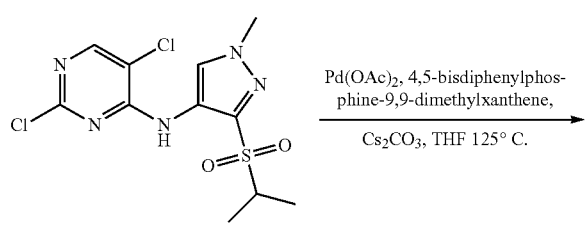

Pd(OAc)₂, 4,5-bisdiphenylphosphine-9,9-dimethylxanthene,
Cs₂CO₃, THF 125° C.

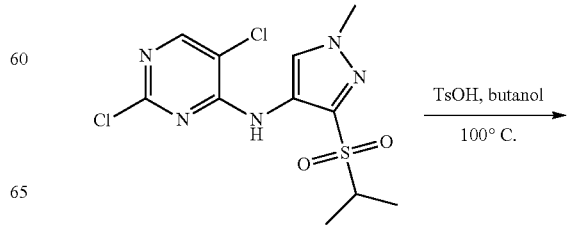

TsOH, butanol
100° C.

-continued

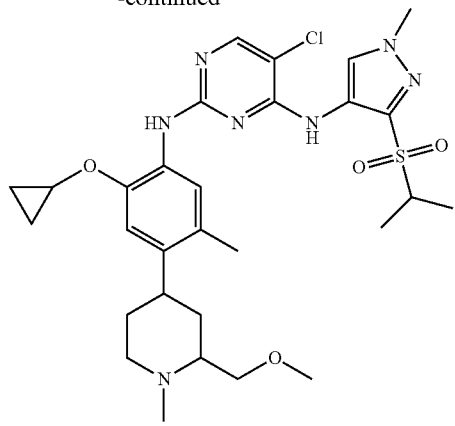

Final product 77

2-cyclopropoxy-4-(2-methoxy-1-methylpiperidin-4-yl)-5-methyl aniline (32.1 mg, 0.105 mmol), 2,5-dichloro-N-(3-(isopropylsulfonyl-1-methyl-1H-pyrazol-4-yl)-pyrimidin-4-amine (36.8 mg, 0.105 mmol), p-toluenesulfonic acid (9.2 mg, 0.053 mmol) and n-butanol (1 mL) were added to a 10 mL reaction flask. The reaction mixture was heated up to 100° C. under the protection of nitrogen and stirred for 3 hours, filtered, dried, concentrated and separated by column chromatography (dichloromethane/methanol=10:1) to obtain the title compound (yellow solid, 34.6 mg, 53%) (MS: [M+1] 618.4)

Examples 180-215: Preparation of Final Products 78-113

Final products 78-113 were synthesized by the above method for preparing final product 77 (table 9).

TABLE 9

| Final Product Nos. | Raw Material Nos. | Structural Formulas of Final Products | NMR or MS |
|---|---|---|---|
| Final product 78 | A56, B3 | 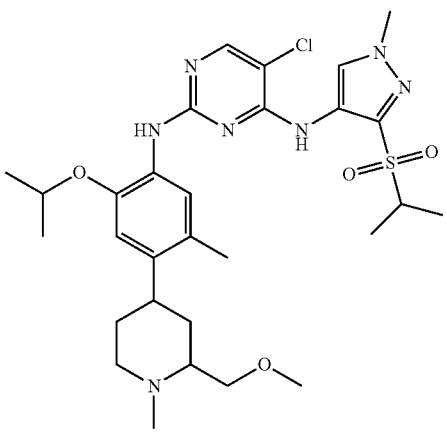 [SMILES: COCC1CC(c2cc(OC(C)C)c(Nc3ncc(Cl)c(Nc4cn(C)nc4S(=O)(=O)C(C)C)n3)cc2C)CCN1C] | MS: [M + 1] 620.2 |
| Final product 79 | A55, B4 | 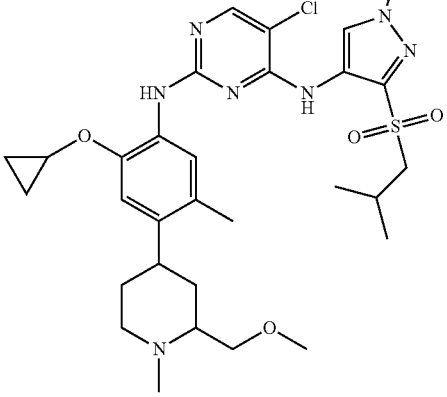 | MS: [M + 1] 631.9 |

US 10,023,593 B2
TABLE 9-continued
Final products 78-113
| Final Product Nos. | Raw Material Nos. | Structural Formulas of Final Products | NMR or MS |
|---|---|---|---|
| Final product 80 | A54, B3 | 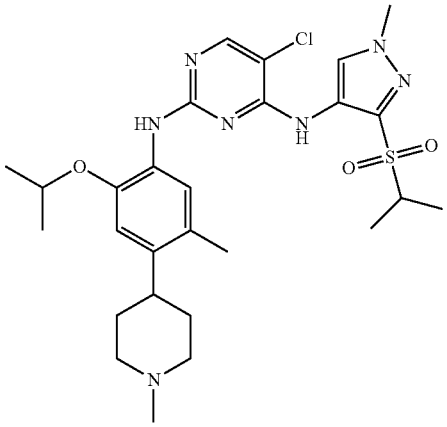 [SMILES: Cc1cc(Nc2ncc(Cl)c(Nc3cn(C)nc3S(=O)(=O)C(C)C)n2)c(OC(C)C)cc1C1CCN(C)CC1] | $^{1}$H NMR (400 MHz MeOD) ppm 1.34-1.39 (m 12H), 2.05-2.11 (m 4H), 2.75 (s 3H), 2.97 (s 3H), 3.12-3.35 (m 3H), 3.41-3.48 (m 1H), 3.67 (d 2H), 3.97 (s 3H), 4.60-4.66 (m 1H), 6.93 (s 1H), 7.69 (s 1H), 8.06 (s 1H), 8.39 (s 1H); MS: [M + 1] 576.3 |
| Final product 81 | A54, B7 | 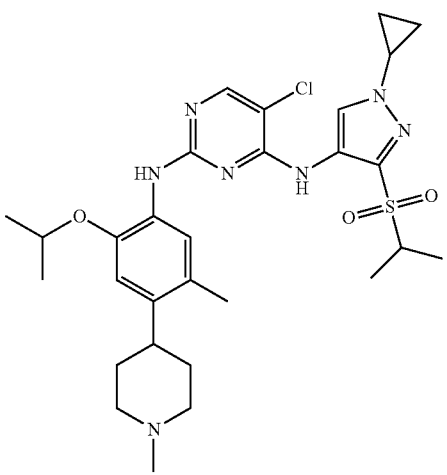 [SMILES: Cc1cc(Nc2ncc(Cl)c(Nc3cn(C4CC4)nc3S(=O)(=O)C(C)C)n2)c(OC(C)C)cc1C1CCN(C)CC1] | MS: [M + 1] 602.3 |
| Final product 82 | A48, B3 | 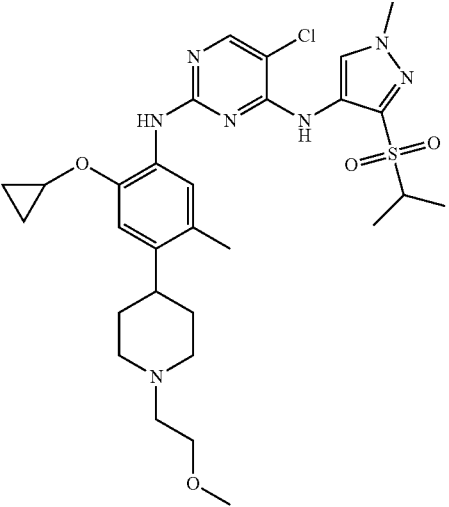 [SMILES: COCCN1CCC(c2cc(OC3CC3)c(Nc3ncc(Cl)c(Nc4cn(C)nc4S(=O)(=O)C(C)C)n3)cc2C)CC1] | MS: [M + 1] 618.4 |

TABLE 9-continued
Final products 78-113
| Final Product Nos. | Raw Material Nos. | Structural Formulas of Final Products | NMR or MS |
|---|---|---|---|
| Final product 83 | A48, B4 | 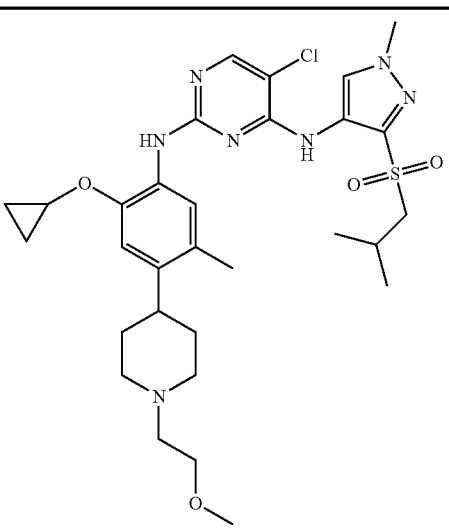 | MS: [M + 1] 632.3 |
| Final product 84 | A49, B4 | 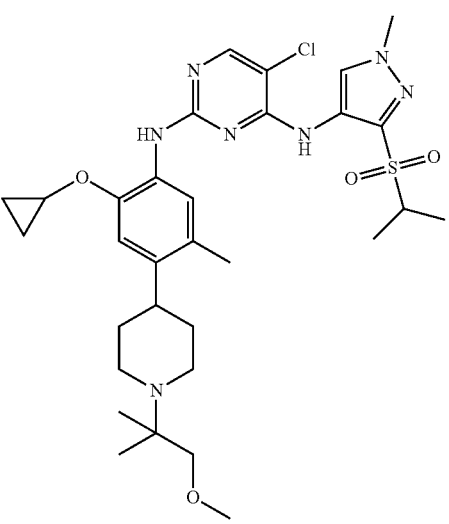 [SMILES: COCC(C)(C)N1CCC(c2cc(OC3CC3)c(Nc3ncc(Cl)c(Nc4cn(C)nc4S(=O)(=O)C(C)C)n3)cc2C)CC1] | MS: [M + 1] 646.3 |
| Final product 85 | A50, B4 | 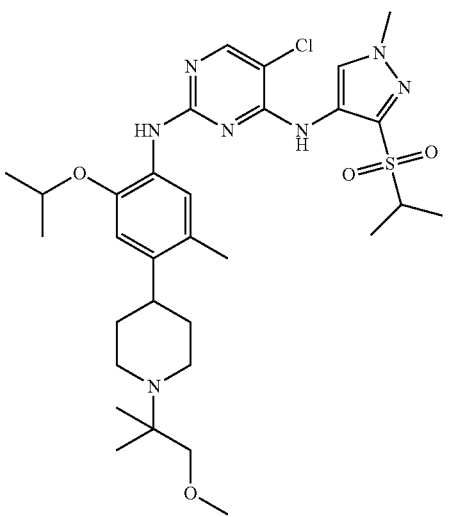 [SMILES: COCC(C)(C)N1CCC(c2cc(OC(C)C)c(Nc3ncc(Cl)c(Nc4cn(C)nc4S(=O)(=O)C(C)C)n3)cc2C)CC1] | MS: [M + 1] 648.3 |

TABLE 9-continued
Final products 78-113
| Final Product Nos. | Raw Material Nos. | Structural Formulas of Final Products | NMR or MS |
|---|---|---|---|
| Final product 86 | A54, B4 | 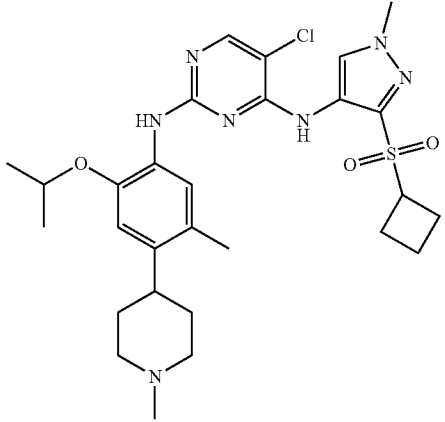 [SMILES: Cc1cc(Nc2ncc(Cl)c(Nc3cn(C)nc3S(=O)(=O)C3CCC3)n2)c(OC(C)C)cc1C1CCN(C)CC1] | MS: [M + 1] 588.3 |
| Final product 87 | A68, B3 | 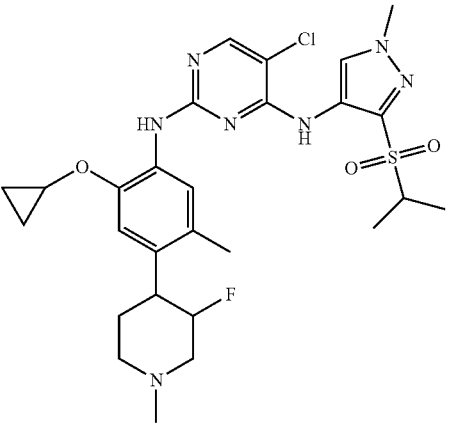 | MS: [M + 1] 592.3 |
| Final product 88 | A69, B3 | 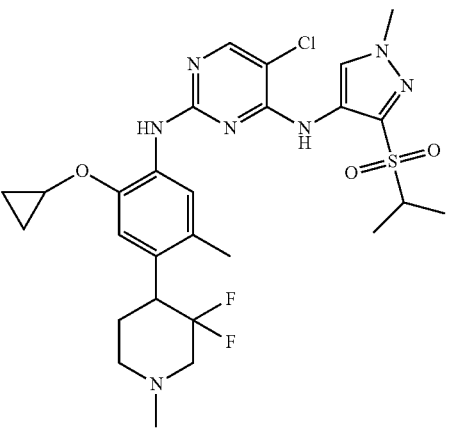 [SMILES: Cc1cc(Nc2ncc(Cl)c(Nc3cn(C)nc3S(=O)(=O)C(C)C)n2)c(OC2CC2)cc1C1CCN(C)CC1(F)F] | MS: [M + 1] 610.1 |

TABLE 9-continued
Final products 78-113
| Final Product Nos. | Raw Material Nos. | Structural Formulas of Final Products | NMR or MS |
|---|---|---|---|
| Final product 89 | A70, B3 | 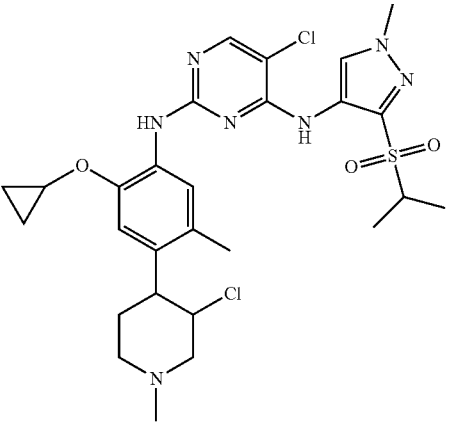 [SMILES: Cc1cc(Nc2ncc(Cl)c(Nc3cn(C)nc3S(=O)(=O)C(C)C)n2)c(OC2CC2)cc1C1CCN(C)CC1Cl] | MS: [M + 1] 608.2 |
| Final product 90 | A57, B3 | 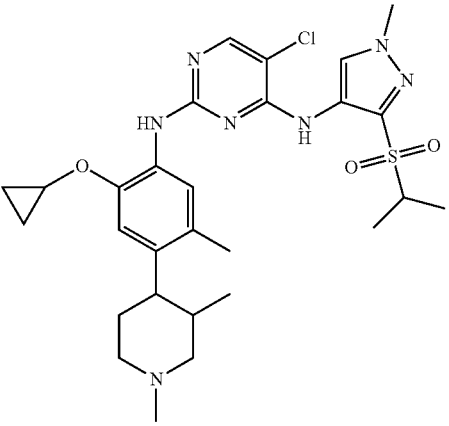 [SMILES: Cc1cc(Nc2ncc(Cl)c(Nc3cn(C)nc3S(=O)(=O)C(C)C)n2)c(OC2CC2)cc1C1CCN(C)CC1C] | MS: [M + 1] 587.9 |
| Final product 91 | A57, B4 | 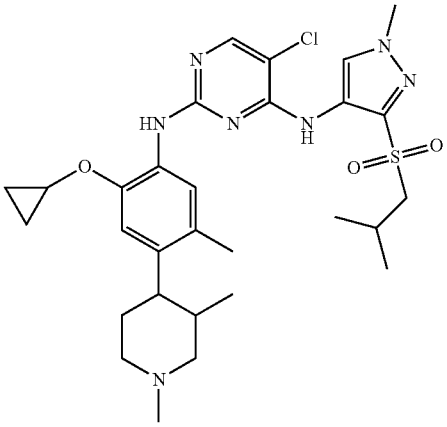 [SMILES: Cc1cc(Nc2ncc(Cl)c(Nc3cn(C)nc3S(=O)(=O)CC(C)C)n2)c(OC2CC2)cc1C1CCN(C)CC1C] | MS: [M + 1] 602.3 |

TABLE 9-continued

Final products 78-113

| Final Product Nos. | Raw Material Nos. | Structural Formulas of Final Products | NMR or MS |
|---|---|---|---|
| Final product 92 | A58, B3 | | MS: [M + 1] 587.9 |
| Final product 93 | A58, B4 | | MS: [M + 1] 602.3 |
| Final product 94 | A59, B3 | | MS: [M + 1] 590.3 |

TABLE 9-continued
Final products 78-113
| Final Product Nos. | Raw Material Nos. | Structural Formulas of Final Products | NMR or MS |
|---|---|---|---|
| Final product 95 | A60, B3 | 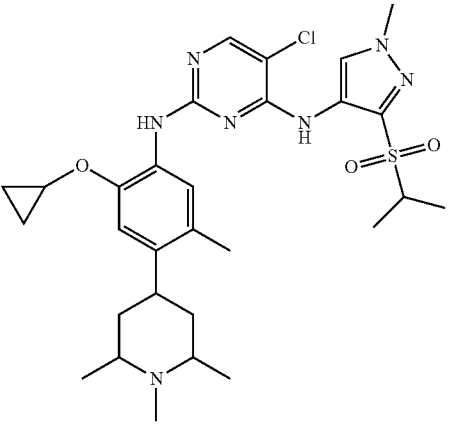 [SMILES: Cc1cc(Nc2ncc(Cl)c(Nc3cn(C)nc3S(=O)(=O)C(C)C)n2)c(OC2CC2)cc1C1CC(C)N(C)C(C)C1] | MS: [M + 1] 602.2 |
| Final product 96 | A60, B4 | 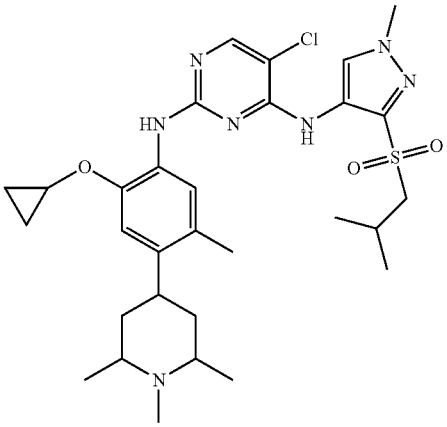 [SMILES: Cc1cc(Nc2ncc(Cl)c(Nc3cn(C)nc3S(=O)(=O)CC(C)C)n2)c(OC2CC2)cc1C1CC(C)N(C)C(C)C1] | MS: [M + 1] 616.3 |
| Final product 97 | A61, B3 | 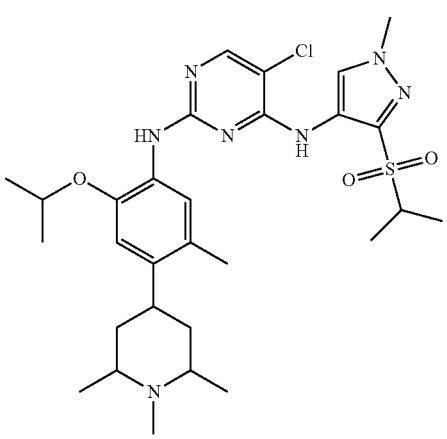 [SMILES: Cc1cc(Nc2ncc(Cl)c(Nc3cn(C)nc3S(=O)(=O)C(C)C)n2)c(OC(C)C)cc1C1CC(C)N(C)C(C)C1] | MS: [M + 1] 604.3 |

TABLE 9-continued
| Final Product Nos. | Raw Material Nos. | Structural Formulas of Final Products | NMR or MS |
|---|---|---|---|
| Final product 98 | A74, B3 | 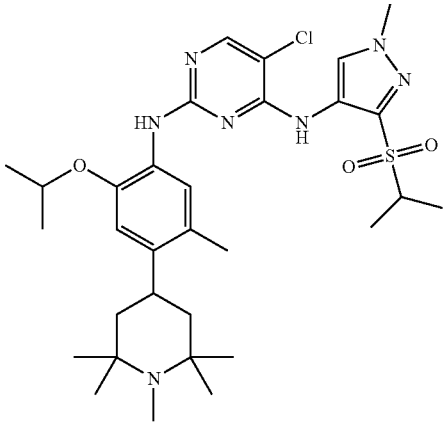 [SMILES: Cc1cc(Nc2ncc(Cl)c(Nc3cn(C)nc3S(=O)(=O)C(C)C)n2)c(OC(C)C)cc1C1CC(C)(C)N(C)C(C)(C)C1] | MS: [M + 1] 632.3 |
| Final product 99 | A73, B3 | 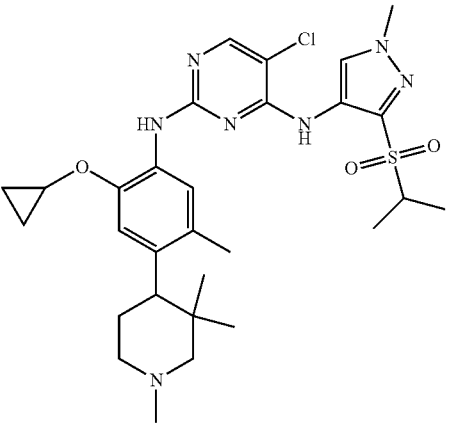 [SMILES: Cc1cc(Nc2ncc(Cl)c(Nc3cn(C)nc3S(=O)(=O)C(C)C)n2)c(OC2CC2)cc1C1CCN(C)CC1(C)C] | MS: [M + 1] 602.3 |
| Final product 100 | A75, B3 | 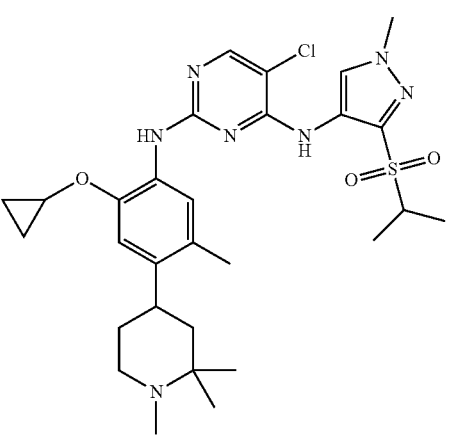 [SMILES: Cc1cc(Nc2ncc(Cl)c(Nc3cn(C)nc3S(=O)(=O)C(C)C)n2)c(OC2CC2)cc1C1CCN(C)C(C)(C)C1] | MS: [M + 1] 602.1 |

TABLE 9-continued
Final products 78-113
| Final Product Nos. | Raw Material Nos. | Structural Formulas of Final Products | NMR or MS |
|---|---|---|---|
| Final product 101 | A63, B3 | 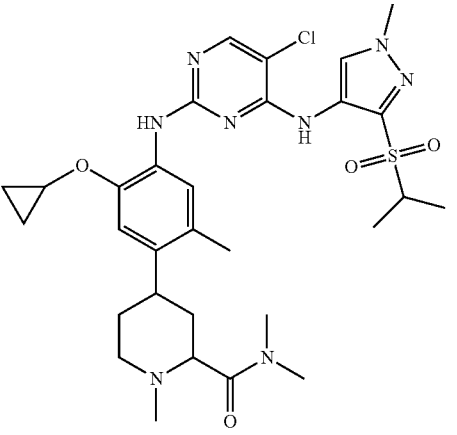 [SMILES: Cc1cc(Nc2ncc(Cl)c(Nc3cn(C)nc3S(=O)(=O)C(C)C)n2)c(OC2CC2)cc1C1CCN(C)C(C(=O)N(C)C)C1] | MS: [M + 1] 645.2 |
| Final product 102 | A62, B3 | 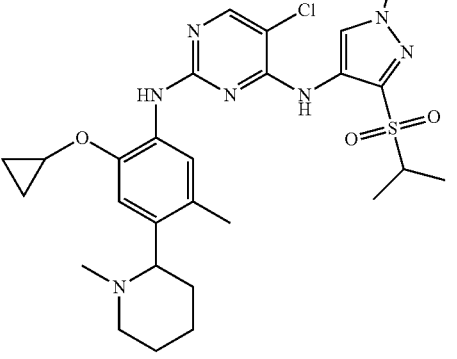 | MS: [M + 1] 574.2 |
| Final product 103 | A72, B3 | 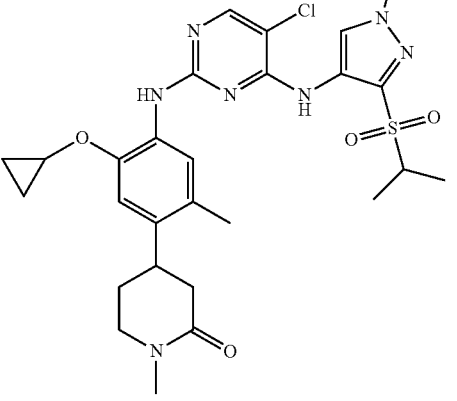 | MS: [M + 1] 587.9 |

TABLE 9-continued
| Final Product Nos. | Raw Material Nos. | Structural Formulas of Final Products | NMR or MS |
|---|---|---|---|
| Final product 104 | A72, B4 | 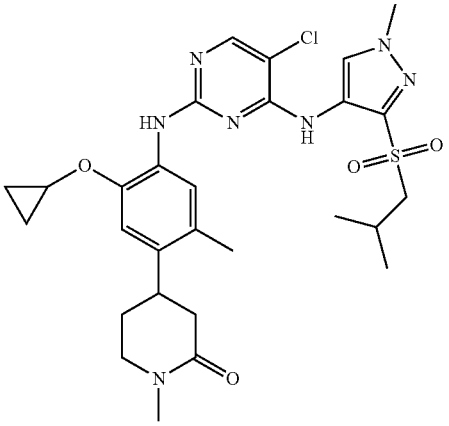 [SMILES: Cc1cc(Nc2ncc(Cl)c(Nc3cn(C)nc3S(=O)(=O)CC(C)C)n2)c(OC2CC2)cc1C1CCN(C)C(=O)C1] | MS: [M + 1] 602.2 |
| Final product 105 | A76, B3 | 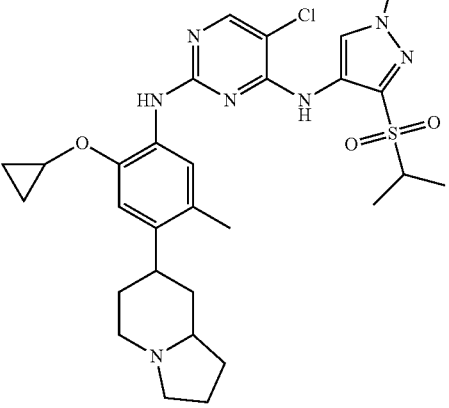 | MS: [M + 1] 600.3 |
| Final product 106 | A78, B3 | 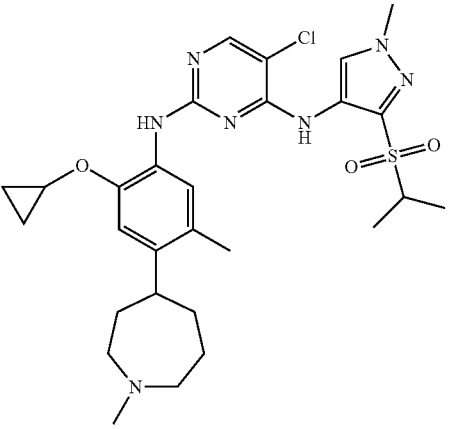 [SMILES: Cc1cc(Nc2ncc(Cl)c(Nc3cn(C)nc3S(=O)(=O)C(C)C)n2)c(OC2CC2)cc1C1CCCN(C)CC1] | MS: [M + 1] 588.2 |

TABLE 9-continued
Final products 78-113
| Final Product Nos. | Raw Material Nos. | Structural Formulas of Final Products | NMR or MS |
|---|---|---|---|
| Final product 107 | A80, B3 | 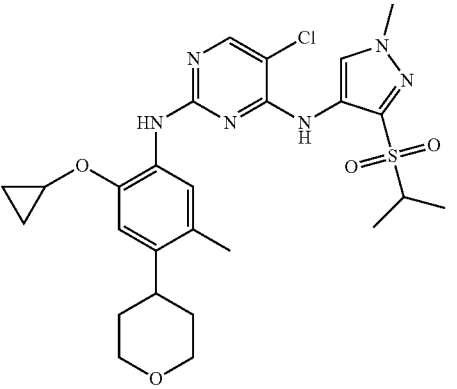 [SMILES: Cc1cc(Nc2ncc(Cl)c(Nc3cn(C)nc3S(=O)(=O)C(C)C)n2)c(OC2CC2)cc1C1CCOCC1] | MS: [M + 1] 560.9 |
| Final product 108 | A79, B3 | 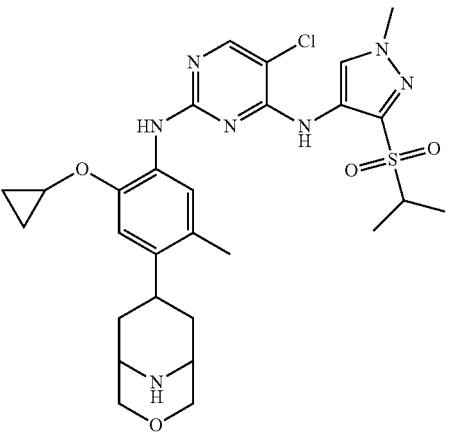 [SMILES: Cc1cc(Nc2ncc(Cl)c(Nc3cn(C)nc3S(=O)(=O)C(C)C)n2)c(OC2CC2)cc1C1CC2COCC(C1)N2] | MS: [M + 1] 602.3 |
| Final product 109 | A77, B3 | 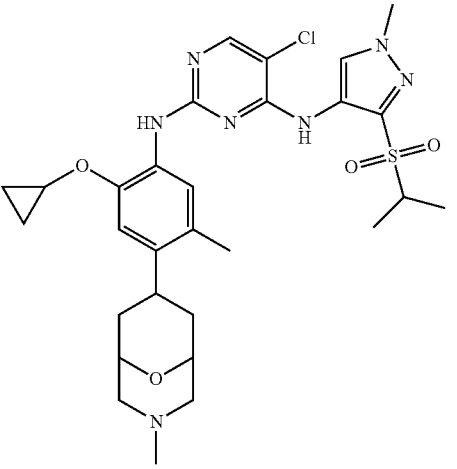 [SMILES: Cc1cc(Nc2ncc(Cl)c(Nc3cn(C)nc3S(=O)(=O)C(C)C)n2)c(OC2CC2)cc1C1CC2CN(C)CC(C1)O2] | MS: [M + 1] 616.3 |

TABLE 9-continued
| | | Final products 78-113 | |
|---|---|---|---|
| Final Product Nos. | Raw Material Nos. | Structural Formulas of Final Products | NMR or MS |
| Final product 110 | A81, B3 | 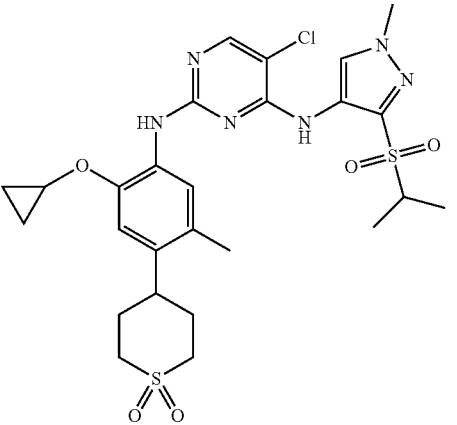 [SMILES: Cc1cc(Nc2ncc(Cl)c(Nc3cn(C)nc3S(=O)(=O)C(C)C)n2)c(OC2CC2)cc1C1CCS(=O)(=O)CC1] | MS: [M + 1] 609.2 |
| Final product 111 | A84, B3 | 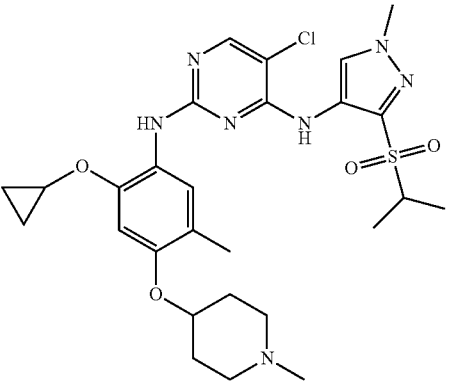 [SMILES: Cc1cc(Nc2ncc(Cl)c(Nc3cn(C)nc3S(=O)(=O)C(C)C)n2)c(OC2CC2)cc1OC1CCN(C)CC1] | MS: [M + 1] 589.9 |
| Final product 112 | A85, B3 | 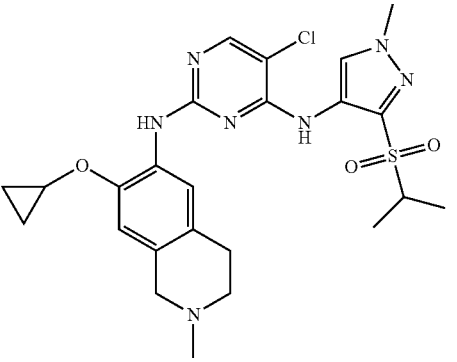 [SMILES: CC(C)S(=O)(=O)c1nn(C)cc1Nc1nc(Nc2cc3c(cc2OC2CC2)CN(C)CC3)ncc1Cl] | MS: [M + 1] 532.2 |

TABLE 9-continued

Final products 78-113

| Final Product Nos. | Raw Material Nos. | Structural Formulas of Final Products | NMR or MS |
|---|---|---|---|
| Final product 113 | A87, B13 | | MS: [M + 1] 591.2 |

Example 216: 5-chloro-$N^2$-[2-cyclopropoxy-4-(1-ethylpiperidin-4-yl)-5-methylphenyl]-$N^4$-[1-methyl-3-(isopropylsulfonyl)-1H-pyrazol-4-yl]-pyrimidin-2,4-diamine (Final Product 114)

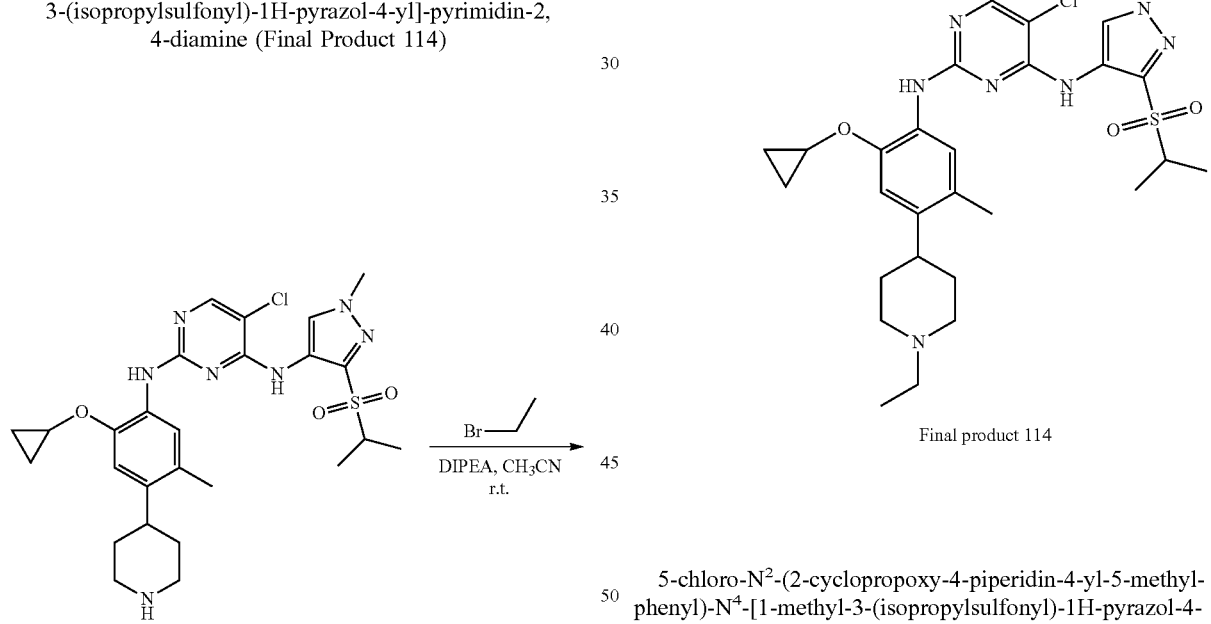

Final product 114

5-chloro-$N^2$-(2-cyclopropoxy-4-piperidin-4-yl-5-methylphenyl)-$N^4$-[1-methyl-3-(isopropylsulfonyl)-1H-pyrazol-4-yl]-pyrimidin-2,4-diamine (30 mg, 0.054 mmol), N,N-diisopropylethylamine (20 mg, 0.15 mmol), bromoethane (10 mg, 0.1 mmol) and acetonitrile (3 mL) were added to a 10 mL reaction flask. The reaction mixture was stirred at room temperature for 18 hours. After completion of the reaction, the reaction solution was filtered and concentrated. The thus obtained crude product was separated by thin layer chromatography (developing solvent: dichloromethane/methanol=9:1) to obtain the title compound (light yellow solid, 14 mg, 44%). (MS: [M+1] 588.2)

Examples 217-224 Preparation of Final Product 115-122

Final products 115-122 were synthesized by using the above method for preparing final product 114 (table 10).

TABLE 10

Final products 115-122

| Final Product Nos. | Structural formulas of Final Products | NMR or MS |
| --- | --- | --- |
| Final product 115 | | MS: [M + 1] 562.2 |
| Final product 116 | | MS: [M + 1] 576.2 |
| Final product 117 | | MS: [M + 1] 602.3 |

TABLE 10-continued

Final products 115-122

| Final Product Nos. | Structural formulas of Final Products | NMR or MS |
|---|---|---|
| Final product 118 | | $^1$H NMR (400 MHz MeOD) ppm 1.28-1.33 (m 12H), 1.39-1.42 (m 3H), 2.03-2.07 (m 4H), 2.34 (s 3H), 2.71 (s 3H), 3.12-3.16 (m 4H), 3.23-3.15 (m 1H), 3.39-3.42 (m 1H), 3.70 (d 2H), 3.94 (s 3H), 4.59-4.63 (m 1H), 6.92 (s 1H), 7.61 (s 1H), 8.04 (s 1H), 8.37 (s 1H)(mesylate); MS: [M + 1] 590.3 |
| Final product 119 | | MS: [M + 1] 590.1 |
| Final product 120 | | MS: [M + 1] 588.2 |

TABLE 10-continued

Final products 115-122

| Final Product Nos. | Structural formulas of Final Products | NMR or MS |
|---|---|---|
| Final product 121 | | MS: [M + 1] 602.3 |
| Final product 122 | | MS: [M + 1] 602.3 |

Example 225: 5-chloro-$N^2$-[2-cyclopropoxy-4-(1-isopropylpiperidin-4-yl)-5-methyl-phenyl]-$N^4$-[1-methyl-3-(isopropylsulfonyl)-1H-pyrazol-4-yl]-pyrimidin-2,4-diamine (Final Product 123)

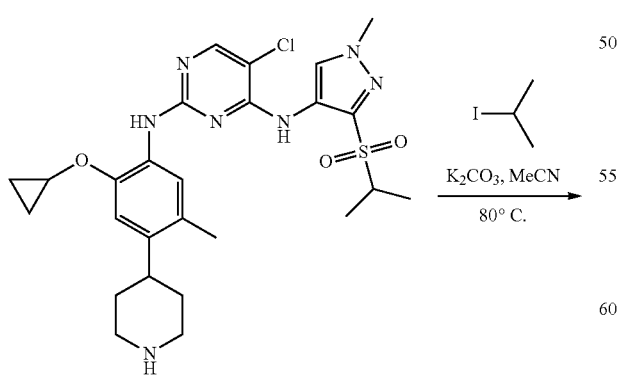

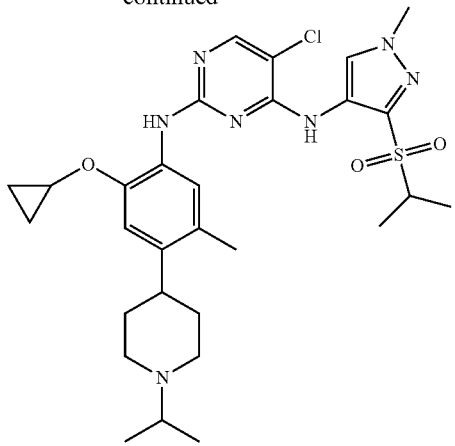

Final product 123

5-chloro-$N^2$-(2-cyclopropoxy-4-piperidin-4-yl-5-methyl-phenyl)-$N^4$-[1-methyl-3-(isopropylsulfonyl)-1H-pyrazol-4-yl]-pyrimidin-2,4-diamine (45 mg, 0.08 mmol), 2-iodo-propane (27 mg, 0.16 mmol), potassium carbonate (22 mg, 0.16 mmol) and acetonitrile (2 mL) were added to a 10 mL reaction flask. The reaction mixture was heated up to 80° C. under the protection of nitrogen and stirred for 7 hours. After completion of the reaction, the reaction solution was filtered and concentrated. The thus obtained crude product was separated by thin layer chromatography (developing solvent:methylene chloride/methanol=9:1) to obtain the title compound (yellow solid, 34.5 mg, 72%). $^1$H NMR (400 MHz MeOD) ppm 0.63-0.67 (m 2H), 0.83-0.87 (m 2H), 1.32-1.35 (m 6H), 1.43-1.49 (m 6H), 2.10-2.24 (m 5H), 2.38 (s 3H), 2.70 (s 3H), 3.25-3.29 (m 2H), 3.45-3.52 (m 1H), 3.68-3.63 (m 3H), 3.90-3.94 (m 1H), 3.98 (s 3H), 7.28 (s 1H), 7.42 (s 1H), 8.08 (s 1H), 8.46 (s 1H)(mesylate); MS: [M+1] 602.3)

Example 226-234 Preparation of Final Product 124-132

Final products 124-132 were synthesized by using the above method for preparing final product 123 (table 11).

TABLE 11

Final products 124-132

| Final Product Nos. | Structural Formulas of Final Products | NMR or MS |
|---|---|---|
| Final product 124 | | MS: [M + 1] 576.2 |
| Final product 125 | | MS: [M + 1] 590.2 |

TABLE 11-continued

Final products 124-132

| Final Product Nos. | Structural Formulas of Final Products | NMR or MS |
|---|---|---|
| Final product 126 | | $^1$H NMR (400 MHz MeOD) ppm 1.29-1.32 (m 12H), 1.41-1.43 (m 6H), 2.14-2.18 (m 4H), 2.35 (s 3H), 2.70 (s 3H), 3.43-3.46 (m 1H), 3.56-3.60 (m 3H), 3.96 (s 3H), 4.61-4.65 (m 1H), 6.96 (s 1H), 7.50 (s 1H), 8.07 (s 1H), 8.41 (s 1H)(mesylate); MS: [M + 1] 604.3 |
| Final product 127 | | $^1$H NMR (400 MHz MeOD) ppm 0.73-0.76 (m 2H), 0.79-0.82 (m 2H), 1.01-1.05 (m 6H), 1.40-1.49 (m 6H), 2.05-2.11 (m 4H), 2.13-2.23 (m 1H), 2.32 (s 3H), 2.68 (s 3H), 3.15-3.22 (m 4H), 3.55-3.59 (m 3H), 3.82-3.86 (m 1H), 3.92 (s 3H), 7.24 (s 1H), 7.53 (s 1H), 8.01 (s 1H), 8.32 (s 1H)(mesylate); MS: [M + 1] 616.0 |
| Final product 128 | | MS: [M + 1] 604.3 |

TABLE 11-continued

Final products 124-132

| Final Product Nos. | Structural Formulas of Final Products | NMR or MS |
|---|---|---|
| Final product 129 | | MS: [M + 1] 602.3 |
| Final product 130 | | MS: [M + 1] 616.3 |
| Final product 131 | | MS: [M + 1] 616.3 |

TABLE 11-continued

Final products 124-132

| Final Product Nos. | Structural Formulas of Final Products | NMR or MS |
|---|---|---|
| Final product 132 | | MS: [M + 1] 576.2 |

Example 235: 2-(4-(4-(5-chloro-4-(3-(isopropylsulfonyl)-1-methyl-1H-pyrazol-4-amino)pyrimidin-2-amino)-5-cyclopropoxy-2-methylphenyl)piperidin-1-yl) ethanol (Final Product 133)

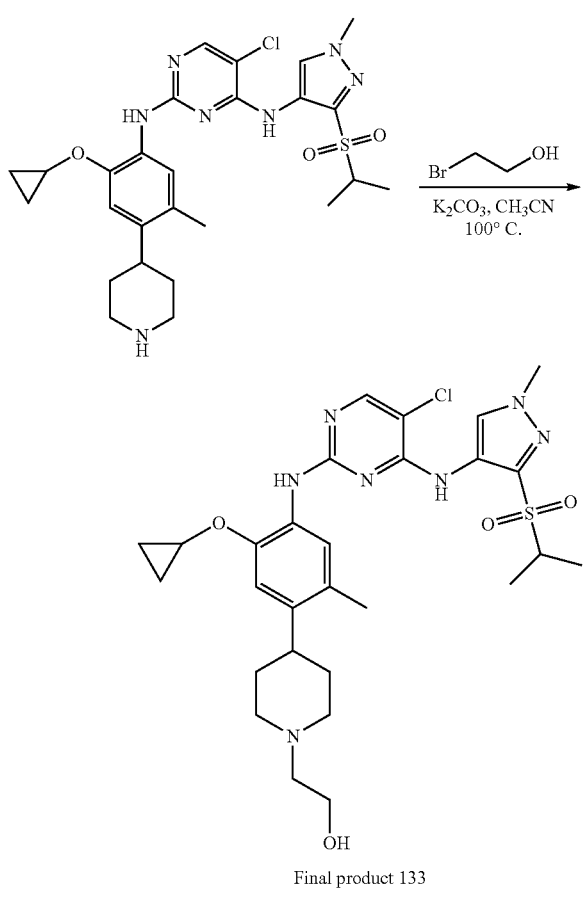

Final product 133

5-chloro-$N^2$-(2-cyclopropoxy-4-piperidin-4-yl-5-methyl-phenyl)-$N^4$-[1-methyl-3-(isopropyl sulfonyl)-1H-pyrazol-4-yl]-pyrimidin-2,4-diamine (30 mg, 0.054 mmol), 2-bromoethanol (17 mg, 0.14 mmol), potassium carbonate (42 mg, 0. mmol) and acetonitrile (2 mL) were added to a 10 mL round-bottomed flask. The reaction solution was stirred at 100° C. for 24 hours and filtered. The filtrate was diluted with water after concentration and extracted with ethyl acetate. The organic phase was dried and concentrated. The thus obtained crude product was washed with diethyl ether to obtain the title compound (13.5 mg, 41%). ($^1$H NMR (400 MHz CD3OD) ppm 0.57-0.61 (m 2H), 0.77-0.82 (m 2H), 1.31-1.33 (m 6H), 2.08-2.19 (m 4H), 2.35 (s 3H), 2.71 (s 3H), 3.19-3.27 (m 4H), 3.39-3.77 (m 2H), 3.80-3.88 (m 3H), 3.94-3.96 (m 5H), 7.26 (s 1H), 7.55 (s 1H), 8.01 (s 1H), 8.37 (s 1H)(mesylate); MS: [M+1] 604.3)

Examples 236-243: Preparation of Final Products 134-141

Final products 134-141 were synthesized by using the above method for preparing final product 133 (table 12).

TABLE 12

Final products 134-141

| Final Product Nos. | Structural Formulas of Final Products | NMR or MS |
|---|---|---|
| Final product 134 | | MS: [M + 1] 578.2 |
| Final product 135 | | MS: [M + 1] 592.2 |
| Final product 136 | | MS: [M + 1] 606.3 |

TABLE 12-continued

Final products 134-141

| Final Product Nos. | Structural Formulas of Final Products | NMR or MS |
|---|---|---|
| Final product 137 | (structure) | MS: [M + 1] 618.3 |
| Final product 138 | (structure) | $^1$H NMR (400 MHz CD3OD) ppm 1.36-1.39 (m 6H), 1.72-1.90 (m 4H), 2.10-2.14 (m 6H), 2.37 (s 3H), 2.45-2.49 (m 2H), 2.70 (s 3H), 3.20-3.27 (m 3H), 3.46-3.50 (m 1H), 3.79 (d 2H), 3.93-3.98 (m 5H), 4.76-4.80 (m 1H), 6.86 (s 1H), 7.33 (s 1H), 8.11 (s 1H), 8.45 (s 1H)(mesylate); MS: [M + 1] 618.2 |
| Final product 139 | (structure) | MS: [M + 1] 604.2 |

TABLE 12-continued

Final products 134-141

| Final Product Nos. | Structural Formulas of Final Products | NMR or MS |
|---|---|---|
| Final product 140 | (structure) | MS: [M + 1] 618.3 |
| Final product 141 | (structure) | MS: [M + 1] 606.1 |

Example 244: 5-chloro-$N^2$-(2-isopropoxy-4-(1-(2-methoxyethyl)piperidin-4-yl)-5-methyl-phenyl)-$N^4$-(3-(isopropyl sulfonyl)-1-methyl-1H-pyrazol-4)-pyrimidin-2,4-diamine (Final Product 142)

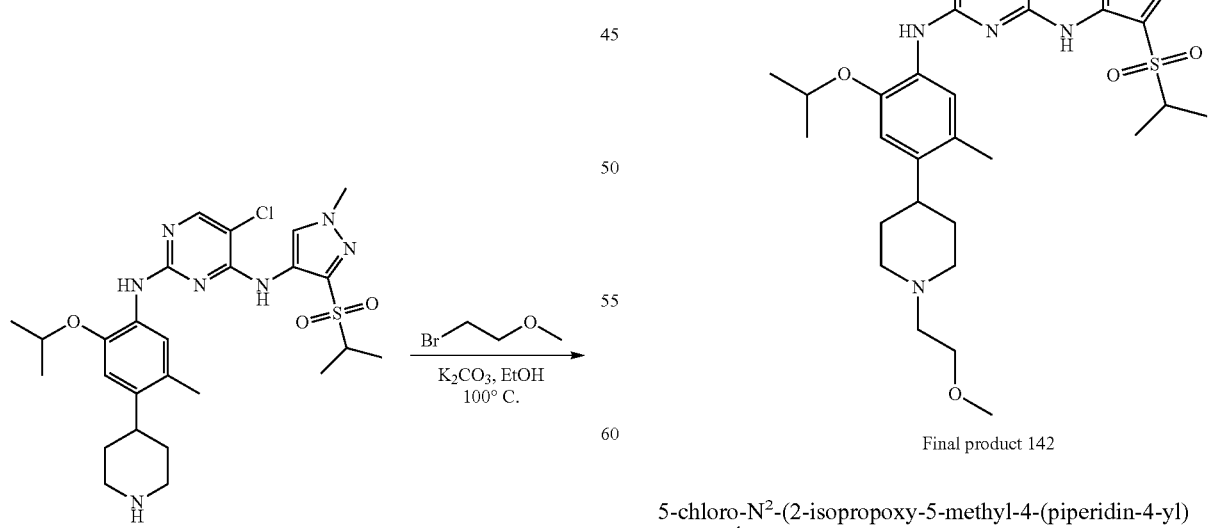

Final product 142

5-chloro-$N^2$-(2-isopropoxy-5-methyl-4-(piperidin-4-yl)phenyl)-$N^4$-(3-(isopropylsulfonyl)-1-methyl-1H-pyrazole-4)-pyrimidin-2,4-diamine (56 mg, 0.1 mmol), 1-bromo-2-methoxy-ethane (28 mg, 0.2 mmol), potassium carbonate (28 mg, 0.2 mmol) and ethanol (5 mL) were added to a 10 mL sealed tube. The reaction mixture was heated up to 100° C. by microwave and reacted for 2 hours under stirring. After completion of the reaction, the obtained crude product by filtration and concentration was separated and purified by preparative HPLC to obtain the title compound (31 mg, 50%). (MS: [M+1] 620.3)

Examples 245, 246: Preparation of Final Products 143 and 144

The above method for synthesizing final product 142 was applied to prepare 5-chloro-N²-(2-ethoxy-4-(1-(2-methoxyethyl) piperidin-4-yl)-5-methyl-phenyl)-N⁴-(3-(isopropyl sulfonyl)-1-methyl-1H-pyrazol-4)-pyrimidin-2,4-diamine (final product 143) and 5-chloro-N²-(2-cyclobutyloxy-4-(1-(2-methoxyethyl) piperidin-4-yl)-5-methyl-phenyl)-N⁴-(3-(isopropyl sulfonyl)-1-methyl-1H-pyrazol-4)-pyrimidin-2,4-diamine (final product 144)

Final product 143

Final product 144

Example 247: 5-chloro-N²-[2-cyclopropoxy-4-(1-(2-fluoroethyl)piperidin-4-yl)-5-methylphenyl]-N⁴-[1-methyl-3-(isopropyl sulfonyl)-1H-pyrazol-4-yl]-pyrimidin-2,4-diamine (Final Product 145)

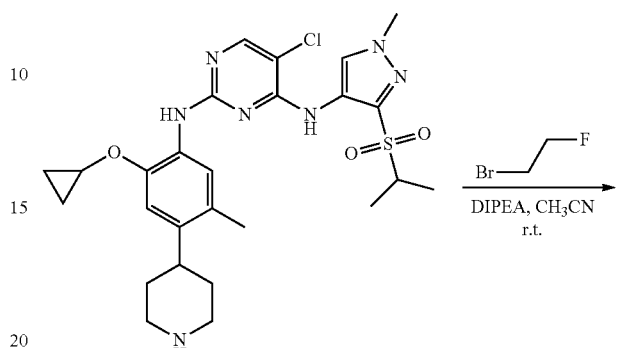

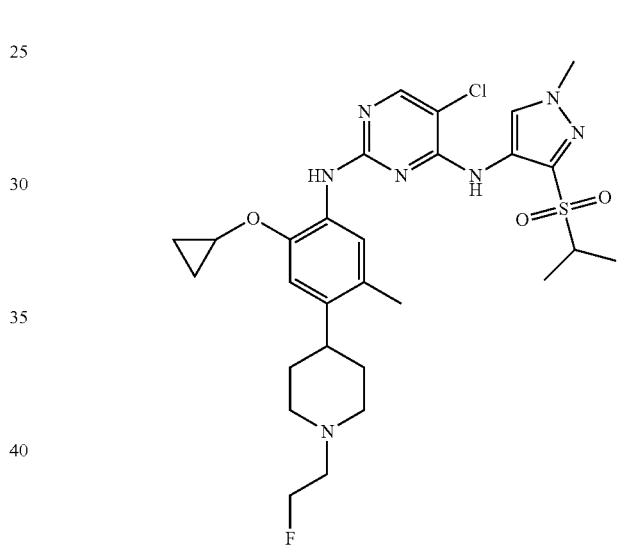

Final product 145

5-chloro-N²-(2-cyclopropoxy-4-piperidin-4-yl-5-methyl-phenyl)-N⁴-[1-methyl-3-(isopropyl sulfonyl)-1H-pyrazol-4-yl]-pyrimidin-2,4 diamine (30 mg, 0.054 mmol), 1-bromo-2-fluoroethane (14.0 mg, 0.11 mmol), diisopropylethylamine (15.0 mg, 0.11 mmol) and acetonitrile (5 mL) were added to a 10 mL reaction flask. The reaction mixture was stirred at room temperature overnight. After completion of the reaction, the reaction solution was added with ethyl acetate, washed with saturated sodium bicarbonate and saturated brine, dried and concentrated. The thus obtained crude product was separated and purified by thin layer chromatography preparative plate (eluent:methanol/dichloromethane=1/10) to obtain the title compound (white solid, 19 mg, 58%). (MS: [M+1] 606.2)

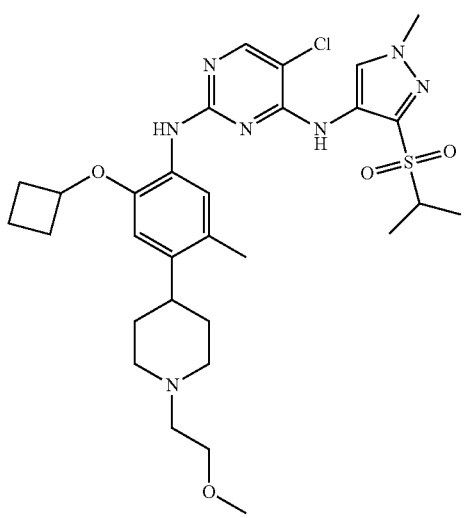

Example 248: 5-chloro-N²-(2-cyclopropoxy-4-(1-(2-(dimethylamino)ethyl)piperidin-4-yl)-5-methylphenyl)-N⁴-(3-(isopropyl sulfonyl)-1-methyl-1H-pyrazol-4-yl)-pyrimidin-2,4-diamine (Final Product 146)

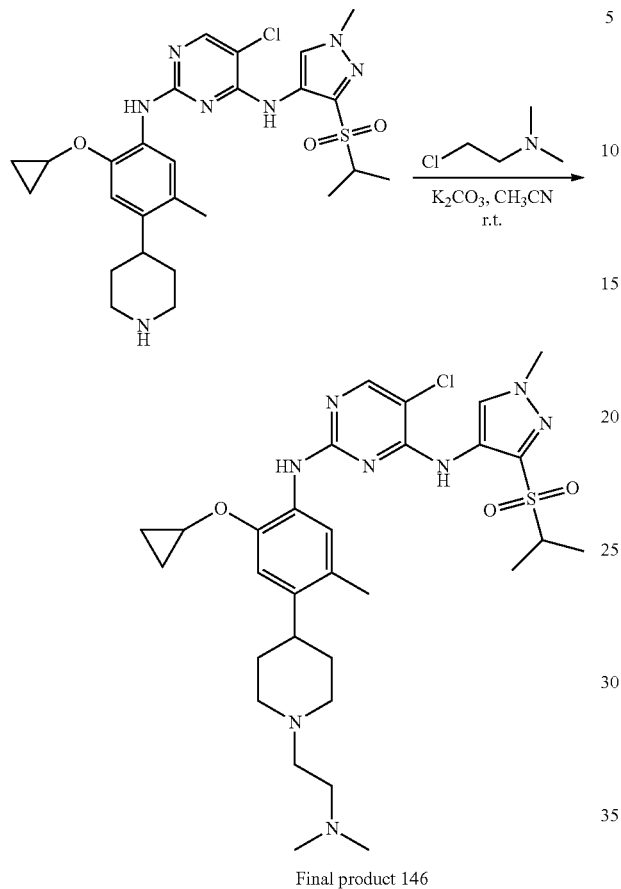

Final product 146

5-chloro-N²-(2-cyclopropoxy-4-piperidin-4-yl-5-methylphenyl)-N⁴-[1-methyl-3-(isopropyl sulfonyl)-1H-pyrazol-4-yl]-pyrimidin-2,4 diamine (40 mg, 0.071 mmol), 2-chloro-N,N-dimethylethylamine hydrochloride (15.7 mg, 0.11 mmol), potassium carbonate (42 mg, 0.3 mmol) and 2 mL acetonitrile were added to a 10 mL round-bottomed flask. The reaction solution was stirred at room temperature for 24 hours, and filtered, concentrated and separated by thin layer chromatography (dichloromethane/methanol=10:1) to obtain the title compound (21.5 mg, 48%) (MS: [M+1] 631.4)

Example 249: 2-(4-(4-(5-chloro-4-(3-(isopropylsulfonyl)-1-methyl-1H-pyrazol-4-amino)pyrimidin-2-amino)-5-propoxy-2-methylphenyl)piperidin-1-yl)-2-methyl-1-propanol (Final Product 147)

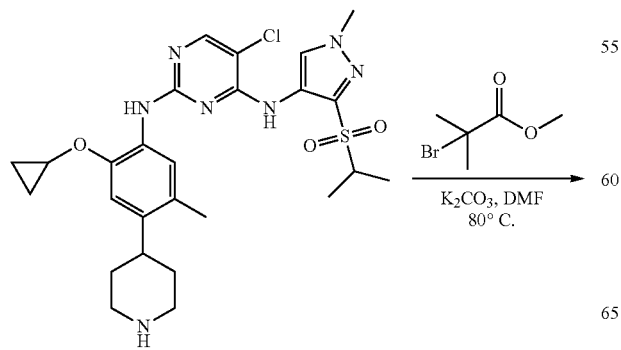

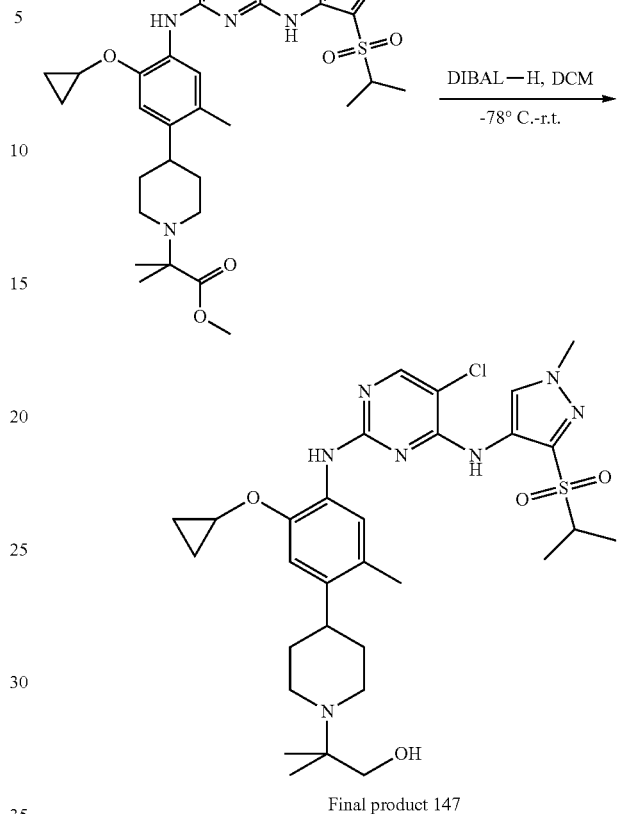

Step 1: methyl 2-(4-(4-(5-chloro-4-(3-(isopropyl sulfonyl)-1-methyl-1H-pyrazol-4-amino)pyrimidin-2-amino)-5-propoxy-2-methylphenyl)piperidin-1-yl)-2-methyl propionate

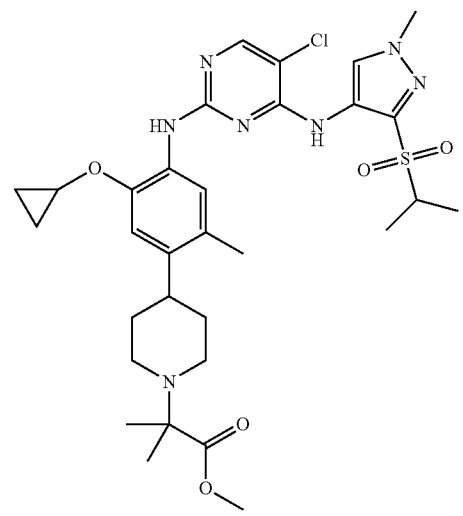 [SMILES: COC(=O)C(C)(C)N1CCC(c2cc(OC3CC3)c(Nc3ncc(Cl)c(Nc4cn(C)nc4S(=O)(=O)C(C)C)n3)cc2C)CC1]

5-chloro-N²-(2-cyclopropoxy-4-piperidin-4-yl-5-methylphenyl)-N⁴-[1-methyl-3-(isopropyl sulfonyl)-1H-pyrazol-4- yl]-pyrimidin-2,4-diamine (56 mg, 0.1 mmol), potassium carbonate (28 mg, 0.2 mmol), N,N-dimethylformamide (4 mL) and 2-bromo-methyl isobutyrate (36 mg, 0.2 mmol) were added to a 10 mL microwave tube. The reaction mixture was heated up to 80° C. and stirred for 18 hours. After completion of the reaction, the reaction mixture was filtered, added with ethyl acetate, washed with saturated brine, dried and concentrated. The thus obtained crude product was separated and purified by column chromatography (silica gel column, eluent:dichloromethane/methanol=10:1) to obtain the title compound (25 mg, 38%). (MS: [M+1] 660.3)

Step 2: 2-(4-(4-(5-chloro-4-(3-(isopropyl sulfonyl)-1-methyl-1H-pyrazol-4-amino)pyrimidin-2-amino)-5-cyclopropoxy-2-methylphenyl)piperidin-1-yl)-2-methyl-1-propanol methyl 2-(4-(4-(5-chloro-4-(3-(isopropylsulfonyl)-1-methyl-1H-pyrazol-4-amino) pyrimidin-2-amino)-5-cyclopropoxy-2-methylphenyl) piperidin-1-yl)-2-methyl propionate (25 mg, 0.038 mmol) and dichloromethane (5 mL) were added to a 25 mL reaction flask. The reaction mixture was cooled down to −78° C. under the protection of nitrogen and diisobutylaluminum hydride in toluene solution (1M, 0.15 mL, 0.15 mmol) was dropped thereinto at this temperature. The reaction mixture was slowly heated up and stirred at room temperature for 10 hours. After completion of the reaction, the reaction solution was dropped with water to quench the reaction, added with ethyl acetate to extract, washed with saturated brine, dried and concentrated. The thus obtained crude product was purified by preparative plate (developing solvent:methylene chloride/methanol=9:1) to obtain the title compound (17 mg, 71%). (MS: [M+1] 632.3)

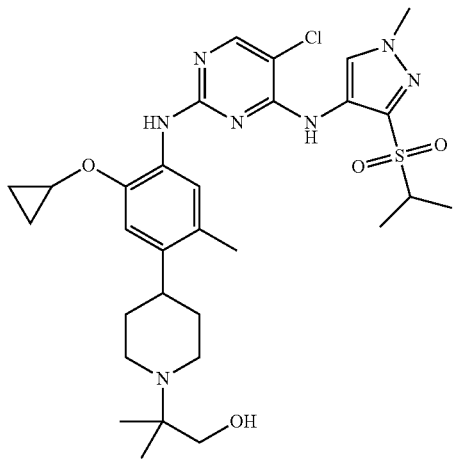 [SMILES: Cc1cc(Nc2ncc(Cl)c(Nc3cn(C)nc3S(=O)(=O)C(C)C)n2)c(OC2CC2)cc1C1CCN(C(C)(C)CO)CC1]

Examples 250-256: Preparation of Final Products 148-154

Final products 148-154 were synthesized by using the above method for preparing final product 147 (table 13).

TABLE 13

| | Final products 148-154 | |
|---|---|---|
| Final Product Nos. | Structural Formula of Final Products | NMR or MS |
| Final product 148 | | MS: [M + 1] 632.3 |

TABLE 13-continued

Final products 148-154

| Final Product Nos. | Structural Formula of Final Products | NMR or MS |
|---|---|---|
| Final product 149 | | MS: [M + 1] 646.3 |
| Final product 150 | | MS: [M + 1] 620.3 |
| Final product 151 | | MS: [M + 1] 620.3 |

TABLE 13-continued
Final products 148-154
| Final Product Nos. | Structural Formula of Final Products | NMR or MS |
|---|---|---|
| Final product 152 | 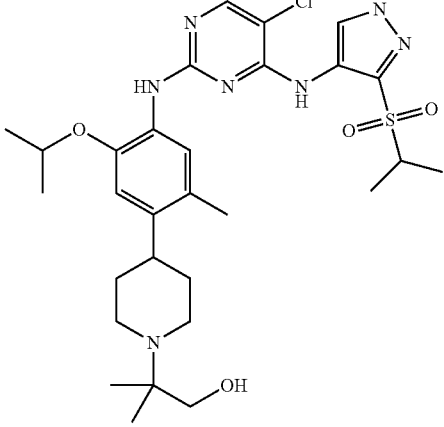 | $^1$H NMR (400 MHz MeOD) ppm 1.30-1.36 (m 12H), 1.43 (s 6H), 2.07-2.19 (m 4H), 2.36 (s 3H), 2.70 (s 3H), 3.20-3.25 (m 3H), 3.43-3.47 (m 1H), 3.97 (s 3H), 4.65-4.68 (m 1H), 7.01 (s 1H), 7.43 (s 1H), 8.08 (s 1H), 8.43 (s 1H)(mesylate); MS: [M + 1] 634.3 |
| Final product 153 | 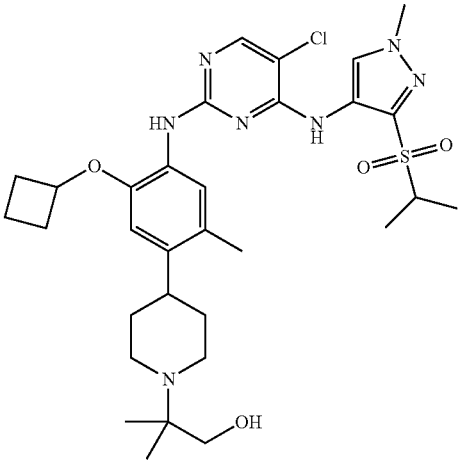 | MS: [M + 1] 646.3 |
| Final product 154 | 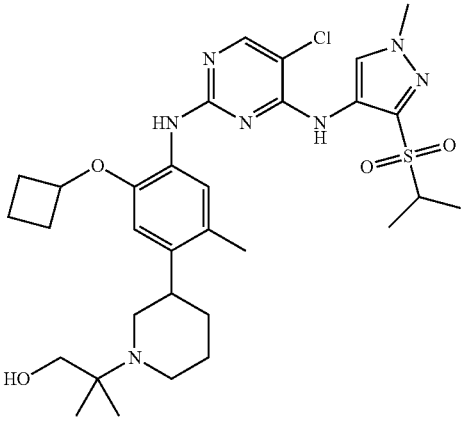 | MS: [M + 1] 646.3 |

Example 257: 2-(4-(4-(5-chloro-4-(3-(isopropoxy sulfonyl)-1-methyl-1H-pyrazol-4-yl-amino)pyrimidin-2-yl-amine)-5-cyclopropoxy-2-methylphenyl)piperidin-1-yl)-N,N-dimethylacetamide (Final Product 155)

Example 258: 5-chloro-N²-(2-cyclopropoxy-4-(1-(oxetane-3-yl)piperidin-4-yl)-5-methylphenyl)-N⁴-(3-(isopropoxy sulfonyl)-1-methyl-1H-pyrazol-4-yl) pyrimidin-2,4-diamine (Final Product 156)

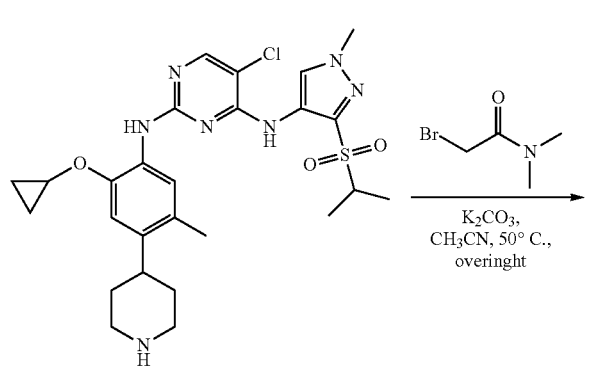

Final product 155

Final product 156

5-chloro-N²-(2-cyclopropoxy-4-piperidin-4-yl-5-methyl-phenyl)-N⁴-[1-methyl-3-(isopropoxy sulfonyl)-1H-pyrazol-4-yl]-pyrimidin-2,4-diamine (30 mg, 0.054 mmol), 2-bromo-N,N-dimethyl acetamide (18 mg, 0.108 mmol), potassium carbonate (20 mg, 0.107 mmol) and acetonitrile (2 mL) were added to a 10 mL reaction flask. The reaction solution was heated up to 50° C. and stirred overnight. After completion of the reaction, the reaction was cooled down, added with ethyl acetate to dilute, washed with saturated brine, dried and concentrated. The thus obtained crude product was separated and purified by thin layer chromatography preparative plate (eluent:methanol/dichloromethane=1/10) to obtain the title compound (white solid, 12.0 mg, 34%). (MS: [M+1] 645.3)

5-chloro-N²-(2-cyclopropoxy-4-piperidin-4-yl-5-methyl-phenyl)-N⁴-[1-methyl-3-(isopropoxy sulfonyl)-1H-pyrazol-4-yl]-pyrimidin-2,4-diamine (20 mg, 0.036 mmol), 3-oxetanone (26 mg, 0.36 mmol) and methanol (1 mL) were added to a 10 ml reaction flask, and sodium cyanoborohydride (6.8 mg, 0.108 mmol) and zinc chloride (7.3 mg, 0.054 mmol) were added to the reaction system in batches. The reaction mixture was heated up to 48° C. and stirred for 22 hours. After completion of the reaction, the reaction solution was concentrated, added with dichloromethane (5 mL), washed with saturated aqueous sodium chloride solution twice and filtered. The organic phase was collected, dried, concentrated and separated by thin layer chromatography (ethyl acetate/methanol=5:1) to obtain the title compound (yellow solid, 20.8 mg, 94%). (MS: [M+1] 616.3)

Example 259: 5-chloro-$N^2$-[2-cyclopropoxy-4-(1-cyclopropylpiperidin-4-yl)-5-methyl-phenyl]-$N^4$-[3-isopropyl sulfonyl)-1H-pyrazol-1-methyl-1H-pyrazol-4-yl]pyrimidin-2,4-diamine (Final Product 157)

Example 260: 5-chloro-$N^2$-(2-cyclopropoxy-5-methyl-4-(1-(1-methyl-piperidin-4-yl) piperidin-4-yl) phenyl)-$N^4$-(3-(isopropyl sulfonyl)-1-methyl-1H-pyrazol-4-yl)pyrimidin-2,4-diamine (Final Product 158)

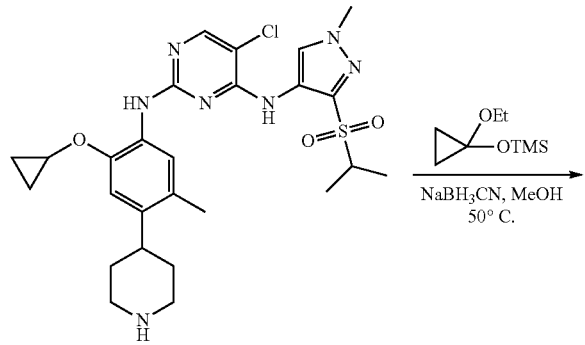

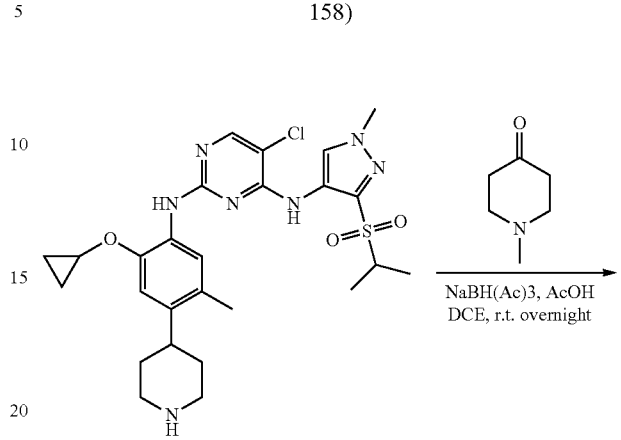

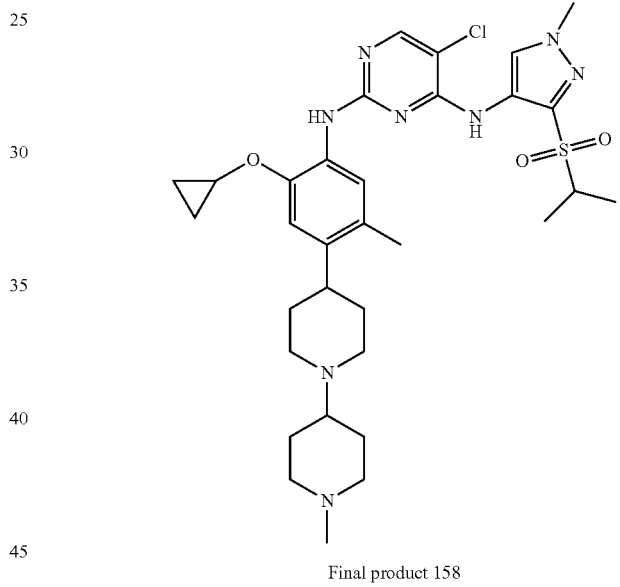

Final product 157

Final product 158

5-chloro-$N^2$-(2-cyclopropoxy-4-piperidin-4-yl-5-methyl-phenyl)-$N^4$-[1-methyl-3-(isopropyl sulfonyl)-1H-pyrazol-4-yl]-pyrimidin-2,4-diamine (56 mg, 0.1 mmol), methanol (1 mL) and acetic acid (1 drop) were added to a 10 ml reaction flask, and sodium cyanoborohydride (32 mg, 0.5 mmol), (1-ethoxycyclopropoxy) trimethyl silane (35 mg, 0.2 mmol) were added to the reaction system. The reaction mixture was heated up to 50° C. and reacted for 24 hours. The reaction was added with water to quench, extracted with ethyl acetate, washed with saturated aqueous sodium bicarbonate, dried and concentrated. The thus obtained crude product was separated by column chromatography (silica gel column, eluent:dichloromethane/methanol, gradient: 0-20% methanol) to obtain the title compound (white solid, 35.9 mg, 60%). (MS: [M+1] 599.9)

5-chloro-$N^2$-(2-cyclopropoxy-4-piperidin-4-yl-5-methyl-phenyl)-$N^4$-[1-methyl-3-(isopropyl sulfonyl)-1H-pyrazol-4-yl]-pyrimidin-2,4-diamine (35 mg, 0.062 mmol), 1-methyl-piperidin-4-one (22 mg, 0.195 mmol), acetic acid (1 drop) and dichloroethane (4 mL) were added to a 10 ml reaction flask. The reaction mixture was reacted at room temperature for 1 hour and added with sodium triacetoxyborohydride (133 mg, 0.626 mmol). The reaction mixture was stirred at room temperature overnight. After completion of the reaction, the reaction solution was added with ethyl acetate, washed with saturated sodium bicarbonate and saturated brine, dried and concentrated. The thus obtained crude product was separated and purified by thin layer chromatography preparative plate (eluent:methanol/dichloromethane=1/10) to obtain the title compound (white solid, 21.0 mg, 51%). (MS: [M+1] 657.3)

Example 261: 4-(4-(5-chloro-4-(3-(isopropyl sulfonyl)-1-methyl-1H-pyrazol-4-amino)pyrimidin-2-amino)-5-cyclopropoxy-2-methylphenyl)piperidin-1-formaldehyde (Final Product 159)

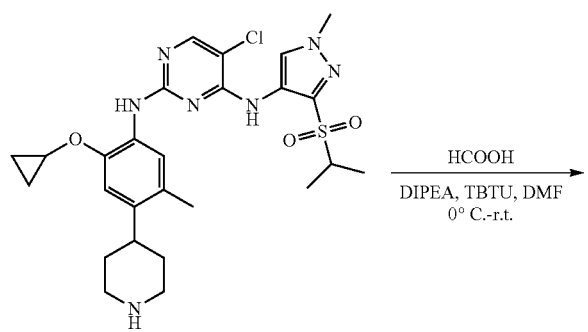

Example 262: 1-acetyl-4-(4-(5-chloro-4-(3-(isopropyl sulfonyl)-1-methyl-1H-pyrazol-4-amino)pyrimidin-2-amine)-5-cyclopropoxy-2-methylphenyl)piperidine (Final Product 160)

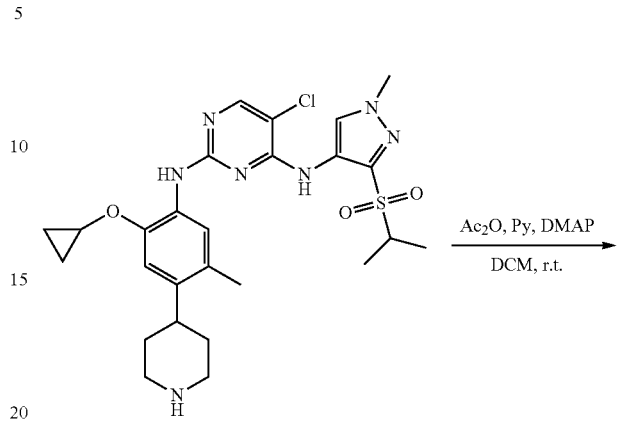

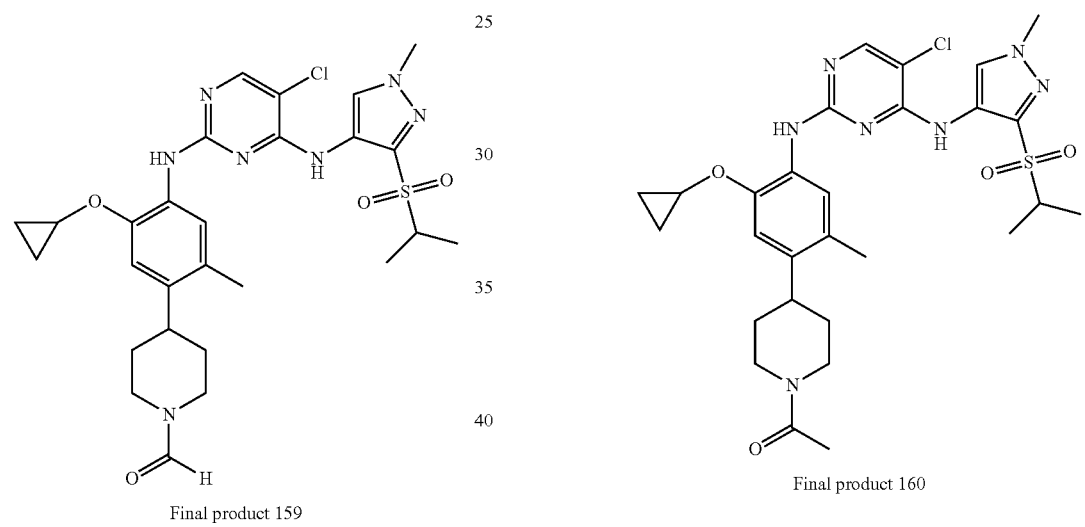

Final product 159

Final product 160

5-chloro-$N^2$-(2-cyclopropoxy-4-piperidin-4-yl-5-methylphenyl)-$N^4$-[1-methyl-3-(isopropyl sulfonyl)-1H-pyrazol-4-yl]-pyrimidin-2,4-diamine (28 mg, 0.05 mmol), diisopropylethylamine (19 mg, 0.15 mmol), formic acid (2.5 mg, 0.05 mmol) and dimethylformamide (1 mL) were added to a 10 ml reaction flask. The reaction mixture was slowly added with O-benzotriazole-N,N,N',N'-tetramethyluronium tetrafluoroborate (16.8 mg, 0.05 mmol) in batches at 0° C. and heated up to room temperature and stirred for 3 hours. After completion of the reaction, the reaction was added with dichloromethane (5 mL), washed with saturated aqueous ammonium chloride solution twice and filtered. The organic phase was collected, dried, concentrated and separated by column chromatography (dichloromethane/methanol=10:1) to obtain the title compound (yellow solid, 27.6 mg, 94%). (MS: [M+1] 588.3)

5-chloro-$N^2$-(2-cyclopropoxy-4-piperidin-4-yl-5-methylphenyl)-$N^4$-[1-methyl-3-(isopropyl sulfonyl)-1H-pyrazol-4-yl]-pyrimidin-2,4-diamine (20 mg, 0.036 mmol), pyridine (17 mg, 0.215 mmol), acetic anhydride (14.6 mg, 0.143 mmol), a catalytic amount of 4-dimethylaminopyridine, and dichloromethane (1 mL) were added to a 10 ml reaction flask. The reaction mixture was stirred at room temperature for 18 hours. After completion of the reaction, the reaction was added with dichloromethane (5 mL) to dilute, washed with saturated aqueous ammonium chloride solution twice and filtered. The organic phase was collected, dried, concentrated and separated by column chromatography (ethyl acetate/methanol=20:1) to obtain the title compound (yellow solid, 12.7 mg, 59%). (MS: [M+1] 602.2)

Example 263: 1-trifluoroacetyl-4-(4-(5-chloro-4-(3-(isopropyl sulfonyl)-1-methyl-1H-pyrazol-4-amino)pyrimidin-2-amine)-5-cyclopropoxy-2-methylphenyl)piperidine (Final Product 161)

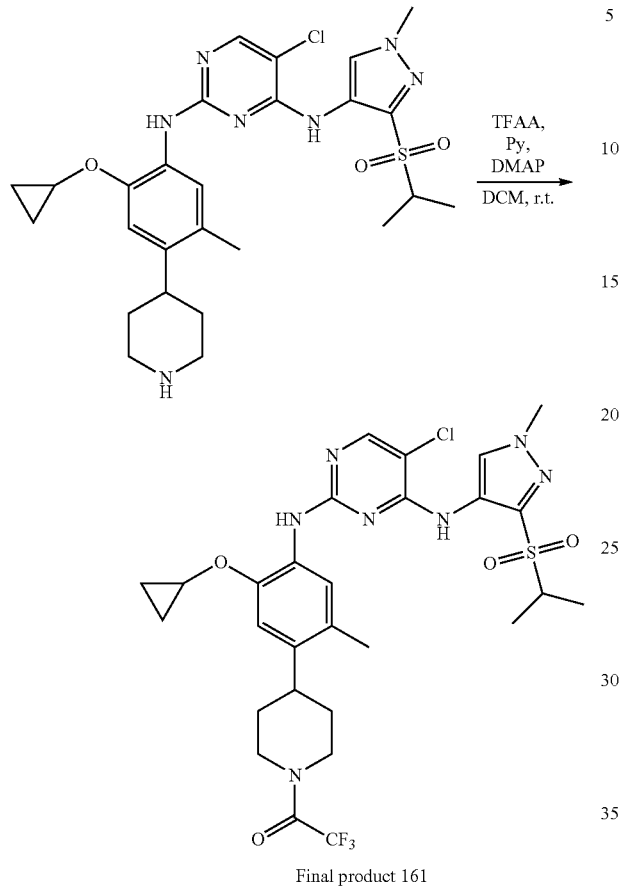

Final product 161

The title compound was synthesized from 5-chloro-N²-(2-cyclopropoxy-4-piperidin-4-yl-5-methylphenyl)-N⁴-[1-methyl-3-(isopropyl sulfonyl)-1H-pyrazol-4-yl]-pyrimidin-2,4-diamine and trifluoroacetic anhydride (white solid, 11.5 mg, 48%) by using the above method for preparing final product 160. (MS: [M+1] 656.1)

Example 264: 1-cyclopropylformyl-4-(4-(5-chloro-4-(3-(isopropyl sulfonyl)-1-methyl-1H-pyrazol-4-amino) pyrimidin-2-amine)-5-cyclopropoxy-2-methylphenyl)piperidine (Final Product 162)

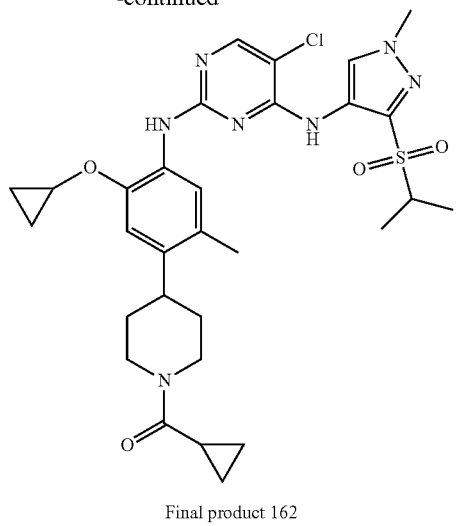

Final product 162

5-chloro-N²-(2-cyclopropoxy-4-piperidin-4-yl-5-methylphenyl)-N⁴-[1-methyl-3-(isopropyl sulfonyl)-1H-pyrazol-4-yl]-pyrimidin-2,4-diamine (22.4 mg, 0.04 mmol), triethylamine (10.1 mg, 0.1 mmol) and dichloromethane (1 ml) were added to a 10 ml reaction flask. The reaction mixture was stirred at 0° C. for 10 minutes, and then cyclopropyl formyl chloride (4.6 mg, 0.044 mmol) was added to the reaction system. The reaction was heated up to room temperature and continued to stir for 1 hour. After completion of the reaction, the reaction solution was concentrated, added with dichloromethane, washed with saturated aqueous sodium chloride solution twice and filtered. The organic phase was collected, dried, concentrated and prepared by reversed-phase high-performance liquid chromatography to obtain the title compound (white solid, 10 mg, 41%). (MS: [M+1] 628.2)

Example 265: 1-isobutyryl-4-(4-(5-chloro-4-(3-(isopropyl sulfonyl)-1-methyl-1H-pyrazol-4-amino) pyrimidin-2-amine)-5-cyclopropoxy-2-methylphenyl)piperidine (Final Product 163)

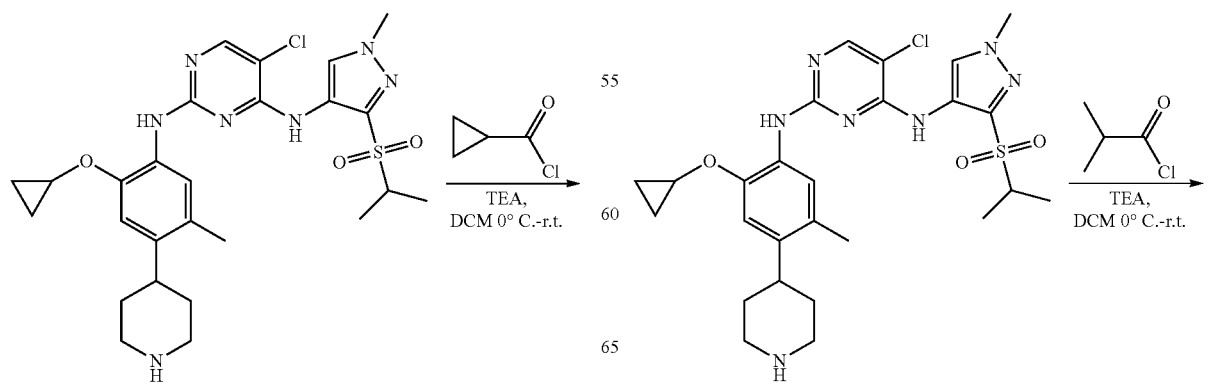

-continued

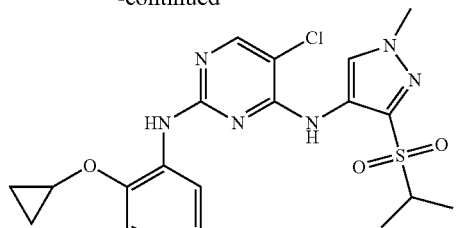

Final product 163

The title compound was synthesized from 5-chloro-N²-(2-cyclopropoxy-4-piperidin-4-yl-5-methylphenyl)-N⁴-[1-methyl-3-(isopropyl sulfonyl)-1H-pyrazol-4-yl]-pyrimidin-2,4-diamine and isobutyryl chloride (white solid, 8.2 mg, 41%) by using the above method for preparing final product 162. (MS: [M+1] 630.2)

Example 266: 1-pivaloyl-4-(4-(5-chloro-4-(3-(isopropyl sulfonyl)-1-methyl-1H-pyrazol-4-amino)pyrimidin-2-amine)-5-cyclopropoxy-2-methylphenyl)piperidine (Final Product 164)

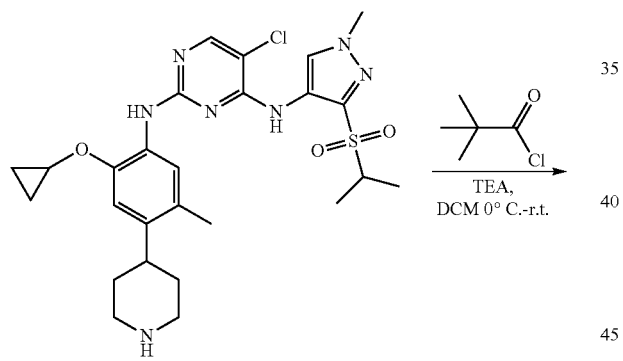

Final product 164

The title compound was synthesized from 5-chloro-N²-(2-cyclopropoxy-4-piperidin-4-yl-5-methylphenyl)-N⁴-[1-methyl-3-(isopropyl sulfonyl)-1H-pyrazol-4-yl]-pyrimidin-2,4-diamine and pivaloyl chloride (white solid, 11.5 mg, 46%) by using the above method for preparing final product 162. (MS: [M+1] 644.2)

Example 267: 1-(2-dimethylamino)acetyl-4-(4-(5-chloro-4-(3-(isopropyl sulfonyl)-1-methyl-1H-pyrazol-4-amino)pyrimidin-2-amino)-5-cyclopropoxy-2-methylphenyl)piperidine (Final Product 165)

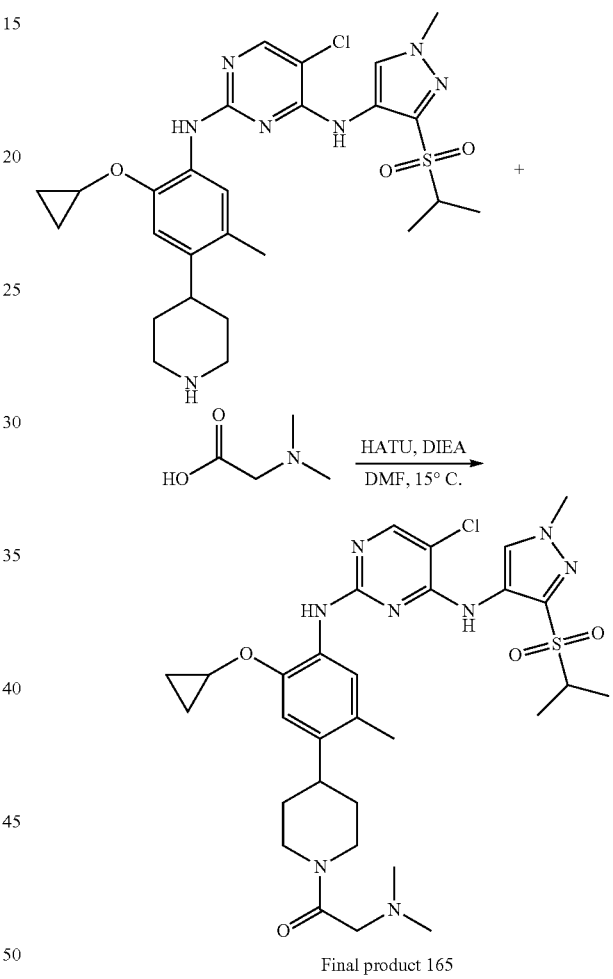

Final product 165

5-chloro-N²-(2-cyclopropoxy-4-piperidin-4-yl-5-methylphenyl)-N⁴-[1-methyl-3-(isopropyl sulfonyl)-1H-pyrazol-4-yl]-pyrimidin-2,4-diamine (35 mg, 0.062 mmol), 2-(dimethylamino) acetic acid (7.1 mg, 0.069 mmol), 2-(7-azo benzotriazole)-N,N,N',N'-tetramethyluronium hexafluorophosphate (35.3 mg, 0.093 mmol), N,N-diisopropylethylamine (24 mg, 0.186 mmol) and N,N-dimethylformamide (2 mL) were added to a 10 ml reaction flask. The reaction mixture was stirred at 15° C. for 16 hours. After completion of the reaction, the reaction solution was added with ethyl acetate (20 ml), washed with water and saturated brine, dried, concentrated and separated by thin layer chromatography (developing solvent: dichloromethane/methanol=20:1) to obtain the title compound (light yellow solid, 30 mg, 76%). (MS: [M+1] 644.9)

Example 268: 1-cyano acetyl-4-(4-(5-chloro-4-(3-(isopropyl sulfonyl)-1-methyl-1H-pyrazol-4-amino)pyrimidin-2-amine)-5-cyclopropoxy-2-methylphenyl)piperidine (Final Product 166)

Example 269: 5-chloro-$N^2$-(2-cyclopropoxy-5-methyl-4-(1-methanesulfonyl-piperidin-4-yl)-phenyl)-$N^4$-(3-(isopropyl sulfonyl)-1-methyl-1H-pyrazol-4-yl)pyrimidin-2,4-diamine (Final Product 167)

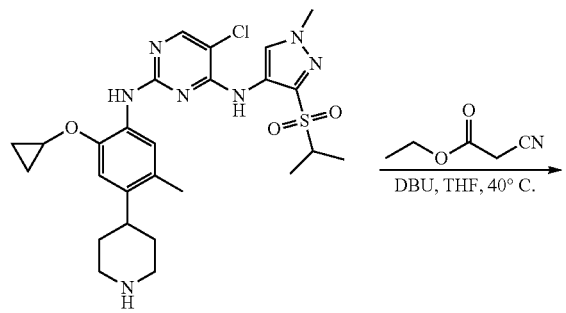

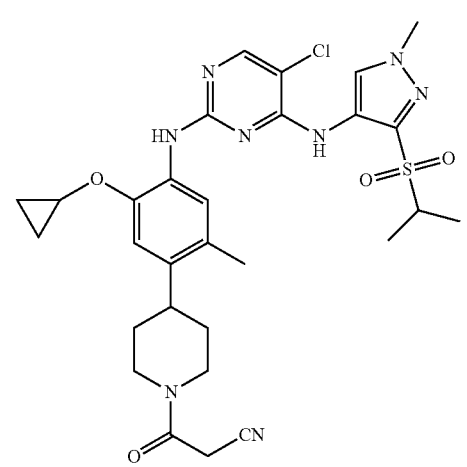

Final product 166

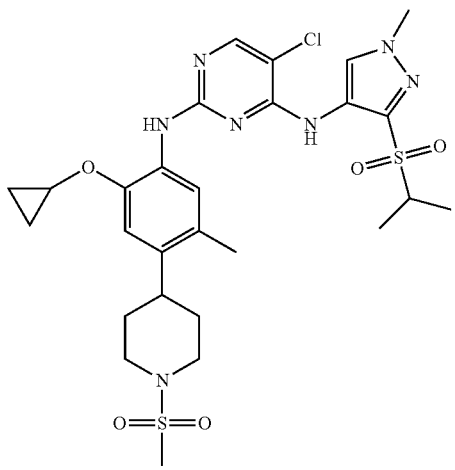

Final product 167

5-chloro-$N^2$-(2-cyclopropoxy-4-piperidin-4-yl-5-methyl-phenyl)-$N^4$-[1-methyl-3-(isopropyl sulfonyl)-1H-pyrazol-4-yl]-pyrimidin-2,4-diamine (33 mg, 0.06 mmol), ethyl cyanoacetate (13.5 mg, 0.12 mmol), 1,8-diazabicyclo[5.4.0]undec-7-ene (15 mg, 0.1 mmol) and tetrahydrofuran (2 mL) were added to a 10 ml reaction flask. The reaction mixture was heated up to 40° C., stirred for 24 hours and poured into water, extracted with ethyl acetate, dried, concentrated and purified by thin layer chromatography (ethyl acetate/petroleum ether=3:1) to obtain the title compound (white solid, 13 mg, 35%). (MS: [M+1] 627.3)

5-chloro-$N^2$-(2-cyclopropoxy-4-piperidin-4-yl-5-methyl-phenyl)-$N^4$-[1-methyl-3-(isopropyl sulfonyl)-1H-pyrazol-4-yl]-pyrimidin-2,4-diamine (22 mg, 0.04 mmol), triethylamine (4 mg, 0.04 mmol) and dichloromethane (1 mL) were added to a 5 ml reaction flask. The reaction was stirred at 0° C. for 2 hours and then poured into water, extracted with ethyl acetate, dried, concentrated and purified by thin layer chromatography (ethyl acetate/petroleum ether=3:1) to obtain the title compound (white solid, 20 mg, 79%). (MS: [M+1] 638.3)

Examples 270-275 Preparation of Final Products 168-173

Final products 168-173 were synthesized by using the method for preparing final product 167 (table 14).

TABLE 14

Final products 168-173

| Final Product Nos. | Structural Formulas of Final Products | NMR or MS |
|---|---|---|
| Final product 168 | | MS: [M + 1] 611.8 |
| Final product 169 | | MS: [M + 1] 625.9 |
| Final product 170 | | MS: [M + 1] 609.8 |

TABLE 14-continued

Final products 168-173

| Final Product Nos. | Structural Formulas of Final Products | NMR or MS |
|---|---|---|
| Final product 171 | | MS: [M + 1] 623.9 |
| Final product 172 | | MS: [M + 1] 610.3 |
| Final product 173 | | MS: [M + 1] 650.2 |

Example 276: 4-(4-(5-chloro-4-(3-(isopropyl sulfonyl)-1-methyl-1H-pyrazol-4-amine)pyrimidin-2-amine)-5-cyclopropoxy-2-methyl-phenyl)-N-ethyl-piperidin-1-carboxamide (Final Product 174)

Example 277: 5-chloro-$N^2$-(2-cyclopropoxy4-(4-(dimethylamino)cyclohexyl)-5-methylphenyl)-$N^4$-(3-(isobutyl sulfonyl)-1-methyl-1H-pyrazol-4-yl)pyrimidin-2,4-diamine(cis Final Product 175, Trans Final Product 176)

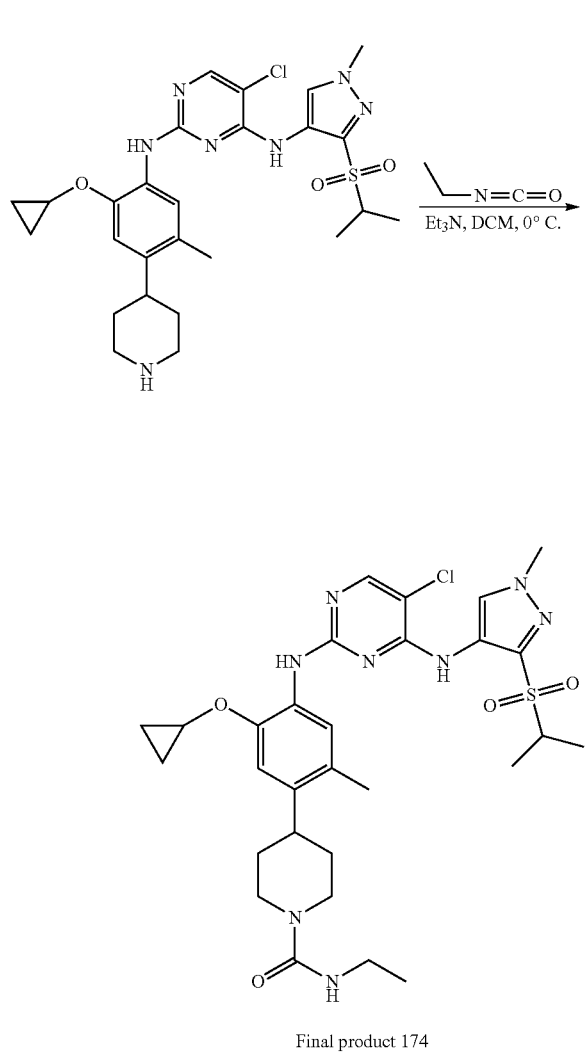

Final product 174

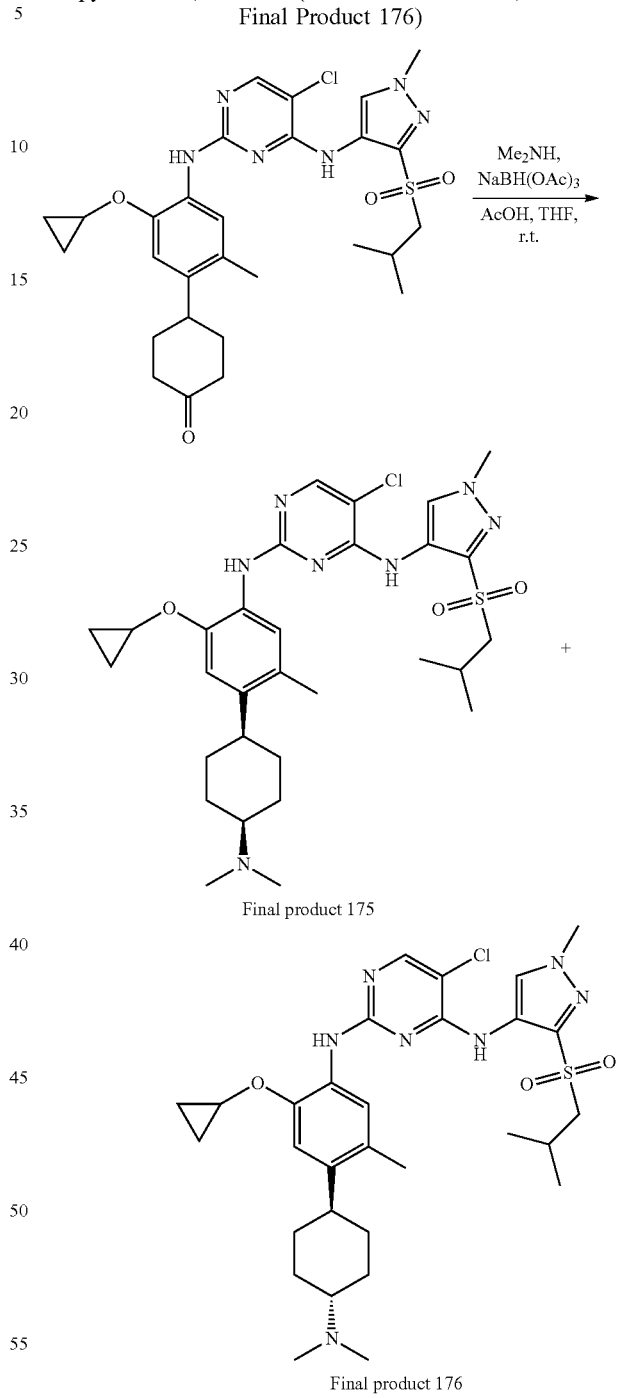

Final product 175

Final product 176

Interminate 5-chloro-$N^2$-(2-cyclopropoxy-4-piperidin-4-yl-5-methylphenyl)-$N^4$-[1-methyl-3-(isopropyl sulfonyl)-1H-pyrazol-4-yl]-pyrimidin-2, 4-diamine (22 mg, 0.04 mmol), triethylamine (8.1 mg, 0.08 mmol) and dichloromethane (1 mL) were added to a 5 ml reaction flask. The reaction mixture was cooled down to 0° C. and dropped with ethyl isocyanate (2.8 mg, 0.04 mmol). The reaction was poured into water after stirring for 2 hours, extracted with ethyl acetate, dried, concentrated and separated by thin layer chromatography (ethyl acetate/petroleum ether=3:1) to obtain the title compound (white solid, 10.2 mg, 40%). (MS: [M+1] 631.3)

4-(4-(5-chloro-4-(3-(isopropyl sulfonyl)-1-methyl-1H-pyrazol-4-amine) pyrimidin-2-amine)-5-cyclopropoxy-2-methyl-phenyl) cyclohexanone (152 mg, 0.26 mmol), dimethylamine (2.0M tetrahydrofuran solution, 1.3 mL, 2.6 mmol), glacial acetic acid (15.6 mg, 0.26 mmol) and tetrahydrofuran (5 mL) were added to a 25 ml reaction flask. The reaction mixture was stirred under the protection of nitrogen at room temperature for 2 hours, and then sodium triacetoxyborohydride (551 mg, 2.6 mmol) was added to the reaction system. The reaction mixture was stirred at room temperature for 24 hours, and added with saturated aqueous sodium bicarbonate solution to neutralize till the pH value to 8 to 9, extracted with ethyl acetate, dried, concentrated and separated by thin layer chromatography (dichloromethane:methanol=14:1) to obtain the title compound 175 with a lower polarity (white solid, 22 mg, 14%). (MS: [M+1] 616.3)

Examples 278-305 Preparation of Final Products 177-204

The final products 177-204 were synthesized from the corresponding ketone and amine through reductive amination by using the method (the reduction system was slightly different) similar to that for preparing final product 175 (table 15).

TABLE 15

| | | | |
|---|---|---|---|
| | | Final products 177-204 | |
| Final Product Nos. | Reduction Systems | Structural Formulas of Final Products | NMR or MS |
| Final product 177 | NaBH(OAc)$_3$, Ti($^i$PrO)$_4$ | 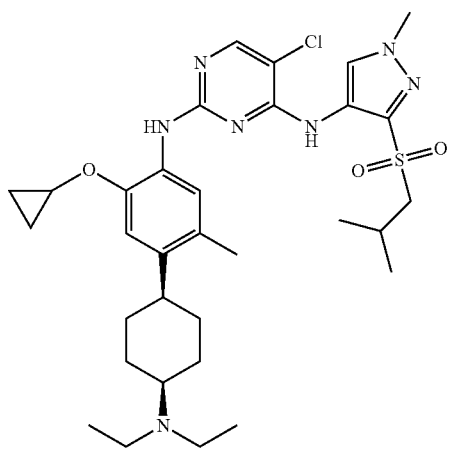 | MS: [M + 1] 644.3 |
| Final product 178 | NaBH(OAc)$_3$, Ti($^i$PrO)$_4$ | 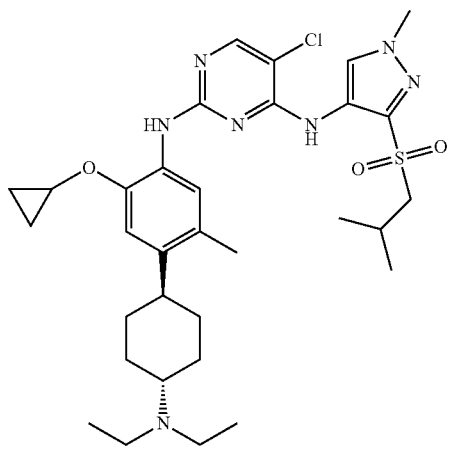 | MS: [M + 1] 644.3 |

TABLE 15-continued

Final products 177-204

| Final Product Nos. | Reduction Systems | Structural Formulas of Final Products | NMR or MS |
|---|---|---|---|
| Final product 179 | NaBH(OAc)₃, AcOH | | MS: [M + 1] 628.3 |
| Final product 180 | NaBH(OAc)₃, AcOH | | MS: [M + 1] 628.3 |
| Final product 181 | NaBH(OAc)₃, AcOH | | MS: [M + 1] 630.3 |

TABLE 15-continued

Final products 177-204

| Final Product Nos. | Reduction Systems | Structural Formulas of Final Products | NMR or MS |
|---|---|---|---|
| Final product 182 | NaBH(OAc)₃, AcOH | | MS: [M + 1] 630.3 |
| Final product 183 | NaBH(OAc)₃, AcOH | | MS: [M + 1] 604.3 |
| Final product 184 | NaBH(OAc)₃, AcOH | | MS: [M + 1] 632.3 |

TABLE 15-continued
Final products 177-204
| Final Product Nos. | Reduction Systems | Structural Formulas of Final Products | NMR or MS |
|---|---|---|---|
| Final product 185 | NaBH(OAc)₃, AcOH | 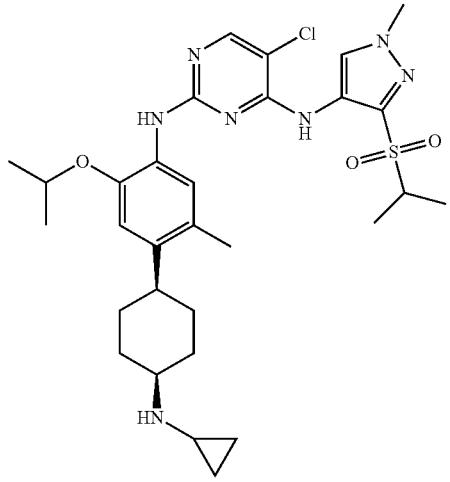 | MS: [M + 1] 616.3 |
| Final product 186 | NaBH(OAc)₃, AcOH | 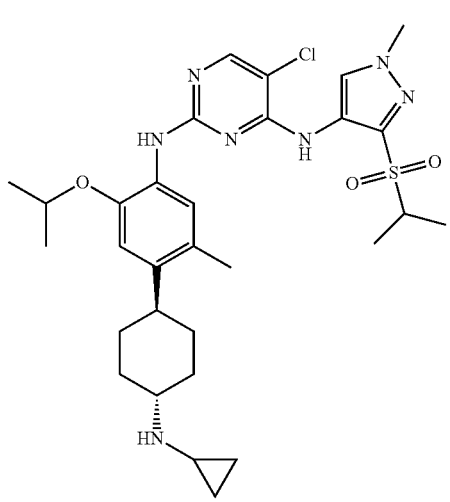 | MS: [M + 1] 616.3 |
| Final product 187 | NaBH(OAc)₃, AcOH | 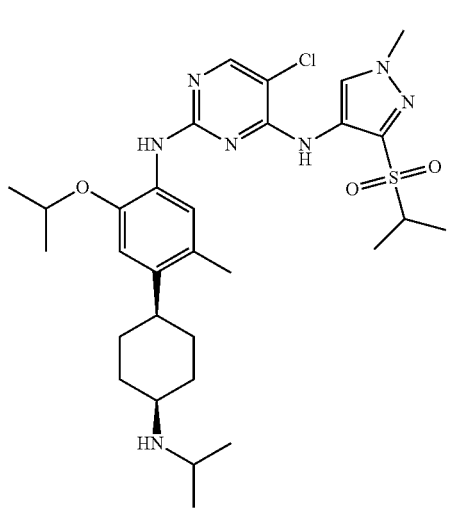 | MS: [M + 1] 618.3 |

TABLE 15-continued
Final products 177-204
| Final Product Nos. | Reduction Systems | Structural Formulas of Final Products | NMR or MS |
|---|---|---|---|
| Final product 188 | NaBH(OAc)₃, AcOH | 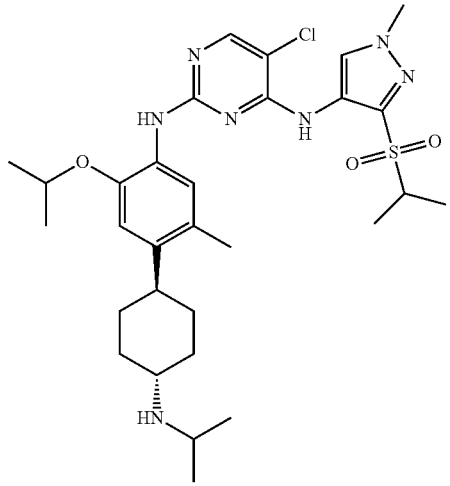 | MS: [M + 1] 618.3 |
| Final product 189 | NaBH₃CN | 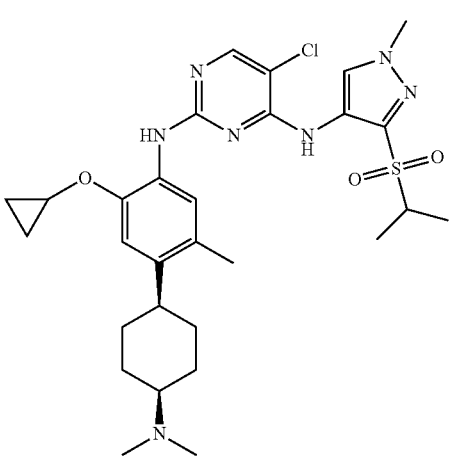 | ¹H NMR(400 MHz CD3OD) ppm 0.72-0.75 (m 2H), 0.79-0.81 (m 2H), 1.27-1.31 (m 6H), 1.83-1.86 (m 4H), 1.98-2.01 (m 2H), 2.31-2.36 (m 5H), 2.68 (s 3H), 3.00-3.07 (m 7H), 3.38-3.43 (m 2H), 3.91 (s 3H), 3.94-3.98 (m 1H), 7.41 (s 1H), 7.43 (s 1H), 7.98 (s 1H), 8.32 (s 1H) (mesylate); MS: [M + 1] 602.3 |
| Final product 190 | NaBH₃CN | 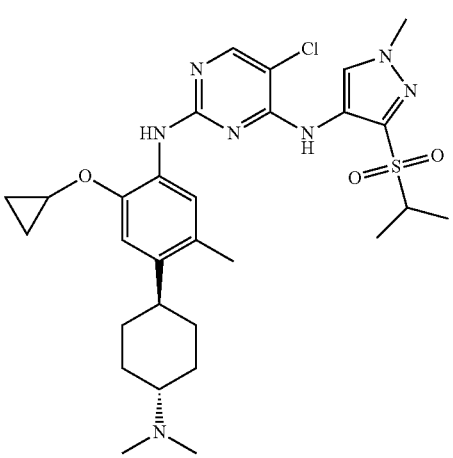 | MS: [M +30 1] 602.3 |

TABLE 15-continued

Final products 177-204

| Final Product Nos. | Reduction Systems | Structural Formulas of Final Products | NMR or MS |
|---|---|---|---|
| Final product 191 | NaBH(OAc)₃, Ti(ⁱPrO)₄ | | ¹H NMR(400 MHz CD3OD) ppm 0.64-0.66 (m 2H), 0.84-0.88 (m 2H), 1.27-1.39 (m 12H), 1.86-1.89 (m 2H), 1.97-2.08 (m 4H), 2.25-2.28 (m 2H), 2.33 (s 3H), 2.68 (s 3H), 3.09-3.11 (m 1H), 3.23-3.26 (m 2H), 3.33-3.53 (m 3H), 3.96 (s 3H), 4.01-4.02 (m 1H), 7.21 (s 1H), 7.60 (s 1H), 8.06 (s 1H), (mesylate); MS: [M + 1] 630.2 |
| Final product 192 | NaBH(OAc)₃, Ti(ⁱPrO)₄ | | ¹H NMR(400 MHz CD3OD) ppm 0.69-0.72 (m 2H), 0.78-0.81 (m 2H), 1.35-1.42 (m 12H), 1.68-1.83 (m 4H), 2.03(d 2H), 2.18-2.21 (m 2H), 2.31 (s 3H), 2.68 (s 3H), 2.84-2.90 (m 1H), 3.17-3.23 (m 2H), 3.30-3.47 (m 3H), 3.50-3.56 (m 1H), 3.80-3.84 (m 1H), 3.91 (s 1H), 7.23 (s 1H), 7.45 (s 1H), 8.00 (s 1H), 8.33 (s 1H) (mesylate); MS: [M + 1] 630.2 |
| Final product 193 | NaBH(OAc)₃, Ti(ⁱPrO)₄ | | MS: [M + 1] 630.3 |

TABLE 15-continued

Final products 177-204

| Final Product Nos. | Reduction Systems | Structural Formulas of Final Products | NMR or MS |
|---|---|---|---|
| Final product 194 | NaBH(OAc)$_3$, Ti($^i$PrO)$_4$ | | MS: [M + 1] 630.3 |
| Final product 195 | LiBH$_4$, TsOH | | MS: [M + 1] 614.3 |
| Final product 196 | LiBH$_4$, TsOH | | $^1$H NMR(400 MHz CD3OD) ppm 0.70-0.72 (m 2H), 0.76-0.78 (m 2H), 0.88-0.90 (m 2H), 0.95-0.97 (m 2H), 1.29-1.33 (m 6H), 1.61-1.73 (m 4H), 2.00-2.03 (m 2H), 2.31 (s 3H), 2.36-2.39 (m 2H), 2.70 (s 3H), 2.81-2.85 (m 2H), 3.39-3.42 (m 2H), 3.81-3.83 (m 1H), 3.91 (s 1H), 7.22 (s 1H), 7.52 (s 1H), 7.99 (s 1H), 8.32 (s 1H) (mesylate); MS: [M + 1] 614.3 |

TABLE 15-continued
Final products 177-204
| Final Product Nos. | Reduction Systems | Structural Formulas of Final Products | NMR or MS |
|---|---|---|---|
| Final product 197 | NaBH(OAc)$_3$, AcOH | 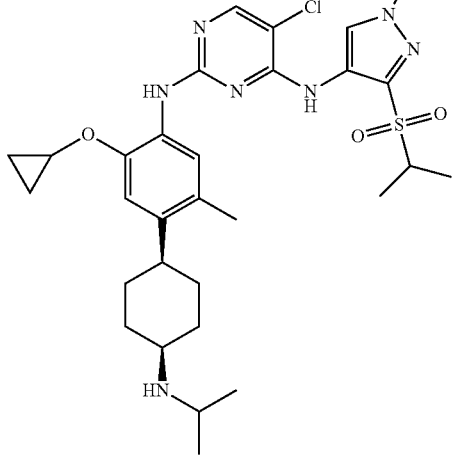 | MS: [M + 1] 616.3 |
| Final product 198 | NaBH(OAc)$_3$, AcOH | 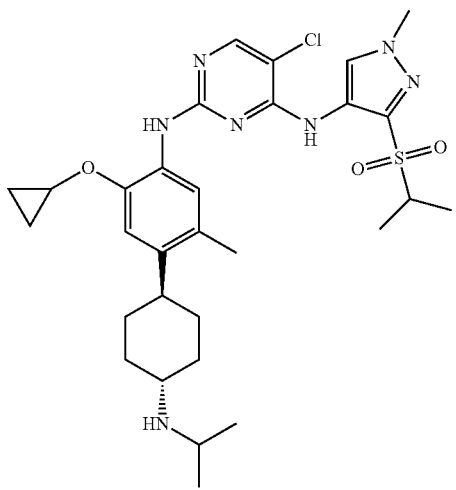 | $^1$H NMR(400 MHz CD3OD) ppm 0.70-0.72 (m 2H), 0.77-0.81 (m 2H), 1.30-1.38 (m 12H), 1.61-1.65 (m 2H), 1.74-1.78 (m 2H), 2.00-2.04 (m 2H), 2.27-2.39 (m 2H), 2.35 (s 3H), 2.70 (s 3H), 2.86-2.93 (m 1H), 3.37-3.40 (m 1H), 3.47-3.50 (m 1H), 3.57-3.60 (m 1H), 3.87-3.90 (m 1H), 3.98 (s 1H), 7.24 (s 1H), 7.37 (s 1H), 8.07 (s 1H) (mesylate); MS: [M + 1] 616.3 |
| Final product 199 | NaBH(OAc)$_3$, AcOH | 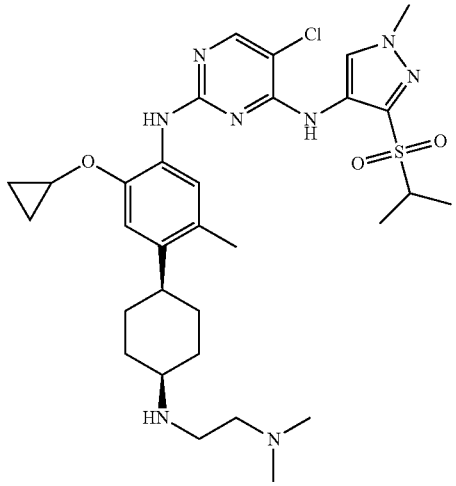 | MS: [M + 1] 645.3 |

TABLE 15-continued
Final products 177-204
| Final Product Nos. | Reduction Systems | Structural Formulas of Final Products | NMR or MS |
|---|---|---|---|
| Final product 200 | NaBH(OAc)$_3$, AcOH | 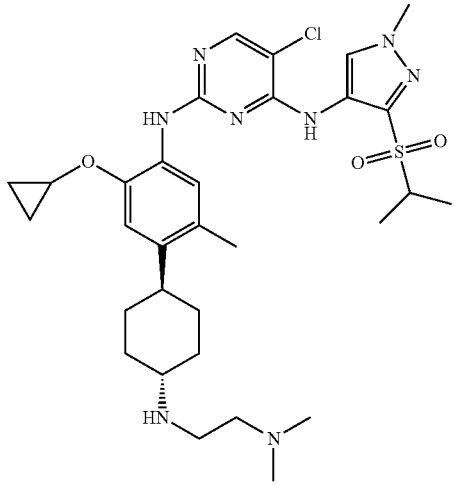 | MS: [M + 1] 645.3 |
| Final product 201 | NaBH$_3$CN | 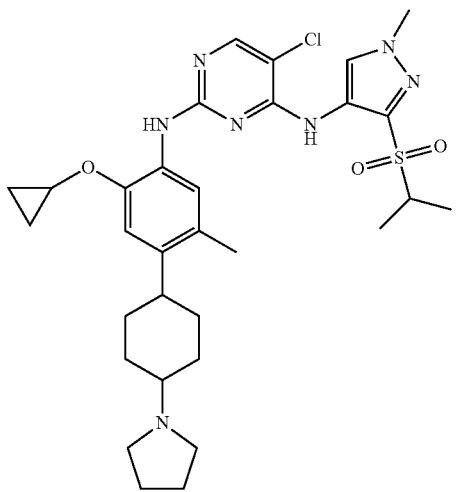 | MS: [M + 1] 628.3 |
| Final product 202 | NaBH$_3$CN | 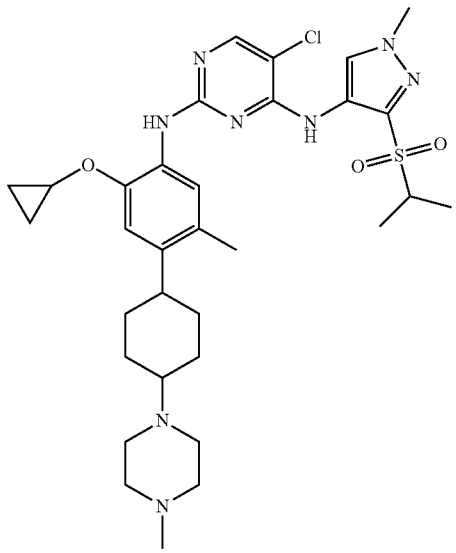 | MS: [M + 1] 657.3 |

TABLE 15-continued

Final products 177-204

| Final Product Nos. | Reduction Systems | Structural Formulas of Final Products | NMR or MS |
|---|---|---|---|
| Final product 203 | NaBH₃CN, Ti(ⁱPrO)₄ | | MS: [M + 1] 685.1 |
| Final product 204 | NaBH₃CN, Ti(ⁱPrO)₄ | | (¹H NMR(400 MHz CD3OD) ppm 0.71-0.75 (m 2H), 0.79-0.84 (m 2H), 1.31-1.33 (m 6H), 1.72-1.78 (m 5H), 2.06(d 2H), 2.17 (s 3H), 2.71 (s 3H), 2.29-2.31 (m 5H), 2.71 (s 3H), 2.85-2.88 (m 1H), 3.12-3.17 (m 2H), 3.49-3.61 (m 7H), 3.80-3.84 (m 1H), 3.92 (s 3H), 7.22 (s 1H), 7.49 (s 1H), 7.99 (s 1H), 8.33 (s 1H) (mesylate); MS: [M + 1] 685.1 |

Example 306: N-(4-(4-(5-chloro-4-(3-(isopropylsulfonyl)-1-methyl-1H-pyrazol-4-amine) pyrimidin-2-amine)-5-cyclopropoxy-2-methylphenyl)cyclohexyl)methanesulfonamide (Final Product 205)

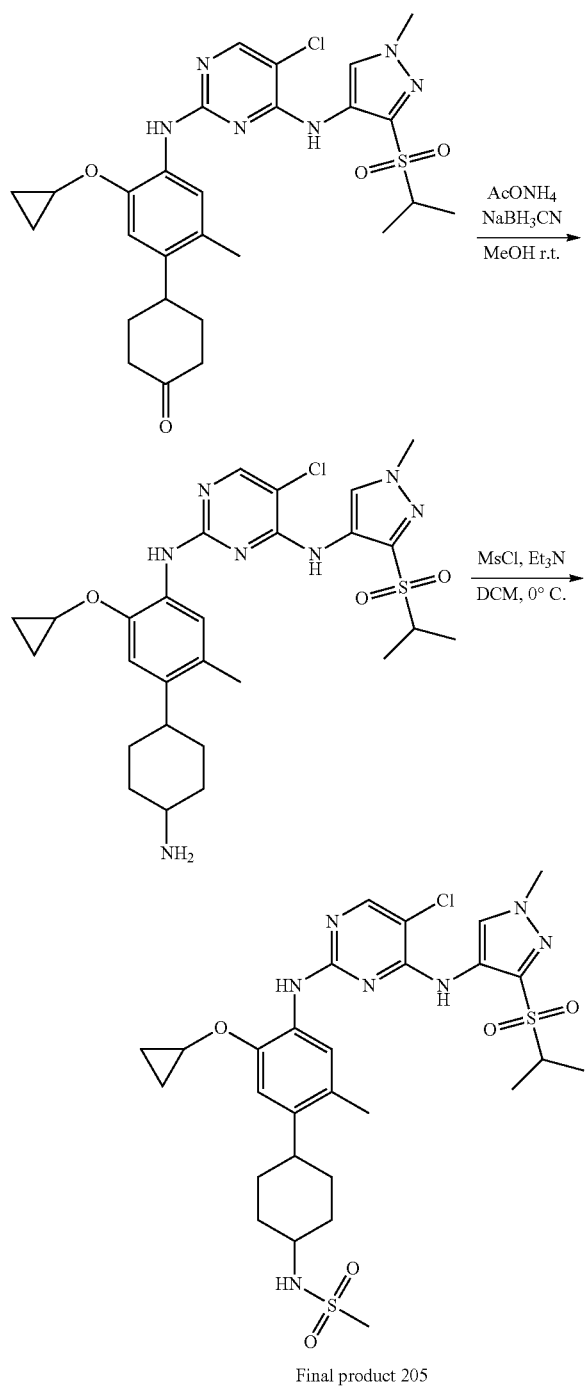

Final product 205

4-(4-(5-chloro-4-(3-(isopropylsulfonyl)-1-methyl-1H-pyrazol-4-amine) pyrimidin-2-amine)-5-cyclopropyloxy-2-methylphenyl) cyclohexanone (27 mg, 0.047 mmol), ammonium acetate (36 mg, 0.47 mmol) and methanol (2 mL) were added to a 5 ml reaction flask. The reaction mixture was stirred under the protection of nitrogen at room temperature for 30 minutes, and sodium cyanoborohydride (30 mg, 0.47 mmol) was added to the reaction system. The reaction mixture was stirred at room temperature for 24 hours, and added with saturated aqueous sodium bicarbonate to neutralize till the pH value was 8 to 9, extracted with ethyl acetate, dried and concentrated to obtain intermediate amine (white solid, 27 mg, 100%), which was used directly for the subsequent reaction. (MS: [M+1] 574.2)

The obtained intermediate (25 mg, 0.044 mmol) above, ethylamine (8.9 mg, 0.088 mmol), dichloromethane (1 mL), tetrahydrofuran (1 mL) were added to a 5 ml reaction flask. The reaction mixture was cooled down to 0° C. under the protection of nitrogen, and methanesulfonyl chloride (7.5 mg, 0.066 mmol) was added to the reaction system. After stirring at 0° C. for 1 hour, saturated aqueous sodium bicarbonate solution was added to neutralize till the pH was 8 to 9, the mixture solution was extracted with ethyl acetate, dried, concentrated and separated by thin layer chromatography (ethyl acetate/petroleum ether=2:1) to obtain the title compound (white solid, 22 mg, 77%). (($^1$H NMR (400 MHz CD3OD) ppm 0.61-0.65 (m 2H), 0.81-0.85 (m 2H), 1.34-1.37 (m 6H), 1.51-1.55 (m 2H), 1.67-1.71 (m 2H), 1.90-1.93 (m 2H), 2.17-2.21 (m 2H), 2.33 (s 3H), 2.70 (s 3H), 2.79-2.86 (m 1H), 2.71 (s 3H), 2.99 (s 3H), 3.30-3.36 (m 1H), 3.41-3.49 (m 1H), 3.87-3.89 (m 1H), 3.97 (s 3H), 7.20 (s 1H), 7.37 (s 1H), 7.46 (s 1H), 8.05 (s 1H)(mesylate); MS: [M+1] 652.1)

Examples 307, 308 Preparation of Final Products 206 and 207

The above method for synthesizing final product 205 was applied to prepare N-(4-(4-(5-chloro-4-(3-(isopropylsulfonyl)-1-methyl-1H-pyrazol-4-amine) pyrimidin-2-amine)-5-cyclopropoxy-2-methylphenyl) cyclohexyl) acetamide (trans final product 206, MS: [M+1] 616.1) and N-(4-(4-(5-chloro-4-(3-(isopropylsulfonyl)-1-methyl-1H-pyrazol-4-amine) pyrimidin-2-amine)-5-cyclopropoxy-2-methylphenyl) cyclohexyl) cyclopropyl carboxamide (trans final product 207, MS: [M+1] 642.3) by reacting the same substituted cyclohexylamine with acetyl chloride and cyclopropyl carbonyl chloride respectively.

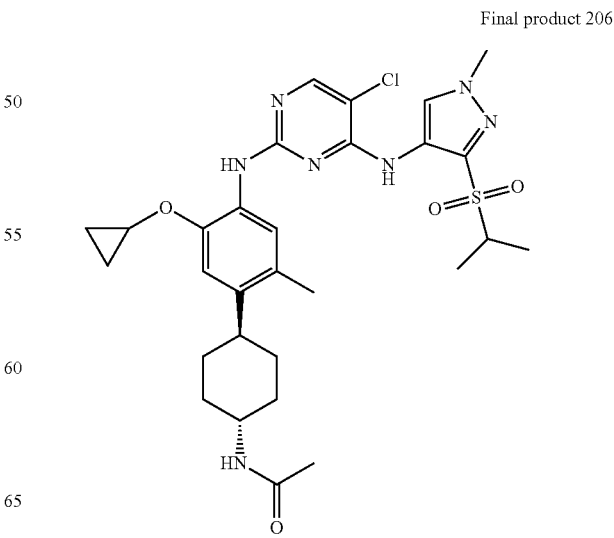

Final product 206

Final product 207

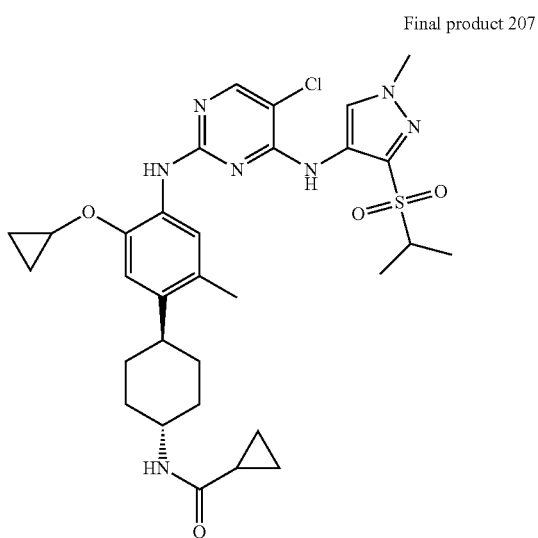

Example 309: 5-chloro-$N^2$-[4-(5-chloro-1-methyl-1,2,3,6-tetrahydro-pyridin-4-yl)-2-cyclopropoxy-5-methyl-phenyl]-$N^4$-[1-methyl-3-(isopropylsulfonyl)-1H-pyrazol-4-yl]-pyrimidin-2,4-diamine (Final Product 208)

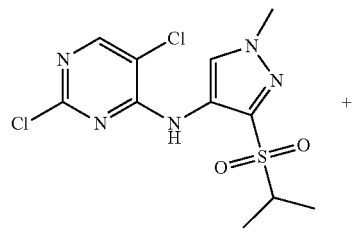

+

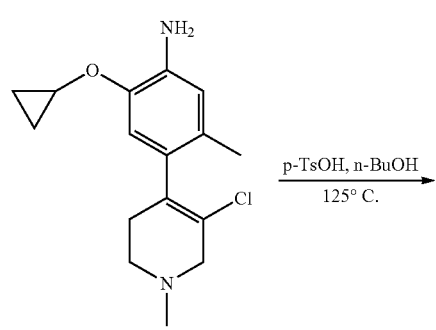

Final product 208

The title compound (yellow solid, 52.7 mg, 64%) was prepared by the above method for preparing final product 77. (MS: [M+1] 605.9)

Example 310: $N^2$-[2-cyclopropoxy-4-(1-methyl-piperidin-4-yl)-5-methylphenyl]-$N^4$-[1-methyl-3-(isopropylsulfonyl)-1H-pyrazol-4-yl]-5-(trifluoromethyl)pyrimidin-2,4-diamine (Final Product 209)

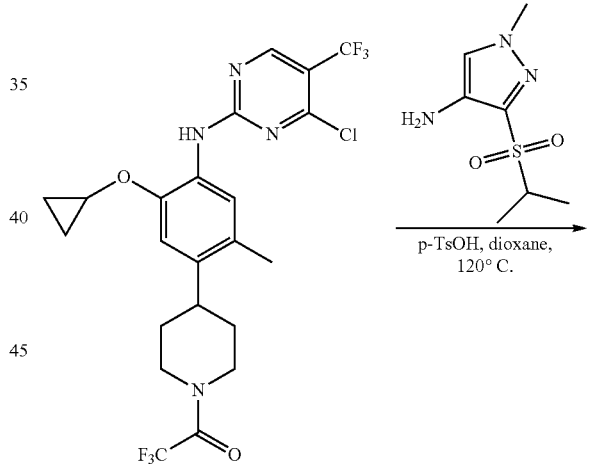

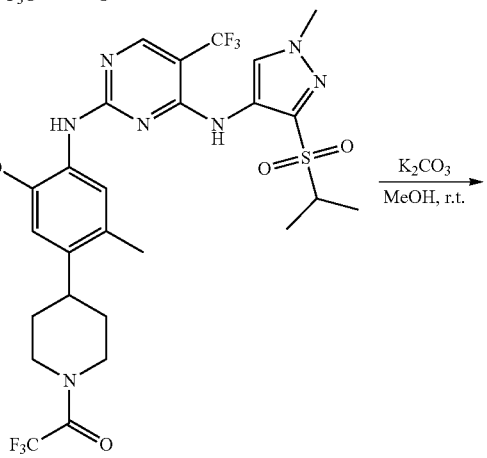

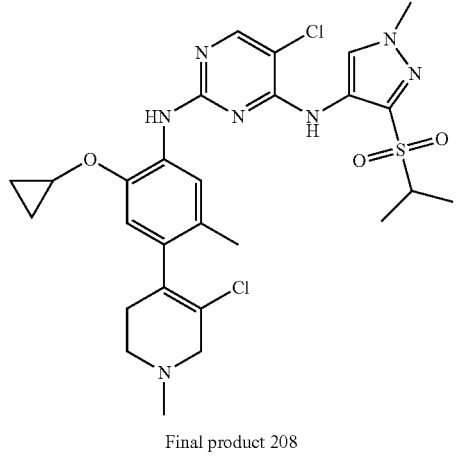

425

-continued

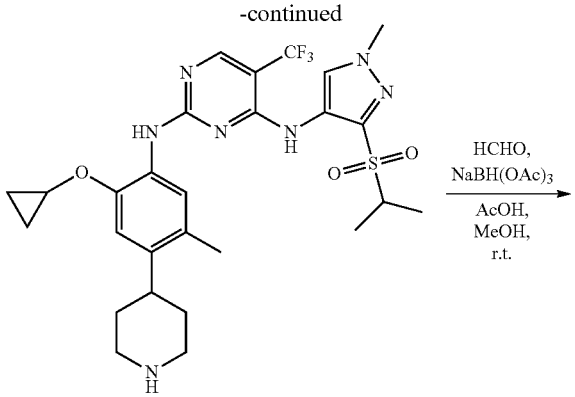

Step 1: $N^2$-[2-cyclopropoxy-4-N-trifluoroacetyl-piperidin-4-yl)phenyl]-$N^4$-(3-isopropylsulfonyl-1-methyl-1H-pyrazol-4-yl) 5-(trifluoromethyl)pyrimidin-2,4-diamine

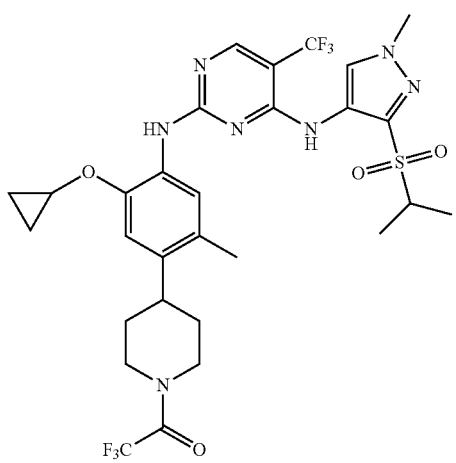

1-(4-(4-(4-chloro-5-(trifluoromethyl) pyrimidin-2-amino)-5-cyclopropoxy-2-methylphenyl)-1-yl)-N-2,2,2-trifluoroacetyl-piperidine (65 mg, 0.124 mmol), 3-(isopropylsulfonyl)-1-methyl-1H-pyrazol-4-amine (49 mg, 0.24 mmol), 1,4-dioxane (5 mL) and p-toluene sulfonic acid (21 mg, 0.12 mmol) were added to a 15 ml reaction flask. The reaction mixture was heated up to 120° C. by microwave and stirred for 18 hours. After completion of the reaction, the reaction solution was added with saturated aqueous sodium bicarbonate solution for alkalization and extracted with ethyl acetate. The organic phase was washed with saturated brine, dried and concentrated. The crude product was separated by column chromatography (silica gel column, eluent:ethyl acetate/petroleum ether=1:1) to obtain the title compound (65 mg, 76%). (MS: [M+1] 690.2)

Step 2: $N^2$-[2-cyclopropoxy-4-(piperidin-4-yl) phenyl]-$N^4$-(3-isopropylsulfonyl-1-methyl-1H-pyrazol-4-yl) 5-(trifluoromethyl)pyrimidin-2,4-diamine

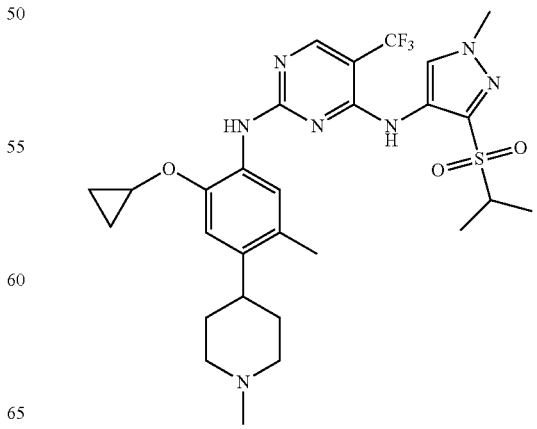

$N^2$-[2-cyclopropoxy-4-N-trifluoroacetyl-piperidin-4-yl)phenyl]-$N^4$-(3-isopropylsulfonyl-1-methyl-1H-pyrazol-4-yl) 5-(trifluoromethyl) pyrimidin-2,4-diamine (65 mg, 0.094 mmol), potassium carbonate (39 mg, 0.28 mmol) and methanol (5 mL) were added to a 15 ml reaction flask. The reaction mixture was stirred at room temperature for 1 hour. After completion of the reaction, ethyl acetate was added, and washed with saturated brine, dried and concentrated to obtain the title compound (56 mg), which was used directly for the subsequent reaction. (MS: [M+1] 594.2)

Step 3: $N^2$-[2-cyclopropoxy-4-(1-methyl-piperidin-4-yl)-5-methyl-phenyl]-$N^4$-[1-methyl-3-(isopropylsulfonyl)-1H-pyrazol-4-yl]-5-(trifluoromethyl)pyrimidin-2,4-diamine

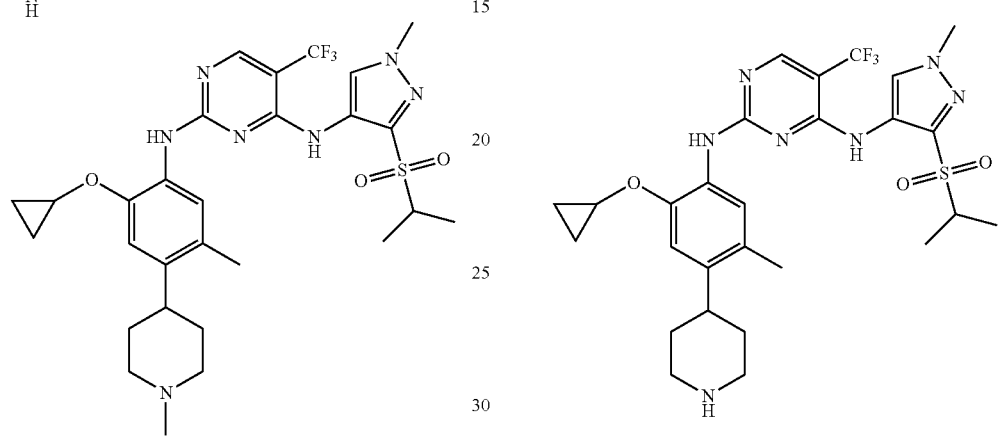

Final product 209

With reference to the method of synthesizing final product 30, the title compound was obtained (51 mg, 89%). (MS: [M+1] 608.3)

Example 311: N²-[2-cyclopropoxy-4-(1-methyl-piperidin-4-yl)-5-methyl-phenyl]-N⁴-[1-methyl-3-(isopropylsulfonyl)-1H-pyrazol-4-yl]-5-(cyano)py-rimidin-2,4-diamine (Final Product 210)

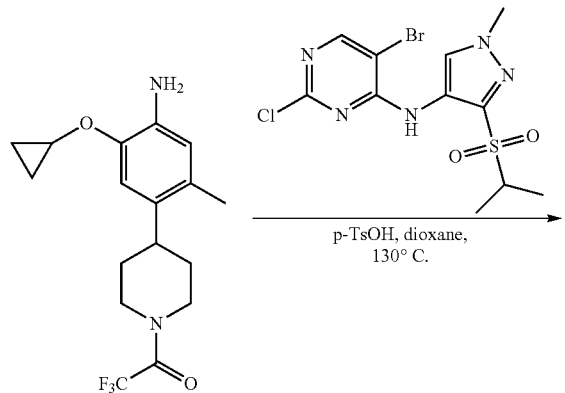

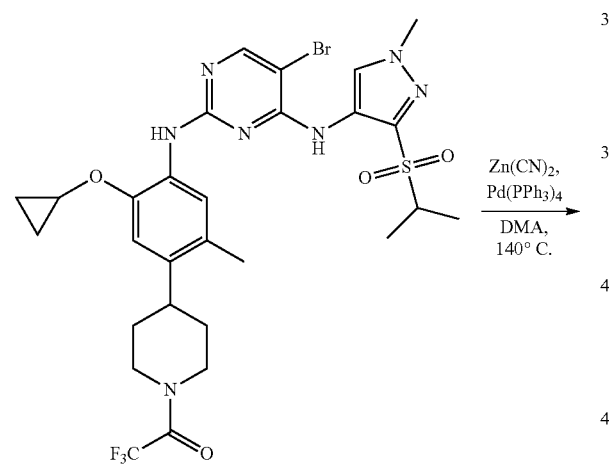

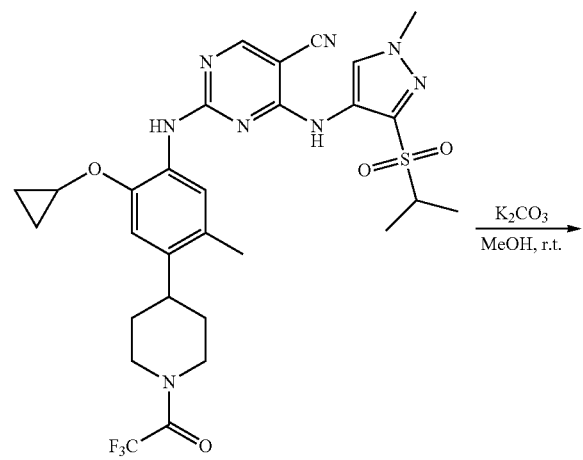

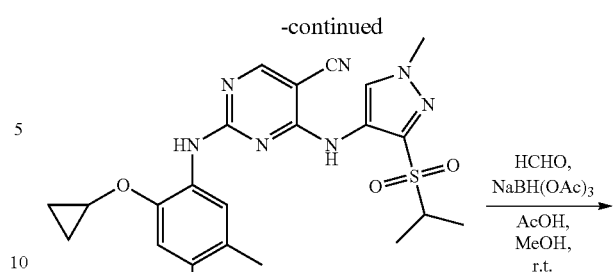

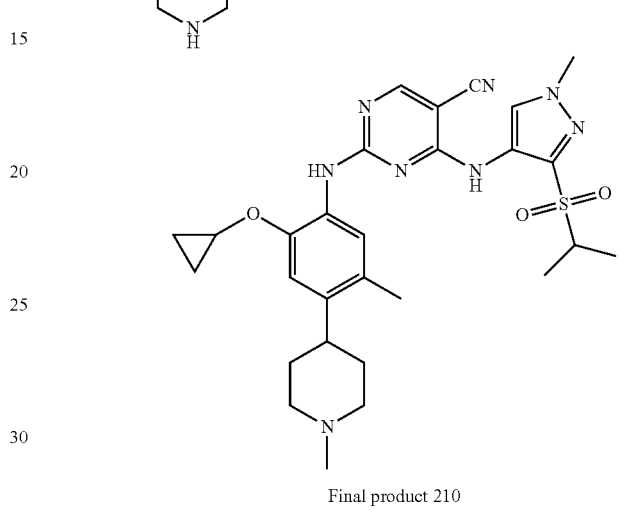

Final product 210

Step 1: N²-[2-cyclopropoxy-4-N-trifluoroacetyl-piperidin-4-yl)phenyl]-N⁴-(3-isopropylsulfonyl-1-methyl-1H-pyrazol-4-yl)5-bromo-pyrimidin-2,4-diamine

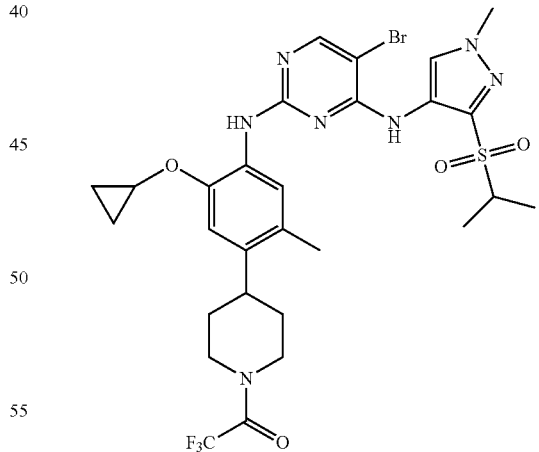

2-chloro-5-bromo-N-(3-(isopropylsulfonyl)-1-methyl-1H-pyrazol-4-yl) pyrimidin-4-amine (100 mg, 0.25 mmol), 1-(4-(4-(4-chloro-5-(trifluoromethyl) pyrimidin-2-amino)-5-cyclopropoxy-2-methyl-phenyl)-1-yl)-N-2,2,2-trifluoro-acetyl-piperidine (79 mg, 0.23 mmol), p-toluenesulfonic acid (36 mg, 0.21 mmol) and 1,4-dioxane (3 mL) were added to a 25 ml reaction flask. The reaction mixture was heated up to 130° C. under the protection of nitrogen and stirred for 3 hours. After completion of the reaction, the reaction solution was added with ethyl acetate, and the organic phase was washed with sodium carbonate solution and saturated brine, dried and concentrated. The thus obtained crude product was separated and purified by column chromatography (silica gel column, eluent:dichloromethane/methanol, gradient: 0-5% methanol) to obtain the title compound (121 mg, 75%). (MS: [M+1] 700.1)

Step 2: N²-[2-cyclopropoxy-4-N-trifluoroacetyl-piperidin-4-yl)phenyl]-N⁴-(3-isopropylsulfonyl-1-methyl-1H-pyrazol-4-yl)5-cyano-pyrimidin-2,4-diamine

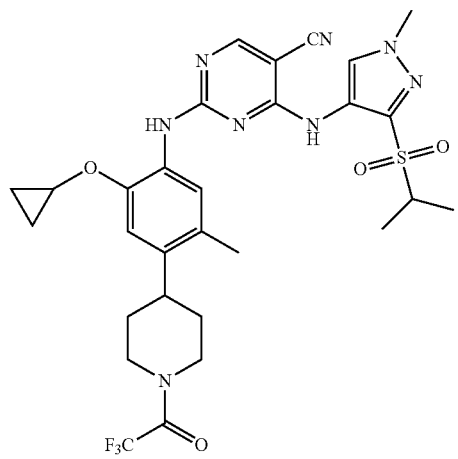

N²-[2-cyclopropoxy-4-N-trifluoroacetyl-piperidin-4-yl)phenyl]-N⁴-(3-isopropylsulfonyl-1-methyl-1H-pyrazol-4-yl)-5-bromo-pyrimidin-2,4-diamine (121 mg, 0.17 mmol), zinc cyanide (120 mg, 1.02 mmol), tetrakis(triphenylphosphine)palladium (20 mg, 0.017 mmol) and N,N-dimethylacetamide (2 mL) were added to a 5 ml microwave tube. The reaction mixture was heated up to 140° C. by microwave under the protection of nitrogen and stirred for 3 hours. After completion of the reaction, the reaction solution was added with ethyl acetate, and the organic phase was washed with sodium carbonate solution and saturated brine, dried and concentrated. The thus obtained crude product was separated and purified by column chromatography (silica gel column, eluent:dichloromethane/methanol, gradient: 0 to 10% methanol) to obtain the title compound (80 mg, 73%). (MS: [M+1] 647.2)

Step 3: N²-[2-cyclopropoxy-4-piperidin-4-yl)phenyl]-N⁴-(3-isopropylsulfonyl-1-methyl-1H-pyrazol-4-yl)-5-cyano-pyrimidin-2,4-diamine

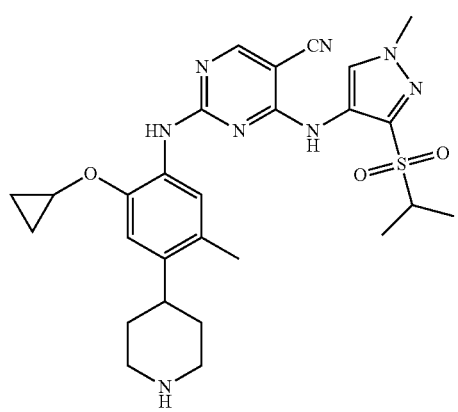

With reference to the second step of synthesizing final product 209, the title compound was obtained (yellow oil, 65 mg, 98%) and the thus obtained crude product was used directly for the subsequent reaction. (MS: [M+1] 551.3)

Step 4: N²-[2-cyclopropoxy-4-(1-methyl-piperidin-4-yl)-5-methyl-phenyl]-N⁴-[1-methyl-3-(isopropylsulfonyl)-1H-pyrazol-4-yl]-5-cyano-pyrimidin-2,4-diamine

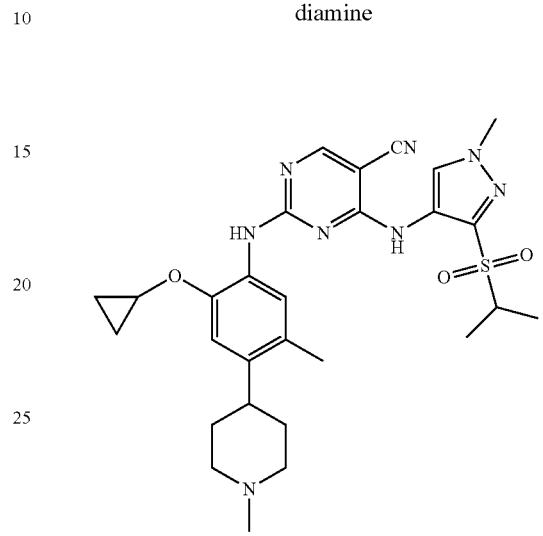

With reference to the method of synthesizing final product 30, the title compound was obtained (21 mg, 31%). (MS: [M+1] 565.4)

Example 312: 5-chloro-N²-[2-cyclopropoxy-4-(1-methyl-piperidin-4-yl)-5-methyl-phenyl]-N⁴-[1-methyl-3-cyano-1H-pyrazol-4-yl]-pyrimidin-2,4-diamine (Final Product 211)

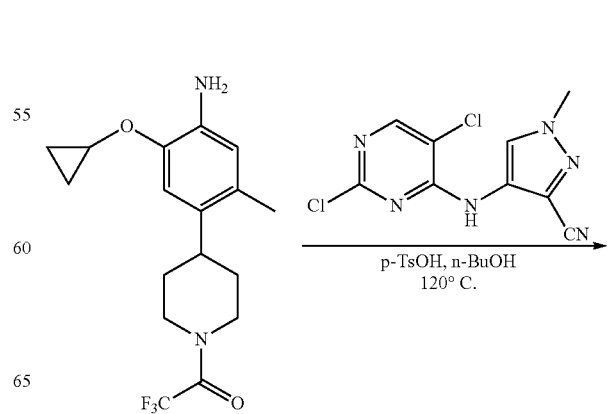

-continued

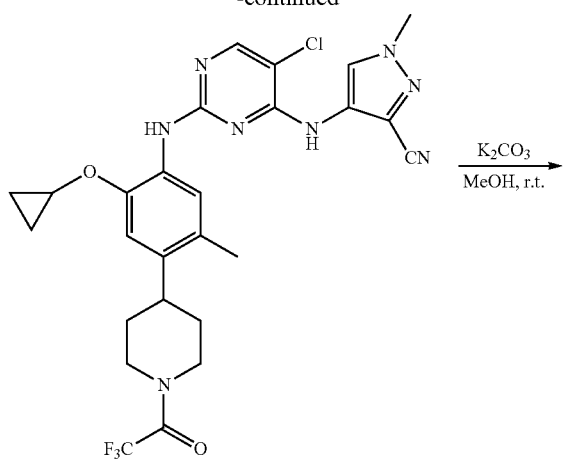

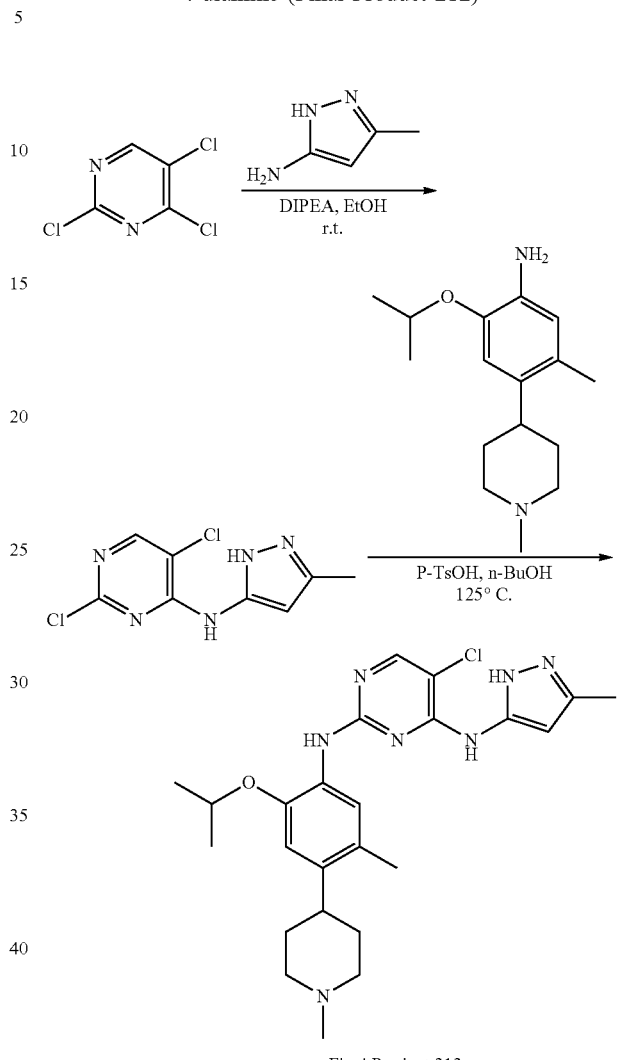

Example 313: Known Compound 5-chloro-$N^2$-[2-cyclopropoxy-4-(1-methyl-piperidin-4-yl)-5-methyl-phenyl]-$N^4$-[5-methyl-1H-pyrazol-3-yl]-pyrimidin-2,4-diamine (Final Product 212)

Final Product 212

Step 1: 2,5-dichloro-N-(3-methyl-1H-pyrazol-5-yl)pyrimidin-4-amine

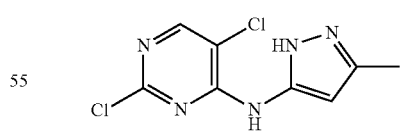

With reference to the method of synthesizing final product 210, the final product 211 was obtained (30 mg). (MS: [M+1] 493.2)

3-methyl-5-aminopyrazole (1.94 g, 20 mmol), ethanol (40 mL) and triethylamine (5.15 g, 51 mmol) were added to a 100 ml reaction flask at room temperature, and then 2,4,5-trichloro-pyrimidine (3.1 g, 17 mmol) was added. The reaction mixture was stirred at room temperature for 18 hours. After completion of the reaction, the reaction solution was filtered, and the filter cake was washed with ethanol and dried to obtain the title compound (3.3 g, 80%). (MS: [M+1] 244.1)

Step 2: 5-chloro-N²-[2-isopropoxy-4-(1-methyl-piperidin-4-yl)-5-methyl-phenyl]-N⁴-[5-methyl-1H-pyrazol-3-yl]-pyrimidin-2,4-diamine

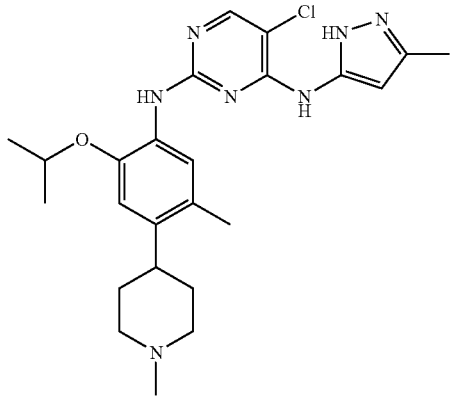

2,5-dichloro-N-(3-methyl-1H-pyrazol-5-yl) pyrimidin-4-amine (139 mg, 0.57 mmol), 2-isopropoxy-5-methyl-4-(1-methyl-piperidin-4-yl) aniline (150 mg, 0.57 mmol), n-butyl alcohol (3 mL) and p-toluenesulfonic acid (97 mg, 0.57 mmol) were added to a 10 ml microwave tube. The reaction mixture was heated up to 125° C. by microwave and stirred for 1 hour. After completion of the reaction, saturated aqueous sodium bicarbonate solution was added for neutralization, ethyl acetate was added for extraction, and the organic phase was washed with saturated brine, dried and concentrated. The thus obtained crude product was separated by preparative HPLC to obtain the title compound (42 mg, 16%). (MS: [M+1] 470.2)

Examples 314-319 Preparation of Final Products 213-217

The known compounds in the present application (final products 213-217) were synthesized by applying the method similar to the examples 46, 2, 6, 39, 11 in CN102112467A (table 16).

The known compound in the present application (final product 218) was synthesized by applying the method similar to example 11 in CN102203083A (table 16).

TABLE 16

Final products 213-218

| Final Product Nos. | Structural Formulas of Final Products | Molecular Ion Peaks $[M + 1]^+$ |
| --- | --- | --- |
| Final product 213 | | 454.3 |
| Final product 214 | | 412.3 |
| Final product 215 | | 456.3 |
| Final product 216 | | 499.3 |

TABLE 16-continued

Final products 213-218

| Final Product Nos. | Structural Formulas of Final Products | Molecular Ion Peaks [M + 1]+ |
|---|---|---|
| Final product 217 | (structure) | 490.3 |
| Final product 218 | (structure) | 513.3 |

TABLE 17

Compounds as ALK kinase inhibitors (final products)

1. (structure)

TABLE 17-continued

Compounds as ALK kinase inhibitors (final products)

2. (structure)
3. (structure)
4. (structure)
5. (structure)

TABLE 17-continued
Compounds as ALK kinase inhibitors (final products)
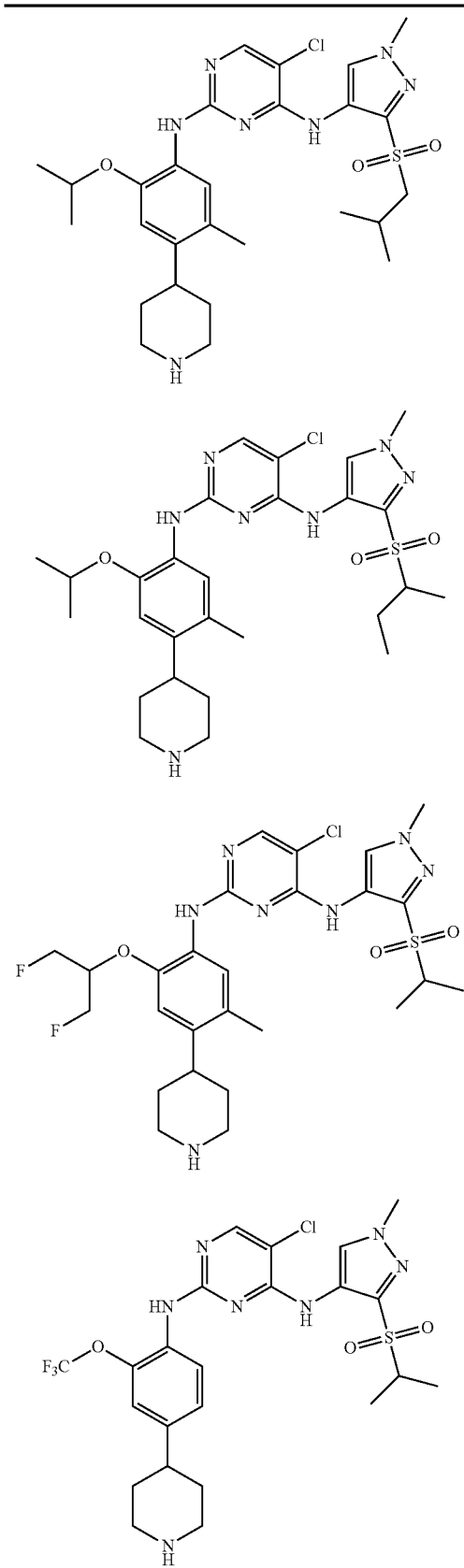
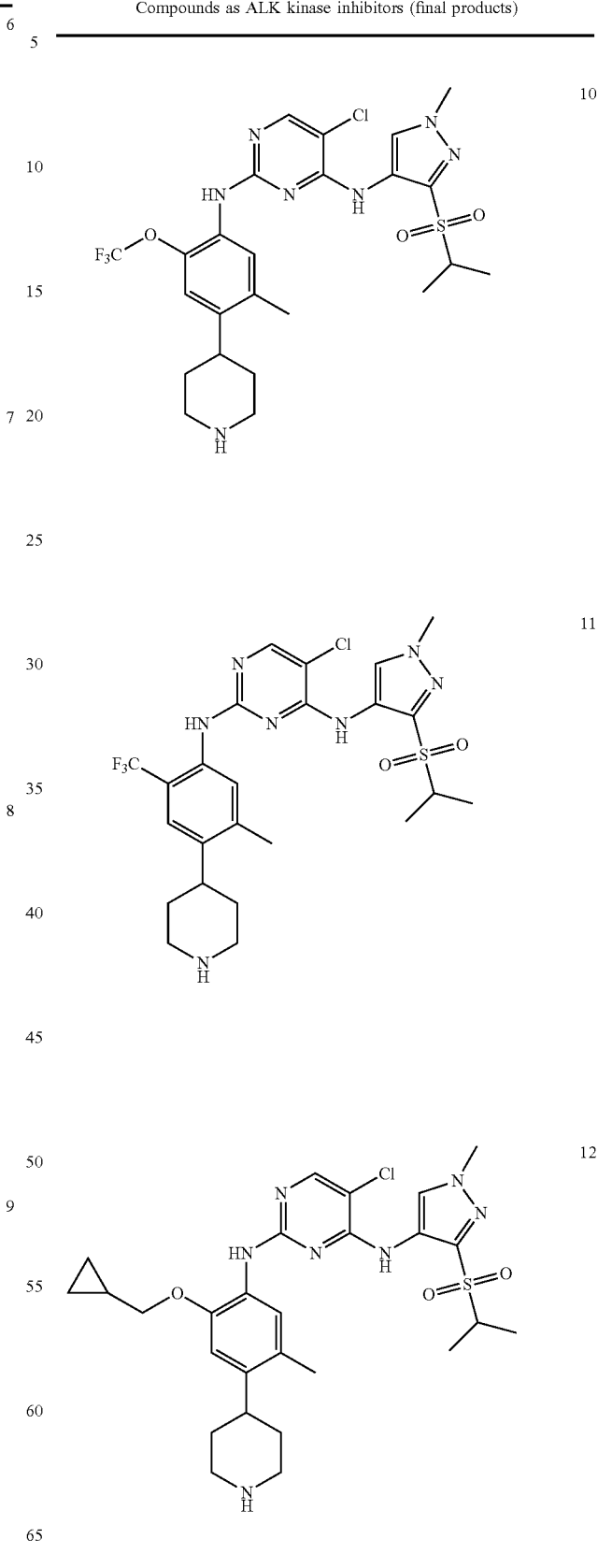

TABLE 17-continued
Compounds as ALK kinase inhibitors (final products)
13
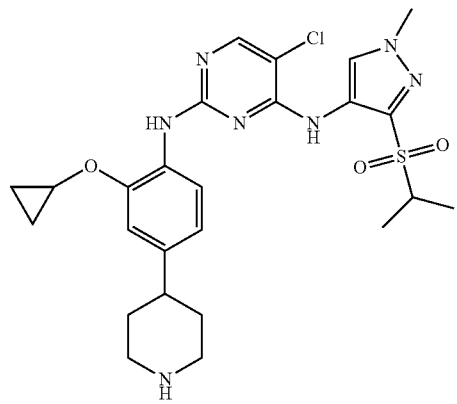
14
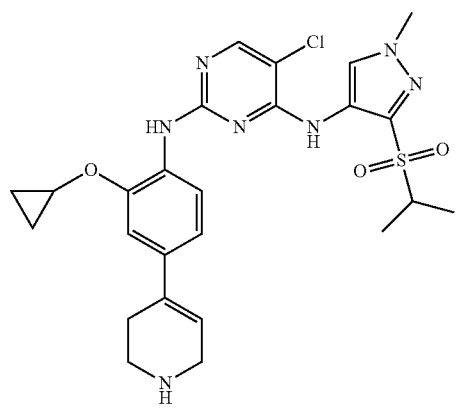
15
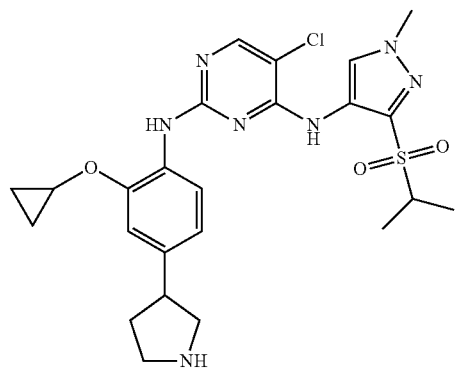
TABLE 17-continued
Compounds as ALK kinase inhibitors (final products)
16
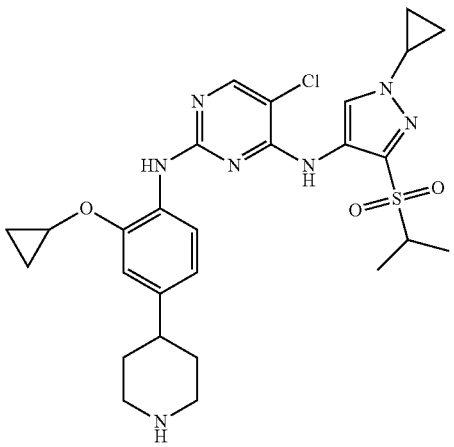
17
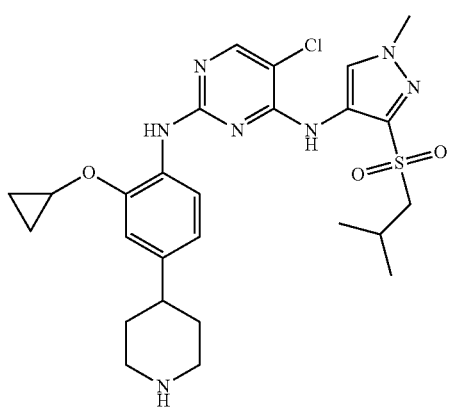
18
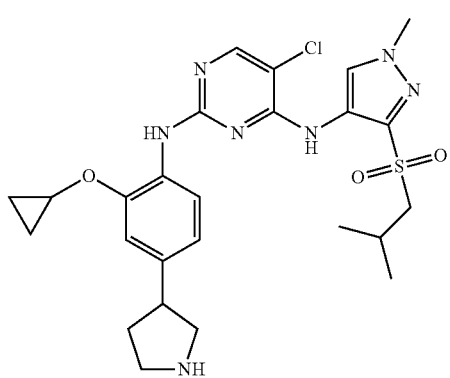

TABLE 17-continued
Compounds as ALK kinase inhibitors (final products)
19
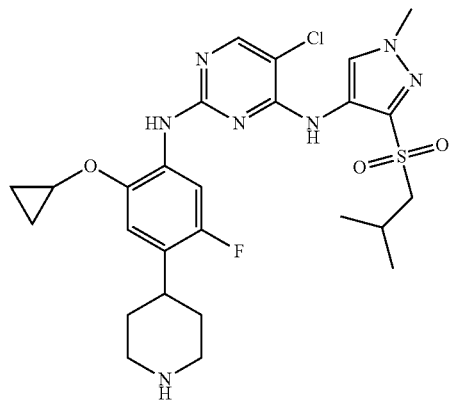
20
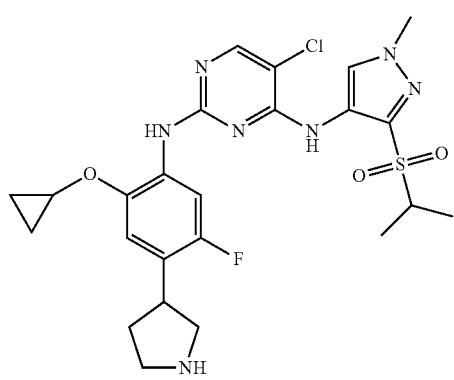
21
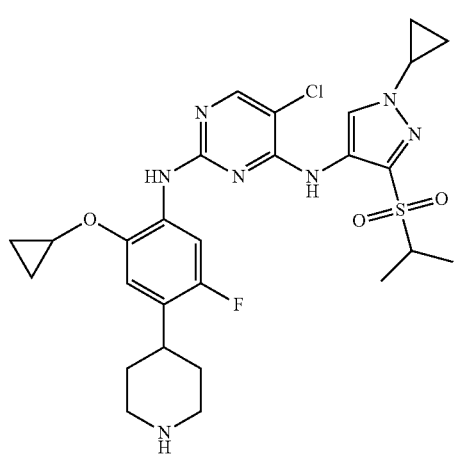
TABLE 17-continued
Compounds as ALK kinase inhibitors (final products)
22
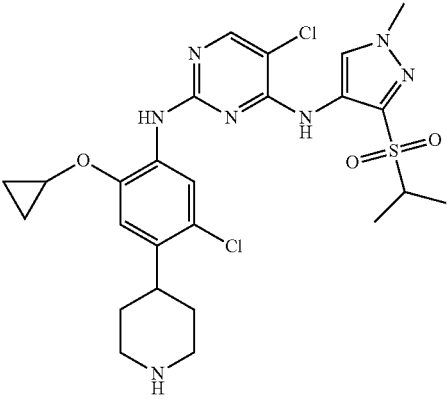
23
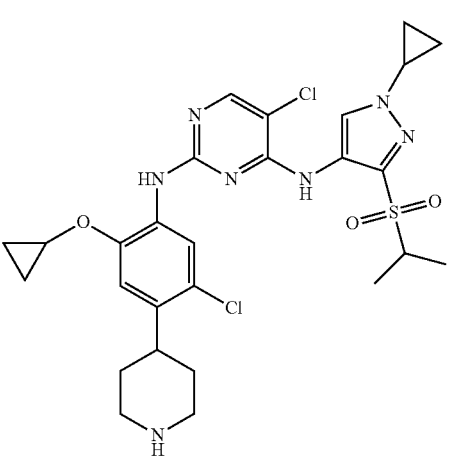
24
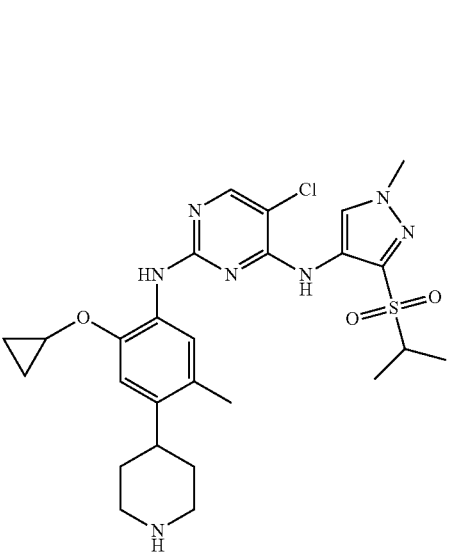

TABLE 17-continued
Compounds as ALK kinase inhibitors (final products)
25
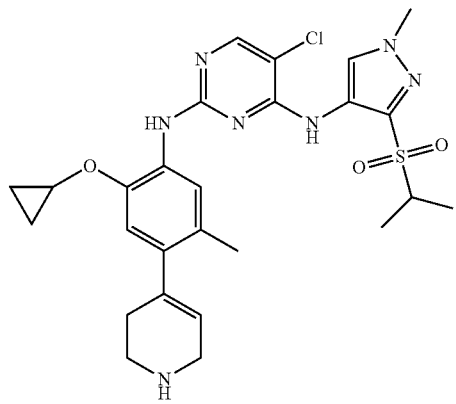
26
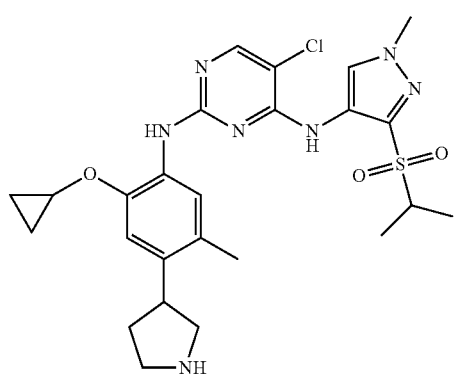
27
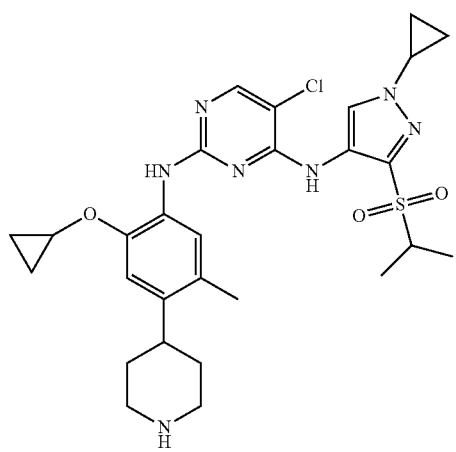
TABLE 17-continued
Compounds as ALK kinase inhibitors (final products)
28
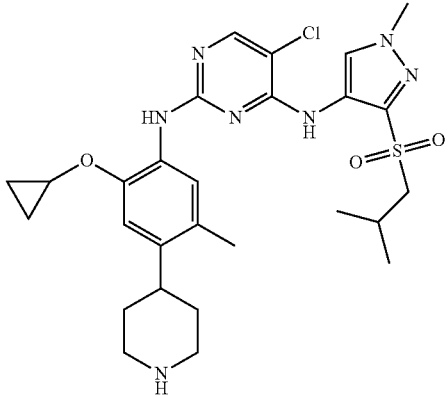
29
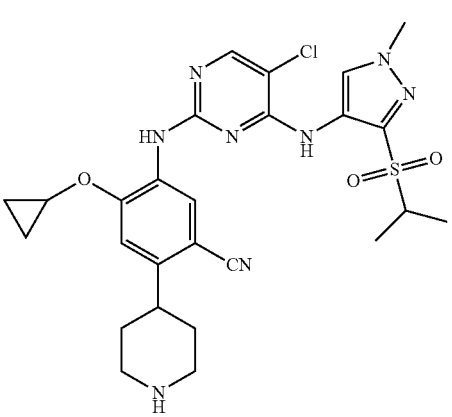
30
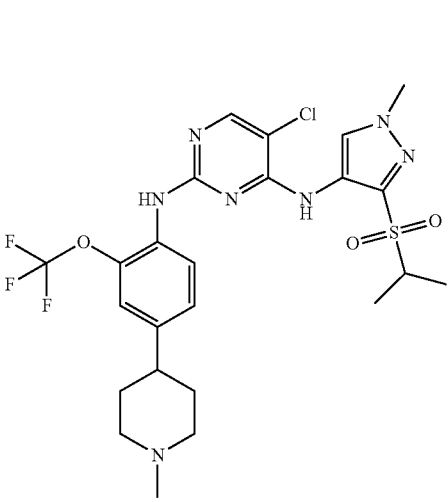

TABLE 17-continued
Compounds as ALK kinase inhibitors (final products)
31
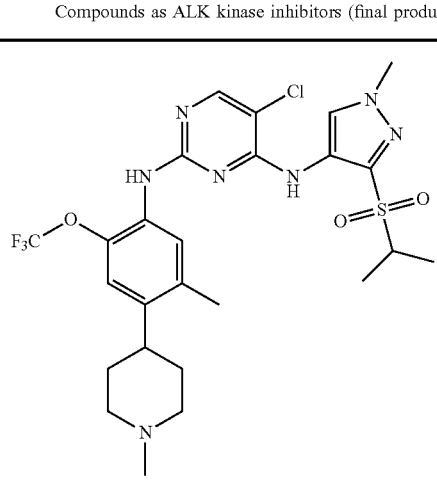
32
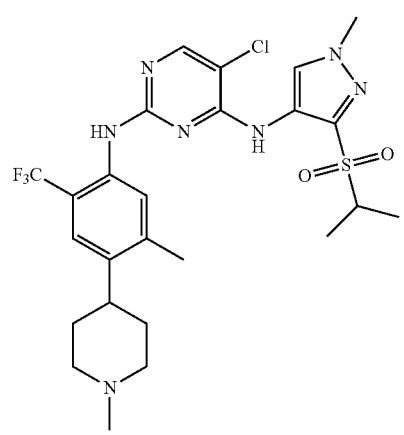
33
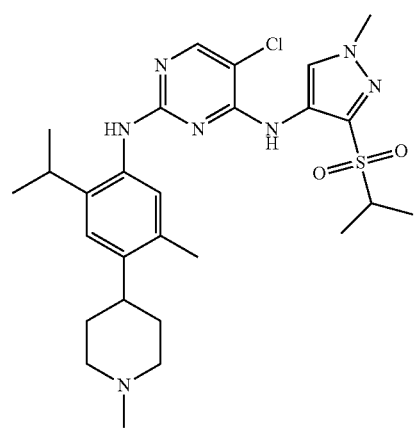
TABLE 17-continued
Compounds as ALK kinase inhibitors (final products)
34
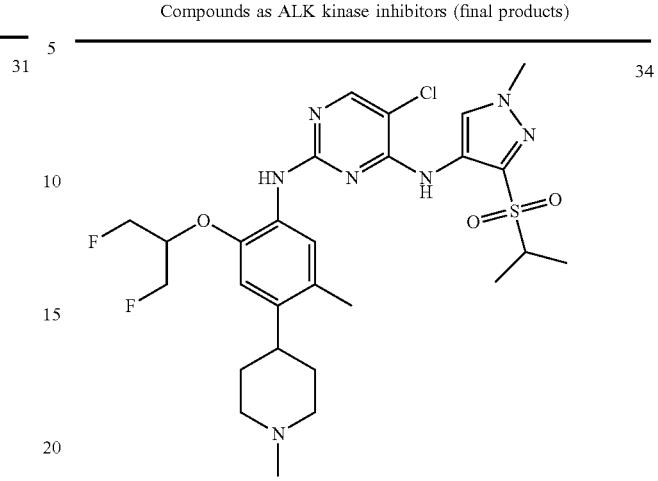
35
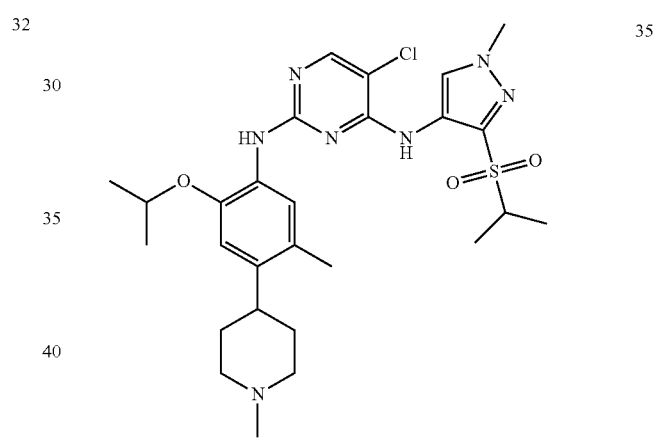
36
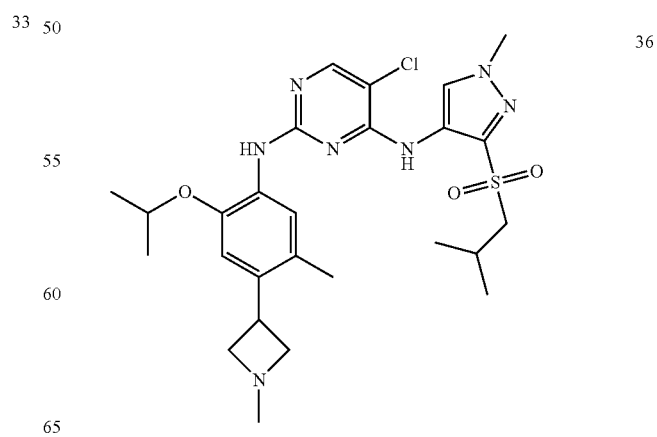

TABLE 17-continued
Compounds as ALK kinase inhibitors (final products)
37
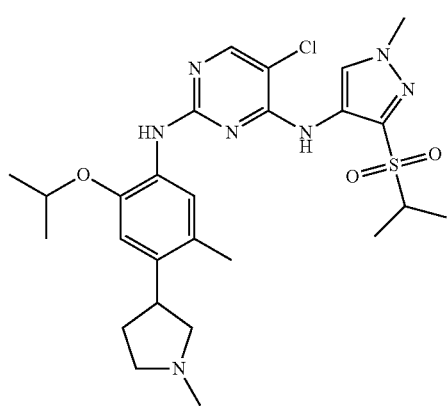
38
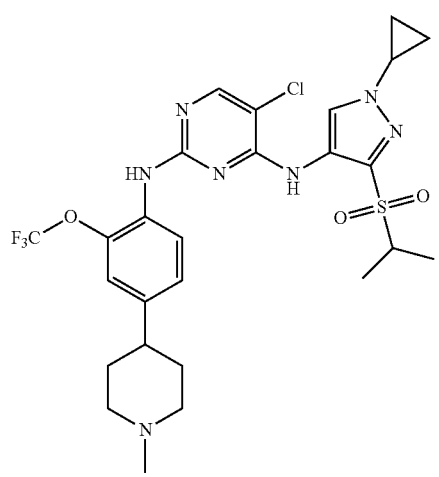
39
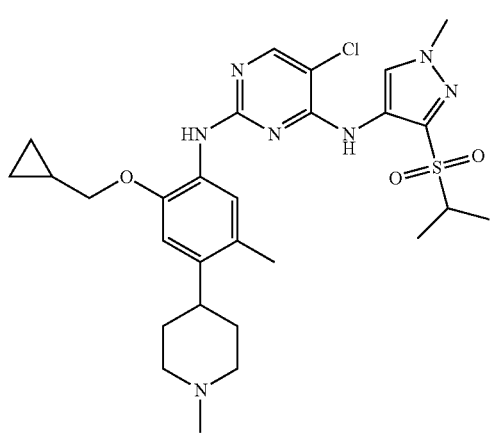
TABLE 17-continued
Compounds as ALK kinase inhibitors (final products)
40
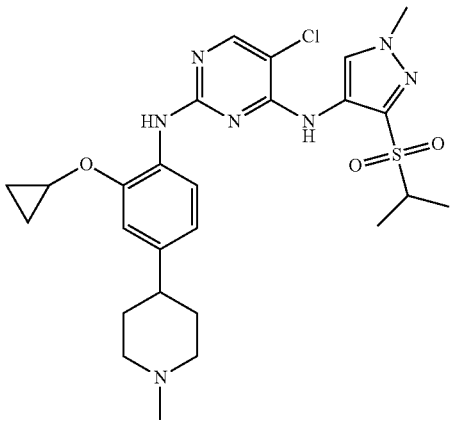
41
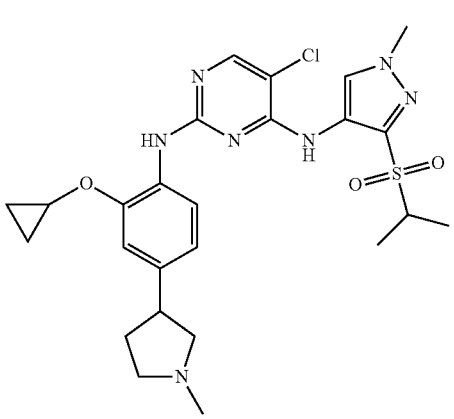
42
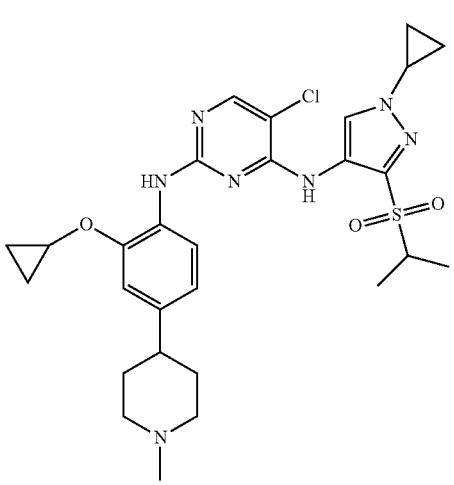

TABLE 17-continued
Compounds as ALK kinase inhibitors (final products)
| | |
|---|---|
| 43 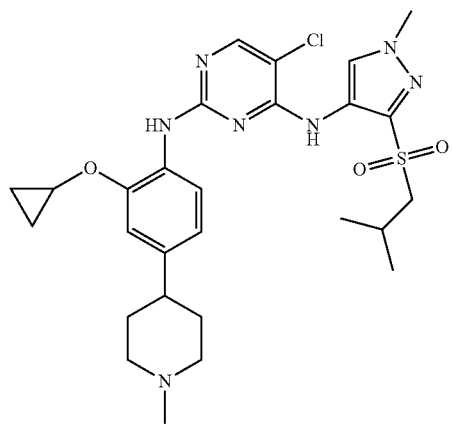 | 46 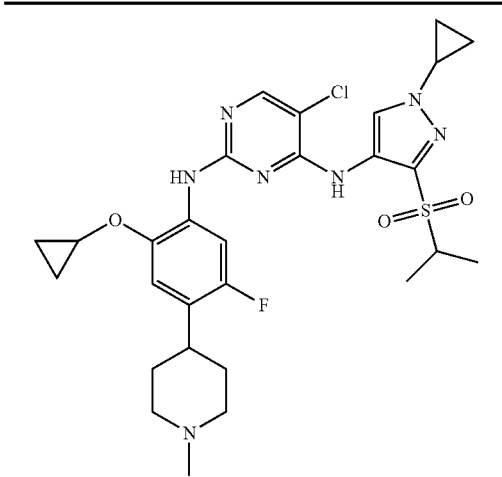 |
| 44 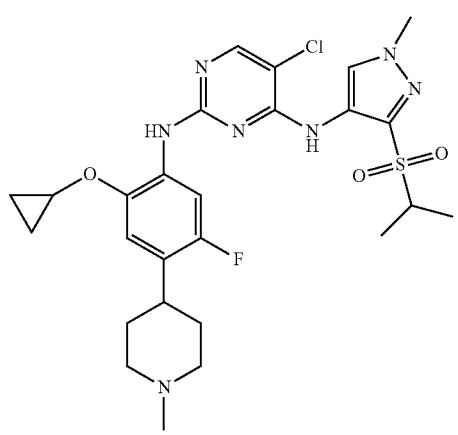 | 47 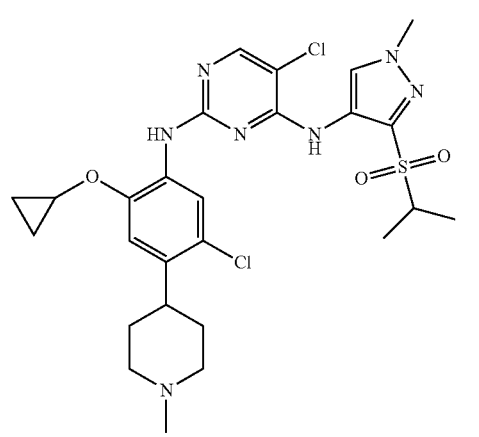 |
| 45 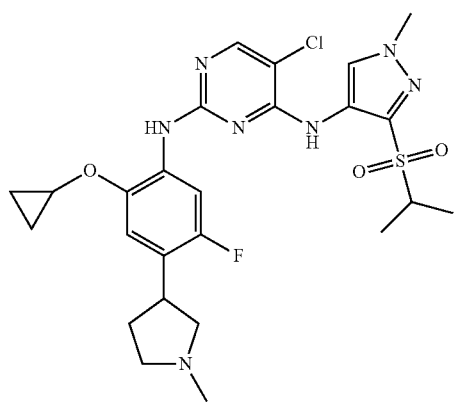 | 48 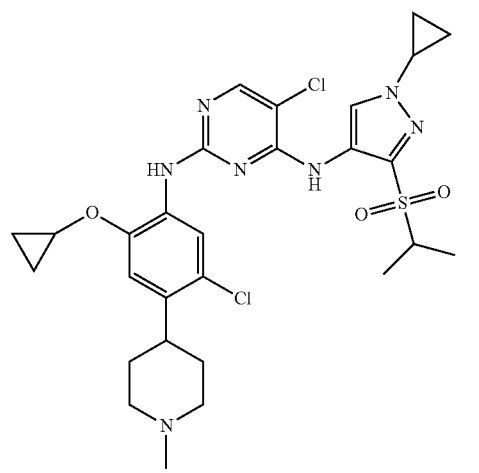 |

TABLE 17-continued
Compounds as ALK kinase inhibitors (final products)
49
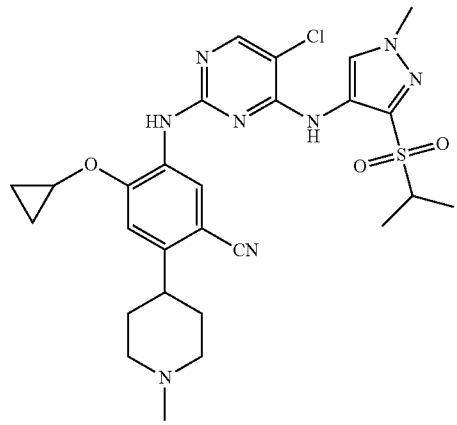
50
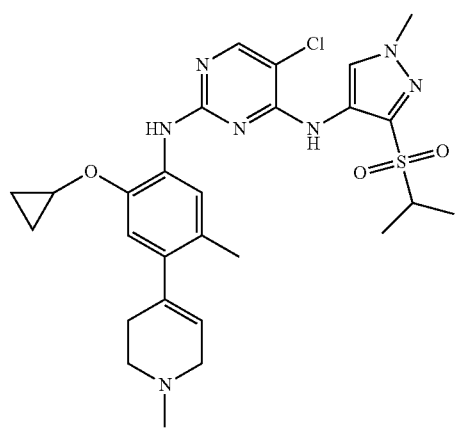
51
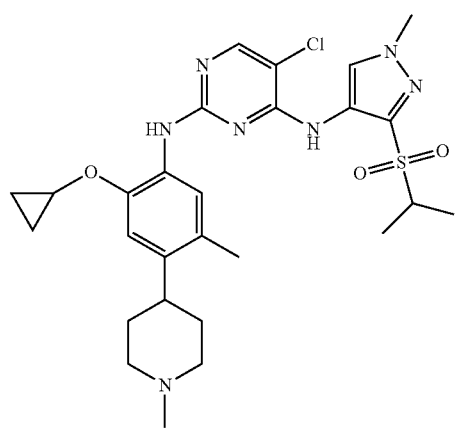
TABLE 17-continued
Compounds as ALK kinase inhibitors (final products)
52
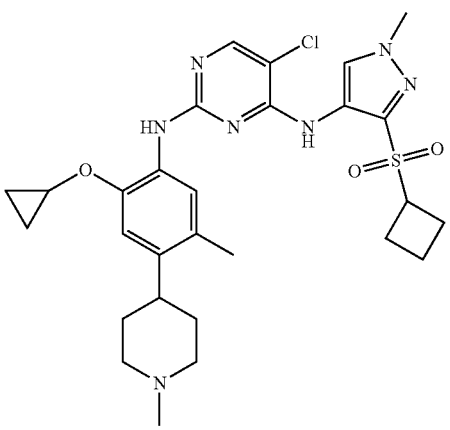
53
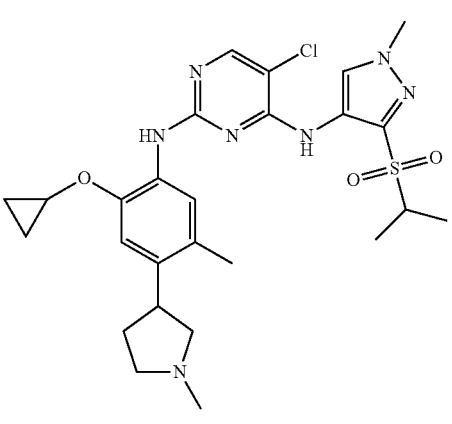
54
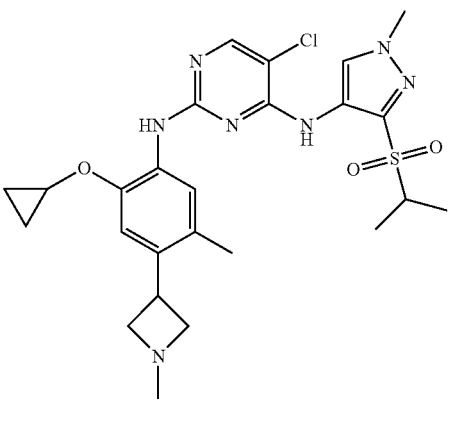

TABLE 17-continued
Compounds as ALK kinase inhibitors (final products)
55
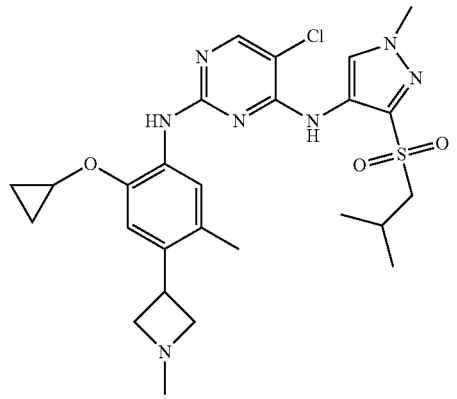
56
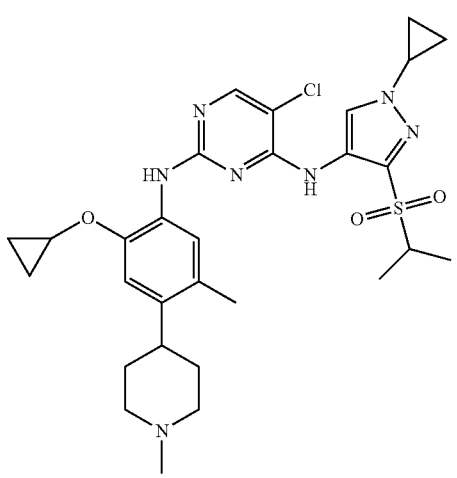
57
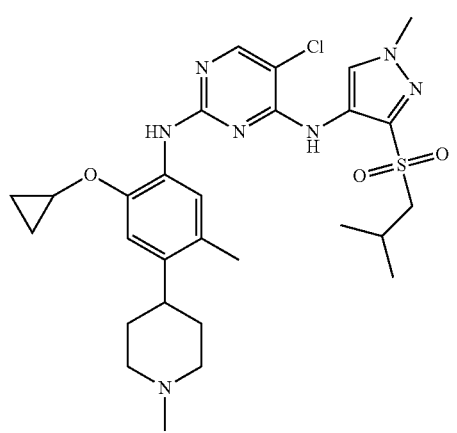
TABLE 17-continued
Compounds as ALK kinase inhibitors (final products)
58
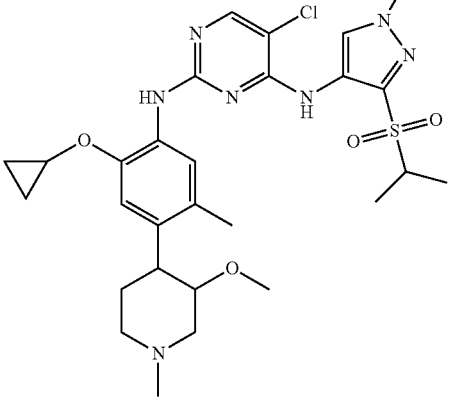
59
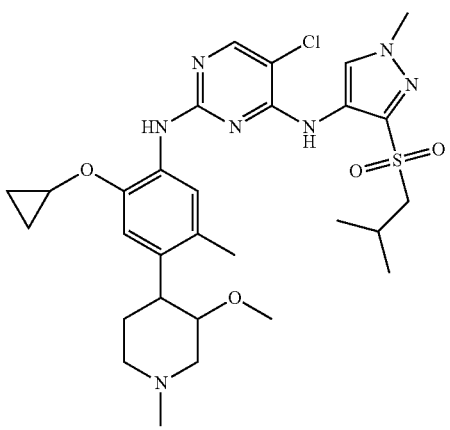
60
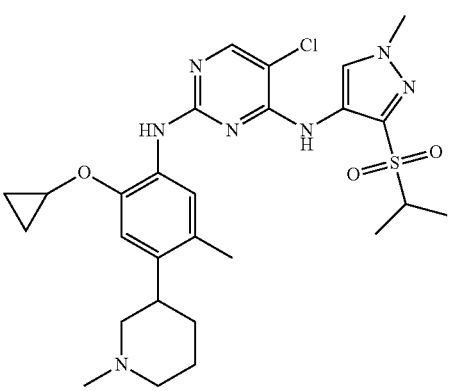
61
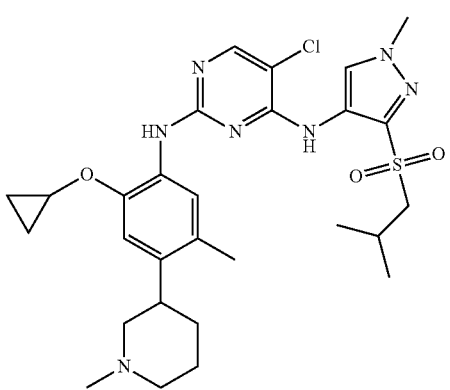

TABLE 17-continued
Compounds as ALK kinase inhibitors (final products)
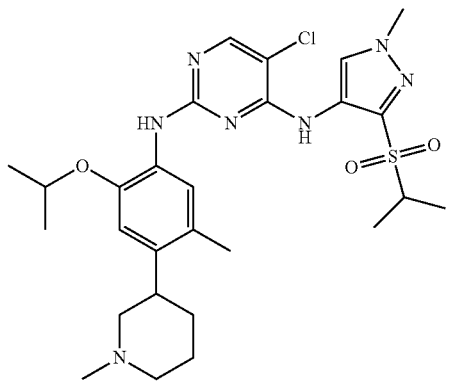
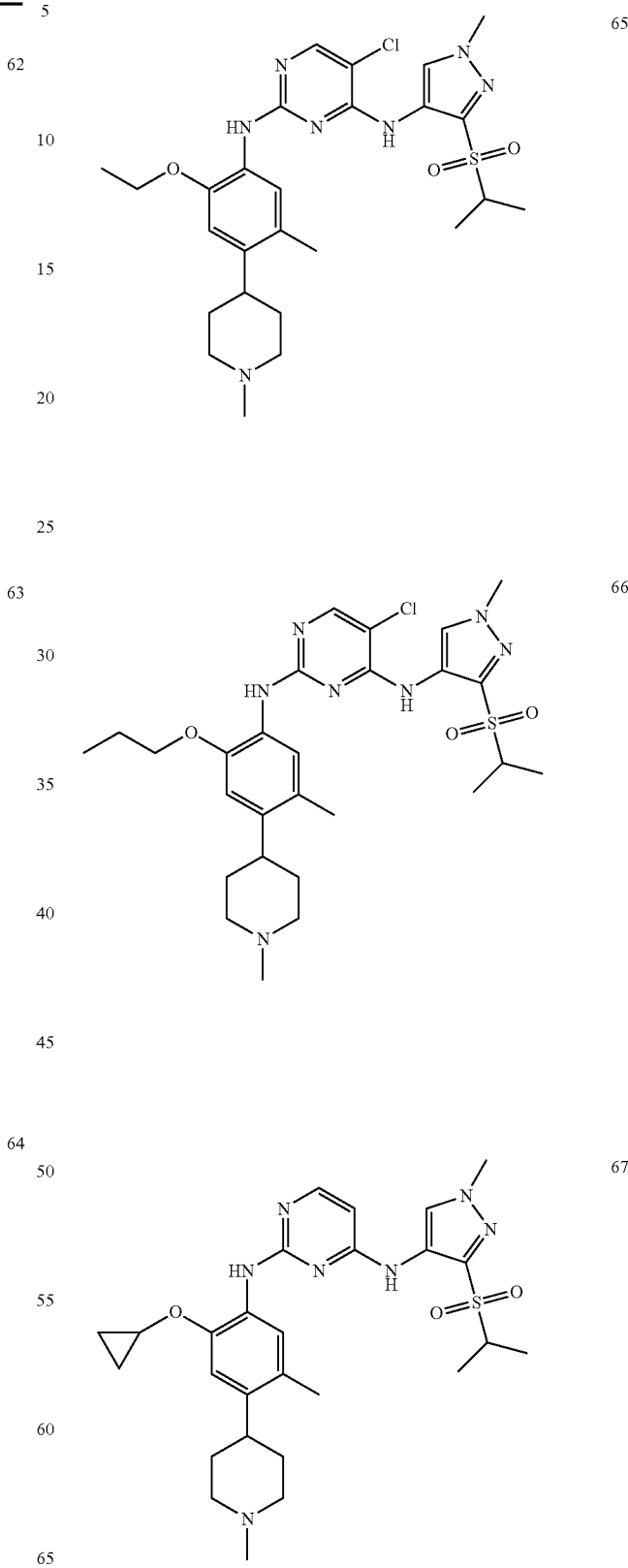

TABLE 17-continued
Compounds as ALK kinase inhibitors (final products)
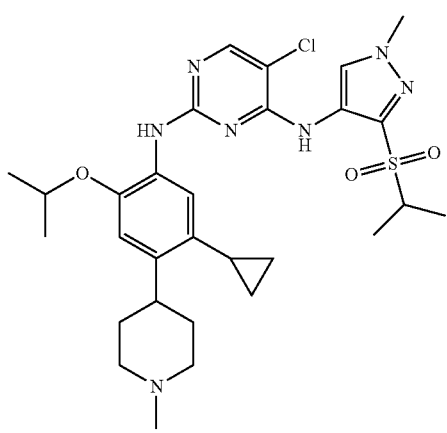
68
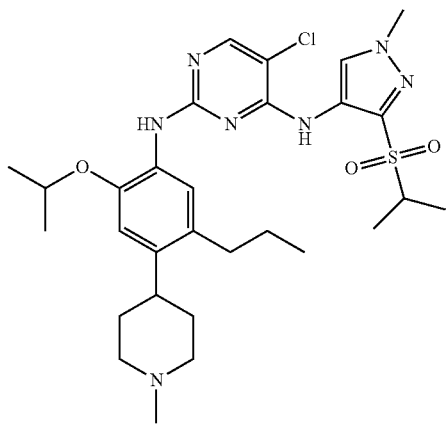
69
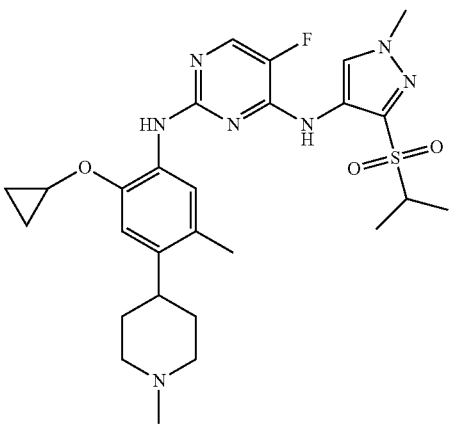
70
TABLE 17-continued
Compounds as ALK kinase inhibitors (final products)
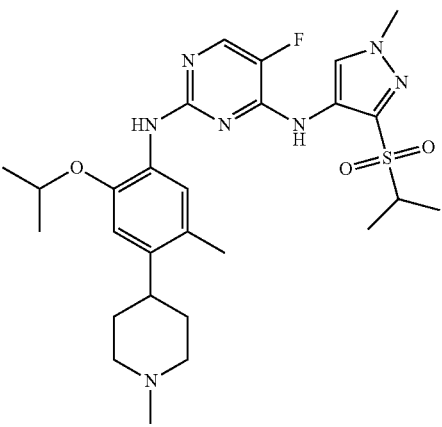
71
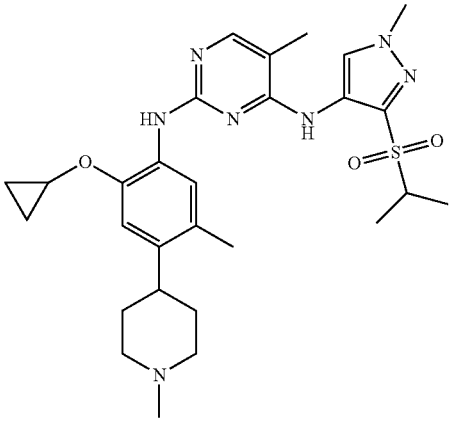
72
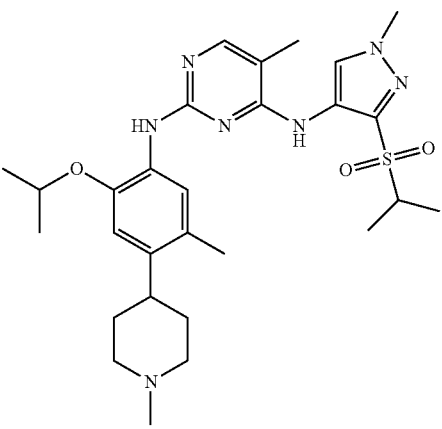
73

TABLE 17-continued
Compounds as ALK kinase inhibitors (final products)
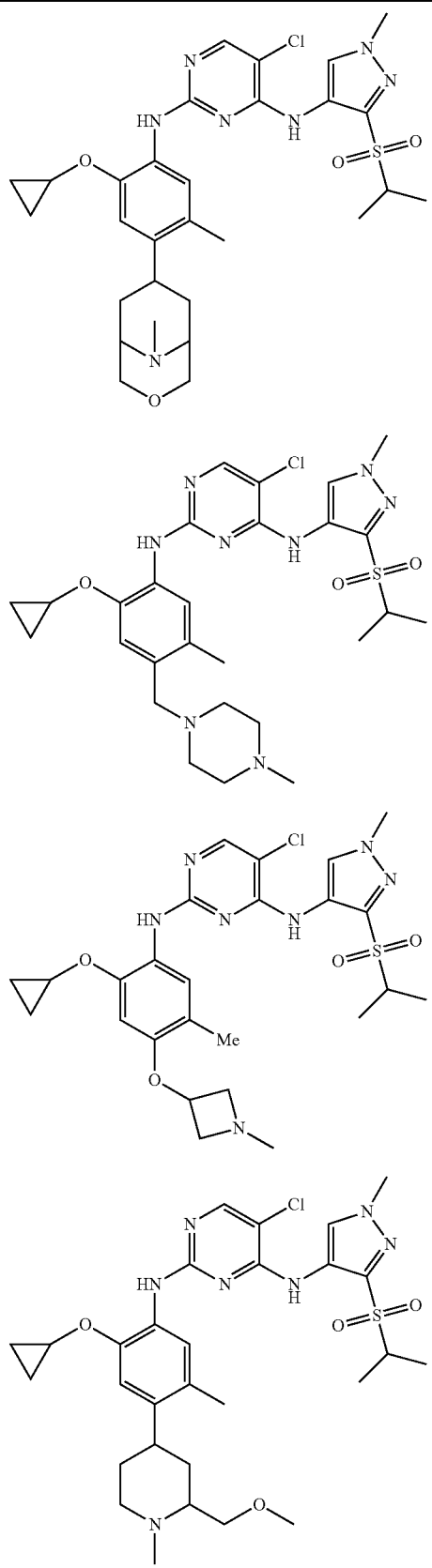
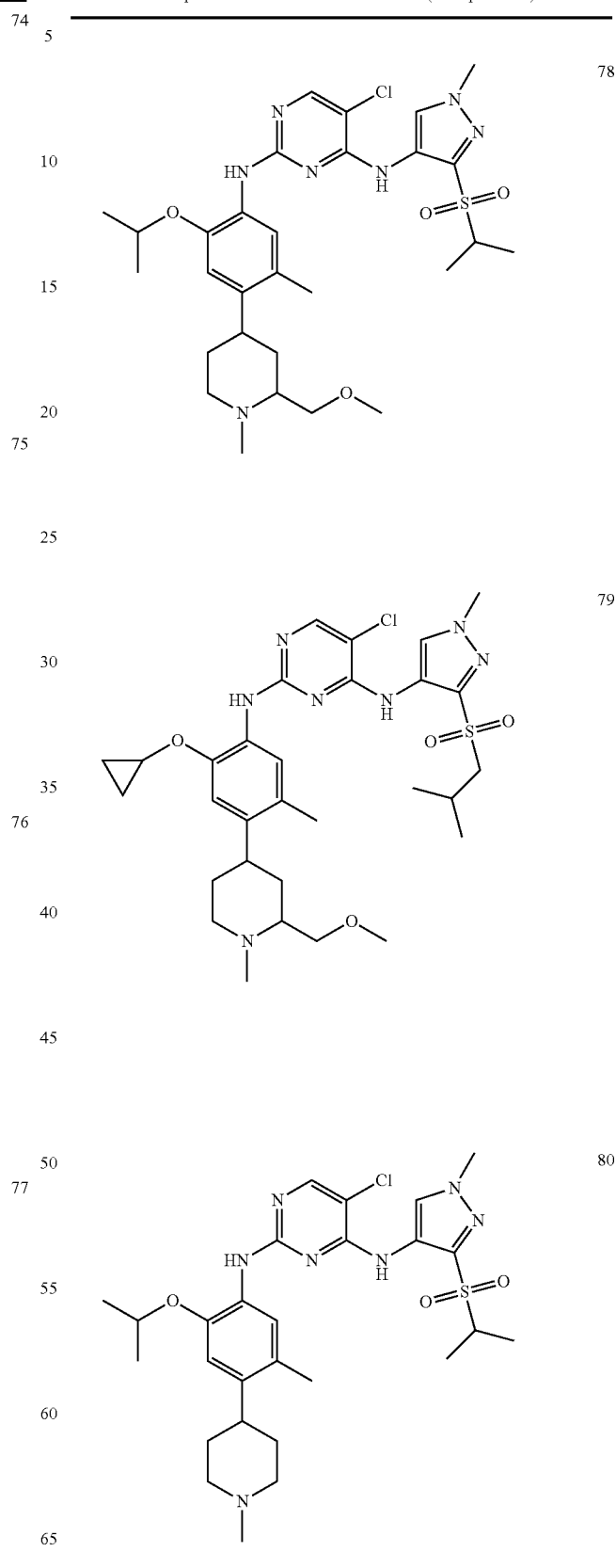

TABLE 17-continued
Compounds as ALK kinase inhibitors (final products)
81
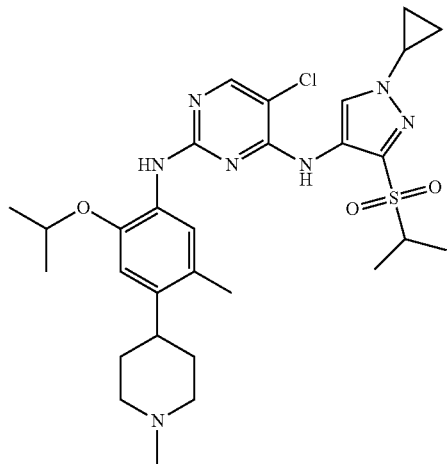
82
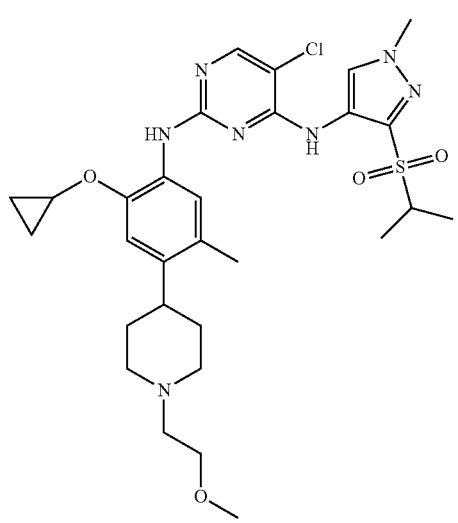
83
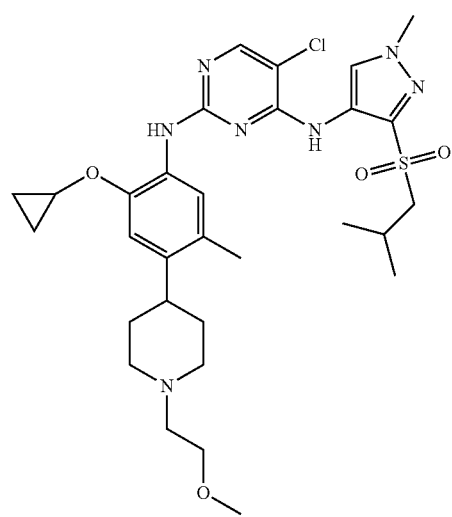
TABLE 17-continued
Compounds as ALK kinase inhibitors (final products)
84
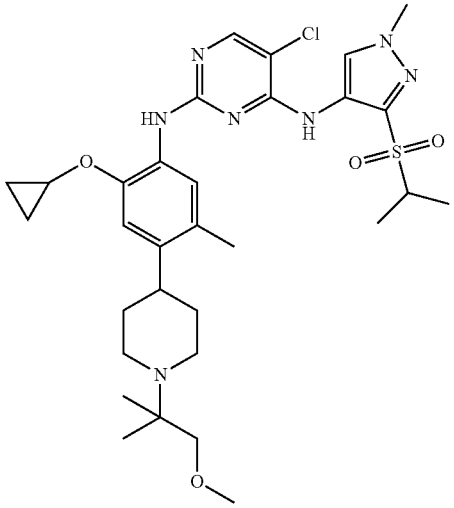
85
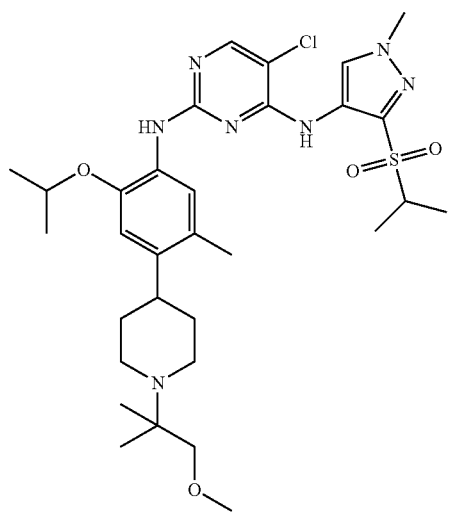
86
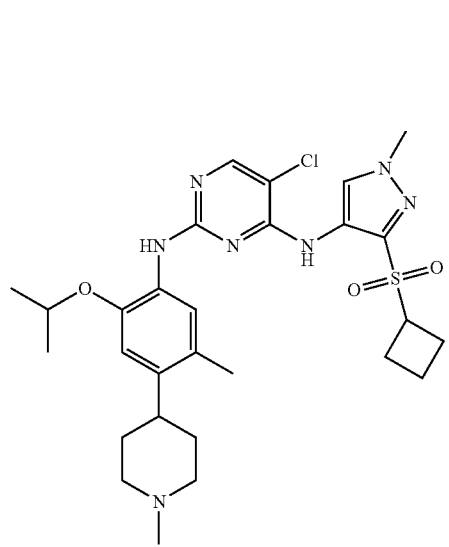

TABLE 17-continued
Compounds as ALK kinase inhibitors (final products)
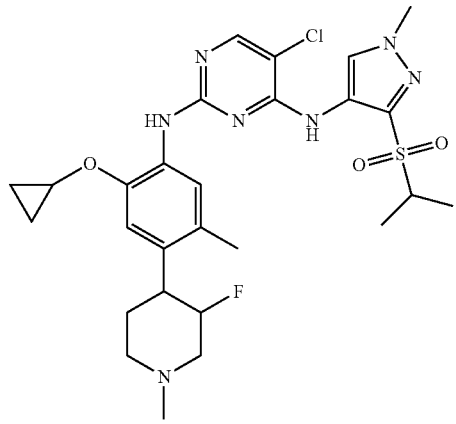
87
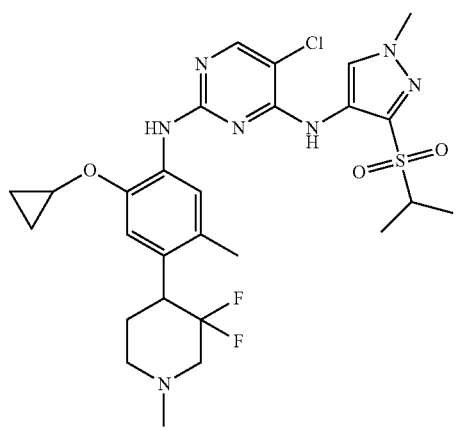
88
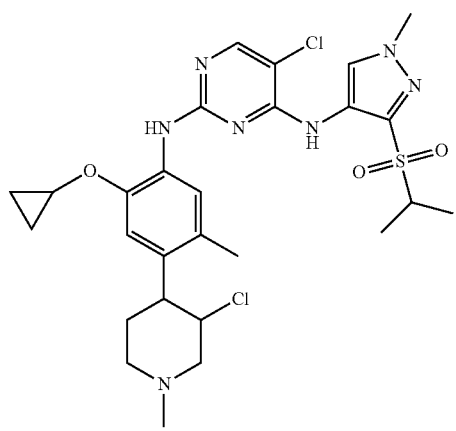
89
TABLE 17-continued
Compounds as ALK kinase inhibitors (final products)
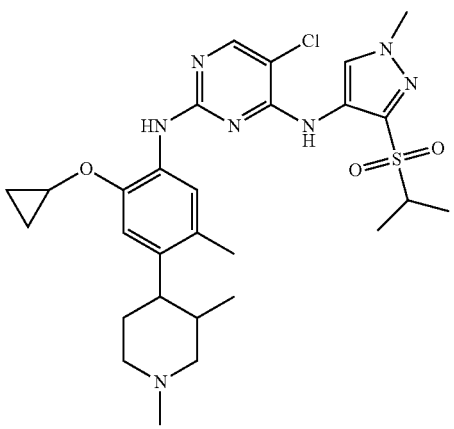
90
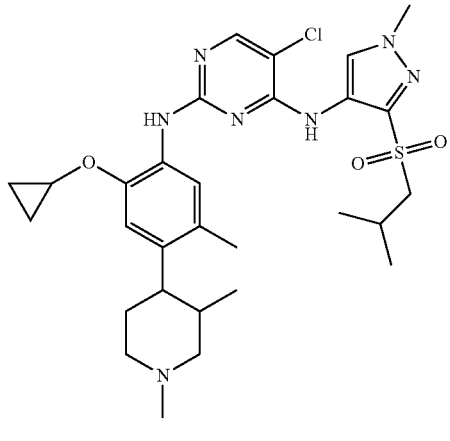
91
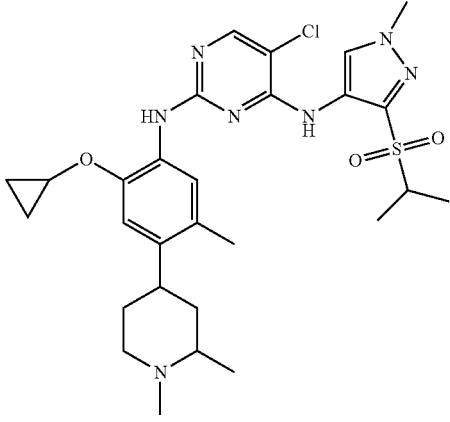
92

TABLE 17-continued
Compounds as ALK kinase inhibitors (final products)
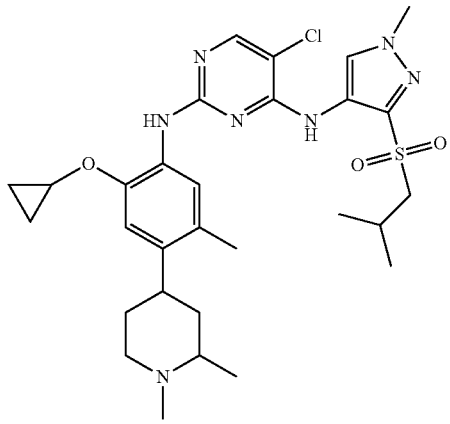
93
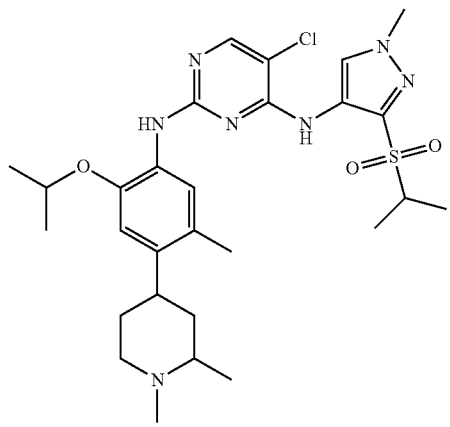
94
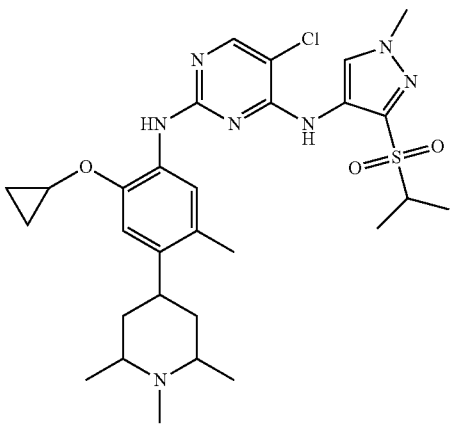
95
TABLE 17-continued
Compounds as ALK kinase inhibitors (final products)
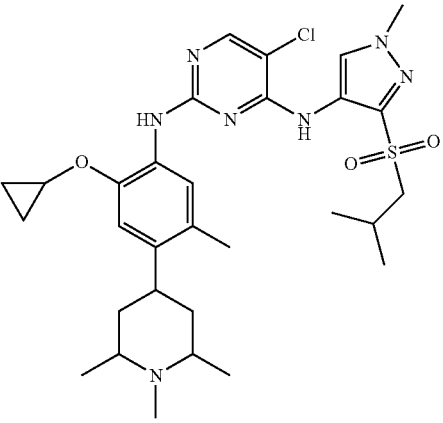
96
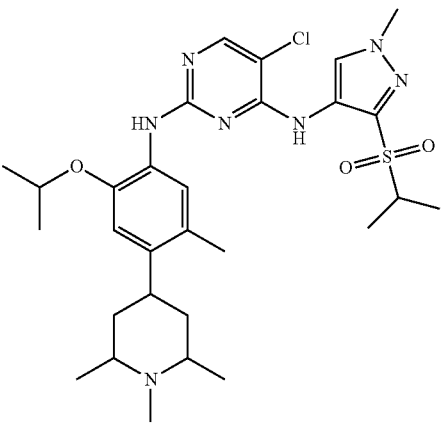
97
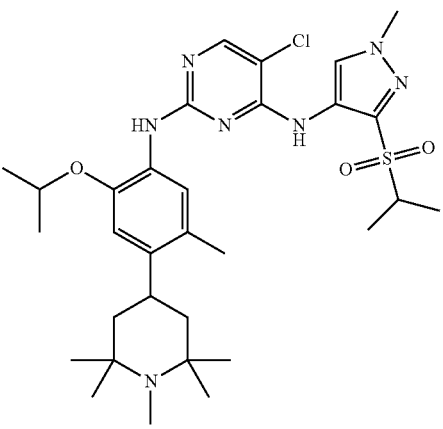
98

TABLE 17-continued
Compounds as ALK kinase inhibitors (final products)
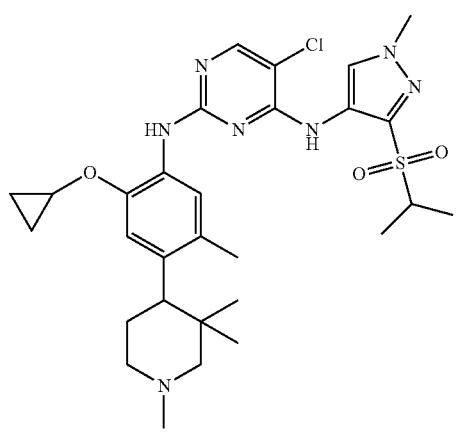
99
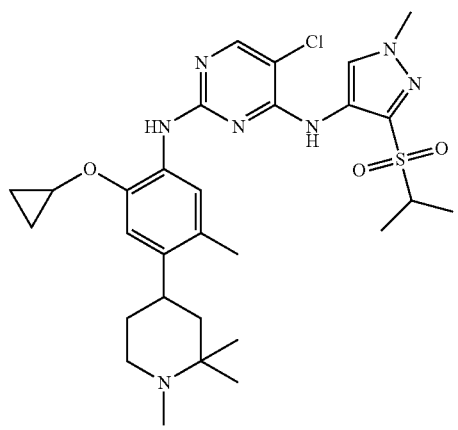
100
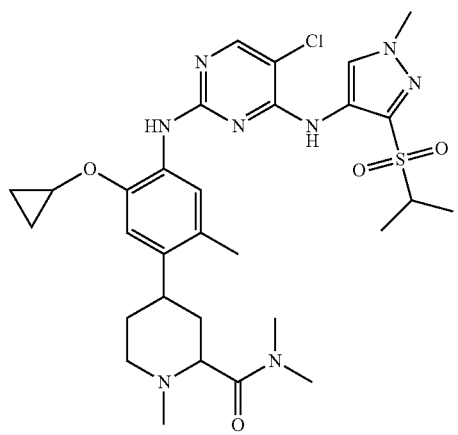
101
TABLE 17-continued
Compounds as ALK kinase inhibitors (final products)
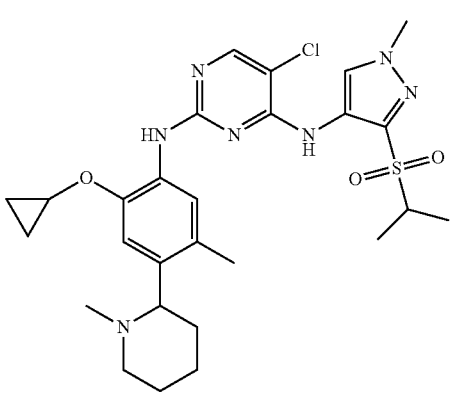
102
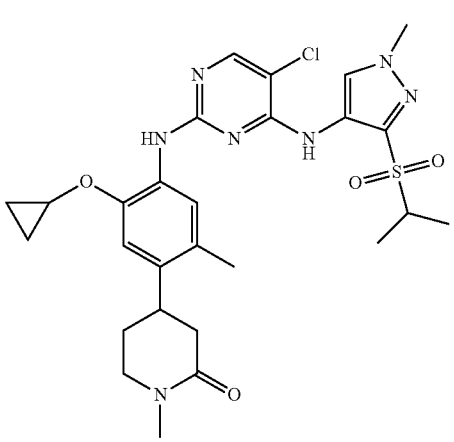
103
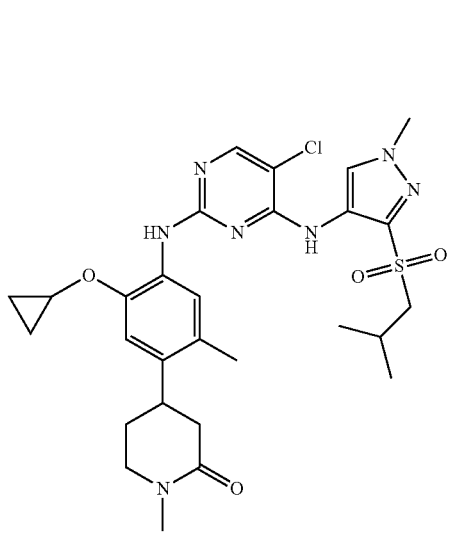
104

TABLE 17-continued
Compounds as ALK kinase inhibitors (final products)
105
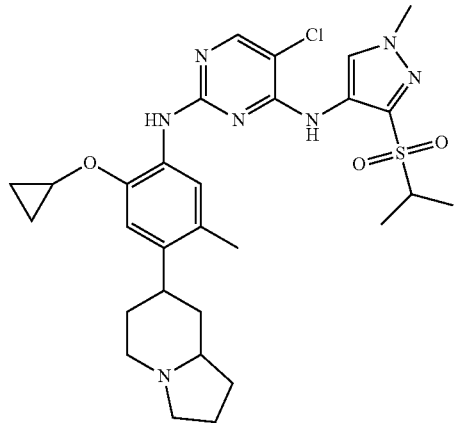
106
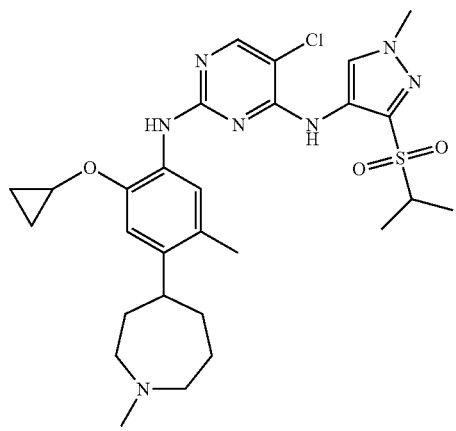
107
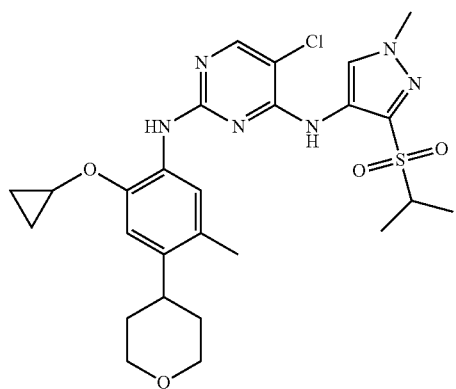
TABLE 17-continued
Compounds as ALK kinase inhibitors (final products)
108
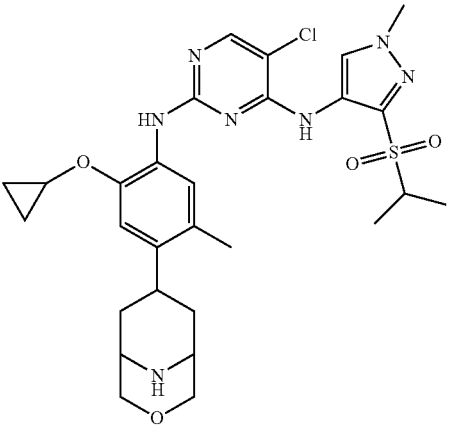
109
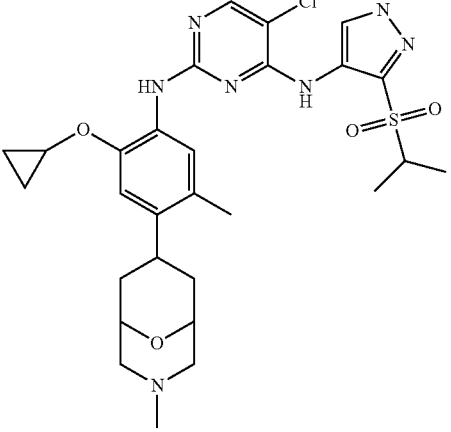
110
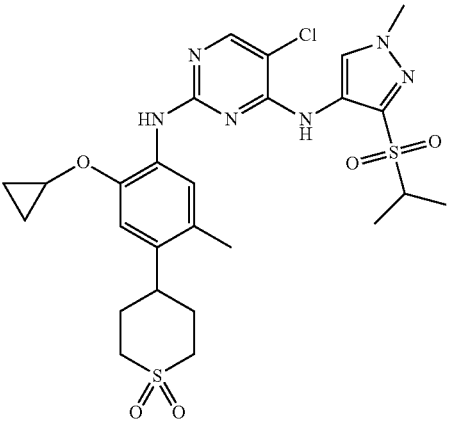

TABLE 17-continued
Compounds as ALK kinase inhibitors (final products)
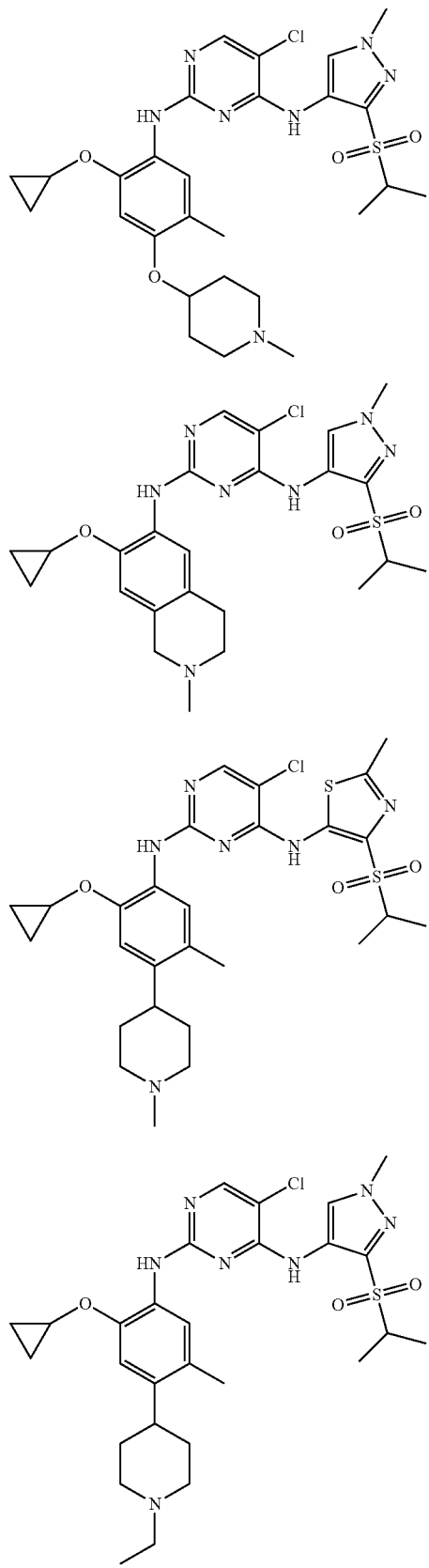
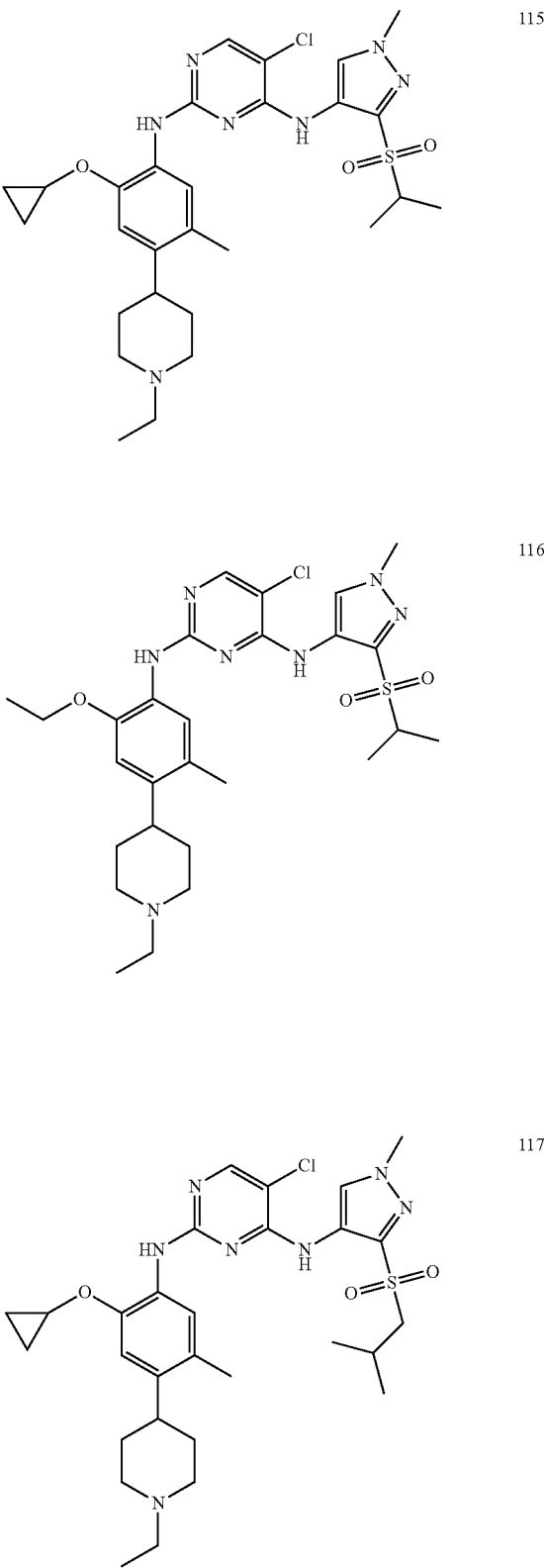

TABLE 17-continued
Compounds as ALK kinase inhibitors (final products)
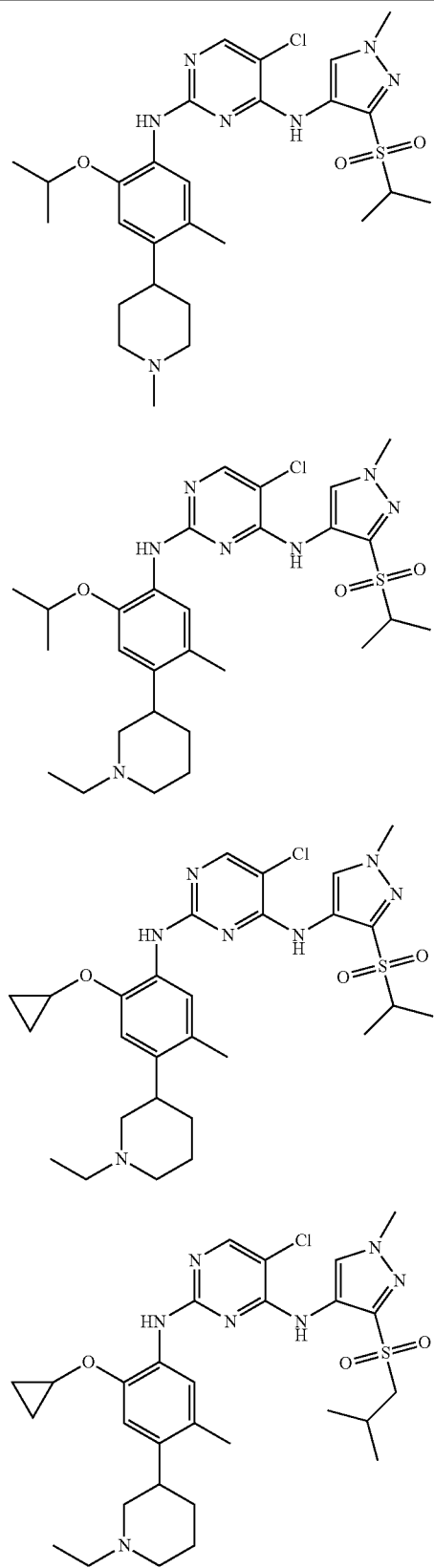
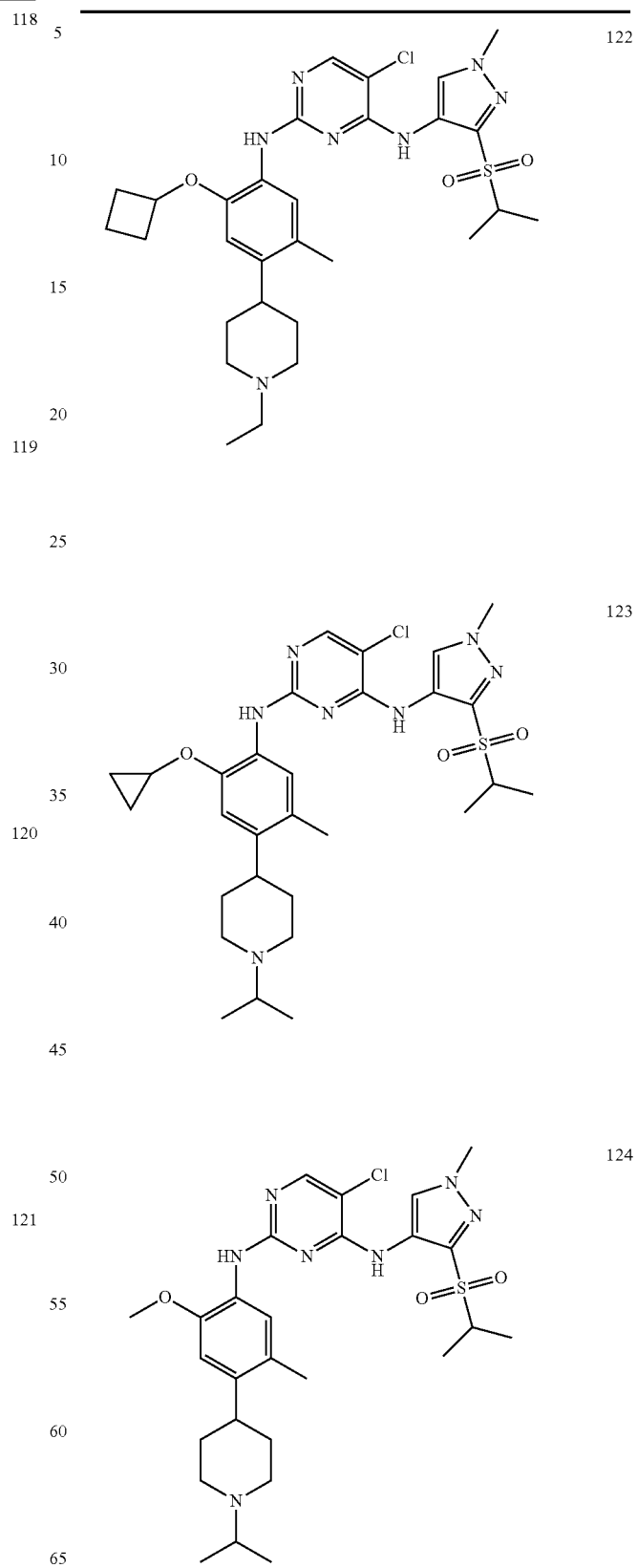

TABLE 17-continued
Compounds as ALK kinase inhibitors (final products)
125
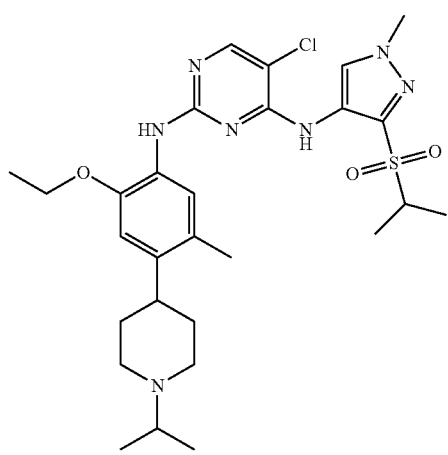
126
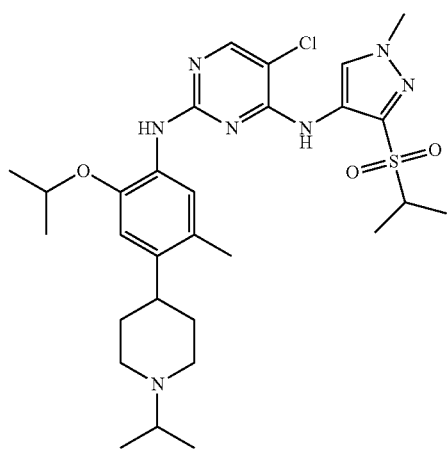
127
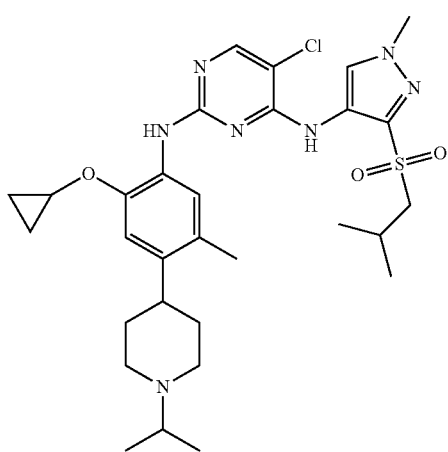
TABLE 17-continued
Compounds as ALK kinase inhibitors (final products)
128
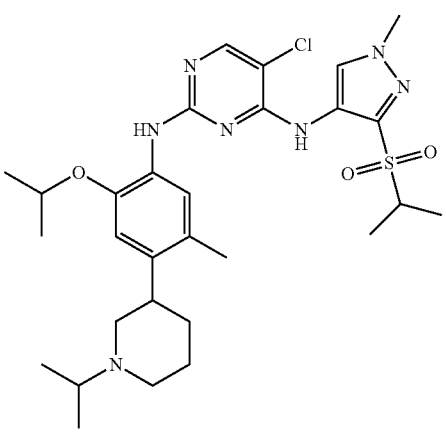
129
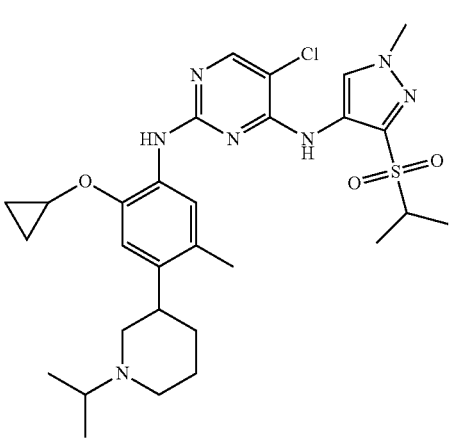
130
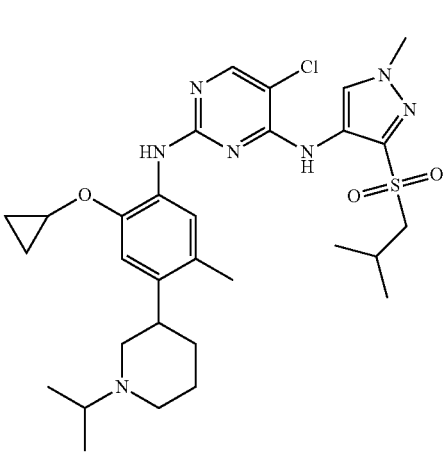

TABLE 17-continued
Compounds as ALK kinase inhibitors (final products)
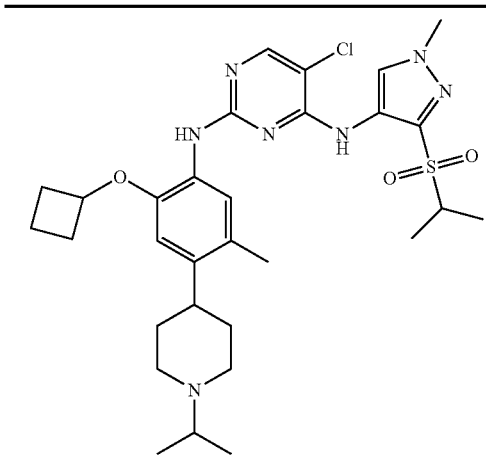
131
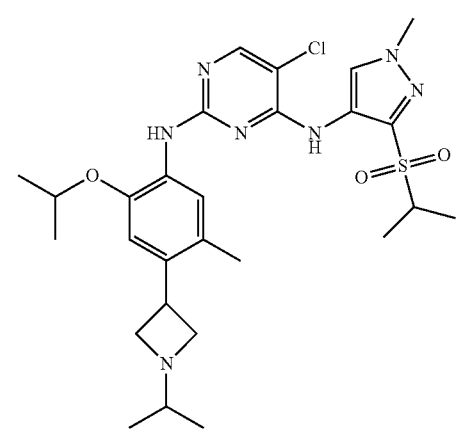
132
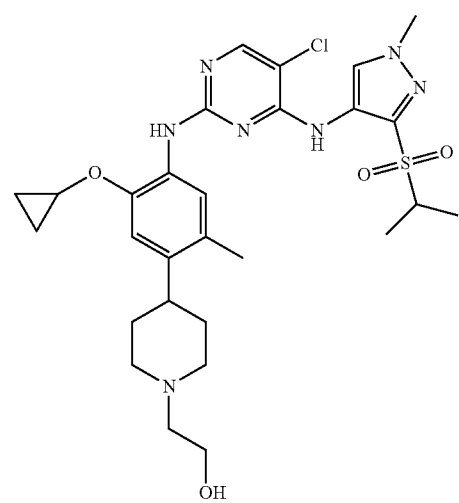
133
TABLE 17-continued
Compounds as ALK kinase inhibitors (final products)
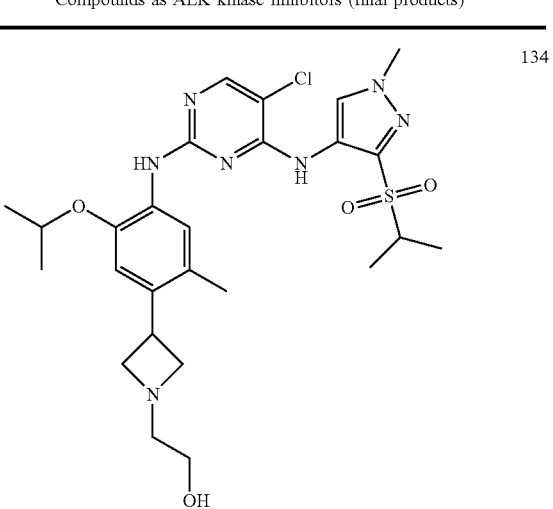
134
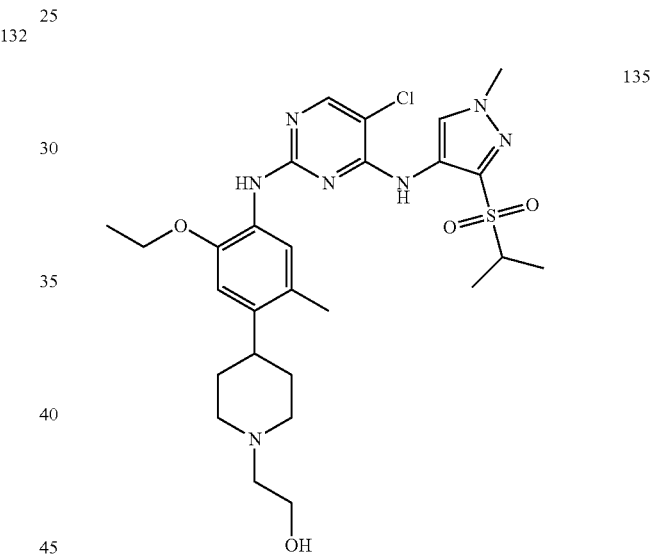
135
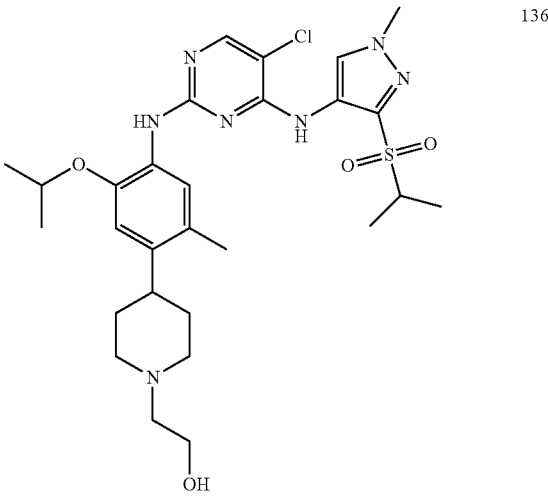
136

TABLE 17-continued
Compounds as ALK kinase inhibitors (final products)
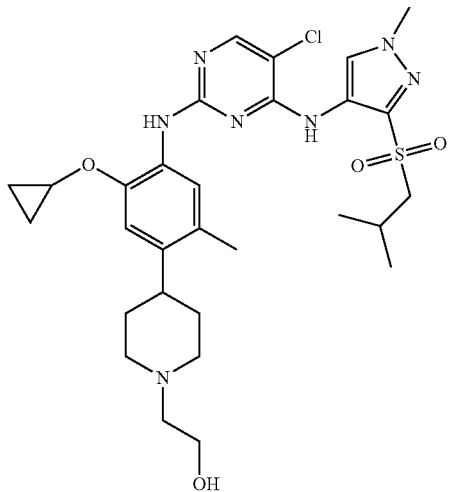
137
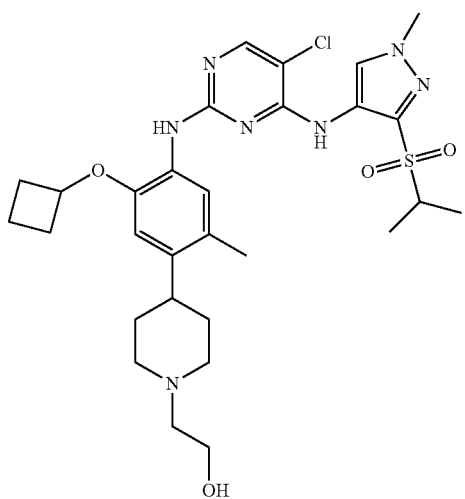
138
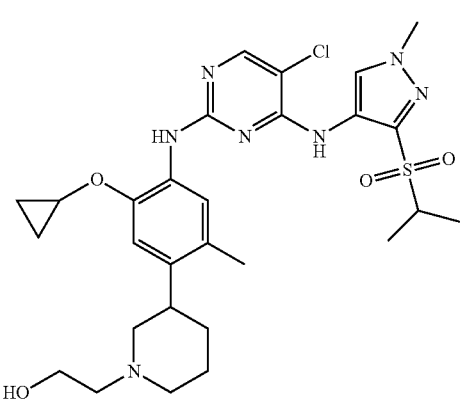
139
TABLE 17-continued
Compounds as ALK kinase inhibitors (final products)
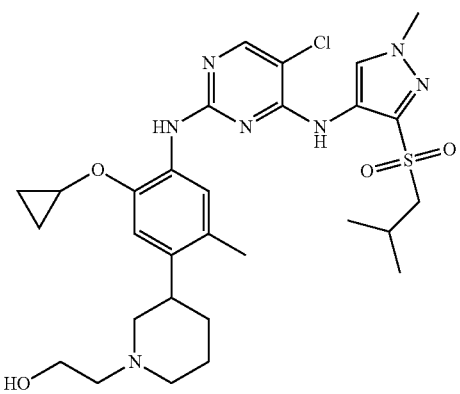
140
141
142

TABLE 17-continued
Compounds as ALK kinase inhibitors (final products)
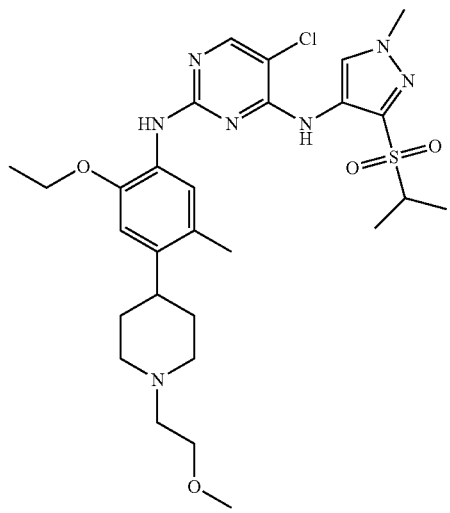
143
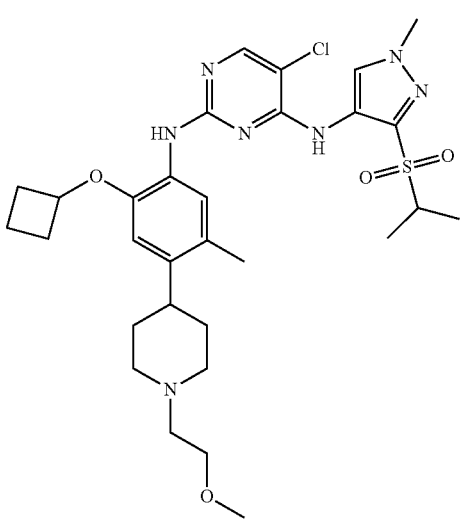
144
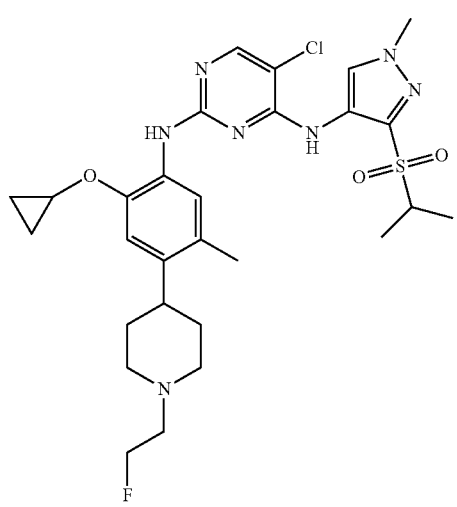
145
TABLE 17-continued
Compounds as ALK kinase inhibitors (final products)
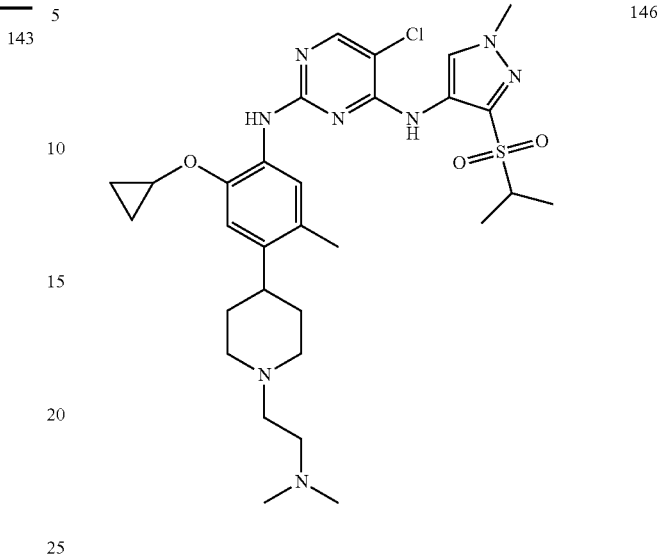
146
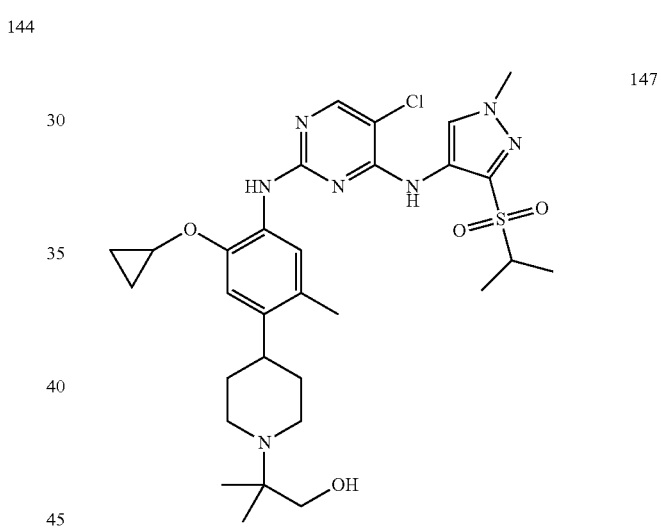
147
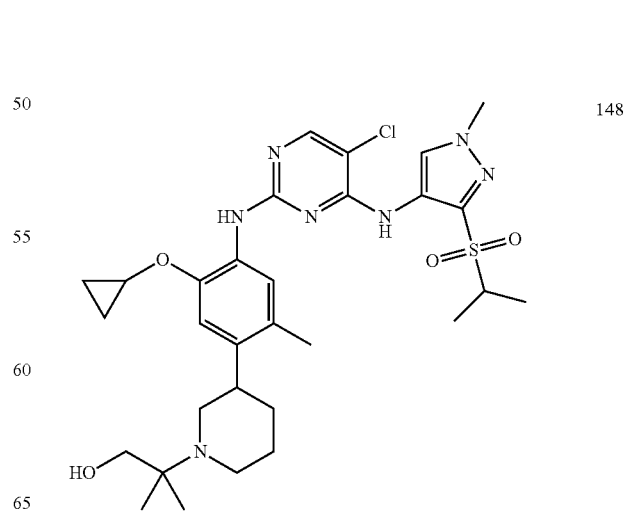
148

TABLE 17-continued
Compounds as ALK kinase inhibitors (final products)
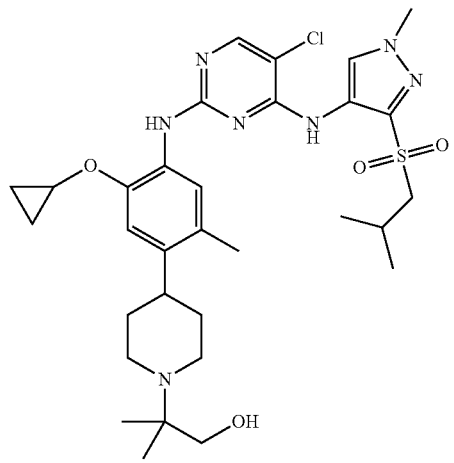 [SMILES: Cc1cc(Nc2ncc(Cl)c(Nc3cn(C)nc3S(=O)(=O)CC(C)C)n2)c(OC2CC2)cc1C1CCN(C(C)(C)CO)CC1]
149
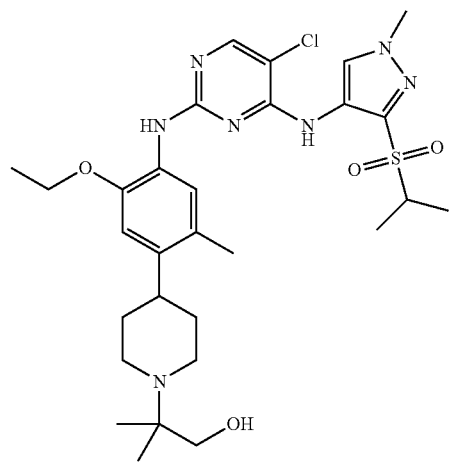
150
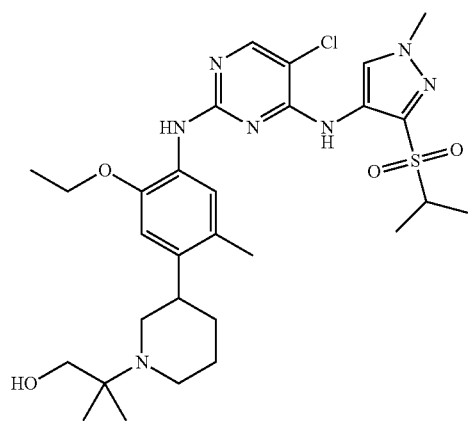
151
TABLE 17-continued
Compounds as ALK kinase inhibitors (final products)
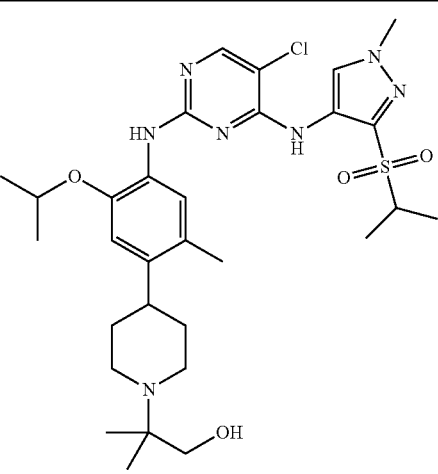
152
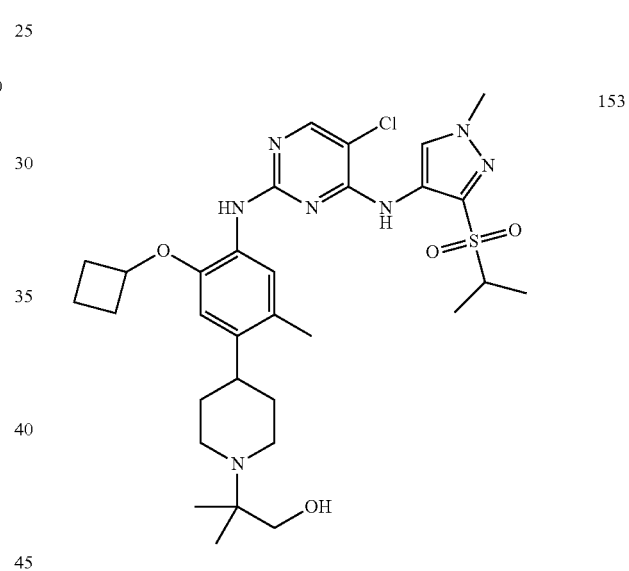
153
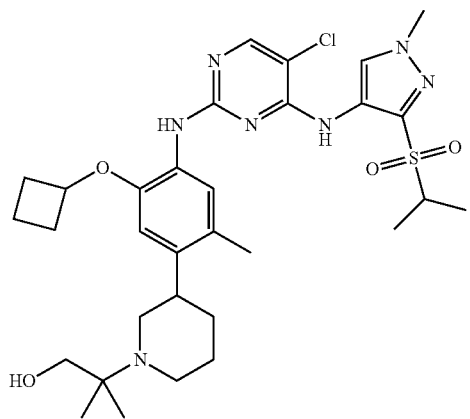
154

TABLE 17-continued
Compounds as ALK kinase inhibitors (final products)
155
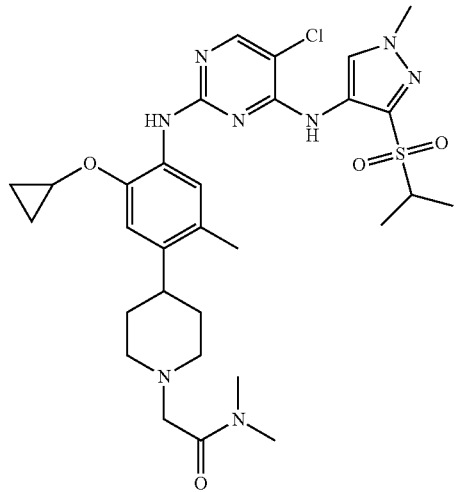
156
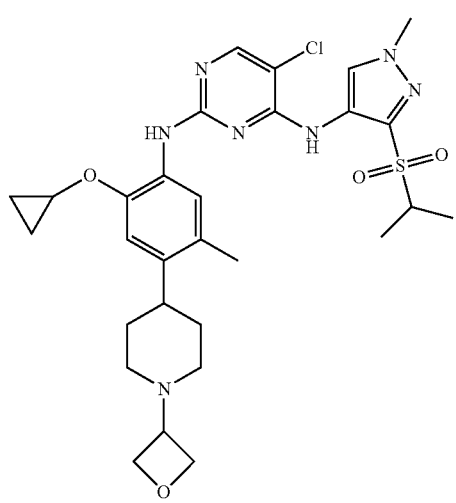
157
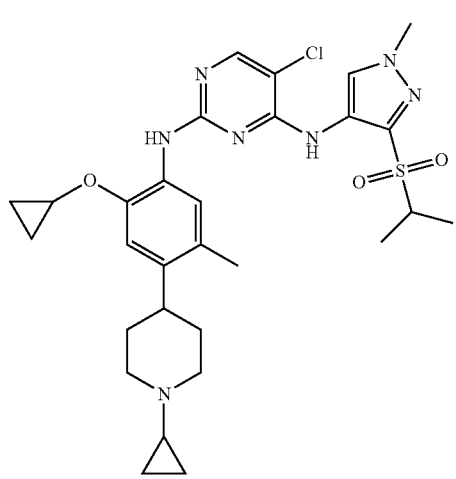
TABLE 17-continued
Compounds as ALK kinase inhibitors (final products)
158
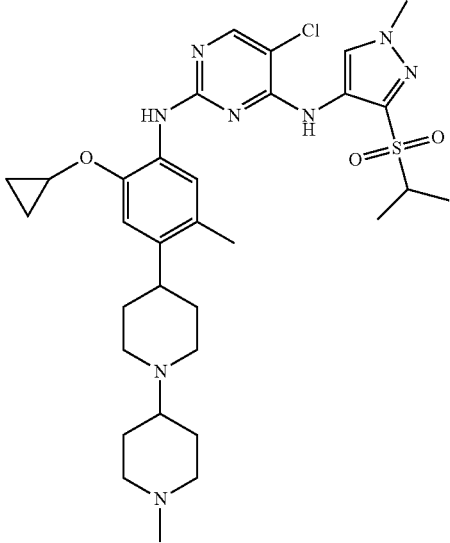
159
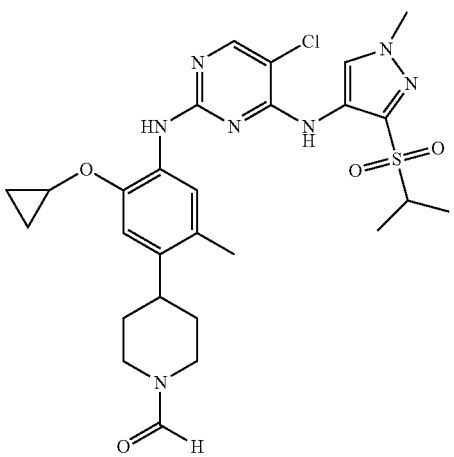
160
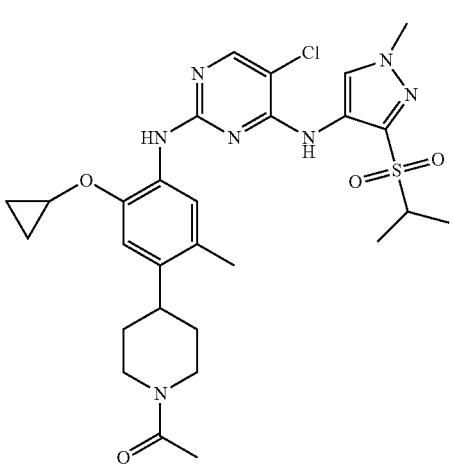

TABLE 17-continued
Compounds as ALK kinase inhibitors (final products)
161
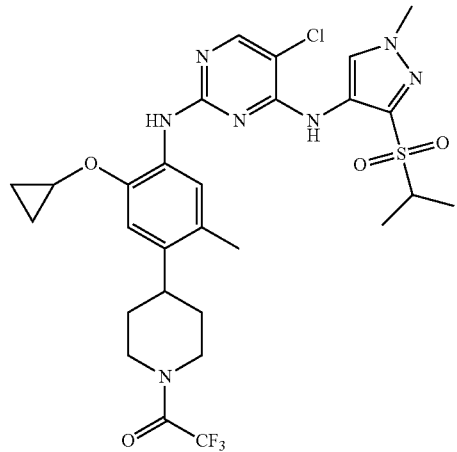
162
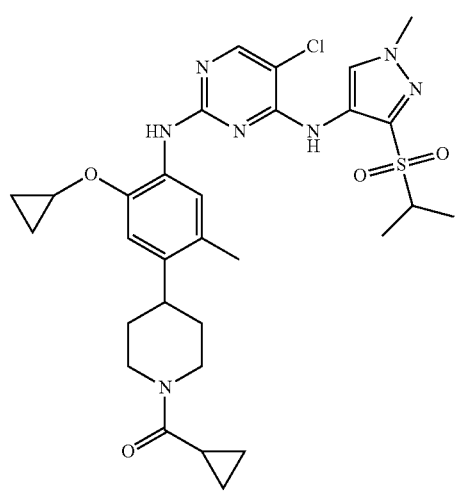
163
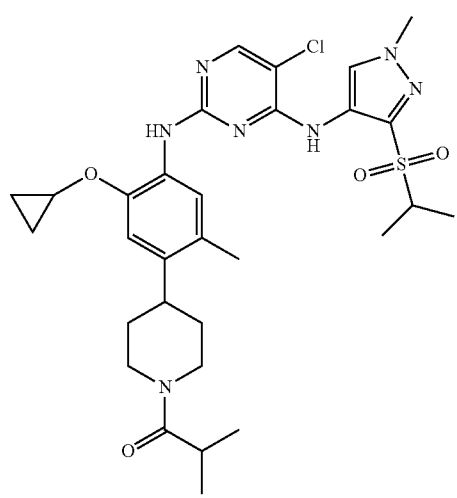
TABLE 17-continued
Compounds as ALK kinase inhibitors (final products)
164
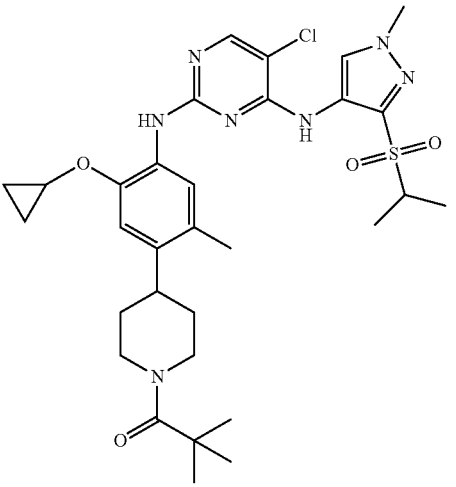
165
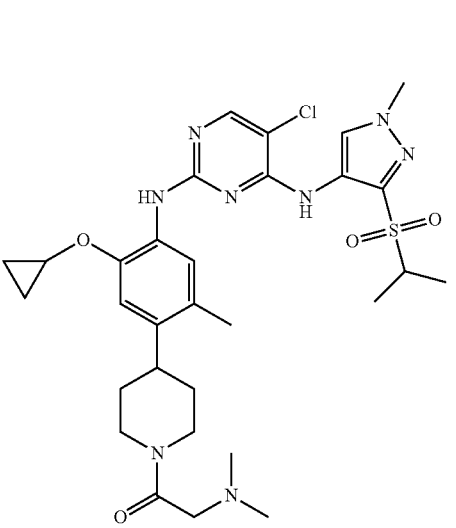
166
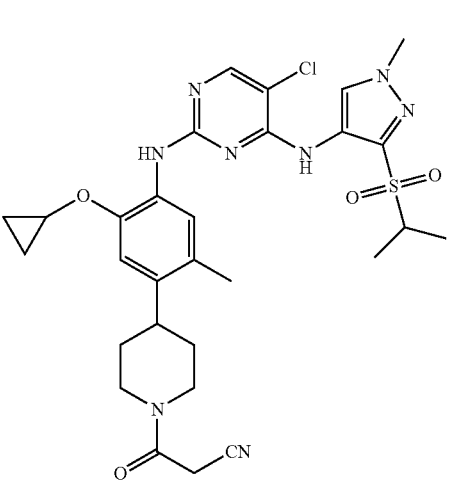

TABLE 17-continued
Compounds as ALK kinase inhibitors (final products)
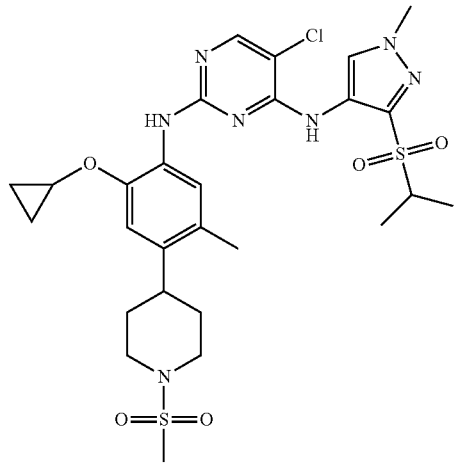
167
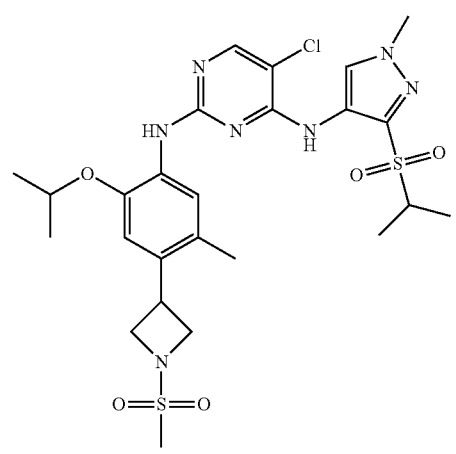
168
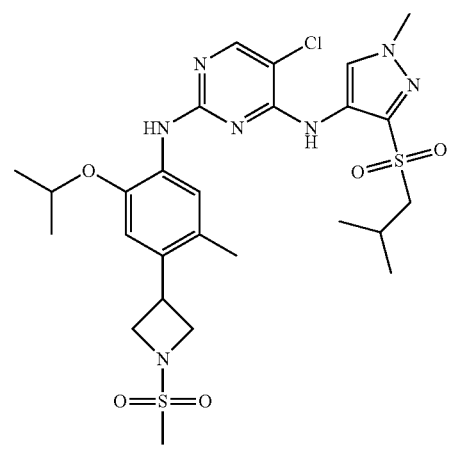
169
TABLE 17-continued
Compounds as ALK kinase inhibitors (final products)
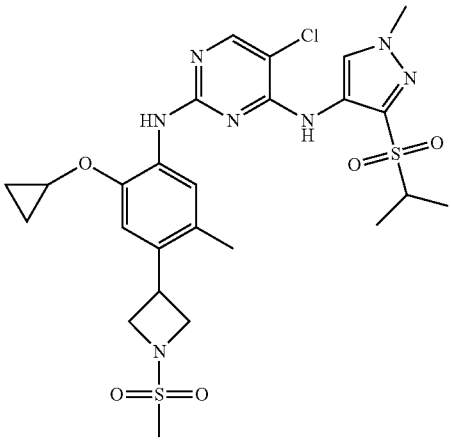 [SMILES: Cc1cc(Nc2ncc(Cl)c(Nc3cn(C)nc3S(=O)(=O)C(C)C)n2)c(OC2CC2)cc1C1CN(S(C)(=O)=O)C1]
170
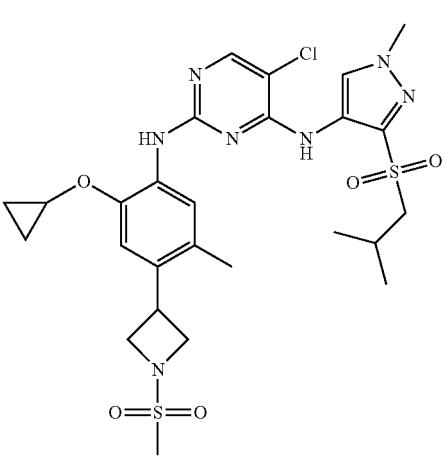
171
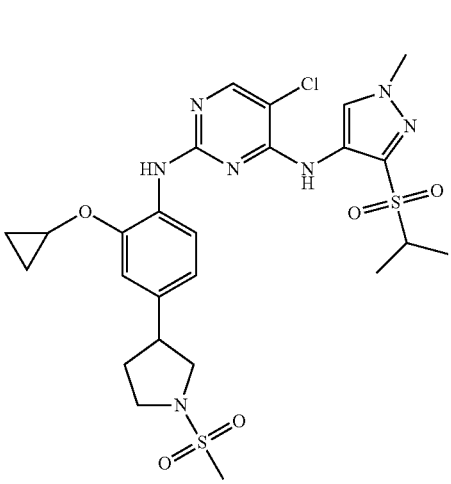
172

TABLE 17-continued
Compounds as ALK kinase inhibitors (final products)
173
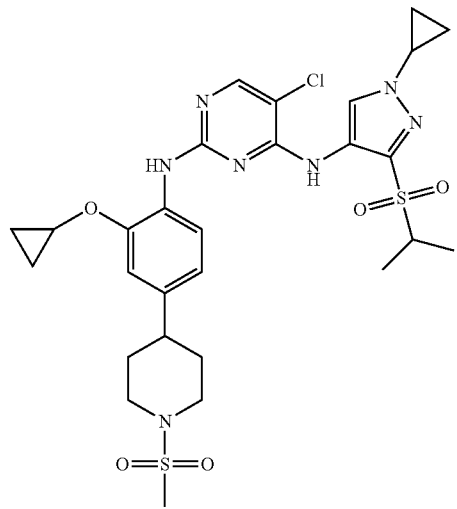 [SMILES: CC(C)S(=O)(=O)c1nn(C2CC2)cc1Nc1nc(Nc2ccc(C3CCN(S(C)(=O)=O)CC3)cc2OC2CC2)ncc1Cl]
174
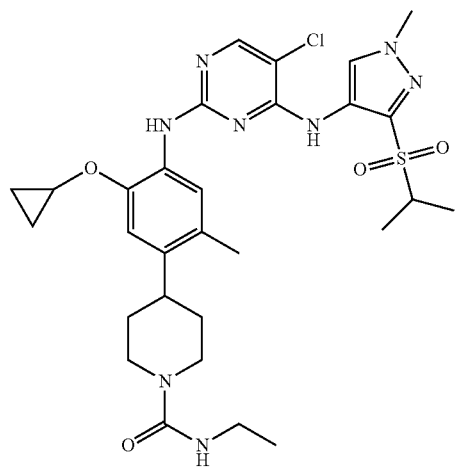
175
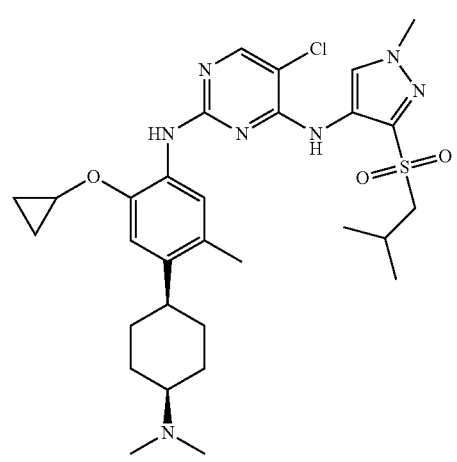
TABLE 17-continued
Compounds as ALK kinase inhibitors (final products)
176
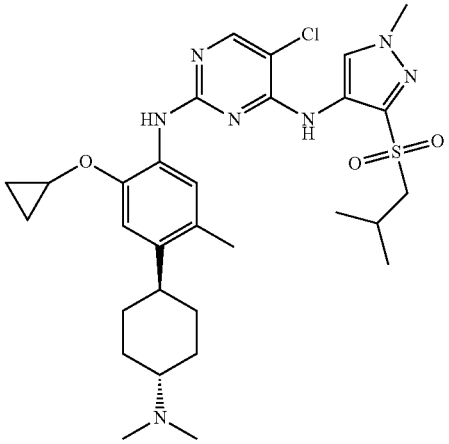
177
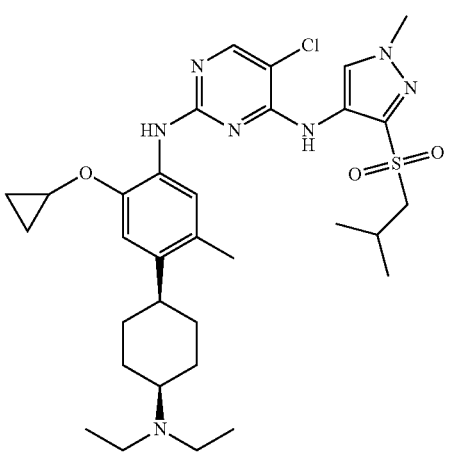 [SMILES: CCN(CC)[C@H]1CC[C@@H](c2cc(OC3CC3)c(Nc3ncc(Cl)c(Nc4cn(C)nc4S(=O)(=O)CC(C)C)n3)cc2C)CC1]
178
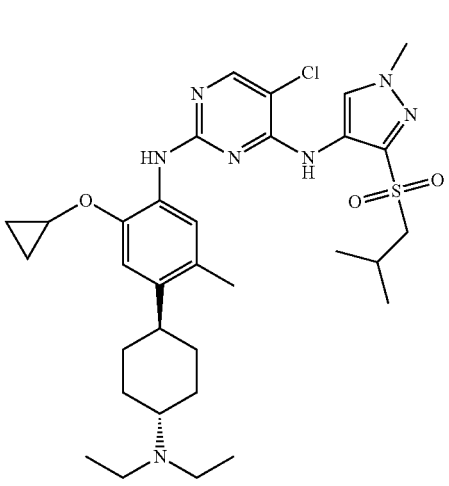 [SMILES: CCN(CC)[C@H]1CC[C@H](c2cc(OC3CC3)c(Nc3ncc(Cl)c(Nc4cn(C)nc4S(=O)(=O)CC(C)C)n3)cc2C)CC1]

TABLE 17-continued
Compounds as ALK kinase inhibitors (final products)
179
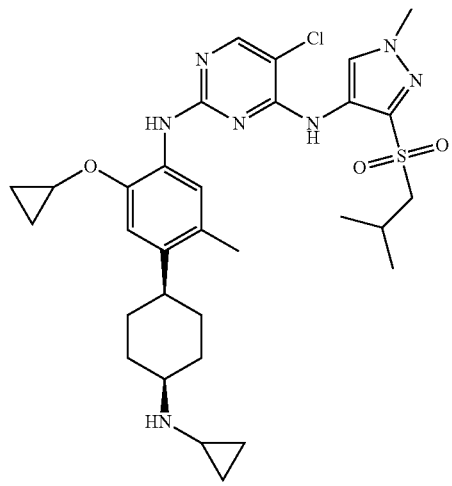 [SMILES: Cc1cc(Nc2ncc(Cl)c(Nc3cn(C)nc3S(=O)(=O)CC(C)C)n2)c(OC2CC2)cc1[C@H]1CC[C@@H](NC2CC2)CC1]
180
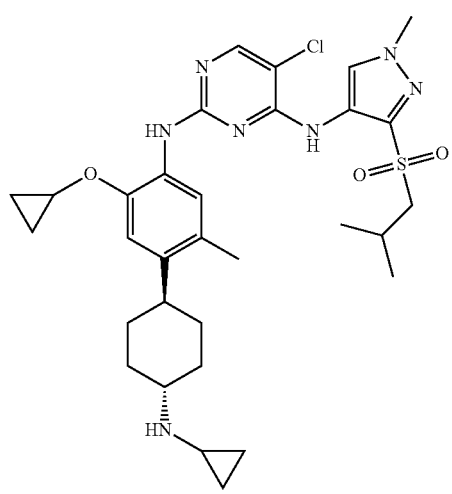 [SMILES: Cc1cc(Nc2ncc(Cl)c(Nc3cn(C)nc3S(=O)(=O)CC(C)C)n2)c(OC2CC2)cc1[C@H]1CC[C@H](NC2CC2)CC1]
181
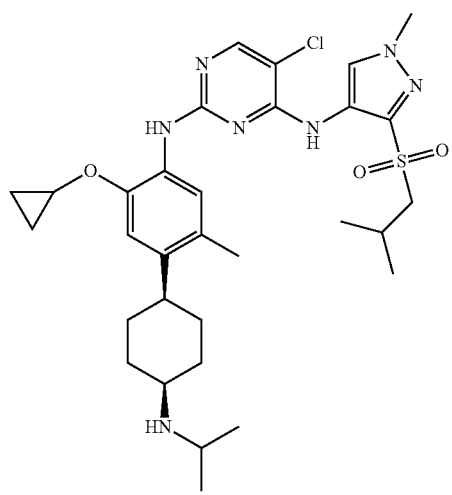 [SMILES: Cc1cc(Nc2ncc(Cl)c(Nc3cn(C)nc3S(=O)(=O)CC(C)C)n2)c(OC2CC2)cc1[C@H]1CC[C@@H](NC(C)C)CC1]
TABLE 17-continued
Compounds as ALK kinase inhibitors (final products)
182
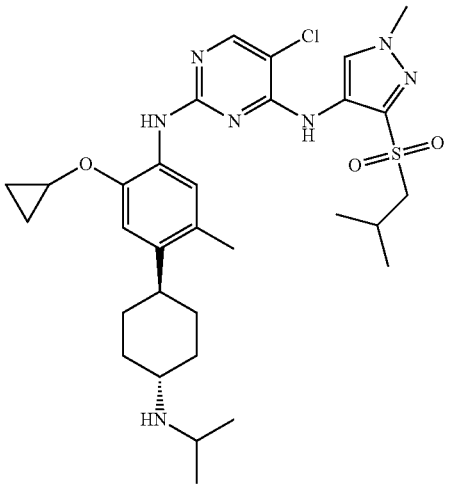 [SMILES: Cc1cc(Nc2ncc(Cl)c(Nc3cn(C)nc3S(=O)(=O)CC(C)C)n2)c(OC2CC2)cc1[C@H]1CC[C@H](NC(C)C)CC1]
183
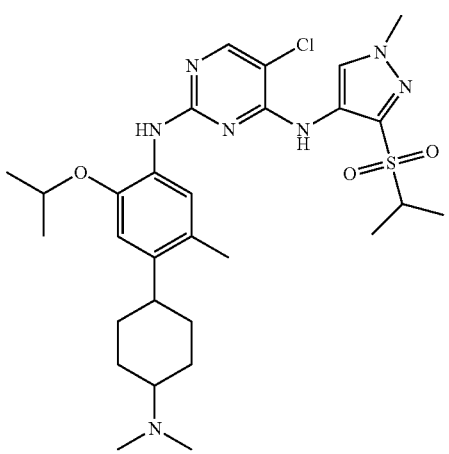 [SMILES: Cc1cc(Nc2ncc(Cl)c(Nc3cn(C)nc3S(=O)(=O)C(C)C)n2)c(OC(C)C)cc1C1CCC(N(C)C)CC1]
184
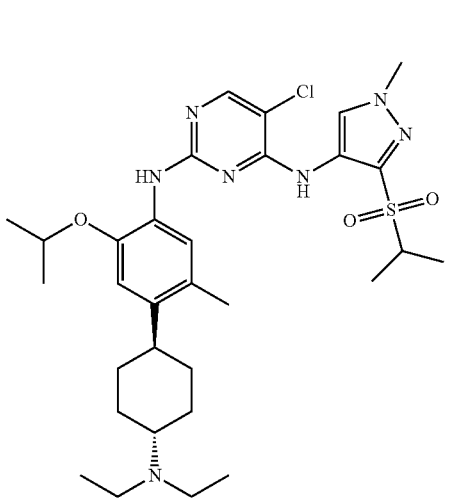 [SMILES: CCN(CC)[C@H]1CC[C@H](c2cc(OC(C)C)c(Nc3ncc(Cl)c(Nc4cn(C)nc4S(=O)(=O)C(C)C)n3)cc2C)CC1]

TABLE 17-continued
Compounds as ALK kinase inhibitors (final products)
185 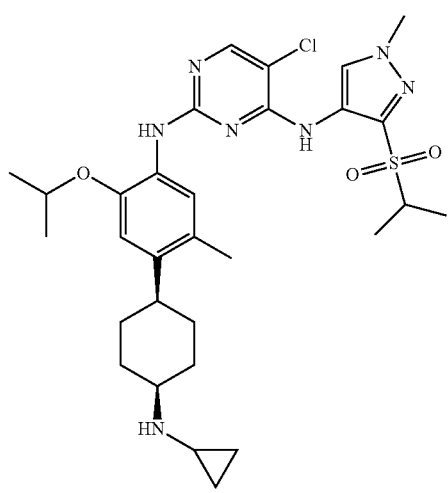 [SMILES: Cc1cc(Nc2ncc(Cl)c(Nc3cn(C)nc3S(=O)(=O)C(C)C)n2)c(OC(C)C)cc1[C@H]1CC[C@@H](NC2CC2)CC1]
186 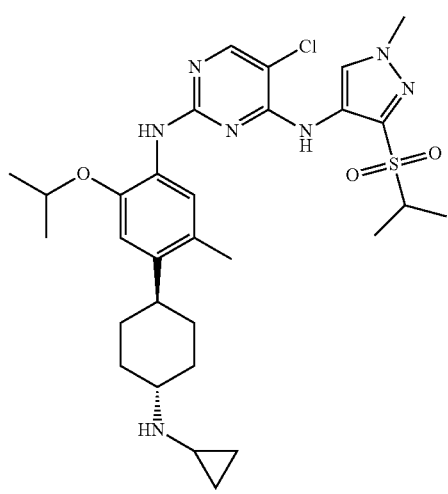 [SMILES: Cc1cc(Nc2ncc(Cl)c(Nc3cn(C)nc3S(=O)(=O)C(C)C)n2)c(OC(C)C)cc1[C@H]1CC[C@H](NC2CC2)CC1]
187 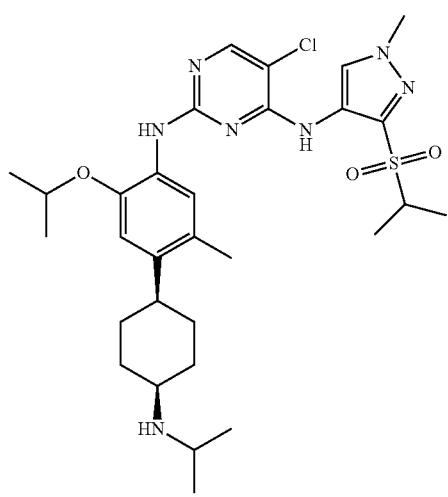 [SMILES: Cc1cc(Nc2ncc(Cl)c(Nc3cn(C)nc3S(=O)(=O)C(C)C)n2)c(OC(C)C)cc1[C@H]1CC[C@@H](NC(C)C)CC1]
TABLE 17-continued
Compounds as ALK kinase inhibitors (final products)
188 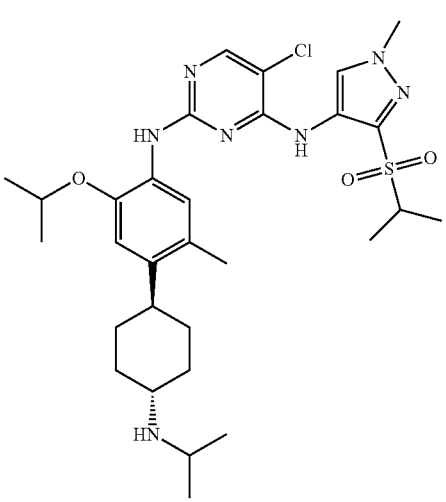 [SMILES: Cc1cc(Nc2ncc(Cl)c(Nc3cn(C)nc3S(=O)(=O)C(C)C)n2)c(OC(C)C)cc1[C@H]1CC[C@H](NC(C)C)CC1]
189 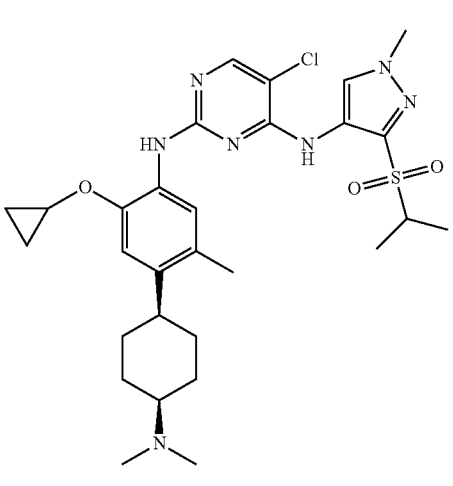 [SMILES: Cc1cc(Nc2ncc(Cl)c(Nc3cn(C)nc3S(=O)(=O)C(C)C)n2)c(OC2CC2)cc1[C@H]1CC[C@@H](N(C)C)CC1]
190 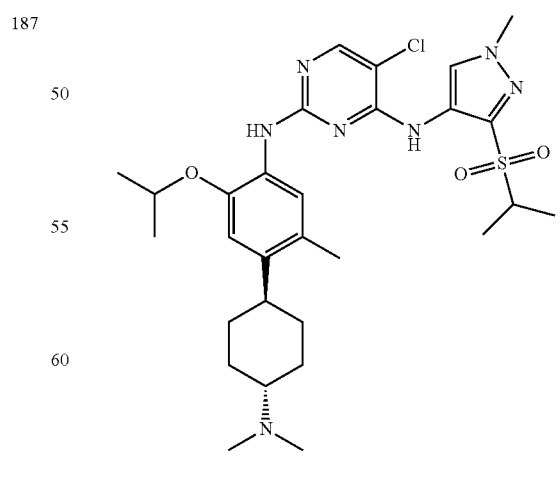

TABLE 17-continued
Compounds as ALK kinase inhibitors (final products)
191
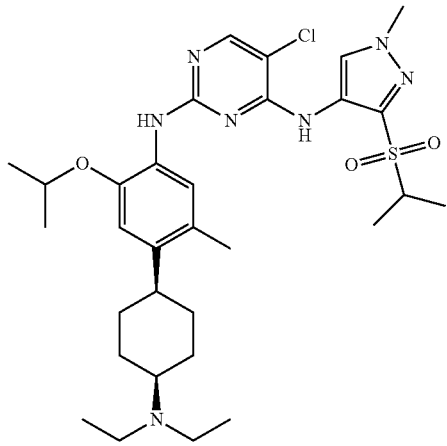
192
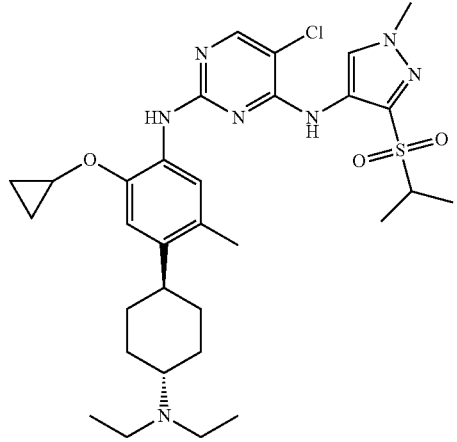 [SMILES: CCN(CC)[C@H]1CC[C@H](c2cc(OC3CC3)c(Nc3ncc(Cl)c(Nc4cn(C)nc4S(=O)(=O)C(C)C)n3)cc2C)CC1]
193
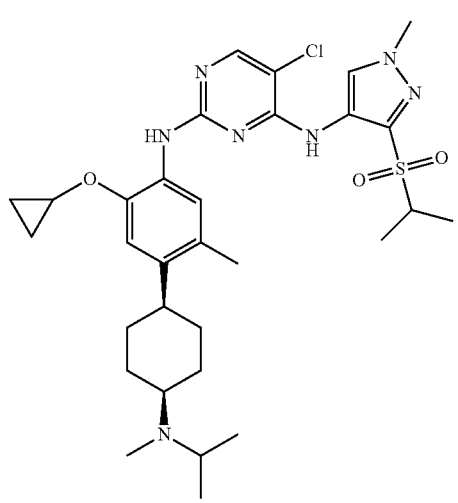 [SMILES: Cc1cc(Nc2ncc(Cl)c(Nc3cn(C)nc3S(=O)(=O)C(C)C)n2)c(OC2CC2)cc1[C@H]1CC[C@@H](N(C)C(C)C)CC1]
TABLE 17-continued
Compounds as ALK kinase inhibitors (final products)
194
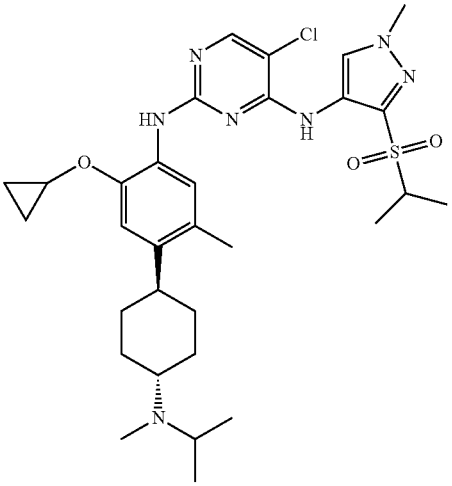 [SMILES: Cc1cc(Nc2ncc(Cl)c(Nc3cn(C)nc3S(=O)(=O)C(C)C)n2)c(OC2CC2)cc1[C@H]1CC[C@H](N(C)C(C)C)CC1]
195
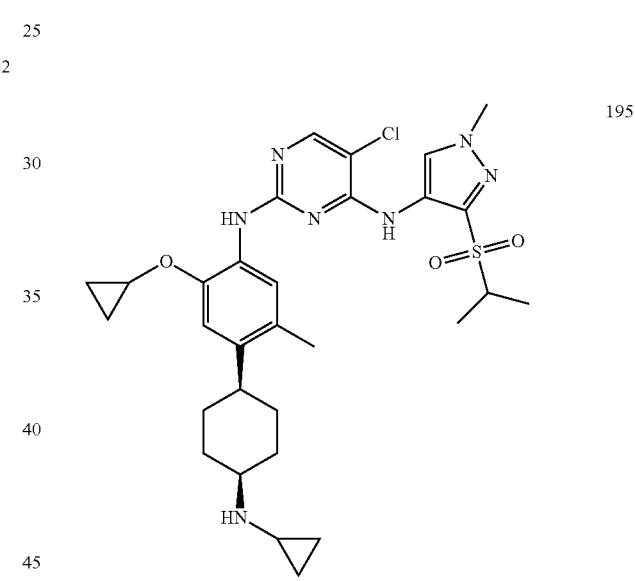
196
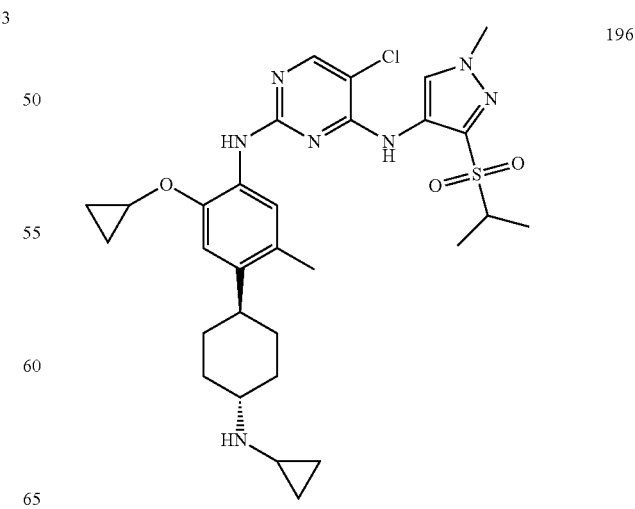

TABLE 17-continued
Compounds as ALK kinase inhibitors (final products)
197
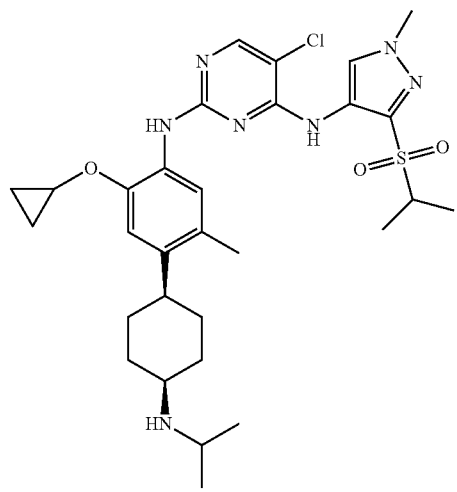 [SMILES: Cc1cc(Nc2ncc(Cl)c(Nc3cn(C)nc3S(=O)(=O)C(C)C)n2)c(OC2CC2)cc1[C@H]1CC[C@@H](NC(C)C)CC1]
198
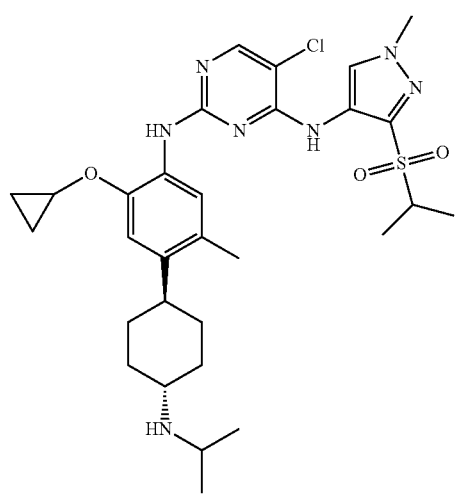 [SMILES: Cc1cc(Nc2ncc(Cl)c(Nc3cn(C)nc3S(=O)(=O)C(C)C)n2)c(OC2CC2)cc1[C@H]1CC[C@H](NC(C)C)CC1]
199
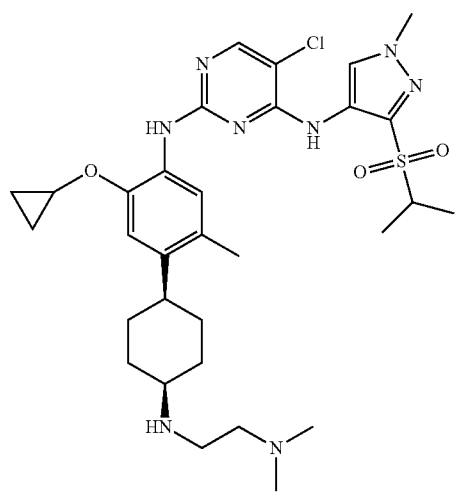 [SMILES: Cc1cc(Nc2ncc(Cl)c(Nc3cn(C)nc3S(=O)(=O)C(C)C)n2)c(OC2CC2)cc1[C@H]1CC[C@@H](NCCN(C)C)CC1]
TABLE 17-continued
Compounds as ALK kinase inhibitors (final products)
200
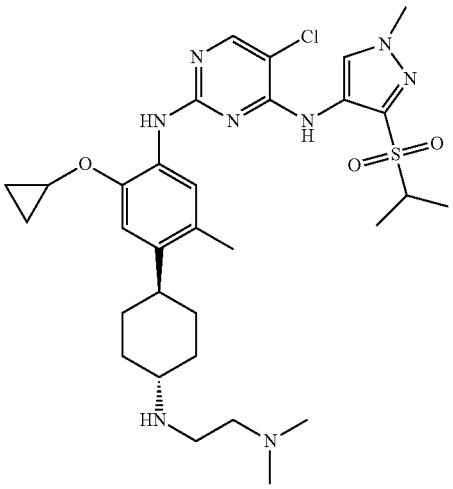 [SMILES: Cc1cc(Nc2ncc(Cl)c(Nc3cn(C)nc3S(=O)(=O)C(C)C)n2)c(OC2CC2)cc1[C@H]1CC[C@H](NCCN(C)C)CC1]
201
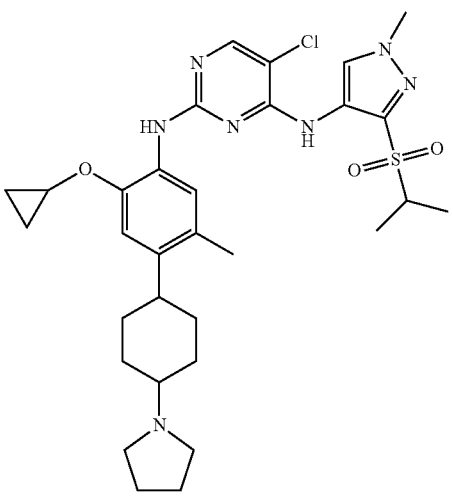 [SMILES: Cc1cc(Nc2ncc(Cl)c(Nc3cn(C)nc3S(=O)(=O)C(C)C)n2)c(OC2CC2)cc1C1CCC(N2CCCC2)CC1]
202
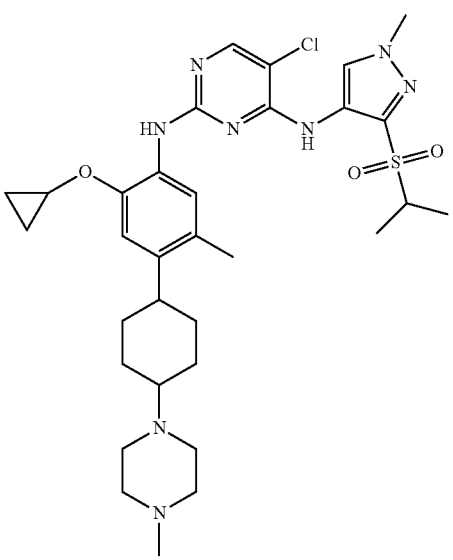 [SMILES: Cc1cc(Nc2ncc(Cl)c(Nc3cn(C)nc3S(=O)(=O)C(C)C)n2)c(OC2CC2)cc1C1CCC(N2CCN(C)CC2)CC1]

TABLE 17-continued
Compounds as ALK kinase inhibitors (final products)
203
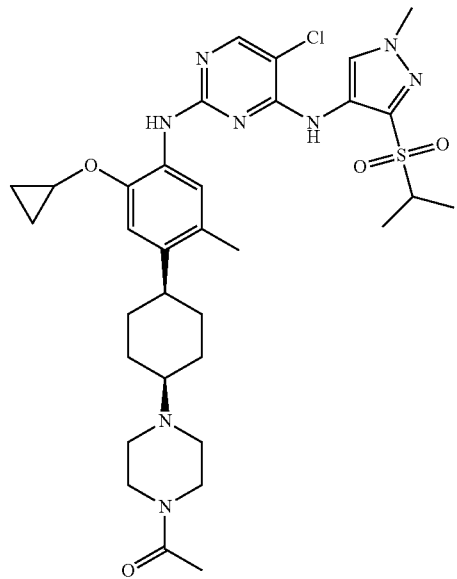 [SMILES: CC(=O)N1CCN([C@H]2CC[C@@H](c3cc(OC4CC4)c(Nc4ncc(Cl)c(Nc5cn(C)nc5S(=O)(=O)C(C)C)n4)cc3C)CC2)CC1]
204
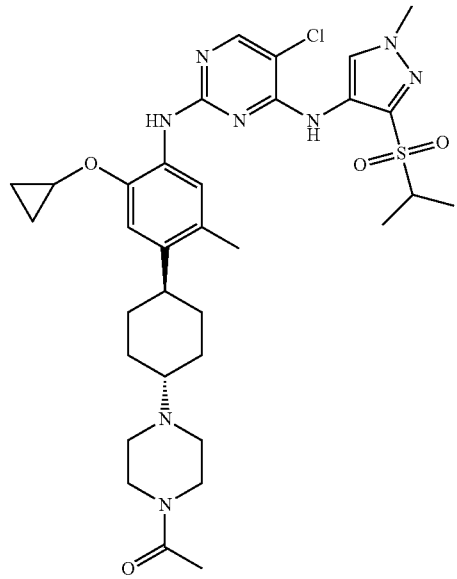 [SMILES: CC(=O)N1CCN([C@H]2CC[C@H](c3cc(OC4CC4)c(Nc4ncc(Cl)c(Nc5cn(C)nc5S(=O)(=O)C(C)C)n4)cc3C)CC2)CC1]
TABLE 17-continued
Compounds as ALK kinase inhibitors (final products)
205
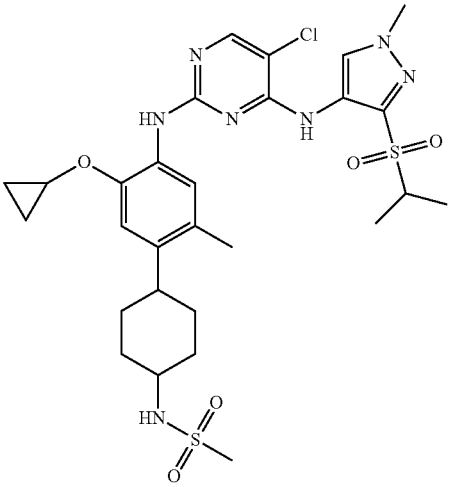
206
207
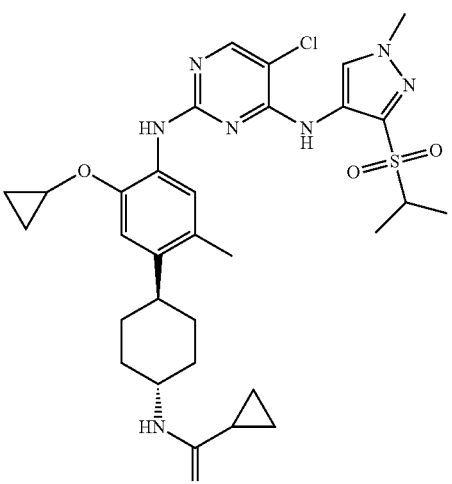

TABLE 17-continued
Compounds as ALK kinase inhibitors (final products)
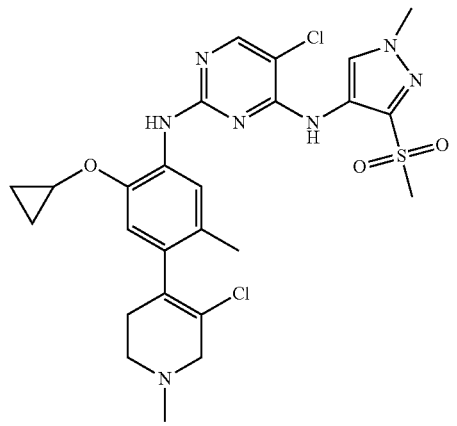
208
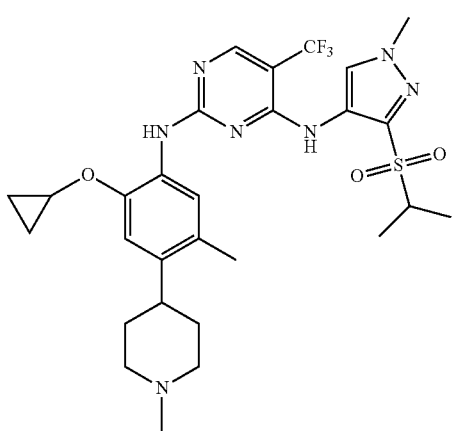 [SMILES: Cc1cc(Nc2ncc(C#N)c(Nc3cn(C)nc3S(=O)(=O)C(C)C)n2)c(OC2CC2)cc1C1CCN(C)CC1]
209
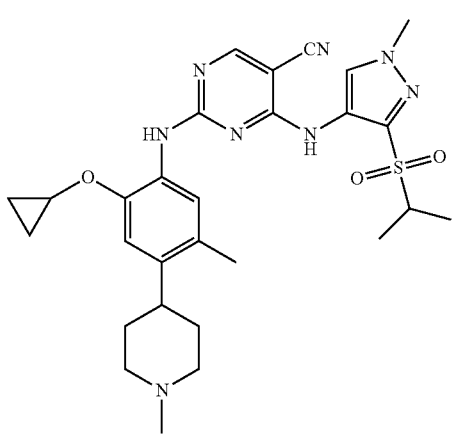
210
TABLE 17-continued
Compounds as ALK kinase inhibitors (final products)
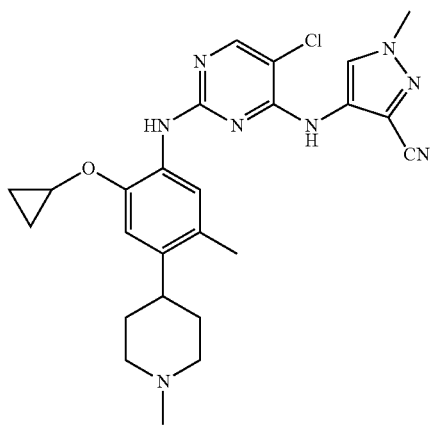
211
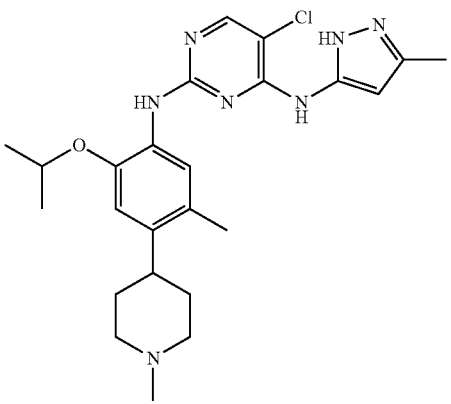 [SMILES: Cc1cc(Nc2nc(Nc3cc(C)c(C4CCN(C)CC4)cc3OC(C)C)ncc2Cl)[nH]n1]
212
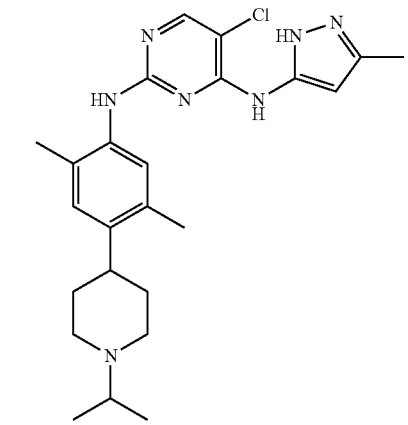
213
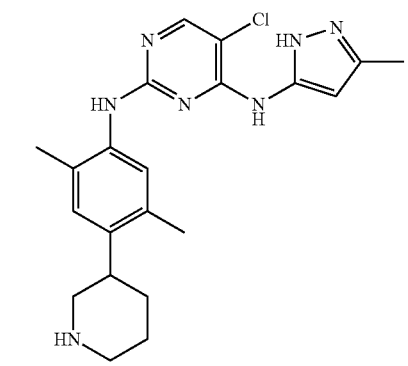
214

TABLE 17-continued

Compounds as ALK kinase inhibitors (final products)

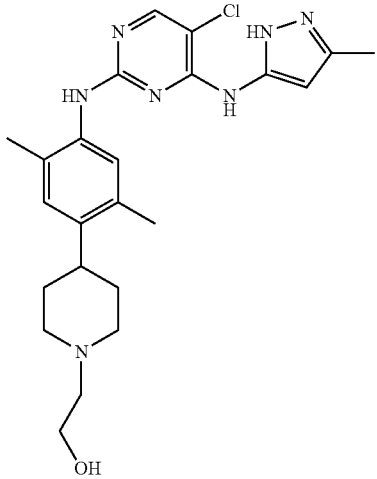

215

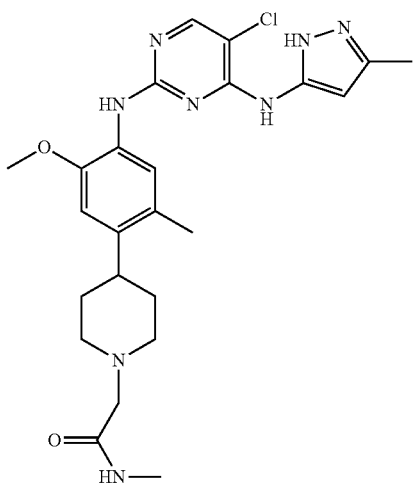

216

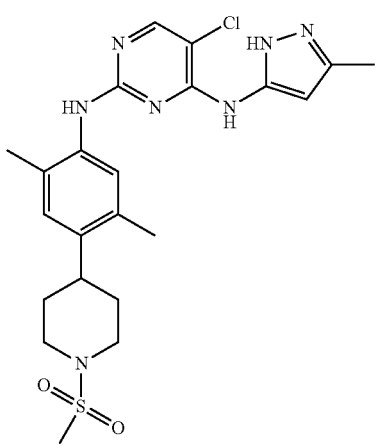

217

TABLE 17-continued

Compounds as ALK kinase inhibitors (final products)

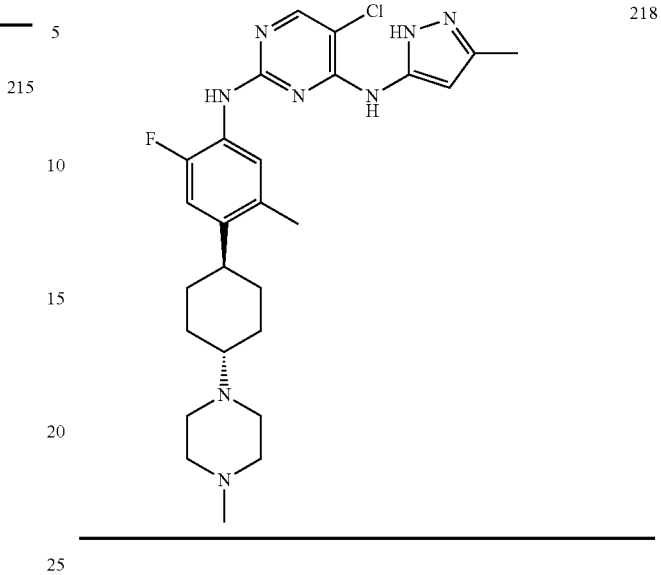

218

Example 320: Inhibitory Activities of the Compounds of the Present Invention on ALK Kinases 1. Inhibitory Activities of the Compounds of the Present Invention on Wild Type ALK Kinases

[experimental method] HTRF KinEASE™-TK Assay kit from Cisbio company was used to detect inhibitory activities of the compounds on wildtype ALK kinases (wild type ALK kinases).

[instrument] Envision 2104 plate reader from PerKinElmer company.

[experiment material] HTRF KinEASE™-TK Assay Kit (Cisbio company, catalog No. 62TK0PEC); Wild Type ALK kinase (produced by Sino-US Crown Bioscience, Inc., batch number ALK 20110607); DTT (Gibco BRL company, catalog No. 15508-012); MgCl$_2$ (Sigma Aldrich company, catalog No. M-2670); ATP (Sigma Aldrich company, catalog No. A-7699); DMSO (AMRESCO company, catalog No. 0231); EDTA (AMRESCO company, catalog No. 0105); 96 wells plates (for diluting compounds) (CITOTEST company, catalog No. Ref36020096D); OptiPlate™-384 (White), PerkinElmer company, catalog No. P12-004)

[experimental condition] Compounds (the final concentration of DMSO was 1%), the reaction substrate (the final concentration was 1 μM), ATP (the final concentration was 2004), and Wildtype ALK kinases (the final concentration was 1 ng/μl) were mixed respectively in a final volume of 10 μl reaction system (containing 5 mM MgCl$_2$, 1× Kinase buffer, and 1 mM DTT). The mixture was reacted at 30° C. for 35 minutes after shaking for 30 seconds. After completion of the reaction, each well was added with 5 μl Sa-XL665 and 5 μl TK Antibody-Eu(K), and placed in the dark for 60 minutes to end the reaction after uniform mixing. The data was read from PerkinElmer EnVision plate reader (615 nM, 665 nM), the 665/615 ratio was calculated, and the data was analyzed.

[tested samples] Compounds from the examples.

[data analysis] Minimum 665/615 ratio (R$_{min}$, 665/615 ratio under the condition that 10.4 μM positive control drug LDK-378 was added)

Maximum 665/615 ratio ($R_{max}$, 665/615 ratio under the condition that no compound was added)

Tested 665/615 ratio ($R_{compound}$, 665/615 ratio under the condition that a given concentration of compound was added)

Inhibition rate (%)=[1−($R_{compound}$−$R_{min}$)/($R_{max}$−$R_{min}$)]×100

【data processing】 IC50 of compounds was calculated by using XLfit program in Excel.

2. Inhibitory Activities of the Compounds of the Present Invention on L1196M Mutant ALK Kinases 【experimental method】 HTRF KinEASE™-TK Assay kit from Cisbio company was used to detect inhibitory activities of the compounds on L1196M mutant ALK kinases.

【instrument】 Envision 2104 plate reader from PerKinElmer company.

【experiment material】 HTRF KinEASE™-TK Assay Kit (Cisbio company, catalog No. 62TK0PEC); L1196M mutant ALK kinase (produced by Sino-US Crown Bioscience, Inc., batch number ALKm_20110923); DTT (Gibco BRL company, catalog No. 15508-012); MgCl$_2$ (Sigma Aldrich company, catalog No. M-2670); ATP (Sigma Aldrich company, catalog No. A-7699, batch number 051M7014V); DMSO (AMRESCO company, catalog No. 0231); EDTA (AMRESCO company, catalog No. 0105); 96 wells plates (for diluting compounds) (CITOTEST company, catalog No. Ref36020096D); OptiPlate™-384 (White), PerkinElmer company, catalog No. P12-004)

【experimental condition】 Compounds (the final concentration of DMSO was 1%), the reaction substrate (the final concentration was 1 µM), ATP (the final concentration was 5 µM), and L1196M mutant ALK kinases (the final concentration was 1 ng/µl) were mixed respectively in a final volume of 10 µl reaction system (containing 5 mM MgCl$_2$, 1× Kinase buffer, and 1 mM DTT). The mixture was reacted at 30° C. for 35 minutes after shaking for 30 seconds. After completion of the reaction, each well was added with 5 µl Sa-XL665 and 5 µl TK Antibody-Eu(K), and placed in the dark for 60 minutes to end the reaction after uniform mixing. The data was read from PerkinElmer EnVision plate reader (615 nM, 665 nM), the 665/615 ratio was calculated, and the data was analyzed.

【tested samples】 Compounds from the examples.

【data analysis】 Minimum 665/615 ratio ($R_{min}$, 665/615 ratio under the condition that 10.4 µM positive control drug LDK-378 was added)

Maximum 665/615 ratio ($R_{max}$, 665/615 ratio under the condition that no compound was added)

Tested 665/615 ratio ($R_{compound}$, 665/615 ratio under the condition that a given concentration of compound was added)

Inhibition rate (%)=[1−($R_{compound}$−$R_{min}$)/($R_{max}$−$R_{min}$)]×100

【data processing】 IC50 of compounds was calculated by using XLfit program in Excel.

3. Cell Proliferation Inhibitory Activities of the Compounds of the Present Invention on NCI-H2228 Cell Line 【experimental method】 CellTiter-Glo® Luminescent Cell Viability Assay kit from Promega company was used to detect cell proliferation inhibitory activities of the compounds on NCI-H2228 cell line.

【instrument】 Envision 2104 plate reader from PerKinElmer company; Vi-Cell XR cell counter from Beckman Counter company; MCO-18AIC CO2 incubator from SANYO company.

【experiment material】 CellTiter-Glo® Luminescent Cell Viability Assay Kit (Promega company, catalog No. G7573); NCI-H2228 cell line (ATCC, catalog No. CRL-5935); RPMI-1640 medium (HyClone company, catalog No. SH30809.01B); fetal bovine serum (FBS) (Gibco company, catalog No. 10099-141); trypsin (Trypsin) (Gibco company, catalog No. 25200-072); PBS (HyClone company, catalog No. SH30256.01B); 96 wells cell culture plate (Corning company, catalog No. 3610); DMSO (AMRESCO company, catalog No. 0231); 96 wells plates (for diluting compounds) (CITOTEST company, catalog No. Ref36020096D);

【experimental condition】 NCI-H2228 cells in exponential growth phase were collected and treated with trypsin (Trypsin), and viable cells were counted by Vi-Cell XR cell counter. Cell suspension was adjusted to 62500 cells/ml with culture medium (RPMI-1640+10% FBS). 80 µl cell suspension was added into each well of 96 wells cell culture plate so that the final cell number of NCI-H2228 cells was 5000 cells/well. The cells were cultivated in an incubator with an atmosphere of 37° C., 5% CO$_2$ and 95% humidity for 2 hours and then each well was added with 20 µl compounds in RPMI-1640 medium solution (the final concentration of DMSO was 0.5%). 4 days after drug treatment, each well was added with 50 µl CellTiter-Glo solution which was previously thawed and equilibrated to room temperature, and mixed for 2 minutes with microplate shaker. After placing at room temperature for 10 minutes, luminescence value was measured by PerkinElmer Envision 2104 plate reader and the data was analyzed.

【tested samples】 Compounds of the examples.

【data analysis】 Luminescence value of DMSO solvent control ($V_{vehicle\ control}$, which is the mean luminescence value from DMSO solvent control group)

Tested luminescence value ($V_{sample}$, which is the luminescence value from given concentration of compounds group)

Inhibition rate (%)=(1−$V_{sample}$/$V_{vehicle\ control}$)×100

【data processing】 IC50 of compounds was calculated by using XLfit program in Excel.

4. Cell Proliferation Inhibitory Activities of the Compounds of the Present Invention on Karpas-299 Cell Line 【experimental method】 CellTiter-Glo® Luminescent Cell Viability Assay kit from Promega company was used to detect cell proliferation inhibitory activities of the compounds on Karpas-299 cell line.

【instrument】 Envision 2104 plate reader from PerKinElmer company; Vi-Cell XR cell counter from Beckman Counter company; MCO-18AIC CO$_2$ incubator from SANYO company.

【experiment material】 CellTiter-Glo® Luminescent Cell Viability Assay Kit (Promega company, catalog No. G7573); Karpas-299 cell line (DSMZ, catalog No. ACC31); RPMI-1640 medium (HyClone company, catalog No. SH30809.01B); fetal bovine serum (FBS) (Gibco company, catalog No. 10099-141); PBS (HyClone company, catalog No. SH30256.01B); 96 wells cell culture plate (Corning company, catalog No. 3610); DMSO (AMRESCO company, catalog No. 0231); 96 wells plates (for diluting compounds) (CITOTEST company, catalog No. Ref36020096D);

【experimental condition】 Karpas-299 cells in exponential growth phase were collected and viable cells were counted by Vi-Cell XR cell counter. Cell suspension was adjusted to 62500 cells/ml with culture medium (RPMI-1640+10% FBS). 80 µl cell suspension was added into each well of 96 wells cell culture plate so that so that the final cell number of Karpas-299 cells was 5000 cells/well. The cells were cultivated in an incubator with an atmosphere of 37° C., 5% CO$_2$ and 95% humidity for 2 hours and then each well was added with 20 μl compounds in RPMI-1640 medium solution (the final concentration of DMSO was 0.5%). 4 days after drug treatment, each well was added with 50 μl CellTiter-Glo solution which was previously thawed and equilibrated to room temperature, and mixed for 2 minutes with microplate shaker. After placing at room temperature for 10 minutes, luminescence reading value was measured with PerkinElmer Envision 2104 plate reader and the data was analyzed.

【tested samples】Compounds of the examples.

Luminescence value of DMSO solvent control ($V_{vehicle\ control}$, which is the mean luminescence value from DMSO solvent control group)

Tested luminescence value ($V_{sample}$, which is the luminescence value from given concentration of compounds group)

$$\text{Inhibition rate (\%)} = (1 - V_{sample}/V_{vehicle\ control}) \times 100$$

【data processing】IC50 of compounds was calculated by using XLfit program in Excel.

TABLE 18

In vitro assay results of final products 1-218 (IC50, nM)

| Final Products | Inhibition on ALK kinases (wildtype) | Inhibition on ALK kinases (L1196M mutant) | Inhibition on H2228 | Inhibition on Karpas-299 |
|---|---|---|---|---|
| 1 | 4 | 8 | 184 | 10 |
| 2 | 6 | 16 | 198 | 16 |
| 3 | 4 | 5 | 364 | 28 |
| 4 | 4 | 13 | 288 | 60 |
| 5 | 6 | 12 | 248 | 37 |
| 6 | 3 | 7 | 193 | 24 |
| 7 | 8 | 12 | 224 | 21 |
| 8 | 9 | 10 | 562 | 67 |
| 9 | 16 | 35 | 652 | 119 |
| 10 | 7 | 13 | 188 | 20 |
| 11 | 22 | 39 | 641 | 61 |
| 12 | 10 | 17 | 262 | 43 |
| 13 | 3 | 7 | 58 | 7 |
| 14 | 4 | 6 | 168 | 19 |
| 15 | 3 | 5 | 48 | 9 |
| 16 | 4 | 7 | 39 | 8 |
| 17 | 11 | 13 | 278 | 36 |
| 18 | 2 | 4 | 157 | 28 |
| 19 | 3 | 8 | 138 | 16 |
| 20 | 9 | 34 | 384 | 56 |
| 21 | 1 | 2 | 62 | 10 |
| 22 | 2 | 12 | 115 | 14 |
| 23 | 4 | 8 | 107 | 38 |
| 24 | 2 | 4 | 122 | 9 |
| 25 | 2 | 5 | 190 | 12 |
| 26 | 5 | 6 | 217 | 16 |
| 27 | 3 | 6 | 168 | 19 |
| 28 | 9 | 15 | 134 | 19 |
| 29 | 4 | 7 | 159 | 35 |
| 30 | 7 | 18 | 93 | 25 |
| 31 | 6 | 10 | 374 | 20 |
| 32 | 22 | 49 | 1078 | 74 |
| 33 | 12 | 28 | 660 | |
| 34 | 10 | 23 | 403 | 62 |
| 35 | 2 | 5 | 270 | 17 |
| 36 | 8 | 15 | 326 | 62 |
| 37 | 7 | 4 | 131 | 11 |
| 38 | 11 | 18 | 146 | 22 |
| 39 | 15 | 48 | 226 | 74 |
| 40 | 3 | 5 | 36 | 7 |
| 41 | 1 | 3 | 33 | 4 |
| 42 | 1 | 3 | 29 | 3 |
| 43 | 5 | 12 | 125 | 26 |
| 44 | 3 | 4 | 125 | 17 |
| 45 | 4 | 10 | 135 | 19 |
| 46 | 2 | 6 | 127 | |
| 47 | 4 | 10 | 103 | 15 |
| 48 | 2 | 5 | 115 | 41 |
| 49 | 8 | 13 | 165 | 100 |
| 50 | 5 | 7 | 86 | 11 |
| 51 | 2 | 4 | 52 | 6 |
| 52 | 2 | 15 | 76 | |
| 53 | 3 | 4 | 133 | 16 |
| 54 | 3 | 5 | 18 | 7 |
| 55 | 4 | 8 | 181 | 25 |
| 56 | 5 | 11 | 142 | 21 |
| 57 | 7 | 11 | 108 | 12 |
| 58 | 4 | 6 | 55 | 11 |
| 59 | | | 156 | 52 |
| 60 | | | 28 | |
| 61 | | | 85 | |
| 62 | | | 122 | |
| 63 | | | 31 | |
| 64 | | | 31 | |
| 65 | | | 38 | |
| 66 | | | 59 | |
| 67 | 6 | 21 | 172 | 32 |
| 68 | | | 150 | |
| 69 | | | 178 | |
| 70 | 2 | 18 | 81 | |
| 71 | | | 199 | |
| 72 | 1 | 6 | 69 | |
| 73 | | | 151 | |
| 74 | | | 19 | |
| 75 | | | 109 | |
| 76 | | | 215 | |
| 77 | 2 | 4 | 25 | 4 |
| 78 | | | 128 | |
| 79 | 3 | 8 | 62 | 12 |
| 80 | 4 | 8 | 96 | 10 |
| 81 | 11 | 25 | 190 | 27 |
| 82 | 4 | 7 | 43 | 14 |
| 83 | | | 53 | 11 |
| 84 | | | 46 | |
| 85 | | | 77 | |
| 86 | | | 120 | |
| 87 | 6 | 10 | 113 | 13 |
| 88 | 6 | 15 | 72 | 17 |
| 89 | | | 108 | |
| 90 | 1 | 4 | 45 | 5 |
| 91 | | | 75 | |
| 92 | 2 | 5 | 48 | |
| 93 | | | 67 | |
| 94 | | | 79 | |
| 95 | 2 | 3 | 26 | 4 |
| 96 | | | 85 | |
| 97 | | | 154 | |
| 98 | | | 240 | |
| 99 | | | 58 | |
| 100 | | | 61 | 6 |
| 101 | | | 26 | |
| 102 | | | 103 | |
| 103 | | | 66 | 10 |
| 104 | | | 70 | |
| 105 | | | 63 | |
| 106 | | | 34 | |
| 107 | 9 | 19 | 174 | 18 |
| 108 | | | 33 | |
| 109 | | | 109 | |
| 110 | | | 97 | |
| 111 | 3 | 7 | 188 | 16 |
| 112 | | | 211 | |
| 113 | 6 | 22 | 150 | |
| 114 | | | 70 | 10 |
| 115 | | | 94 | |
| 116 | | | 34 | |
| 117 | | | 158 | |
| 118 | 5 | 10 | 101 | 9 |
| 119 | | | 193 | |

TABLE 18-continued

In vitro assay results of final products 1-218 (IC50, nM)

| Final Products | Inhibition on ALK kinases (wildtype) | Inhibition on ALK kinases (L1196M mutant) | Inhibition on H2228 | Inhibition on Karpas-299 |
|---|---|---|---|---|
| 120 | | | 93 | |
| 121 | | | 168 | |
| 122 | | | 79 | |
| 123 | 2 | 5 | 58 | 9 |
| 124 | | | 86 | |
| 125 | | | 47 | |
| 126 | 7 | 12 | 142 | 12 |
| 127 | 5 | 12 | 142 | 30 |
| 128 | | | 128 | |
| 129 | | | 32 | |
| 130 | | | 28 | |
| 131 | | | 52 | |
| 132 | | | 207 | |
| 133 | 2 | 6 | 41 | 4 |
| 134 | | | 134 | |
| 135 | 3 | 7 | 33 | 3 |
| 136 | | | 112 | |
| 137 | 4 | 11 | 103 | 12 |
| 138 | 4 | 8 | 60 | 6 |
| 139 | | | 90 | |
| 140 | | | 105 | |
| 141 | | | 147 | |
| 142 | | | 140 | |
| 143 | | | 32 | |
| 144 | | | 48 | |
| 145 | | | 54 | |
| 146 | 2 | 5 | 199 | 15 |
| 147 | | | 41 | |
| 148 | | | 44 | |
| 149 | | | 57 | |
| 150 | | | 43 | |
| 151 | | | 70 | |
| 152 | 4 | 9 | 86 | 7 |
| 153 | | | 60 | |
| 154 | | | 128 | |
| 155 | | | 75 | |
| 156 | 10 | 10 | 44 | 19 |
| 157 | 7 | 11 | 142 | 13 |
| 158 | | | 170 | |
| 159 | 9 | 9 | 43 | 11 |
| 160 | 7 | 9 | 35 | 14 |
| 161 | 32 | 43 | 47 | 27 |
| 162 | 19 | 21 | 34 | 24 |
| 163 | 26 | 29 | 149 | |
| 164 | 56 | 56 | 87 | 15 |
| 165 | 2 | 3 | 35 | 3 |
| 166 | 3 | 6 | 42 | 8 |
| 167 | 9 | 11 | 59 | 18 |
| 168 | 14 | 25 | 440 | 68 |
| 169 | 68 | 43 | 133 | |
| 170 | 40 | 95 | 381 | 86 |
| 171 | 86 | 156 | 251 | 69 |
| 172 | 8 | 9 | 111 | 17 |
| 173 | 37 | 28 | 34 | 19 |
| 174 | 4 | 6 | 82 | 20 |
| 175 | | | 256 | |
| 176 | | | 91 | |
| 177 | | | 73 | |
| 178 | 18 | 17 | 101 | 18 |
| 179 | | | 137 | |
| 180 | 35 | 40 | 127 | 26 |
| 181 | | | 106 | |
| 182 | 14 | 22 | 89 | 15 |
| 183 | | | 172 | |
| 184 | | | 188 | |
| 185 | | | 296 | |
| 186 | | | 253 | |
| 187 | | | 111 | |
| 188 | 5 | 8 | 89 | 10 |
| 189 | 4 | 7 | 76 | 6 |
| 190 | | | 115 | |
| 191 | 8 | 17 | 60 | 9 |
| 192 | 9 | 12 | 68 | 8 |
| 193 | | | 116 | |
| 194 | | | 78 | |
| 195 | | | 116 | |
| 196 | 9 | 18 | 88 | 9 |
| 197 | | | 72 | |
| 198 | 5 | 9 | 54 | 5 |
| 199 | | | 225 | |
| 200 | | | 210 | |
| 201 | | | 149 | |
| 202 | | | 141 | |
| 203 | | | 189 | |
| 204 | 7 | 18 | 76 | 7 |
| 205 | 16 | 20 | 151 | 18 |
| 206 | | | 81 | |
| 207 | | | 154 | |
| 208 | 6 | 36 | 152 | 35 |
| 209 | 3 | 9 | 71 | |
| 210 | 2 | 4 | 87 | |
| 211 | 3 | 11 | 272 | |
| 212 | 13 | 37 | 725 | |
| 213 | 19 | 22 | 964 | |
| 214 | 22 | 54 | 1240 | |
| 215 | 28 | 39 | 1038 | |
| 216 | 17 | 28 | 948 | |
| 217 | 20 | 69 | 1134 | |
| 218 | 27 | 49 | 1068 | |

What is claimed is:

1. A compound of Formula I or pharmaceutically acceptable salts thereof,

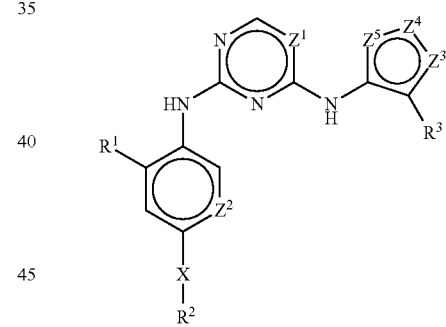

Formula I wherein $R^1$ is alkyl, haloalkyl or —O—$R^4$, wherein $R^4$ is hydrogen, $C_{1-8}$ alkyl, halo $C_{1-8}$ alkyl, $C_{3-8}$ cycloalkyl, halo $C_{3-8}$ cycloalkyl, $C_{1-8}$ alkyl-$C_{3-8}$ cycloalkyl, $C_{3-8}$ cycloalkyl-$C_{1-8}$ alkyl, substituted or unsubstituted heterocyclyl, or substituted or unsubstituted heterocyclyl —$C_{1-8}$ alkyl;

$R^2$ is alkyl, cycloalkyl, heterocycloalkyl or heterocycloalkenyl, which may optionally be substituted with 1 to 3 substituents independently selected from the group consisting of oxo, $C_{1-8}$ alkyl, halo $C_{1-8}$ alkyl, $C_{1-8}$ alkoxy, halo $C_{1-8}$ alkoxy, $C_{3-8}$ cycloalkyl, halo $C_{3-8}$ cycloalkyl, $C_{3-8}$ cycloalkoxy, halo $C_{3-8}$ cycloalkoxy, $C_{1-8}$ alkoxy-$C_{1-8}$ alkyl, hydroxy-$C_{1-8}$ alkyl, amino-$C_{1-8}$ alkyl, carboxy-$C_{1-8}$ alkyl, $C_{1-8}$ alkyl-amino-$C_{1-8}$ alkyl, halogen, hydroxy, cyano, cyano-$C_{1-8}$ alkyl, amino, $C_{1-8}$-alkylamino, di ($C_{1-8}$ alkyl)-amino, $C_{3-8}$ cycloalkyl amino, substituted or unsubstituted aromatic group, substituted or unsubstituted heteroaromatic group, substituted or unsubstituted heterocyclyl, substituted or unsubstituted heterocyclyl-alkyl, $(CH_2)_n CONR^5R^6$, —$COR^5$, —$SO_2R^5$ and —$NR^5SO_2R^6$, wherein n is an integer of 0-8, $R^5$ and $R^6$ are independently hydrogen, alkyl, haloalkyl, cycloalkyl, halocycloalkyl, amino, $C_{1-8}$ alkyl-amino, di ($C_{1-8}$ alkyl)-amino, cyano-$C_{1-8}$ alkyl, $C_{1-8}$ alkyl-amino-$C_{1-8}$ alkyl or di ($C_{1-8}$ alkyl)-amino-$C_{1-8}$ alkyl, wherein the substituents may optionally form a ring with the carbon atoms to which they are attached;

$R^3$ is-$SO_2R^7$, —$SO_2NR^7R^8$, —CN, —$CONR^7R^8$, or —$COR^7$, wherein $R^7$ and $R^8$ are independently hydrogen, alkyl or cycloalkyl;

X is a chemical bond, O, S, CO, $NR^9$, $SO_2$ or S(O), wherein $R^9$ is hydrogen, $C_{1-8}$ alkyl, halo $C_{1-8}$ alkyl, $C_{3-8}$ cycloalkyl, halo $C_{3-8}$ cycloalkyl, $C_{1-8}$ alkyl-CO or 4-6 membered heterocyclyl;

$Z^1$ is N or C—$R^{10}$, wherein $R^{10}$ is hydrogen, halogen, alkyl, haloalkyl, cycloalkyl, halocycloalkyl, alkoxy, haloalkoxy or cyano;

$Z^2$ is C—$R^{11}$ or N, wherein $R^{11}$ is hydrogen, $C_{1-8}$ alkyl, halo $C_{1-8}$ alkyl, $C_{3-8}$ cycloalkyl, halo $C_{3-8}$ cycloalkyl, $C_{1-8}$ alkoxy, halo $C_{1-8}$ alkoxy, $C_{3-8}$ cycloalkoxy, halo $C_{3-8}$ cycloalkoxy, halogen, amino, $C_{1-8}$ alkyl-amino, di($C_{1-8}$ alkyl)-amino or cyano, wherein $R^{11}$ anti $R^2$ may optionally form a 5- or 6-membered ring fused to the phenyl ring together with the atoms to which they are attached, the ring may be optionally substituted with 1 to 3 substituents independently selected from the group consisting of oxo, $C_{1-8}$ alkyl, halo $C_{1-8}$ alkyl, $C_{1-8}$ alkoxy, halo $C_{1-8}$ alkoxy, $C_{3-3}$ cycloalkyl, halo $C_{3-8}$ cycloalkyl, $C_{3-8}$ cycloalkoxy, halo $C_{3-8}$ cycloalkoxy, $C_{1-8}$ alkoxy-$C_{1-8}$ alkyl, hydroxy-$C_{1-8}$ alkyl, amino-$C_{1-8}$ alkyl, carboxy-$C_{1-8}$ alkyl, $C_{1-8}$ alkyl-amino-$C_{1-8}$ alkyl, halogen, hydroxy, cyano, cyano-$C_{1-8}$ alkyl, amino, $C_{1-8}$ alkyl-amino, di($C_{1-8}$ alkyl)-amino, $C_{3-8}$ cycloalkyl-amino, substituted or unsubstituted aromatic group, substituted or unsubstituted heteroaromatic group, substituted or unsubstituted heterocyclyl, substituted or unsubstituted heterocyclyl alkyl, $(CH_2)nCONR^{12}R^{13}$, —$SO_2R^{12}$ and —$NR^{12}SO_2R^{13}$, wherein n is an integer of 0-8, $R^{12}$ and $R^{13}$ are independently hydrogen, alkyl, haloalkyl, cycloalkyl, halocycloalkyl, amino, $C_{1-8}$ alkyl-amino, di($C_{1-8}$ alkyl)-amino, cyano-$C_{1-8}$ alkyl, $C_{1-8}$ alkyl-amino-$C_{1-8}$ alkyl or di($C_{1-8}$ alkyl)-amino-$C_{1-8}$ alkyl;

$Z^3$, $Z^4$ and $Z^5$ are selected from the following groups:
$Z^3$ is N, $Z^4$ is N—$R^{14}$, $Z^5$ is CH or N;
$Z^3$ is N, $Z^4$ is C—$R^{14}$, $Z^5$ is N, O or S;
$Z^3$ is O or S, $Z^4$ is N—$R^{14}$, $Z^5$ is CH;
$Z^3$ is O or S, $Z^4$ is C—$R^{14}$, $Z^5$ is N; and
$Z^3$ is C, $Z^4$ is N—$R^{14}$, $Z^5$ is O or S;
wherein $R^{14}$ is hydrogen, alkyl, haloalkyl, $C_{3-8}$ cycloalkyl, halo-$C_{3-8}$ cycloalkyl or 4-6 membered heterocyclyl.

2. The compound or pharmaceutically acceptable salts thereof according to claim 1, wherein $R^1$ is $C_{1-8}$ alkyl, $C_{1-8}$ halo alkyl or —O—$R^4$, wherein $R^4$ is hydrogen, $C_{1-8}$ alkyl, halo $C_{1-8}$ alkyl, $C_{3-8}$ cycloalkyl, halo $C_{3-8}$ cycloalkyl, $C_{1-8}$ alkyl-$C_{3-8}$ cycloalkyl, $C_{3-8}$ cycloalkyl-$C_{1-8}$ alkyl, substituted or unsubstituted 4-7 membered heterocyclyl or substituted or unsubstituted 4-7 membered heterocyclyl-$C_{1-8}$ alkyl.

3. The compound or pharmaceutically acceptable salts thereof according to claim 1, wherein $R^2$ is $C_{1-8}$ alkyl, $C_{3-8}$ cycloalkyl, 4-7 membered heterocycloalkyl or 4-7 membered heterocycloalkenyl, which may optionally be substituted by 1-3 substituents independently selected from the group consisting of oxo, $C_{1-8}$ alkyl, halo $C_{1-8}$ alkyl, $C_{1-8}$ alkoxy, halo $C_{1-8}$ alkoxy, $C_{3-8}$ cycloalkyl, halo $C_{3-8}$ cycloalkyl, $C_{3-8}$ cycloalkoxy, halo-$C_{3-8}$ cycloalkoxy, $C_{1-8}$ alkoxy-$C_{1-8}$ alkyl, hydroxy-$C_{1-8}$ alkyl, amino-$C_{1-8}$ alkyl, carboxy-$C_{1-8}$ alkyl, $C_{1-8}$ alkyl-amino-$C_{1-8}$ alkyl, halogen, hydroxy, cyano, cyano-$C_{1-8}$ alkyl, amino, $C_{1-8}$ alkyl-amino, di ($C_{1-8}$ alkyl)-amino, $C_{3-8}$ cycloalkyl-amino, substituted or unsubstituted aromatic group, substituted or unsubstituted heteroaromatic group, substituted or unsubstituted 4-7 membered heterocyclyl, substituted or unsubstituted 4-7 membered heterocyclyl-$C_{1-8}$ alkyl, —$(CH_2)_n CONR^5R^6$, —$COR^5$, —$SO_2R^5$ and —$NR^5SO_2R^6$, wherein n is an integer of 0-8, $R^5$ and $R^6$ are independently hydrogen, $C_{1-8}$ alkyl, halo $C_{1-8}$ alkyl, $C_{3-8}$ cycloalkyl, halo $C_{3-8}$ cycloalkyl, amino, $C_{1-8}$ alkyl-amino, di ($C_{1-8}$ alkyl)-amino, cyano-$C_{1-8}$ alkyl, $C_{1-8}$ alkyl-amino —$C_{1-8}$ alkyl or di- ($C_{1-8}$ alkyl)-amino-$C_{1-8}$ alkyl, wherein the substituent groups and the carbon atoms to which they are attached form a substituted or unsubstituted ring.

4. The compound or pharmaceutically acceptable salts thereof according to claim 1, wherein $R^3$ is —$SO_2R^7$, —$SO_2NR^7R^8$, —CN, —$CONR^7R^8$, or —$COR^7$, wherein $R^7$ and $R^8$ are independently hydrogen, $C_{1-8}$ alkyl or $C_{3-8}$ cycloalkyl.

5. The compound or pharmaceutically acceptable salts thereof according to claim 1, wherein X is a chemical bond or CO.

6. The compound or pharmaceutically acceptable salts thereof according to claim 1, wherein $Z^1$ is C—$R^{10}$, wherein $R^{10}$ is hydrogen, halogen, $C_{1-8}$ alkyl, halo $C_{1-8}$ alkyl, $C_{3-8}$ cycloalkyl, halo $C_{3-8}$ cycloalkyl, $C_{1-8}$ alkoxy, halo $C_{1-8}$ alkoxy, or cyano.

7. The compound or pharmaceutically acceptable salts thereof according to claim 1, wherein $Z^2$ is C—$R^{11}$, wherein $R^{11}$ is hydrogen, $C_{1-8}$ alkyl, halogen or cyano, wherein $R^{11}$ and $R^2$ may optionally together form a 5- or 6-membered ring fused to the phenyl ring with the atoms to which they are attached, the ring may be optionally substituted with 1-3 substituents independently selected from the group consisting of: oxo, $C_{1-8}$ alkyl, halo $C_{1-8}$ alkyl, $C_{1-8}$ alkoxy, halo $C_{1-8}$ alkoxy, $C_{3-8}$ cycloalkyl, halo $C_{3-8}$ cycloalkyl, $C_{3-8}$ cycloalkoxy, halo $C_{3-8}$ cycloalkoxy, $C_{1-8}$ alkoxy-$C_{1-8}$ alkyl, hydroxy-$C_{1-8}$ alkyl, amino-$C_{1-8}$ alkyl, carboxyl-$C_{1-8}$ alkyl, $C_{1-8}$ alkyl-amino-$C_{1-8}$ alkyl, halogen, hydroxy, cyano, cyano-$C_{1-8}$ alkyl, amino, $C_{1-8}$ alkyl-amino, di ($C_{1-8}$ alkyl) amino, $C_{3-8}$ cycloalkyl-amino, substituted or unsubstituted aromatic group, substituted or unsubstituted heteroaromatic group, substituted or unsubstituted heterocyclyl, substituted or unsubstituted heterocyclyl-alkyl, —$(CH_2)_n$—$CONR^{12}R^{13}$, —$COR^{12}$, —$SO_2R^{12}$ and —$NR^{12}SO_2R^{13}$, wherein n is an integer of 0-8, $R^{12}$ and $R^{13}$ are independently hydrogen, alkyl, haloalkyl, cycloalkyl, halocycloalkyl, amino, $C_{1-8}$ alkyl-amino, di ($C_{1-8}$ alkyl)-amino, cyano alkyl-amino-$C_{1-8}$ alkyl or di- ($C_{1-8}$ alkyl)-amino-$C_{1-8}$ alkyl.

8. The compound or pharmaceutically acceptable salts thereof according to claim 1, wherein $Z^3$, $Z^4$ and $Z^5$ are selected from the following groups:
$Z^3$ is N, $Z^4$ is N—$R^{14}$, $Z^5$ is CH or N;
$Z^3$ is N, $Z^4$ is C—$R^{14}$, $Z^5$ is N, O or S;
$Z^3$ is O or S, $Z^4$ is N—$R^{14}$, $Z^5$ is CH;
$Z^3$ is O or S, $Z^4$ is C—$R^{14}$, $Z^5$ is N; and
$Z^3$ is C, $Z^4$ is N—$R^{14}$, $Z^5$ is O or S,
wherein $R^{14}$ is hydrogen, $C_{1-8}$ alkyl, $C_{3-8}$ cycloalkyl, halo $C_{3-8}$ cycloalkyl, 4-6 membered heterocyclyl containing 1 or 2 heteroatoms selected from the group consisting of N, O and S or halo 4-6 membered heterocyclyl containing 1 or 2 heteroatoms selected from the group consisting of N, O and S.

9. The compound or pharmaceutically acceptable salts thereof according to claim 1, wherein $Z^3$ is N, $Z^4$ is N—$R^{14}$, $Z^5$ is CH, wherein $R^{14}$ is hydrogen, $C_{1-8}$ alkyl, $C_{3-8}$ cycloalkyl, halo $C_{3-8}$ cycloalkyl, 4-6 membered heterocyclyl containing 1 or 2 heteroatoms selected from the group consisting of N, O and S or halo 4-6 membered heterocyclyl containing 1 or 2 heteroatoms selected from the group consisting of N, O and S.

10. The compound or pharmaceutically acceptable salts thereof according to claim 1, wherein $Z^3$ is N, $Z^4$ is C—$R^{14}$, $Z^5$ is S, wherein $R^{14}$ is $C_{1-8}$ alkyl or $C_{3-8}$ cycloalkyl.

11. The compound or pharmaceutically acceptable salts thereof according to claim 1, wherein the structures of the compounds are selected from the following:

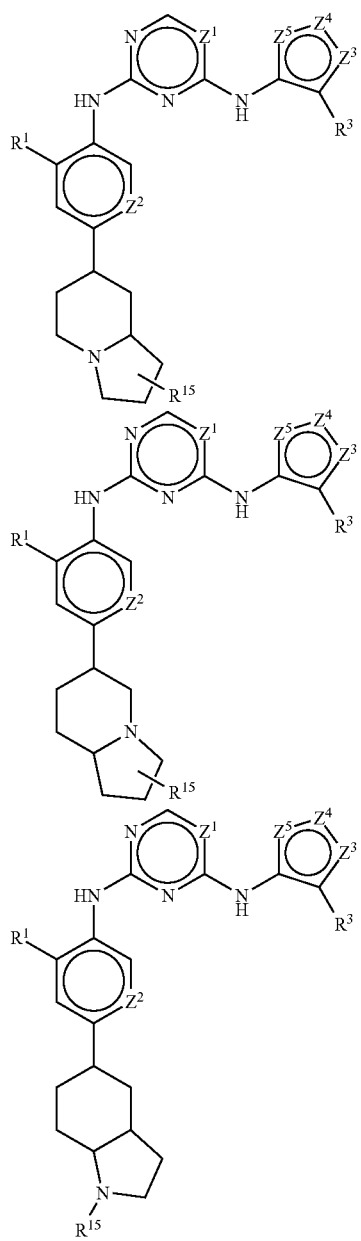

-continued

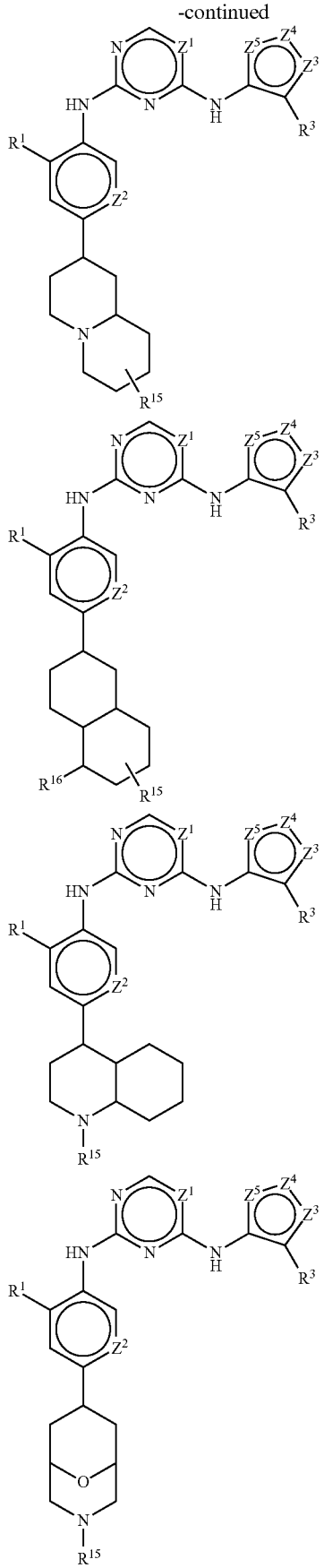

517

-continued

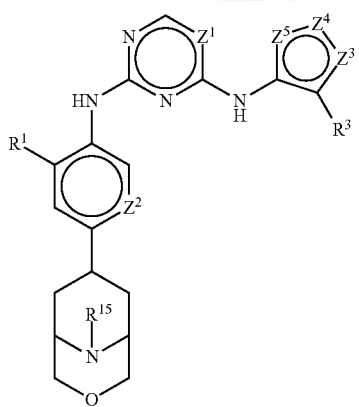

wherein $R^{15}$ and $R^{16}$ are independently $C_{1-8}$ alkyl, $C_{3-8}$ cycloalkyl, $C_{1-8}$ alkoxy-$C_{1-8}$ alkyl, hydroxy-$C_{1-8}$ alkyl, amino-$C_{1-8}$ alkyl, $C_{1-8}$ alkyl —CO, $C_{1-8}$ alkyl-amino-$C_{1-8}$ alkyl or di ($C_{1-8}$ alkyl)-amino-$C_{1-8}$ alkyl;

$R^1$, $R^3$, $Z^1$, $Z^2$, $Z^3$, $Z^4$, $Z^5$ are defined as with Formula I.

12. The compound or pharmaceutically acceptable salts thereof according to claim 1, wherein the structures of the compounds are selected from the following:

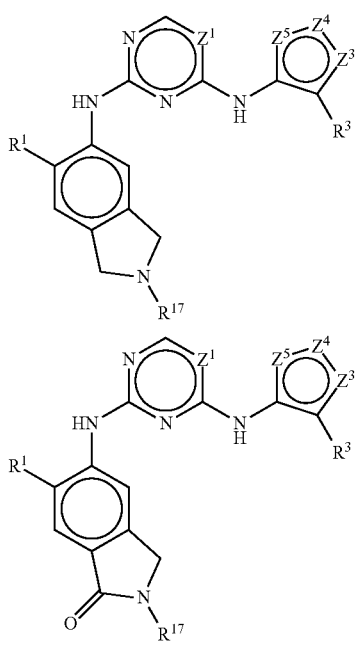

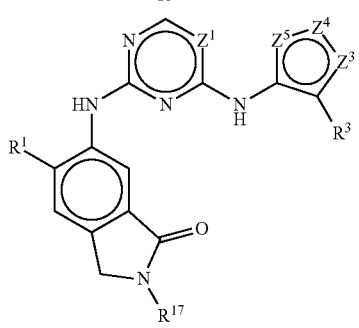

518

-continued

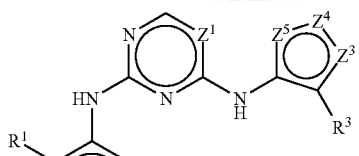

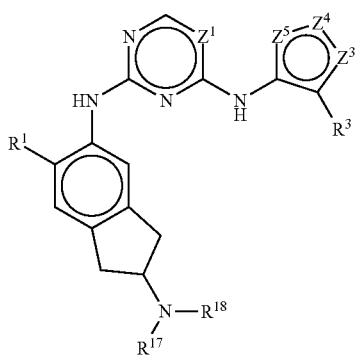

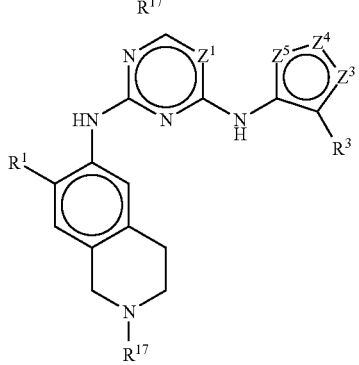

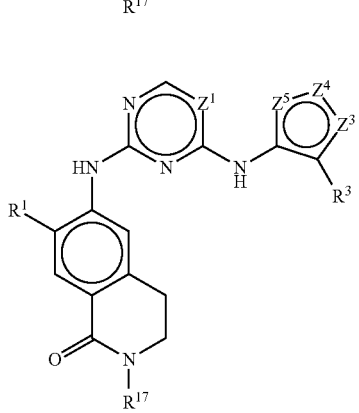

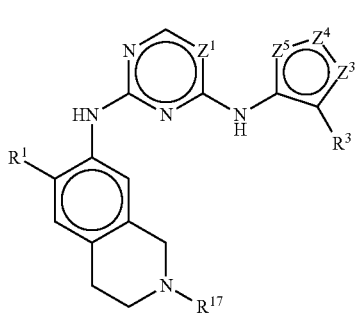

-continued
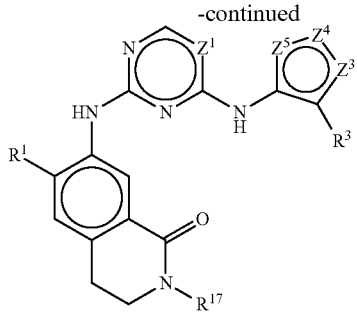
wherein R[17] and R[18] are independently $C_{1-8}$ alkyl, $C_{3-8}$ cycloalkyl, $C_{1-8}$ alkoxy-$C_{1-8}$ alkyl, hydroxy-$C_{1-8}$ alkyl, amino-$C_{1-8}$ alkyl, $C_{1-8}$ alkyl —CO, $C_{1-8}$ alkyl-amino-$C_{1-8}$ alkyl or di ($C_{1-8}$ alkyl)-amino-$C_{1-8}$ alkyl;
R[1], R[3], Z[1], Z[3], Z[4], Z[5] are defined as with Formula I.
13. A compound selected from the following:
1
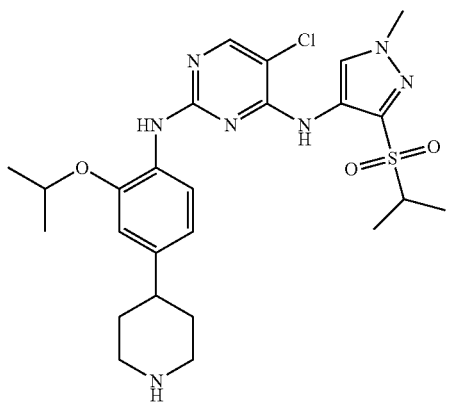 [SMILES: CC(C)Oc1cc(C2CCNCC2)ccc1Nc1ncc(Cl)c(Nc2cn(C)nc2S(=O)(=O)C(C)C)n1]
2
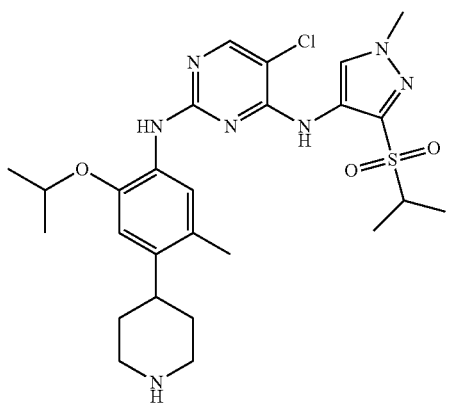 [SMILES: Cc1cc(Nc2ncc(Cl)c(Nc3cn(C)nc3S(=O)(=O)C(C)C)n2)c(OC(C)C)cc1C1CCNCC1]
3
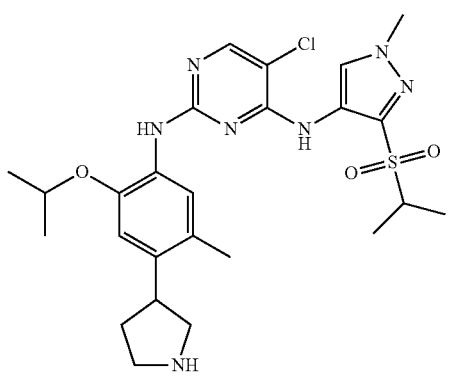 [SMILES: Cc1cc(Nc2ncc(Cl)c(Nc3cn(C)nc3S(=O)(=O)C(C)C)n2)c(OC(C)C)cc1C1CCNC1]
-continued
4
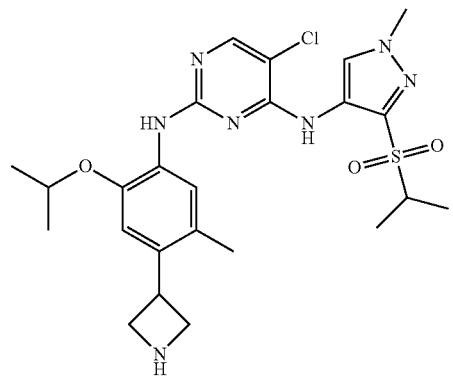 [SMILES: Cc1cc(Nc2ncc(Cl)c(Nc3cn(C)nc3S(=O)(=O)C(C)C)n2)c(OC(C)C)cc1C1CNC1]
5
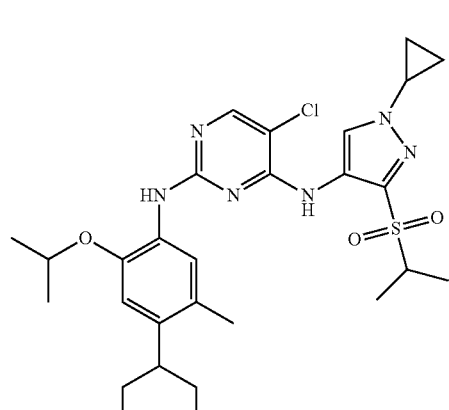
6
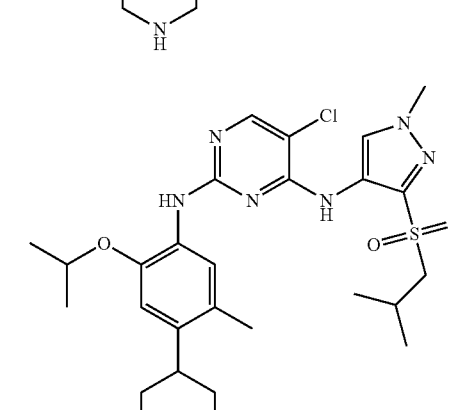
7
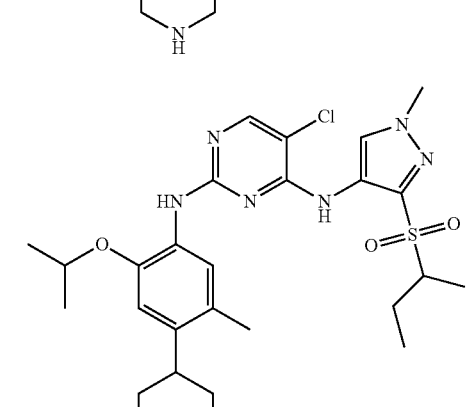

-continued
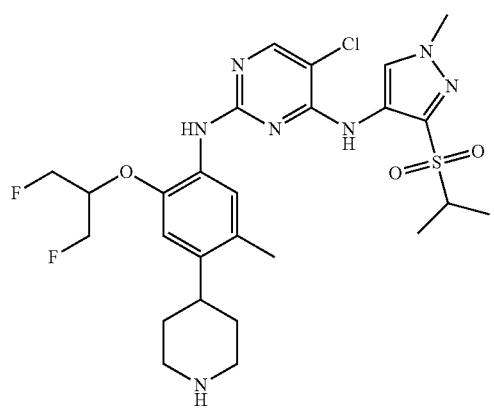 [SMILES: Cc1cc(Nc2ncc(Cl)c(Nc3cn(C)nc3S(=O)(=O)C(C)C)n2)c(OC(CF)CF)cc1C1CCNCC1]
8
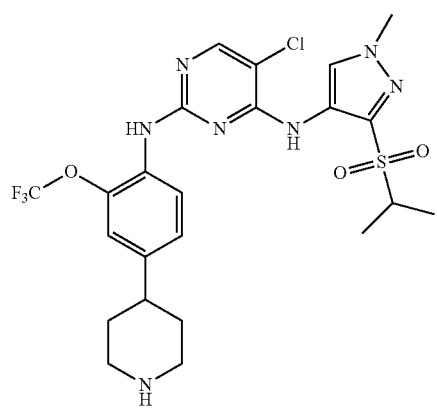 [SMILES: CC(C)S(=O)(=O)c1nn(C)cc1Nc1nc(Nc2ccc(C3CCNCC3)cc2OC(F)(F)F)ncc1Cl]
9
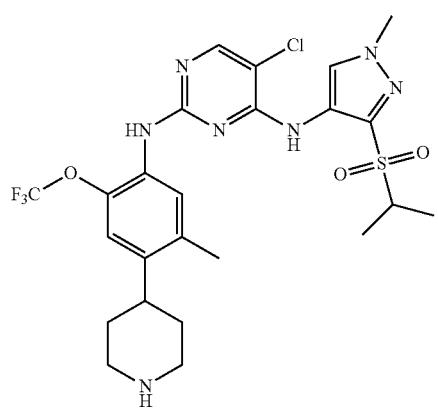 [SMILES: Cc1cc(Nc2ncc(Cl)c(Nc3cn(C)nc3S(=O)(=O)C(C)C)n2)c(OC(F)(F)F)cc1C1CCNCC1]
10
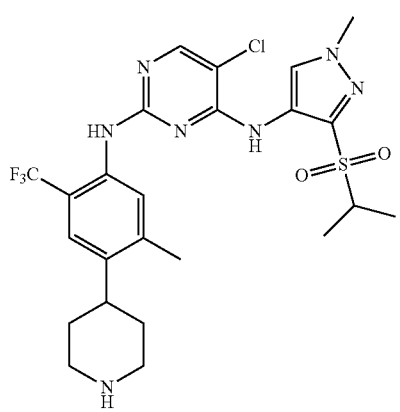 [SMILES: Cc1cc(Nc2ncc(Cl)c(Nc3cn(C)nc3S(=O)(=O)C(C)C)n2)c(C(F)(F)F)cc1C1CCNCC1]
11
-continued
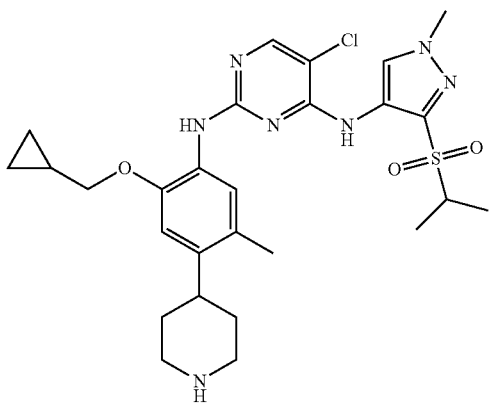 [SMILES: Cc1cc(Nc2ncc(Cl)c(Nc3cn(C)nc3S(=O)(=O)C(C)C)n2)c(OCC2CC2)cc1C1CCNCC1]
12
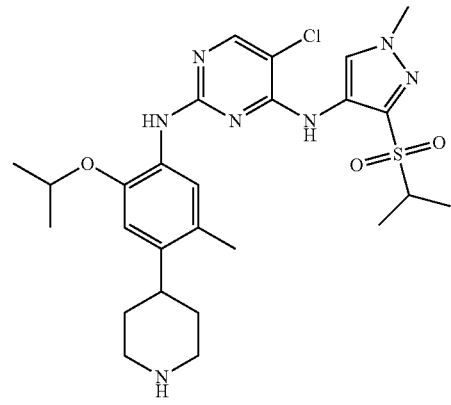
13
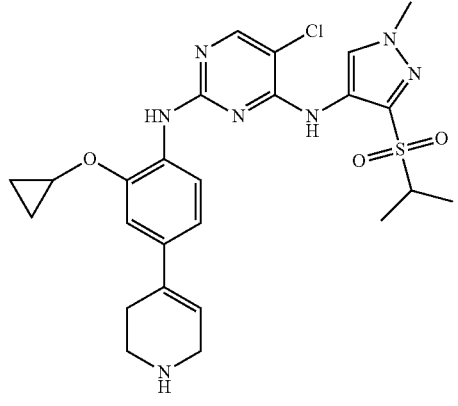 [SMILES: CC(C)S(=O)(=O)c1nn(C)cc1Nc1nc(Nc2ccc(C3=CCNCC3)cc2OC2CC2)ncc1Cl]
14
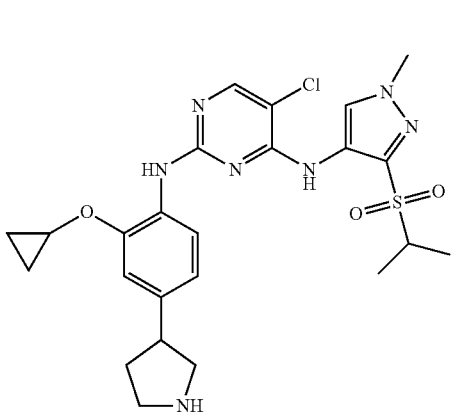 [SMILES: CC(C)S(=O)(=O)c1nn(C)cc1Nc1nc(Nc2ccc(C3CCNC3)cc2OC2CC2)ncc1Cl]
15

-continued
16
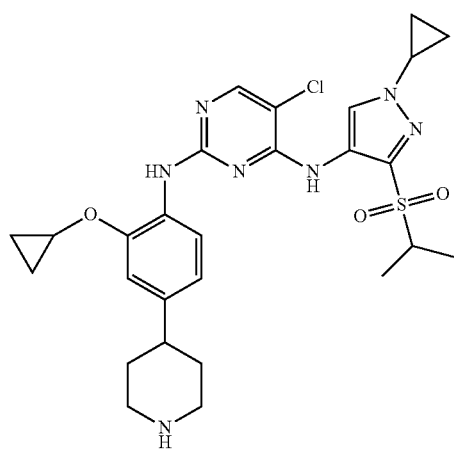 [SMILES: CC(C)S(=O)(=O)c1nn(C2CC2)cc1Nc1nc(Nc2ccc(C3CCNCC3)cc2OC2CC2)ncc1Cl]
17
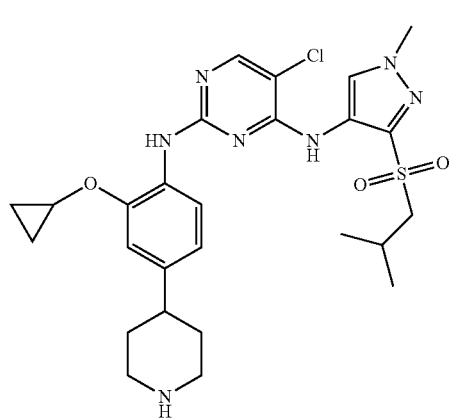 [SMILES: CC(C)CS(=O)(=O)c1nn(C)cc1Nc1nc(Nc2ccc(C3CCNCC3)cc2OC2CC2)ncc1Cl]
18
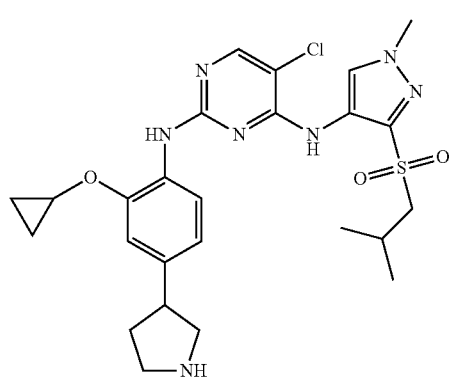 [SMILES: CC(C)CS(=O)(=O)c1nn(C)cc1Nc1nc(Nc2ccc(C3CCNC3)cc2OC2CC2)ncc1Cl]
19
-continued
20
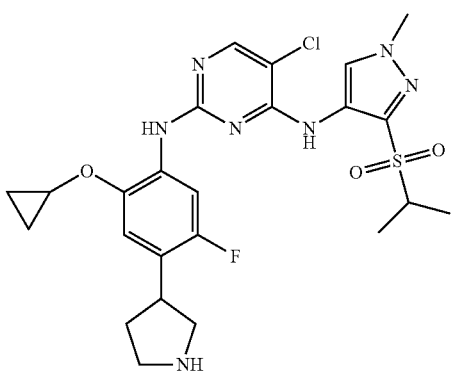
21
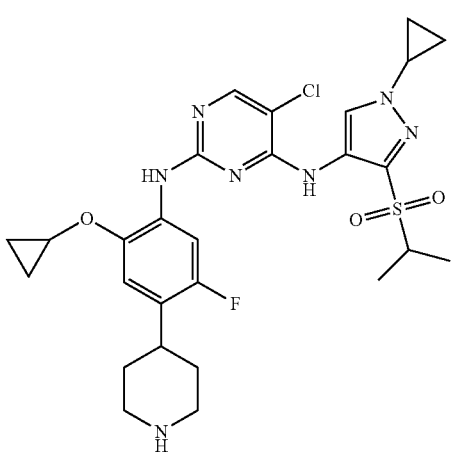
22
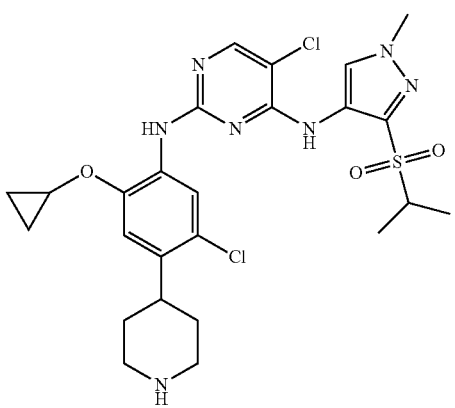

23
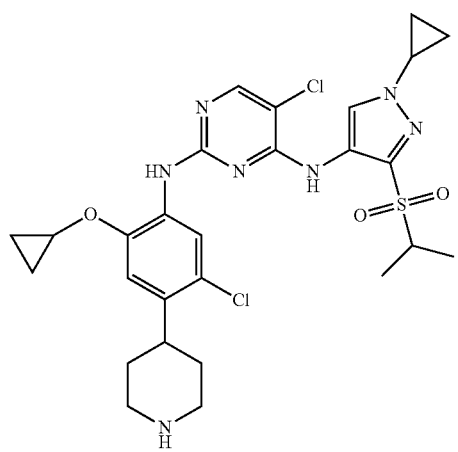 [SMILES: CC(C)S(=O)(=O)c1nn(C2CC2)cc1Nc1nc(Nc2cc(Cl)c(C3CCNCC3)cc2OC2CC2)ncc1Cl]
24
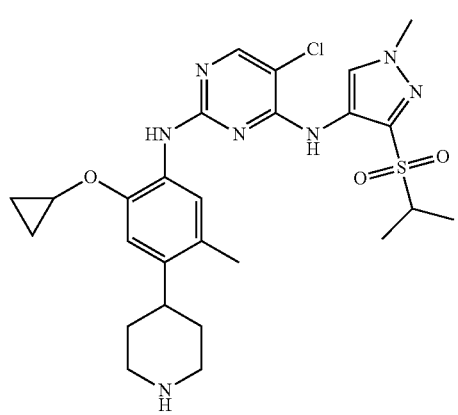 [SMILES: Cc1cc(Nc2ncc(Cl)c(Nc3cn(C)nc3S(=O)(=O)C(C)C)n2)c(OC2CC2)cc1C1CCNCC1]
25
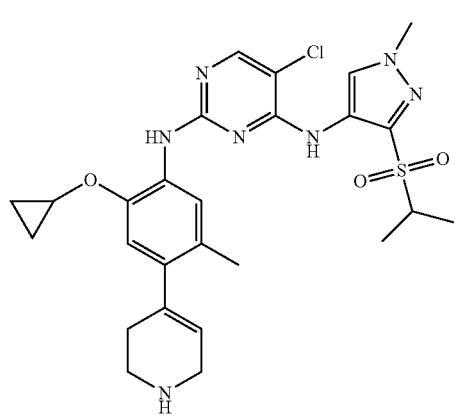 [SMILES: Cc1cc(Nc2ncc(Cl)c(Nc3cn(C)nc3S(=O)(=O)C(C)C)n2)c(OC2CC2)cc1C1=CCNCC1]
26
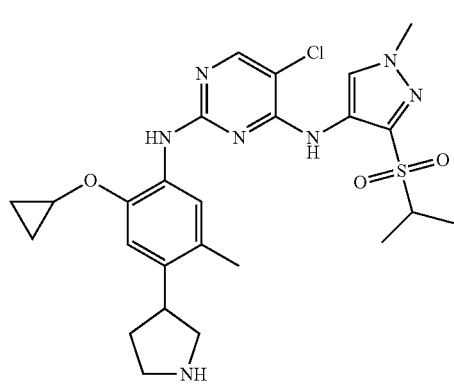 [SMILES: Cc1cc(Nc2ncc(Cl)c(Nc3cn(C)nc3S(=O)(=O)C(C)C)n2)c(OC2CC2)cc1C1CCNC1]
27
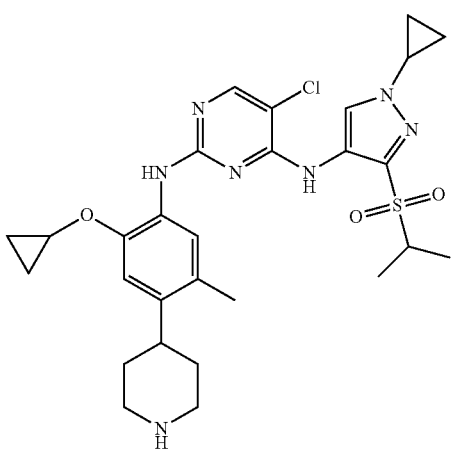 [SMILES: Cc1cc(Nc2ncc(Cl)c(Nc3cn(C4CC4)nc3S(=O)(=O)C(C)C)n2)c(OC2CC2)cc1C1CCNCC1]
28
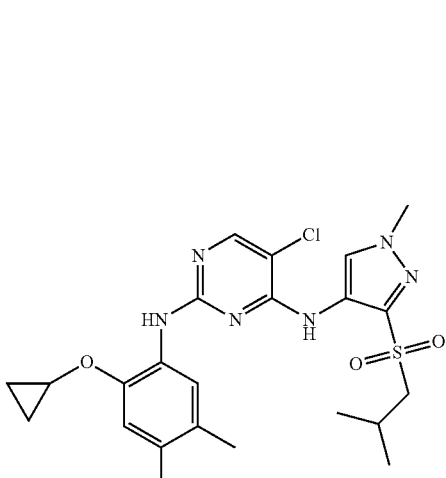
29
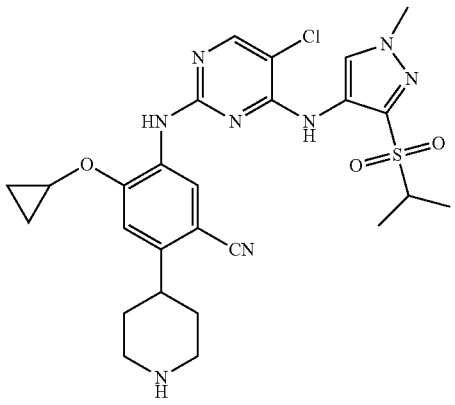

| 30 | 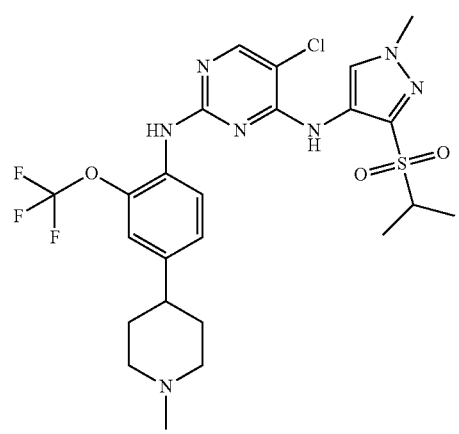 [SMILES: CC(C)S(=O)(=O)c1nn(C)cc1Nc1nc(Nc2ccc(C3CCN(C)CC3)cc2OC(F)(F)F)ncc1Cl] | 33 | 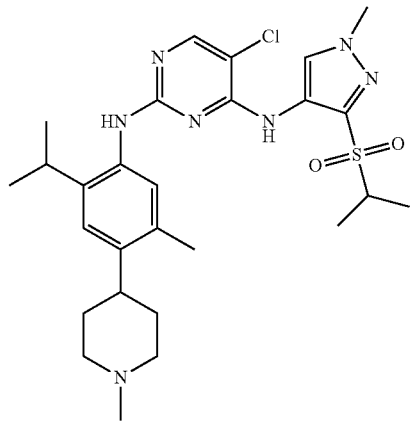 [SMILES: Cc1cc(Nc2ncc(Cl)c(Nc3cn(C)nc3S(=O)(=O)C(C)C)n2)c(C(C)C)cc1C1CCN(C)CC1] |
| 31 | 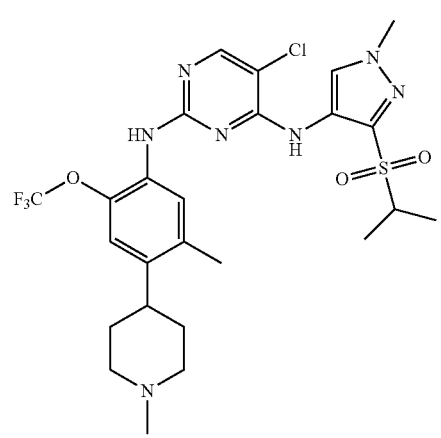 [SMILES: Cc1cc(Nc2ncc(Cl)c(Nc3cn(C)nc3S(=O)(=O)C(C)C)n2)c(OC(F)(F)F)cc1C1CCN(C)CC1] | 34 | 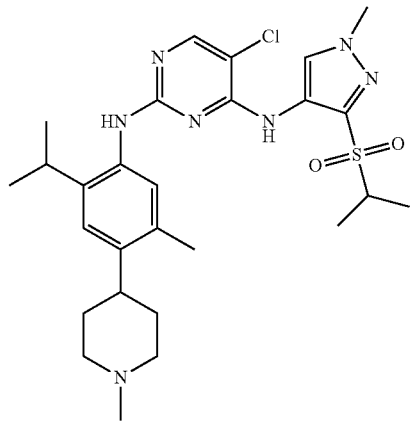 [SMILES: Cc1cc(Nc2ncc(Cl)c(Nc3cn(C)nc3S(=O)(=O)C(C)C)n2)c(C(C)C)cc1C1CCN(C)CC1] |
| 32 | 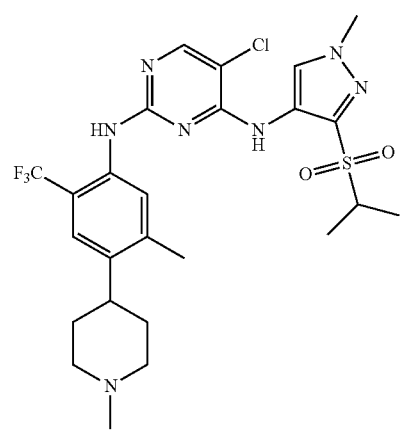 | 35 | 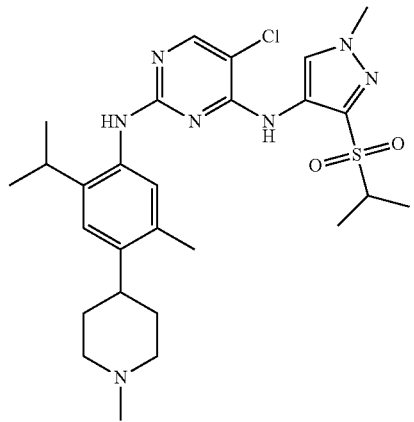 |
| | | 36 | 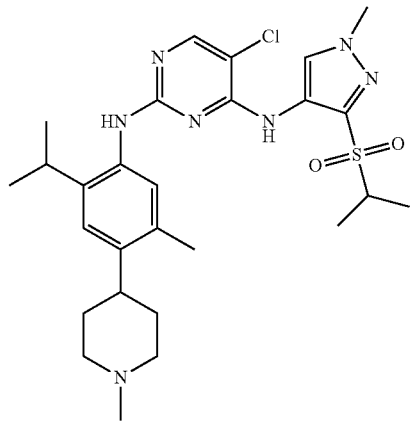 [SMILES: Cc1cc(Nc2ncc(Cl)c(Nc3cn(C)nc3S(=O)(=O)C(C)C)n2)c(C(C)C)cc1C1CCN(C)CC1] |

37
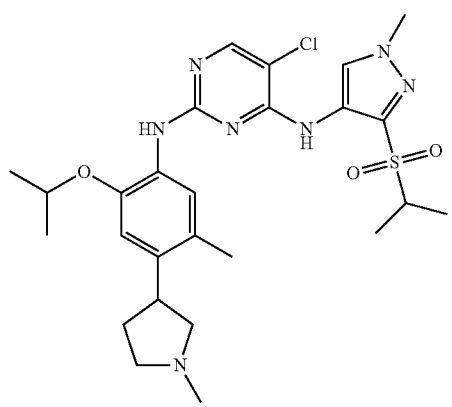 [SMILES: Cc1cc(Nc2ncc(Cl)c(Nc3cn(C)nc3S(=O)(=O)C(C)C)n2)c(OC(C)C)cc1C1CCN(C)C1]
38
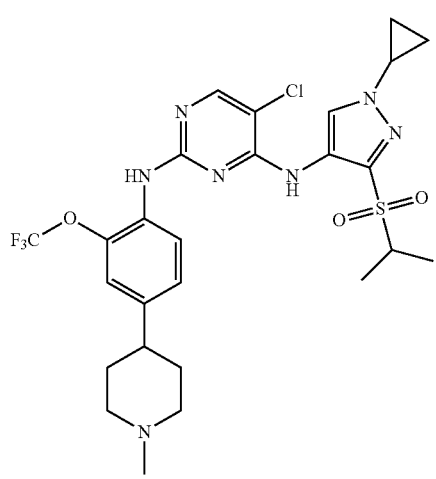 [SMILES: CC(C)S(=O)(=O)c1nn(C2CC2)cc1Nc1nc(Nc2ccc(C3CCN(C)CC3)cc2OC(F)(F)F)ncc1Cl]
39
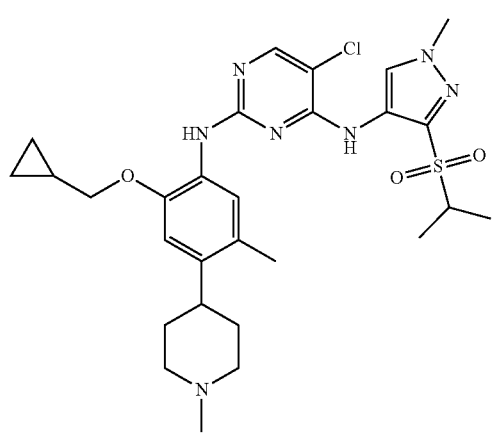 [SMILES: Cc1cc(Nc2ncc(Cl)c(Nc3cn(C)nc3S(=O)(=O)C(C)C)n2)c(OCC2CC2)cc1C1CCN(C)CC1]
40
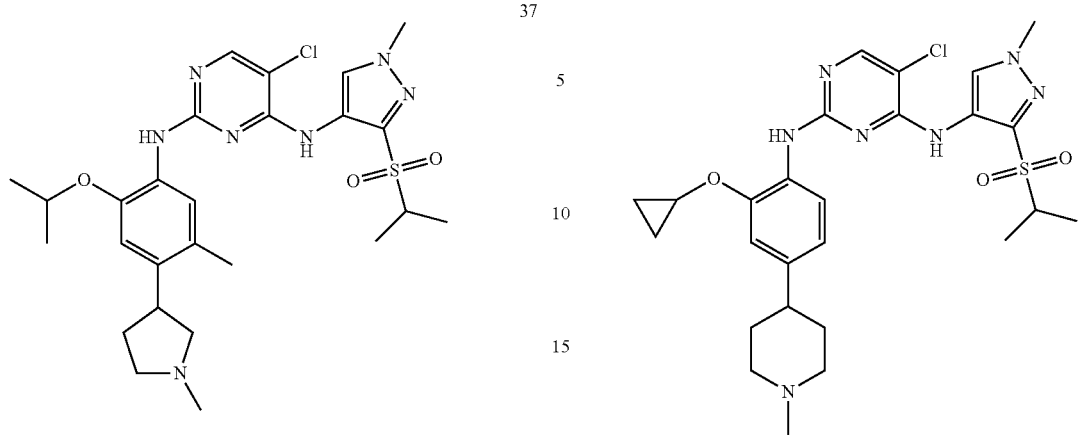
41
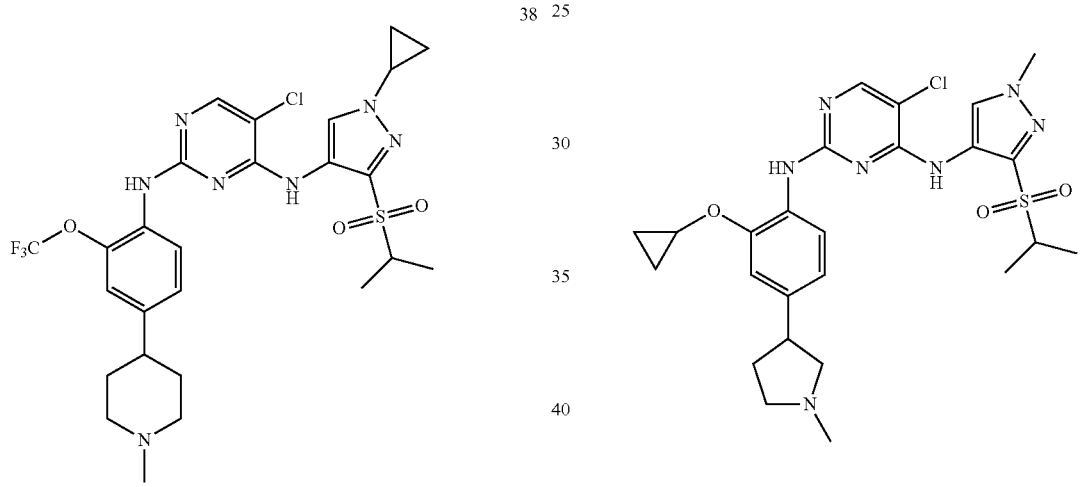
42
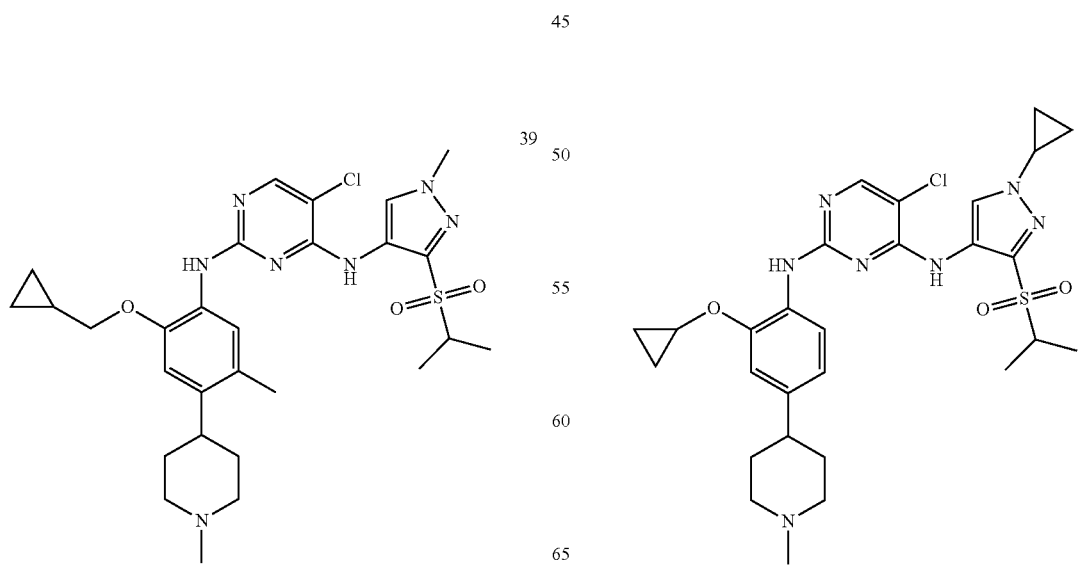

-continued
43
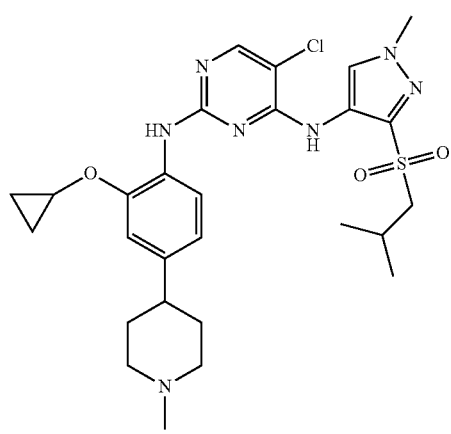 [SMILES: CC(C)CS(=O)(=O)c1nn(C)cc1Nc1nc(Nc2ccc(C3CCN(C)CC3)cc2OC2CC2)ncc1Cl]
44
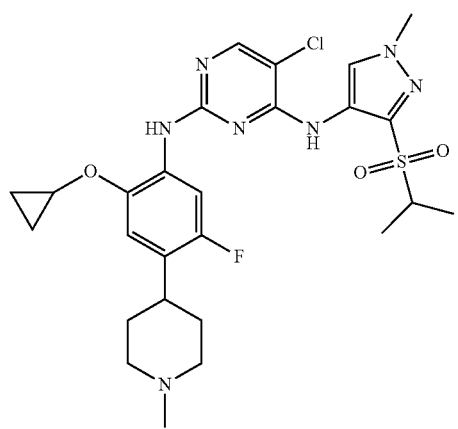 [SMILES: CC(C)S(=O)(=O)c1nn(C)cc1Nc1nc(Nc2cc(F)c(C3CCN(C)CC3)cc2OC2CC2)ncc1Cl]
45
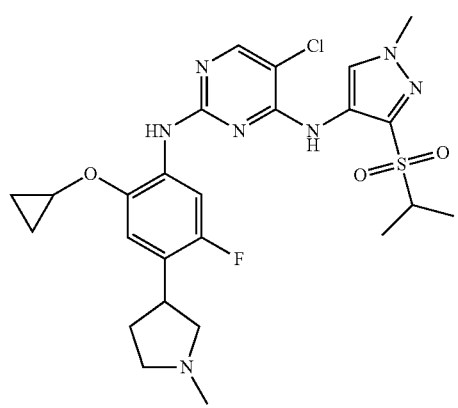 [SMILES: CC(C)S(=O)(=O)c1nn(C)cc1Nc1nc(Nc2cc(F)c(C3CCN(C)C3)cc2OC2CC2)ncc1Cl]
-continued
46
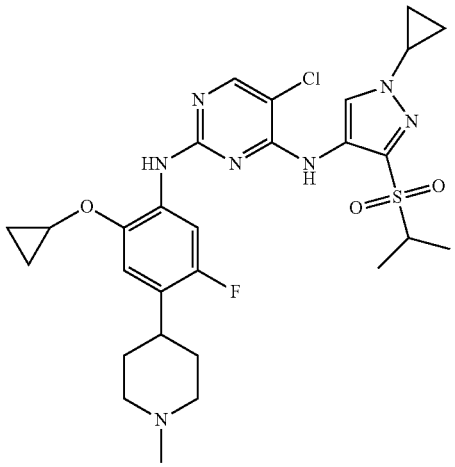
47
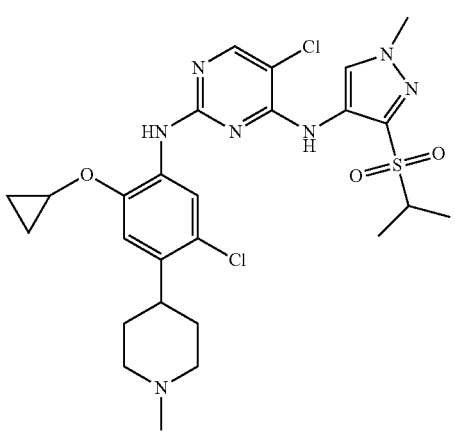
48
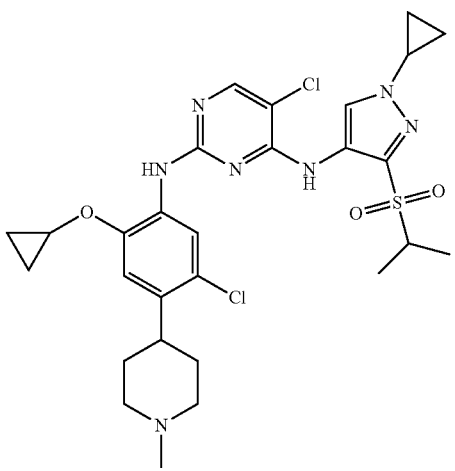

49
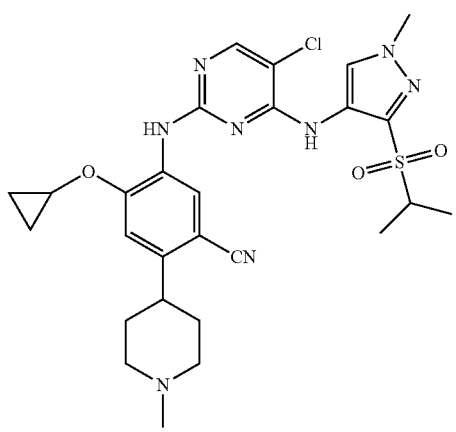 [SMILES: CC(C)S(=O)(=O)c1nn(C)cc1Nc1nc(Nc2cc(C#N)c(C3CCN(C)CC3)cc2OC2CC2)ncc1Cl]
50
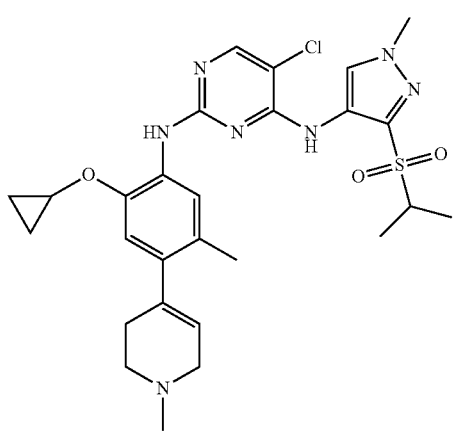 [SMILES: Cc1cc(Nc2ncc(Cl)c(Nc3cn(C)nc3S(=O)(=O)C(C)C)n2)c(OC2CC2)cc1C1=CCN(C)CC1]
51
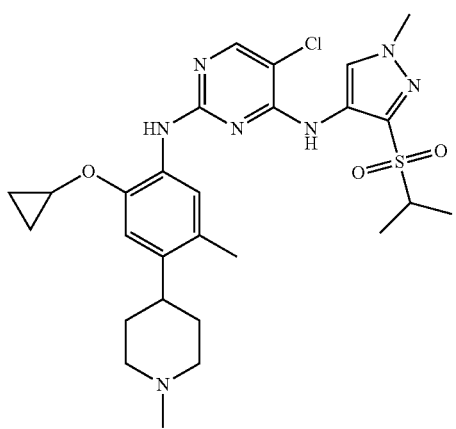 [SMILES: Cc1cc(Nc2ncc(Cl)c(Nc3cn(C)nc3S(=O)(=O)C(C)C)n2)c(OC2CC2)cc1C1CCN(C)CC1]
52
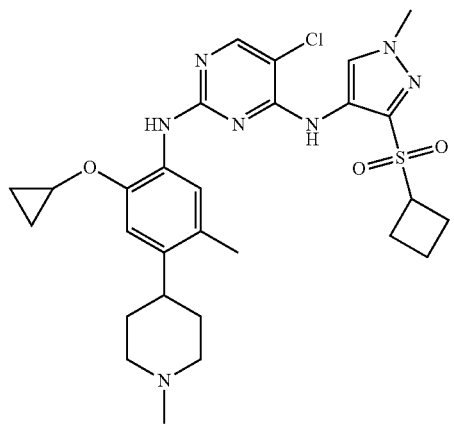 [SMILES: Cc1cc(Nc2ncc(Cl)c(Nc3cn(C)nc3S(=O)(=O)C3CCC3)n2)c(OC2CC2)cc1C1CCN(C)CC1]
53
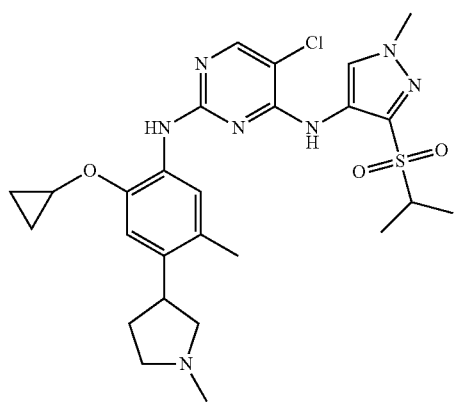 [SMILES: Cc1cc(Nc2ncc(Cl)c(Nc3cn(C)nc3S(=O)(=O)C(C)C)n2)c(OC2CC2)cc1C1CCN(C)C1]
54
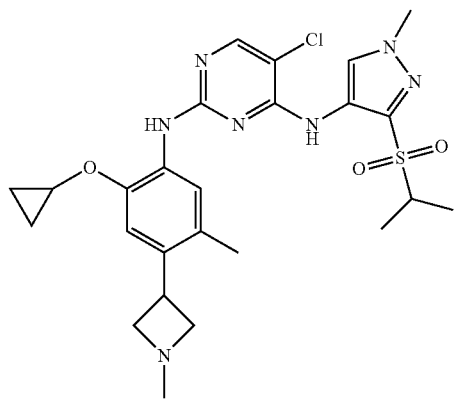 [SMILES: Cc1cc(Nc2ncc(Cl)c(Nc3cn(C)nc3S(=O)(=O)C(C)C)n2)c(OC2CC2)cc1C1CN(C)C1]
55
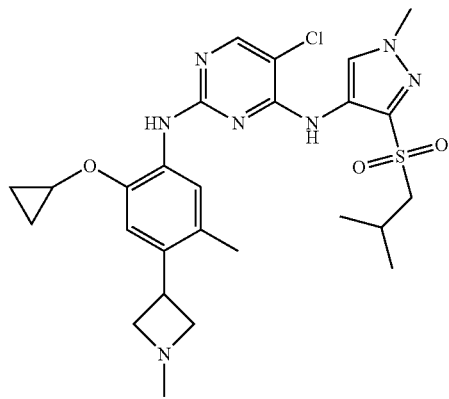 [SMILES: Cc1cc(Nc2ncc(Cl)c(Nc3cn(C)nc3S(=O)(=O)CC(C)C)n2)c(OC2CC2)cc1C1CN(C)C1]

535
-continued
56
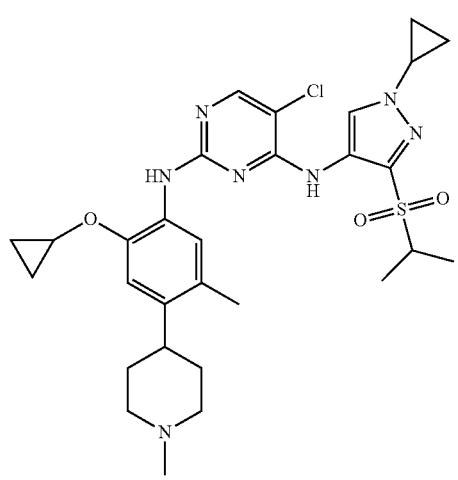 [SMILES: Cc1cc(Nc2ncc(Cl)c(Nc3cn(C4CC4)nc3S(=O)(=O)C(C)C)n2)c(OC2CC2)cc1C1CCN(C)CC1]
57
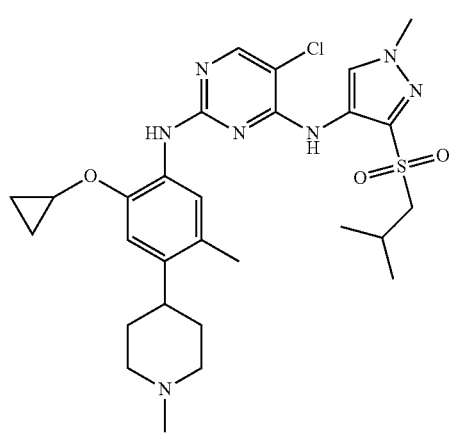 [SMILES: Cc1cc(Nc2ncc(Cl)c(Nc3cn(C)nc3S(=O)(=O)CC(C)C)n2)c(OC2CC2)cc1C1CCN(C)CC1]
58
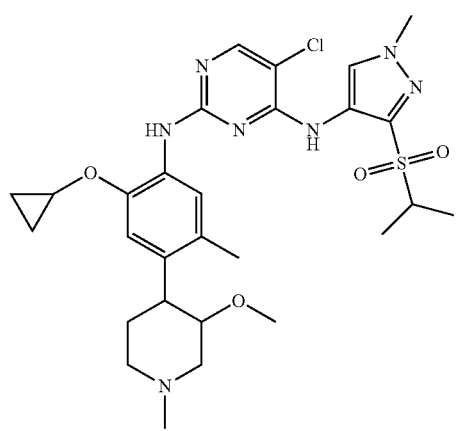 [SMILES: COC1CN(C)CCC1c1cc(OC2CC2)c(Nc2ncc(Cl)c(Nc3cn(C)nc3S(=O)(=O)C(C)C)n2)cc1C]
536
-continued
59
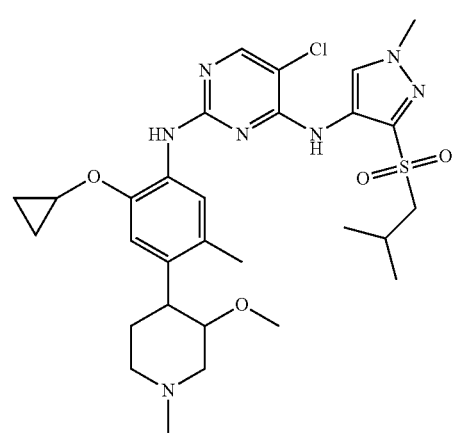 [SMILES: COC1CN(C)CCC1c1cc(OC2CC2)c(Nc2ncc(Cl)c(Nc3cn(C)nc3S(=O)(=O)CC(C)C)n2)cc1C]
60
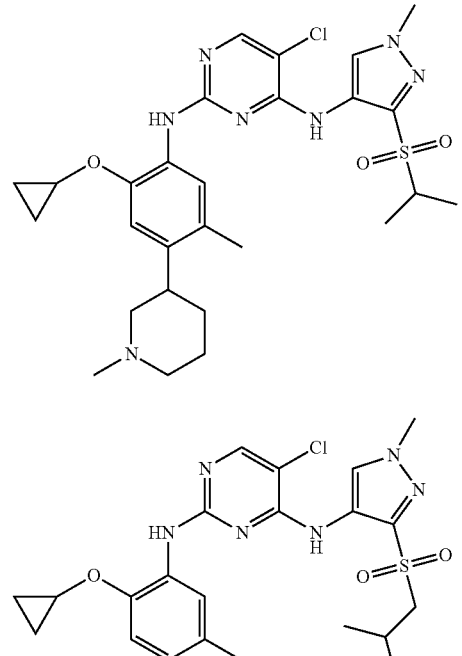
61
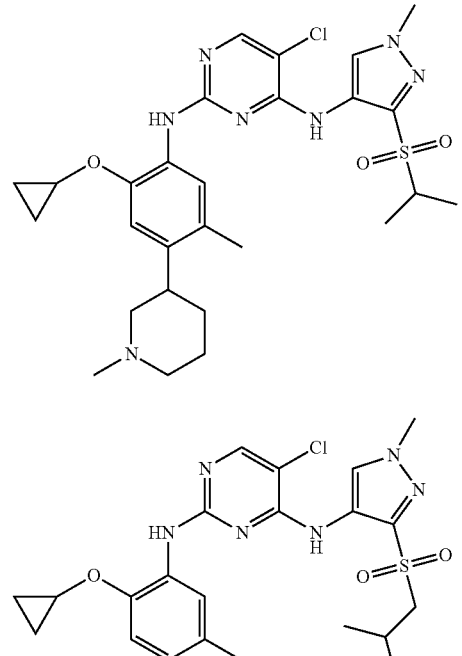
62
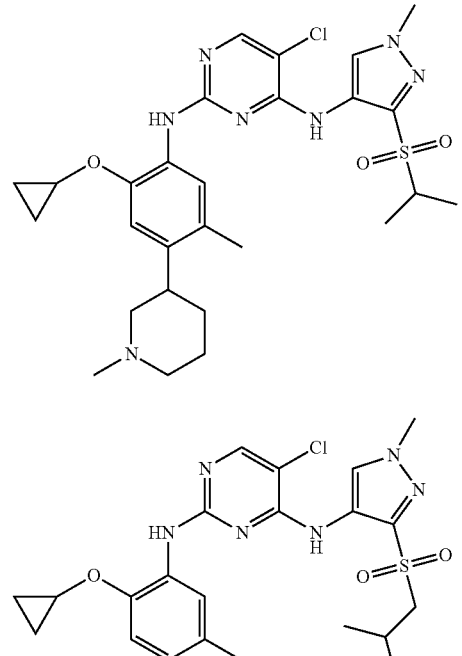

537
63
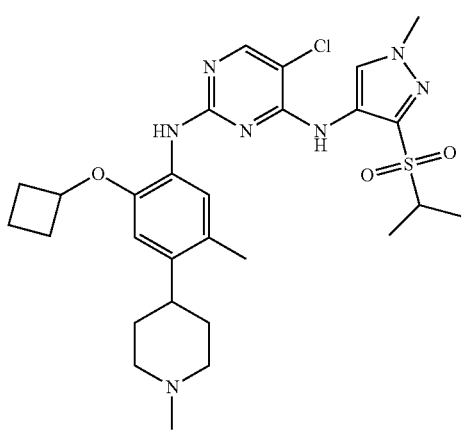 [SMILES: Cc1cc(Nc2ncc(Cl)c(Nc3cn(C)nc3S(=O)(=O)C(C)C)n2)c(OC2CCC2)cc1C1CCN(C)CC1]
64
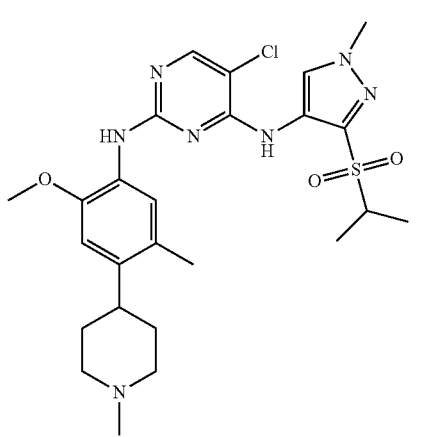 [SMILES: COc1cc(C2CCN(C)CC2)c(C)cc1Nc1ncc(Cl)c(Nc2cn(C)nc2S(=O)(=O)C(C)C)n1]
65
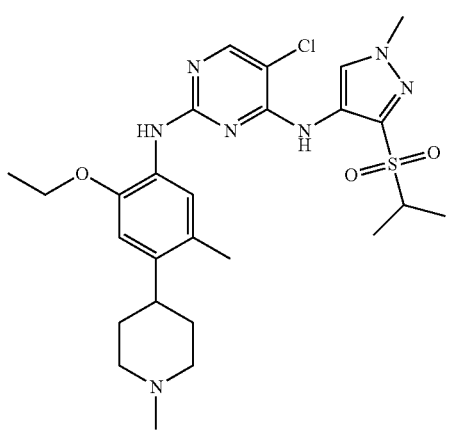 [SMILES: CCOc1cc(C2CCN(C)CC2)c(C)cc1Nc1ncc(Cl)c(Nc2cn(C)nc2S(=O)(=O)C(C)C)n1]
538
66
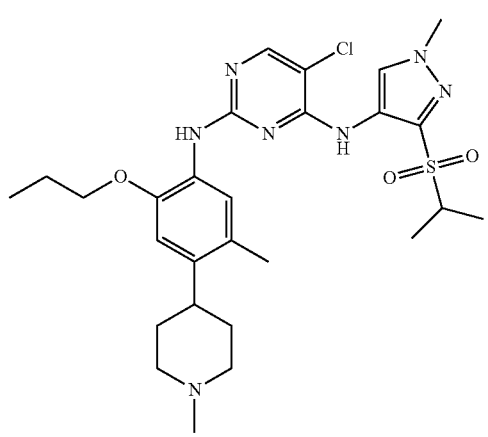 [SMILES: CCCOc1cc(C2CCN(C)CC2)c(C)cc1Nc1ncc(Cl)c(Nc2cn(C)nc2S(=O)(=O)C(C)C)n1]
67
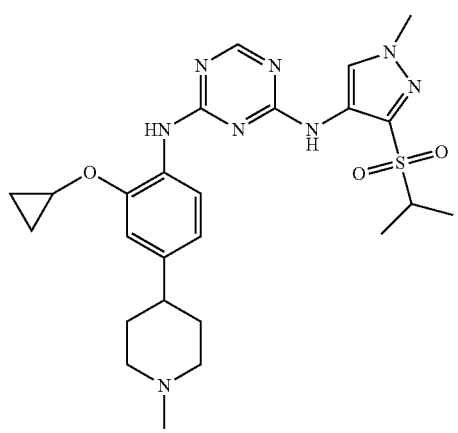 [SMILES: Cc1cc(Nc2nccc(Nc3cn(C)nc3S(=O)(=O)C(C)C)n2)c(OC2CC2)cc1C1CCN(C)CC1]
68
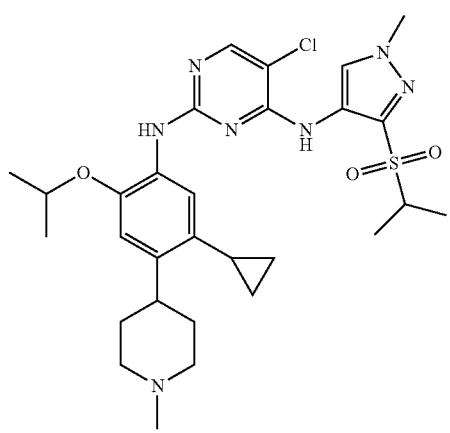 [SMILES: CC(C)Oc1cc(C2CCN(C)CC2)c(C2CC2)cc1Nc1ncc(Cl)c(Nc2cn(C)nc2S(=O)(=O)C(C)C)n1]

69
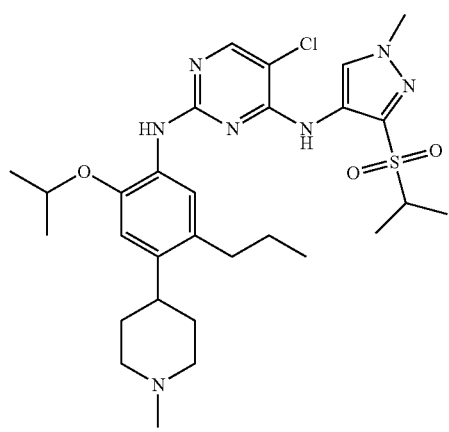 [SMILES: CCCc1cc(Nc2ncc(Cl)c(Nc3cn(C)nc3S(=O)(=O)C(C)C)n2)c(OC(C)C)cc1C1CCN(C)CC1]
70
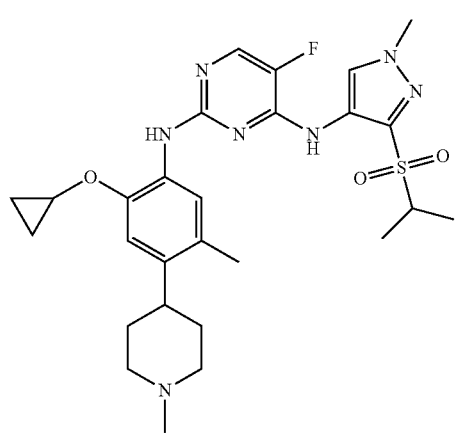 [SMILES: Cc1cc(Nc2ncc(F)c(Nc3cn(C)nc3S(=O)(=O)C(C)C)n2)c(OC2CC2)cc1C1CCN(C)CC1]
71
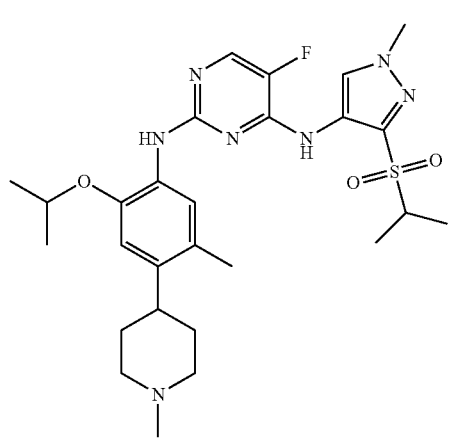 [SMILES: Cc1cc(Nc2ncc(F)c(Nc3cn(C)nc3S(=O)(=O)C(C)C)n2)c(OC(C)C)cc1C1CCN(C)CC1]
72
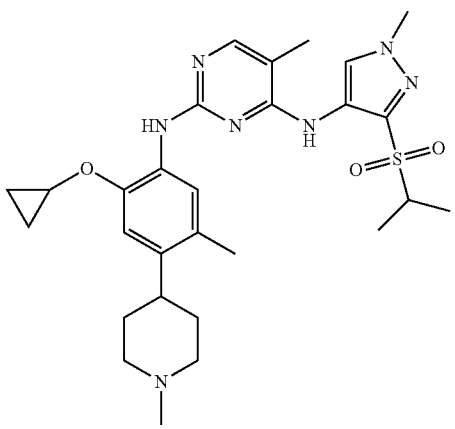 [SMILES: Cc1cc(Nc2ncc(C)c(Nc3cn(C)nc3S(=O)(=O)C(C)C)n2)c(OC2CC2)cc1C1CCN(C)CC1]
73
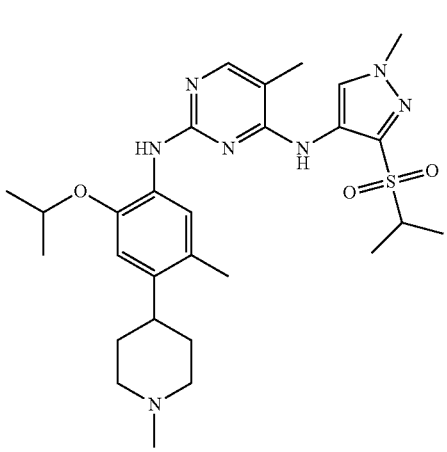 [SMILES: Cc1cc(Nc2ncc(C)c(Nc3cn(C)nc3S(=O)(=O)C(C)C)n2)c(OC(C)C)cc1C1CCN(C)CC1]
74
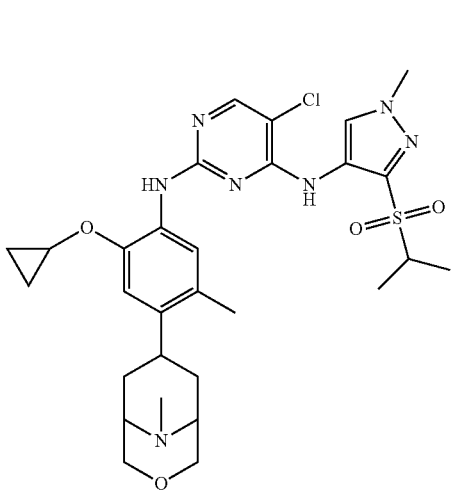 [SMILES: Cc1cc(Nc2ncc(Cl)c(Nc3cn(C)nc3S(=O)(=O)C(C)C)n2)c(OC2CC2)cc1C1CC2COCC(C1)N2C]

75
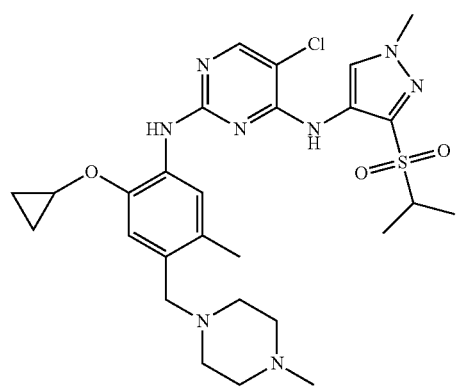 [SMILES: Cc1cc(Nc2ncc(Cl)c(Nc3cn(C)nc3S(=O)(=O)C(C)C)n2)c(OC2CC2)cc1CN1CCN(C)CC1]
76
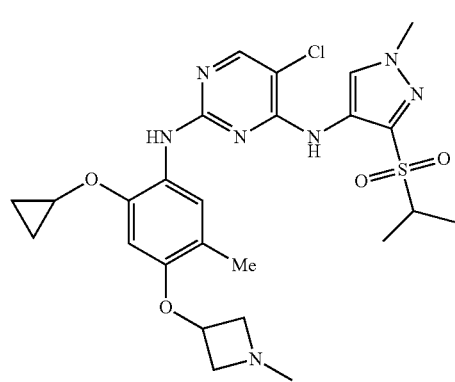 [SMILES: Cc1cc(Nc2ncc(Cl)c(Nc3cn(C)nc3S(=O)(=O)C(C)C)n2)c(OC2CC2)cc1OC1CN(C)C1]
77
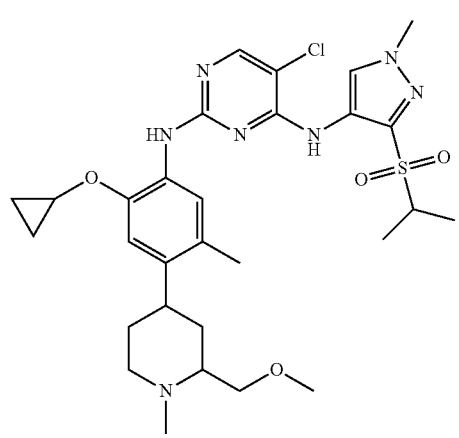 [SMILES: COCC1CC(c2cc(OC3CC3)c(Nc3ncc(Cl)c(Nc4cn(C)nc4S(=O)(=O)C(C)C)n3)cc2C)CCN1C]
78
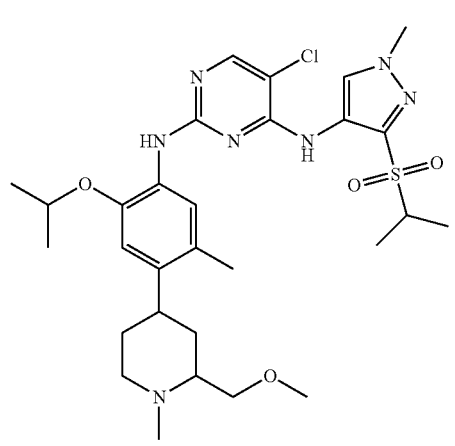 [SMILES: COCC1CC(c2cc(OC(C)C)c(Nc3ncc(Cl)c(Nc4cn(C)nc4S(=O)(=O)C(C)C)n3)cc2C)CCN1C]
79
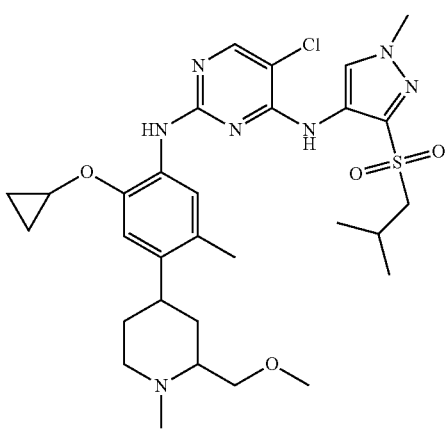 [SMILES: COCC1CC(c2cc(OC3CC3)c(Nc3ncc(Cl)c(Nc4cn(C)nc4S(=O)(=O)CC(C)C)n3)cc2C)CCN1C]
80
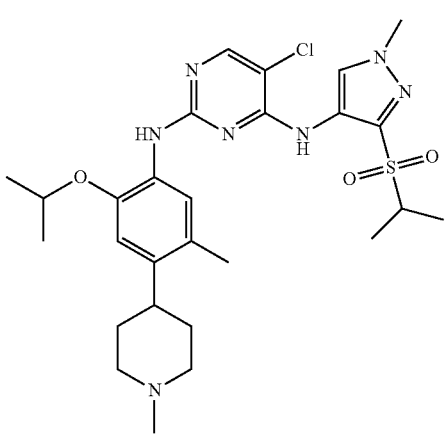
81
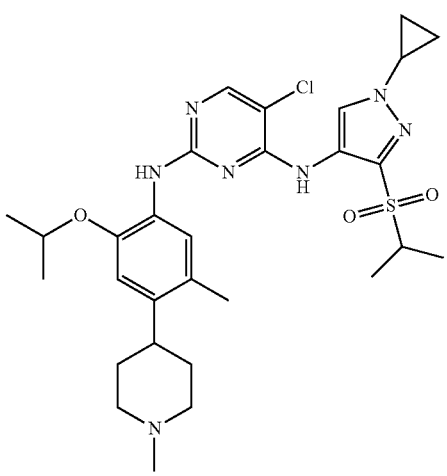 [SMILES: Cc1cc(Nc2ncc(Cl)c(Nc3cn(C4CC4)nc3S(=O)(=O)C(C)C)n2)c(OC(C)C)cc1C1CCN(C)CC1]

82
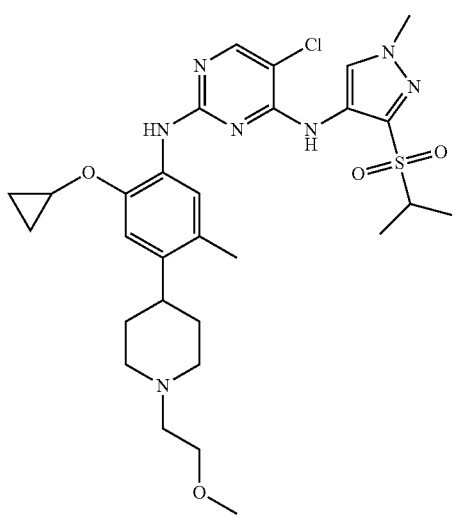 [SMILES: COCCN1CCC(c2cc(OC3CC3)c(Nc3ncc(Cl)c(Nc4cn(C)nc4S(=O)(=O)C(C)C)n3)cc2C)CC1]
83
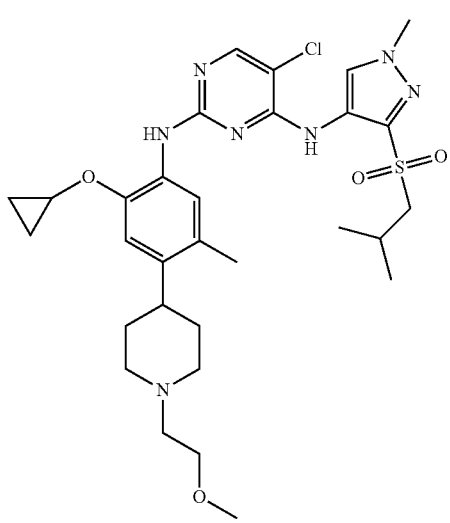 [SMILES: COCCN1CCC(c2cc(OC3CC3)c(Nc3ncc(Cl)c(Nc4cn(C)nc4S(=O)(=O)CC(C)C)n3)cc2C)CC1]
84
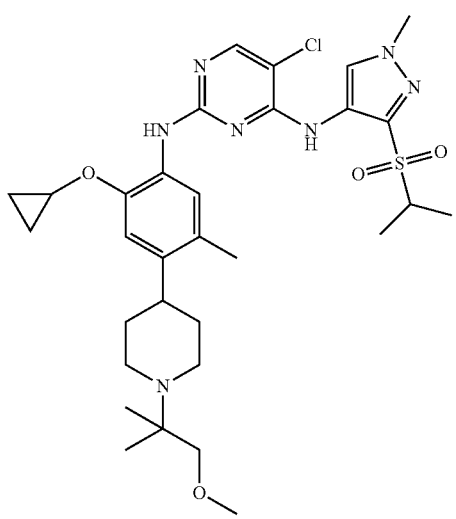 [SMILES: COCC(C)(C)N1CCC(c2cc(OC3CC3)c(Nc3ncc(Cl)c(Nc4cn(C)nc4S(=O)(=O)C(C)C)n3)cc2C)CC1]
85
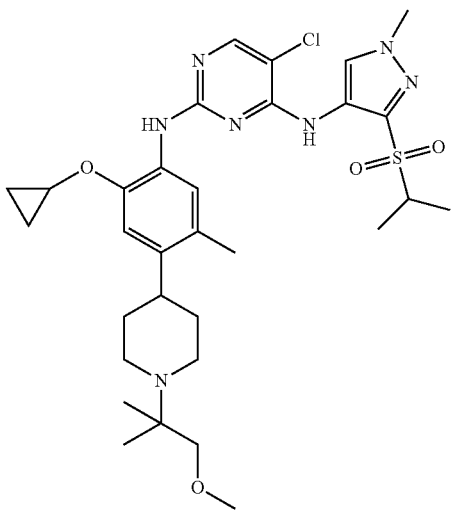
86
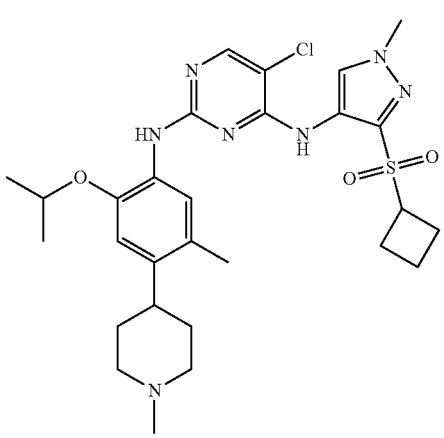 [SMILES: Cc1cc(Nc2ncc(Cl)c(Nc3cn(C)nc3S(=O)(=O)C3CCC3)n2)c(OC(C)C)cc1C1CCN(C)CC1]
87
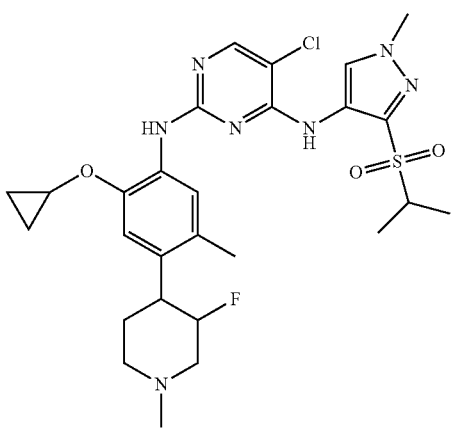 [SMILES: Cc1cc(Nc2ncc(Cl)c(Nc3cn(C)nc3S(=O)(=O)C(C)C)n2)c(OC2CC2)cc1C1CCN(C)CC1C]

88
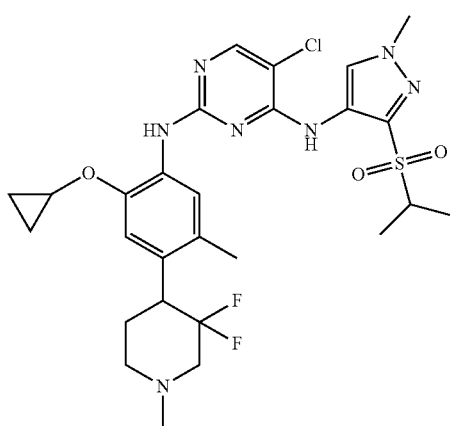
89
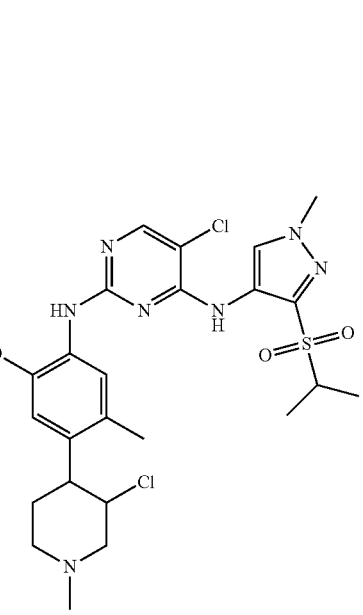
90
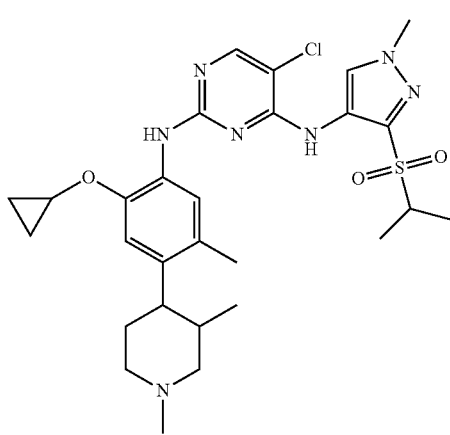
91
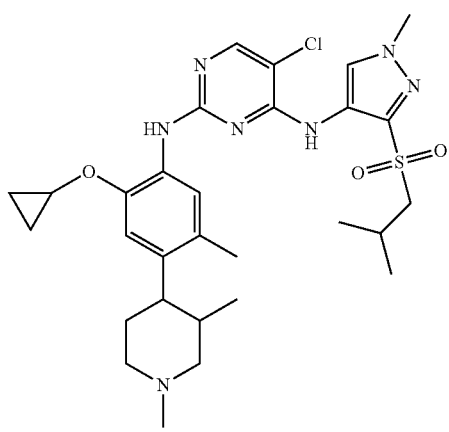 [SMILES: Cc1cc(Nc2ncc(Cl)c(Nc3cn(C)nc3S(=O)(=O)CC(C)C)n2)c(OC2CC2)cc1C1CCN(C)CC1C]
92
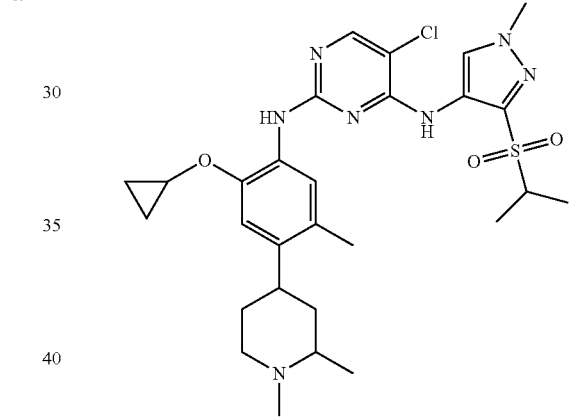
93
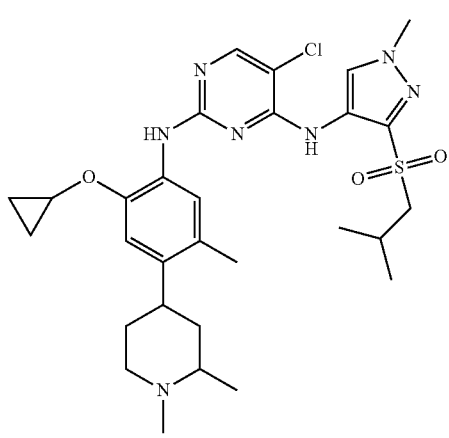 [SMILES: Cc1cc(Nc2ncc(Cl)c(Nc3cn(C)nc3S(=O)(=O)CC(C)C)n2)c(OC2CC2)cc1C1CCN(C)C(C)C1]

94
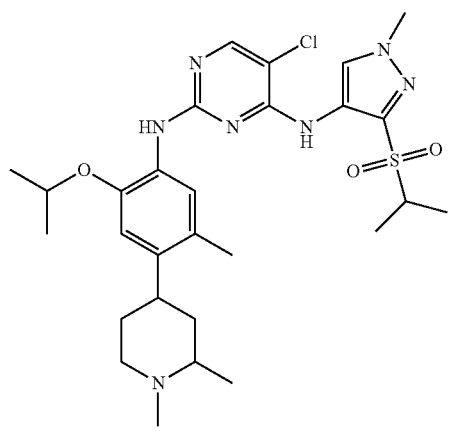 [SMILES: Cc1cc(Nc2ncc(Cl)c(Nc3cn(C)nc3S(=O)(=O)C(C)C)n2)c(OC(C)C)cc1C1CCN(C)C(C)C1]
95
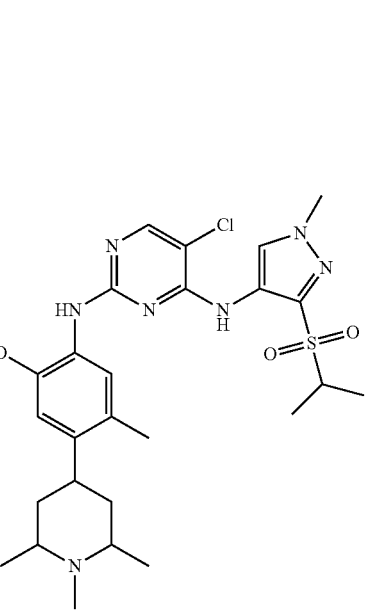
96
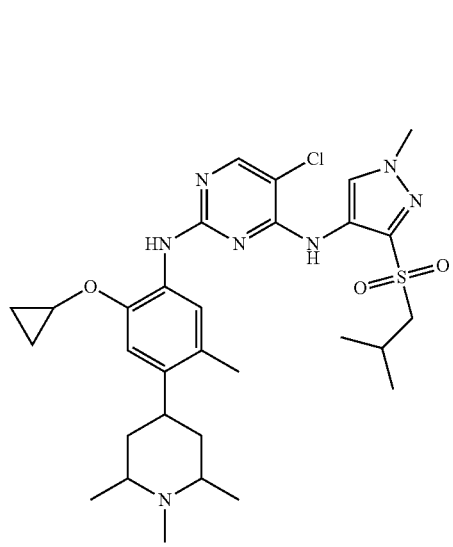 [SMILES: Cc1cc(Nc2ncc(Cl)c(Nc3cn(C)nc3S(=O)(=O)CC(C)C)n2)c(OC2CC2)cc1C1CC(C)N(C)C(C)C1]
97
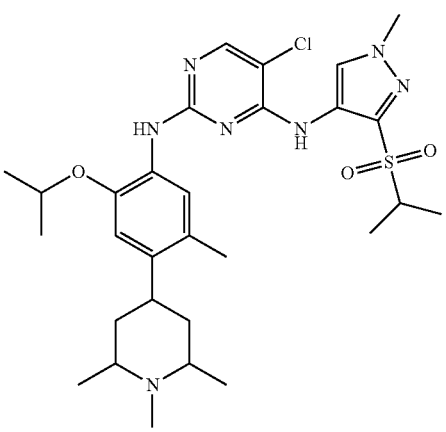 [SMILES: Cc1cc(Nc2ncc(Cl)c(Nc3cn(C)nc3S(=O)(=O)C(C)C)n2)c(OC(C)C)cc1C1CC(C)N(C)C(C)C1]
98
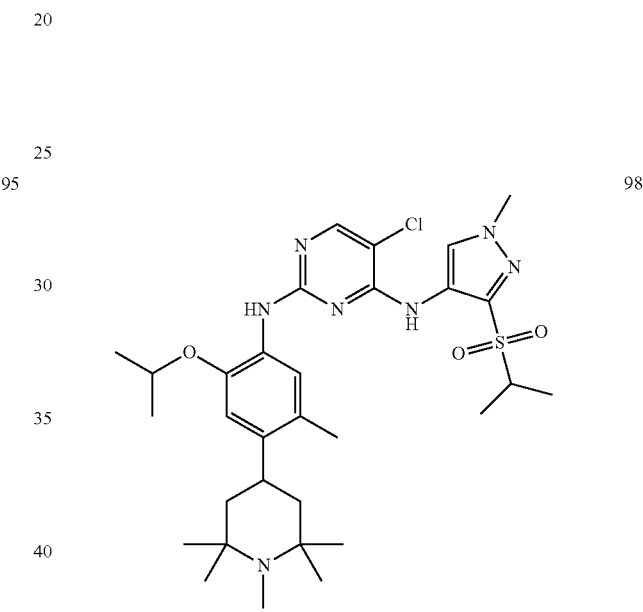
99
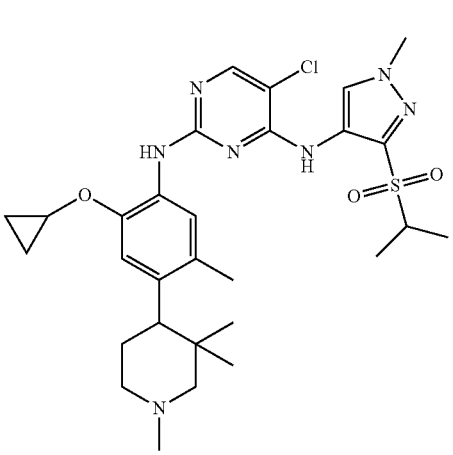 [SMILES: Cc1cc(Nc2ncc(Cl)c(Nc3cn(C)nc3S(=O)(=O)C(C)C)n2)c(OC2CC2)cc1C1CCN(C)CC1(C)C]

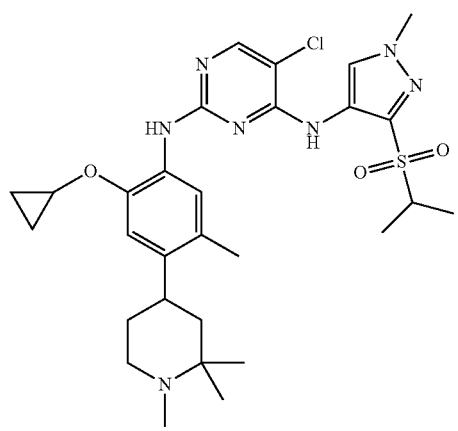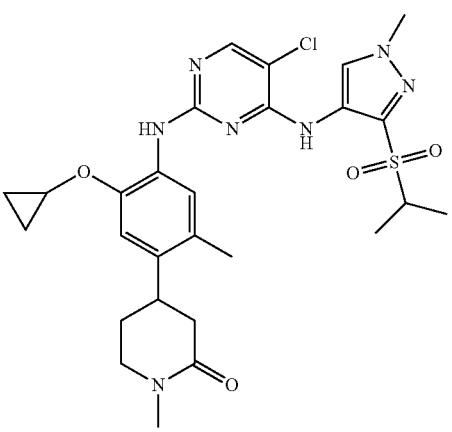 [SMILES: Cc1cc(Nc2ncc(Cl)c(Nc3cn(C)nc3S(=O)(=O)C(C)C)n2)c(OC2CC2)cc1C1CCN(C)C(=O)C1]

106 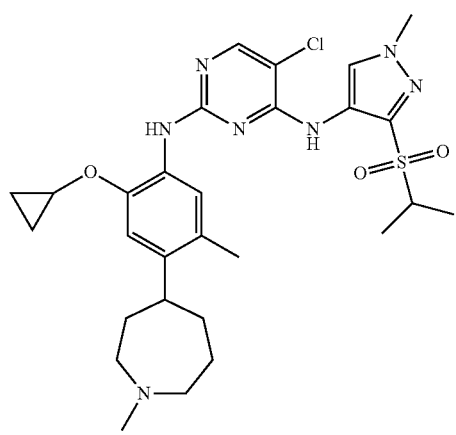 [SMILES: Cc1cc(Nc2ncc(Cl)c(Nc3cn(C)nc3S(=O)(=O)C(C)C)n2)c(OC2CC2)cc1C1CCCN(C)CC1]
107 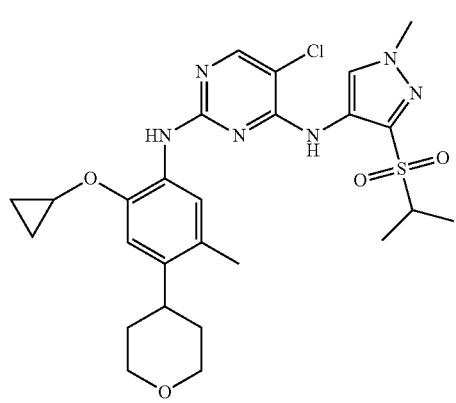 [SMILES: Cc1cc(Nc2ncc(Cl)c(Nc3cn(C)nc3S(=O)(=O)C(C)C)n2)c(OC2CC2)cc1C1CCOCC1]
108 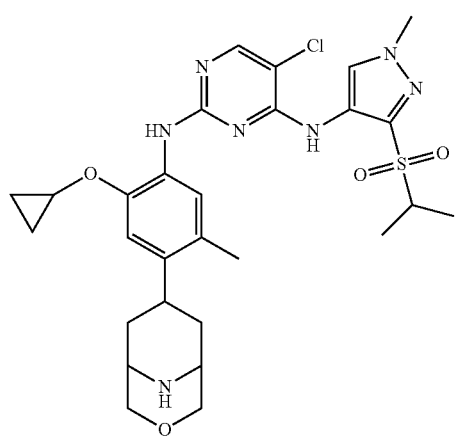 [SMILES: Cc1cc(Nc2ncc(Cl)c(Nc3cn(C)nc3S(=O)(=O)C(C)C)n2)c(OC2CC2)cc1C1CC2COCC(C1)N2]
109 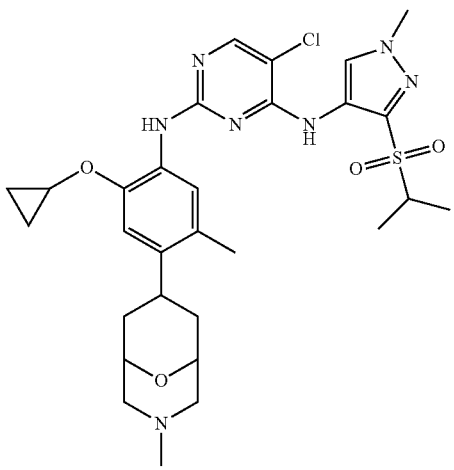 [SMILES: Cc1cc(Nc2ncc(Cl)c(Nc3cn(C)nc3S(=O)(=O)C(C)C)n2)c(OC2CC2)cc1C1CC2CN(C)CC(C1)O2]
110 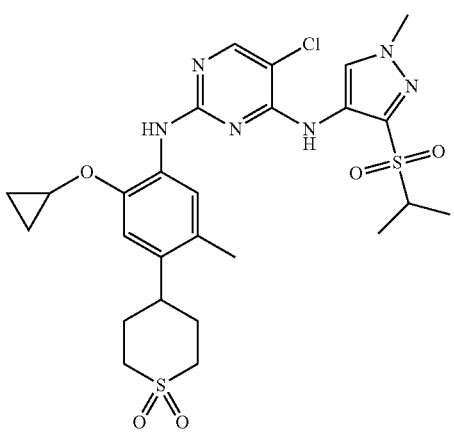 [SMILES: Cc1cc(Nc2ncc(Cl)c(Nc3cn(C)nc3S(=O)(=O)C(C)C)n2)c(OC2CC2)cc1C1CCS(=O)(=O)CC1]
111 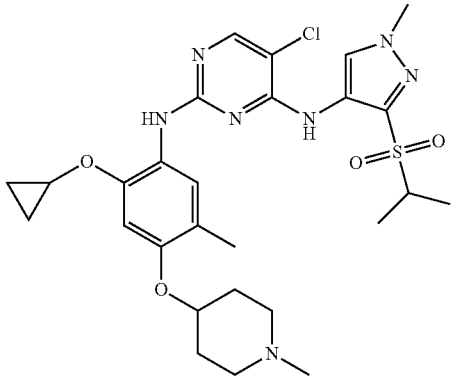 [SMILES: Cc1cc(Nc2ncc(Cl)c(Nc3cn(C)nc3S(=O)(=O)C(C)C)n2)c(OC2CC2)cc1OC1CCN(C)CC1]
112 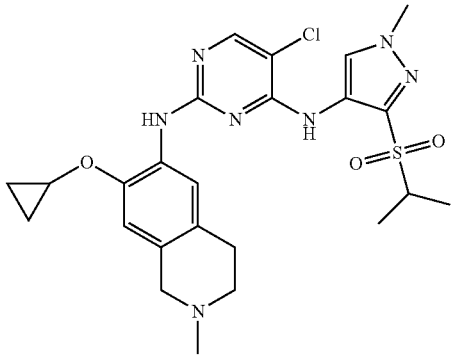 [SMILES: CC(C)S(=O)(=O)c1nn(C)cc1Nc1nc(Nc2cc3c(cc2OC2CC2)CN(C)CC3)ncc1Cl]

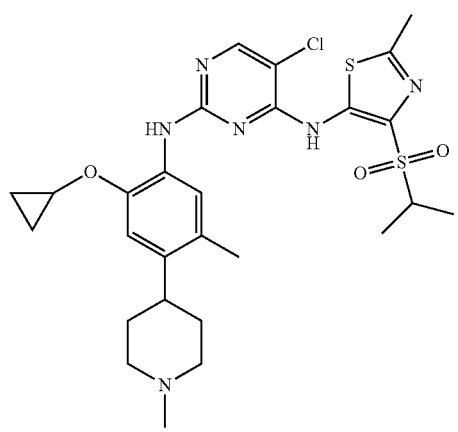 [SMILES: Cc1nc(S(=O)(=O)C(C)C)c(Nc2nc(Nc3cc(C)c(C4CCN(C)CC4)cc3OC3CC3)ncc2Cl)s1]
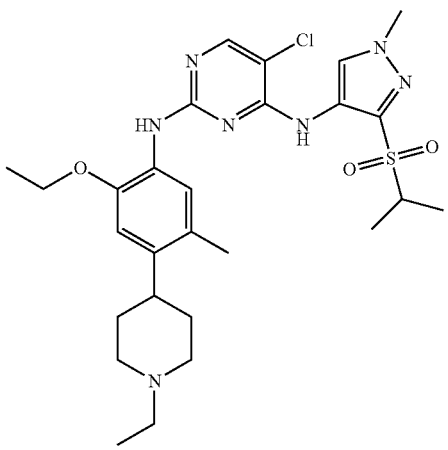 [SMILES: CCOc1cc(C2CCN(CC)CC2)c(C)cc1Nc1ncc(Cl)c(Nc2cn(C)nc2S(=O)(=O)C(C)C)n1]

119 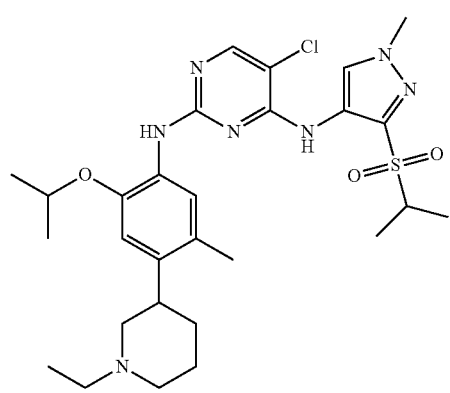 [SMILES: CCN1CCCC(c2cc(OC(C)C)c(Nc3ncc(Cl)c(Nc4cn(C)nc4S(=O)(=O)C(C)C)n3)cc2C)C1]
120 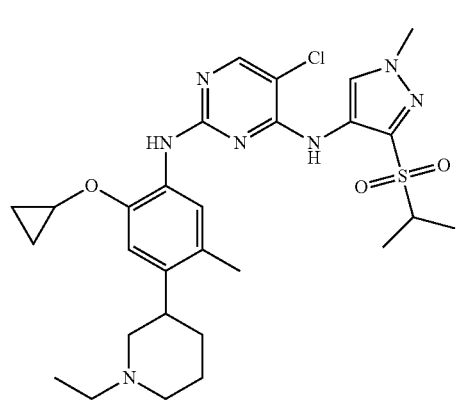 [SMILES: CCN1CCCC(c2cc(OC3CC3)c(Nc3ncc(Cl)c(Nc4cn(C)nc4S(=O)(=O)C(C)C)n3)cc2C)C1]
121 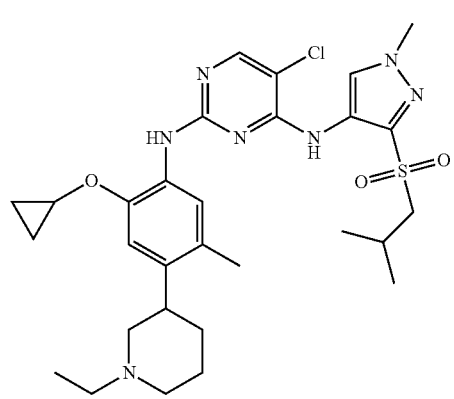 [SMILES: CCN1CCCC(c2cc(OC3CC3)c(Nc3ncc(Cl)c(Nc4cn(C)nc4S(=O)(=O)CC(C)C)n3)cc2C)C1]
122 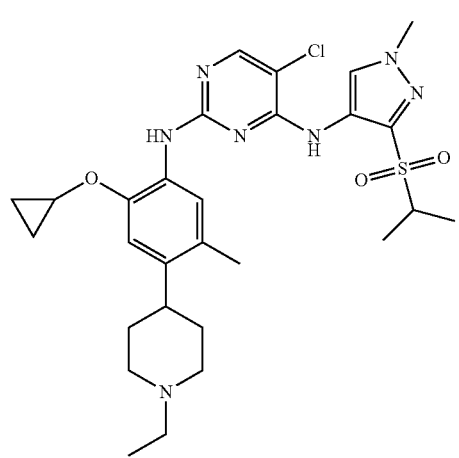
123 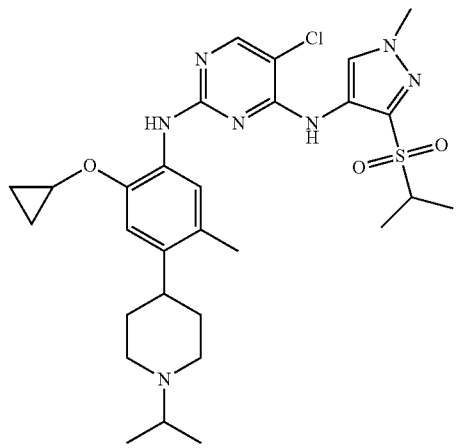 [SMILES: Cc1cc(Nc2ncc(Cl)c(Nc3cn(C)nc3S(=O)(=O)C(C)C)n2)c(OC2CC2)cc1C1CCN(C(C)C)CC1]
124 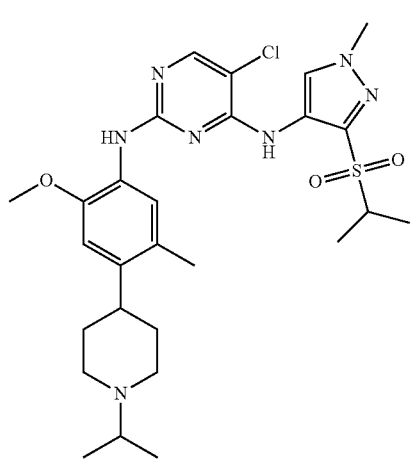 [SMILES: COc1cc(C2CCN(C(C)C)CC2)c(C)cc1Nc1ncc(Cl)c(Nc2cn(C)nc2S(=O)(=O)C(C)C)n1]
125 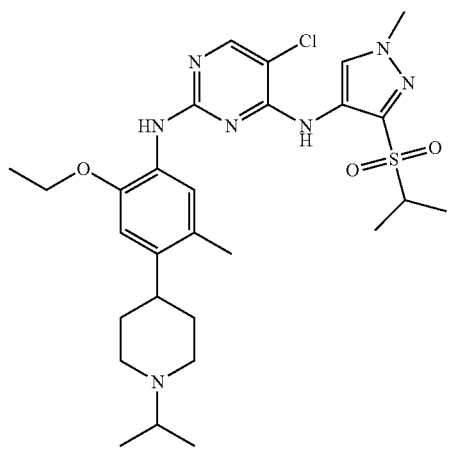 [SMILES: CCOc1cc(C2CCN(C(C)C)CC2)c(C)cc1Nc1ncc(Cl)c(Nc2cn(C)nc2S(=O)(=O)C(C)C)n1]

126
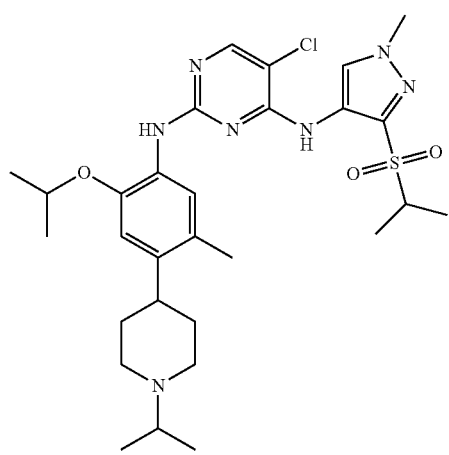 [SMILES: Cc1cc(Nc2ncc(Cl)c(Nc3cn(C)nc3S(=O)(=O)C(C)C)n2)c(OC(C)C)cc1C1CCN(C(C)C)CC1]
127
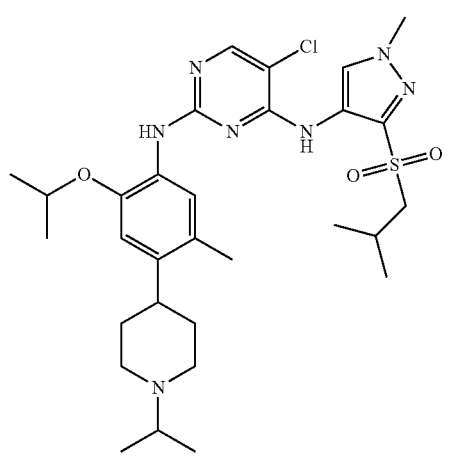
128
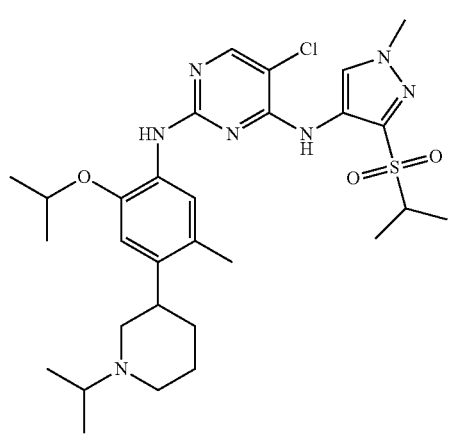 [SMILES: Cc1cc(Nc2ncc(Cl)c(Nc3cn(C)nc3S(=O)(=O)C(C)C)n2)c(OC(C)C)cc1C1CCCN(C(C)C)C1]
129
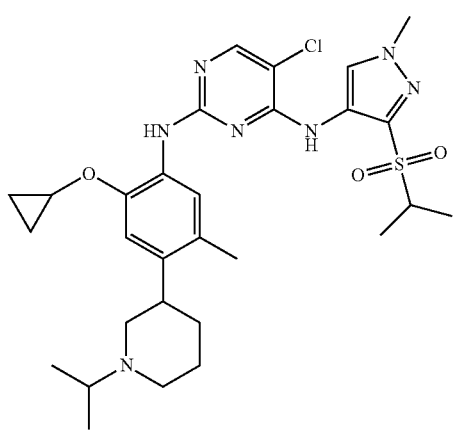 [SMILES: Cc1cc(Nc2ncc(Cl)c(Nc3cn(C)nc3S(=O)(=O)C(C)C)n2)c(OC2CC2)cc1C1CCCN(C(C)C)C1]
130
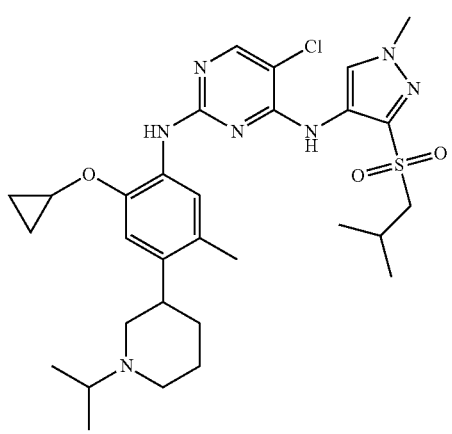 [SMILES: Cc1cc(Nc2ncc(Cl)c(Nc3cn(C)nc3S(=O)(=O)CC(C)C)n2)c(OC2CC2)cc1C1CCCN(C(C)C)C1]
131
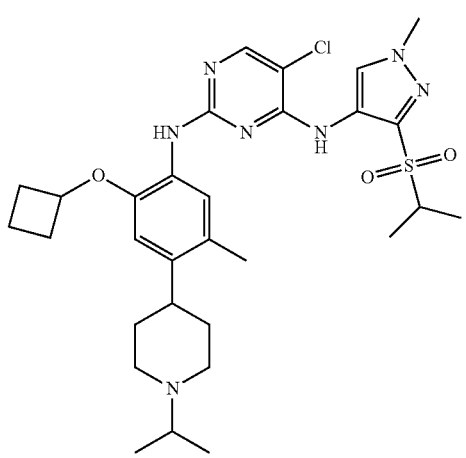 [SMILES: Cc1cc(Nc2ncc(Cl)c(Nc3cn(C)nc3S(=O)(=O)C(C)C)n2)c(OC2CCC2)cc1C1CCN(C(C)C)CC1]

132
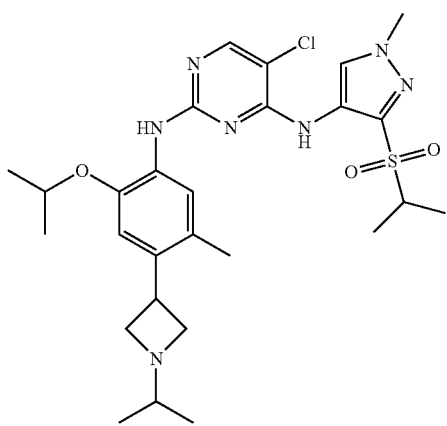 [SMILES: Cc1cc(Nc2ncc(Cl)c(Nc3cn(C)nc3S(=O)(=O)C(C)C)n2)c(OC(C)C)cc1C1CN(C(C)C)C1]
133
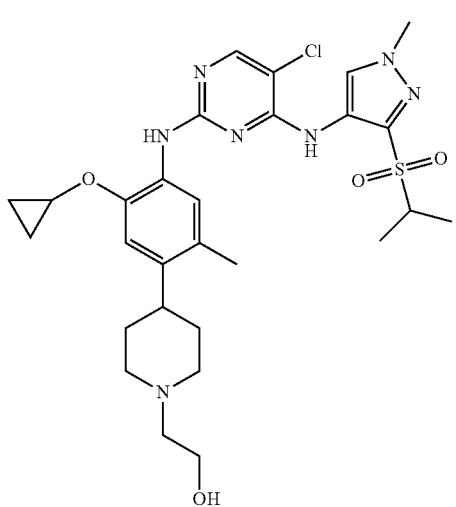 [SMILES: Cc1cc(Nc2ncc(Cl)c(Nc3cn(C)nc3S(=O)(=O)C(C)C)n2)c(OC2CC2)cc1C1CCN(CCO)CC1]
134
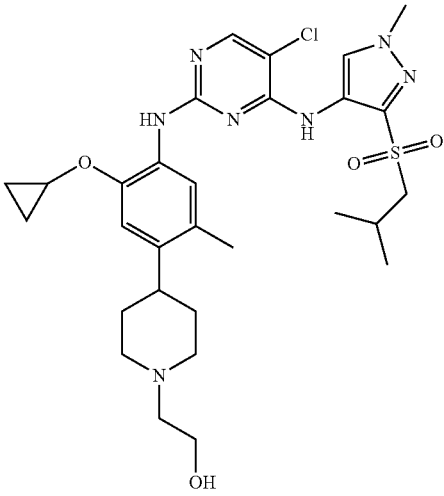
135
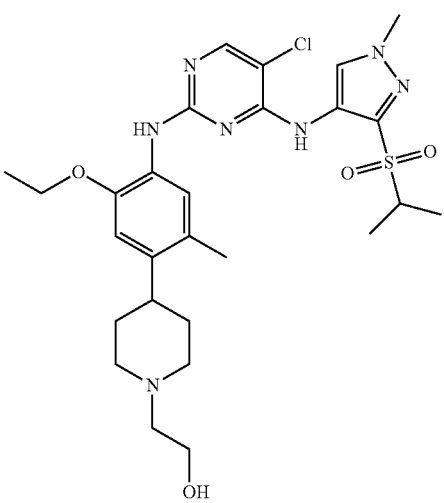 [SMILES: CCOc1cc(C2CCN(CCO)CC2)c(C)cc1Nc1ncc(Cl)c(Nc2cn(C)nc2S(=O)(=O)C(C)C)n1]
136
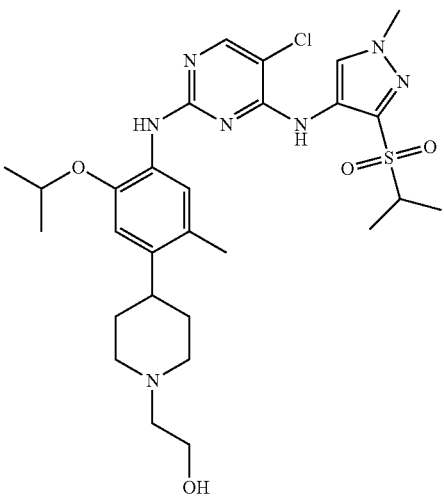 [SMILES: Cc1cc(Nc2ncc(Cl)c(Nc3cn(C)nc3S(=O)(=O)C(C)C)n2)c(OC(C)C)cc1C1CCN(CCO)CC1]
137

138
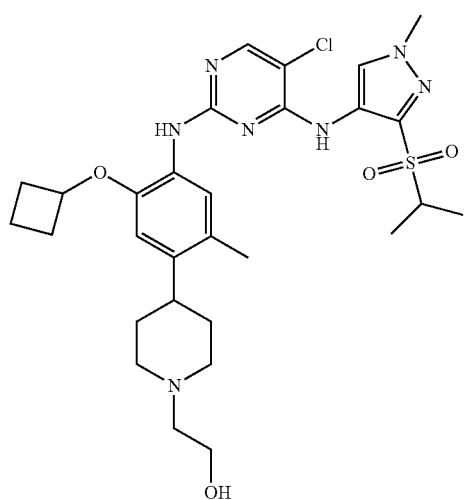 [SMILES: Cc1cc(Nc2ncc(Cl)c(Nc3cn(C)nc3S(=O)(=O)C(C)C)n2)c(OC2CCC2)cc1C1CCN(CCO)CC1]
139
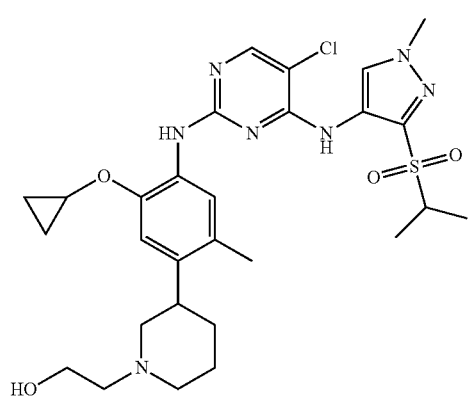
140
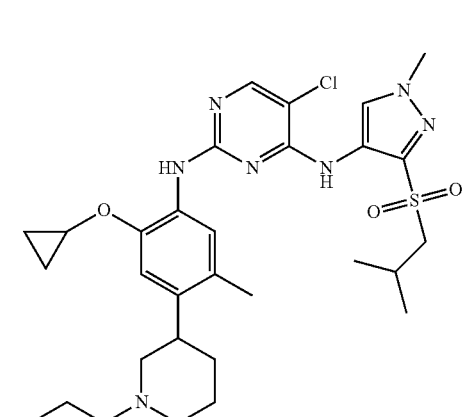
141
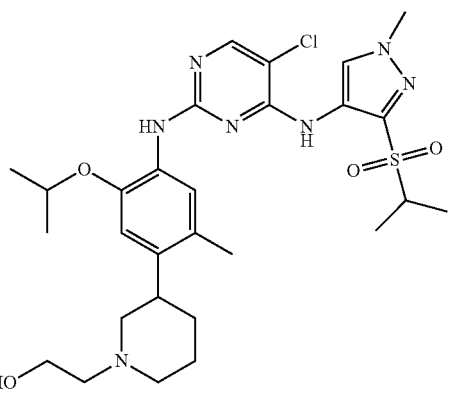
142
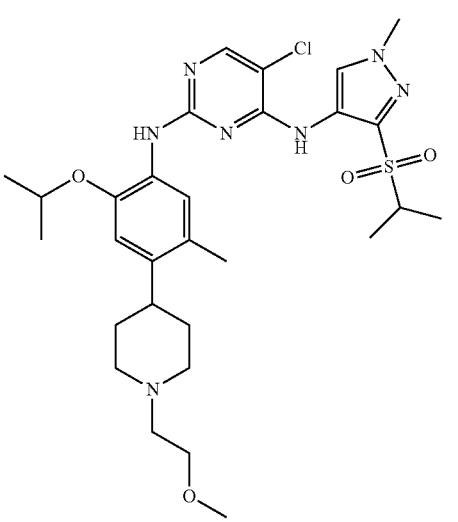 [SMILES: COCCN1CCC(c2cc(OC(C)C)c(Nc3ncc(Cl)c(Nc4cn(C)nc4S(=O)(=O)C(C)C)n3)cc2C)CC1]
143
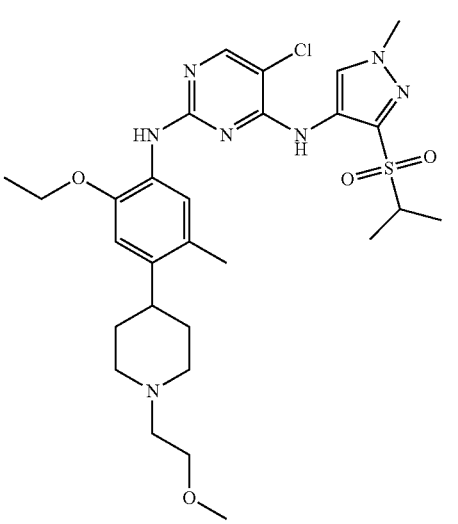 [SMILES: CCOc1cc(C2CCN(CCOC)CC2)c(C)cc1Nc1ncc(Cl)c(Nc2cn(C)nc2S(=O)(=O)C(C)C)n1]

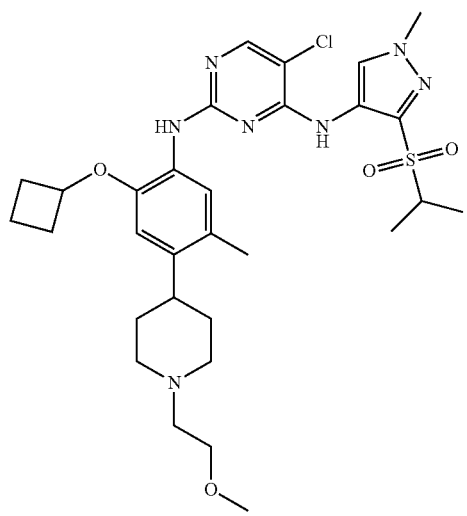 [SMILES: COCCN1CCC(c2cc(OC3CCC3)c(Nc3ncc(Cl)c(Nc4cn(C)nc4S(=O)(=O)C(C)C)n3)cc2C)CC1]
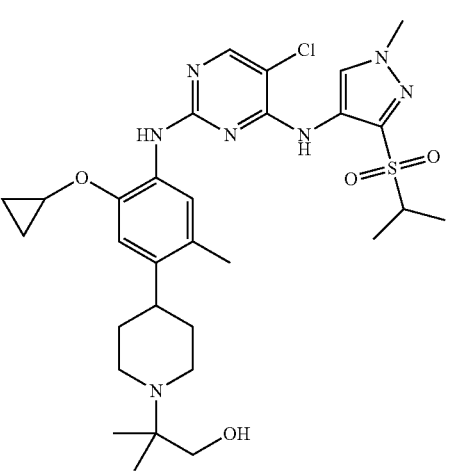
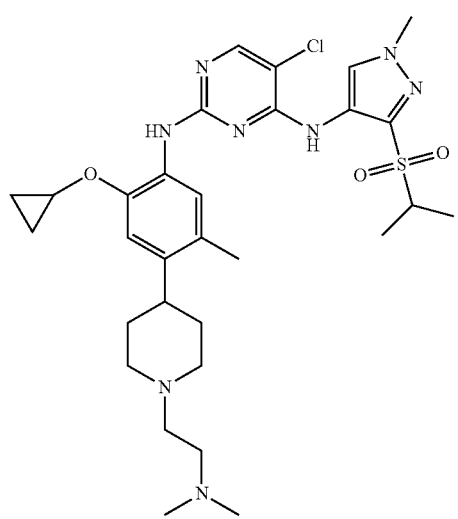 [SMILES: Cc1cc(Nc2ncc(Cl)c(Nc3cn(C)nc3S(=O)(=O)C(C)C)n2)c(OC2CC2)cc1C1CCN(CCN(C)C)CC1]

150
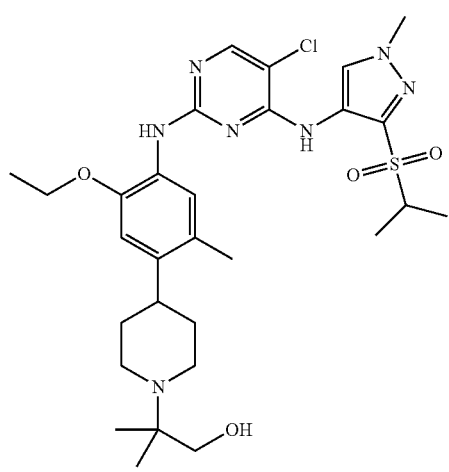 [SMILES: CCOc1cc(C2CCN(C(C)(C)CO)CC2)c(C)cc1Nc1ncc(Cl)c(Nc2cn(C)nc2S(=O)(=O)C(C)C)n1]
151
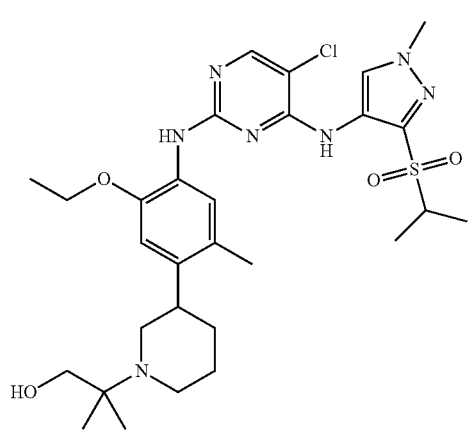
152
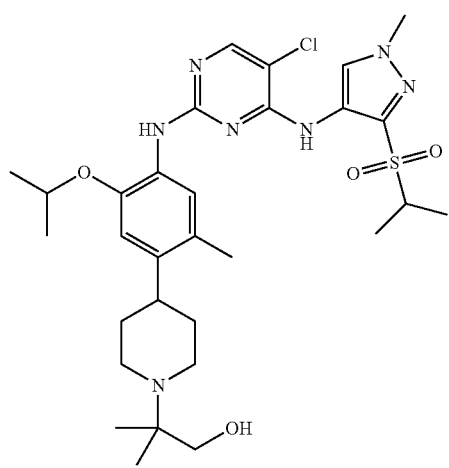 [SMILES: Cc1cc(Nc2ncc(Cl)c(Nc3cn(C)nc3S(=O)(=O)C(C)C)n2)c(OC(C)C)cc1C1CCN(C(C)(C)CO)CC1]
153
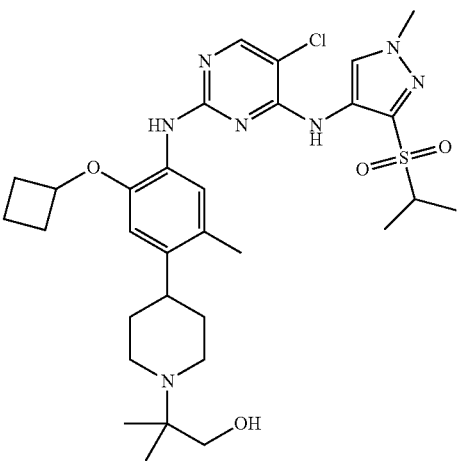 [SMILES: Cc1cc(Nc2ncc(Cl)c(Nc3cn(C)nc3S(=O)(=O)C(C)C)n2)c(OC2CCC2)cc1C1CCN(C(C)(C)CO)CC1]
154
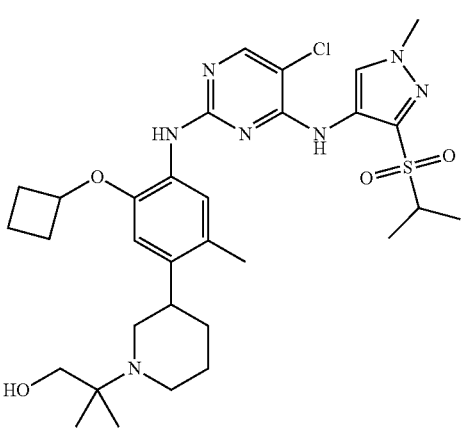 [SMILES: Cc1cc(Nc2ncc(Cl)c(Nc3cn(C)nc3S(=O)(=O)C(C)C)n2)c(OC2CCC2)cc1C1CCCN(C(C)(C)CO)C1]
155
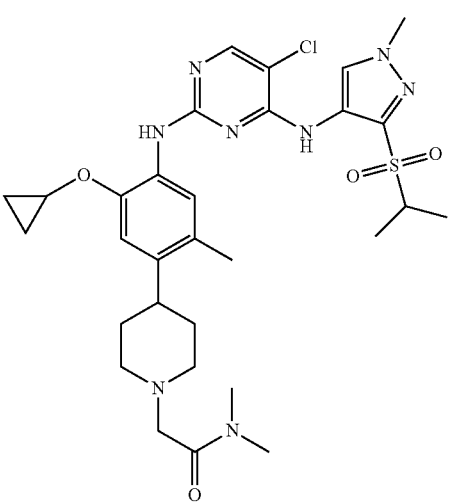 [SMILES: Cc1cc(Nc2ncc(Cl)c(Nc3cn(C)nc3S(=O)(=O)C(C)C)n2)c(OC2CC2)cc1C1CCN(CC(=O)N(C)C)CC1]

156
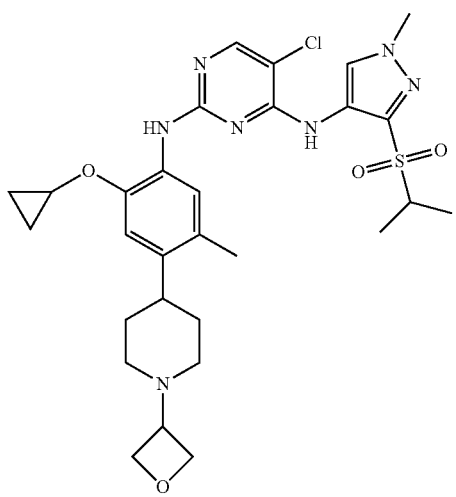 [SMILES: Cc1cc(Nc2ncc(Cl)c(Nc3cn(C)nc3S(=O)(=O)C(C)C)n2)c(OC2CC2)cc1C1CCN(C2COC2)CC1]
157
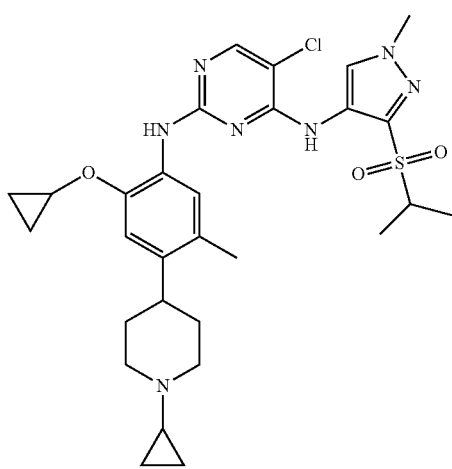 [SMILES: Cc1cc(Nc2ncc(Cl)c(Nc3cn(C)nc3S(=O)(=O)C(C)C)n2)c(OC2CC2)cc1C1CCN(C2CC2)CC1]
158
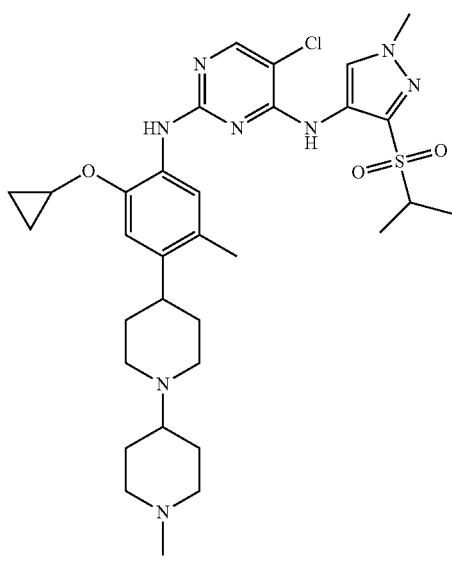 [SMILES: Cc1cc(Nc2ncc(Cl)c(Nc3cn(C)nc3S(=O)(=O)C(C)C)n2)c(OC2CC2)cc1C1CCN(C2CCN(C)CC2)CC1]
159
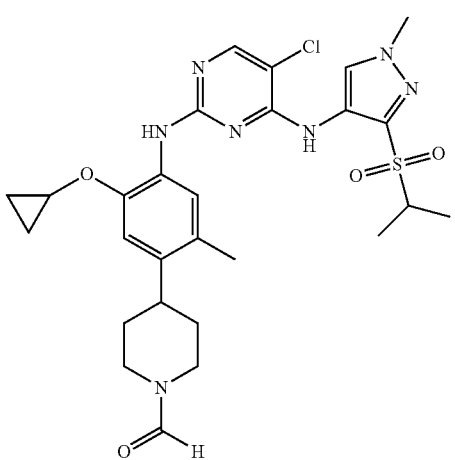 [SMILES: Cc1cc(Nc2ncc(Cl)c(Nc3cn(C)nc3S(=O)(=O)C(C)C)n2)c(OC2CC2)cc1C1CCN(C=O)CC1]
160
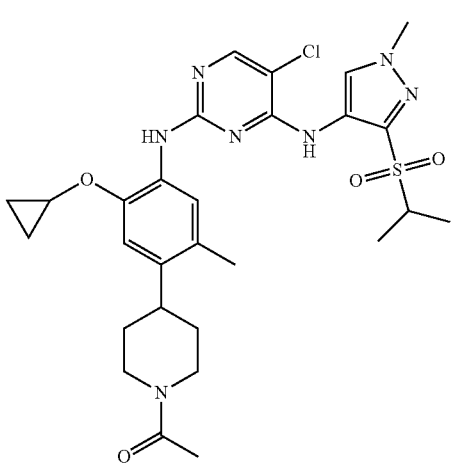 [SMILES: CC(=O)N1CCC(c2cc(OC3CC3)c(Nc3ncc(Cl)c(Nc4cn(C)nc4S(=O)(=O)C(C)C)n3)cc2C)CC1]
161
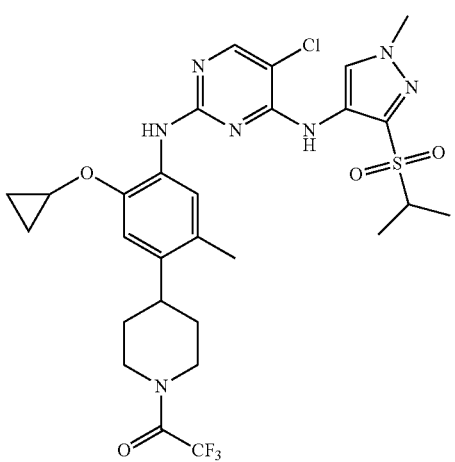 [SMILES: Cc1cc(Nc2ncc(Cl)c(Nc3cn(C)nc3S(=O)(=O)C(C)C)n2)c(OC2CC2)cc1C1CCN(C(=O)C(F)(F)F)CC1]

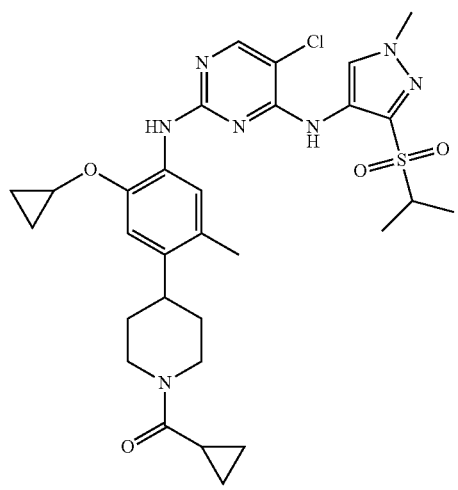 [SMILES: Cc1cc(Nc2ncc(Cl)c(Nc3cn(C)nc3S(=O)(=O)C(C)C)n2)c(OC2CC2)cc1C1CCN(C(=O)C2CC2)CC1]
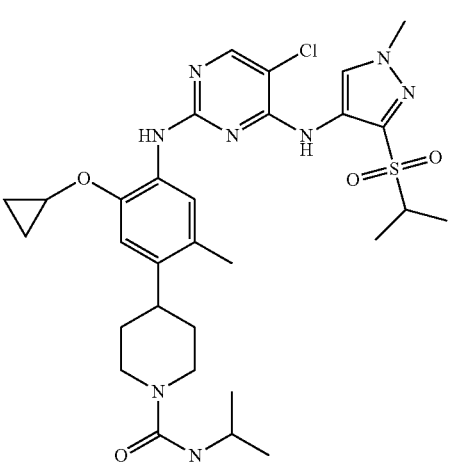 [SMILES: Cc1cc(Nc2ncc(Cl)c(Nc3cn(C)nc3S(=O)(=O)C(C)C)n2)c(OC2CC2)cc1C1CCN(C(=O)CN(C)C)CC1]

168
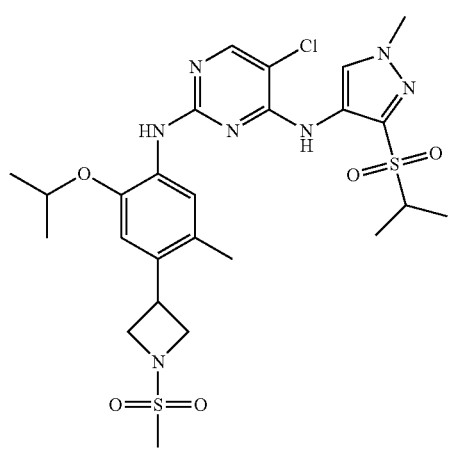 [SMILES: Cc1cc(Nc2ncc(Cl)c(Nc3cn(C)nc3S(=O)(=O)C(C)C)n2)c(OC(C)C)cc1C1CN(S(C)(=O)=O)C1]
169
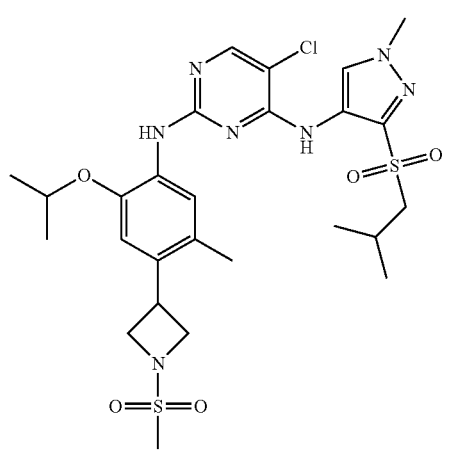 [SMILES: Cc1cc(Nc2ncc(Cl)c(Nc3cn(C)nc3S(=O)(=O)CC(C)C)n2)c(OC(C)C)cc1C1CN(S(C)(=O)=O)C1]
170
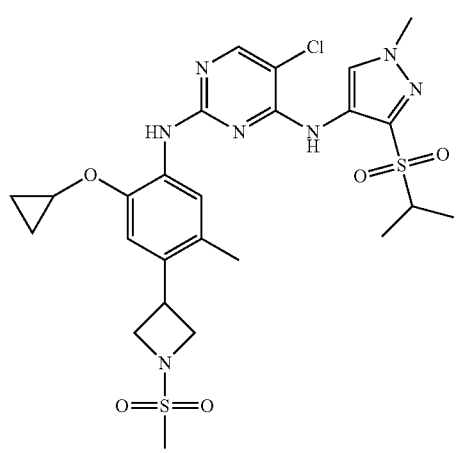 [SMILES: Cc1cc(Nc2ncc(Cl)c(Nc3cn(C)nc3S(=O)(=O)C(C)C)n2)c(OC2CC2)cc1C1CN(S(C)(=O)=O)C1]
171
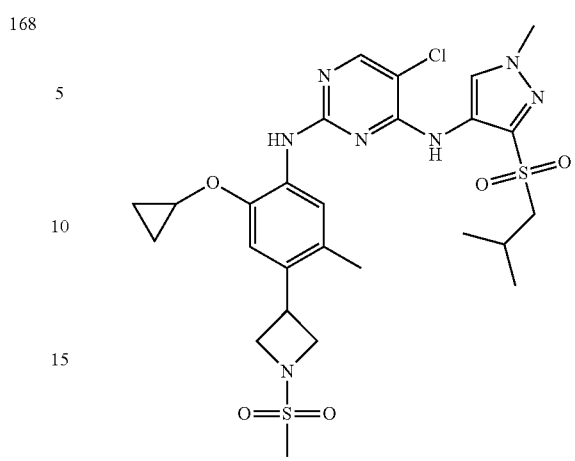
172
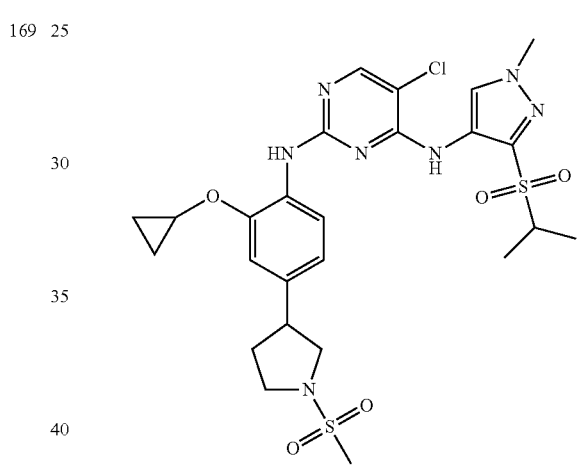
173
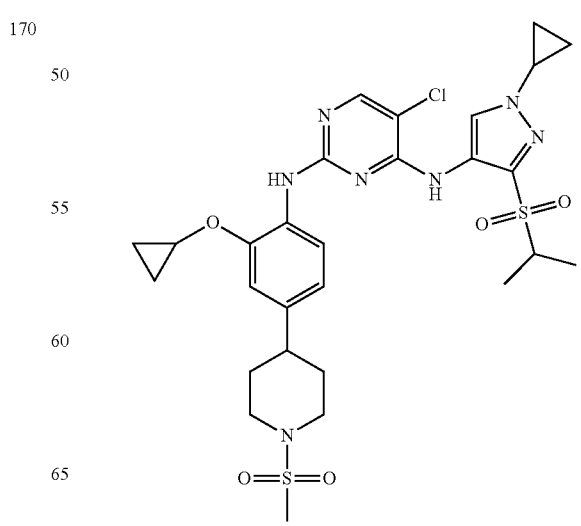

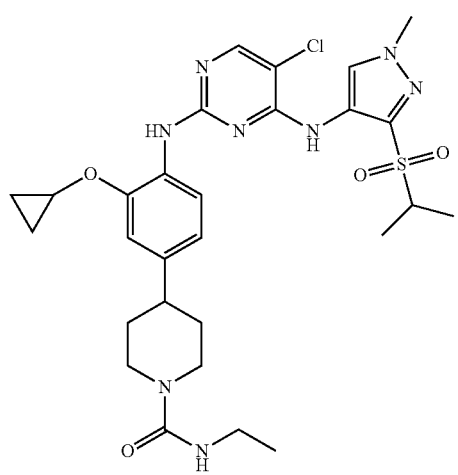 [SMILES: CCNC(=O)N1CCC(c2cc(OC3CC3)c(Nc3ncc(Cl)c(Nc4cn(C)nc4S(=O)(=O)C(C)C)n3)cc2C)CC1]
174
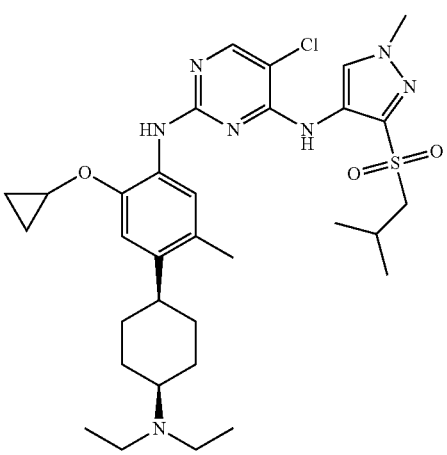
177
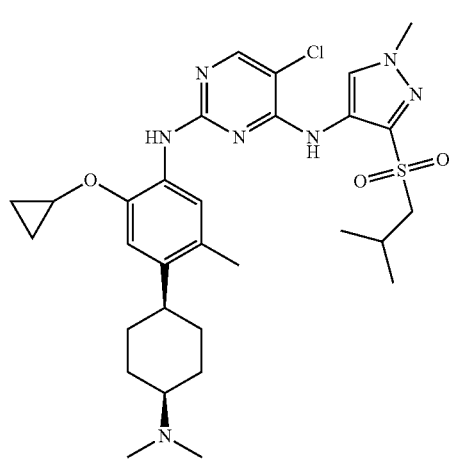 [SMILES: Cc1cc(Nc2ncc(Cl)c(Nc3cn(C)nc3S(=O)(=O)CC(C)C)n2)c(OC2CC2)cc1[C@H]1CC[C@@H](N(C)C)CC1]
175
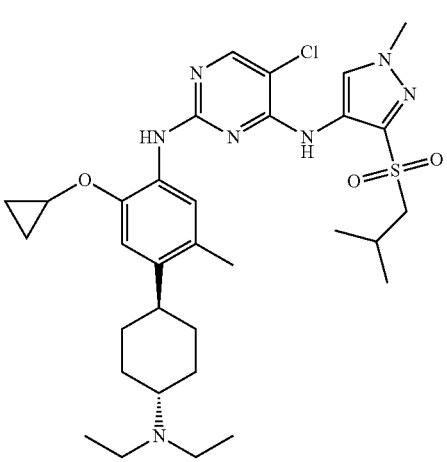
178
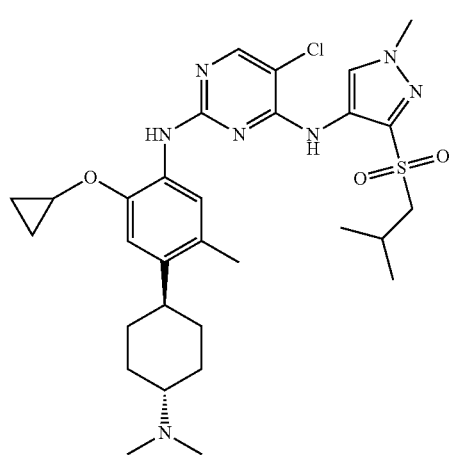 [SMILES: Cc1cc(Nc2ncc(Cl)c(Nc3cn(C)nc3S(=O)(=O)CC(C)C)n2)c(OC2CC2)cc1[C@H]1CC[C@H](N(C)C)CC1]
176
179

180
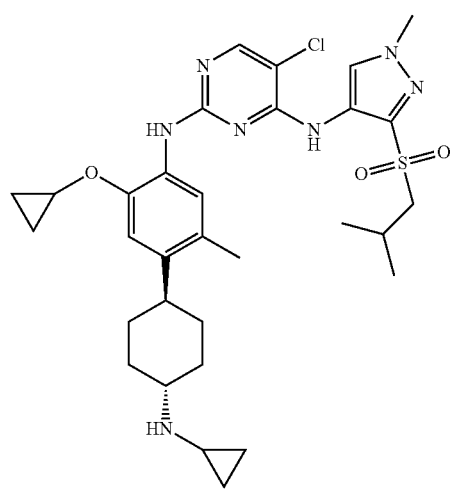 [SMILES: Cc1cc(Nc2ncc(Cl)c(Nc3cn(C)nc3S(=O)(=O)CC(C)C)n2)c(OC2CC2)cc1[C@H]1CC[C@H](NC2CC2)CC1]
181
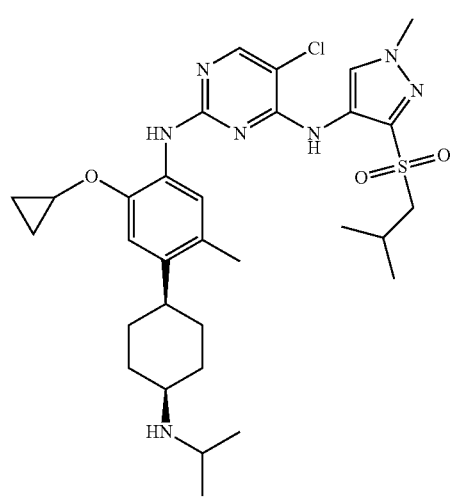 [SMILES: Cc1cc(Nc2ncc(Cl)c(Nc3cn(C)nc3S(=O)(=O)CC(C)C)n2)c(OC2CC2)cc1[C@H]1CC[C@@H](NC(C)C)CC1]
182
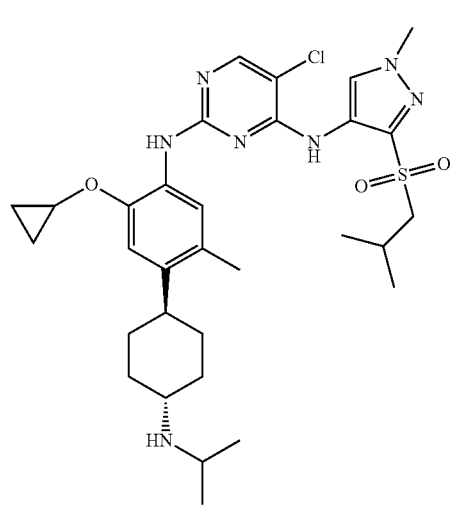 [SMILES: Cc1cc(Nc2ncc(Cl)c(Nc3cn(C)nc3S(=O)(=O)CC(C)C)n2)c(OC2CC2)cc1[C@H]1CC[C@H](NC(C)C)CC1]
183
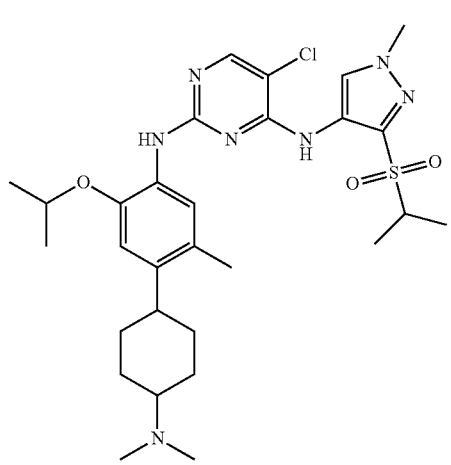 [SMILES: Cc1cc(Nc2ncc(Cl)c(Nc3cn(C)nc3S(=O)(=O)C(C)C)n2)c(OC(C)C)cc1C1CCC(N(C)C)CC1]
184
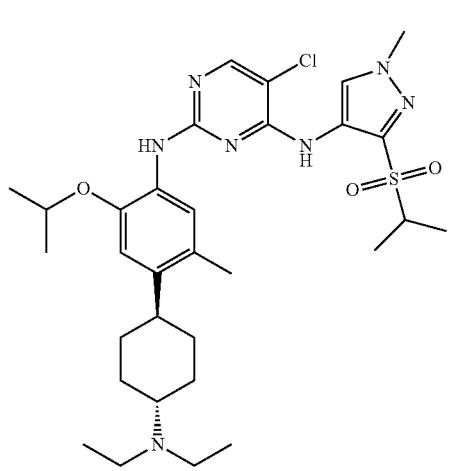 [SMILES: CCN(CC)[C@H]1CC[C@H](c2cc(OC(C)C)c(Nc3ncc(Cl)c(Nc4cn(C)nc4S(=O)(=O)C(C)C)n3)cc2C)CC1]
185
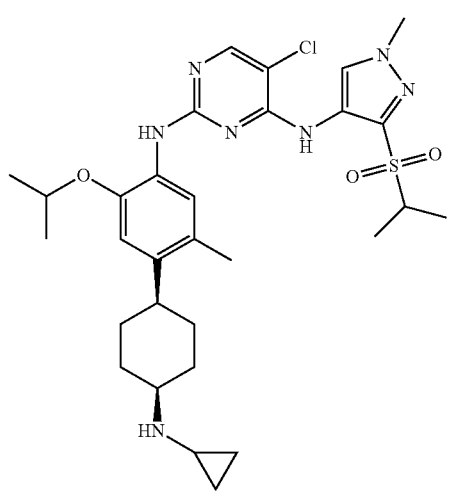 [SMILES: Cc1cc(Nc2ncc(Cl)c(Nc3cn(C)nc3S(=O)(=O)C(C)C)n2)c(OC(C)C)cc1[C@H]1CC[C@@H](NC2CC2)CC1]

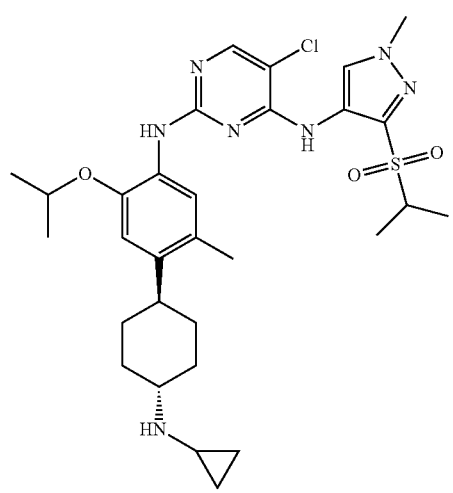 [SMILES: Cc1cc(Nc2ncc(Cl)c(Nc3cn(C)nc3S(=O)(=O)C(C)C)n2)c(OC(C)C)cc1[C@H]1CC[C@H](NC2CC2)CC1]
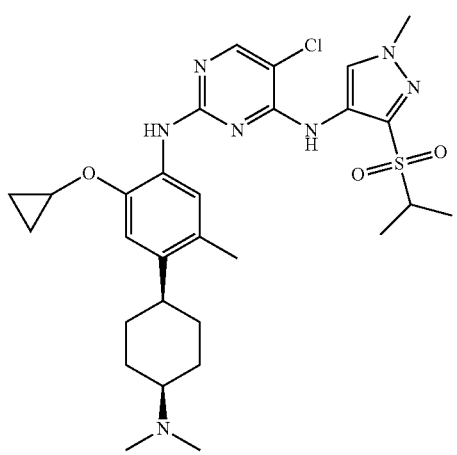 [SMILES: Cc1cc(Nc2ncc(Cl)c(Nc3cn(C)nc3S(=O)(=O)C(C)C)n2)c(OC2CC2)cc1[C@H]1CC[C@@H](N(C)C)CC1]

192 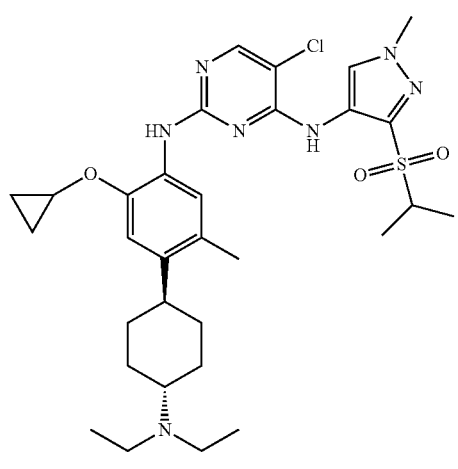 [SMILES: CCN(CC)[C@H]1CC[C@H](c2cc(OC3CC3)c(Nc3ncc(Cl)c(Nc4cn(C)nc4S(=O)(=O)C(C)C)n3)cc2C)CC1]
193 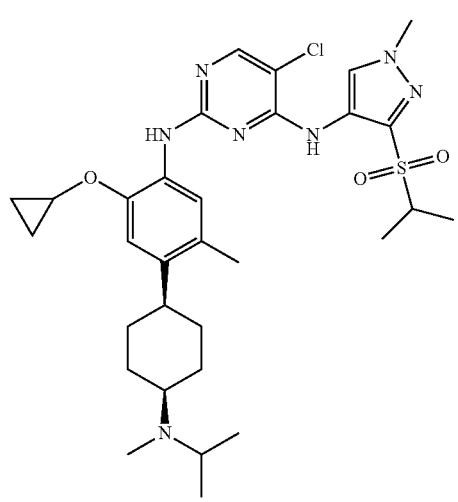 [SMILES: Cc1cc(Nc2ncc(Cl)c(Nc3cn(C)nc3S(=O)(=O)C(C)C)n2)c(OC2CC2)cc1[C@H]1CC[C@@H](N(C)C(C)C)CC1]
194 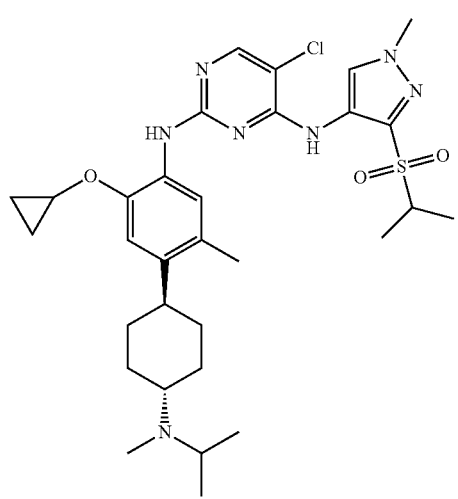 [SMILES: Cc1cc(Nc2ncc(Cl)c(Nc3cn(C)nc3S(=O)(=O)C(C)C)n2)c(OC2CC2)cc1[C@H]1CC[C@H](N(C)C(C)C)CC1]
195 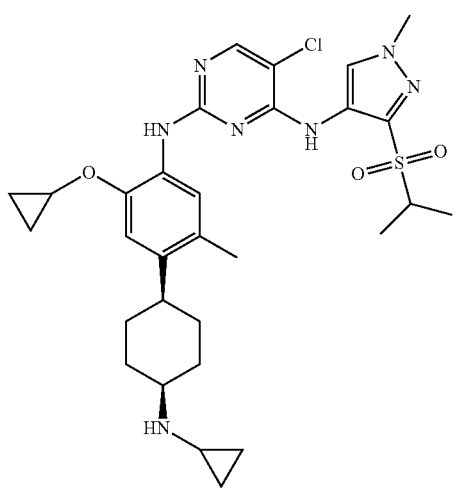 [SMILES: Cc1cc(Nc2ncc(Cl)c(Nc3cn(C)nc3S(=O)(=O)C(C)C)n2)c(OC2CC2)cc1[C@H]1CC[C@@H](NC2CC2)CC1]
196 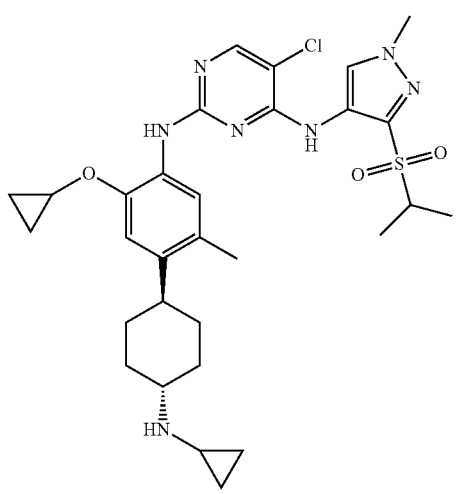 [SMILES: Cc1cc(Nc2ncc(Cl)c(Nc3cn(C)nc3S(=O)(=O)C(C)C)n2)c(OC2CC2)cc1[C@H]1CC[C@H](NC2CC2)CC1]
197 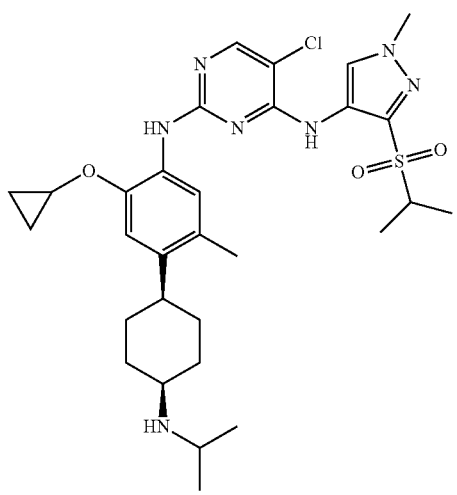 [SMILES: Cc1cc(Nc2ncc(Cl)c(Nc3cn(C)nc3S(=O)(=O)C(C)C)n2)c(OC2CC2)cc1[C@H]1CC[C@@H](NC(C)C)CC1]

| 198 | 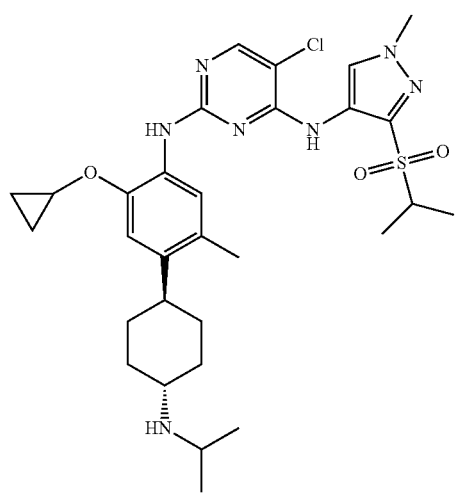 [SMILES: Cc1cc(Nc2ncc(Cl)c(Nc3cn(C)nc3S(=O)(=O)C(C)C)n2)c(OC2CC2)cc1[C@H]1CC[C@H](NC(C)C)CC1] |
| 199 | 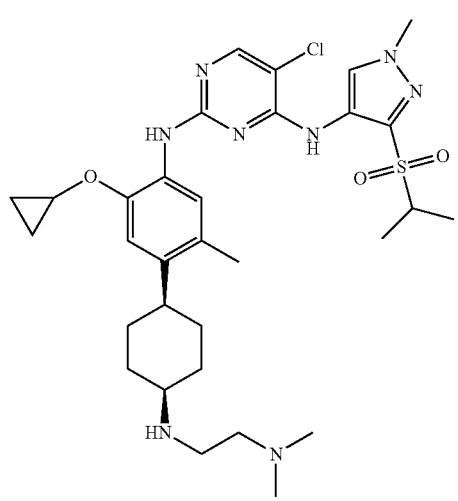 [SMILES: Cc1cc(Nc2ncc(Cl)c(Nc3cn(C)nc3S(=O)(=O)C(C)C)n2)c(OC2CC2)cc1[C@H]1CC[C@@H](NCCN(C)C)CC1] |
| 201 | 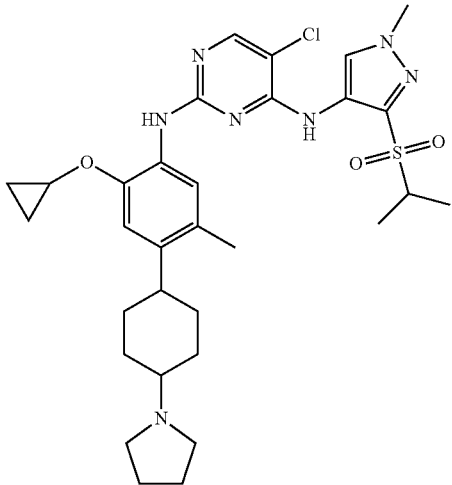 [SMILES: Cc1cc(Nc2ncc(Cl)c(Nc3cn(C)nc3S(=O)(=O)C(C)C)n2)c(OC2CC2)cc1C1CCC(N2CCCC2)CC1] |
| 202 | 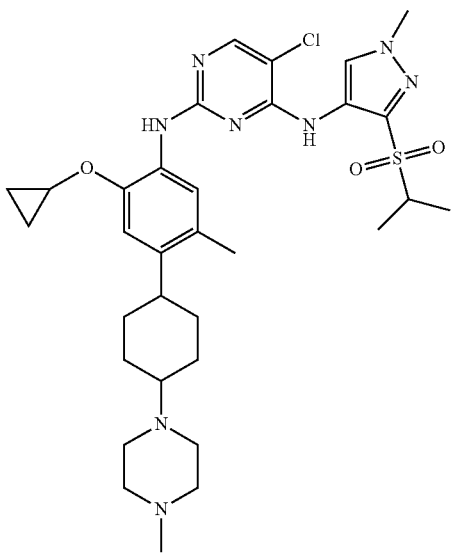 [SMILES: Cc1cc(Nc2ncc(Cl)c(Nc3cn(C)nc3S(=O)(=O)C(C)C)n2)c(OC2CC2)cc1C1CCC(N2CCN(C)CC2)CC1] |
| 203 | 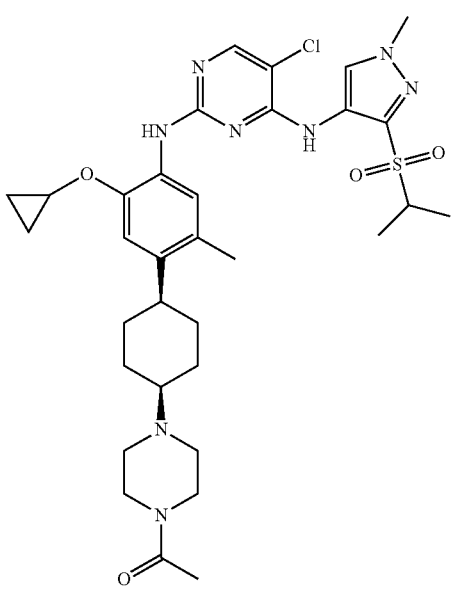 [SMILES: CC(=O)N1CCN([C@H]2CC[C@@H](c3cc(OC4CC4)c(Nc4ncc(Cl)c(Nc5cn(C)nc5S(=O)(=O)C(C)C)n4)cc3C)CC2)CC1] |

204 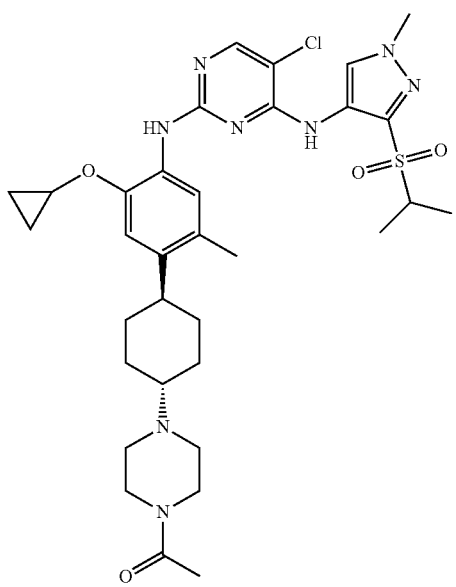 [SMILES: CC(=O)N1CCN([C@H]2CC[C@H](c3cc(OC4CC4)c(Nc4ncc(Cl)c(Nc5cn(C)nc5S(=O)(=O)C(C)C)n4)cc3C)CC2)CC1]
205 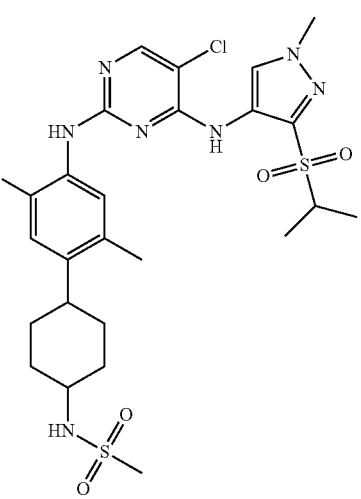
206 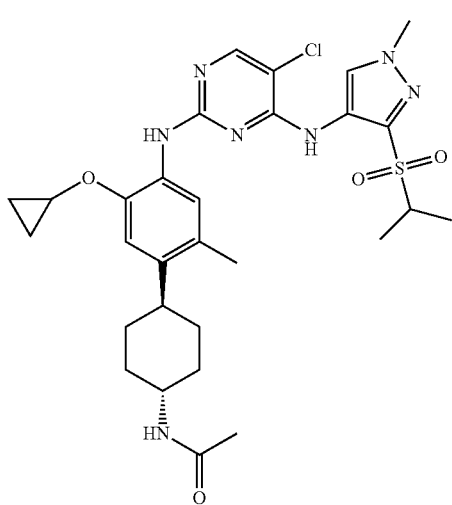
207 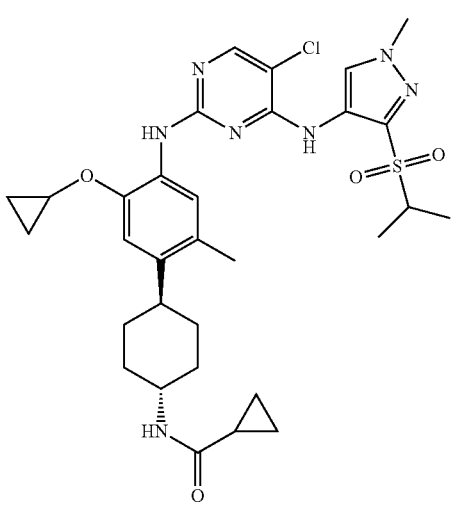 [SMILES: Cc1cc(Nc2ncc(Cl)c(Nc3cn(C)nc3S(=O)(=O)C(C)C)n2)c(OC2CC2)cc1[C@H]1CC[C@H](NC(=O)C2CC2)CC1]
208 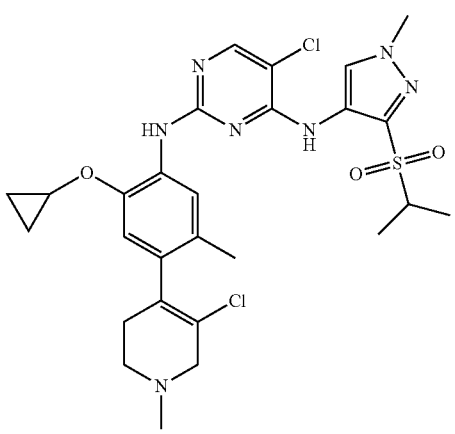
209 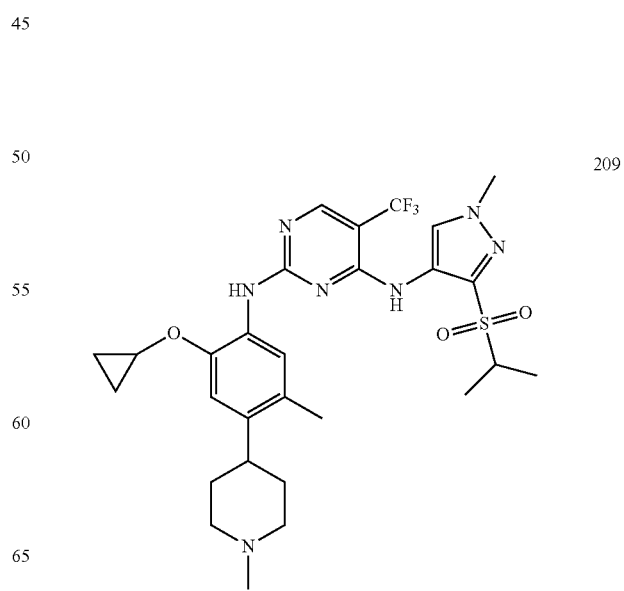

585
-continued

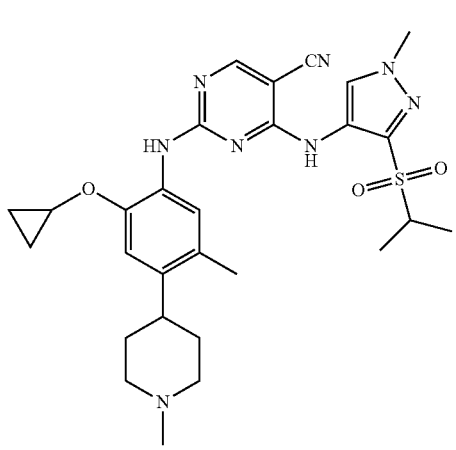
210

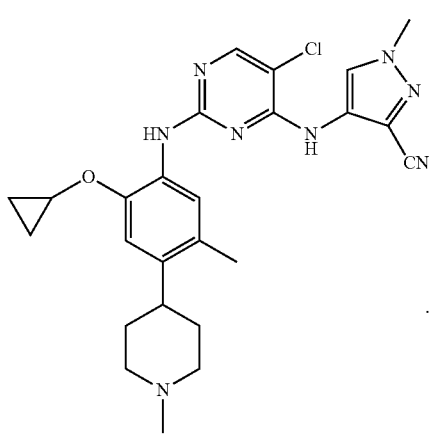 [SMILES: Cc1cc(Nc2ncc(Cl)c(Nc3cn(C)nc3C#N)n2)c(OC2CC2)cc1C1CCN(C)CC1]
211

-continued

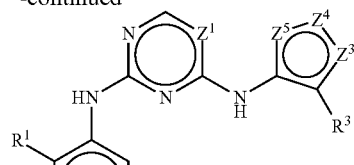

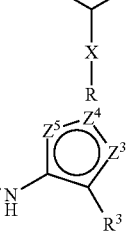

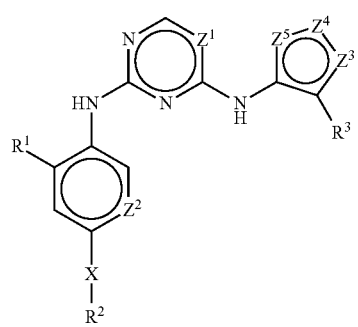

wherein $R^1$, $R^2$, $R^3$, X, $Z^1$, $Z^2$, $Z^3$, $Z^4$ and $Z^5$ are defined as with Formula I, R is the precursor of $R^2$.

15. A pharmaceutical composition comprising the compound or the pharmaceutical salts thereof according to claim 1.

16. The pharmaceutical composition according to claim 15, wherein the pharmaceutical composition is in the form of a tablet, a capsule, a pill, a granule, a powder, a suppository, an injection, a solution, a suspension, an ointment, a patch, a lotion, a drop, a liniment or a spray.

17. A method of treating anaplastic lame cell lymphoma, diffuse lame B-cell lymphoma or non-small cell lung cancer in subject, comprising administering to the subject a therapeutically effective amount of the compound or pharmaceutically acceptable salts thereof according to claim 1.

18. The method according to claim 17, wherein the subject is a mammal.

19. The method according to claim 17, wherein the modes of administration include oral, mucosal, sublingual, ocular, topical, parenteral, rectal, intracisternal, vagina, peritoneum, bladder, nasal administration.

20. The compound or pharmaceutically acceptable salts thereof according to claim 1, wherein $R^1$ is $C_{1-8}$ alkyl, $C_{1-8}$ halo alkyl or —O—$R^4$, wherein $R^4$ is hydrogen, $C_{1-5}$ alkyl, halo $C_{1-8}$ alkyl, $C_{3-8}$ cycloalkyl, halo $C_{3-8}$ cycloalkyl, $C_{1-8}$ alkyl-$C_{3-8}$ cycloalkyl, $C_{3-8}$ cycloalkyl-$C_{1-8}$ alkyl, substituted or unsubstituted 4-7 membered heterocyclyl containing one or two heteroatoms selected from a group consisting of N, O, and S or substituted or unsubstituted 4-7 membered 14. A method of preparing the compound according to claim 1, comprising the following steps:

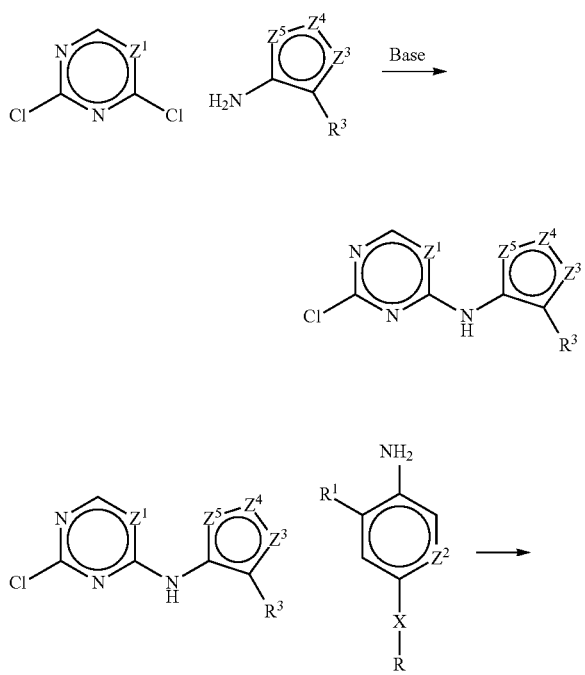

heterocyclyl-$C_{1-8}$ alkyl containing one or two heteroatoms selected from a group consisting of N, O, and S.

21. The compound or pharmaceutically acceptable salts thereof according to claim 1, wherein $R^1$ is $C_{1-8}$ alkyl, $C_{1-8}$ halo alkyl or —O—$R^4$, wherein $R^4$ is $C_{1-5}$ alkyl, halo $C_{1-5}$ alkyl, $C_{3-7}$ cycloalkyl, halo $C_{3-7}$ cycloalkyl or $C_{3-7}$ cycloalkyl-methyl.

22. The compound or pharmaceutically acceptable salts thereof according to claim 1, wherein $R^1$ is $C_{1-8}$ alkyl, $C_{1-8}$ halo alkyl or —O—$R^4$, wherein $R^4$ is methyl, ethyl, n-propyl, isopropyl, cyclopropyl, trifluoromethyl, cyclobutyl or cyclopropyl methyl.

23. The compound or pharmaceutically acceptable salts thereof according to claim 1, wherein $R^2$ is $C_{1-8}$ alkyl, $C_{3-8}$ cycloalkyl, 4-7 membered heterocycloalkyl containing one or two heteroatoms selected from a group consisting of N, O and S or 4-7 membered heterocycloalkenyl containing one or two heteroatoms selected from a group consisting of N, O and S, which may optionally be substituted with 1-3 substituents independently selected from the following group: oxo, $C_{1-8}$ alkyl, halo $C_{1-8}$ alkyl, $C_{1-8}$ alkoxy, halo $C_{1-8}$ alkoxy, $C_{3-8}$ cycloalkyl, halo $C_{3-8}$ cycloalkyl, $C_{3-8}$ cycloalkoxy, halo $C_{3-8}$ cycloalkoxy, $C_{1-8}$ alkoxy-$C_{1-8}$ alkyl, hydroxy-$C_{1-8}$ alkyl, amino-$C_{1-8}$ alkyl, carboxy-$C_{1-8}$ alkyl, $C_{1-8}$ alkyl-amino-$C_{1-8}$ alkyl, halogen, hydroxy, cyano, cyano-$C_{1-8}$ alkyl, amino, $C_{1-8}$ alkyl-amino, di ($C_{1-8}$ alkyl)-amino, $C_{3-8}$ cycloalkyl-amino, substituted or unsubstituted aromatic group, substituted or unsubstituted heteroaromatic group, substituted or unsubstituted 4-7 membered heterocyclyl, substituted or unsubstituted 4-7 membered heterocyclyl-$C_{1-8}$ alkyl, —(CH$_2$)$_n$CONR$^5$R$^6$, —COR$^5$, —SO$_2$R$^5$ and —NR$^5$SO$_2$R$^6$, wherein n is an integer of 0-8, $R^5$ and $R^6$ are independently hydrogen, $C_{1-8}$ alkyl, halo $C_{1-8}$ alkyl, $C_{3-8}$ cycloalkyl, halo $C_{3-8}$ cycloalkyl, amino, $C_{1-8}$ alkyl-amino, di ($C_{1-8}$ alkyl)-amino, or cyano-$C_{1-8}$ alkyl, $C_{1-8}$ alkyl-amino-$C_{1-8}$ alkyl or di- ($C_{1-8}$ alkyl)-amino-$C_{1-8}$ alkyl, wherein the substituents optionally form a substituted or unsubstituted ring with the carbon atoms to which they are attached.

24. The compound or pharmaceutically acceptable salts thereof according to claim 1, wherein $R^2$ is $C_{3-8}$ cycloalkyl, 4-7 membered heterocycloalkyl containing one or two heteroatoms selected from a group consisting of N, O and S or 4-7 membered heterocycloalkenyl containing one or two heteroatoms selected from a group consisting of N, O and S, which may optionally be substituted with 1-3 substituents independently selected from the following group: $C_{1-8}$ alkyl, halo $C_{1-8}$ alkyl, $C_{1-8}$alkoxy, $C_{3-8}$ cycloalkyl, halo $C_{3-8}$ cycloalkoxy, $C_{1-8}$ alkoxy-$C_{1-8}$ alkyl, hydroxy-$C_{1-8}$ alkyl, amino-$C_{1-8}$ alkyl, $C_{1-8}$ alkyl-amino-$C_{1-8}$ alkyl, halogen, cyano, cyano-$C_{1-8}$ alkyl, amino, $C_{1-8}$ alkyl-amino, di ($C_{1-8}$ alkyl)-amino, $C_{3-8}$ cycloalkyl-amino, substituted or unsubstituted 4-7 membered heterocyclyl, —CONR$^5$R$^6$, —COR$^5$, —SO$_2$R$^5$ and —NR$^5$SO$_2$R$^6$, wherein $R^5$ and $R^6$ are independently hydrogen, $C_{1-8}$ alkyl, halo $C_{1-8}$ alkyl, $C_{3-8}$ cycloalkyl, amino, $C_{1-8}$ alkyl-amino, di ($C_{1-8}$ alkyl)-amino, cyano-$C_{1-8}$ alkyl, $C_{1-8}$ alkyl-amino-$C_{1-8}$ alkyl or di- ($C_{1-8}$ alkyl)-amino-$C_{1-8}$ alkyl.

25. The compound or pharmaceutically acceptable salts thereof according to claim 1, wherein $R^2$ is cyclohexyl, piperidinyl, pyrrolidinyl, azetidinyl, tetrahydropyranyl, morpholinyl or 3-4 alkenyl piperidinyl, which are optionally substituted with 1-3 substituents independently selected from the following group: methyl, ethyl, n-propyl, isopropyl, n-butyl, sec-butyl, isobutyl, tert-butyl, cyclopropyl, cyclobutyl, oxetane, methoxy, methoxymethyl, methoxyethyl, fluoro, chloro, cyano, amino, cyclopropylamino, (isopropyl, methyl)-amino, formyl, acetyl, trifluoroacetyl, cyclopropanecarbonyl, —COR$^5$, —SO$_2$R$^5$ and —NR$^5$SO$_2$R$^6$, wherein $R^5$ and $R^6$ are independently hydrogen, $C_{1-5}$ alkyl, dimethylamino, dimethylamino methyl, ethylamino or cyanomethyl.

26. The compound or pharmaceutically acceptable salts thereof according to claim 1, wherein $R^3$ is —SO$_2$R$^7$, wherein $R^7$ is hydrogen, $C_{1-8}$ alkyl or $C_{3-8}$ cycloalkyl.

27. The compound or pharmaceutically acceptable salts thereof according to claim 1, wherein $R^3$ is —SO$_2$R$^7$, wherein $R^7$ is isopropyl, sec-butyl or isobutyl.

28. The compound or pharmaceutically acceptable salts thereof according to claim 1, wherein Z' is C—$R^{10}$, wherein $R^{10}$ is halogen.

29. The compound or pharmaceutically acceptable salts thereof according to claim 1, wherein Z' is C—$R^{10}$, wherein $R^{10}$ is chloro.

30. The compound or pharmaceutically acceptable salts thereof according to claim 1, wherein $Z^2$ is C—$R^{11}$, wherein $R^{11}$ and $R^2$ together with the atoms to which they are attached form a 5- or 6-membered ring fused to the phenyl ring.

31. The compound or pharmaceutically acceptable salts thereof according to claim 1, wherein $Z^2$ is C—$R^{11}$, wherein $R^{11}$ is hydrogen, methyl, fluoro, chloro or cyano.

32. The compound or pharmaceutically acceptable salts thereof according to claim 1, wherein $Z^3$ is N, $Z^4$ is N—$R^{14}$, $Z^5$ is CH, wherein $R^{14}$ is $C_{1-8}$ alkyl or $C_{3-8}$ cycloalkyl.

33. The compound or pharmaceutically acceptable salts thereof according to claim 1, wherein $Z^3$ is N, $Z^4$ is N—$R^{14}$, $Z^5$ is CH, wherein $R^{14}$ is methyl or cyclopropyl.

34. The compound or pharmaceutically acceptable salts thereof according to claim 1, wherein $Z^3$ is N, $Z^4$ is C—$R^{14}$, $Z^5$ is S, wherein $R^{14}$ is methyl or cyclopropyl.

35. The method according to claim 14, wherein the method comprises the following steps:

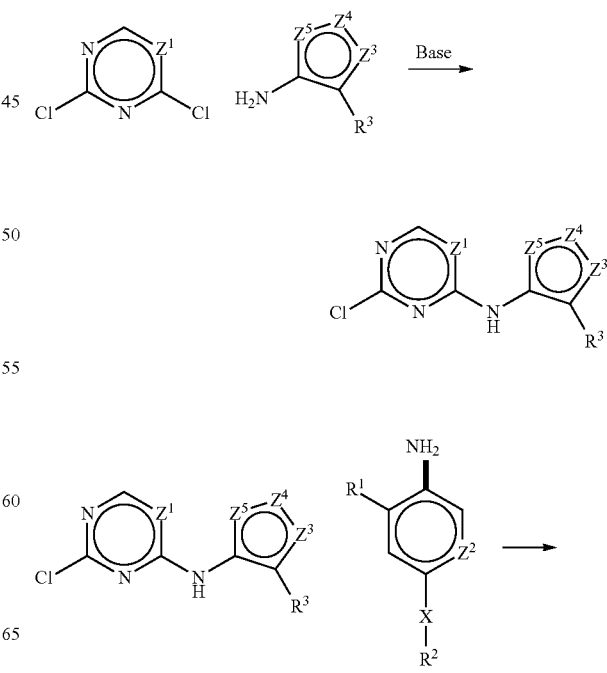

-continued
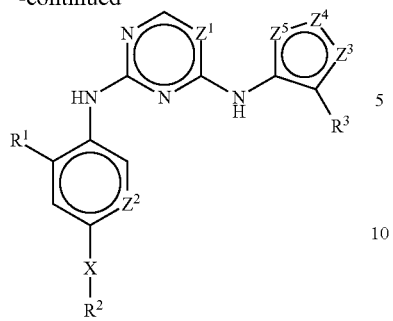
wherein $R^1$, $R^2$, $R^3$, X, $Z^1$, $Z^2$, $Z^3$, $Z^4$ and $Z^5$ are defined as with Formula I.
36. The pharmaceutical composition according to claim 15, wherein the pharmaceutical composition comprises a pharmaceutical acceptable carrier or excipient.
37. The method according to claim 18, wherein the subject is a human.
* * * * *